(12) United States Patent
Prongay et al.

(10) Patent No.: US 8,088,611 B2
(45) Date of Patent: Jan. 3, 2012

(54) KINASE DOMAIN POLYPEPTIDE OF HUMAN PROTEIN KINASE B GAMMA (AKT3)

(75) Inventors: Andrew J. Prongay, Billerica, MA (US); Thierry O. Fischmann, Scotch Plains, NJ (US); Chandra C. Kumar, Raritan, NJ (US); Vincent S. Madison, Ukiah, CA (US); Joseph E. Myers, Edison, NJ (US); Paul Reichert, Montville, NJ (US); Rosalinda Syto, Nutley, NJ (US); William T. Windsor, East Brunswick, NJ (US); Li Xiao, Cranbury, NJ (US); Todd W. Mayhood, Randolph, NJ (US)

(73) Assignee: Schering Corp., Kenilworth, NJ (US)

( * ) Notice: Subject to any disclaimer, the term of this patent is extended or adjusted under 35 U.S.C. 154(b) by 0 days.

(21) Appl. No.: 12/784,760

(22) Filed: May 21, 2010

(65) Prior Publication Data

US 2010/0267053 A1 Oct. 21, 2010

Related U.S. Application Data

(62) Division of application No. 11/847,801, filed on Aug. 30, 2007, now Pat. No. 7,776,589.

(60) Provisional application No. 60/841,703, filed on Aug. 31, 2006.

(51) Int. Cl.
*C12N 9/12* (2006.01)

(52) U.S. Cl. ........................................ 435/194

(58) Field of Classification Search ................ None
See application file for complete search history.

(56) References Cited

U.S. PATENT DOCUMENTS

| 5,300,435 | A | 4/1994 | Granados |
| 6,831,175 | B2 | 12/2004 | Li et al. |
| 7,303,892 | B1 * | 12/2007 | Adam et al. ............... 435/15 |
| 2003/0100049 | A1 | 5/2003 | Guo et al. |
| 2003/0187026 | A1 | 10/2003 | Li et al. |
| 2003/0199511 | A1 | 10/2003 | Li et al. |
| 2008/0201123 | A1 * | 8/2008 | Cosgrove ................... 703/11 |

FOREIGN PATENT DOCUMENTS

WO WO 03/051366 6/2003

OTHER PUBLICATIONS

Koseoglu S, Lu Z, Kumar C, Kirschmeier P, Zou J., AKT1, AKT2 and AKT3-dependent cell survival is cell line-specific and knockdown of all three isoforms selectively induces apoptosis in 20 human tumor cell lines, Cancer Biol Ther. May 2007;6(5):755-62.
Genbank sequence disclosure; accession No. NP_005456, Dec. 2008.
Kandel et al., The regulation and activities of the multifunctional serine/threonine kinase Akt/PKB, Exp Cell Res. Nov. 25, 1999;253(1):210-29.
Genbank sequence disclosure No. Q9Y243, Apr. 8, 2008.
Genbank sequence disclosure No. NP_005456, Mar. 27, 2008.
International Protein Index sequence disclosure No. IPI00031747.3, Apr. 17, 2008.
Masure et al., "Molecular cloning, expression and characterization of the human serine/threonine kinase Akt-3", Eur. J. Biochem. 265:353-360, 1999.
Merriam-Webster online dictionary definition of "encode", obtained from www.merriam-webster.com/medical/encode, last viewed on Mar. 9, 2009, 2 pages.

* cited by examiner

*Primary Examiner* — David J Steadman

(57) ABSTRACT

The present invention provides, in part, AKT3 polypeptides and methods of use thereof along with nucleic acids encoding the polypeptides. For example, methods for screening for AKT3 inhibitors are provided herein.

5 Claims, No Drawings

KINASE DOMAIN POLYPEPTIDE OF HUMAN PROTEIN KINASE B GAMMA (AKT3)

This application is a divisional of U.S. application Ser. No. 11/847,801, filed Aug. 30, 2007, now U.S. Pat. No. 7,776,589, which claims the benefit of U.S. provisional patent application No. 60/841,703; filed Aug. 31, 2006; which is herein incorporated by reference in its entirety.

FIELD OF THE INVENTION

The present invention relates to AKT3 polypeptides.

BACKGROUND OF THE INVENTION

Protein kinase B or AKT (PKB/AKT) is a serine/threonine kinase which, in mammals, comprises three highly homologous members known as PKBα (AKT1), PKBβ (AKT2), and PKBγ (AKT3). PKB/AKT is activated in cells exposed to diverse stimuli such as hormones, growth factors, and extracellular matrix components. Constitutive PKB/AKT activation can occur due to amplification of PKB/AKT genes or as a result of mutations in components of the signaling pathway that activates PKB/AKT. Constitutive PKB/AKT signaling is believed to promote proliferation and increased cell survival and thereby contributing to cancer progression.

AKT3 is a promising target for use in identifying compounds to treat cancer. Such compounds inhibit the enzymatic activity of AKT3 and thereby disrupt the cell cycle and proliferation of cells. Structure-assisted drug design is one way to optimize the success of identifying such compounds. But use of this powerful methodology requires three-dimensional structural information (e.g., as obtained via X-ray diffraction of the target protein). Alternatively, inhibitors of AKT3 can be identified using assays which utilize soluble, non-crystalline AKT3.

SUMMARY OF THE INVENTION

The present invention provides, in part, AKT3 (e.g., human AKT3) polypeptides that are useful for the determination of the three dimensional structure of AKT3 and the design of AKT3 inhibitors. Assay methods for identifying inhibitors of AKT3 are also provided along with polypeptides for use therein.

The present invention provides isolated crystalline and non-crystalline polypeptides consisting of AKT3 (e.g., human ATK3) amino acids 139-458; comprising AKT3 amino acids 139-458, comprising the mutation T305X; comprising AKT3 amino acids 139-458, phosphorylated on amino acid T305; consisting of AKT3 amino acids 139-479; comprising AKT3 amino acids 139-479, phosphorylated on amino acids T305 and S472; comprising AKT3 amino acids 139-479 comprising the mutations T305X and S472X; or comprising AKT3 amino acids 139-479, phosphorylated on amino acids T305 and comprising the mutation S472D. In an embodiment of the invention, the polypeptide comprises a three-dimensional structure characterized by structural coordinates comprising a root mean square deviation of conserved residue backbone atoms or of alpha carbon atoms of less than about 1.5 Å when superimposed on backbone atoms described in Table 2, 3, 4 or 5. In an embodiment of the invention, the polypeptide comprises a three-dimensional structure characterized by the structural coordinates of Table 2, 3, 4 or 5. In an embodiment of the invention, the polypeptide consists of or comprises amino acids selected from the group consisting of SEQ ID NO: 1; SEQ ID NO: 2; amino acids 24-347 of SEQ ID NO: 1; amino acids 24-368 of SEQ ID NO: 2; amino acids 28-347 of SEQ ID NO: 1 and amino acids 28-368 of SEQ ID NO: 2. In an embodiment of the invention, the polypeptide is complexed with a member selected from the group consisting of a polypeptide comprising the amino acid sequence of SEQ ID NO: 6 and 14. The scope of the present invention also includes an aqueous solution comprising the polypeptide and a buffer. The present invention also comprises any isolated polynucleotide encoding the polypeptide wherein the polynucleotide is optionally operably linked to an expression control sequence such as a transcriptional control sequence (e.g., promoter). A recombinant vector comprising the polynucleotide is also within the scope of the present invention along with an isolated host cell comprising the vector.

The present invention also provides a crystalline composition comprising a polypeptide selected from the group consisting of: (a) human AKT3 short kinase domain polypeptide, wherein said crystal is in $P2_12_12_1$ space group and comprises unit cell dimensions a=49.070, b=73.350, c=95.570, α=β=γ=90.0; a=48.679, b=73.357, c=95.468, α=β=γ=90.0; a=49.093, b=73.528, c=95.559, α=β=γ=90.0; or a=49.015, b=73.365, c=95.375, α=β=γ=90.0; (b) human AKT3 long kinase domain (pT305, pS472) polypeptide, wherein said crystal is in $P2_12_12_1$ space group and comprises unit cell dimensions a=48.760, b=73.080, c=95.110, α=β=γ=90.0; (c) human AKT3 long kinase domain (T305D, S472D) polypeptide, wherein said crystal is in $P2_12_12_1$ space group and comprises unit cell dimensions a=48.680, b=72.890, c=95.210, α=β=γ=90.0; and (d) human AKT3 long kinase domain (pT305, S472D) polypeptide, wherein said crystal is in $P2_12_12_1$ space group and comprises unit cell dimensions a=48.830, b=72.970, c=95.220, α=β=γ=90.0. In an embodiment of the invention, the short kinase domain polypeptide comprises the amino acid sequence of SEQ ID NO: 1 or the long kinase domain polypeptide comprises the amino acid sequence of SEQ ID NO: 2. In an embodiment of the invention, the human AKT3 short or long kinase domain polypeptide comprises a three-dimensional structure characterized by structural coordinates comprising a root mean square deviation of conserved residue backbone atoms or of alpha carbon atoms of less than about 1.5 Å when superimposed on backbone atoms or alpha carbon atoms described in Table 2, 3, 4 or 5. In an embodiment of the invention, the AKT3 short or long kinase domain polypeptide comprises a three-dimensional structure characterized by the structural coordinates of Table 2, 3, 4 or 5.

The present invention also provides a method for identifying a substance that reduces the occurrence or growth of a cancer cell or that inhibits AKT3 comprising: (a) contacting a composition comprising AKT3lkd or AKT3skd with a substance to be tested for the presence of the inhibitor; and (b) determining the ellipticity of said composition; whereby the substance is selected if the ellipticity and/or the Tm of said composition alone is different from the ellipticity and/or Tm of the composition that is in contact with said substance.

The present invention also provides a method for identifying a substance that reduces the occurrence or growth of a cancer cell or that inhibits AKT3 comprising: (a) contacting a composition comprising AKT3lkd or AKT3skd with a substance to be tested for the presence of an inhibitor; and (b) determining if the substance binds to said AKT3lkd or AKT3skd or fragment or fusion thereof; whereby the substance is selected if binding is observed.

The present invention also provides a method for identifying a substance that reduces the occurrence or growth of a cancer cell or that inhibits AKT3 comprising (a) contacting a composition comprising AKT3lkd or AKT3skd with a substrate or ligand that is known to bind AKT3lkd or AKT3skd and with a substance to be tested for the presence of an inhibitor; and (b) determining if the substance being tested reduces binding of the substrate or ligand to AKT3lkd or AKT3skd; whereby the substance is selected if binding of the substrate or ligand to AKT3lkd or AKT3skd is reduced as compared to substrate or ligand binding to AKT3lkd or AKT3skd in the absence of the substance.

The present invention also provides a method for identifying a substance that reduces the occurrence or growth of a cancer cell or that inhibits AKT3 comprising (a) contacting a composition comprising AKT3lkd or AKT3skd with an AKT3 substrate, with adenosine triphosphate (ATP; e.g., $[\gamma^{32}P]ATP$) and $Mg^{2+}$ (e.g., $MgCl_2$) and with a substance to be tested for the presence of an AKT3 inhibitor; and (b) determining if the substrate is phosphorylated (e.g., with $^{32}P$); wherein the substance is selected if the substrate is phosphorylated at a lower level in the presence of the substance than in the absence of the substance.

The present invention also provides a method for evaluating the potential of a candidate AKT3 inhibitor to associate with an AKT3 polypeptide or fragment thereof or structural homologue thereof comprising a three dimensional structure characterized by structural coordinates comprising a root mean square deviation of common residue backbone atoms or alpha carbon atoms of less than about 1.5 Å (e.g., 1 Å, 0.5 Å, 0.25 Å, 0.1 Å, 0.05 Å) when superimposed on backbone atoms or alpha carbon atoms described by structural coordinates of Table 2, 3, 4, or 5 comprising the steps of: (i) employing computational means to perform a fitting operation between the candidate and the polypeptide; and (ii) analyzing the results of said fitting operation to quantify the association between the candidate and the polypeptide.

The present invention also provides a method for identifying a substance that reduces the occurrence or growth of a cancer cell or that inhibits AKT3 comprising measuring the rate of decrease in $A_{340}$ over time of a composition comprising AKT3skd or AKT3lkd, and AKT3 substrate, ATP, PEP, NADH, $Mg^{2+}$, pyruvate kinase and lactate dehydrogenase in the presence of a substance to be tested for the presence of an AKT3 inhibitor; wherein the substance is selected if the rate of decrease in $A_{340}$ over time is less than the rate of decrease observed in the absence of the substance.

DETAILED DESCRIPTION OF THE INVENTION

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1996) (herein "Ausubel et al., 1996").

TABLE 1

| Sequence Summary | |
|---|---|
| Sequence | SEQ ID NO: |
| AKT3 short kinase domain | 1 |
| AKT3 long kinase domain | 2 |
| AKT3 full length sequence | 3 |
| TEV cleavage site | 4 |
| HHK | 5 |
| GSK-3 peptide | 6 |
| primer | 7 |
| primer | 8 |
| primer | 9 |
| HHKRK | 10 |
| N-terminal sequence | 11 |
| TEV consensus sequence | 12 |
| FLAG tag | 13 |
| AKT3 substrate peptide | 14 |
| domain boundary | 15 |
| domain boundary | 16 |
| Polynucleotide encoding AKT3 short kinase domain | 17 |
| Polynucleotide encoding AKT3 long kinase domain | 18 |

AKT3 Polypeptides and Crystals

The present invention comprises various fragments and mutants of AKT3 (e.g., any of the lkd or skd constructs set forth herein) which are optionally complexed with any other molecule, for example any small organic molecule such as

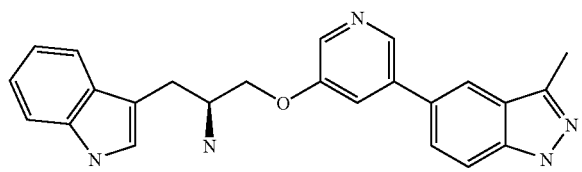

(see e.g., WO2003/51366 or US2003/0199511).

In an embodiment of the invention, full length human AKT3 comprises the amino acid sequence:

```
MSDVTIVKEG WVQKRGEYIK NWRPRYFLLK TDGSFIGYKE KPQDVDLPYP LNNFSVAKCQ  60

LMKTERPKPN TFIIRCLQWT TVIERTFHVD TPEEREEWTE AIQAVADRLQ RQEEERMNCS 120

PTSQIDNIGE EEMDASTTHH KRKTMNDFDY LKLLGKGTFG KVILVREKAS GKYYAMKILK 180

KEVIAKDEV  AHTLTESRVL KNTRHPFLTS LKYSFQTKDR LCFVMEYVNG GELFFHLSRE 240

RVFSEDRTRF YGAEIVSALD YLHSGKIVYR DLKLENLMLD KDGHIKITDF GLCKEGITDA 300

ATMKTFCGTP EYLAPEVLED NDYGRAVDWW GLGVVMYEMM CGRLPFYNQD HEKLFELILM 360
```

-continued

EDIKFPRTLS SDAKSLLSGL LIKDPNKRLG GGPDDAKEIM RHSFFSGVNW QDVYDKKLVP420

PFKPQVTSET DTRYFDEEFT AQTITITPPE KYDEDGMDCM DNERRPHFPQ FSYSASGRE 479

See also accession nos. IPI00031747.3; Q9Y243; and NP_005456.

As set forth herein, the scope of the present invention comprises both crystalline and non-crystalline polypeptides comprising the AKT3 long or short kinase domain as well as post-translationally modified versions and mutants thereof (e.g., as set forth herein).

In an embodiment of the invention, the AKT3 short kinase domain (AKT3skd) comprises the following amino acid sequence:

<u>MSYYHHHHHHDYDIPTTENLYFQGAMD</u>HHKRKTMNDFDYLKLLGKGTEGK

VILVREKASGKYYAMKILKKEVIIAKDEVAHTLTESRVLKNTRHPFLTSL

KYSFQTKDRLCFVMEYVNGGELFFHLSRERVESEDRTRFYGAEIVSALDY

LHSGKIVYRDLKLENLMLDKDGHIKITDEGLCKEGITDAATMK<u><u>T</u></u>FCGTPE

YLAPEVLEDNDYGRAVDWWGLGVVMYEMMCGRLPFYNQDHEKLFELILME

DIKFPRTLSSDAKSLLSGLLIKDPNKRLGGGPDDAKEIMRHSFFSGVNWQ

DVYDKKLVPPFKPQVTSETDTRYFDEEFTAQTITITPPEKYDEDG

In an embodiment of the invention, AKT3 skd (excluding the underscored N-terminal tag) comprises amino acids 139-458 of human AKT3.

The double underlined threonine (T) at position 194 of SEQ ID NO: 1 is referred to as threonine 305 or T305. In an embodiment, the N-terminal tag (underlined) is cleaved after the Q of the TEV cleavage site (ENLYFQ) (SEQ ID NO: 4) resulting in yet another polypeptide of the invention. The human AKT3 short kinase domain sequence starts at HHK (SEQ ID NO: 5).

Another embodiment of the present invention comprises any polynucleotide that encodes the AKT3 short kinase domain. For example:

(SEQ ID NO: 17)
atgwsntayt aycaycayca ycaycaycay gaytaygaya thccnacnac ngaraayytn tayttycarg gngcnatgga ycaycayaar mgnaaracna tgaaygaytt ygaytayytn aarytnytng gnaarggnac nttyggnaar gtnathytng tnmgngaraa rgcnwsnggn aartaytayg cnatgaarat hytnaaraar gargtnatha thgcnaarga ygargtngcn cayacnytna cngarwsnmg ngtnytnaar aayacnmgnc ayccnttyyt nacnwsnytn aartaywsnt tycaracnaa rgaymgnytn tgyttygtna tggartaygt naayggnggn garytnttyt tycayytnws nmgngarmgn gtnttywsng argaymgnac nmgnttytay ggngcngara thgtnwsngc nytngaytay ytncaywsng gnaarathgt ntaymgngay ytnaarytng araayytnat gytngayaar gayggncaya thaarathac ngayttyggn ytntgyaarg arggnathac ngaygcngcn acnatgaara cnttytgygg nacnccngar tayytngcnc cngargtnyt ngargayaay gaytayggnm gngcngtnga ytggtgggn ytnggngtng tnatgtayga ratgatgtgy ggnmgnytnc cnttytayaa ycargaycay garaarytnt tygarytnat hytnatggar gayathaart tyccnmgnac nytnwsnwsn gaygcnaarw snytnytnws nggnytnytn athaargayc cnaayaarmg nytnggnggn ggnccngayg aygcnaarga rathatgmgn caywsnttyt tywsnggngt naaytggcar gaygtntayg ayaaraaryt ngtnccnccn ttyaarccnc argtnacnws ngaracngay acnmgntayt tygaygarga rttyacngcn caracnatha cnathacncc nccngaraar taygaygarg ayggnatgga y In an embodiment of the invention, the AKT3 long kinase domain (AKT3lkd) comprises the following amino acid sequence:

(SEQ ID NO: 2)
<u>MSYYHHHHHHDYDIPTTENLYFQGAMD</u>HHKRKTMNDFDYLKLLGKGT

FGKVILVREKASGKYYAMKILKKEVIIAKDEVAHTLTESRVLKNTRH

PFLTSLKYSFQTKDRLCFVMEYVNGGELFFHLSRERVFSEDRTRFYG

AEIVSALDYLHSGKIVYRDLKLENLMLDKDGHIKITDFGLCKEGITD

AATMK<u><u>T</u></u>FCGTPEYLAPEVLEDNDYGRAVDWWGLGVVMYEMMCGRLPF

YNQDHEKLFELILMEDIKFPRTLSSDAKSLLSGLLIKDPNKRLGGGP

DDAKEIMRHSFFSGVNWQDVYDKKLVPPFKPQVTSETDTRYFDEEFT

AQTITITPPEKYDEDGMDCMDNERRPHFPQF<u><u>S</u></u>YSASGRE

In an embodiment of the invention, AKT3lkd (excluding the underscored N-terminal tag) comprises amino acids 139-479 of human AKT3.

The double underlined threonine (T) at position 194 of SEQ ID NO: 2 is referred to as threonine 305 or T305. The double underlined serine (S) at position 361 of SEQ ID NO: 2 is referred to as serine 472 or S472.

In an embodiment, the N-terminal tag (underlined) is cleaved after the Q of the TEV cleavage site (ENLYFQ) (SEQ ID NO: 4) resulting in yet another polypeptide of the invention. The human AKT3 long kinase domain sequence starts at HHK (SEQ ID NO: 5).

Another embodiment of the present invention comprises any polynucleotide that encodes the AKT3 long kinase domain. For example:

(SEQ ID NO: 18)

```
atgwsntayt aycaycayca ycaycaycay gaytaygaya
thccnacnac ngaraayytn tayttycarg gngcnatgga
ycaycayaar mgnaaracna tgaaygaytt ygaytayytn
aarytnytng gnaarggnac nttyggnaar gtnathytng
tnmgngaraa rgcnwsnggn aartaytayg cnatgaarat
hytnaaraar gargtnatha thgcnaarga ygargtngcn
cayacnytna cngarwsnmg ngtnytnaar aayacnmgnc
ayccnttyyt nacnwsnytn aartaywsnt tycaracnaa
rgaymgnytn tgyttygtna tggartaygt naayggnggn
garytnttyt tycayytnws nmgngarmgn gtnttywsng
argaymgnac nmgnttytay ggngcngara thgtnwsngc
nytngaytay ytncaywsng gnaarathgt ntaymgngay
ytnaarytng araayytnat gytngayaar gayggncaya
thaarathac ngayttyggn ytntgyaarg arggnathac
ngaygcngcn acnatgaara cnttytgygg nacnccngar
tayytngcnc cngargtnyt ngargayaay gaytayggnm
gngcngtnga ytggtggggn ytnggngtng tnatgtayga
ratgatgtgy ggnmgnytnc cnttytayaa ycargaycay
garaarytnt tygarytnat hytnatggar gayathaart
tyccnmgnac nytnwsnwsn gaygcnaarw snytnytnws
nggnytnytn athaargayc cnaayaarmg nytnggnggn
ggnccngayg aygcnaarga rathatgmgn caywsnttyt
tywsnggngt naaytggcar gaygtntayg ayaaraaryt
ngtnccnccn ttyaarccnc argtnacnws ngaracngay
acnmgntayt tygaygarga rttyacngcn caracnatha
cnathacncc nccngaraar taygaygarg ayggnatgga
ytgyatggay aaygarmgnm gnccncaytt yccncartty
wsntaywsng cnwsnggnmg ngar
```

Polypeptides of the present invention include soluble form (e.g., in an aqueous or non-aqueous, desiccated form) polypeptides as well as polypeptides in crystalline form.

The terms "AKT3lkd" and "AKT3skd" include any AKT3 long kinase domain or AKT3 short kinase domain sequence, respectively, including any post-translational modification and/or mutation thereof. For example, the terms include AKT3lkd or AKT3skd comprising a phosphorylated T305 and/or phosphorylated S472 and/or a T305D mutation and/or a S472D mutation including any combination thereof, for example, as set forth herein (e.g., AKT3lkd, AKT3skd, AKT3lkd(pT305, pS472); AKT3lkd(pT305, S472D); AKT3lkd(T305D, S472D); AKT3skd or AKT3skd(T305D)). The terms include any polypeptide comprising an amino acid sequence selected from the group consisting of SEQ ID NO: 1; SEQ ID NO: 2; amino acids 24-347 of SEQ ID NO: 1 (TEV cleaved SEQ ID NO: 1); amino acids 24-368 of SEQ ID NO: 2 (TEV cleaved SEQ ID NO: 2); amino acids 28-347 of SEQ ID NO: 1 (AKT3 short kinase domain lacking N-terminal peptide) and amino acids 28-368 of SEQ ID NO: 2 (AKT3 long kinase domain lacking N-terminal peptide), again, including any post-translational modification (e.g., phosphorylation of S472 and/or T305) or mutation thereof (e.g., mutation of S472 and/or T305 to aspartic acid (D)).

"AKT3skd" refers to the short kinase domain. "AKT3lkd" refers to the long kinase domain. "AKT3lkdPP" refers to the long kinase domain with T305 and S472 phosphorylated; this is also written/labeled as "AKT3lkd(pT305, pS472)". "AKT3lkdPD" refers to the long kinase domain with S305 phosphorylated and T472 mutated to aspartic acid; this is also written/labeled as "AKT3lkd(pT305, S472D)". "AKT3lkdDD" refers to the long kinase domain with T305 and S472 mutated to aspartic acid; this is also written/labeled as "AKT3lkd(T305D, S472D)".

In an embodiment of the invention, a phosphorylated serine (pS) or threonine (pT) is phosphorylated on the sidechain γ-hydroxyl group.

In an embodiment of the invention, a mutation is expressed as A#B wherein A represents the residue which exists in the natural, beginning or unmutated polypeptide, # represents the amino acid position and B represents the residue in the final or mutated protein. For example, T305X represents a mutation wherein position 305 is any residue other than threonine or serine; and S472X represents a mutation wherein position 305 is any residue other than threonine or serine (e.g., alanine, arginine, asparagine, aspartic acid, cysteine, glutamine, glutamic acid, glycine, histidine, isoleucine, leucine, lysine, methionine, phenylalanine, proline, tryptophan, tyrosine, valine).

An "enzymatically active" AKT3 or domain or mutant thereof (e.g., AKT3skd or AKT3lkd) comprises any of the activities that characterize AKT3, including, but not limited to phosphorylation of natural or synthetic substrates such as a peptide comprising the amino acid sequence of SEQ ID NO: 6 or 14. A substance inhibits AKT3 when, for example, it reduces the ability of the enzyme to bind or phosphorylate a substrate or to perform any other function. The terms "mutant" and "mutation" refer to any detectable change in genetic material or amino acid sequence. This includes gene mutations, in which the structure (e.g., DNA sequence) of a gene is altered, any gene or DNA arising from any mutation process, and any expression product (e.g., RNA or protein) expressed by a modified gene or DNA sequence. The term "variant" may also be used to indicate a modified or altered gene, DNA sequence, polypeptide or enzyme, etc., i.e., any kind of mutant. Sequence- and function-conservative variants of AKT3lkd and AKT3skd polypeptides (e.g., SEQ ID NO: 1 or 2) are contemplated for use in the present invention and the present invention includes any crystal comprising any AKT3lkd or AKT3skd variant. A natural allelic variant is one of several alternate naturally occurring forms of a gene occupying a given locus on a chromosome of an organism (Genes II, Lewin, B., ed., John Wiley & Sons, New York (1985)). "Function-conservative variants" of AKT3lkd or AKT3skd (e.g., SEQ ID NO: 1 or 2) are those in which a given amino acid residue in a AKT3lkd or AKT3skd polypeptide has been changed without significantly altering the overall conformation and/or function of the polypeptide, including, but not limited to, replacement of an amino acid with one having similar properties (such as, for example, polarity, hydrogen bonding potential, acidic, basic, hydrophobic, aromatic (see infra)). A sequence conservative variant is a variant wherein the DNA sequence encoding a polypeptide is changed or mutated in a manner wherein the encoded amino acid sequence is unchanged.

Protein or polypeptide sequence homology, or sequence identity, is determined by optimizing residue matches, if necessary, by introducing gaps as required. See, e.g., Needleham, et al. *J. Mol. Biol.* 48:443-453 (1970); Sankoff et al., "Time Warps, String Edits, and Macromolecules: The Theory and Practice of Sequence Comparison", Ch. 1, Addison-Wesley, Reading, Mass. (1983); and software packages from Intelli-Genetics, Mountain View, Calif. and the University of Wisconsin Genetics Computer Group (GCG), Madison, Wis.

The present invention includes any AKT3lkd or AKT3skd polypeptide or crystal wherein the amino acid sequence comprises less than 100% similarity or identity to, for example, the AKT3lkd or AKT3skd sequence of SEQ ID NO: 1 or 2 (e.g., natural allelic variations or homologues of AKT3lkd or AKT3skd). In an embodiment of the invention, an AKT3lkd or AKT3skd polypeptide that is less than 100% similar or identical to SEQ ID NO: 1 or 2 is enzymatically active. Sequence "identity" refers to exact matches between the amino acids of two sequences which are being compared. Sequence "similarity" refers to both exact matches between the amino acids of two polypeptides which are being compared in addition to matches between nonidentical, biochemically related amino acids. For example, biochemically related amino acids which share similar properties can fall, in an embodiment of the invention, within the following groups: polar/hydrophilic amino acids including asparagine, glutamine, serine, cysteine, threonine, lysine, arginine, histidine, aspartic acid and glutamic acid; nonpolar/hydrophobic amino acids including glycine, alanine, valine, leucine, isoleucine, proline, tyrosine, phenylalanine, tryptophan and methionine; acidic amino acids including aspartic acid and glutamic acid and basic amino acids including histidine, lysine and arginine. Typical AKT3lkd or AKT3skd polypeptides and homologues thereof used in this invention will have from 50-100% similarity or identity, to 60-100% similarity or identity, e.g., with AKT3lkd or AKT3skd comprising the amino acid sequence of SEQ ID NO: 1 or 2. The present invention includes polypeptides and crystals comprising polypeptides or homologues thereof comprising at least about 70% similarity or identity, generally at least 76% similarity or identity, more generally at least 81% similarity or identity, often at least 85% similarity or identity, more often at least 88% similarity or identity, typically at least 90% similarity or identity, more typically at least 92% similarity or identity, usually at least 94% similarity or identity, more usually at least 95% similarity or identity, preferably at least 96% similarity or identity, and more preferably at least 97% similarity or identity, and in particularly preferred embodiments, at least 98% or more (e.g., 99%) similarity or identity to the amino acid sequence of SEQ ID NO: 1 or 2.

Also included in the present invention are polynucleotides comprising nucleotide sequences which are at least about 70% identical, preferably at least about 80% identical, more preferably at least about 90% identical and most preferably at least about 95% identical (e.g., 95%, 96%, 97%, 98%, 99%, 100%) to a reference AKT3lkd or AKT3skd nucleotide sequence (e.g., any of SEQ ID NOs: 17 or 18) when the comparison is performed by a BLASTN algorithm wherein the parameters of the algorithm are selected to give the largest match between the respective sequences over the entire length of the respective reference sequences.

The terms "express" and "expression" mean, in an embodiment of the invention, allowing or causing the information in a gene or DNA sequence to become manifest, e.g., producing a protein by activating the cellular functions involved in transcription and, optionally, translation of a corresponding gene or DNA sequence. A DNA sequence can be expressed using in vitro translation systems (e.g., rabbit reticulocyte lysate-based systems) or in or by a cell (e.g., an insect cell or bacterial cell such as *E. coli* to form an "expression product" such as a mRNA or a protein. The expression product, e.g. the resulting protein, may also be referred to as "expressed".

An insect cell used in this invention includes any cell derived from an organism of the class Insecta. In an embodiment of the invention, the insect is *Spodoptera fruigiperda* (e.g., Sf9 or Sf21) or *Trichoplusia ni* (e.g., High Five™ cells; Invitrogen; Carlsbad, Calif.)). Other examples of insect expression systems that can be used with the present invention, for example to produce a polypeptide, include Bac-To-Bac (Invitrogen Corporation, Carlsbad, Calif.) or Gateway (Invitrogen Corporation, Carlsbad, Calif.).

An AKT3lkd or AKT3skd polypeptide (e.g., SEQ ID NO: 1 or 2) can also be produced by any conventional method, including synthetic methods and recombinant DNA methods.

It may also be desirable to add amino acids at the amino- or carboxy-terminus of a AKT3lkd or AKT3skd polypeptide (e.g., SEQ ID NO: 1 or 2), e.g., to prepare a fusion protein. In one embodiment, the addition is a polyhistidine tag of 5-20 amino acids (e.g., 6 amino acids) in length. For example, the present invention includes crystals comprising AKT3lkd or AKT3skd, wherein MYS-$H_6$-DYDIPTTENLYFQGAMD (SEQ ID NO: 11) is appended to the AKT3lkd or AKT3skd N-terminus (e.g., SEQ ID NO: 1 or 2) and crystals wherein the N-terminal sequence has been cleaved off. The sequence ENLYFQ (SEQ ID NO: 4) is a TEV NIa protease (TEV) cleavage site. The seven amino acid TEV consensus sequence is Glu-X-X-Tyr-X-Gln (SEQ ID NO: 12). TEV cleaves after the Gln. The scope of the present invention includes polypeptides wherein ENLYFQ (SEQ ID NO: 4) is replaced by any sequence fitting the TEV consensus sequence. X can be various amino acyl residues. A detailed analysis of altered cleavage sites is described in Dougherty et al. Virology 171:356-364 (1989). A histidine tag for aiding in purification of a AKT3lkd or AKT3skd polypeptide can be located at the carboxy-terminus. Other tags include glutathione-S-transferase, myc, FLAG (i.e., DYKDDDDK; SEQ ID NO: 13), calmodulin-binding peptide (CBP), maltose binding protein (MBP); hemagglutinin influenza virus (HAI); green fluorescent protein (GFP); thioredoxin; streptococcal protein G and streptococcal protein A.

In an embodiment of the invention, a protease cleavage site is located between any tag appended to a polypeptide of the present invention (e.g., an AKT3 polypeptide). For example any of the following cleavage sites can, in an embodiment of the invention be incorporated into a polypeptide of the invention: enterokinase (DDDDK*) (SEQ ID NO: 19); factor Xa (IDGR*) (SEQ ID NO: 20); thrombin (LVPR*GS) (SEQ ID NO: 21); preScission (LEVLFQ*GP) (SEQ ID NO: 22); TEV protease (EQLYFQ*G) (SEQ ID NO: 23); 3C protease (ETLFQ*GP) (SEQ ID NO: 24); sortase A (LPET*G) (SEQ ID NO: 25) or granzyme B (D*X, N*X, M*N, S*X); wherein * indicates the protease cleavage point (see e.g., Arnau et al., (2006) Protein Expression and Purification 48, 1-13).

The present invention comprises any of the AKT3 polypeptide set forth herein in a crystallizable composition or solution. An AKT3lkd or AKT3skd (e.g., SEQ ID NO: 1 or 2) preparation can contain one or more members selected from the group consisting of a precipitant, a protein stabilizing agent, a salt, a buffering agent and a reducing agent or oxygen scavenger. Examples of reducing agents are dithiothreitol (DTT), dithioerythritol (DET), β-mercaptoethanol (BME) and Tris(2-carboxyethyl)phosphine (TCEP). A "precipitant" is a compound that decreases the solubility of a polypeptide in a concentrated solution. Alternatively, the term "precipitant" can be used to refer to a change in physical or chemical parameters which decreases polypeptide solubility, including temperature, pH and salt concentrations. Precipitants induce crystallization by forming an energetically unfavorable precipitant-depleted layer around the polypeptide molecules. To minimize the relative amount of this depletion layer, the polypeptides form associations and, ultimately, crystals. This process is explained in Weber, *Advances in Protein Chemistry* 41:1-36 (1991) which is incorporated by reference. In addition to precipitants, other materials are sometimes added to the polypeptide crystallization solution. These include buffers, such as Tris or Hepes, to adjust the pH of the solution (and hence surface charge on the peptide) and salts, such as sodium chloride, lithium chloride and sodium citrate, to reduce the solubility of the polypeptide. Other additives include glycerol and ethylene glycol, and detergents, such as n-octyl-β-D-glucopyranoside. Various precipitants are known in the art and include the following: ammonium sulfate, ethanol, isopropanol, 3-ethyl-2,4 pentanediol; and many of the polyglycols, such as polyethylene glycol (e.g., PEG 400).

Crystallization may be accomplished by using known methods in the art (Giegé, et al., (1994) *Acta Crystallogr.* D50: 339-350; McPherson, (1990) *Eur. J. Biochem.* 189: 1-23). Such techniques include hanging drop vapor diffusion, sitting drop vapor diffusion, microbatch and dialysis. In an embodiment, hanging-drop vapor diffusion (see e.g., McPherson, (1976) *J. Biol. Chem.* 251: 6300-6303) is used. Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water and other volatile organic components vaporize from the drop and transfers to the reservoir, the precipitant concentration increases to a level optimal for crystallization. This may occur prior to or after reaching equilibrium. Once the system is in equilibrium, these optimum conditions are maintained until the crystallization is complete. The hanging drop method differs from the sitting drop method in the vertical orientation of the protein solution drop within the system. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels. It is desirable to use a AKT3lkd or AKT3skd protein preparation having a concentration of at least about 1 mg/mL; for example, about 10 mg/mL to about 20 mg/mL (e.g., 12 mg/mL).

The crystals of the present invention have a wide range of uses. For example, high quality crystals are suitable for X-ray or neutron diffraction analysis to determine the three dimensional structure of AKT3lkd or AKT3skd (e.g., SEQ ID NO: 1 or 2). Knowledge of these structures and solvent accessible residues allow structure-based design and construction of agonists and antagonists for AKT3.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals which are preferred for diffraction analysis.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of a AKT3lkd or AKT3skd polypeptide (e.g., SEQ ID NO: 1 or 2). The present invention includes crystals which effectively diffract X-rays for the determination of the atomic coordinates of AKT3lkd or AKT3skd to a resolution of greater than about 5.0 Ångströms (e.g., about 4.5 Å, about 4.0 Å, about 3 Å, about 2.5 Å, about 2 Å, about 1 Å, about 0.5 Å), preferably greater than about 4.0 Ångströms (e.g., about 3 Å, about 2.5 Å, about 2 Å, about 1 Å, about 0.5 Å), more preferably greater than about 2.8 Ångströms (e.g., about 2.5 Å, about 2 Å, about 1 Å, about 0.5 Å) and most preferably greater than about 2.0 Ångströms (e.g., about 1.5 Å, about 1.0 Å, about 0.5 Å).

The present invention includes AKT3lkd or AKT3skd crystals whose three-dimensional structure is described by the structure coordinates set forth in any of Tables 2-5. The scope of the present invention also includes crystals which possess structural coordinates which are similar to those set forth in any of Tables 2-5. In an embodiment, the crystals include a polypeptide which includes the amino acid sequence of SEQ ID NO: 1 or 2. Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for an enzyme or an enzyme-complex or a portion thereof, is a relative set of points that define a shape in three dimensions.

The present invention includes crystals exhibiting structural coordinates which are similar to those set forth in any of Tables 2-5 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Tables 2-5, the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in Tables 2-5 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results.

Generally, each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) or alpha carbon atoms (Cα) only for all conserved residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any set of structure coordinates of a molecule that has a RMSD of conserved residue backbone atoms (N, Cα, C, O) or alpha carbon atoms (Cα) only of less than about 1.5 Å when superimposed—using backbone atoms or alpha carbon atoms—on the relevant structure coordinates of Table 2, 3, 4, or 5 are considered identical and the crystals which they characterize are both within the scope of the present invention. In an embodiment of the invention, the root mean square deviation is less than about 1.0 Å, e.g., less than about 0.5 Å, e.g., less than about 0.1 Å.

The term "least squares" refers to a method based on the principle that the best estimate of a value is that in which the sum of the squares of the deviations of observed values is a minimum.

Computers

In accordance with the present invention, the structure coordinates of the a AKT3lkd or AKT3skd polypeptides (e.g., SEQ ID NO: 1 or 2) may be stored in a machine-readable storage medium. Such data may be used for a variety of purposes, such as drug discovery and X-ray crystallographic analysis of a protein crystal. Accordingly, one aspect of this invention provides a machine-readable data storage medium comprising a data storage material encoded with the structure coordinates set forth in Table 2, 3, 4 or 5. The machine-readable data storage medium may also include any set of structure coordinates of a molecule that has a root mean square deviation of conserved residue backbone atoms (N, Cα, C, O) of less than about 1.5 Å, preferably, less than about 1.0 Å, more preferably less than about 0.5 Å and even more preferably less than about 0.1 Å when superimposed—using backbone atoms—on the relevant structure coordinates of Table 2, 3, 4 or 5.

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of AKT3lkd or AKT3skd or a portion thereof using a program such as INSIGHT (Molecular Simulations Inc., San Diego, Calif.) or QUANTA as described herein. Output hardware might also include a printer, so that hard copy output may be produced, or a disk drive, to store system output for later use. In preferred embodiments, the computer possesses a display that is displaying a three dimensional representation of AKT3lkd or AKT3skd or a homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

"Structure factors" are mathematical expressions derived from three-dimensional structure coordinates of a molecule. These mathematical expressions include, for example, amplitude and phase information. The term "structure factors" is known to those of ordinary skill in the art.

The present invention permits the use of structure-assisted drug design techniques to design, select, and synthesize chemical entities, including inhibitory compounds that are capable of binding to a AKT3lkd or AKT3skd polypeptide (e.g., SEQ ID NO: 1 or 2). Also, de novo and iterative drug design methods can be used to develop drugs from the structure of the AKT3lkd or AKT3skd crystals of this invention.

The present method comprises a method by which the three-dimensional structure of any AKT3 crystal of the invention (e.g., AKT3lkd or AKT3skd, e.g., characterized by coordinates in table 2, 3, 4 or 5) can be used to identify an AKT3 antagonist or substance that binds to AKT3. For example, the present invention comprises a method for identifying an AKT3lkd or AKT3skd antagonist comprising the steps of: a) crystallizing AKT3lkd or AKT3skd (e.g., SEQ ID NO: 1 or 2) to form at least one crystal; b) irradiating the crystal produced by step (a) to obtain a diffraction pattern of said crystal; c) determining the atomic coordinates of the three-dimensional structure of the AKT3lkd or AKT3skd from the diffraction pattern; d) using the atomic coordinates (e.g., as set forth herein) and one or more molecular modeling techniques to identify a substance that interacts with the AKT3lkd or AKT3skd or a binding pocket thereof; and, optionally, e) determining if the substance antagonizes the ability of AKT3lkd or AKT3skd to phosphorylate a substrate (e.g., polypeptide comprising the amino acids sequence of SEQ ID NO: 6 or 14); wherein the substance is selected if it antagonizes the phosphorylation activity of AKT3lkd or AKT3skd. The ability of AKT3lkd or AKT3skd to phosphorylate a substrate can be determined by any of the assays set forth in the "Assays" section herein (e.g., the peptide phosphorylation assay). Another optional step comprises generating a crystalline complex between the substance and the polypeptide and examining the three-dimensional structure of the complex. For example, the crystalline complex is, in an embodiment of the invention, generated by soaking a crystal of AKT3lkd or AKT3skd with a solution containing the substance. Soaking is performed by either adding the substance directly to a droplet the crystals grew in, or by transferring the uncomplexed crystals into a solution containing the substance; cryoprotection of the crystals e.g., by adding ethylene glycol to the crystal then subjecting the suspension to a liquid nitrogen bath or stream to freeze; followed by irradiating the crystal to obtain a diffraction pattern of the crystal from which the atomic coordinates of the three-dimensional structure of the complex is obtained. These data confirm the existence of the complex, provide valuable data regarding the design of future inhibitors and provide insight as to the mechanism of inhibition by the substance.

One particularly useful drug design technique enabled by this invention is structure-assisted drug design. Structure-assisted drug design is a method for optimizing associations between a protein and a compound by determining and evaluating the three-dimensional structures of successive sets of protein/compound complexes.

Numerous computer programs are available and suitable for structure-assisted drug design and the processes of computer modeling, model building, and computationally identifying, selecting and evaluating potential inhibitors in the methods described herein. These include, for example, GOLD (available from CCDC, Cambridge, UK), Glide (available from SCHRODINGER, Portland, Oreg.), AUTODOCK (available from Art Olson at The Scripps Research Institute, La Jolla, Calif.), FlexX (available from Tripos, St. Louis. Mo.), DOCK (available from University of California, San Francisco, Calif.), ICM (available from MolSoft, San Diego, Calif.), GRID (available form Oxford University, UK), Fred (available from OpenEye Scientific Software, Santa Fe, N. Mex.), Slide (available from L. Kuhn, MSU, East Lansing, Mich.), Surflex (available from Discovery Partners International, San Diego, Calif.) and QXP (available from C. McMartin, Conn.), and 3D database systems such as MACCS-3D (available from MDL Information Systems, San Leandro, Calif.), UNITY (available from Tripos), and CATALYST (available from Accelrys, San Diego, Calif.), CoMFA (available from Tripos), Phase (available from SCHRODINGER).

Potential inhibitors may also be computationally designed "de novo" using such software packages as Cerius2/LUDI and AutoLudi (available from Accelrys), LeapFrog (Tripos), SPROUT (available from SimBioSys Inc. Canada), ALLE-GROW (available from Regine S. Bohacek, Boston De Novo Design, MA), BOMB (available from W. Jorgensen, Yale University, New Haven, Conn.) and CombiSMoG (available from Concurrent Pharmaceuticals, MA). Compound deformation energy and electrostatic repulsion, may be evaluated using the programs based on QM/Semiempirical methods, such as: GAUSSIAN 98 (available from Gaussian, Inc.), Jaguar (available from SCHRODINGER), or based on Forcefield methods, such as: AMBER, QUANTA/CHARMM, INSIGHT II/DISCOVER, MacroModel, and Sybyl. These computer evaluation and modeling techniques may be performed on any suitable hardware including for example, workstations available from Silicon Graphics, Sun Microsystems, PC or IBM Linux workstations and the like. These techniques, methods, hardware and software packages are representative and are not intended to be comprehensive listing. Other modeling techniques known in the art may also be employed in accordance with this invention. See for example, N. C. Cohen, Molecular Modeling in Drug Design, Academic Press (1996) (and references therein).

Those skilled in the art will appreciate that association of natural ligands or substrates with the binding pockets of their corresponding receptors or enzymes is the basis of many biological mechanisms of action. The term "binding pocket", as used herein, includes any region of a molecule or molecular complex, that, as a result of its shape, favorably associates with another chemical entity or compound. Similarly, drugs may exert their biological effects through association with the binding pockets of receptors and enzymes. Such association may occur with all or any part of the binding pockets. An understanding of such associations will help lead to the design of drugs having more favorable associations with the target enzyme, and thus, improved biological effects. Therefore, this information is valuable in designing potential enzyme inhibitors, such as inhibitors of AKT3.

In an embodiment of the invention, the human AKT3 binding pocket comprises residues Leu151, Val162, Ala175, Lys177, Thr209, Met225, Glu226, Tyr227, Val228, Glu232, Met278, Thr288, Asp289, Phe290, Gly291 and Phe435. These residues contribute to the pocket either with their peptide backbone or with their side chains or both. Asp289, Phe290, Gly291 undergo movement upon inhibitor binding, with some inhibitors.

In iterative structure-assisted drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of a new polypeptide, solving the three-dimensional structure of the polypeptide, and comparing the associations between the new protein and previously solved protein. By observing how changes in the compound affected the protein/compound associations, these associations may be optimized.

In some cases, iterative structure-assisted drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. In an embodiment of the invention, AKT3lkd or AKT3skd crystals provided by this invention may be soaked in the presence of a compound or compounds, such as an AKT3 inhibitor or ligand or substrate (e.g., polypeptide of SEQ ID NO: 6 or 14), to provide novel AKT3lkd or AKT3skd/compound crystal complexes. As used herein, the term "soaked" includes a process in which the crystal is transferred to a solution containing the compound of interest.

The structure coordinates set forth in any of Tables 2-5 can also be used to aid in obtaining structural information about another crystallized molecule or molecular complex. This may be achieved by any of a number of well-known techniques, including molecular replacement.

The structure coordinates set forth in any of Tables 2-5 can also be used for determining at least a portion of the three-dimensional structure of molecules or molecular complexes which contain at least some structurally similar features to AKT3lkd or AKT3skd. In particular, structural information about another crystallized molecule or molecular complex may be obtained by well-known techniques, including molecular replacement.

Therefore, another aspect of this invention provides a method of utilizing molecular replacement to obtain structural information about a crystallized molecule or molecular complex, whose structure is unknown, comprising the steps of generating an X-ray diffraction pattern from said crystallized molecule or molecular complex and applying crystallographic phases derived from at least a portion of the structure coordinates set forth in Table 2, 3, 4 or 5 to the X-ray diffraction pattern to generate a three-dimensional electron density map of the molecule or molecular complex whose structure is unknown. Once the structure coordinates of a protein crystal have been determined, they are useful in solving the structures of other crystals. For example, polypeptides may be crystallized and their structure elucidated by, for example, difference Fourier techniques and molecular replacement.

By using molecular replacement, all or part of the structure coordinates of, for example, the AKT3lkd or AKT3skd polypeptide provided by this invention (and set forth in any of Tables 2-5) can be used to determine the previously unknown structure of a crystallized molecule or molecular complex more quickly and efficiently than attempting to determine such information ab initio.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the AKT3lkd or AKT3skd crystal according to Table 2, 3, 4 or 5 within the unit cell of the crystal of the unknown molecule or molecular complex so as best to account for the observed X-ray diffraction pattern amplitudes to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in Meth. Enzymol., 115: 55-77 (1985); Rossman, ed., "The Molecular Replacement Method", Int. Sci. Rev. Ser., No. 13, Gordon & Breach, New York (1972)).

Phase information from the structure coordinates of the present invention may be used to elucidate the structure of other crystals. For example, the structure of AKT3lkd or AKT3skd in complex with other atoms or molecules may be elucidated. Such complexes include, for example, those containing atoms soaked into or co-crystallized within the crystal lattice. Other structures which can be elucidated using the phase information of the present invention include for example other kinases or homologues or mutants thereof having sufficient three-dimensional structure similarity to AKT3lkd or AKT3skd complex as to be solved using molecular replacement. Also, these protein molecules in a complex with a small molecule substrate(s), inhibitor(s), transition state analog(s), product(s) or analog(s) of any of these may also be solved using the phase information of the present invention.

The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

AKT3lkd or AKT3skd crystals may be studied using well-known X-ray diffraction techniques and may be refined versus X-ray data to 3 Å resolution or better to an $R_{free}$ value of about 0.40 or less using computer software such as X-PLOR (Yale University, 1992, distributed by Molecular Simulations, Inc.; see e.g., Blundell & Johnson, supra; Meth, Enzymol., vol. 114 & 115, H. W. Wyckoff et al., eds., Academic Press (1985)) and BUSTER (Bricogne, G. (1993). Acta Cryst. D49, 37-60, "Direct Phase Determination by Entropy Maximisation and Likelihood Ranking: Status Report and Perspectives"; Bricogne, G. (1997) "The Bayesian Statistical Viewpoint on Structure Determination: Basic Concepts and Examples", in Methods in Enzymology, 276A, 361-423, C. W. Carter & R. M. Sweet, eds.; and Roversi et al., (2000), "Modelling prior distributions of atoms for Macromolecular Refinement and Completion", Acta Cryst., D56, 1313-1323). This information may be used to optimize known AKT3 inhibitors and to design new ATK3 inhibitors.

Assays

A use for soluble AKT3lkd and AKT3skd polypeptides (e.g., SEQ ID NO: 1 or 2) is for the identification of AKT3 inhibitors. AKT3lkd or AKT3skd can be used in various assays known in the art for the identification of AKT3 inhibitors. AKT3 inhibitors are useful, for example, as anti-cancer agents. An AKT3 inhibitor identified using an assay of the present invention can be administered to a subject to treat or prevent the occurrence of cancer.

The binding of a substance to be tested for the presence of AKT3 antagonist to AKT3skd or AKT3lkd can be monitored by temperature-dependent circular dichroism. Circular dichroism is observed when optically active matter (e.g., protein) absorbs left and right hand circular polarized light slightly differently. In an embodiment of the invention, it is measured with a CD spectropolarimeter. Generally, the instrument needs to be able to measure accurately in the far UV at wavelengths down to 190-170 nm since the difference in left and right handed absorbance A(l)–A(r) is very small corresponding to an ellipticity of a few thousandths of a degree (mdeg). The analysis of temperature-dependent circular dichroism spectra therefore yields valuable information about secondary structure of biological macromolecules as well as the melting temperature (Tm) of the substance being analyzed. Generally, the temperature-dependent circular dichroism spectrum of a given substance takes a sigmoidal shape and the melting temperature of the substance is the point of inflection on the sigmoid curve. Changes in AKT3lkd or AKT3skd secondary structure can be monitored over a range of temperatures using temperature-dependent circular dichroism. As temperature increases, the temperature-dependent circular dichroism spectra of the protein and/or the Tm will change. Binding of inhibitors to AKT3lkd or AKT3skd can be monitored by comparing the temperature-dependent circular dichroism spectrum and/or Tm of native AKT3lkd or AKT3skd to that of AKT3lkd or AKT3skd that has been contacted with a substance to be tested for the presence of a modulator. Specifically, a change in the AKT3lkd or AKT3skd temperature-dependent circular dichroism spectra and/or Tm, in the presence of a substance being tested for the presence of a modulator, as compared to the temperature-dependent circular dichroism spectra of native AKT3lkd or AKT3skd, will indicate binding.

In an embodiment of the invention, a method for identifying a substance that reduces the occurrence or growth of a cancer cell or that inhibits or binds to AKT3 (e.g., AKT3 substrate phosphorylation) comprises:
 (a) contacting a composition comprising AKT3lkd or AKT3skd (e.g., SEQ ID NO: 1 or 2) with a substance to be tested for the presence of the inhibitor;
 (b) determining the ellipticity of said composition;
whereby the substance is selected if the ellipticity and/or the Tm of said composition alone is different from the ellipticity and/or Tm of the composition that is in contact with said substance.

In an embodiment of the invention, ellipticity is measured at several different temperatures (e.g., between 30° C. and 80° C.).

In an embodiment of the invention, the temperature-dependent circular dichroism assay is performed along with a negative-control method comprising:
 (a) contacting a composition comprising AKT3lkd or AKT3skd (e.g., SEQ ID NO: 1 or 2) with a negative-control substance known not bind to AKT3lkd or AKT3skd; and
 (b) determining the ellipticity of the composition and said negative-control substance;
whereby the method is determined to be functioning properly if the ellipticity and/or Tm of the composition alone is substantially the same as that of the composition that is in contact with the negative-control substance.

In an embodiment of the invention, the temperature-dependent circular dichroism assay is performed along with a positive-control method comprising:
 (a) contacting a composition comprising AKT3lkd or AKT3skd (e.g., SEQ ID NO: 1 or 2) with a positive-control substance known to bind AKT3lkd or AKT3skd; and
 (b) determining the ellipticity of the composition and said positive-control substance;
whereby the method is determined to be functioning properly if the ellipticity and/or Tm of the composition alone is different from that of the composition that is in contact with the positive-control substance.

The temperature-dependent circular dichroism methods set forth above can be modified to replace temperature variation with the addition of some other stimulus that affects AKT3lkd or AKT3skd secondary structure. For example, instead of measuring ellipticity at various temperatures, ellipticity can be measured at different concentrations of protein denaturant. For example, the protein denaturants urea or guanidine HCl can be used.

Inhibitors of AKT3 and substances that inhibit cancer cell occurrence or proliferation can also be identified by direct binding assay. For example, in an embodiment of the invention, a method for identifying a substance that reduces the occurrence or growth of a cancer cell or that binds to or inhibits AKT3 (e.g., AKT3 substrate phosphorylation) comprises:
 (1) contacting a composition comprising AKT3lkd or AKT3skd (e.g., SEQ ID NO: 1 or 2) with a substance (e.g., a detectably labeled substance such as a radiolabeled substance) to be tested for the presence of an inhibitor; and
 (2) determining if the substance binds to said AKT3lkd or AKT3skd; whereby the substance is selected if binding is observed.

In an embodiment of the invention, the direct binding assay is performed along with a negative-control assay comprising:
 (1) contacting a composition comprising AKT3lkd or AKT3skd (e.g., SEQ ID NO: 1 or 2) with a negative-control substance (e.g., a detectably labeled negative-control substance such as a radiolabeled negative-control substance) that is known not to bind AKT3lkd or AKT3skd; and
 (2) determining if the negative-control substance binds to said AKT3lkd or AKT3skd;
whereby the method is determined to be functioning properly if no direct binding of the negative-control substance is detected.

In an embodiment of the invention, the direct binding assay is performed along with a positive-control assay comprising:
 (1) contacting a composition comprising AKT3lkd or AKT3skd (e.g., SEQ ID NO: 1 or 2) with a positive-control substance (e.g., a detectably labeled positive-control substance such as a radiolabeled positive-control substance) that is known to bind AKT3lkd or AKT3skd; and
 (2) determining if the positive-control substance binds to said AKT3lkd or AKT3skd;
whereby the method is determined to be functioning properly if direct binding of the positive-control substance is detected.

The substance being tested in any of the foregoing assays can be detectably labeled with any of many labels known in the art including, for example, $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

In an embodiment of the invention, binding is determined by chromatographically binding the AKT3lkd or AKT3skd/inhibitor complex to a solid support, optionally washing the bound complex, optionally drying the washed complex (e.g., under a vacuum) and then detecting the presence of the substance being tested on the support. In an embodiment, the solid support is a positively charged membrane or filter such as a nylon (e.g., Immobilon-Ny+transfer membrane; Millipore; Billerica, Mass.).

Bound, radiolabeled complex may be detected by any of several methods known in the art. For example, if the complex comprises a radiolabel, the bound complex can be detected chemiluminescently (e.g., using Opti-Fluor Scintillation cocktail; PerkinElmer Life and Analytical Sciences, Inc.; Boston, Mass.). Chemiluminescence can be detected, for example, in a scintillation counter (Packard Top-counter). Specifically, the bound complex can be contacted with scintillant and then analyzed for the occurrence of scintillation.

In an embodiment of the invention, inhibitors of AKT3 and substances that inhibit cancer cell occurrence or proliferation are identified by competition or competitive inhibition assay. In a competition assay, an inhibitor is identified based upon its ability to compete for binding with a substance known to bind AKT3lkd or AKT3skd (this substance will be referred to as "ligand" or "substrate" for the purposes of discussing this method). In an embodiment of the invention, a method for identifying a substance that reduces the occurrence or growth of a cancer cell or that inhibits AKT3 (e.g., AKT3 substrate phosphorylation) comprises:
  (i) contacting a composition comprising AKT3lkd or AKT3skd (e.g., SEQ ID NO: 1 or 2) with a substrate or ligand that is known to bind AKT3lkd or AKT3skd and with a substance to be tested for the presence of an inhibitor; and
  (ii) determining if the substance being tested reduces binding of the substrate or ligand to AKT3lkd or AKT3skd;
whereby the substance is selected if binding of the substrate or ligand to AKT3lkd or AKT3skd is reduced as compared to substrate or ligand binding to AKT3lkd or AKT3skd in the absence of the substance.

In an embodiment of the invention, the competition assay is performed along with a positive-control assay. In an embodiment, such a positive-control assay comprises:
  (i) contacting a composition comprising AKT3lkd or AKT3skd (e.g., SEQ ID NO: 1 or 2) with a substrate or ligand that is known to bind AKT3lkd or AKT3skd and with a positive-control substance also known to bind to AKT3lkd or AKT3skd; and
  (ii) determining if said positive-control substance reduces the binding of the substrate or ligand;
whereby the assay is determined to function properly if the binding of said substrate or ligand is reduced in the presence of the positive-control substance as compared to the binding of the substrate or ligand in the absence of the positive-control substance.

In an embodiment, the positive-control substance is a known inhibitor of AKT3 such as

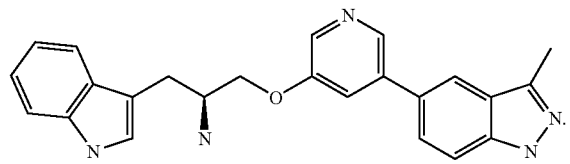

In an embodiment of the invention, the competition assay is performed along with a negative-control assay. In an embodiment, such a negative-control assay comprises:
  (i) contacting a composition comprising AKT3lkd or AKT3skd (e.g., SEQ ID NO: 1 or 2) with a substrate or ligand that is known to bind AKT3lkd or AKT3skd and with a negative-control substance known not to bind to AKT3lkd or AKT3skd; and
  (ii) determining if said negative-control substance reduces that binding of said substrate or ligand;
whereby the assay is determined to function properly if the binding of said substrate or ligand is substantially the same as the binding that is observed in the absence of the negative-control substance.

During a competition assay, a complex between AKT3lkd or AKT3skd (e.g., SEQ ID NO: 1 or 2) and the substrate or ligand or the positive-control substance/known inhibitor is formed. Such a complex is within the scope of the present invention. For example, the scope of the present invention includes a complex between AKT3lkd or AKT3skd (e.g., SEQ ID NO: 1 or 2) and a polypeptide comprising the amino acids sequence of SEQ ID NO: 6 or 14. Such complexes are useful, for example, for preparation of crystals which are useful for the design of inhibitors.

In an embodiment of the invention, a method for identifying a substance that reduces the occurrence or growth of a cancer cell or that inhibits AKT3 is a peptide phosphorylation assay. Such an assay comprises:
  (A) contacting a composition comprising AKT3lkd or AKT3skd (e.g., SEQ ID NO: 1 or 2) with an AKT3 substrate or ligand (e.g., a GSK-3 peptide such as GRPRTSSFAEG; SEQ ID NO: 6), with radiolabeled adenosine triphosphate (ATP) and $Mg^{2+}$ (e.g., $MgCl_2$) and with a substance to be tested for the presence of an AKT3 inhibitor; and
  (B) determining if the substrate or ligand is radiolabeled;
wherein the substance is selected if the peptide is radiolabeled at a lower level in the presence of the substance than in the absence of the substance.

In an embodiment of the invention, a positive-control assay is performed in conjunction with the phosphorylation assay. Such an assay comprises:
  (A) contacting a composition comprising AKT3lkd or AKT3skd (e.g., SEQ ID NO: 1 or 2) with an AKT3 substrate or ligand (e.g., a GSK-3 peptide such as GRPRTSSFAEG; SEQ ID NO: 6), with a positive-control substance that is known to inhibit AKT3 mediated phosphorylation of the substrate and with radiolabeled adenosine triphosphate (ATP) and $Mg^{2+}$ (e.g., $MgCl_2$); and
  (B) determining if the substrate or ligand is radiolabeled;
wherein the assay is determined to be functioning correctly if the substrate is phosphorylated at a level that is less than that of a substrate assayed in the absence of the positive-control substance.

In an embodiment of the invention, a negative-control assay is performed in conjunction with the phosphorylation assay. Such an assay comprises:
  (A) contacting a composition comprising AKT3lkd or AKT3skd (e.g., SEQ ID NO: 1 or 2) with an AKT3 substrate or ligand (e.g., a GSK-3 peptide such as GRPRTSSFAEG; SEQ ID NO: 6), with a negative-control substance that is known not to inhibit AKT3 mediated phosphorylation of the substrate and with radiolabeled adenosine triphosphate (ATP) and $Mg^{2+}$ (e.g., $MgCl_2$); and
  (B) determining if the substrate or ligand is radiolabeled;

wherein the assay is determined to be functioning correctly if the substrate is phosphorylated at a level that is substantially the same as that of a substrate assayed in the absence of the negative-control substance.

In another embodiment of the invention, a negative-control assay is performed in conjunction with the phosphorylation assay. Such an assay comprises:
(A) contacting a composition comprising AKT3lkd or AKT3skd (e.g., SEQ ID NO: 1 or 2) with a negative-control substance (e.g., a peptide) that is known not to be phosphorylated by AKT3 and with radiolabeled adenosine triphosphate (ATP) and $Mg^{2+}$ (e.g., $MgCl_2$); and
(B) determining if the substrate or ligand is radiolabeled; wherein the assay is determined to be functioning correctly if no phosphorylation of the negative-control substance is observed.

The peptide phosphorylation assay can also be used to confirm that substances previously determined to bind to AKT3lkd or AKT3skd, for example, by structure-based drug design, do inhibit AKT3, AKT3lkd or AKT3skd kinase activity.

In an embodiment of the invention, the radiolabeled ATP is [$\gamma^{32}P$]-ATP. For example, the assay can be carried out under the general conditions as set forth in Nakatani et al., Biochem. and Biophys. Res. Comm. 257, 906-910 (1999). In an embodiment of the invention, the AKT3 substrate is RPRAATF (SEQ ID NO: 14) which is available from Upstate Biotechnology (Lake Placid, N.Y.).

In an embodiment of the invention, the AKT3 substrate or ligand is histone H2b polypeptide. The histone H2b assay can be carried out using the general conditions set forth in Masure et al. (European Journal of Biochemistry 265(1):353-360 (1999)). Other substrates of AKT3 include GSK-3, IKKa, mdm2, forkhead transcription factor, BAD, caspase 9, Phosphofructokinase2, p21, p27, TSC2 and PRASP40.

In an embodiment of the invention, the presence of the radiolabeled substrate is determined by chromatographically binding the substrate to a solid support, optionally washing the bound substrate, optionally drying the washed substrate (e.g., under a vacuum) and then detecting the presence of the substrate on the support. In an embodiment, the solid support is a positively- or negatively-charged membrane or filter such as a nylon (e.g., Immobilon-Ny+transfer membrane; Millipore; Billerica, Mass.).

Bound substrate may be detected by any of several methods known in the art. For example, the bound, radiolabeled substrate (e.g., GSK-3 peptide) can be detected chemilluminescently (e.g., using Opti-Fluor Scintillation cocktail; PerkinElmer Life and Analytical Sciences, Inc.; Boston, Mass.). Chemilluminescence can be detected, for example, in a scintillation counter (Packard Top-counter). Specifically, the bound, radiolabeled substrate can be contacted with scintillant and then analyzed for the occurrence of scintillation.

In an embodiment of the invention, the presence of phosphorylated substrate peptide can be detected by mass spectrographic analysis; for example by the method described by Zeller et al., J. Exp. Ther. Oncol. 3(2):59-61 (2003).

In an embodiment of the invention, a method for identifying a substance that reduces the occurrence or growth of a cancer cell or that inhibits AKT3 is an ATP/NADH coupled assay. In general, the assay is based on a reaction in which the regeneration of hydrolyzed ATP (ADP) is coupled to the oxidation of NADH. Following each cycle of ATP hydrolysis, the regeneration system, comprising phosphoenolpyruvate (PEP) and pyruvate kinase (PK), converts one molecule of PEP to pyruvate when the ADP is converted back to the ATP. The pyruvate is subsequently converted to lactate by Lactate dehydrogenase (LDH) resulting in the oxidation of one NADH molecule. The assay measures the rate of NADH absorbance decrease at 340 nm, which is proportional to the rate of steady-state ATP hydrolysis. The extinction coefficient of NADH is 6220 $M^{-1}$ $cm^{-1}$ for absorbance at 340 nm. The constant regeneration of ATP allows monitoring the ATP hydrolysis rate over the entire course of the assay. In an embodiment of the invention, a coupled assay for identifying a substance that reduces the occurrence or growth of a cancer cell or that inhibits AKT3 comprises measuring the rate of decrease in $A_{340}$ over time of a composition comprising AKT3skd or AKT3lkd (e.g., SEQ ID NO: 1 or 2), and AKT3 substrate (e.g., GSK-3 peptide), ATP, PEP, NADH, and $Mg^{2+}$ (e.g., $MgCl_2$), pyruvate kinase and lactate dehydrogenase in the presence of a substance to be tested for the presence of an AKT3 inhibitor; wherein the substance is selected if the rate of decrease in $A_{340}$ over time is less than the rate of decrease observed in the absence of the substance.

In an embodiment, a reducing agent such as dithiothreitol (DTT) is added to the assay. In an embodiment of the invention, the assay is carried out at 16° C., 20° C., 23° C., 25° C., 30° C. or at 37° C. In an embodiment of the invention, the concentration of the AKT3 substrate and of ATP is about 5× to about 10× its Km. In an embodiment of the invention, only the initial velocity of the reaction, before 10% of the substrate is consumed, is measured and the rate of $A_{340}$ decrease is calculated from these data.

In an embodiment of the invention, the coupled assay is performed in conjunction with a positive-control assay comprising measuring the rate of decrease in $A_{340}$ over time of a composition comprising AKT3skd or AKT3lkd, and AKT3 substrate, ATP, PEP, NADH, and $Mg^{2+}$ (e.g., $MgCl_2$), pyruvate kinase and lactate dehydrogenase in the presence of a positive-control substance that is known to inhibit AKT3; wherein the substance is selected if the rate of decrease in $A_{340}$ over time is less than the rate of decrease observed in the absence of the positive-control substance.

In an embodiment of the invention, the coupled assay is performed in conjunction with a negative-control assay comprising measuring the rate of decrease in $A_{340}$ over time of a composition comprising AKT3skd or AKT3lkd, and AKT3 substrate, ATP, PEP, NADH, and $Mg^{2+}$ (e.g., $MgCl_2$), pyruvate kinase and lactate dehydrogenase in the presence of a negative-control substance that is known not to inhibit AKT3; wherein the substance is selected if the rate of decrease in $A_{340}$ over time is substantially the same as the rate of decrease observed in the absence of the negative-control substance.

EXAMPLES

The following examples are intended to exemplify the present invention and should not be construed to limit it. The scope of the invention included all polypeptides and polynucleotides, including crystals, described in the examples along with all methods exemplified.

Example 1

Domain Selection and Activation Mutants for AKT3 Constructs

1. The 3D structures of 15 distinct kinases were examined and divided into two classes: (A) CK2, CDK2, CDK6, ERK2, JNK & p38 have an insertion of ~35 residues in the C-terminal domain and (B) calmodulin-dependent-kinase, CK1, LCK, HCK, SRC, twitchin kinase, FGFRK, insulin-receptor-kinase & PKA lack this insertion. Using Clustal W, the sequences of each of these classes align well, corresponding to the structural alignment. In order to get correspondence of the sequence and structural alignments for the full 15 kinases, the ~35 inserted residues must be deleted from the 6 kinases in class A.

2. A Blast search shows that PKA, PKC and related kinases are most closely related to AKT's. Seven of these kinases were included in the sequence alignment to help illustrate conserved elements in the family. A Clustal W multi-sequence alignment was performed using AKT1, AKT2, AKT3, the seven related kinases and the 15 distinct kinases of known structure.

3. From the multi-sequence analysis the consensus kinase domain for AKT3 was deduced. The domain boundaries are:
  (A) N-terminus—Δ138-HHKRKTMND (SEQ ID NO: 16) corresponding to the consensus structural domain and an observed enzymatic fragmentation site in AKT1. PKA has an additional N-terminal helix, but the AKT's do not have sequence homology to this helix. This eliminates the Pleckstrin Homology (PH) domain and linker for AKT3.
  (B) C-terminus—(i) Long—full length
    (ii) Short—447-TPPEKYDEDGMD-Δ21 (SEQ ID NO: 15). This corresponds in length to the C-terminus of PKA and also eliminates C459 that may yield disulfide-linked aggregates and S472 a regulatory site that might be partially phosphorylated thereby giving heterogeneity.

To partially or fully-activate the catalytic kinase activity of the AKT3 kinase domain constructs, the following variants were selected:
  1) AKT3 short kinase domain (AKT3skd):
    a) T305D mutant (AKT3skd(T305D))
    b) phosphorylated-T305 (AKT3skd(pT305))
  2) AKT3 long kinase domain (AKT3lkd):
    a) phosphorylated T305, phosphorylated S472 (AKT3lkd(pT305, pS472))
    b) phosphorylated T305, S472D (AKT3lkd(pT305, S472D))
    c) T305D, S472D double mutant (AKT3lkd(T305D, S472D))

Example 2

Cloning of AKT3 Constructs for Expression in High-Five and *Escherichia coli* Cells A plasmid encoding human AKT3 cDNA in the pcDNA3 vector was used to amplify the short kinase domain (AKT3skd, corresponding to AKT3 residues 139-458) and the long kinase domain (AKT3lkd, corresponding to AKT3 residues 139-479) fragments. The amplifications were performed with the following PCR primers: 5'ACTGCCATG-GATCATCATAAAAGAAAGACAATGAAT3' (common 5' primer) (SEQ ID NO: 7); 5'GATCGAATTCTTAT-TCTCGTCCACTTGCAGA3' (AKT3skd, 3' primer); (SEQ ID NO: 8) and 5'GATCGAATTCTCAGTCCATACCATC-CTCATCATATTTTTC3' (AKT3lkd 3' primer) (SEQ ID NO: 9). The resulting PCR fragments were digested with NcoI and EcoRI restriction enzymes and sub-cloned into the pFAST-BAC HTa vector. Each resulting construct was then used to generate recombinant baculovirus using the Bac-to-Bac system (Gibco/Life sciences) following instructions provided by the manufacturer. The NcoI and EcoRI digested PCR fragments were also cloned into *E. coli* expression constructs based on the pHis-parallel vectors (Sheffield et al., (1999), Protein Express Purif. 10, 309-319). Site-directed mutagenesis was performed using a Quick change kit (Stratagene; La Jolla, Calif.) following instructions provided by the manufacturer. DNA constructs used for transfection were purified from bacteria using Qiagen plasmid Mega kit (Qiagen, Inc; Valencia, Calif.) according to the manufacturer's protocol.

Example 3

Amino Acid Sequence of AKT3Skd and AKT3lkd

The amino sequence of the AKT3skd construct, as it was expressed, is presented below. This construct contains an N-terminal His-tag that is removable by cleavage with the TEV protease. The TEV cleavage site is at ENLYFQ (underscored) (SEQ ID NO: 4) with cleavage after the Q residue. The sequence corresponding to the actual AKT3 sequence starts with His139 (bold font) at HHKRK . . . (SEQ ID NO: 10).

(SEQ. ID NO: 1)
MSYYHHHHHHDYDIPTT<u>ENLYFQ</u>GAMDHHKRKTMNDFDYLKLLGKGT

FGKVILVREKASGKYYAMKILKKEVIIAKDEVAHTLTESRVLKNTRH

PFLTSLKYSFQTKDRLCFVMEYVNGGELFFHLSRERVFSEDRTRFYG

AEIVSALDYLHSGKIVYRDLKLENLMLDKDGHIKITDFGLCKEGITD

AATMKTFCGTPEYLAPEVLEDNDYGRAVDWWGLGVVMYEMMCGRLPF

YNQDHEKLFELILMEDIKFPRTLSSDAKSLLSGLLIKDPNKRLGGGP

DDAKEIMRHSFFSGVNWQDVYDKKLVPPFKPQVTSETDTRYFDEEFT

AQTITITPPEKYDEDGMD

The AKT3 long kinase domain is as follows:

(SEQ ID NO: 2)
MSYYHHHHHHDYDIPTT<u>ENLYFQ</u>GAMDHHKRKTMNDFDYLKLLGKGTF

GKVILVREKASGKYYAMKILKKEVIIAKDEVAHTLTESRVLKNTRHPF

LTSLKYSFQTKDRLCFVMEYVNGGELFFHLSRERVFSEDRTRFYGAEI

VSALDYLHSGKIVYRDLKLENLMLDKDGHIKITDFGLCKEGITDAATM

KTFCGTPEYLAPEVLEDNDYGRAVDWWGLGVVMYEMMCGRLPFYNQDH

EKLFELILMEDIKFPRTLSSDAKSLLSGLLIKDPNKRLGGGPDDAKEI

MRHSFFSGVNWQDVYDKKLVPPFKPQVTSETDTRYFDEEFTAQTITIT

PPEKYDEDGMDCMDNERRPHFPQFSYSASGRE

Example 4

Expression of AKT3 Constructs in High-Five Cells

In this example, AKT3skd, AKT3skd(T305D), AKT3lkd (pT305, S472), AKT3lkd(pT305, S472D) and AKT3lkd (T305D, S472D) are expressed in High-Five insect cells.

High-five cells were grown in suspension at 27° C. in Express Five SFM medium supplemented with 20 mM L-glutamine (Gibco-BRL). The cells were maintained at a density of 1-6×10⁶ cells/mL and were passaged every 2-3 days. For infections, cells were infected at a density of 2.0× 10⁶ cells/mL. Infections were carried out using a multiplicity of infection (MOI) of ~2-4 with a final cell viability of ~85%. Cells were harvested 48 hours post-infection by centrifugation at 500×g for 10 minutes.

Example 5

Purification of AKT3 Constructs Expressed in High-Five Cells

The pelleted cells were resuspended and microfluidized in 50 mM Iris-HCl (pH 7.9), containing 50 mM NaCl, 10% glycerol, 10 mM 2-mercaptoethanol, 1 mM EDTA, and 1× protease inhibitor cocktail set III (Calbiochem; San Diego, Calif.). The supernatant obtained by centrifugation at 125,000×g for 1 hour at 4° C. was applied to a Q-Sepharose Fast-Flow column (Amersham Biosciences Co.; Piscataway, N.J.) which had been equilibrated in 20 mM Tris-HCl (pH 7.9), 50 mM NaCl, 10% glycerol, 10 mM 2-mercaptoethanol. All constructs eluted at 200-250 mM NaCl using a 10 bed volume gradient of 20 mM Tris-HCl (pH 7.9), 500 mM NaCl, 10% glycerol, 10 mM 2-beta-mercaptoethanol. The eluted fractions containing the AKT3 polypeptide were adjusted to contain 20 mM imidazole then applied to a Ni-NTA column (Qiagen; Valencia, Calif.) equilibrated in 20 mM Tris-HCl (pH 8.0), 300 mM NaCl, 10% glycerol, 5 mM 2-mercaptoethanol, 20 mM imidazole. The AKT3 was eluted with the linear gradient of imidazole from 0 to 200 mM. Fractions were pooled and dialyzed in 50 mM Tris-HCl (pH 7.9), 0.5 mM EDTA, 1 mM OTT at 4° C. overnight. TEV protease (Invitrogen; Carlsbad, Calif.) was added in a 115:1 ratio (activity unit:weight) to AKT. Cleavage was allowed to occur simultaneous with further dialysis into 20 mM Tris-HCl (pH 7.9), 100 mM NaCl, 10% glycerol, 5 mM 2-mercaptoethanol overnight at 4° C. The cleaved AKT sample was adjusted to 0.3 M NaCl and purified over a second Ni-NTA column. The flow-through fractions containing AKT were pooled and treated with λ-phosphatase (Calbiochem; San Diego, Calif.) at a 1:200 enzyme:substrate weight ratio overnight at 4° C. Dephosphorylated AKT3skd, AKT3lkd and AKT3lkd (T305D, S472D) were further purified on a Superdex-75 gel-filtration column (Amersham Biosciences Co.; Piscataway, N.J.) equilibrated in 20 mM Iris (pH 7.5), 100 mM NaCl, 1 mM DTT. Pooled fractions were concentrated to 10-15 mg/ml using a stirred cell with a YM-10 ultrafiltration membrane (Millipore; Billerica, Mass.) and then used for crystallization. AKT3lkd protein was phosphorylated with purified PDK1 at a weight ratio of 1:50 enzyme:substrate in 20 mM Tris-HCl (pH 7.5), 100 mM NaCl, 1.25 mM ATP, and 50 μM PIFtide peptide at 30° C. for 2 hours. Phosphorylated AKT3 was purified using gel-filtration and concentrated as described above. The mass and extent of phosphorylation for each sample was determined by liquid chromatography mass spectrometry (LC-MS) using a Waters Micromass ZQ 4000 electrospray mass spectrometer.

Example 6

Crystallization of AKT3 Constructs Expressed in High-Five Cells

The crystals were grown by vapor diffusion in hanging drops. Typically 1 μL AKT3skd at 10 mg/mL in 20 mM TRIS pH 7.5, 0.1 M NaCl, 1 mM OTT were mixed with 1 μL of reservoir solution: 0.1 M MES pH 5.3-5.5, 10-15% Isopropanol. Optimal crystal growth occurred with a reservoir solution of 0.1 M MES pH 5.3, 12% Isopropanol.

Example 7

Expression of AKT3 Constructs in *E. coli*

*E. coli* BL21(DE3) cells containing the plasmid expressing the AKT3 construct were grown in 1 liter of Terrific Broth containing 100 μg/mL Ampicillin to an OD of 2.0. The expression of AKT3 was induced by the addition of IPTG to a final concentration of 1 mM. Once induced, the temperature is lowered from 37+ C to 16° C. and the cells continued to incubate overnight.

Example 8

Purification of *E. coli* Derived AKT3 Constructs

This protocol has been used to purify the following AKT3 constructs: AKT3skd, AKT3skd(T305D), AKT3lkd(T305, S472)-to be phosphorylated at T305 and at S472, AKT3lkd (T305, S472D)-to be phosphorylated at T305, and AKT3lkd (T305D, S4720).

The cells were pelleted by centrifugation (4000 rpm for 15 min.) and resuspended in Lysis Buffer: 25 mM HEPES pH 7.6, 1 M NaCl, 10% glycerol, 0.1% n-octyl-β-D-glucopyranoside, and 1 mM TCEP. The cells were lysed by passage twice through a microfluidizer. The cell lysate was adjusted to 20 mM imidazole and 4 Complete EDTA-free Protease Inhibitor Cocktail tablets (Roche Applied Science; Indianapolis, Ind.) were added. To this was added 25 mL of Ni-NTA Agarose resin that had been pre-equilibrated in Buffer A: 25 mM HEPES pH 7.6, 1 M NaCl, 10% glycerol, 0.1% n-octyl-β-D-glucopyranoside, 1 mM TCEP, and 20 mM imidazole. The lysate-resin mixture was mixed by rotation overnight at 4° C.

The Ni-NTA agarose resin was allowed to settle from the lysate by gravity while on ice. The resin was washed by resuspension in Buffer A and allowed to settle. This was repeated twice, and following the 3$^{rd}$ wash the resin was pelleted by centrifugation at 2000 rpm for 5 min. The supernatant was decanted and the resin packed in a XK26 column. The packed resin was washed with Buffer A until the OD$_{280}$ reached a baseline, then the protein was eluted with Buffer B (Buffer A containing 300 mM Imidazole). The protein was dispensed into 3 mg aliquots at 0.5 mg/mL concentration and stored at −80° C. Prior to crystallization trials, the protein was chromatographed at a flow rate of 0.25 mL/min through a Sephacryl S-100H/R 26/60 column, pre-equilibrated with Buffer C: 20 mM HEPES pH 7.5, 0.3 M NaCl, 1 mM DTT.

The protein was concentrated to ~12 mg/mL using an Ultrafree centrifugal filter unit with a Biomax 10,000 MWCO membrane. The final concentration of the protein solution was determined from its UV absorbance at 280 nm using an A280 0.1%=0.957 and a molecular weight of 42843.7 Daltons for the long kinase domain construct. An A280 0.1%=0.980 and a molecular weight of 40347 Daltons were used for the short kinase domain construct.

Example 9

Enzymatic Modification of AKT3 Constructs Expressed in *Escherichia coli*

1.) Dephosphorylation of AKT3 with Lambda PP

For some of the samples, the protein was treated with Lambda Phosphatase to remove all phosphorylations. Typically, 2 μL of lambda PP (20,000 U/50 μL) were added per 100 μg of AKT3 and the reaction was carried out in 50 mM HEPES pH 7.5, 5 mM DU, 2 mM MnCl$_2$ at room temperature for 2 hours or overnight on ice. The phosphatase reaction was performed simultaneously with a cleavage by TEV Protease. Following the reaction, the Lambda phosphatase was removed from the AKT3 by gel filtration through a Sephacryl S-100H/R resin in a 26/60 column at a flow rate of 0.25 mL/min with 20 mM HEPES pH 7.5, 0.3 M NaCl, 5 mM OTT.

2.) TEV Protease Cleavage of AKT3

The various AKT3 constructs were treated with TEV protease to remove the N-terminal His-tag. The reaction was carried out by adding 2 Units of TEV Protease for each 10 µg of AKT3 in 50 mM Tris, pH 8.0-0.5 mM EDTA-1 mM OTT and incubating overnight on ice. The TEV protease and the cleaved His-Tag were removed by adjusting the reaction to 20 mM Imidazole and passing it over a Ni-NTA Agarose resin. A buffer exchange was performed by passage over a Sephacryl 5-1001-1/13 resin in a 26/60 column at a flow rate of 0.25 mL/min with 20 mM HEPES pH 7.5, 0.3 M NaCl, 5 mM OTT.

3.) Phosphorylation of AKT3 with PDK1

The AKT3 constructs are specifically phosphorylated at Thr305 and Ser472 by treatment with PDK1. The reaction was carried out in 50 mM HEPES pH 7.5, 20 mM MgCl$_2$, 1 mM DTT by adding 1 µg of full length PDK1 for each 25 µg of AKT3 at a final concentration of 1 mg/mL. The reaction was initiated by the addition of 1.25 mM ATP (neutralized) final concentration and incubating at room temperature for 2 hrs. The PDK1 was removed from the AKT3 by gel filtration through a Sephacryl S-100H/R resin in a 26/60 column at a flow rate of 0.25 mL/min with 20 mM HEPES pH 7.5, 0.3 M NaCl, 5 mM OTT. The extent of phosphorylation was confirmed by mass spectrometry analysis.

Example 10

Crystallization of AKT3skd Construct Expressed in *Escherichia coli*

The crystals were grown by vapor diffusion in hanging drops. 2 µL AKT3skd at 8-12 mg/mL in 20 mM HEPES pH 7.5, 0.3 M NaCl, 5 mM OTT were mixed with 2 µL of reservoir solution: 0.1 M MES pH 5.3-5.5, 10-15% Isopropanol. Optimal crystal growth occurred with a reservoir solution of 0.1 M MES pH 5.3, 12% Isopropanol.

Example 11

Crystallization of Phosphorylated and/or Mutant AKT3 Constructs Expressed in *Escherichia coli*

The crystals were grown by vapor diffusion in hanging drops.

1) AKT3lkd(T305D,S47213): 2 µL AKT3 at 8-12 mg/mL in 20 mM HEPES pH 7.5, 0.3 M NaCl, 5 mM DTT were mixed with 2 µL of reservoir solution: 0.1 M MES pH 5.3-5.5, 10-18% Isopropanol. Optimal growth of crystals occurred with a reservoir solution of 0.1 M MES pH 5.3, 12% Isopropanol.

2) AKT3lkd(pT305,S472D): 1 µL AKT3 at 8-12 mg/mL in 20 mM HEPES pH 7.5, 0.3 M NaCl, 5 mM DTT were mixed with 0.3 µL Seed Solution (containing crushed crystals of either AKT3lkd (T305D, S472D) or AKT3lkd (pT305, pS472)) and 0.7 µL of reservoir solution: 0.1 M MES pH 5.3-5.5, 10-18% isopropanol. The seed solution was prepared by crushing a crystal. Optimal growth of AKT3lkd(pT305, S472D) crystals occurred with a reservoir solution of 0.1 M MES pH 5.5, 8% Isopropanol, 2 mM OTT.

3) AKT3lkd(pT305,pS472): 1 µL AKT3 at 8-12 mg/mL in 20 mM HEPES pH 7.5, 0.3 M NaCl, 5 mM DTT were mixed with 0.3 µL seed solution containing crushed AKT3skd crystals and 0.7 µL of reservoir solution: 0.1 M MES pH 5.3-5.5, 10-18% isopropanol. The initial seed crystals were grown with AKT3skd expressed in High 5 cells. Optimal growth of AKT3lkd(pT305, pS472) crystals occurred with a reservoir solution of 0.1 M MES pH 5.5, 12% Isopropanol, 1 mM DTT. Subsequently, crystals obtained from this method were used, in turn, as seeds to crystallize other *E. coli* expressed constructs.

4) AKT3skd(T305D): 2 µL AKT3skd at 8-12 mg/mL in 20 mM HEPES pH 7.5, 0.3 M NaCl, 5 mM DTT were mixed with 2 µL of reservoir solution: 0.1 M MES pH 5.3-5.5, 10-15% Isopropanol. Optimal growth of AKT3skd(T305D) crystals occurred with a reservoir solution of 0.1 M MES pH 5.3, 11% Isopropanol.

Example 12

Photomicrograph of Crystals of AKT3skd Expressed in *Escherichia coli*

Photomicrographic analysis of the AKT3skd(T305) crystal was performed. The AKT3skd(T305) crystal was observed to have the following dimensions: 110 µm×110 µm.

Example 13

Crystallographic Analysis of AKT3 Short Kinase Domain

Prior to data collection, crystals were either transferred into a series of cryoprotectant solutions containing 10% (V/V) ethanol −0.1 M MES, pH 5.5 with 5, 10 and 25% (V/V) ethylene glycol. The crystals were then flash-cooled in a nitrogen stream at 95° K. Alternatively, ethylene glycol was added stepwise to the original drop containing the crystal until a final concentration of 25% (V/V) was obtained. X-ray diffraction was collected using a Rigaku generator equipped with a Raxis 4++ detector. The data were integrated and scaled using the HKL package. Three data sets were used to determine the structure. This procedure was used for all crystals set forth herein wherein data collection was conducted.

|  | High-Five expressed AKT3 Short Kinase Domain | *E. coli* expressed AKT3 Short Kinase Domain | *E. coli* expressed AKT3 Short Kinase Domain |
|---|---|---|---|
| Resolution Å | 50-1.80 | 50-2.0 | 50-1.80 |
| Resolution of Last Shell Å | 1.82-1.80 | 2.02-2.00 | 1.82-1.80 |
| Total Reflections | 103887 | 107017 | 144045 |
| Unique Reflections | 32001 | 21055 | 31560 |
| I/σ Overall | 16.7 | 20 | 25.8 |
| I/σ Last Shell | 2.1 | 2.5 | 1.9 |
| Rsym Overall | 0.064 | 0.068 | 0.048 |
| Rsym in Last Shell | 0.554 | 0.509 | 0.447 |
| % Completeness Overall | 98.6 | 86.9 | 97.6 |
| % Completeness Last Shell | 100 | 87.3 | 77.7 |
| Unit Cell | a = 48.679<br>b = 73.357<br>c = 95.468<br>α = β = γ = 90.0 | a = 49.093<br>b = 73.528<br>c = 95.559<br>α = β = γ = 90.0 | a = 49.015<br>b = 73.365<br>c = 95.375<br>α = β = γ = 90.0 |
| Spacegroup | P2$_1$2$_1$2$_1$ | P2$_1$2$_1$2$_1$ | P2$_1$2$_1$2$_1$ |

Example 14

Structure Determination of AKT3skd

The crystal structure was solved by molecular replacement using the search models described below. The chain was traced using the program ARPWARP. Refinement was done using the programs XPLOR and BUSTER.

Search Probes for Molecular Replacement

Clustal W sequence alignment established the residue to residue correspondence between AKT3 and PKA or AKT2. Search probes based on either the PKA (PDB code 1ATP) or AKT2 (PDB code 1O6K) structures were truncated to correspond to the AKT3 sequence. Coordinates were retained for side chains of residues that were identical in AKT3 and the probe, Additional modifications were made:

Probe 1—PKA with non-identical residues were truncated to Alanyl, or Glycyl residues if a Glycyl residue occurred in either sequence.

Probe 2—probe 1 with helix B, helix C and the T-loop deleted.

Probe 3—AKT2 with the 56 residues that differ between AKT2 and AKT3 truncated: Arginine to Lysine, Threonine to Serine, and all others to Alanine except if either sequence has Glycine.

Probe 4—probe 3 but with deletion of disordered segments 189-197, 297-312 and 442-479.

The final structure of AKT3skd had the following statistical values:

| | |
|---|---|
| #C, O, N, S Atoms in ASU | 2332 |
| Rcryst | 23.7 |
| Rfree | 26.4 |
| r.m.s.d Bond Length | 0.010 |
| r.m.s.d Bond Angles | 0.903 |

TABLE 2

Structural coordinates of AKT3skd
(amino acids 28-347 of SEQ ID NO:1)

Rfree = 25.7 Rwork = 23.2 Resolution = 1.70
CRYST1 Unit Cell Dimensions: a = 49.070 b = 73.350 c = 95.570
$\alpha$ = 90.00 $\beta$ = 90.00 $\gamma$ = 90.00 Space group: $P2_12_12_1$

| | | | | |
|---|---|---|---|---|
| ORIGX1 | 1.000000 | 0.000000 | 0.000000 | 0.00000 |
| ORIGX2 | 0.000000 | 1.000000 | 0.000000 | 0.00000 |
| ORIGX3 | 0.000000 | 0.000000 | 1.000000 | 0.00000 |
| SCALE1 | 0.020379 | 0.000000 | 0.000000 | 0.00000 |
| SCALE2 | 0.000000 | 0.013633 | 0.000000 | 0.00000 |
| SCALE3 | 0.000000 | 0.000000 | 0.010464 | 0.00000 |

| Col. # | Reference* |
|---|---|
| 1 | Atomic coordinate records for standard groups |
| 2 | Atom serial number |
| 3 | Atom name |
| 4 | Residue name |
| 5 | Molecule |
| 6 | Residue sequence number |
| 7 | Orthogonal coordinates for X in Angstroms |
| 8 | Orthogonal coordinates for Y in Angstroms |
| 9 | Orthogonal coordinates for Z in Angstroms |
| 10 | Occupancy |
| 11 | Temperature factor |

*This key applies to each set of structural coordinates set forth herein.

| | | | | | | | | | | |
|---|---|---|---|---|---|---|---|---|---|---|
| ATOM | 1 | N | ARG | A | 142 | 19.144 | 53.882 | 16.854 | 1.00 | 56.47 |
| ATOM | 2 | CA | ARG | A | 142 | 20.560 | 53.876 | 17.207 | 1.00 | 56.28 |
| ATOM | 3 | C | ARG | A | 142 | 20.756 | 53.423 | 18.648 | 1.00 | 59.29 |
| ATOM | 4 | O | ARG | A | 142 | 19.956 | 53.747 | 19.529 | 1.00 | 58.52 |
| ATOM | 5 | CB | ARG | A | 142 | 21.176 | 55.266 | 17.008 | 1.00 | 57.58 |
| ATOM | 6 | CG | ARG | A | 142 | 20.610 | 56.038 | 15.826 | 1.00 | 71.75 |
| ATOM | 7 | CD | ARG | A | 142 | 19.372 | 56.843 | 16.222 | 1.00 | 86.34 |
| ATOM | 8 | NE | ARG | A | 142 | 18.811 | 57.581 | 15.091 | 1.00 | 97.85 |
| ATOM | 9 | CZ | ARG | A | 142 | 17.567 | 57.436 | 14.644 | 1.00 | 113.90 |
| ATOM | 10 | NH1 | ARG | A | 142 | 16.745 | 56.573 | 15.227 | 1.00 | 101.58 |
| ATOM | 11 | NH2 | ARG | A | 142 | 17.147 | 58.148 | 13.606 | 1.00 | 101.92 |
| ATOM | 12 | N | LYS | A | 143 | 21.821 | 52.665 | 18.884 | 1.00 | 55.03 |
| ATOM | 13 | CA | LYS | A | 143 | 22.120 | 52.182 | 20.225 | 1.00 | 53.93 |
| ATOM | 14 | C | LYS | A | 143 | 22.963 | 53.210 | 20.965 | 1.00 | 55.82 |
| ATOM | 15 | O | LYS | A | 143 | 23.557 | 54.106 | 20.346 | 1.00 | 54.58 |
| ATOM | 16 | CB | LYS | A | 143 | 22.851 | 50.839 | 20.159 | 1.00 | 55.99 |
| ATOM | 17 | CG | LYS | A | 143 | 22.063 | 49.736 | 19.461 | 1.00 | 62.70 |
| ATOM | 18 | CD | LYS | A | 143 | 20.655 | 49.615 | 20.016 | 1.00 | 70.14 |
| ATOM | 19 | CE | LYS | A | 143 | 20.346 | 48.185 | 20.430 | 1.00 | 78.24 |
| ATOM | 20 | NZ | LYS | A | 143 | 19.278 | 47.583 | 19.589 | 1.00 | 86.16 |
| ATOM | 21 | N | THR | A | 144 | 23.008 | 53.090 | 22.288 | 1.00 | 51.40 |
| ATOM | 22 | CA | THR | A | 144 | 23.784 | 54.014 | 23.104 | 1.00 | 50.82 |
| ATOM | 23 | C | THR | A | 144 | 24.792 | 53.300 | 23.985 | 1.00 | 53.32 |
| ATOM | 24 | O | THR | A | 144 | 24.662 | 52.106 | 24.262 | 1.00 | 51.95 |
| ATOM | 25 | CB | THR | A | 144 | 22.880 | 54.871 | 24.022 | 1.00 | 58.30 |
| ATOM | 26 | OG1 | THR | A | 144 | 21.703 | 54.130 | 24.377 | 1.00 | 57.78 |

TABLE 2-continued

| | | | | | | | | | |
|---|---|---|---|---|---|---|---|---|---|
| ATOM | 27 | CG2 | THR | A | 144 | 22.484 | 56.160 | 23.328 | 1.00 | 57.47 |
| ATOM | 28 | N | MET | A | 145 | 25.774 | 54.061 | 24.459 | 1.00 | 50.10 |
| ATOM | 29 | CA | MET | A | 145 | 26.787 | 53.549 | 25.365 | 1.00 | 50.30 |
| ATOM | 30 | C | MET | A | 145 | 26.081 | 52.968 | 26.586 | 1.00 | 52.44 |
| ATOM | 31 | O | MET | A | 145 | 26.645 | 52.158 | 27.318 | 1.00 | 52.48 |
| ATOM | 32 | CB | MET | A | 145 | 27.699 | 54.696 | 25.809 | 1.00 | 52.94 |
| ATOM | 33 | CG | MET | A | 145 | 29.183 | 54.476 | 25.588 | 1.00 | 57.43 |
| ATOM | 34 | SD | MET | A | 145 | 29.598 | 52.903 | 24.840 | 1.00 | 62.51 |
| ATOM | 35 | CE | MET | A | 145 | 29.171 | 51.722 | 26.198 | 1.00 | 58.98 |
| ATOM | 36 | N | ASN | A | 146 | 24.837 | 53.399 | 26.803 | 1.00 | 47.48 |
| ATOM | 37 | CA | ASN | A | 146 | 24.042 | 52.950 | 27.951 | 1.00 | 46.70 |
| ATOM | 38 | C | ASN | A | 146 | 23.175 | 51.728 | 27.648 | 1.00 | 48.54 |
| ATOM | 39 | O | ASN | A | 146 | 22.445 | 51.249 | 28.515 | 1.00 | 47.47 |
| ATOM | 40 | CB | ASN | A | 146 | 23.158 | 54.097 | 28.474 | 1.00 | 47.91 |
| ATOM | 41 | CG | ASN | A | 146 | 23.844 | 55.452 | 28.388 | 1.00 | 76.94 |
| ATOM | 42 | OD1 | ASN | A | 146 | 24.346 | 55.972 | 29.388 | 1.00 | 73.39 |
| ATOM | 43 | ND2 | ASN | A | 146 | 23.850 | 56.041 | 27.195 | 1.00 | 70.24 |
| ATOM | 44 | N | ASP | A | 147 | 23.276 | 51.213 | 26.423 | 1.00 | 44.28 |
| ATOM | 45 | CA | ASP | A | 147 | 22.490 | 50.050 | 25.999 | 1.00 | 43.00 |
| ATOM | 46 | C | ASP | A | 147 | 23.156 | 48.718 | 26.353 | 1.00 | 44.27 |
| ATOM | 47 | O | ASP | A | 147 | 22.553 | 47.657 | 26.207 | 1.00 | 42.65 |
| ATOM | 48 | CB | ASP | A | 147 | 22.264 | 50.096 | 24.486 | 1.00 | 45.02 |
| ATOM | 49 | CG | ASP | A | 147 | 21.002 | 50.846 | 24.102 | 1.00 | 56.42 |
| ATOM | 50 | OD1 | ASP | A | 147 | 19.903 | 50.247 | 24.179 | 1.00 | 56.39 |
| ATOM | 51 | OD2 | ASP | A | 147 | 21.117 | 52.018 | 23.679 | 1.00 | 62.76 |
| ATOM | 52 | N | PHE | A | 148 | 24.405 | 48.775 | 26.798 | 1.00 | 39.94 |
| ATOM | 53 | CA | PHE | A | 148 | 25.135 | 47.558 | 27.115 | 1.00 | 38.95 |
| ATOM | 54 | C | PHE | A | 148 | 25.743 | 47.530 | 28.507 | 1.00 | 41.85 |
| ATOM | 55 | O | PHE | A | 148 | 26.051 | 48.576 | 29.090 | 1.00 | 42.10 |
| ATOM | 56 | CB | PHE | A | 148 | 26.260 | 47.346 | 26.095 | 1.00 | 40.18 |
| ATOM | 57 | CG | PHE | A | 148 | 25.834 | 47.552 | 24.673 | 1.00 | 40.99 |
| ATOM | 58 | CD1 | PHE | A | 148 | 25.582 | 46.465 | 23.847 | 1.00 | 43.68 |
| ATOM | 59 | CD2 | PHE | A | 148 | 25.710 | 48.828 | 24.154 | 1.00 | 42.93 |
| ATOM | 60 | CE1 | PHE | A | 148 | 25.188 | 46.655 | 22.531 | 1.00 | 44.64 |
| ATOM | 61 | CE2 | PHE | A | 148 | 25.311 | 49.022 | 22.836 | 1.00 | 45.79 |
| ATOM | 62 | CZ | PHE | A | 148 | 25.059 | 47.932 | 22.029 | 1.00 | 43.70 |
| ATOM | 63 | N | ASP | A | 149 | 26.010 | 46.315 | 28.977 | 1.00 | 37.25 |
| ATOM | 64 | CA | ASP | A | 149 | 26.705 | 46.077 | 30.244 | 1.00 | 36.19 |
| ATOM | 65 | C | ASP | A | 149 | 28.175 | 45.898 | 29.883 | 1.00 | 37.63 |
| ATOM | 66 | O | ASP | A | 149 | 28.503 | 45.125 | 28.975 | 1.00 | 36.53 |
| ATOM | 67 | CB | ASP | A | 149 | 26.232 | 44.761 | 30.870 | 1.00 | 38.00 |
| ATOM | 68 | CG | ASP | A | 149 | 24.832 | 44.852 | 31.453 | 1.00 | 47.00 |
| ATOM | 69 | OD1 | ASP | A | 149 | 24.398 | 45.968 | 31.806 | 1.00 | 47.02 |
| ATOM | 70 | OD2 | ASP | A | 149 | 24.188 | 43.791 | 31.586 | 1.00 | 50.39 |
| ATOM | 71 | N | TYR | A | 150 | 29.057 | 46.599 | 30.585 | 1.00 | 32.59 |
| ATOM | 72 | CA | TYR | A | 150 | 30.485 | 46.477 | 30.341 | 1.00 | 31.96 |
| ATOM | 73 | C | TYR | A | 150 | 31.021 | 45.290 | 31.142 | 1.00 | 32.06 |
| ATOM | 74 | O | TYR | A | 150 | 31.033 | 45.308 | 32.384 | 1.00 | 32.39 |
| ATOM | 75 | CB | TYR | A | 150 | 31.194 | 47.773 | 30.722 | 1.00 | 34.97 |
| ATOM | 76 | CG | TYR | A | 150 | 32.697 | 47.660 | 30.871 | 1.00 | 39.83 |
| ATOM | 77 | CD1 | TYR | A | 150 | 33.455 | 46.942 | 29.957 | 1.00 | 42.29 |
| ATOM | 78 | CD2 | TYR | A | 150 | 33.361 | 48.330 | 31.879 | 1.00 | 41.32 |
| ATOM | 79 | CE1 | TYR | A | 150 | 34.833 | 46.873 | 30.076 | 1.00 | 43.71 |
| ATOM | 80 | CE2 | TYR | A | 150 | 34.734 | 48.261 | 32.001 | 1.00 | 42.34 |
| ATOM | 81 | CZ | TYR | A | 150 | 35.461 | 47.539 | 31.100 | 1.00 | 48.64 |
| ATOM | 82 | OH | TYR | A | 150 | 36.833 | 47.490 | 31.219 | 1.00 | 50.74 |
| ATOM | 83 | N | LEU | A | 151 | 31.395 | 44.223 | 30.443 | 1.00 | 26.02 |
| ATOM | 84 | CA | LEU | A | 151 | 31.847 | 43.028 | 31.125 | 1.00 | 25.34 |
| ATOM | 85 | C | LEU | A | 151 | 33.342 | 42.973 | 31.391 | 1.00 | 28.00 |
| ATOM | 86 | O | LEU | A | 151 | 33.753 | 42.594 | 32.475 | 1.00 | 25.44 |
| ATOM | 87 | CB | LEU | A | 151 | 31.356 | 41.753 | 30.418 | 1.00 | 24.92 |
| ATOM | 88 | CG | LEU | A | 151 | 29.825 | 41.586 | 30.351 | 1.00 | 28.95 |
| ATOM | 89 | CD1 | LEU | A | 151 | 29.444 | 40.300 | 29.640 | 1.00 | 28.56 |
| ATOM | 90 | CD2 | LEU | A | 151 | 29.232 | 41.603 | 31.750 | 1.00 | 31.96 |
| ATOM | 91 | N | LYS | A | 152 | 34.164 | 43.286 | 30.391 | 1.00 | 23.26 |
| ATOM | 92 | CA | LYS | A | 152 | 35.609 | 43.197 | 30.592 | 1.00 | 22.71 |
| ATOM | 93 | C | LYS | A | 152 | 36.396 | 43.888 | 29.495 | 1.00 | 27.82 |
| ATOM | 94 | O | LYS | A | 152 | 36.006 | 43.862 | 28.325 | 1.00 | 28.43 |
| ATOM | 95 | CB | LYS | A | 152 | 36.024 | 41.717 | 30.641 | 1.00 | 25.10 |
| ATOM | 96 | CG | LYS | A | 152 | 37.495 | 41.477 | 30.939 | 1.00 | 29.48 |
| ATOM | 97 | CD | LYS | A | 152 | 37.720 | 40.034 | 31.344 | 1.00 | 29.73 |
| ATOM | 98 | CE | LYS | A | 152 | 39.077 | 39.833 | 31.983 | 1.00 | 34.59 |
| ATOM | 99 | NZ | LYS | A | 152 | 39.326 | 38.377 | 32.221 | 1.00 | 43.40 |
| ATOM | 100 | N | LEU | A | 153 | 37.522 | 44.471 | 29.870 | 1.00 | 25.46 |
| ATOM | 101 | CA | LEU | A | 153 | 38.421 | 45.091 | 28.888 | 1.00 | 26.22 |
| ATOM | 102 | C | LEU | A | 153 | 39.199 | 43.976 | 28.176 | 1.00 | 30.03 |
| ATOM | 103 | O | LEU | A | 153 | 39.823 | 43.131 | 28.827 | 1.00 | 29.33 |
| ATOM | 104 | CB | LEU | A | 153 | 39.394 | 46.043 | 29.583 | 1.00 | 27.21 |
| ATOM | 105 | CG | LEU | A | 153 | 40.452 | 46.637 | 28.640 | 1.00 | 32.57 |
| ATOM | 106 | CD1 | LEU | A | 153 | 39.802 | 47.674 | 27.735 | 1.00 | 32.34 |

TABLE 2-continued

| | | | | | | | | | |
|---|---|---|---|---|---|---|---|---|---|
| ATOM | 107 | CD2 | LEU | A | 153 | 41.583 | 47.247 | 29.427 | 1.00 | 34.26 |
| ATOM | 108 | N | LEU | A | 154 | 39.130 | 43.956 | 26.840 | 1.00 | 26.49 |
| ATOM | 109 | CA | LEU | A | 154 | 39.786 | 42.919 | 26.048 | 1.00 | 26.69 |
| ATOM | 110 | C | LEU | A | 154 | 41.137 | 43.354 | 25.480 | 1.00 | 34.11 |
| ATOM | 111 | O | LEU | A | 154 | 42.004 | 42.521 | 25.225 | 1.00 | 34.84 |
| ATOM | 112 | CB | LEU | A | 154 | 38.868 | 42.451 | 24.913 | 1.00 | 26.68 |
| ATOM | 113 | CG | LEU | A | 154 | 37.531 | 41.834 | 25.341 | 1.00 | 30.42 |
| ATOM | 114 | CD1 | LEU | A | 154 | 36.664 | 41.550 | 24.146 | 1.00 | 30.42 |
| ATOM | 115 | CD2 | LEU | A | 154 | 37.738 | 40.592 | 26.193 | 1.00 | 32.36 |
| ATOM | 116 | N | GLY | A | 155 | 41.306 | 44.653 | 25.277 | 1.00 | 32.72 |
| ATOM | 117 | CA | GLY | A | 155 | 42.549 | 45.174 | 24.724 | 1.00 | 33.91 |
| ATOM | 118 | C | GLY | A | 155 | 42.534 | 46.684 | 24.648 | 1.00 | 38.77 |
| ATOM | 119 | O | GLY | A | 155 | 41.476 | 47.303 | 24.580 | 1.00 | 36.57 |
| ATOM | 120 | N | LYS | A | 156 | 43.721 | 47.274 | 24.695 | 1.00 | 39.11 |
| ATOM | 121 | CA | LYS | A | 156 | 43.870 | 48.722 | 24.629 | 1.00 | 40.88 |
| ATOM | 122 | C | LYS | A | 156 | 45.040 | 49.069 | 23.713 | 1.00 | 48.96 |
| ATOM | 123 | O | LYS | A | 156 | 46.007 | 48.309 | 23.604 | 1.00 | 48.86 |
| ATOM | 124 | CB | LYS | A | 156 | 44.106 | 49.295 | 26.028 | 1.00 | 44.00 |
| ATOM | 125 | CG | LYS | A | 156 | 43.270 | 50.523 | 26.346 | 1.00 | 61.11 |
| ATOM | 126 | CD | LYS | A | 156 | 43.943 | 51.385 | 27.399 | 1.00 | 73.52 |
| ATOM | 127 | CE | LYS | A | 156 | 43.145 | 52.650 | 27.681 | 1.00 | 84.99 |
| ATOM | 128 | NZ | LYS | A | 156 | 43.896 | 53.594 | 28.553 | 1.00 | 93.90 |
| ATOM | 129 | N | GLY | A | 157 | 44.940 | 50.210 | 23.042 | 1.00 | 48.29 |
| ATOM | 130 | CA | GLY | A | 157 | 45.992 | 50.648 | 22.135 | 1.00 | 49.02 |
| ATOM | 131 | C | GLY | A | 157 | 45.893 | 52.140 | 21.880 | 1.00 | 54.26 |
| ATOM | 132 | O | GLY | A | 157 | 44.988 | 52.807 | 22.381 | 1.00 | 53.41 |
| ATOM | 133 | N | THR | A | 158 | 46.834 | 52.663 | 21.097 | 1.00 | 52.01 |
| ATOM | 134 | CA | THR | A | 158 | 46.855 | 54.088 | 20.784 | 1.00 | 51.75 |
| ATOM | 135 | C | THR | A | 158 | 45.551 | 54.524 | 20.123 | 1.00 | 54.32 |
| ATOM | 136 | O | THR | A | 158 | 45.066 | 55.631 | 20.358 | 1.00 | 53.18 |
| ATOM | 137 | CB | THR | A | 158 | 48.043 | 54.449 | 19.878 | 1.00 | 61.68 |
| ATOM | 138 | OG1 | THR | A | 158 | 48.102 | 53.532 | 18.776 | 1.00 | 63.91 |
| ATOM | 139 | CG2 | THR | A | 158 | 49.347 | 54.375 | 20.661 | 1.00 | 59.65 |
| ATOM | 140 | N | PHE | A | 159 | 44.976 | 53.641 | 19.308 | 1.00 | 50.69 |
| ATOM | 141 | CA | PHE | A | 159 | 43.726 | 53.951 | 18.618 | 1.00 | 49.94 |
| ATOM | 142 | C | PHE | A | 159 | 42.518 | 53.930 | 19.549 | 1.00 | 50.02 |
| ATOM | 143 | O | PHE | A | 159 | 41.511 | 54.578 | 19.280 | 1.00 | 49.07 |
| ATOM | 144 | CB | PHE | A | 159 | 43.497 | 52.998 | 17.441 | 1.00 | 52.45 |
| ATOM | 145 | CG | PHE | A | 159 | 44.236 | 53.389 | 16.189 | 1.00 | 54.71 |
| ATOM | 146 | CD1 | PHE | A | 159 | 44.890 | 52.430 | 15.423 | 1.00 | 58.25 |
| ATOM | 147 | CD2 | PHE | A | 159 | 44.269 | 54.712 | 15.769 | 1.00 | 57.30 |
| ATOM | 148 | CE1 | PHE | A | 159 | 45.574 | 52.787 | 14.266 | 1.00 | 59.20 |
| ATOM | 149 | CE2 | PHE | A | 159 | 44.951 | 55.075 | 14.617 | 1.00 | 60.26 |
| ATOM | 150 | CZ | PHE | A | 159 | 45.607 | 54.110 | 13.867 | 1.00 | 58.36 |
| ATOM | 151 | N | GLY | A | 160 | 42.613 | 53.174 | 20.639 | 1.00 | 43.77 |
| ATOM | 152 | CA | GLY | A | 160 | 41.502 | 53.080 | 21.589 | 1.00 | 42.15 |
| ATOM | 153 | C | GLY | A | 160 | 41.523 | 51.750 | 22.347 | 1.00 | 42.87 |
| ATOM | 154 | O | GLY | A | 160 | 42.586 | 51.291 | 22.802 | 1.00 | 41.88 |
| ATOM | 155 | N | LYS | A | 161 | 40.351 | 51.136 | 22.476 | 1.00 | 37.42 |
| ATOM | 156 | CA | LYS | A | 161 | 40.229 | 49.869 | 23.191 | 1.00 | 35.51 |
| ATOM | 157 | C | LYS | A | 161 | 39.050 | 49.035 | 22.692 | 1.00 | 35.58 |
| ATOM | 158 | O | LYS | A | 161 | 38.211 | 49.503 | 21.910 | 1.00 | 33.42 |
| ATOM | 159 | CB | LYS | A | 161 | 40.072 | 50.137 | 24.688 | 1.00 | 38.09 |
| ATOM | 160 | CG | LYS | A | 161 | 38.668 | 50.553 | 25.081 | 1.00 | 43.06 |
| ATOM | 161 | CD | LYS | A | 161 | 38.682 | 51.511 | 26.272 | 1.00 | 52.66 |
| ATOM | 162 | CE | LYS | A | 161 | 37.358 | 52.240 | 26.403 | 1.00 | 62.61 |
| ATOM | 163 | NZ | LYS | A | 161 | 36.224 | 51.388 | 25.948 | 1.00 | 73.03 |
| ATOM | 164 | N | VAL | A | 162 | 39.006 | 47.780 | 23.137 | 1.00 | 29.99 |
| ATOM | 165 | CA | VAL | A | 162 | 37.920 | 46.879 | 22.783 | 1.00 | 28.18 |
| ATOM | 166 | C | VAL | A | 162 | 37.453 | 46.256 | 24.091 | 1.00 | 30.32 |
| ATOM | 167 | O | VAL | A | 162 | 38.274 | 45.829 | 24.893 | 1.00 | 29.29 |
| ATOM | 168 | CB | VAL | A | 162 | 38.412 | 45.763 | 21.830 | 1.00 | 31.70 |
| ATOM | 169 | CG1 | VAL | A | 162 | 37.295 | 44.795 | 21.535 | 1.00 | 30.75 |
| ATOM | 170 | CG2 | VAL | A | 162 | 38.945 | 46.372 | 20.518 | 1.00 | 32.21 |
| ATOM | 171 | N | ILE | A | 163 | 36.143 | 46.237 | 24.308 | 1.00 | 26.32 |
| ATOM | 172 | CA | ILE | A | 163 | 35.579 | 45.708 | 25.536 | 1.00 | 26.53 |
| ATOM | 173 | C | ILE | A | 163 | 34.479 | 44.682 | 25.259 | 1.00 | 28.24 |
| ATOM | 174 | O | ILE | A | 163 | 33.720 | 44.812 | 24.285 | 1.00 | 28.80 |
| ATOM | 175 | CB | ILE | A | 163 | 34.973 | 46.869 | 26.379 | 1.00 | 29.90 |
| ATOM | 176 | CG1 | ILE | A | 163 | 33.890 | 47.589 | 25.574 | 1.00 | 31.53 |
| ATOM | 177 | CG2 | ILE | A | 163 | 36.055 | 47.884 | 26.753 | 1.00 | 30.81 |
| ATOM | 178 | CD1 | ILE | A | 163 | 33.254 | 48.752 | 26.312 | 1.00 | 40.10 |
| ATOM | 179 | N | LEU | A | 164 | 34.385 | 43.656 | 26.114 | 1.00 | 21.55 |
| ATOM | 180 | CA | LEU | A | 164 | 33.348 | 42.646 | 25.988 | 1.00 | 21.61 |
| ATOM | 181 | C | LEU | A | 164 | 32.120 | 43.216 | 26.613 | 1.00 | 28.46 |
| ATOM | 182 | O | LEU | A | 164 | 32.180 | 43.724 | 27.744 | 1.00 | 28.36 |
| ATOM | 183 | CB | LEU | A | 164 | 33.762 | 41.341 | 26.737 | 1.00 | 22.70 |
| ATOM | 184 | CG | LEU | A | 164 | 32.708 | 40.254 | 26.917 | 1.00 | 26.84 |
| ATOM | 185 | CD1 | LEU | A | 164 | 32.190 | 39.703 | 25.571 | 1.00 | 27.21 |
| ATOM | 186 | CD2 | LEU | A | 164 | 33.240 | 39.126 | 27.791 | 1.00 | 28.50 |

TABLE 2-continued

| | | | | | | | | | |
|---|---|---|---|---|---|---|---|---|---|
| ATOM | 187 | N | VAL | A | 165 | 31.011 | 43.207 | 25.872 | 1.00 | 25.89 |
| ATOM | 188 | CA | VAL | A | 165 | 29.757 | 43.756 | 26.387 | 1.00 | 27.04 |
| ATOM | 189 | C | VAL | A | 165 | 28.608 | 42.778 | 26.214 | 1.00 | 33.03 |
| ATOM | 190 | O | VAL | A | 165 | 28.659 | 41.855 | 25.404 | 1.00 | 31.74 |
| ATOM | 191 | CB | VAL | A | 165 | 29.357 | 45.088 | 25.675 | 1.00 | 30.26 |
| ATOM | 192 | CG1 | VAL | A | 165 | 30.417 | 46.174 | 25.867 | 1.00 | 29.42 |
| ATOM | 193 | CG2 | VAL | A | 165 | 29.066 | 44.844 | 24.161 | 1.00 | 30.19 |
| ATOM | 194 | N | ARG | A | 166 | 27.550 | 43.003 | 26.978 | 1.00 | 32.82 |
| ATOM | 195 | CA | ARG | A | 166 | 26.346 | 42.212 | 26.866 | 1.00 | 33.85 |
| ATOM | 196 | C | ARG | A | 166 | 25.246 | 43.208 | 26.529 | 1.00 | 39.84 |
| ATOM | 197 | O | ARG | A | 166 | 25.175 | 44.295 | 27.120 | 1.00 | 38.75 |
| ATOM | 198 | CB | ARG | A | 166 | 26.034 | 41.507 | 28.203 | 1.00 | 36.13 |
| ATOM | 199 | CG | ARG | A | 166 | 24.808 | 40.601 | 28.179 | 1.00 | 43.62 |
| ATOM | 200 | CD | ARG | A | 166 | 24.346 | 40.246 | 29.602 | 1.00 | 50.37 |
| ATOM | 201 | NE | ARG | A | 166 | 25.148 | 39.167 | 30.195 | 1.00 | 50.11 |
| ATOM | 202 | CZ | ARG | A | 166 | 25.782 | 39.260 | 31.357 | 1.00 | 51.16 |
| ATOM | 203 | NH1 | ARG | A | 166 | 25.710 | 40.385 | 32.065 | 1.00 | 37.53 |
| ATOM | 204 | NH2 | ARG | A | 166 | 26.506 | 38.237 | 31.807 | 1.00 | 32.50 |
| ATOM | 205 | N | GLU | A | 167 | 24.462 | 42.892 | 25.507 | 1.00 | 38.25 |
| ATOM | 206 | CA | GLU | A | 167 | 23.362 | 43.752 | 25.107 | 1.00 | 38.77 |
| ATOM | 207 | C | GLU | A | 167 | 22.249 | 43.530 | 26.112 | 1.00 | 44.44 |
| ATOM | 208 | O | GLU | A | 167 | 21.732 | 42.424 | 26.234 | 1.00 | 44.65 |
| ATOM | 209 | CB | GLU | A | 167 | 22.868 | 43.382 | 23.704 | 1.00 | 39.90 |
| ATOM | 210 | CG | GLU | A | 167 | 21.815 | 44.339 | 23.153 | 1.00 | 51.34 |
| ATOM | 211 | CD | GLU | A | 167 | 21.483 | 44.061 | 21.702 | 1.00 | 65.78 |
| ATOM | 212 | OE1 | GLU | A | 167 | 21.334 | 45.029 | 20.930 | 1.00 | 59.64 |
| ATOM | 213 | OE2 | GLU | A | 167 | 21.386 | 42.874 | 21.330 | 1.00 | 58.02 |
| ATOM | 214 | N | LYS | A | 168 | 21.924 | 44.575 | 26.862 | 1.00 | 43.29 |
| ATOM | 215 | CA | LYS | A | 168 | 20.895 | 44.506 | 27.908 | 1.00 | 44.16 |
| ATOM | 216 | C | LYS | A | 168 | 19.621 | 43.777 | 27.480 | 1.00 | 50.20 |
| ATOM | 217 | O | LYS | A | 168 | 19.195 | 42.810 | 28.121 | 1.00 | 50.40 |
| ATOM | 218 | CB | LYS | A | 168 | 20.543 | 45.920 | 28.394 | 1.00 | 46.13 |
| ATOM | 219 | CG | LYS | A | 168 | 21.535 | 46.507 | 29.383 | 1.00 | 52.37 |
| ATOM | 220 | CD | LYS | A | 168 | 21.484 | 48.023 | 29.382 | 1.00 | 59.75 |
| ATOM | 221 | CE | LYS | A | 168 | 21.993 | 48.589 | 30.694 | 1.00 | 66.33 |
| ATOM | 222 | NZ | LYS | A | 168 | 22.822 | 47.598 | 31.431 | 1.00 | 74.39 |
| ATOM | 223 | N | ALA | A | 169 | 18.999 | 44.266 | 26.416 | 1.00 | 47.65 |
| ATOM | 224 | CA | ALA | A | 169 | 17.742 | 43.697 | 25.930 | 1.00 | 47.83 |
| ATOM | 225 | C | ALA | A | 169 | 17.833 | 42.229 | 25.494 | 1.00 | 51.73 |
| ATOM | 226 | O | ALA | A | 169 | 17.019 | 41.398 | 25.904 | 1.00 | 51.80 |
| ATOM | 227 | CB | ALA | A | 169 | 17.172 | 44.556 | 24.807 | 1.00 | 48.62 |
| ATOM | 228 | N | SER | A | 170 | 18.817 | 41.921 | 24.655 | 1.00 | 47.63 |
| ATOM | 229 | CA | SER | A | 170 | 18.965 | 40.581 | 24.097 | 1.00 | 46.94 |
| ATOM | 230 | C | SER | A | 170 | 19.723 | 39.579 | 24.962 | 1.00 | 48.90 |
| ATOM | 231 | O | SER | A | 170 | 19.469 | 38.375 | 24.886 | 1.00 | 48.29 |
| ATOM | 232 | CB | SER | A | 170 | 19.614 | 40.658 | 22.717 | 1.00 | 51.27 |
| ATOM | 233 | OG | SER | A | 170 | 20.997 | 40.958 | 22.826 | 1.00 | 59.08 |
| ATOM | 234 | N | GLY | A | 171 | 20.694 | 40.064 | 25.730 | 1.00 | 44.12 |
| ATOM | 235 | CA | GLY | A | 171 | 21.521 | 39.190 | 26.561 | 1.00 | 43.25 |
| ATOM | 236 | C | GLY | A | 171 | 22.700 | 38.607 | 25.757 | 1.00 | 45.45 |
| ATOM | 237 | O | GLY | A | 171 | 23.517 | 37.842 | 26.288 | 1.00 | 45.23 |
| ATOM | 238 | N | LYS | A | 172 | 22.763 | 38.951 | 24.473 | 1.00 | 40.40 |
| ATOM | 239 | CA | LYS | A | 172 | 23.822 | 38.462 | 23.596 | 1.00 | 39.35 |
| ATOM | 240 | C | LYS | A | 172 | 25.140 | 39.209 | 23.832 | 1.00 | 40.40 |
| ATOM | 241 | O | LYS | A | 172 | 25.139 | 40.397 | 24.170 | 1.00 | 39.95 |
| ATOM | 242 | CB | LYS | A | 172 | 23.396 | 38.583 | 22.129 | 1.00 | 41.81 |
| ATOM | 243 | CG | LYS | A | 172 | 22.112 | 37.840 | 21.802 | 1.00 | 57.53 |
| ATOM | 244 | CD | LYS | A | 172 | 21.606 | 38.187 | 20.407 | 1.00 | 68.99 |
| ATOM | 245 | CE | LYS | A | 172 | 20.756 | 37.059 | 19.835 | 1.00 | 80.49 |
| ATOM | 246 | NZ | LYS | A | 172 | 19.596 | 37.577 | 19.056 | 1.00 | 90.51 |
| ATOM | 247 | N | TYR | A | 173 | 26.258 | 38.504 | 23.639 | 1.00 | 35.04 |
| ATOM | 248 | CA | TYR | A | 173 | 27.593 | 39.069 | 23.853 | 1.00 | 33.70 |
| ATOM | 249 | C | TYR | A | 173 | 28.190 | 39.614 | 22.583 | 1.00 | 35.82 |
| ATOM | 250 | O | TYR | A | 173 | 28.048 | 39.020 | 21.512 | 1.00 | 36.48 |
| ATOM | 251 | CB | TYR | A | 173 | 28.533 | 38.016 | 24.448 | 1.00 | 34.16 |
| ATOM | 252 | CG | TYR | A | 173 | 28.018 | 37.461 | 25.749 | 1.00 | 35.17 |
| ATOM | 253 | CD1 | TYR | A | 173 | 28.093 | 38.216 | 26.918 | 1.00 | 36.62 |
| ATOM | 254 | CD2 | TYR | A | 173 | 27.336 | 36.263 | 25.788 | 1.00 | 35.61 |
| ATOM | 255 | CE1 | TYR | A | 173 | 27.556 | 37.755 | 28.103 | 1.00 | 35.33 |
| ATOM | 256 | CE2 | TYR | A | 173 | 26.777 | 35.797 | 26.969 | 1.00 | 36.77 |
| ATOM | 257 | CZ | TYR | A | 173 | 26.913 | 36.549 | 28.130 | 1.00 | 42.14 |
| ATOM | 258 | OH | TYR | A | 173 | 26.394 | 36.086 | 29.310 | 1.00 | 39.68 |
| ATOM | 259 | N | TYR | A | 174 | 28.881 | 40.736 | 22.706 | 1.00 | 30.54 |
| ATOM | 260 | CA | TYR | A | 174 | 29.513 | 41.369 | 21.569 | 1.00 | 29.95 |
| ATOM | 261 | C | TYR | A | 174 | 30.835 | 41.952 | 21.990 | 1.00 | 30.10 |
| ATOM | 262 | O | TYR | A | 174 | 31.106 | 42.113 | 23.178 | 1.00 | 28.55 |
| ATOM | 263 | CB | TYR | A | 174 | 28.624 | 42.517 | 21.031 | 1.00 | 31.38 |
| ATOM | 264 | CG | TYR | A | 174 | 27.300 | 42.062 | 20.472 | 1.00 | 34.52 |
| ATOM | 265 | CD1 | TYR | A | 174 | 27.231 | 41.383 | 19.259 | 1.00 | 36.54 |
| ATOM | 266 | CD2 | TYR | A | 174 | 26.112 | 42.318 | 21.151 | 1.00 | 35.93 |

TABLE 2-continued

| | | | | | | | | | |
|---|---|---|---|---|---|---|---|---|---|
| ATOM | 267 | CE1 | TYR | A | 174 | 26.038 | 40.950 | 18.755 | 1.00 | 38.28 |
| ATOM | 268 | CE2 | TYR | A | 174 | 24.902 | 41.895 | 20.648 | 1.00 | 36.77 |
| ATOM | 269 | CZ | TYR | A | 174 | 24.868 | 41.208 | 19.447 | 1.00 | 45.26 |
| ATOM | 270 | OH | TYR | A | 174 | 23.665 | 40.782 | 18.935 | 1.00 | 47.55 |
| ATOM | 271 | N | ALA | A | 175 | 31.654 | 42.319 | 21.012 | 1.00 | 25.39 |
| ATOM | 272 | CA | ALA | A | 175 | 32.883 | 43.014 | 21.318 | 1.00 | 25.19 |
| ATOM | 273 | C | ALA | A | 175 | 32.700 | 44.450 | 20.836 | 1.00 | 31.42 |
| ATOM | 274 | O | ALA | A | 175 | 32.352 | 44.669 | 19.684 | 1.00 | 31.85 |
| ATOM | 275 | CB | ALA | A | 175 | 34.054 | 42.374 | 20.609 | 1.00 | 25.80 |
| ATOM | 276 | N | MET | A | 176 | 32.896 | 45.431 | 21.717 | 1.00 | 27.53 |
| ATOM | 277 | CA | MET | A | 176 | 32.764 | 46.820 | 21.286 | 1.00 | 25.89 |
| ATOM | 278 | C | MET | A | 176 | 34.091 | 47.498 | 21.119 | 1.00 | 30.98 |
| ATOM | 279 | O | MET | A | 176 | 34.881 | 47.590 | 22.061 | 1.00 | 31.28 |
| ATOM | 280 | CB | MET | A | 176 | 31.862 | 47.649 | 22.222 | 1.00 | 27.16 |
| ATOM | 281 | CG | MET | A | 176 | 31.747 | 49.083 | 21.768 | 1.00 | 29.64 |
| ATOM | 282 | SD | MET | A | 176 | 30.941 | 50.150 | 22.993 | 1.00 | 33.77 |
| ATOM | 283 | CE | MET | A | 176 | 29.455 | 49.511 | 23.043 | 1.00 | 29.36 |
| ATOM | 284 | N | LYS | A | 177 | 34.361 | 47.961 | 19.905 | 1.00 | 27.97 |
| ATOM | 285 | CA | LYS | A | 177 | 35.603 | 48.657 | 19.642 | 1.00 | 28.59 |
| ATOM | 286 | C | LYS | A | 177 | 35.333 | 50.137 | 19.795 | 1.00 | 36.11 |
| ATOM | 287 | O | LYS | A | 177 | 34.397 | 50.662 | 19.200 | 1.00 | 36.72 |
| ATOM | 288 | CB | LYS | A | 177 | 36.139 | 48.340 | 18.228 | 1.00 | 30.23 |
| ATOM | 289 | CG | LYS | A | 177 | 37.427 | 49.081 | 17.887 | 1.00 | 38.47 |
| ATOM | 290 | CD | LYS | A | 177 | 38.093 | 48.521 | 16.612 | 1.00 | 43.33 |
| ATOM | 291 | CE | LYS | A | 177 | 37.210 | 48.737 | 15.379 | 1.00 | 45.14 |
| ATOM | 292 | NZ | LYS | A | 177 | 38.007 | 48.831 | 14.107 | 1.00 | 38.05 |
| ATOM | 293 | N | ILE | A | 178 | 36.101 | 50.779 | 20.670 | 1.00 | 35.56 |
| ATOM | 294 | CA | ILE | A | 178 | 35.940 | 52.198 | 20.958 | 1.00 | 36.26 |
| ATOM | 295 | C | ILE | A | 178 | 37.178 | 52.945 | 20.519 | 1.00 | 41.12 |
| ATOM | 296 | O | ILE | A | 178 | 38.237 | 52.842 | 21.143 | 1.00 | 40.35 |
| ATOM | 297 | CB | ILE | A | 178 | 35.655 | 52.440 | 22.462 | 1.00 | 39.75 |
| ATOM | 298 | CG1 | ILE | A | 178 | 34.229 | 51.983 | 22.806 | 1.00 | 40.17 |
| ATOM | 299 | CG2 | ILE | A | 178 | 35.868 | 53.915 | 22.819 | 1.00 | 41.09 |
| ATOM | 300 | CD1 | ILE | A | 178 | 34.096 | 51.301 | 24.146 | 1.00 | 50.12 |
| ATOM | 301 | N | LEU | A | 179 | 37.050 | 53.664 | 19.403 | 1.00 | 39.57 |
| ATOM | 302 | CA | LEU | A | 179 | 38.168 | 54.394 | 18.815 | 1.00 | 40.28 |
| ATOM | 303 | C | LEU | A | 179 | 38.148 | 55.881 | 19.152 | 1.00 | 46.35 |
| ATOM | 304 | O | LEU | A | 179 | 37.080 | 56.504 | 19.222 | 1.00 | 45.17 |
| ATOM | 305 | CB | LEU | A | 179 | 38.174 | 54.209 | 17.291 | 1.00 | 40.03 |
| ATOM | 306 | CG | LEU | A | 179 | 38.078 | 52.772 | 16.776 | 1.00 | 43.82 |
| ATOM | 307 | CD1 | LEU | A | 179 | 38.113 | 52.746 | 15.258 | 1.00 | 43.60 |
| ATOM | 308 | CD2 | LEU | A | 179 | 39.192 | 51.912 | 17.357 | 1.00 | 45.74 |
| ATOM | 309 | N | LYS | A | 180 | 39.338 | 56.443 | 19.356 | 1.00 | 45.40 |
| ATOM | 310 | CA | LYS | A | 180 | 39.473 | 57.859 | 19.682 | 1.00 | 46.21 |
| ATOM | 311 | C | LYS | A | 180 | 39.541 | 58.675 | 18.394 | 1.00 | 50.71 |
| ATOM | 312 | O | LYS | A | 180 | 40.525 | 58.607 | 17.668 | 1.00 | 49.90 |
| ATOM | 313 | CB | LYS | A | 180 | 40.729 | 58.098 | 20.528 | 1.00 | 49.50 |
| ATOM | 314 | CG | LYS | A | 180 | 40.622 | 57.581 | 21.966 | 1.00 | 65.80 |
| ATOM | 315 | CD | LYS | A | 180 | 40.185 | 56.115 | 22.002 | 1.00 | 76.85 |
| ATOM | 316 | CE | LYS | A | 180 | 39.479 | 55.769 | 23.316 | 1.00 | 85.41 |
| ATOM | 317 | NZ | LYS | A | 180 | 38.887 | 54.395 | 23.307 | 1.00 | 89.60 |
| ATOM | 318 | N | LYS | A | 181 | 38.474 | 59.416 | 18.109 | 1.00 | 49.19 |
| ATOM | 319 | CA | LYS | A | 181 | 38.394 | 60.239 | 16.899 | 1.00 | 49.93 |
| ATOM | 320 | C | LYS | A | 181 | 39.661 | 61.059 | 16.660 | 1.00 | 55.89 |
| ATOM | 321 | O | LYS | A | 181 | 40.226 | 61.037 | 15.566 | 1.00 | 56.00 |
| ATOM | 322 | CB | LYS | A | 181 | 37.172 | 61.158 | 16.952 | 1.00 | 52.25 |
| ATOM | 323 | CG | LYS | A | 181 | 35.841 | 60.416 | 16.926 | 1.00 | 62.29 |
| ATOM | 324 | CD | LYS | A | 181 | 34.705 | 61.325 | 16.489 | 1.00 | 70.58 |
| ATOM | 325 | CE | LYS | A | 181 | 33.362 | 60.806 | 16.979 | 1.00 | 80.70 |
| ATOM | 326 | NZ | LYS | A | 181 | 32.503 | 61.898 | 17.512 | 1.00 | 88.79 |
| ATOM | 327 | N | GLU | A | 182 | 40.124 | 61.753 | 17.696 | 1.00 | 53.48 |
| ATOM | 328 | CA | GLU | A | 182 | 41.327 | 62.578 | 17.590 | 1.00 | 53.63 |
| ATOM | 329 | C | GLU | A | 182 | 42.533 | 61.795 | 17.075 | 1.00 | 57.30 |
| ATOM | 330 | O | GLU | A | 182 | 43.373 | 62.339 | 16.357 | 1.00 | 56.84 |
| ATOM | 331 | CB | GLU | A | 182 | 41.654 | 63.240 | 18.929 | 1.00 | 55.25 |
| ATOM | 332 | CG | GLU | A | 182 | 40.434 | 63.561 | 19.777 | 1.00 | 67.00 |
| ATOM | 333 | CD | GLU | A | 182 | 40.265 | 62.601 | 20.943 | 1.00 | 92.53 |
| ATOM | 334 | OE1 | GLU | A | 182 | 41.265 | 62.338 | 21.650 | 1.00 | 89.82 |
| ATOM | 335 | OE2 | GLU | A | 182 | 39.131 | 62.117 | 21.155 | 1.00 | 86.50 |
| ATOM | 336 | N | VAL | A | 183 | 42.622 | 60.520 | 17.440 | 1.00 | 53.46 |
| ATOM | 337 | CA | VAL | A | 183 | 43.733 | 59.681 | 16.989 | 1.00 | 53.27 |
| ATOM | 338 | C | VAL | A | 183 | 43.542 | 59.249 | 15.537 | 1.00 | 57.11 |
| ATOM | 339 | O | VAL | A | 183 | 44.504 | 59.176 | 14.769 | 1.00 | 56.93 |
| ATOM | 340 | CB | VAL | A | 183 | 43.906 | 58.422 | 17.872 | 1.00 | 57.04 |
| ATOM | 341 | CG1 | VAL | A | 183 | 43.353 | 57.199 | 17.160 | 1.00 | 56.93 |
| ATOM | 342 | CG2 | VAL | A | 183 | 45.371 | 58.210 | 18.216 | 1.00 | 56.72 |
| ATOM | 343 | N | ILE | A | 184 | 42.297 | 58.963 | 15.165 | 1.00 | 53.83 |
| ATOM | 344 | CA | ILE | A | 184 | 41.991 | 58.542 | 13.799 | 1.00 | 53.63 |
| ATOM | 345 | C | ILE | A | 184 | 42.374 | 59.642 | 12.806 | 1.00 | 57.93 |
| ATOM | 346 | O | ILE | A | 184 | 43.090 | 59.394 | 11.833 | 1.00 | 57.55 |

TABLE 2-continued

| | | | | | | | | | |
|---|---|---|---|---|---|---|---|---|---|
| ATOM | 347 | CB | ILE | A | 184 | 40.493 | 58.179 | 13.633 | 1.00 | 56.58 |
| ATOM | 348 | CG1 | ILE | A | 184 | 40.193 | 56.847 | 14.318 | 1.00 | 56.65 |
| ATOM | 349 | CG2 | ILE | A | 184 | 40.121 | 58.096 | 12.156 | 1.00 | 57.47 |
| ATOM | 350 | CD1 | ILE | A | 184 | 40.916 | 55.686 | 13.705 | 1.00 | 61.36 |
| ATOM | 351 | N | ILE | A | 185 | 41.912 | 60.860 | 13.074 | 1.00 | 54.79 |
| ATOM | 352 | CA | ILE | A | 185 | 42.232 | 62.000 | 12.222 | 1.00 | 54.50 |
| ATOM | 353 | C | ILE | A | 185 | 43.744 | 62.165 | 12.155 | 1.00 | 57.67 |
| ATOM | 354 | O | ILE | A | 185 | 44.335 | 62.142 | 11.078 | 1.00 | 56.93 |
| ATOM | 355 | CB | ILE | A | 185 | 41.614 | 63.316 | 12.768 | 1.00 | 57.78 |
| ATOM | 356 | CG1 | ILE | A | 185 | 42.043 | 63.548 | 14.218 | 1.00 | 58.51 |
| ATOM | 357 | CG2 | ILE | A | 185 | 40.099 | 63.279 | 12.677 | 1.00 | 58.42 |
| ATOM | 358 | CD1 | ILE | A | 185 | 43.148 | 64.580 | 14.378 | 1.00 | 67.26 |
| ATOM | 359 | N | ALA | A | 186 | 44.367 | 62.293 | 13.322 | 1.00 | 54.32 |
| ATOM | 360 | CA | ALA | A | 186 | 45.804 | 62.490 | 13.412 | 1.00 | 54.15 |
| ATOM | 361 | C | ALA | A | 186 | 46.606 | 61.383 | 12.737 | 1.00 | 58.05 |
| ATOM | 362 | O | ALA | A | 186 | 47.703 | 61.623 | 12.227 | 1.00 | 57.96 |
| ATOM | 363 | CB | ALA | A | 186 | 46.223 | 62.646 | 14.864 | 1.00 | 54.98 |
| ATOM | 364 | N | LYS | A | 187 | 46.071 | 60.167 | 12.751 | 1.00 | 54.15 |
| ATOM | 365 | CA | LYS | A | 187 | 46.772 | 59.030 | 12.158 | 1.00 | 53.77 |
| ATOM | 366 | C | LYS | A | 187 | 46.495 | 58.887 | 10.666 | 1.00 | 56.84 |
| ATOM | 367 | O | LYS | A | 187 | 47.082 | 58.031 | 9.994 | 1.00 | 56.16 |
| ATOM | 368 | CB | LYS | A | 187 | 46.423 | 57.734 | 12.894 | 1.00 | 56.48 |
| ATOM | 369 | CG | LYS | A | 187 | 46.853 | 57.717 | 14.365 | 1.00 | 70.45 |
| ATOM | 370 | CD | LYS | A | 187 | 48.334 | 58.028 | 14.517 | 1.00 | 79.18 |
| ATOM | 371 | CE | LYS | A | 187 | 48.804 | 57.782 | 15.941 | 1.00 | 89.97 |
| ATOM | 372 | NZ | LYS | A | 187 | 49.940 | 58.671 | 16.312 | 1.00 | 98.59 |
| ATOM | 373 | N | ASP | A | 188 | 45.607 | 59.735 | 10.153 | 1.00 | 52.93 |
| ATOM | 374 | CA | ASP | A | 188 | 45.249 | 59.719 | 8.739 | 1.00 | 52.79 |
| ATOM | 375 | C | ASP | A | 188 | 44.488 | 58.450 | 8.384 | 1.00 | 55.44 |
| ATOM | 376 | O | ASP | A | 188 | 44.688 | 57.875 | 7.318 | 1.00 | 55.36 |
| ATOM | 377 | CB | ASP | A | 188 | 46.505 | 59.841 | 7.869 | 1.00 | 54.90 |
| ATOM | 378 | CG | ASP | A | 188 | 47.091 | 61.253 | 7.873 | 1.00 | 67.05 |
| ATOM | 379 | OD1 | ASP | A | 188 | 46.328 | 62.214 | 8.131 | 1.00 | 67.91 |
| ATOM | 380 | OD2 | ASP | A | 188 | 48.317 | 61.397 | 7.652 | 1.00 | 71.93 |
| ATOM | 381 | N | GLU | A | 189 | 43.609 | 58.019 | 9.285 | 1.00 | 50.65 |
| ATOM | 382 | CA | GLU | A | 189 | 42.837 | 56.793 | 9.081 | 1.00 | 49.89 |
| ATOM | 383 | C | GLU | A | 189 | 41.338 | 57.051 | 8.995 | 1.00 | 51.41 |
| ATOM | 384 | O | GLU | A | 189 | 40.533 | 56.175 | 9.302 | 1.00 | 50.14 |
| ATOM | 385 | CB | GLU | A | 189 | 43.117 | 55.801 | 10.213 | 1.00 | 51.27 |
| ATOM | 386 | CG | GLU | A | 189 | 44.582 | 55.682 | 10.580 | 1.00 | 61.97 |
| ATOM | 387 | CD | GLU | A | 189 | 45.141 | 54.312 | 10.283 | 1.00 | 84.11 |
| ATOM | 388 | OE1 | GLU | A | 189 | 45.930 | 53.800 | 11.104 | 1.00 | 82.29 |
| ATOM | 389 | OE2 | GLU | A | 189 | 44.783 | 53.739 | 9.233 | 1.00 | 78.76 |
| ATOM | 390 | N | VAL | A | 190 | 40.963 | 58.256 | 8.584 | 1.00 | 46.79 |
| ATOM | 391 | CA | VAL | A | 190 | 39.550 | 58.610 | 8.494 | 1.00 | 45.55 |
| ATOM | 392 | C | VAL | A | 190 | 38.809 | 57.873 | 7.373 | 1.00 | 47.96 |
| ATOM | 393 | O | VAL | A | 190 | 37.840 | 57.159 | 7.625 | 1.00 | 47.06 |
| ATOM | 394 | CB | VAL | A | 190 | 39.350 | 60.130 | 8.378 | 1.00 | 49.21 |
| ATOM | 395 | CG1 | VAL | A | 190 | 37.890 | 60.452 | 8.160 | 1.00 | 48.87 |
| ATOM | 396 | CG2 | VAL | A | 190 | 39.880 | 60.828 | 9.643 | 1.00 | 49.06 |
| ATOM | 397 | N | ALA | A | 191 | 39.273 | 58.039 | 6.142 | 1.00 | 45.20 |
| ATOM | 398 | CA | ALA | A | 191 | 38.654 | 57.363 | 5.004 | 1.00 | 45.44 |
| ATOM | 399 | C | ALA | A | 191 | 38.725 | 55.852 | 5.216 | 1.00 | 49.04 |
| ATOM | 400 | O | ALA | A | 191 | 37.766 | 55.123 | 4.929 | 1.00 | 47.69 |
| ATOM | 401 | CB | ALA | A | 191 | 39.349 | 57.749 | 3.711 | 1.00 | 46.41 |
| ATOM | 402 | N | HIS | A | 192 | 39.857 | 55.393 | 5.747 | 1.00 | 46.53 |
| ATOM | 403 | CA | HIS | A | 192 | 40.054 | 53.969 | 6.022 | 1.00 | 46.82 |
| ATOM | 404 | C | HIS | A | 192 | 39.008 | 53.419 | 6.991 | 1.00 | 46.73 |
| ATOM | 405 | O | HIS | A | 192 | 38.434 | 52.359 | 6.758 | 1.00 | 45.80 |
| ATOM | 406 | CB | HIS | A | 192 | 41.481 | 53.713 | 6.573 | 1.00 | 49.13 |
| ATOM | 407 | CG | HIS | A | 192 | 41.617 | 52.423 | 7.327 | 1.00 | 53.57 |
| ATOM | 408 | ND1 | HIS | A | 192 | 42.061 | 52.365 | 8.631 | 1.00 | 55.81 |
| ATOM | 409 | CD2 | HIS | A | 192 | 41.355 | 51.146 | 6.962 | 1.00 | 56.09 |
| ATOM | 410 | CE1 | HIS | A | 192 | 42.067 | 51.107 | 9.037 | 1.00 | 55.54 |
| ATOM | 411 | NE2 | HIS | A | 192 | 41.643 | 50.347 | 8.043 | 1.00 | 55.94 |
| ATOM | 412 | N | THR | A | 193 | 38.781 | 54.126 | 8.093 | 1.00 | 41.16 |
| ATOM | 413 | CA | THR | A | 193 | 37.813 | 53.682 | 9.077 | 1.00 | 40.29 |
| ATOM | 414 | C | THR | A | 193 | 36.404 | 53.581 | 8.492 | 1.00 | 43.05 |
| ATOM | 415 | O | THR | A | 193 | 35.705 | 52.587 | 8.697 | 1.00 | 41.02 |
| ATOM | 416 | CB | THR | A | 193 | 37.769 | 54.616 | 10.305 | 1.00 | 49.18 |
| ATOM | 417 | OG1 | THR | A | 193 | 39.045 | 54.621 | 10.956 | 1.00 | 45.36 |
| ATOM | 418 | CG2 | THR | A | 193 | 36.714 | 54.139 | 11.286 | 1.00 | 49.09 |
| ATOM | 419 | N | LEU | A | 194 | 35.981 | 54.612 | 7.774 | 1.00 | 40.20 |
| ATOM | 420 | CA | LEU | A | 194 | 34.628 | 54.618 | 7.221 | 1.00 | 40.35 |
| ATOM | 421 | C | LEU | A | 194 | 34.393 | 53.547 | 6.164 | 1.00 | 42.08 |
| ATOM | 422 | O | LEU | A | 194 | 33.351 | 52.904 | 6.153 | 1.00 | 42.52 |
| ATOM | 423 | CB | LEU | A | 194 | 34.234 | 55.995 | 6.718 | 1.00 | 40.79 |
| ATOM | 424 | CG | LEU | A | 194 | 33.314 | 56.764 | 7.673 | 1.00 | 46.18 |
| ATOM | 425 | CD1 | LEU | A | 194 | 33.978 | 56.970 | 9.033 | 1.00 | 46.57 |
| ATOM | 426 | CD2 | LEU | A | 194 | 32.892 | 58.097 | 7.066 | 1.00 | 49.25 |

TABLE 2-continued

| | | | | | | | | | |
|---|---|---|---|---|---|---|---|---|---|
| ATOM | 427 | N | THR | A | 195 | 35.387 | 53.341 | 5.310 | 1.00 | 37.92 |
| ATOM | 428 | CA | THR | A | 195 | 35.336 | 52.316 | 4.263 | 1.00 | 37.52 |
| ATOM | 429 | C | THR | A | 195 | 35.230 | 50.935 | 4.900 | 1.00 | 40.35 |
| ATOM | 430 | O | THR | A | 195 | 34.361 | 50.129 | 4.536 | 1.00 | 38.60 |
| ATOM | 431 | CB | THR | A | 195 | 36.612 | 52.362 | 3.392 | 1.00 | 46.87 |
| ATOM | 432 | OG1 | THR | A | 195 | 36.604 | 53.549 | 2.591 | 1.00 | 48.87 |
| ATOM | 433 | CG2 | THR | A | 195 | 36.692 | 51.136 | 2.478 | 1.00 | 43.82 |
| ATOM | 434 | N | GLU | A | 196 | 36.112 | 50.670 | 5.862 | 1.00 | 37.18 |
| ATOM | 435 | CA | GLU | A | 196 | 36.102 | 49.393 | 6.579 | 1.00 | 38.40 |
| ATOM | 436 | C | GLU | A | 196 | 34.739 | 49.152 | 7.203 | 1.00 | 42.60 |
| ATOM | 437 | O | GLU | A | 196 | 34.178 | 48.057 | 7.106 | 1.00 | 42.17 |
| ATOM | 438 | CB | GLU | A | 196 | 37.152 | 49.406 | 7.697 | 1.00 | 40.26 |
| ATOM | 439 | CG | GLU | A | 196 | 36.554 | 49.140 | 9.102 | 1.00 | 54.56 |
| ATOM | 440 | CD | GLU | A | 196 | 37.369 | 49.761 | 10.230 | 1.00 | 78.58 |
| ATOM | 441 | OE1 | GLU | A | 196 | 36.863 | 49.805 | 11.379 | 1.00 | 70.46 |
| ATOM | 442 | OE2 | GLU | A | 196 | 38.518 | 50.187 | 9.970 | 1.00 | 74.99 |
| ATOM | 443 | N | SER | A | 197 | 34.239 | 50.160 | 7.908 | 1.00 | 40.14 |
| ATOM | 444 | CA | SER | A | 197 | 32.965 | 50.051 | 8.599 | 1.00 | 40.49 |
| ATOM | 445 | C | SER | A | 197 | 31.859 | 49.624 | 7.662 | 1.00 | 45.16 |
| ATOM | 446 | O | SER | A | 197 | 31.090 | 48.706 | 7.966 | 1.00 | 45.31 |
| ATOM | 447 | CB | SER | A | 197 | 32.595 | 51.379 | 9.257 | 1.00 | 44.50 |
| ATOM | 448 | OG | SER | A | 197 | 31.277 | 51.325 | 9.786 | 1.00 | 55.05 |
| ATOM | 449 | N | ARG | A | 198 | 31.765 | 50.306 | 6.530 | 1.00 | 40.98 |
| ATOM | 450 | CA | ARG | A | 198 | 30.734 | 50.011 | 5.548 | 1.00 | 41.20 |
| ATOM | 451 | C | ARG | A | 198 | 30.783 | 48.558 | 5.095 | 1.00 | 44.29 |
| ATOM | 452 | O | ARG | A | 198 | 29.752 | 47.887 | 4.995 | 1.00 | 44.16 |
| ATOM | 453 | CB | ARG | A | 198 | 30.873 | 50.936 | 4.346 | 1.00 | 41.67 |
| ATOM | 454 | CG | ARG | A | 198 | 29.917 | 52.125 | 4.371 | 1.00 | 56.17 |
| ATOM | 455 | CD | ARG | A | 198 | 30.618 | 53.416 | 3.965 | 1.00 | 72.34 |
| ATOM | 456 | NE | ARG | A | 198 | 31.212 | 53.327 | 2.632 | 1.00 | 83.81 |
| ATOM | 457 | CZ | ARG | A | 198 | 32.007 | 54.253 | 2.106 | 1.00 | 100.90 |
| ATOM | 458 | NH1 | ARG | A | 198 | 32.307 | 55.345 | 2.799 | 1.00 | 88.26 |
| ATOM | 459 | NH2 | ARG | A | 198 | 32.507 | 54.085 | 0.888 | 1.00 | 90.28 |
| ATOM | 460 | N | VAL | A | 199 | 31.986 | 48.083 | 4.810 | 1.00 | 40.54 |
| ATOM | 461 | CA | VAL | A | 199 | 32.173 | 46.720 | 4.349 | 1.00 | 39.33 |
| ATOM | 462 | C | VAL | A | 199 | 31.678 | 45.706 | 5.381 | 1.00 | 43.11 |
| ATOM | 463 | O | VAL | A | 199 | 30.879 | 44.834 | 5.062 | 1.00 | 41.77 |
| ATOM | 464 | CB | VAL | A | 199 | 33.669 | 46.444 | 4.001 | 1.00 | 42.63 |
| ATOM | 465 | CG1 | VAL | A | 199 | 33.924 | 44.951 | 3.836 | 1.00 | 42.13 |
| ATOM | 466 | CG2 | VAL | A | 199 | 34.081 | 47.219 | 2.745 | 1.00 | 42.42 |
| ATOM | 467 | N | LEU | A | 200 | 32.156 | 45.822 | 6.620 | 1.00 | 40.97 |
| ATOM | 468 | CA | LEU | A | 200 | 31.777 | 44.866 | 7.670 | 1.00 | 41.12 |
| ATOM | 469 | C | LEU | A | 200 | 30.301 | 44.948 | 8.038 | 1.00 | 45.45 |
| ATOM | 470 | O | LEU | A | 200 | 29.736 | 44.000 | 8.584 | 1.00 | 45.00 |
| ATOM | 471 | CB | LEU | A | 200 | 32.636 | 45.059 | 8.926 | 1.00 | 40.96 |
| ATOM | 472 | CG | LEU | A | 200 | 34.057 | 44.493 | 8.886 | 1.00 | 45.51 |
| ATOM | 473 | CD1 | LEU | A | 200 | 34.165 | 43.319 | 7.916 | 1.00 | 45.52 |
| ATOM | 474 | CD2 | LEU | A | 200 | 35.076 | 45.578 | 8.555 | 1.00 | 48.09 |
| ATOM | 475 | N | LYS | A | 201 | 29.690 | 46.088 | 7.750 | 1.00 | 43.58 |
| ATOM | 476 | CA | LYS | A | 201 | 28.292 | 46.317 | 8.078 | 1.00 | 43.73 |
| ATOM | 477 | C | LYS | A | 201 | 27.366 | 45.668 | 7.074 | 1.00 | 47.34 |
| ATOM | 478 | O | LYS | A | 201 | 26.372 | 45.054 | 7.445 | 1.00 | 47.63 |
| ATOM | 479 | CB | LYS | A | 201 | 28.000 | 47.823 | 8.119 | 1.00 | 46.71 |
| ATOM | 480 | CG | LYS | A | 201 | 27.946 | 48.423 | 9.516 | 1.00 | 60.10 |
| ATOM | 481 | CD | LYS | A | 201 | 27.981 | 49.945 | 9.460 | 1.00 | 69.78 |
| ATOM | 482 | CE | LYS | A | 201 | 26.582 | 50.529 | 9.503 | 1.00 | 78.71 |
| ATOM | 483 | NZ | LYS | A | 201 | 25.692 | 49.761 | 10.423 | 1.00 | 86.65 |
| ATOM | 484 | N | ASN | A | 202 | 27.693 | 45.833 | 5.796 | 1.00 | 42.21 |
| ATOM | 485 | CA | ASN | A | 202 | 26.859 | 45.366 | 4.699 | 1.00 | 40.93 |
| ATOM | 486 | C | ASN | A | 202 | 27.289 | 44.058 | 4.047 | 1.00 | 41.79 |
| ATOM | 487 | O | ASN | A | 202 | 26.997 | 43.827 | 2.878 | 1.00 | 42.65 |
| ATOM | 488 | CB | ASN | A | 202 | 26.764 | 46.442 | 3.631 | 1.00 | 42.30 |
| ATOM | 489 | CG | ASN | A | 202 | 25.388 | 47.069 | 3.561 | 1.00 | 74.14 |
| ATOM | 490 | OD1 | ASN | A | 202 | 24.991 | 47.819 | 4.456 | 1.00 | 67.81 |
| ATOM | 491 | ND2 | ASN | A | 202 | 24.635 | 46.735 | 2.514 | 1.00 | 68.69 |
| ATOM | 492 | N | THR | A | 203 | 27.994 | 43.223 | 4.792 | 1.00 | 33.93 |
| ATOM | 493 | CA | THR | A | 203 | 28.425 | 41.925 | 4.284 | 1.00 | 32.01 |
| ATOM | 494 | C | THR | A | 203 | 28.072 | 40.898 | 5.325 | 1.00 | 34.47 |
| ATOM | 495 | O | THR | A | 203 | 28.000 | 41.215 | 6.525 | 1.00 | 35.05 |
| ATOM | 496 | CB | THR | A | 203 | 29.939 | 41.889 | 4.103 | 1.00 | 38.09 |
| ATOM | 497 | OG1 | THR | A | 203 | 30.558 | 42.407 | 5.283 | 1.00 | 33.24 |
| ATOM | 498 | CG2 | THR | A | 203 | 30.349 | 42.729 | 2.921 | 1.00 | 36.27 |
| ATOM | 499 | N | ARG | A | 204 | 27.858 | 39.666 | 4.877 | 1.00 | 28.53 |
| ATOM | 500 | CA | ARG | A | 204 | 27.536 | 38.563 | 5.761 | 1.00 | 28.30 |
| ATOM | 501 | C | ARG | A | 204 | 28.211 | 37.321 | 5.207 | 1.00 | 28.75 |
| ATOM | 502 | O | ARG | A | 204 | 27.858 | 36.835 | 4.124 | 1.00 | 29.00 |
| ATOM | 503 | CB | ARG | A | 204 | 26.022 | 38.335 | 5.824 | 1.00 | 33.73 |
| ATOM | 504 | CG | ARG | A | 204 | 25.610 | 36.862 | 5.845 | 1.00 | 49.96 |
| ATOM | 505 | CD | ARG | A | 204 | 24.099 | 36.698 | 6.024 | 1.00 | 62.83 |
| ATOM | 506 | NE | ARG | A | 204 | 23.622 | 37.358 | 7.235 | 1.00 | 75.75 |

TABLE 2-continued

| | | | | | | | | | |
|---|---|---|---|---|---|---|---|---|---|
| ATOM | 507 | CZ | ARG | A | 204 | 23.304 | 36.723 | 8.360 | 1.00 | 89.97 |
| ATOM | 508 | NH1 | ARG | A | 204 | 23.403 | 35.400 | 8.429 | 1.00 | 74.79 |
| ATOM | 509 | NH2 | ARG | A | 204 | 22.887 | 37.411 | 9.417 | 1.00 | 77.06 |
| ATOM | 510 | N | HIS | A | 205 | 29.188 | 36.820 | 5.940 | 1.00 | 23.27 |
| ATOM | 511 | CA | HIS | A | 205 | 29.889 | 35.615 | 5.513 | 1.00 | 21.14 |
| ATOM | 512 | C | HIS | A | 205 | 30.377 | 34.879 | 6.753 | 1.00 | 23.21 |
| ATOM | 513 | O | HIS | A | 205 | 30.773 | 35.505 | 7.720 | 1.00 | 22.25 |
| ATOM | 514 | CB | HIS | A | 205 | 31.094 | 36.001 | 4.629 | 1.00 | 21.41 |
| ATOM | 515 | CG | HIS | A | 205 | 31.780 | 34.819 | 4.016 | 1.00 | 23.10 |
| ATOM | 516 | ND1 | HIS | A | 205 | 31.430 | 34.326 | 2.779 | 1.00 | 24.06 |
| ATOM | 517 | CD2 | HIS | A | 205 | 32.732 | 33.985 | 4.500 | 1.00 | 23.62 |
| ATOM | 518 | CE1 | HIS | A | 205 | 32.167 | 33.261 | 2.503 | 1.00 | 22.30 |
| ATOM | 519 | NE2 | HIS | A | 205 | 32.968 | 33.035 | 3.528 | 1.00 | 23.98 |
| ATOM | 520 | N | PRO | A | 206 | 30.407 | 33.550 | 6.691 | 1.00 | 21.36 |
| ATOM | 521 | CA | PRO | A | 206 | 30.875 | 32.742 | 7.808 | 1.00 | 21.09 |
| ATOM | 522 | C | PRO | A | 206 | 32.229 | 33.125 | 8.381 | 1.00 | 22.63 |
| ATOM | 523 | O | PRO | A | 206 | 32.452 | 33.025 | 9.595 | 1.00 | 22.37 |
| ATOM | 524 | CB | PRO | A | 206 | 30.921 | 31.305 | 7.232 | 1.00 | 23.23 |
| ATOM | 525 | CG | PRO | A | 206 | 30.090 | 31.309 | 6.084 | 1.00 | 28.04 |
| ATOM | 526 | CD | PRO | A | 206 | 29.946 | 32.738 | 5.562 | 1.00 | 22.95 |
| ATOM | 527 | N | PHE | A | 207 | 33.140 | 33.575 | 7.522 | 1.00 | 19.03 |
| ATOM | 528 | CA | PHE | A | 207 | 34.468 | 33.903 | 7.963 | 1.00 | 18.41 |
| ATOM | 529 | C | PHE | A | 207 | 34.828 | 35.394 | 8.089 | 1.00 | 21.83 |
| ATOM | 530 | O | PHE | A | 207 | 36.001 | 35.754 | 8.233 | 1.00 | 20.12 |
| ATOM | 531 | CB | PHE | A | 207 | 35.512 | 33.107 | 7.148 | 1.00 | 19.00 |
| ATOM | 532 | CG | PHE | A | 207 | 35.194 | 31.640 | 7.052 | 1.00 | 18.96 |
| ATOM | 533 | CD1 | PHE | A | 207 | 35.034 | 30.881 | 8.201 | 1.00 | 19.63 |
| ATOM | 534 | CD2 | PHE | A | 207 | 34.914 | 31.056 | 5.815 | 1.00 | 19.28 |
| ATOM | 535 | CE1 | PHE | A | 207 | 34.698 | 29.524 | 8.131 | 1.00 | 19.76 |
| ATOM | 536 | CE2 | PHE | A | 207 | 34.553 | 29.697 | 5.726 | 1.00 | 20.62 |
| ATOM | 537 | CZ | PHE | A | 207 | 34.451 | 28.937 | 6.871 | 1.00 | 18.73 |
| ATOM | 538 | N | LEU | A | 208 | 33.820 | 36.251 | 8.017 | 1.00 | 20.30 |
| ATOM | 539 | CA | LEU | A | 208 | 34.023 | 37.680 | 8.169 | 1.00 | 20.52 |
| ATOM | 540 | C | LEU | A | 208 | 33.328 | 38.098 | 9.471 | 1.00 | 22.69 |
| ATOM | 541 | O | LEU | A | 208 | 32.183 | 37.701 | 9.716 | 1.00 | 21.75 |
| ATOM | 542 | CB | LEU | A | 208 | 33.376 | 38.426 | 6.997 | 1.00 | 22.02 |
| ATOM | 543 | CG | LEU | A | 208 | 34.112 | 38.465 | 5.674 | 1.00 | 29.30 |
| ATOM | 544 | CD1 | LEU | A | 208 | 33.253 | 39.222 | 4.627 | 1.00 | 30.59 |
| ATOM | 545 | CD2 | LEU | A | 208 | 35.453 | 39.183 | 5.867 | 1.00 | 33.47 |
| ATOM | 546 | N | THR | A | 209 | 34.025 | 38.885 | 10.289 | 1.00 | 20.41 |
| ATOM | 547 | CA | THR | A | 209 | 33.457 | 39.395 | 11.553 | 1.00 | 21.25 |
| ATOM | 548 | C | THR | A | 209 | 32.296 | 40.304 | 11.238 | 1.00 | 28.31 |
| ATOM | 549 | O | THR | A | 209 | 32.416 | 41.192 | 10.405 | 1.00 | 28.91 |
| ATOM | 550 | CB | THR | A | 209 | 34.511 | 40.159 | 12.341 | 1.00 | 27.85 |
| ATOM | 551 | OG1 | THR | A | 209 | 35.527 | 39.231 | 12.767 | 1.00 | 27.75 |
| ATOM | 552 | CG2 | THR | A | 209 | 33.875 | 40.815 | 13.568 | 1.00 | 31.06 |
| ATOM | 553 | N | SER | A | 210 | 31.143 | 40.034 | 11.846 | 1.00 | 26.45 |
| ATOM | 554 | CA | SER | A | 210 | 29.976 | 40.845 | 11.575 | 1.00 | 28.21 |
| ATOM | 555 | C | SER | A | 210 | 29.912 | 42.065 | 12.467 | 1.00 | 34.77 |
| ATOM | 556 | O | SER | A | 210 | 30.171 | 41.983 | 13.675 | 1.00 | 33.21 |
| ATOM | 557 | CB | SER | A | 210 | 28.696 | 40.024 | 11.699 | 1.00 | 31.90 |
| ATOM | 558 | OG | SER | A | 210 | 28.648 | 39.329 | 12.924 | 1.00 | 46.37 |
| ATOM | 559 | N | LEU | A | 211 | 29.593 | 43.204 | 11.861 | 1.00 | 33.80 |
| ATOM | 560 | CA | LEU | A | 211 | 29.461 | 44.482 | 12.586 | 1.00 | 35.22 |
| ATOM | 561 | C | LEU | A | 211 | 27.967 | 44.727 | 12.754 | 1.00 | 40.72 |
| ATOM | 562 | O | LEU | A | 211 | 27.251 | 44.874 | 11.762 | 1.00 | 40.34 |
| ATOM | 563 | CB | LEU | A | 211 | 30.115 | 45.615 | 11.767 | 1.00 | 35.55 |
| ATOM | 564 | CG | LEU | A | 211 | 29.924 | 47.073 | 12.191 | 1.00 | 41.00 |
| ATOM | 565 | CD1 | LEU | A | 211 | 29.490 | 47.152 | 13.640 | 1.00 | 41.06 |
| ATOM | 566 | CD2 | LEU | A | 211 | 31.231 | 47.858 | 11.957 | 1.00 | 43.10 |
| ATOM | 567 | N | LYS | A | 212 | 27.486 | 44.687 | 14.004 | 1.00 | 37.52 |
| ATOM | 568 | CA | LYS | A | 212 | 26.045 | 44.787 | 14.291 | 1.00 | 37.69 |
| ATOM | 569 | C | LYS | A | 212 | 25.500 | 46.208 | 14.504 | 1.00 | 42.49 |
| ATOM | 570 | O | LYS | A | 212 | 24.413 | 46.546 | 14.019 | 1.00 | 43.34 |
| ATOM | 571 | CB | LYS | A | 212 | 25.665 | 43.890 | 15.463 | 1.00 | 40.14 |
| ATOM | 572 | CG | LYS | A | 212 | 24.172 | 43.890 | 15.780 | 1.00 | 53.82 |
| ATOM | 573 | CD | LYS | A | 212 | 23.696 | 42.512 | 16.211 | 1.00 | 61.64 |
| ATOM | 574 | CE | LYS | A | 212 | 22.232 | 42.538 | 16.633 | 1.00 | 69.79 |
| ATOM | 575 | NZ | LYS | A | 212 | 21.393 | 41.610 | 15.817 | 1.00 | 77.87 |
| ATOM | 576 | N | TYR | A | 213 | 26.227 | 47.016 | 15.261 | 1.00 | 37.95 |
| ATOM | 577 | CA | TYR | A | 213 | 25.824 | 48.395 | 15.495 | 1.00 | 37.24 |
| ATOM | 578 | C | TYR | A | 213 | 27.030 | 49.311 | 15.397 | 1.00 | 41.96 |
| ATOM | 579 | O | TYR | A | 213 | 28.165 | 48.910 | 15.660 | 1.00 | 41.00 |
| ATOM | 580 | CB | TYR | A | 213 | 25.162 | 48.572 | 16.872 | 1.00 | 37.77 |
| ATOM | 581 | CG | TYR | A | 213 | 24.100 | 47.555 | 17.212 | 1.00 | 38.38 |
| ATOM | 582 | CD1 | TYR | A | 213 | 22.922 | 47.475 | 16.485 | 1.00 | 40.50 |
| ATOM | 583 | CD2 | TYR | A | 213 | 24.231 | 46.745 | 18.329 | 1.00 | 38.50 |
| ATOM | 584 | CE1 | TYR | A | 213 | 21.939 | 46.566 | 16.822 | 1.00 | 41.41 |
| ATOM | 585 | CE2 | TYR | A | 213 | 23.266 | 45.842 | 18.673 | 1.00 | 39.40 |
| ATOM | 586 | CZ | TYR | A | 213 | 22.111 | 45.759 | 17.928 | 1.00 | 48.51 |

TABLE 2-continued

| | | | | | | | | | |
|---|---|---|---|---|---|---|---|---|---|
| ATOM | 587 | OH | TYR | A | 213 | 21.142 | 44.849 | 18.283 | 1.00 | 50.94 |
| ATOM | 588 | N | SER | A | 214 | 26.764 | 50.559 | 15.034 | 1.00 | 38.98 |
| ATOM | 589 | CA | SER | A | 214 | 27.779 | 51.586 | 14.932 | 1.00 | 39.88 |
| ATOM | 590 | C | SER | A | 214 | 27.123 | 52.832 | 15.533 | 1.00 | 47.24 |
| ATOM | 591 | O | SER | A | 214 | 25.978 | 53.137 | 15.218 | 1.00 | 46.64 |
| ATOM | 592 | CB | SER | A | 214 | 28.117 | 51.842 | 13.455 | 1.00 | 44.60 |
| ATOM | 593 | OG | SER | A | 214 | 29.302 | 52.614 | 13.325 | 1.00 | 56.95 |
| ATOM | 594 | N | PHE | A | 215 | 27.796 | 53.490 | 16.466 | 1.00 | 46.55 |
| ATOM | 595 | CA | PHE | A | 215 | 27.207 | 54.676 | 17.078 | 1.00 | 47.62 |
| ATOM | 596 | C | PHE | A | 215 | 28.166 | 55.793 | 17.369 | 1.00 | 55.78 |
| ATOM | 597 | O | PHE | A | 215 | 29.389 | 55.648 | 17.227 | 1.00 | 55.62 |
| ATOM | 598 | CB | PHE | A | 215 | 26.293 | 54.351 | 18.258 | 1.00 | 49.30 |
| ATOM | 599 | CG | PHE | A | 215 | 27.013 | 53.834 | 19.459 | 1.00 | 50.94 |
| ATOM | 600 | CD1 | PHE | A | 215 | 27.091 | 52.476 | 19.702 | 1.00 | 53.77 |
| ATOM | 601 | CD2 | PHE | A | 215 | 27.596 | 54.705 | 20.361 | 1.00 | 53.21 |
| ATOM | 602 | CE1 | PHE | A | 215 | 27.743 | 51.999 | 20.813 | 1.00 | 54.62 |
| ATOM | 603 | CE2 | PHE | A | 215 | 28.258 | 54.227 | 21.476 | 1.00 | 55.97 |
| ATOM | 604 | CZ | PHE | A | 215 | 28.331 | 52.879 | 21.700 | 1.00 | 54.02 |
| ATOM | 605 | N | GLN | A | 216 | 27.598 | 56.927 | 17.748 | 1.00 | 55.38 |
| ATOM | 606 | CA | GLN | A | 216 | 28.328 | 58.162 | 17.899 | 1.00 | 56.83 |
| ATOM | 607 | C | GLN | A | 216 | 28.484 | 58.695 | 19.320 | 1.00 | 62.63 |
| ATOM | 608 | O | GLN | A | 216 | 27.619 | 58.505 | 20.177 | 1.00 | 62.18 |
| ATOM | 609 | CB | GLN | A | 216 | 27.659 | 59.232 | 17.029 | 1.00 | 58.49 |
| ATOM | 610 | CG | GLN | A | 216 | 26.382 | 58.741 | 16.289 | 1.00 | 80.96 |
| ATOM | 611 | CD | GLN | A | 216 | 25.244 | 58.313 | 17.238 | 1.00 | 104.60 |
| ATOM | 612 | OE1 | GLN | A | 216 | 25.370 | 58.402 | 18.462 | 1.00 | 101.24 |
| ATOM | 613 | NE2 | GLN | A | 216 | 24.161 | 57.795 | 16.665 | 1.00 | 97.25 |
| ATOM | 614 | N | THR | A | 217 | 29.582 | 59.417 | 19.527 | 1.00 | 61.13 |
| ATOM | 615 | CA | THR | A | 217 | 29.886 | 60.078 | 20.793 | 1.00 | 61.96 |
| ATOM | 616 | C | THR | A | 217 | 30.846 | 61.231 | 20.501 | 1.00 | 67.55 |
| ATOM | 617 | O | THR | A | 217 | 31.546 | 61.216 | 19.487 | 1.00 | 67.56 |
| ATOM | 618 | CB | THR | A | 217 | 30.528 | 59.121 | 21.817 | 1.00 | 71.98 |
| ATOM | 619 | OG1 | THR | A | 217 | 31.230 | 58.077 | 21.131 | 1.00 | 74.31 |
| ATOM | 620 | CG2 | THR | A | 217 | 29.465 | 58.513 | 22.711 | 1.00 | 70.27 |
| ATOM | 621 | N | LYS | A | 218 | 30.845 | 62.233 | 21.378 | 1.00 | 64.97 |
| ATOM | 622 | CA | LYS | A | 218 | 31.666 | 63.442 | 21.220 | 1.00 | 65.08 |
| ATOM | 623 | C | LYS | A | 218 | 33.045 | 63.277 | 20.565 | 1.00 | 68.49 |
| ATOM | 624 | O | LYS | A | 218 | 33.406 | 64.052 | 19.676 | 1.00 | 68.49 |
| ATOM | 625 | CB | LYS | A | 218 | 31.788 | 64.193 | 22.551 | 1.00 | 68.03 |
| ATOM | 626 | CG | LYS | A | 218 | 30.482 | 64.822 | 23.032 | 1.00 | 82.23 |
| ATOM | 627 | CD | LYS | A | 218 | 30.703 | 66.236 | 23.565 | 1.00 | 90.86 |
| ATOM | 628 | CE | LYS | A | 218 | 29.681 | 66.589 | 24.643 | 1.00 | 98.44 |
| ATOM | 629 | NZ | LYS | A | 218 | 29.849 | 67.983 | 25.142 | 1.00 | 105.38 |
| ATOM | 630 | N | ASP | A | 219 | 33.813 | 62.280 | 20.999 | 1.00 | 64.06 |
| ATOM | 631 | CA | ASP | A | 219 | 35.154 | 62.068 | 20.437 | 1.00 | 63.24 |
| ATOM | 632 | C | ASP | A | 219 | 35.555 | 60.599 | 20.289 | 1.00 | 64.78 |
| ATOM | 633 | O | ASP | A | 219 | 36.744 | 60.279 | 20.212 | 1.00 | 64.42 |
| ATOM | 634 | CB | ASP | A | 219 | 36.205 | 62.815 | 21.258 | 1.00 | 65.39 |
| ATOM | 635 | CG | ASP | A | 219 | 35.843 | 62.899 | 22.727 | 1.00 | 77.64 |
| ATOM | 636 | OD1 | ASP | A | 219 | 34.809 | 62.309 | 23.120 | 1.00 | 78.43 |
| ATOM | 637 | OD2 | ASP | A | 219 | 36.583 | 63.562 | 23.488 | 1.00 | 83.95 |
| ATOM | 638 | N | ARG | A | 220 | 34.567 | 59.713 | 20.231 | 1.00 | 59.41 |
| ATOM | 639 | CA | ARG | A | 220 | 34.843 | 58.287 | 20.086 | 1.00 | 58.09 |
| ATOM | 640 | C | ARG | A | 220 | 33.949 | 57.628 | 19.039 | 1.00 | 59.11 |
| ATOM | 641 | O | ARG | A | 220 | 32.779 | 57.991 | 18.878 | 1.00 | 58.21 |
| ATOM | 642 | CB | ARG | A | 220 | 34.691 | 57.568 | 21.433 | 1.00 | 58.38 |
| ATOM | 643 | CG | ARG | A | 220 | 35.369 | 58.280 | 22.608 | 1.00 | 68.86 |
| ATOM | 644 | CD | ARG | A | 220 | 36.746 | 57.689 | 22.902 | 1.00 | 79.81 |
| ATOM | 645 | NE | ARG | A | 220 | 37.282 | 58.151 | 24.183 | 1.00 | 90.92 |
| ATOM | 646 | CZ | ARG | A | 220 | 37.564 | 57.352 | 25.211 | 1.00 | 106.59 |
| ATOM | 647 | NH1 | ARG | A | 220 | 37.356 | 56.043 | 25.118 | 1.00 | 92.96 |
| ATOM | 648 | NH2 | ARG | A | 220 | 38.047 | 57.863 | 26.339 | 1.00 | 94.08 |
| ATOM | 649 | N | LEU | A | 221 | 34.509 | 56.648 | 18.336 | 1.00 | 53.37 |
| ATOM | 650 | CA | LEU | A | 221 | 33.759 | 55.893 | 17.337 | 1.00 | 51.97 |
| ATOM | 651 | C | LEU | A | 221 | 33.542 | 54.484 | 17.883 | 1.00 | 51.52 |
| ATOM | 652 | O | LEU | A | 221 | 34.506 | 53.783 | 18.187 | 1.00 | 51.66 |
| ATOM | 653 | CB | LEU | A | 221 | 34.536 | 55.832 | 16.018 | 1.00 | 52.24 |
| ATOM | 654 | CG | LEU | A | 221 | 33.695 | 55.988 | 14.752 | 1.00 | 57.25 |
| ATOM | 655 | CD1 | LEU | A | 221 | 33.029 | 57.360 | 14.732 | 1.00 | 57.61 |
| ATOM | 656 | CD2 | LEU | A | 221 | 34.552 | 55.781 | 13.511 | 1.00 | 59.61 |
| ATOM | 657 | N | CYS | A | 222 | 32.276 | 54.097 | 18.039 | 1.00 | 44.68 |
| ATOM | 658 | CA | CYS | A | 222 | 31.923 | 52.787 | 18.595 | 1.00 | 43.77 |
| ATOM | 659 | C | CYS | A | 222 | 31.340 | 51.787 | 17.585 | 1.00 | 42.42 |
| ATOM | 660 | O | CYS | A | 222 | 30.351 | 52.067 | 16.901 | 1.00 | 40.76 |
| ATOM | 661 | CB | CYS | A | 222 | 30.979 | 52.951 | 19.776 | 1.00 | 44.77 |
| ATOM | 662 | SG | CYS | A | 222 | 31.569 | 54.176 | 20.987 | 1.00 | 49.19 |
| ATOM | 663 | N | PHE | A | 223 | 31.932 | 50.596 | 17.551 | 1.00 | 36.24 |
| ATOM | 664 | CA | PHE | A | 223 | 31.499 | 49.529 | 16.651 | 1.00 | 33.73 |
| ATOM | 665 | C | PHE | A | 223 | 31.255 | 48.271 | 17.446 | 1.00 | 34.05 |
| ATOM | 666 | O | PHE | A | 223 | 32.176 | 47.733 | 18.052 | 1.00 | 32.89 |

TABLE 2-continued

| | | | | | | | | | |
|---|---|---|---|---|---|---|---|---|---|
| ATOM | 667 | CB | PHE | A | 223 | 32.569 | 49.262 | 15.596 | 1.00 | 35.79 |
| ATOM | 668 | CG | PHE | A | 223 | 32.936 | 50.474 | 14.789 | 1.00 | 38.06 |
| ATOM | 669 | CD1 | PHE | A | 223 | 32.071 | 50.968 | 13.825 | 1.00 | 41.37 |
| ATOM | 670 | CD2 | PHE | A | 223 | 34.116 | 51.157 | 15.039 | 1.00 | 40.99 |
| ATOM | 671 | CE1 | PHE | A | 223 | 32.399 | 52.092 | 13.097 | 1.00 | 42.41 |
| ATOM | 672 | CE2 | PHE | A | 223 | 34.445 | 52.288 | 14.314 | 1.00 | 44.29 |
| ATOM | 673 | CZ | PHE | A | 223 | 33.592 | 52.750 | 13.341 | 1.00 | 42.07 |
| ATOM | 674 | N | VAL | A | 224 | 30.010 | 47.818 | 17.455 | 1.00 | 28.45 |
| ATOM | 675 | CA | VAL | A | 224 | 29.631 | 46.619 | 18.179 | 1.00 | 28.53 |
| ATOM | 676 | C | VAL | A | 224 | 29.733 | 45.451 | 17.219 | 1.00 | 32.84 |
| ATOM | 677 | O | VAL | A | 224 | 28.959 | 45.346 | 16.287 | 1.00 | 32.03 |
| ATOM | 678 | CB | VAL | A | 224 | 28.216 | 46.736 | 18.728 | 1.00 | 32.61 |
| ATOM | 679 | CG1 | VAL | A | 224 | 27.858 | 45.522 | 19.568 | 1.00 | 32.49 |
| ATOM | 680 | CG2 | VAL | A | 224 | 28.087 | 48.019 | 19.554 | 1.00 | 32.14 |
| ATOM | 681 | N | MET | A | 225 | 30.728 | 44.599 | 17.433 | 1.00 | 29.93 |
| ATOM | 682 | CA | MET | A | 225 | 30.979 | 43.489 | 16.516 | 1.00 | 31.21 |
| ATOM | 683 | C | MET | A | 225 | 30.788 | 42.132 | 17.194 | 1.00 | 33.15 |
| ATOM | 684 | O | MET | A | 225 | 30.808 | 42.035 | 18.416 | 1.00 | 30.59 |
| ATOM | 685 | CB | MET | A | 225 | 32.396 | 43.631 | 15.966 | 1.00 | 35.04 |
| ATOM | 686 | CG | MET | A | 225 | 32.612 | 44.933 | 15.204 | 1.00 | 41.42 |
| ATOM | 687 | SD | MET | A | 225 | 34.305 | 45.500 | 15.283 | 1.00 | 48.61 |
| ATOM | 688 | CE | MET | A | 225 | 35.012 | 44.618 | 13.856 | 1.00 | 45.47 |
| ATOM | 689 | N | GLU | A | 226 | 30.619 | 41.072 | 16.407 | 1.00 | 29.08 |
| ATOM | 690 | CA | GLU | A | 226 | 30.428 | 39.767 | 17.010 | 1.00 | 28.72 |
| ATOM | 691 | C | GLU | A | 226 | 31.689 | 39.426 | 17.848 | 1.00 | 30.26 |
| ATOM | 692 | O | GLU | A | 226 | 32.771 | 39.891 | 17.540 | 1.00 | 29.47 |
| ATOM | 693 | CB | GLU | A | 226 | 30.111 | 38.696 | 15.933 | 1.00 | 31.09 |
| ATOM | 694 | CG | GLU | A | 226 | 31.252 | 37.826 | 15.540 | 1.00 | 40.43 |
| ATOM | 695 | CD | GLU | A | 226 | 30.901 | 36.911 | 14.352 | 1.00 | 43.06 |
| ATOM | 696 | OE1 | GLU | A | 226 | 30.904 | 37.396 | 13.195 | 1.00 | 27.54 |
| ATOM | 697 | OE2 | GLU | A | 226 | 30.615 | 35.711 | 14.577 | 1.00 | 34.34 |
| ATOM | 698 | N | TYR | A | 227 | 31.492 | 38.762 | 18.990 | 1.00 | 28.82 |
| ATOM | 699 | CA | TYR | A | 227 | 32.599 | 38.417 | 19.902 | 1.00 | 27.94 |
| ATOM | 700 | C | TYR | A | 227 | 33.269 | 37.108 | 19.459 | 1.00 | 31.28 |
| ATOM | 701 | O | TYR | A | 227 | 32.612 | 36.103 | 19.346 | 1.00 | 32.92 |
| ATOM | 702 | CB | TYR | A | 227 | 32.064 | 38.254 | 21.323 | 1.00 | 28.19 |
| ATOM | 703 | CG | TYR | A | 227 | 33.123 | 37.867 | 22.342 | 1.00 | 28.76 |
| ATOM | 704 | CD1 | TYR | A | 227 | 34.284 | 38.617 | 22.488 | 1.00 | 29.75 |
| ATOM | 705 | CD2 | TYR | A | 227 | 32.972 | 36.732 | 23.127 | 1.00 | 29.75 |
| ATOM | 706 | CE1 | TYR | A | 227 | 35.276 | 38.238 | 23.407 | 1.00 | 30.28 |
| ATOM | 707 | CE2 | TYR | A | 227 | 33.924 | 36.376 | 24.063 | 1.00 | 30.48 |
| ATOM | 708 | CZ | TYR | A | 227 | 35.066 | 37.133 | 24.201 | 1.00 | 32.81 |
| ATOM | 709 | OH | TYR | A | 227 | 36.038 | 36.738 | 25.095 | 1.00 | 32.43 |
| ATOM | 710 | N | VAL | A | 228 | 34.575 | 37.158 | 19.206 | 1.00 | 27.19 |
| ATOM | 711 | CA | VAL | A | 228 | 35.343 | 35.988 | 18.740 | 1.00 | 27.28 |
| ATOM | 712 | C | VAL | A | 228 | 36.441 | 35.726 | 19.778 | 1.00 | 27.50 |
| ATOM | 713 | O | VAL | A | 228 | 37.245 | 36.617 | 20.071 | 1.00 | 26.38 |
| ATOM | 714 | CB | VAL | A | 228 | 35.987 | 36.305 | 17.345 | 1.00 | 32.11 |
| ATOM | 715 | CG1 | VAL | A | 228 | 36.582 | 35.070 | 16.747 | 1.00 | 32.40 |
| ATOM | 716 | CG2 | VAL | A | 228 | 34.937 | 36.896 | 16.400 | 1.00 | 32.17 |
| ATOM | 717 | N | ASN | A | 229 | 36.448 | 34.532 | 20.383 | 1.00 | 25.89 |
| ATOM | 718 | CA | ASN | A | 229 | 37.332 | 34.291 | 21.512 | 1.00 | 26.07 |
| ATOM | 719 | C | ASN | A | 229 | 38.311 | 33.113 | 21.403 | 1.00 | 28.21 |
| ATOM | 720 | O | ASN | A | 229 | 38.835 | 32.621 | 22.428 | 1.00 | 25.91 |
| ATOM | 721 | CB | ASN | A | 229 | 36.492 | 34.164 | 22.801 | 1.00 | 27.56 |
| ATOM | 722 | CG | ASN | A | 229 | 35.728 | 32.838 | 22.880 | 1.00 | 39.97 |
| ATOM | 723 | OD1 | ASN | A | 229 | 35.381 | 32.246 | 21.860 | 1.00 | 30.20 |
| ATOM | 724 | ND2 | ASN | A | 229 | 35.479 | 32.365 | 24.106 | 1.00 | 31.31 |
| ATOM | 725 | N | GLY | A | 230 | 38.602 | 32.695 | 20.169 | 1.00 | 25.10 |
| ATOM | 726 | CA | GLY | A | 230 | 39.534 | 31.606 | 19.936 | 1.00 | 25.34 |
| ATOM | 727 | C | GLY | A | 230 | 40.964 | 32.079 | 19.840 | 1.00 | 25.64 |
| ATOM | 728 | O | GLY | A | 230 | 41.892 | 31.264 | 19.707 | 1.00 | 24.79 |
| ATOM | 729 | N | GLY | A | 231 | 41.160 | 33.389 | 19.919 | 1.00 | 24.47 |
| ATOM | 730 | CA | GLY | A | 231 | 42.504 | 33.954 | 19.938 | 1.00 | 25.11 |
| ATOM | 731 | C | GLY | A | 231 | 43.032 | 34.476 | 18.607 | 1.00 | 28.83 |
| ATOM | 732 | O | GLY | A | 231 | 42.639 | 34.000 | 17.537 | 1.00 | 28.08 |
| ATOM | 733 | N | GLU | A | 232 | 43.968 | 35.421 | 18.687 | 1.00 | 25.66 |
| ATOM | 734 | CA | GLU | A | 232 | 44.596 | 35.989 | 17.492 | 1.00 | 26.26 |
| ATOM | 735 | C | GLU | A | 232 | 45.535 | 34.973 | 16.824 | 1.00 | 27.20 |
| ATOM | 736 | O | GLU | A | 232 | 46.348 | 34.335 | 17.495 | 1.00 | 27.68 |
| ATOM | 737 | CB | GLU | A | 232 | 45.384 | 37.233 | 17.875 | 1.00 | 28.25 |
| ATOM | 738 | CG | GLU | A | 232 | 44.526 | 38.463 | 18.071 | 1.00 | 40.38 |
| ATOM | 739 | CD | GLU | A | 232 | 45.346 | 39.701 | 18.353 | 1.00 | 68.56 |
| ATOM | 740 | OE1 | GLU | A | 232 | 45.826 | 40.333 | 17.387 | 1.00 | 72.91 |
| ATOM | 741 | OE2 | GLU | A | 232 | 45.531 | 40.031 | 19.541 | 1.00 | 64.12 |
| ATOM | 742 | N | LEU | A | 233 | 45.444 | 34.817 | 15.499 | 1.00 | 22.76 |
| ATOM | 743 | CA | LEU | A | 233 | 46.347 | 33.869 | 14.832 | 1.00 | 22.81 |
| ATOM | 744 | C | LEU | A | 233 | 47.800 | 34.289 | 14.959 | 1.00 | 28.58 |
| ATOM | 745 | O | LEU | A | 233 | 48.693 | 33.449 | 14.994 | 1.00 | 28.59 |
| ATOM | 746 | CB | LEU | A | 233 | 45.959 | 33.660 | 13.346 | 1.00 | 23.09 |

TABLE 2-continued

| | | | | | | | | | |
|---|---|---|---|---|---|---|---|---|---|
| ATOM | 747 | CG | LEU | A | 233 | 44.968 | 32.499 | 13.143 | 1.00 | 30.23 |
| ATOM | 748 | CD1 | LEU | A | 233 | 44.626 | 32.366 | 11.675 | 1.00 | 31.50 |
| ATOM | 749 | CD2 | LEU | A | 233 | 45.536 | 31.165 | 13.683 | 1.00 | 32.01 |
| ATOM | 750 | N | PHE | A | 234 | 48.040 | 35.590 | 15.030 | 1.00 | 28.95 |
| ATOM | 751 | CA | PHE | A | 234 | 49.392 | 36.084 | 15.184 | 1.00 | 31.04 |
| ATOM | 752 | C | PHE | A | 234 | 49.990 | 35.468 | 16.454 | 1.00 | 35.21 |
| ATOM | 753 | O | PHE | A | 234 | 51.119 | 34.998 | 16.452 | 1.00 | 35.10 |
| ATOM | 754 | CB | PHE | A | 234 | 49.402 | 37.617 | 15.270 | 1.00 | 34.42 |
| ATOM | 755 | CG | PHE | A | 234 | 50.751 | 38.189 | 15.577 | 1.00 | 37.95 |
| ATOM | 756 | CD1 | PHE | A | 234 | 51.217 | 38.233 | 16.888 | 1.00 | 42.52 |
| ATOM | 757 | CD2 | PHE | A | 234 | 51.573 | 38.659 | 14.558 | 1.00 | 42.14 |
| ATOM | 758 | CE1 | PHE | A | 234 | 52.478 | 38.745 | 17.179 | 1.00 | 44.76 |
| ATOM | 759 | CE2 | PHE | A | 234 | 52.838 | 39.174 | 14.842 | 1.00 | 45.70 |
| ATOM | 760 | CZ | PHE | A | 234 | 53.293 | 39.210 | 16.153 | 1.00 | 44.21 |
| ATOM | 761 | N | PHE | A | 235 | 49.195 | 35.399 | 17.517 | 1.00 | 33.14 |
| ATOM | 762 | CA | PHE | A | 235 | 49.676 | 34.821 | 18.765 | 1.00 | 33.73 |
| ATOM | 763 | C | PHE | A | 235 | 49.824 | 33.313 | 18.702 | 1.00 | 32.74 |
| ATOM | 764 | O | PHE | A | 235 | 50.832 | 32.766 | 19.143 | 1.00 | 31.27 |
| ATOM | 765 | CB | PHE | A | 235 | 48.820 | 35.280 | 19.949 | 1.00 | 36.92 |
| ATOM | 766 | CG | PHE | A | 235 | 48.972 | 36.753 | 20.258 | 1.00 | 40.71 |
| ATOM | 767 | CD1 | PHE | A | 235 | 50.235 | 37.339 | 20.295 | 1.00 | 45.75 |
| ATOM | 768 | CD2 | PHE | A | 235 | 47.858 | 37.562 | 20.476 | 1.00 | 44.42 |
| ATOM | 769 | CE1 | PHE | A | 235 | 50.385 | 38.700 | 20.550 | 1.00 | 47.27 |
| ATOM | 770 | CE2 | PHE | A | 235 | 48.000 | 38.917 | 20.720 | 1.00 | 47.89 |
| ATOM | 771 | CZ | PHE | A | 235 | 49.261 | 39.489 | 20.754 | 1.00 | 46.39 |
| ATOM | 772 | N | HIS | A | 236 | 48.863 | 32.641 | 18.072 | 1.00 | 27.11 |
| ATOM | 773 | CA | HIS | A | 236 | 48.957 | 31.192 | 17.895 | 1.00 | 25.48 |
| ATOM | 774 | C | HIS | A | 236 | 50.200 | 30.830 | 17.074 | 1.00 | 30.28 |
| ATOM | 775 | O | HIS | A | 236 | 50.919 | 29.897 | 17.407 | 1.00 | 31.16 |
| ATOM | 776 | CB | HIS | A | 236 | 47.710 | 30.659 | 17.200 | 1.00 | 25.40 |
| ATOM | 777 | CG | HIS | A | 236 | 46.506 | 30.607 | 18.081 | 1.00 | 28.09 |
| ATOM | 778 | ND1 | HIS | A | 236 | 46.460 | 29.844 | 19.233 | 1.00 | 29.60 |
| ATOM | 779 | CD2 | HIS | A | 236 | 45.311 | 31.240 | 17.997 | 1.00 | 28.56 |
| ATOM | 780 | CE1 | HIS | A | 236 | 45.271 | 29.983 | 19.797 | 1.00 | 28.76 |
| ATOM | 781 | NE2 | HIS | A | 236 | 44.557 | 30.826 | 19.068 | 1.00 | 28.66 |
| ATOM | 782 | N | LEU | A | 237 | 50.444 | 31.569 | 15.994 | 1.00 | 27.97 |
| ATOM | 783 | CA | LEU | A | 237 | 51.601 | 31.280 | 15.139 | 1.00 | 26.70 |
| ATOM | 784 | C | LEU | A | 237 | 52.932 | 31.565 | 15.847 | 1.00 | 34.74 |
| ATOM | 785 | O | LEU | A | 237 | 53.884 | 30.793 | 15.718 | 1.00 | 34.17 |
| ATOM | 786 | CB | LEU | A | 237 | 51.512 | 32.048 | 13.804 | 1.00 | 25.76 |
| ATOM | 787 | CG | LEU | A | 237 | 52.638 | 31.802 | 12.788 | 1.00 | 27.67 |
| ATOM | 788 | CD1 | LEU | A | 237 | 52.676 | 30.329 | 12.283 | 1.00 | 25.91 |
| ATOM | 789 | CD2 | LEU | A | 237 | 52.496 | 32.760 | 11.604 | 1.00 | 27.14 |
| ATOM | 790 | N | SER | A | 238 | 52.982 | 32.655 | 16.608 | 1.00 | 34.93 |
| ATOM | 791 | CA | SER | A | 238 | 54.204 | 33.027 | 17.331 | 1.00 | 36.89 |
| ATOM | 792 | C | SER | A | 238 | 54.594 | 31.952 | 18.345 | 1.00 | 43.29 |
| ATOM | 793 | O | SER | A | 238 | 55.779 | 31.616 | 18.489 | 1.00 | 44.71 |
| ATOM | 794 | CB | SER | A | 238 | 54.043 | 34.386 | 18.013 | 1.00 | 41.20 |
| ATOM | 795 | OG | SER | A | 238 | 53.102 | 34.318 | 19.068 | 1.00 | 54.27 |
| ATOM | 796 | N | ARG | A | 239 | 53.591 | 31.378 | 19.004 | 1.00 | 39.48 |
| ATOM | 797 | CA | ARG | A | 239 | 53.808 | 30.313 | 19.974 | 1.00 | 39.38 |
| ATOM | 798 | C | ARG | A | 239 | 54.238 | 28.990 | 19.314 | 1.00 | 42.03 |
| ATOM | 799 | O | ARG | A | 239 | 55.131 | 28.300 | 19.810 | 1.00 | 40.74 |
| ATOM | 800 | CB | ARG | A | 239 | 52.543 | 30.095 | 20.810 | 1.00 | 39.60 |
| ATOM | 801 | CG | ARG | A | 239 | 52.261 | 31.192 | 21.827 | 1.00 | 52.83 |
| ATOM | 802 | CD | ARG | A | 239 | 51.018 | 30.869 | 22.658 | 1.00 | 64.56 |
| ATOM | 803 | NE | ARG | A | 239 | 51.280 | 30.944 | 24.093 | 1.00 | 75.33 |
| ATOM | 804 | CZ | ARG | A | 239 | 50.465 | 30.462 | 25.027 | 1.00 | 92.15 |
| ATOM | 805 | NH1 | ARG | A | 239 | 49.333 | 29.866 | 24.677 | 1.00 | 82.52 |
| ATOM | 806 | NH2 | ARG | A | 239 | 50.782 | 30.575 | 26.310 | 1.00 | 78.69 |
| ATOM | 807 | N | GLU | A | 240 | 53.604 | 28.642 | 18.193 | 1.00 | 37.32 |
| ATOM | 808 | CA | GLU | A | 240 | 53.910 | 27.400 | 17.501 | 1.00 | 35.71 |
| ATOM | 809 | C | GLU | A | 240 | 55.094 | 27.509 | 16.551 | 1.00 | 36.64 |
| ATOM | 810 | O | GLU | A | 240 | 55.630 | 26.495 | 16.117 | 1.00 | 36.52 |
| ATOM | 811 | CB | GLU | A | 240 | 52.689 | 26.881 | 16.743 | 1.00 | 37.49 |
| ATOM | 812 | CG | GLU | A | 240 | 51.928 | 25.780 | 17.469 | 1.00 | 50.50 |
| ATOM | 813 | CD | GLU | A | 240 | 50.453 | 25.775 | 17.129 | 1.00 | 68.20 |
| ATOM | 814 | OE1 | GLU | A | 240 | 49.709 | 24.956 | 17.705 | 1.00 | 67.00 |
| ATOM | 815 | OE2 | GLU | A | 240 | 50.037 | 26.598 | 16.291 | 1.00 | 62.65 |
| ATOM | 816 | N | ARG | A | 241 | 55.456 | 28.742 | 16.200 | 1.00 | 32.79 |
| ATOM | 817 | CA | ARG | A | 241 | 56.554 | 29.033 | 15.270 | 1.00 | 32.24 |
| ATOM | 818 | C | ARG | A | 241 | 56.139 | 28.883 | 13.795 | 1.00 | 32.18 |
| ATOM | 819 | O | ARG | A | 241 | 56.367 | 29.774 | 12.981 | 1.00 | 31.36 |
| ATOM | 820 | CB | ARG | A | 241 | 57.783 | 28.170 | 15.570 | 1.00 | 36.80 |
| ATOM | 821 | CG | ARG | A | 241 | 58.837 | 28.192 | 14.476 | 1.00 | 53.66 |
| ATOM | 822 | CD | ARG | A | 241 | 60.182 | 28.666 | 15.018 | 1.00 | 72.58 |
| ATOM | 823 | NE | ARG | A | 241 | 61.279 | 28.371 | 14.098 | 1.00 | 89.69 |
| ATOM | 824 | CZ | ARG | A | 241 | 62.372 | 27.686 | 14.429 | 1.00 | 108.21 |
| ATOM | 825 | NH1 | ARG | A | 241 | 62.513 | 27.209 | 15.661 | 1.00 | 94.79 |
| ATOM | 826 | NH2 | ARG | A | 241 | 63.323 | 27.474 | 13.528 | 1.00 | 98.37 |

TABLE 2-continued

| | | | | | | | | | |
|---|---|---|---|---|---|---|---|---|---|
| ATOM | 827 | N | VAL | A | 242 | 55.551 | 27.742 | 13.469 | 1.00 | 28.42 |
| ATOM | 828 | CA | VAL | A | 242 | 55.103 | 27.463 | 12.105 | 1.00 | 27.80 |
| ATOM | 829 | C | VAL | A | 242 | 53.903 | 26.497 | 12.170 | 1.00 | 28.65 |
| ATOM | 830 | O | VAL | A | 242 | 53.763 | 25.720 | 13.131 | 1.00 | 27.39 |
| ATOM | 831 | CB | VAL | A | 242 | 56.261 | 26.833 | 11.285 | 1.00 | 33.22 |
| ATOM | 832 | CG1 | VAL | A | 242 | 56.625 | 25.463 | 11.841 | 1.00 | 33.54 |
| ATOM | 833 | CG2 | VAL | A | 242 | 55.917 | 26.756 | 9.835 | 1.00 | 34.04 |
| ATOM | 834 | N | PHE | A | 243 | 52.964 | 26.642 | 11.232 | 1.00 | 22.36 |
| ATOM | 835 | CA | PHE | A | 243 | 51.805 | 25.738 | 11.174 | 1.00 | 19.84 |
| ATOM | 836 | C | PHE | A | 243 | 52.120 | 24.672 | 10.130 | 1.00 | 21.64 |
| ATOM | 837 | O | PHE | A | 243 | 52.853 | 24.929 | 9.167 | 1.00 | 22.27 |
| ATOM | 838 | CB | PHE | A | 243 | 50.534 | 26.494 | 10.682 | 1.00 | 20.59 |
| ATOM | 839 | CG | PHE | A | 243 | 49.959 | 27.471 | 11.674 | 1.00 | 21.02 |
| ATOM | 840 | CD1 | PHE | A | 243 | 50.177 | 27.343 | 13.046 | 1.00 | 23.63 |
| ATOM | 841 | CD2 | PHE | A | 243 | 49.202 | 28.548 | 11.226 | 1.00 | 21.57 |
| ATOM | 842 | CE1 | PHE | A | 243 | 49.638 | 28.269 | 13.951 | 1.00 | 23.75 |
| ATOM | 843 | CE2 | PHE | A | 243 | 48.663 | 29.481 | 12.123 | 1.00 | 23.41 |
| ATOM | 844 | CZ | PHE | A | 243 | 48.907 | 29.352 | 13.495 | 1.00 | 22.37 |
| ATOM | 845 | N | SER | A | 244 | 51.490 | 23.506 | 10.254 | 1.00 | 18.76 |
| ATOM | 846 | CA | SER | A | 244 | 51.664 | 22.477 | 9.263 | 1.00 | 18.85 |
| ATOM | 847 | C | SER | A | 244 | 51.026 | 22.953 | 7.935 | 1.00 | 21.35 |
| ATOM | 848 | O | SER | A | 244 | 50.224 | 23.909 | 7.923 | 1.00 | 21.09 |
| ATOM | 849 | CB | SER | A | 244 | 50.968 | 21.202 | 9.714 | 1.00 | 22.70 |
| ATOM | 850 | OG | SER | A | 244 | 49.566 | 21.358 | 9.634 | 1.00 | 23.66 |
| ATOM | 851 | N | GLU | A | 245 | 51.368 | 22.291 | 6.836 | 1.00 | 19.30 |
| ATOM | 852 | CA | GLU | A | 245 | 50.768 | 22.662 | 5.554 | 1.00 | 17.74 |
| ATOM | 853 | C | GLU | A | 245 | 49.272 | 22.424 | 5.590 | 1.00 | 20.16 |
| ATOM | 854 | O | GLU | A | 245 | 48.526 | 23.212 | 5.032 | 1.00 | 18.60 |
| ATOM | 855 | CB | GLU | A | 245 | 51.392 | 21.898 | 4.385 | 1.00 | 19.09 |
| ATOM | 856 | CG | GLU | A | 245 | 52.842 | 22.327 | 4.088 | 1.00 | 19.06 |
| ATOM | 857 | CD | GLU | A | 245 | 53.385 | 21.750 | 2.815 | 1.00 | 28.50 |
| ATOM | 858 | OE1 | GLU | A | 245 | 52.595 | 21.507 | 1.880 | 1.00 | 21.05 |
| ATOM | 859 | OE2 | GLU | A | 245 | 54.626 | 21.551 | 2.747 | 1.00 | 21.97 |
| ATOM | 860 | N | ASP | A | 246 | 48.818 | 21.340 | 6.229 | 1.00 | 18.76 |
| ATOM | 861 | CA | ASP | A | 246 | 47.368 | 21.108 | 6.246 | 1.00 | 19.08 |
| ATOM | 862 | C | ASP | A | 246 | 46.627 | 22.106 | 7.115 | 1.00 | 21.36 |
| ATOM | 863 | O | ASP | A | 246 | 45.474 | 22.440 | 6.821 | 1.00 | 19.50 |
| ATOM | 864 | CB | ASP | A | 246 | 47.019 | 19.672 | 6.644 | 1.00 | 20.63 |
| ATOM | 865 | CG | ASP | A | 246 | 45.578 | 19.305 | 6.273 | 1.00 | 27.03 |
| ATOM | 866 | OD1 | ASP | A | 246 | 45.178 | 19.574 | 5.121 | 1.00 | 23.28 |
| ATOM | 867 | OD2 | ASP | A | 246 | 44.798 | 18.915 | 7.179 | 1.00 | 29.89 |
| ATOM | 868 | N | ARG | A | 247 | 47.241 | 22.535 | 8.221 | 1.00 | 19.24 |
| ATOM | 869 | CA | ARG | A | 247 | 46.589 | 23.532 | 9.086 | 1.00 | 18.58 |
| ATOM | 870 | C | ARG | A | 247 | 46.501 | 24.840 | 8.282 | 1.00 | 20.42 |
| ATOM | 871 | O | ARG | A | 247 | 45.468 | 25.508 | 8.233 | 1.00 | 19.01 |
| ATOM | 872 | CB | ARG | A | 247 | 47.394 | 23.758 | 10.368 | 1.00 | 18.77 |
| ATOM | 873 | CG | ARG | A | 247 | 46.770 | 24.818 | 11.288 | 1.00 | 23.52 |
| ATOM | 874 | CD | ARG | A | 247 | 47.245 | 24.675 | 12.697 | 1.00 | 25.93 |
| ATOM | 875 | NE | ARG | A | 247 | 46.637 | 25.683 | 13.547 | 1.00 | 23.85 |
| ATOM | 876 | CZ | ARG | A | 247 | 47.070 | 25.995 | 14.756 | 1.00 | 33.95 |
| ATOM | 877 | NH1 | ARG | A | 247 | 48.129 | 25.375 | 15.260 | 1.00 | 33.00 |
| ATOM | 878 | NH2 | ARG | A | 247 | 46.452 | 26.933 | 15.454 | 1.00 | 25.10 |
| ATOM | 879 | N | THR | A | 248 | 47.582 | 25.152 | 7.586 | 1.00 | 16.69 |
| ATOM | 880 | CA | THR | A | 248 | 47.600 | 26.350 | 6.740 | 1.00 | 16.66 |
| ATOM | 881 | C | THR | A | 248 | 46.560 | 26.259 | 5.615 | 1.00 | 19.00 |
| ATOM | 882 | O | THR | A | 248 | 45.950 | 27.244 | 5.257 | 1.00 | 18.74 |
| ATOM | 883 | CB | THR | A | 248 | 48.986 | 26.617 | 6.184 | 1.00 | 22.19 |
| ATOM | 884 | OG1 | THR | A | 248 | 49.914 | 26.755 | 7.284 | 1.00 | 18.93 |
| ATOM | 885 | CG2 | THR | A | 248 | 48.987 | 27.945 | 5.347 | 1.00 | 22.25 |
| ATOM | 886 | N | ARG | A | 249 | 46.412 | 25.064 | 5.033 | 1.00 | 16.82 |
| ATOM | 887 | CA | ARG | A | 249 | 45.401 | 24.808 | 3.982 | 1.00 | 15.30 |
| ATOM | 888 | C | ARG | A | 249 | 43.995 | 25.108 | 4.493 | 1.00 | 17.49 |
| ATOM | 889 | O | ARG | A | 249 | 43.198 | 25.736 | 3.808 | 1.00 | 17.96 |
| ATOM | 890 | CB | ARG | A | 249 | 45.482 | 23.348 | 3.567 | 1.00 | 16.22 |
| ATOM | 891 | CG | ARG | A | 249 | 44.438 | 22.922 | 2.525 | 1.00 | 19.04 |
| ATOM | 892 | CD | ARG | A | 249 | 44.621 | 21.433 | 2.211 | 1.00 | 19.55 |
| ATOM | 893 | NE | ARG | A | 249 | 45.748 | 21.244 | 1.323 | 1.00 | 20.77 |
| ATOM | 894 | CZ | ARG | A | 249 | 46.903 | 20.678 | 1.689 | 1.00 | 20.07 |
| ATOM | 895 | NH1 | ARG | A | 249 | 47.047 | 20.144 | 2.911 | 1.00 | 21.74 |
| ATOM | 896 | NH2 | ARG | A | 249 | 47.896 | 20.608 | 0.816 | 1.00 | 18.17 |
| ATOM | 897 | N | PHE | A | 250 | 43.711 | 24.669 | 5.710 | 1.00 | 15.66 |
| ATOM | 898 | CA | PHE | A | 250 | 42.412 | 24.899 | 6.348 | 1.00 | 15.55 |
| ATOM | 899 | C | PHE | A | 250 | 42.128 | 26.385 | 6.479 | 1.00 | 17.94 |
| ATOM | 900 | O | PHE | A | 250 | 41.090 | 26.887 | 6.000 | 1.00 | 16.60 |
| ATOM | 901 | CB | PHE | A | 250 | 42.400 | 24.275 | 7.742 | 1.00 | 16.83 |
| ATOM | 902 | CG | PHE | A | 250 | 41.171 | 24.603 | 8.533 | 1.00 | 17.02 |
| ATOM | 903 | CD1 | PHE | A | 250 | 40.005 | 23.859 | 8.363 | 1.00 | 21.42 |
| ATOM | 904 | CD2 | PHE | A | 250 | 41.197 | 25.615 | 9.478 | 1.00 | 20.49 |
| ATOM | 905 | CE1 | PHE | A | 250 | 38.886 | 24.156 | 9.097 | 1.00 | 21.68 |
| ATOM | 906 | CE2 | PHE | A | 250 | 40.057 | 25.942 | 10.197 | 1.00 | 23.34 |

TABLE 2-continued

| | | | | | | | | | |
|---|---|---|---|---|---|---|---|---|---|
| ATOM | 907 | CZ | PHE | A | 250 | 38.898 | 25.232 | 9.978 | 1.00 | 21.53 |
| ATOM | 908 | N | TYR | A | 251 | 43.074 | 27.114 | 7.047 | 1.00 | 15.82 |
| ATOM | 909 | CA | TYR | A | 251 | 42.871 | 28.559 | 7.205 | 1.00 | 15.70 |
| ATOM | 910 | C | TYR | A | 251 | 42.799 | 29.258 | 5.858 | 1.00 | 18.42 |
| ATOM | 911 | O | TYR | A | 251 | 41.957 | 30.144 | 5.647 | 1.00 | 15.57 |
| ATOM | 912 | CB | TYR | A | 251 | 43.976 | 29.172 | 8.043 | 1.00 | 16.40 |
| ATOM | 913 | CG | TYR | A | 251 | 43.993 | 28.685 | 9.470 | 1.00 | 16.66 |
| ATOM | 914 | CD1 | TYR | A | 251 | 42.792 | 28.420 | 10.172 | 1.00 | 18.03 |
| ATOM | 915 | CD2 | TYR | A | 251 | 45.210 | 28.474 | 10.124 | 1.00 | 19.14 |
| ATOM | 916 | CE1 | TYR | A | 251 | 42.823 | 27.961 | 11.529 | 1.00 | 16.97 |
| ATOM | 917 | CE2 | TYR | A | 251 | 45.251 | 28.003 | 11.437 | 1.00 | 20.52 |
| ATOM | 918 | CZ | TYR | A | 251 | 44.049 | 27.734 | 12.123 | 1.00 | 20.20 |
| ATOM | 919 | OH | TYR | A | 251 | 44.105 | 27.273 | 13.415 | 1.00 | 20.93 |
| ATOM | 920 | N | GLY | A | 252 | 43.696 | 28.889 | 4.950 | 1.00 | 15.58 |
| ATOM | 921 | CA | GLY | A | 252 | 43.719 | 29.511 | 3.611 | 1.00 | 15.19 |
| ATOM | 922 | C | GLY | A | 252 | 42.418 | 29.273 | 2.837 | 1.00 | 17.20 |
| ATOM | 923 | O | GLY | A | 252 | 41.878 | 30.195 | 2.192 | 1.00 | 15.82 |
| ATOM | 924 | N | ALA | A | 253 | 41.881 | 28.066 | 2.950 | 1.00 | 15.69 |
| ATOM | 925 | CA | ALA | A | 253 | 40.633 | 27.743 | 2.281 | 1.00 | 15.41 |
| ATOM | 926 | C | ALA | A | 253 | 39.511 | 28.652 | 2.819 | 1.00 | 17.32 |
| ATOM | 927 | O | ALA | A | 253 | 38.697 | 29.187 | 2.045 | 1.00 | 15.70 |
| ATOM | 928 | CB | ALA | A | 253 | 40.303 | 26.272 | 2.496 | 1.00 | 16.93 |
| ATOM | 929 | N | GLU | A | 254 | 39.437 | 28.812 | 4.143 | 1.00 | 14.94 |
| ATOM | 930 | CA | GLU | A | 254 | 38.399 | 29.682 | 4.719 | 1.00 | 14.67 |
| ATOM | 931 | C | GLU | A | 254 | 38.545 | 31.139 | 4.296 | 1.00 | 17.69 |
| ATOM | 932 | O | GLU | A | 254 | 37.555 | 31.799 | 3.937 | 1.00 | 17.27 |
| ATOM | 933 | CB | GLU | A | 254 | 38.334 | 29.509 | 6.214 | 1.00 | 15.31 |
| ATOM | 934 | CG | GLU | A | 254 | 37.901 | 28.035 | 6.552 | 1.00 | 16.98 |
| ATOM | 935 | CD | GLU | A | 254 | 37.491 | 27.843 | 8.005 | 1.00 | 20.29 |
| ATOM | 936 | OE1 | GLU | A | 254 | 36.715 | 26.884 | 8.289 | 1.00 | 20.45 |
| ATOM | 937 | OE2 | GLU | A | 254 | 37.964 | 28.589 | 8.846 | 1.00 | 21.55 |
| ATOM | 938 | N | ILE | A | 255 | 39.780 | 31.606 | 4.200 | 1.00 | 14.62 |
| ATOM | 939 | CA | ILE | A | 255 | 40.042 | 32.968 | 3.708 | 1.00 | 14.40 |
| ATOM | 940 | C | ILE | A | 255 | 39.636 | 33.087 | 2.215 | 1.00 | 17.63 |
| ATOM | 941 | O | ILE | A | 255 | 39.017 | 34.062 | 1.809 | 1.00 | 18.34 |
| ATOM | 942 | CB | ILE | A | 255 | 41.484 | 33.349 | 3.913 | 1.00 | 15.82 |
| ATOM | 943 | CG1 | ILE | A | 255 | 41.833 | 33.347 | 5.432 | 1.00 | 15.41 |
| ATOM | 944 | CG2 | ILE | A | 255 | 41.804 | 34.724 | 3.273 | 1.00 | 17.37 |
| ATOM | 945 | CD1 | ILE | A | 255 | 43.335 | 33.368 | 5.725 | 1.00 | 16.74 |
| ATOM | 946 | N | VAL | A | 256 | 39.983 | 32.085 | 1.411 | 1.00 | 13.92 |
| ATOM | 947 | CA | VAL | A | 256 | 39.628 | 32.104 | −0.006 | 1.00 | 13.61 |
| ATOM | 948 | C | VAL | A | 256 | 38.103 | 32.223 | −0.177 | 1.00 | 17.28 |
| ATOM | 949 | O | VAL | A | 256 | 37.616 | 32.990 | −0.990 | 1.00 | 19.34 |
| ATOM | 950 | CB | VAL | A | 256 | 40.136 | 30.855 | −0.700 | 1.00 | 16.25 |
| ATOM | 951 | CG1 | VAL | A | 256 | 39.473 | 30.694 | −2.155 | 1.00 | 15.82 |
| ATOM | 952 | CG2 | VAL | A | 256 | 41.696 | 30.966 | −0.824 | 1.00 | 15.50 |
| ATOM | 953 | N | SER | A | 257 | 37.383 | 31.481 | 0.631 | 1.00 | 15.81 |
| ATOM | 954 | CA | SER | A | 257 | 35.906 | 31.502 | 0.604 | 1.00 | 16.17 |
| ATOM | 955 | C | SER | A | 257 | 35.383 | 32.936 | 0.845 | 1.00 | 19.09 |
| ATOM | 956 | O | SER | A | 257 | 34.496 | 33.426 | 0.131 | 1.00 | 19.11 |
| ATOM | 957 | CB | SER | A | 257 | 35.361 | 30.547 | 1.673 | 1.00 | 19.40 |
| ATOM | 958 | OG | SER | A | 257 | 33.916 | 30.459 | 1.576 | 1.00 | 20.70 |
| ATOM | 959 | N | ALA | A | 258 | 35.926 | 33.597 | 1.857 | 1.00 | 16.82 |
| ATOM | 960 | CA | ALA | A | 258 | 35.476 | 34.968 | 2.184 | 1.00 | 18.22 |
| ATOM | 961 | C | ALA | A | 258 | 35.843 | 35.956 | 1.052 | 1.00 | 20.30 |
| ATOM | 962 | O | ALA | A | 258 | 35.045 | 36.811 | 0.661 | 1.00 | 20.15 |
| ATOM | 963 | CB | ALA | A | 258 | 36.067 | 35.421 | 3.495 | 1.00 | 19.74 |
| ATOM | 964 | N | LEU | A | 259 | 37.050 | 35.827 | 0.531 | 1.00 | 17.82 |
| ATOM | 965 | CA | LEU | A | 259 | 37.498 | 36.720 | −0.541 | 1.00 | 17.63 |
| ATOM | 966 | C | LEU | A | 259 | 36.675 | 36.514 | −1.819 | 1.00 | 20.15 |
| ATOM | 967 | O | LEU | A | 259 | 36.385 | 37.492 | −2.540 | 1.00 | 22.52 |
| ATOM | 968 | CB | LEU | A | 259 | 38.999 | 36.564 | −0.813 | 1.00 | 17.77 |
| ATOM | 969 | CG | LEU | A | 259 | 39.939 | 37.044 | 0.293 | 1.00 | 21.15 |
| ATOM | 970 | CD1 | LEU | A | 259 | 41.407 | 36.668 | −0.052 | 1.00 | 22.54 |
| ATOM | 971 | CD2 | LEU | A | 259 | 39.793 | 38.576 | 0.552 | 1.00 | 22.64 |
| ATOM | 972 | N | ASP | A | 260 | 36.342 | 35.255 | −2.129 | 1.00 | 18.41 |
| ATOM | 973 | CA | ASP | A | 260 | 35.498 | 34.926 | −3.303 | 1.00 | 19.25 |
| ATOM | 974 | C | ASP | A | 260 | 34.194 | 35.712 | −3.128 | 1.00 | 22.97 |
| ATOM | 975 | O | ASP | A | 260 | 33.776 | 36.472 | −4.022 | 1.00 | 21.45 |
| ATOM | 976 | CB | ASP | A | 260 | 35.233 | 33.406 | −3.304 | 1.00 | 21.12 |
| ATOM | 977 | CG | ASP | A | 260 | 34.417 | 32.925 | −4.506 | 1.00 | 26.51 |
| ATOM | 978 | OD1 | ASP | A | 260 | 34.380 | 33.617 | −5.547 | 1.00 | 28.71 |
| ATOM | 979 | OD2 | ASP | A | 260 | 33.825 | 31.830 | −4.392 | 1.00 | 26.42 |
| ATOM | 980 | N | TYR | A | 261 | 33.605 | 35.599 | −1.942 | 1.00 | 19.78 |
| ATOM | 981 | CA | TYR | A | 261 | 32.352 | 36.305 | −1.627 | 1.00 | 19.37 |
| ATOM | 982 | C | TYR | A | 261 | 32.487 | 37.811 | −1.787 | 1.00 | 22.24 |
| ATOM | 983 | O | TYR | A | 261 | 31.631 | 38.471 | −2.443 | 1.00 | 23.75 |
| ATOM | 984 | CB | TYR | A | 261 | 31.929 | 35.962 | −0.208 | 1.00 | 20.11 |
| ATOM | 985 | CG | TYR | A | 261 | 30.878 | 36.895 | 0.380 | 1.00 | 22.92 |
| ATOM | 986 | CD1 | TYR | A | 261 | 29.541 | 36.772 | 0.019 | 1.00 | 25.99 |

TABLE 2-continued

| | | | | | | | | | |
|---|---|---|---|---|---|---|---|---|---|
| ATOM | 987 | CD2 | TYR | A | 261 | 31.235 | 37.897 | 1.282 | 1.00 | 23.29 |
| ATOM | 988 | CE1 | TYR | A | 261 | 28.570 | 37.610 | 0.575 | 1.00 | 27.42 |
| ATOM | 989 | CE2 | TYR | A | 261 | 30.271 | 38.759 | 1.827 | 1.00 | 23.47 |
| ATOM | 990 | CZ | TYR | A | 261 | 28.951 | 38.593 | 1.484 | 1.00 | 28.17 |
| ATOM | 991 | OH | TYR | A | 261 | 28.001 | 39.469 | 2.008 | 1.00 | 29.87 |
| ATOM | 992 | N | LEU | A | 262 | 33.532 | 38.386 | −1.203 | 1.00 | 19.84 |
| ATOM | 993 | CA | LEU | A | 262 | 33.736 | 39.840 | −1.285 | 1.00 | 20.60 |
| ATOM | 994 | C | LEU | A | 262 | 33.934 | 40.278 | −2.724 | 1.00 | 24.98 |
| ATOM | 995 | O | LEU | A | 262 | 33.328 | 41.253 | −3.171 | 1.00 | 26.15 |
| ATOM | 996 | CB | LEU | A | 262 | 34.935 | 40.265 | −0.447 | 1.00 | 20.59 |
| ATOM | 997 | CG | LEU | A | 262 | 34.674 | 40.171 | 1.059 | 1.00 | 24.14 |
| ATOM | 998 | CD1 | LEU | A | 262 | 35.950 | 40.294 | 1.868 | 1.00 | 25.70 |
| ATOM | 999 | CD2 | LEU | A | 262 | 33.614 | 41.227 | 1.507 | 1.00 | 26.56 |
| ATOM | 1000 | N | HIS | A | 263 | 34.794 | 39.573 | −3.454 | 1.00 | 20.65 |
| ATOM | 1001 | CA | HIS | A | 263 | 35.054 | 39.944 | −4.860 | 1.00 | 20.24 |
| ATOM | 1002 | C | HIS | A | 263 | 33.785 | 39.841 | −5.705 | 1.00 | 25.37 |
| ATOM | 1003 | O | HIS | A | 263 | 33.593 | 40.623 | −6.652 | 1.00 | 25.73 |
| ATOM | 1004 | CB | HIS | A | 263 | 36.146 | 39.046 | −5.477 | 1.00 | 20.03 |
| ATOM | 1005 | CG | HIS | A | 263 | 37.525 | 39.243 | −4.896 | 1.00 | 20.75 |
| ATOM | 1006 | ND1 | HIS | A | 263 | 37.824 | 40.203 | −3.950 | 1.00 | 21.81 |
| ATOM | 1007 | CD2 | HIS | A | 263 | 38.678 | 38.575 | −5.130 | 1.00 | 18.47 |
| ATOM | 1008 | CE1 | HIS | A | 263 | 39.106 | 40.108 | −3.632 | 1.00 | 18.93 |
| ATOM | 1009 | NE2 | HIS | A | 263 | 39.646 | 39.147 | −4.358 | 1.00 | 20.20 |
| ATOM | 1010 | N | SER | A | 264 | 32.950 | 38.854 | −5.413 | 1.00 | 23.92 |
| ATOM | 1011 | CA | SER | A | 264 | 31.714 | 38.664 | −6.163 | 1.00 | 26.16 |
| ATOM | 1012 | C | SER | A | 264 | 30.787 | 39.866 | −5.992 | 1.00 | 31.90 |
| ATOM | 1013 | O | SER | A | 264 | 29.911 | 40.125 | −6.846 | 1.00 | 33.09 |
| ATOM | 1014 | CB | SER | A | 264 | 31.019 | 37.387 | −5.724 | 1.00 | 30.75 |
| ATOM | 1015 | OG | SER | A | 264 | 31.722 | 36.237 | −6.202 | 1.00 | 42.03 |
| ATOM | 1016 | N | GLY | A | 265 | 30.981 | 40.594 | −4.898 | 1.00 | 29.40 |
| ATOM | 1017 | CA | GLY | A | 265 | 30.211 | 41.801 | −4.597 | 1.00 | 29.20 |
| ATOM | 1018 | C | GLY | A | 265 | 30.980 | 43.064 | −4.981 | 1.00 | 32.30 |
| ATOM | 1019 | O | GLY | A | 265 | 30.623 | 44.185 | −4.556 | 1.00 | 31.20 |
| ATOM | 1020 | N | LYS | A | 266 | 32.044 | 42.879 | −5.766 | 1.00 | 28.31 |
| ATOM | 1021 | CA | LYS | A | 266 | 32.897 | 43.972 | −6.232 | 1.00 | 27.92 |
| ATOM | 1022 | C | LYS | A | 266 | 33.629 | 44.731 | −5.131 | 1.00 | 32.40 |
| ATOM | 1023 | O | LYS | A | 266 | 33.904 | 45.926 | −5.269 | 1.00 | 33.44 |
| ATOM | 1024 | CB | LYS | A | 266 | 32.096 | 44.940 | −7.138 | 1.00 | 30.12 |
| ATOM | 1025 | CG | LYS | A | 266 | 31.292 | 44.216 | −8.204 | 1.00 | 37.01 |
| ATOM | 1026 | CD | LYS | A | 266 | 32.158 | 43.282 | −9.017 | 1.00 | 49.73 |
| ATOM | 1027 | CE | LYS | A | 266 | 31.413 | 41.986 | −9.356 | 1.00 | 64.13 |
| ATOM | 1028 | NZ | LYS | A | 266 | 32.238 | 41.066 | −10.203 | 1.00 | 73.15 |
| ATOM | 1029 | N | ILE | A | 267 | 33.962 | 44.030 | −4.040 | 1.00 | 26.20 |
| ATOM | 1030 | CA | ILE | A | 267 | 34.645 | 44.638 | −2.930 | 1.00 | 25.00 |
| ATOM | 1031 | C | ILE | A | 267 | 36.052 | 44.096 | −2.884 | 1.00 | 27.70 |
| ATOM | 1032 | O | ILE | A | 267 | 36.239 | 42.890 | −2.988 | 1.00 | 27.01 |
| ATOM | 1033 | CB | ILE | A | 267 | 33.987 | 44.260 | −1.602 | 1.00 | 28.52 |
| ATOM | 1034 | CG1 | ILE | A | 267 | 32.628 | 44.957 | −1.453 | 1.00 | 29.78 |
| ATOM | 1035 | CG2 | ILE | A | 267 | 34.900 | 44.593 | −0.451 | 1.00 | 28.39 |
| ATOM | 1036 | CD1 | ILE | A | 267 | 31.768 | 44.378 | −0.350 | 1.00 | 36.43 |
| ATOM | 1037 | N | VAL | A | 268 | 37.030 | 44.982 | −2.761 | 1.00 | 23.21 |
| ATOM | 1038 | CA | VAL | A | 268 | 38.432 | 44.566 | −2.620 | 1.00 | 23.46 |
| ATOM | 1039 | C | VAL | A | 268 | 38.725 | 44.768 | −1.148 | 1.00 | 27.36 |
| ATOM | 1040 | O | VAL | A | 268 | 38.520 | 45.861 | −0.609 | 1.00 | 28.49 |
| ATOM | 1041 | CB | VAL | A | 268 | 39.358 | 45.411 | −3.443 | 1.00 | 28.36 |
| ATOM | 1042 | CG1 | VAL | A | 268 | 40.825 | 45.004 | −3.209 | 1.00 | 28.30 |
| ATOM | 1043 | CG2 | VAL | A | 268 | 38.969 | 45.311 | −4.935 | 1.00 | 29.11 |
| ATOM | 1044 | N | TYR | A | 269 | 39.127 | 43.715 | −0.457 | 1.00 | 22.81 |
| ATOM | 1045 | CA | TYR | A | 269 | 39.270 | 43.835 | 0.982 | 1.00 | 22.34 |
| ATOM | 1046 | C | TYR | A | 269 | 40.413 | 44.733 | 1.454 | 1.00 | 26.36 |
| ATOM | 1047 | O | TYR | A | 269 | 40.244 | 45.528 | 2.415 | 1.00 | 25.61 |
| ATOM | 1048 | CB | TYR | A | 269 | 39.339 | 42.466 | 1.647 | 1.00 | 23.22 |
| ATOM | 1049 | CG | TYR | A | 269 | 39.139 | 42.560 | 3.118 | 1.00 | 25.43 |
| ATOM | 1050 | CD1 | TYR | A | 269 | 37.899 | 42.952 | 3.651 | 1.00 | 27.66 |
| ATOM | 1051 | CD2 | TYR | A | 269 | 40.195 | 42.380 | 3.980 | 1.00 | 25.91 |
| ATOM | 1052 | CE1 | TYR | A | 269 | 37.732 | 43.114 | 5.036 | 1.00 | 28.67 |
| ATOM | 1053 | CE2 | TYR | A | 269 | 40.039 | 42.544 | 5.364 | 1.00 | 27.04 |
| ATOM | 1054 | CZ | TYR | A | 269 | 38.810 | 42.886 | 5.873 | 1.00 | 31.81 |
| ATOM | 1055 | OH | TYR | A | 269 | 38.657 | 43.048 | 7.242 | 1.00 | 33.19 |
| ATOM | 1056 | N | ARG | A | 270 | 41.567 | 44.586 | 0.807 | 1.00 | 23.37 |
| ATOM | 1057 | CA | ARG | A | 270 | 42.761 | 45.400 | 1.066 | 1.00 | 23.44 |
| ATOM | 1058 | C | ARG | A | 270 | 43.488 | 45.153 | 2.383 | 1.00 | 27.63 |
| ATOM | 1059 | O | ARG | A | 270 | 44.707 | 45.320 | 2.466 | 1.00 | 29.47 |
| ATOM | 1060 | CB | ARG | A | 270 | 42.414 | 46.914 | 0.963 | 1.00 | 24.18 |
| ATOM | 1061 | CG | ARG | A | 270 | 41.623 | 47.306 | −0.268 | 1.00 | 31.32 |
| ATOM | 1062 | CD | ARG | A | 270 | 41.440 | 48.833 | −0.258 | 1.00 | 45.43 |
| ATOM | 1063 | NE | ARG | A | 270 | 40.862 | 49.362 | −1.488 | 1.00 | 58.32 |
| ATOM | 1064 | CZ | ARG | A | 270 | 40.778 | 50.664 | −1.763 | 1.00 | 70.58 |
| ATOM | 1065 | NH1 | ARG | A | 270 | 41.248 | 51.557 | −0.895 | 1.00 | 53.46 |
| ATOM | 1066 | NH2 | ARG | A | 270 | 40.231 | 51.074 | −2.904 | 1.00 | 54.22 |

TABLE 2-continued

| | | | | | | | | | |
|---|---|---|---|---|---|---|---|---|---|
| ATOM | 1067 | N | ASP | A | 271 | 42.742 | 44.792 | 3.414 | 1.00 | 24.53 |
| ATOM | 1068 | CA | ASP | A | 271 | 43.294 | 44.683 | 4.766 | 1.00 | 24.88 |
| ATOM | 1069 | C | ASP | A | 271 | 43.674 | 43.278 | 5.229 | 1.00 | 28.77 |
| ATOM | 1070 | O | ASP | A | 271 | 43.923 | 43.064 | 6.419 | 1.00 | 28.24 |
| ATOM | 1071 | CB | ASP | A | 271 | 42.331 | 45.333 | 5.771 | 1.00 | 26.45 |
| ATOM | 1072 | CG | ASP | A | 271 | 42.266 | 46.855 | 5.622 | 1.00 | 38.63 |
| ATOM | 1073 | OD1 | ASP | A | 271 | 43.054 | 47.418 | 4.824 | 1.00 | 38.00 |
| ATOM | 1074 | OD2 | ASP | A | 271 | 41.422 | 47.479 | 6.295 | 1.00 | 43.62 |
| ATOM | 1075 | N | LEU | A | 272 | 43.760 | 42.328 | 4.304 | 1.00 | 25.56 |
| ATOM | 1076 | CA | LEU | A | 272 | 44.165 | 40.975 | 4.704 | 1.00 | 25.45 |
| ATOM | 1077 | C | LEU | A | 272 | 45.614 | 40.960 | 5.216 | 1.00 | 28.81 |
| ATOM | 1078 | O | LEU | A | 272 | 46.552 | 41.267 | 4.485 | 1.00 | 29.75 |
| ATOM | 1079 | CB | LEU | A | 272 | 44.007 | 39.997 | 3.530 | 1.00 | 25.41 |
| ATOM | 1080 | CG | LEU | A | 272 | 44.387 | 38.549 | 3.859 | 1.00 | 28.64 |
| ATOM | 1081 | CD1 | LEU | A | 272 | 43.649 | 38.067 | 5.052 | 1.00 | 28.61 |
| ATOM | 1082 | CD2 | LEU | A | 272 | 44.138 | 37.663 | 2.686 | 1.00 | 29.35 |
| ATOM | 1083 | N | LYS | A | 273 | 45.790 | 40.573 | 6.476 | 1.00 | 24.44 |
| ATOM | 1084 | CA | LYS | A | 273 | 47.121 | 40.436 | 7.072 | 1.00 | 23.93 |
| ATOM | 1085 | C | LYS | A | 273 | 46.961 | 39.544 | 8.291 | 1.00 | 25.00 |
| ATOM | 1086 | O | LYS | A | 273 | 45.860 | 39.350 | 8.779 | 1.00 | 22.88 |
| ATOM | 1087 | CB | LYS | A | 273 | 47.698 | 41.783 | 7.495 | 1.00 | 28.18 |
| ATOM | 1088 | CG | LYS | A | 273 | 46.835 | 42.524 | 8.485 | 1.00 | 29.93 |
| ATOM | 1089 | CD | LYS | A | 273 | 47.451 | 43.903 | 8.816 | 1.00 | 41.19 |
| ATOM | 1090 | CE | LYS | A | 273 | 47.156 | 44.916 | 7.710 | 1.00 | 52.29 |
| ATOM | 1091 | NZ | LYS | A | 273 | 47.284 | 46.329 | 8.186 | 1.00 | 62.01 |
| ATOM | 1092 | N | LEU | A | 274 | 48.059 | 38.969 | 8.760 | 1.00 | 23.25 |
| ATOM | 1093 | CA | LEU | A | 274 | 47.977 | 38.043 | 9.902 | 1.00 | 22.52 |
| ATOM | 1094 | C | LEU | A | 274 | 47.323 | 38.673 | 11.127 | 1.00 | 25.92 |
| ATOM | 1095 | O | LEU | A | 274 | 46.576 | 38.015 | 11.850 | 1.00 | 23.95 |
| ATOM | 1096 | CB | LEU | A | 274 | 49.356 | 37.522 | 10.267 | 1.00 | 22.75 |
| ATOM | 1097 | CG | LEU | A | 274 | 49.420 | 36.425 | 11.323 | 1.00 | 27.08 |
| ATOM | 1098 | CD1 | LEU | A | 274 | 48.699 | 35.162 | 10.862 | 1.00 | 27.84 |
| ATOM | 1099 | CD2 | LEU | A | 274 | 50.892 | 36.133 | 11.628 | 1.00 | 29.18 |
| ATOM | 1100 | N | GLU | A | 275 | 47.656 | 39.936 | 11.385 | 1.00 | 25.52 |
| ATOM | 1101 | CA | GLU | A | 275 | 47.114 | 40.648 | 12.543 | 1.00 | 26.58 |
| ATOM | 1102 | C | GLU | A | 275 | 45.596 | 40.779 | 12.493 | 1.00 | 28.33 |
| ATOM | 1103 | O | GLU | A | 275 | 44.969 | 41.109 | 13.491 | 1.00 | 28.02 |
| ATOM | 1104 | CB | GLU | A | 275 | 47.752 | 42.038 | 12.658 | 1.00 | 28.15 |
| ATOM | 1105 | CG | GLU | A | 275 | 49.293 | 42.047 | 12.896 | 1.00 | 43.34 |
| ATOM | 1106 | CD | GLU | A | 275 | 50.097 | 41.189 | 11.895 | 1.00 | 64.43 |
| ATOM | 1107 | OE1 | GLU | A | 275 | 49.950 | 41.364 | 10.654 | 1.00 | 35.05 |
| ATOM | 1108 | OE2 | GLU | A | 275 | 50.945 | 40.395 | 12.364 | 1.00 | 68.44 |
| ATOM | 1109 | N | ASN | A | 276 | 45.014 | 40.575 | 11.310 | 1.00 | 24.34 |
| ATOM | 1110 | CA | ASN | A | 276 | 43.562 | 40.674 | 11.139 | 1.00 | 22.91 |
| ATOM | 1111 | C | ASN | A | 276 | 42.844 | 39.321 | 11.047 | 1.00 | 24.93 |
| ATOM | 1112 | O | ASN | A | 276 | 41.706 | 39.239 | 10.575 | 1.00 | 23.98 |
| ATOM | 1113 | CB | ASN | A | 276 | 43.190 | 41.562 | 9.951 | 1.00 | 23.31 |
| ATOM | 1114 | CG | ASN | A | 276 | 43.409 | 43.047 | 10.234 | 1.00 | 34.82 |
| ATOM | 1115 | OD1 | ASN | A | 276 | 43.365 | 43.480 | 11.380 | 1.00 | 30.59 |
| ATOM | 1116 | ND2 | ASN | A | 276 | 43.569 | 43.832 | 9.183 | 1.00 | 28.99 |
| ATOM | 1117 | N | LEU | A | 277 | 43.499 | 38.264 | 11.530 | 1.00 | 20.25 |
| ATOM | 1118 | CA | LEU | A | 277 | 42.901 | 36.956 | 11.534 | 1.00 | 19.21 |
| ATOM | 1119 | C | LEU | A | 277 | 42.808 | 36.476 | 12.962 | 1.00 | 22.16 |
| ATOM | 1120 | O | LEU | A | 277 | 43.805 | 36.466 | 13.671 | 1.00 | 21.53 |
| ATOM | 1121 | CB | LEU | A | 277 | 43.799 | 35.971 | 10.748 | 1.00 | 17.98 |
| ATOM | 1122 | CG | LEU | A | 277 | 43.969 | 36.321 | 9.262 | 1.00 | 21.63 |
| ATOM | 1123 | CD1 | LEU | A | 277 | 44.943 | 35.390 | 8.601 | 1.00 | 23.16 |
| ATOM | 1124 | CD2 | LEU | A | 277 | 42.592 | 36.258 | 8.545 | 1.00 | 22.69 |
| ATOM | 1125 | N | MET | A | 278 | 41.626 | 36.032 | 13.356 | 1.00 | 21.79 |
| ATOM | 1126 | CA | MET | A | 278 | 41.412 | 35.464 | 14.686 | 1.00 | 22.30 |
| ATOM | 1127 | C | MET | A | 278 | 40.693 | 34.116 | 14.520 | 1.00 | 24.88 |
| ATOM | 1128 | O | MET | A | 278 | 40.214 | 33.792 | 13.427 | 1.00 | 24.08 |
| ATOM | 1129 | CB | MET | A | 278 | 40.541 | 36.410 | 15.530 | 1.00 | 26.11 |
| ATOM | 1130 | CG | MET | A | 278 | 41.190 | 37.771 | 15.786 | 1.00 | 32.44 |
| ATOM | 1131 | SD | MET | A | 278 | 40.313 | 38.740 | 17.049 | 1.00 | 39.70 |
| ATOM | 1132 | CE | MET | A | 278 | 40.065 | 37.538 | 18.316 | 1.00 | 36.52 |
| ATOM | 1133 | N | LEU | A | 279 | 40.664 | 33.313 | 15.581 | 1.00 | 21.70 |
| ATOM | 1134 | CA | LEU | A | 279 | 39.914 | 32.057 | 15.540 | 1.00 | 21.67 |
| ATOM | 1135 | C | LEU | A | 279 | 38.658 | 32.215 | 16.381 | 1.00 | 25.57 |
| ATOM | 1136 | O | LEU | A | 279 | 38.685 | 32.901 | 17.405 | 1.00 | 25.55 |
| ATOM | 1137 | CB | LEU | A | 279 | 40.743 | 30.918 | 16.148 | 1.00 | 21.27 |
| ATOM | 1138 | CG | LEU | A | 279 | 42.049 | 30.556 | 15.422 | 1.00 | 23.75 |
| ATOM | 1139 | CD1 | LEU | A | 279 | 42.711 | 29.304 | 16.065 | 1.00 | 22.91 |
| ATOM | 1140 | CD2 | LEU | A | 279 | 41.725 | 30.263 | 13.936 | 1.00 | 27.93 |
| ATOM | 1141 | N | ASP | A | 280 | 37.580 | 31.563 | 15.986 | 1.00 | 23.09 |
| ATOM | 1142 | CA | ASP | A | 280 | 36.376 | 31.554 | 16.828 | 1.00 | 23.09 |
| ATOM | 1143 | C | ASP | A | 280 | 36.524 | 30.401 | 17.821 | 1.00 | 26.78 |
| ATOM | 1144 | O | ASP | A | 280 | 37.541 | 29.696 | 17.808 | 1.00 | 23.93 |
| ATOM | 1145 | CB | ASP | A | 280 | 35.056 | 31.524 | 16.046 | 1.00 | 24.52 |
| ATOM | 1146 | CG | ASP | A | 280 | 34.856 | 30.243 | 15.211 | 1.00 | 25.11 |

TABLE 2-continued

| | | | | | | | | | |
|---|---|---|---|---|---|---|---|---|---|
| ATOM | 1147 | OD1 | ASP | A | 280 | 35.445 | 29.192 | 15.542 | 1.00 | 25.18 |
| ATOM | 1148 | OD2 | ASP | A | 280 | 33.998 | 30.281 | 14.314 | 1.00 | 25.18 |
| ATOM | 1149 | N | LYS | A | 281 | 35.545 | 30.236 | 18.705 | 1.00 | 26.55 |
| ATOM | 1150 | CA | LYS | A | 281 | 35.615 | 29.187 | 19.747 | 1.00 | 26.87 |
| ATOM | 1151 | C | LYS | A | 281 | 35.831 | 27.786 | 19.191 | 1.00 | 30.67 |
| ATOM | 1152 | O | LYS | A | 281 | 36.428 | 26.917 | 19.870 | 1.00 | 31.90 |
| ATOM | 1153 | CB | LYS | A | 281 | 34.328 | 29.202 | 20.594 | 1.00 | 29.29 |
| ATOM | 1154 | CG | LYS | A | 281 | 33.076 | 28.862 | 19.817 | 1.00 | 40.02 |
| ATOM | 1155 | CD | LYS | A | 281 | 31.854 | 28.791 | 20.726 | 1.00 | 49.28 |
| ATOM | 1156 | CE | LYS | A | 281 | 30.602 | 29.219 | 19.989 | 1.00 | 58.10 |
| ATOM | 1157 | NZ | LYS | A | 281 | 29.793 | 28.054 | 19.558 | 1.00 | 69.05 |
| ATOM | 1158 | N | ASP | A | 282 | 35.352 | 27.558 | 17.961 | 1.00 | 25.17 |
| ATOM | 1159 | CA | ASP | A | 282 | 35.446 | 26.242 | 17.321 | 1.00 | 24.53 |
| ATOM | 1160 | C | ASP | A | 282 | 36.741 | 26.041 | 16.525 | 1.00 | 26.85 |
| ATOM | 1161 | O | ASP | A | 282 | 37.073 | 24.909 | 16.145 | 1.00 | 26.02 |
| ATOM | 1162 | CB | ASP | A | 282 | 34.242 | 25.996 | 16.451 | 1.00 | 26.67 |
| ATOM | 1163 | CG | ASP | A | 282 | 32.945 | 25.992 | 17.246 | 1.00 | 38.42 |
| ATOM | 1164 | OD1 | ASP | A | 282 | 32.912 | 25.339 | 18.304 | 1.00 | 38.72 |
| ATOM | 1165 | OD2 | ASP | A | 282 | 31.991 | 26.676 | 16.834 | 1.00 | 41.20 |
| ATOM | 1166 | N | GLY | A | 283 | 37.482 | 27.124 | 16.305 | 1.00 | 22.06 |
| ATOM | 1167 | CA | GLY | A | 283 | 38.748 | 27.032 | 15.566 | 1.00 | 21.85 |
| ATOM | 1168 | C | GLY | A | 283 | 38.607 | 27.451 | 14.090 | 1.00 | 23.13 |
| ATOM | 1169 | O | GLY | A | 283 | 39.580 | 27.309 | 13.312 | 1.00 | 20.88 |
| ATOM | 1170 | N | HIS | A | 284 | 37.434 | 27.974 | 13.706 | 1.00 | 18.75 |
| ATOM | 1171 | CA | HIS | A | 284 | 37.263 | 28.467 | 12.300 | 1.00 | 19.50 |
| ATOM | 1172 | C | HIS | A | 284 | 37.779 | 29.882 | 12.258 | 1.00 | 23.07 |
| ATOM | 1173 | O | HIS | A | 284 | 37.776 | 30.586 | 13.270 | 1.00 | 22.89 |
| ATOM | 1174 | CB | HIS | A | 284 | 35.796 | 28.427 | 11.851 | 1.00 | 19.91 |
| ATOM | 1175 | CG | HIS | A | 284 | 35.277 | 27.044 | 11.644 | 1.00 | 22.20 |
| ATOM | 1176 | ND1 | HIS | A | 284 | 35.572 | 26.298 | 10.525 | 1.00 | 23.36 |
| ATOM | 1177 | CD2 | HIS | A | 284 | 34.522 | 26.254 | 12.442 | 1.00 | 23.40 |
| ATOM | 1178 | CE1 | HIS | A | 284 | 34.995 | 25.107 | 10.632 | 1.00 | 23.10 |
| ATOM | 1179 | NE2 | HIS | A | 284 | 34.348 | 25.060 | 11.789 | 1.00 | 23.22 |
| ATOM | 1180 | N | ILE | A | 285 | 38.238 | 30.315 | 11.097 | 1.00 | 19.68 |
| ATOM | 1181 | CA | ILE | A | 285 | 38.832 | 31.637 | 10.972 | 1.00 | 21.83 |
| ATOM | 1182 | C | ILE | A | 285 | 37.784 | 32.752 | 10.990 | 1.00 | 23.48 |
| ATOM | 1183 | O | ILE | A | 285 | 36.603 | 32.555 | 10.598 | 1.00 | 22.61 |
| ATOM | 1184 | CB | ILE | A | 285 | 39.634 | 31.695 | 9.607 | 1.00 | 26.46 |
| ATOM | 1185 | CG1 | ILE | A | 285 | 41.110 | 32.134 | 9.801 | 1.00 | 28.85 |
| ATOM | 1186 | CG2 | ILE | A | 285 | 38.913 | 32.491 | 8.608 | 1.00 | 28.05 |
| ATOM | 1187 | CD1 | ILE | A | 285 | 41.388 | 32.882 | 11.060 | 1.00 | 38.75 |
| ATOM | 1188 | N | LYS | A | 286 | 38.211 | 33.930 | 11.454 | 1.00 | 19.89 |
| ATOM | 1189 | CA | LYS | A | 286 | 37.381 | 35.114 | 11.426 | 1.00 | 20.36 |
| ATOM | 1190 | C | LYS | A | 286 | 38.296 | 36.271 | 10.978 | 1.00 | 22.55 |
| ATOM | 1191 | O | LYS | A | 286 | 39.305 | 36.536 | 11.604 | 1.00 | 23.48 |
| ATOM | 1192 | CB | LYS | A | 286 | 36.842 | 35.433 | 12.817 | 1.00 | 23.06 |
| ATOM | 1193 | CG | LYS | A | 286 | 35.626 | 36.313 | 12.787 | 1.00 | 32.03 |
| ATOM | 1194 | CD | LYS | A | 286 | 34.478 | 35.658 | 12.008 | 1.00 | 35.54 |
| ATOM | 1195 | CE | LYS | A | 286 | 33.795 | 34.575 | 12.817 | 1.00 | 31.71 |
| ATOM | 1196 | NZ | LYS | A | 286 | 32.401 | 34.318 | 12.326 | 1.00 | 31.54 |
| ATOM | 1197 | N | ILE | A | 287 | 37.965 | 36.903 | 9.872 | 1.00 | 19.84 |
| ATOM | 1198 | CA | ILE | A | 287 | 38.737 | 38.063 | 9.408 | 1.00 | 18.87 |
| ATOM | 1199 | C | ILE | A | 287 | 38.154 | 39.248 | 10.150 | 1.00 | 26.04 |
| ATOM | 1200 | O | ILE | A | 287 | 36.951 | 39.455 | 10.108 | 1.00 | 25.08 |
| ATOM | 1201 | CB | ILE | A | 287 | 38.563 | 38.259 | 7.893 | 1.00 | 22.27 |
| ATOM | 1202 | CG1 | ILE | A | 287 | 39.132 | 37.039 | 7.166 | 1.00 | 22.31 |
| ATOM | 1203 | CG2 | ILE | A | 287 | 39.242 | 39.542 | 7.441 | 1.00 | 23.64 |
| ATOM | 1204 | CD1 | ILE | A | 287 | 38.670 | 36.889 | 5.725 | 1.00 | 30.08 |
| ATOM | 1205 | N | THR | A | 288 | 39.007 | 39.958 | 10.894 | 1.00 | 25.94 |
| ATOM | 1206 | CA | THR | A | 288 | 38.553 | 41.013 | 11.811 | 1.00 | 28.25 |
| ATOM | 1207 | C | THR | A | 288 | 39.246 | 42.322 | 11.608 | 1.00 | 38.54 |
| ATOM | 1208 | O | THR | A | 288 | 39.999 | 42.504 | 10.655 | 1.00 | 38.18 |
| ATOM | 1209 | CB | THR | A | 288 | 38.811 | 40.599 | 13.293 | 1.00 | 35.97 |
| ATOM | 1210 | OG1 | THR | A | 288 | 40.225 | 40.565 | 13.549 | 1.00 | 36.46 |
| ATOM | 1211 | CG2 | THR | A | 288 | 38.239 | 39.216 | 13.586 | 1.00 | 35.89 |
| ATOM | 1212 | N | ASP | A | 289 | 38.992 | 43.235 | 12.541 | 1.00 | 39.22 |
| ATOM | 1213 | CA | ASP | A | 289 | 39.648 | 44.527 | 12.569 | 1.00 | 40.66 |
| ATOM | 1214 | C | ASP | A | 289 | 39.464 | 45.143 | 13.929 | 1.00 | 45.19 |
| ATOM | 1215 | O | ASP | A | 289 | 38.635 | 46.033 | 14.117 | 1.00 | 45.33 |
| ATOM | 1216 | CB | ASP | A | 289 | 39.115 | 45.458 | 11.501 | 1.00 | 43.65 |
| ATOM | 1217 | CG | ASP | A | 289 | 39.852 | 46.778 | 11.476 | 1.00 | 54.04 |
| ATOM | 1218 | OD1 | ASP | A | 289 | 41.047 | 46.791 | 11.836 | 1.00 | 54.69 |
| ATOM | 1219 | OD2 | ASP | A | 289 | 39.220 | 47.811 | 11.184 | 1.00 | 62.96 |
| ATOM | 1220 | N | PHE | A | 290 | 40.198 | 44.617 | 14.901 | 1.00 | 42.49 |
| ATOM | 1221 | CA | PHE | A | 290 | 40.143 | 45.132 | 16.262 | 1.00 | 42.91 |
| ATOM | 1222 | C | PHE | A | 290 | 41.495 | 45.767 | 16.530 | 1.00 | 49.38 |
| ATOM | 1223 | O | PHE | A | 290 | 41.907 | 45.937 | 17.676 | 1.00 | 49.38 |
| ATOM | 1224 | CB | PHE | A | 290 | 39.876 | 43.992 | 17.248 | 1.00 | 44.69 |
| ATOM | 1225 | CG | PHE | A | 290 | 38.510 | 43.368 | 17.097 | 1.00 | 46.21 |
| ATOM | 1226 | CD1 | PHE | A | 290 | 38.355 | 42.139 | 16.468 | 1.00 | 49.35 |

TABLE 2-continued

| | | | | | | | | | |
|---|---|---|---|---|---|---|---|---|---|
| ATOM | 1227 | CD2 | PHE | A | 290 | 37.380 | 44.015 | 17.581 | 1.00 | 48.03 |
| ATOM | 1228 | CE1 | PHE | A | 290 | 37.085 | 41.562 | 16.323 | 1.00 | 50.01 |
| ATOM | 1229 | CE2 | PHE | A | 290 | 36.113 | 43.439 | 17.456 | 1.00 | 50.84 |
| ATOM | 1230 | CZ | PHE | A | 290 | 35.968 | 42.213 | 16.825 | 1.00 | 49.01 |
| ATOM | 1231 | N | GLY | A | 291 | 42.190 | 46.100 | 15.441 | 1.00 | 47.33 |
| ATOM | 1232 | CA | GLY | A | 291 | 43.519 | 46.695 | 15.506 | 1.00 | 47.70 |
| ATOM | 1233 | C | GLY | A | 291 | 43.479 | 48.054 | 16.174 | 1.00 | 52.09 |
| ATOM | 1234 | O | GLY | A | 291 | 42.793 | 48.965 | 15.710 | 1.00 | 52.16 |
| ATOM | 1235 | N | LEU | A | 292 | 44.222 | 48.185 | 17.266 | 1.00 | 49.20 |
| ATOM | 1236 | CA | LEU | A | 292 | 44.268 | 49.423 | 18.029 | 1.00 | 49.14 |
| ATOM | 1237 | CB | LEU | A | 292 | 43.892 | 49.154 | 19.491 | 1.00 | 49.15 |
| ATOM | 1238 | CG | LEU | A | 292 | 42.562 | 48.435 | 19.749 | 1.00 | 53.31 |
| ATOM | 1239 | CD1 | LEU | A | 292 | 42.448 | 48.050 | 21.213 | 1.00 | 53.09 |
| ATOM | 1240 | CD2 | LEU | A | 292 | 41.379 | 49.296 | 19.329 | 1.00 | 54.70 |
| ATOM | 1241 | C | THR | A | 309 | 52.251 | 47.535 | 5.969 | 1.00 | 50.06 |
| ATOM | 1242 | O | THR | A | 309 | 51.742 | 46.793 | 5.127 | 1.00 | 49.22 |
| ATOM | 1243 | N | PRO | A | 310 | 53.540 | 47.867 | 5.952 | 1.00 | 46.15 |
| ATOM | 1244 | CA | PRO | A | 310 | 54.259 | 48.078 | 4.700 | 1.00 | 45.01 |
| ATOM | 1245 | C | PRO | A | 310 | 54.706 | 46.743 | 4.089 | 1.00 | 45.06 |
| ATOM | 1246 | O | PRO | A | 310 | 54.795 | 46.605 | 2.872 | 1.00 | 44.27 |
| ATOM | 1247 | CB | PRO | A | 310 | 55.487 | 48.881 | 5.141 | 1.00 | 46.86 |
| ATOM | 1248 | CG | PRO | A | 310 | 55.030 | 49.636 | 6.384 | 1.00 | 51.78 |
| ATOM | 1249 | CD | PRO | A | 310 | 53.768 | 48.962 | 6.912 | 1.00 | 47.49 |
| ATOM | 1250 | N | GLU | A | 311 | 55.007 | 45.776 | 4.951 | 1.00 | 39.05 |
| ATOM | 1251 | CA | GLU | A | 311 | 55.468 | 44.461 | 4.512 | 1.00 | 37.52 |
| ATOM | 1252 | C | GLU | A | 311 | 54.370 | 43.706 | 3.767 | 1.00 | 38.16 |
| ATOM | 1253 | O | GLU | A | 311 | 54.621 | 42.655 | 3.162 | 1.00 | 36.95 |
| ATOM | 1254 | CB | GLU | A | 311 | 55.931 | 43.636 | 5.711 | 1.00 | 38.80 |
| ATOM | 1255 | CG | GLU | A | 311 | 54.958 | 43.652 | 6.887 | 1.00 | 49.37 |
| ATOM | 1256 | CD | GLU | A | 311 | 55.202 | 44.814 | 7.839 | 1.00 | 65.62 |
| ATOM | 1257 | OE1 | GLU | A | 311 | 54.559 | 44.849 | 8.911 | 1.00 | 65.07 |
| ATOM | 1258 | OE2 | GLU | A | 311 | 56.027 | 45.695 | 7.511 | 1.00 | 51.13 |
| ATOM | 1259 | N | TYR | A | 312 | 53.158 | 44.242 | 3.808 | 1.00 | 33.43 |
| ATOM | 1260 | CA | TYR | A | 312 | 52.039 | 43.597 | 3.149 | 1.00 | 33.81 |
| ATOM | 1261 | C | TYR | A | 312 | 51.680 | 44.253 | 1.825 | 1.00 | 37.14 |
| ATOM | 1262 | O | TYR | A | 312 | 50.871 | 43.728 | 1.070 | 1.00 | 37.21 |
| ATOM | 1263 | CB | TYR | A | 312 | 50.823 | 43.584 | 4.065 | 1.00 | 35.56 |
| ATOM | 1264 | CG | TYR | A | 312 | 50.821 | 42.435 | 5.035 | 1.00 | 37.01 |
| ATOM | 1265 | CD1 | TYR | A | 312 | 51.395 | 42.563 | 6.295 | 1.00 | 39.06 |
| ATOM | 1266 | CD2 | TYR | A | 312 | 50.226 | 41.222 | 4.702 | 1.00 | 37.81 |
| ATOM | 1267 | CE1 | TYR | A | 312 | 51.389 | 41.502 | 7.196 | 1.00 | 39.79 |
| ATOM | 1268 | CE2 | TYR | A | 312 | 50.226 | 40.157 | 5.588 | 1.00 | 39.07 |
| ATOM | 1269 | CZ | TYR | A | 312 | 50.804 | 40.304 | 6.834 | 1.00 | 47.08 |
| ATOM | 1270 | OH | TYR | A | 312 | 50.779 | 39.253 | 7.727 | 1.00 | 47.95 |
| ATOM | 1271 | N | LEU | A | 313 | 52.262 | 45.417 | 1.554 | 1.00 | 32.81 |
| ATOM | 1272 | CA | LEU | A | 313 | 51.947 | 46.131 | 0.328 | 1.00 | 31.09 |
| ATOM | 1273 | C | LEU | A | 313 | 52.273 | 45.349 | −0.937 | 1.00 | 30.92 |
| ATOM | 1274 | O | LEU | A | 313 | 53.381 | 44.859 | −1.106 | 1.00 | 29.22 |
| ATOM | 1275 | CB | LEU | A | 313 | 52.638 | 47.496 | 0.314 | 1.00 | 31.52 |
| ATOM | 1276 | CG | LEU | A | 313 | 52.168 | 48.379 | 1.466 | 1.00 | 36.75 |
| ATOM | 1277 | CD1 | LEU | A | 313 | 52.993 | 49.650 | 1.552 | 1.00 | 37.96 |
| ATOM | 1278 | CD2 | LEU | A | 313 | 50.679 | 48.692 | 1.299 | 1.00 | 38.86 |
| ATOM | 1279 | N | ALA | A | 314 | 51.312 | 45.298 | −1.850 | 1.00 | 27.40 |
| ATOM | 1280 | CA | ALA | A | 314 | 51.484 | 44.588 | −3.123 | 1.00 | 27.20 |
| ATOM | 1281 | C | ALA | A | 314 | 52.331 | 45.424 | −4.087 | 1.00 | 32.64 |
| ATOM | 1282 | O | ALA | A | 314 | 52.329 | 46.667 | −4.014 | 1.00 | 32.36 |
| ATOM | 1283 | CB | ALA | A | 314 | 50.116 | 44.277 | −3.745 | 1.00 | 27.94 |
| ATOM | 1284 | N | PRO | A | 315 | 53.039 | 44.752 | −4.992 | 1.00 | 29.75 |
| ATOM | 1285 | CA | PRO | A | 315 | 53.906 | 45.450 | −5.955 | 1.00 | 29.72 |
| ATOM | 1286 | C | PRO | A | 315 | 53.167 | 46.551 | −6.714 | 1.00 | 34.02 |
| ATOM | 1287 | O | PRO | A | 315 | 53.699 | 47.659 | −6.873 | 1.00 | 35.35 |
| ATOM | 1288 | CB | PRO | A | 315 | 54.337 | 44.339 | −6.910 | 1.00 | 31.74 |
| ATOM | 1289 | CG | PRO | A | 315 | 54.350 | 43.102 | −6.039 | 1.00 | 35.45 |
| ATOM | 1290 | CD | PRO | A | 315 | 53.133 | 43.288 | −5.127 | 1.00 | 30.09 |
| ATOM | 1291 | N | GLU | A | 316 | 51.945 | 46.251 | −7.171 | 1.00 | 30.17 |
| ATOM | 1292 | CA | GLU | A | 316 | 51.145 | 47.207 | −7.932 | 1.00 | 30.24 |
| ATOM | 1293 | C | GLU | A | 316 | 50.678 | 48.399 | −7.114 | 1.00 | 36.29 |
| ATOM | 1294 | O | GLU | A | 316 | 50.389 | 49.473 | −7.673 | 1.00 | 37.82 |
| ATOM | 1295 | CB | GLU | A | 316 | 49.970 | 46.532 | −8.638 | 1.00 | 31.26 |
| ATOM | 1296 | CG | GLU | A | 316 | 48.917 | 45.998 | −7.710 | 1.00 | 30.87 |
| ATOM | 1297 | CD | GLU | A | 316 | 49.136 | 44.525 | −7.391 | 1.00 | 31.00 |
| ATOM | 1298 | OE1 | GLU | A | 316 | 50.296 | 44.083 | −7.418 | 1.00 | 25.65 |
| ATOM | 1299 | OE2 | GLU | A | 316 | 48.144 | 43.822 | −7.126 | 1.00 | 25.62 |
| ATOM | 1300 | N | VAL | A | 317 | 50.614 | 48.233 | −5.797 | 1.00 | 32.45 |
| ATOM | 1301 | CA | VAL | A | 317 | 50.224 | 49.332 | −4.932 | 1.00 | 32.91 |
| ATOM | 1302 | C | VAL | A | 317 | 51.424 | 50.258 | −4.792 | 1.00 | 39.20 |
| ATOM | 1303 | O | VAL | A | 317 | 51.289 | 51.480 | −4.873 | 1.00 | 39.18 |
| ATOM | 1304 | CB | VAL | A | 317 | 49.737 | 48.854 | −3.559 | 1.00 | 36.67 |
| ATOM | 1305 | CG1 | VAL | A | 317 | 49.687 | 50.030 | −2.573 | 1.00 | 36.71 |
| ATOM | 1306 | CG2 | VAL | A | 317 | 48.356 | 48.195 | −3.688 | 1.00 | 36.06 |

TABLE 2-continued

| | | | | | | | | | |
|---|---|---|---|---|---|---|---|---|---|
| ATOM | 1307 | N | LEU | A | 318 | 52.609 | 49.658 | −4.686 | 1.00 | 36.97 |
| ATOM | 1308 | CA | LEU | A | 318 | 53.875 | 50.403 | −4.598 | 1.00 | 38.00 |
| ATOM | 1309 | C | LEU | A | 318 | 54.178 | 51.155 | −5.894 | 1.00 | 45.05 |
| ATOM | 1310 | O | LEU | A | 318 | 54.624 | 52.309 | −5.867 | 1.00 | 44.02 |
| ATOM | 1311 | CB | LEU | A | 318 | 55.032 | 49.448 | −4.311 | 1.00 | 37.78 |
| ATOM | 1312 | CG | LEU | A | 318 | 55.041 | 48.843 | −2.914 | 1.00 | 41.95 |
| ATOM | 1313 | CD1 | LEU | A | 318 | 56.315 | 48.063 | −2.685 | 1.00 | 41.74 |
| ATOM | 1314 | CD2 | LEU | A | 318 | 54.878 | 49.942 | −1.886 | 1.00 | 45.78 |
| ATOM | 1315 | N | GLU | A | 319 | 53.967 | 50.484 | −7.029 | 1.00 | 44.23 |
| ATOM | 1316 | CA | GLU | A | 319 | 54.217 | 51.092 | −8.331 | 1.00 | 45.51 |
| ATOM | 1317 | C | GLU | A | 319 | 53.244 | 52.234 | −8.543 | 1.00 | 55.18 |
| ATOM | 1318 | O | GLU | A | 319 | 53.292 | 52.942 | −9.553 | 1.00 | 55.17 |
| ATOM | 1319 | CB | GLU | A | 319 | 54.109 | 50.062 | −9.445 | 1.00 | 46.61 |
| ATOM | 1320 | CG | GLU | A | 319 | 55.138 | 48.952 | −9.341 | 1.00 | 56.09 |
| ATOM | 1321 | CD | GLU | A | 319 | 55.991 | 48.826 | −10.585 | 1.00 | 75.09 |
| ATOM | 1322 | OE1 | GLU | A | 319 | 57.081 | 49.433 | −10.621 | 1.00 | 73.18 |
| ATOM | 1323 | OE2 | GLU | A | 319 | 55.578 | 48.110 | −11.522 | 1.00 | 65.77 |
| ATOM | 1324 | N | ASP | A | 320 | 52.362 | 52.409 | −7.566 | 1.00 | 55.67 |
| ATOM | 1325 | CA | ASP | A | 320 | 51.424 | 53.516 | −7.534 | 1.00 | 57.45 |
| ATOM | 1326 | C | ASP | A | 320 | 50.163 | 53.373 | −8.363 | 1.00 | 63.43 |
| ATOM | 1327 | O | ASP | A | 320 | 50.077 | 52.547 | −9.281 | 1.00 | 63.09 |
| ATOM | 1328 | CB | ASP | A | 320 | 52.134 | 54.841 | −7.857 | 1.00 | 59.74 |
| ATOM | 1329 | CG | ASP | A | 320 | 51.767 | 55.956 | −6.880 | 1.00 | 72.73 |
| ATOM | 1330 | OD1 | ASP | A | 320 | 51.372 | 55.640 | −5.735 | 1.00 | 73.67 |
| ATOM | 1331 | OD2 | ASP | A | 320 | 51.882 | 57.144 | −7.257 | 1.00 | 78.96 |
| ATOM | 1332 | N | ASN | A | 321 | 49.186 | 54.204 | −8.019 | 1.00 | 61.34 |
| ATOM | 1333 | CA | ASN | A | 321 | 47.920 | 54.278 | −8.722 | 1.00 | 61.44 |
| ATOM | 1334 | C | ASN | A | 321 | 47.055 | 53.025 | −8.663 | 1.00 | 64.05 |
| ATOM | 1335 | O | ASN | A | 321 | 46.559 | 52.635 | −7.592 | 1.00 | 64.03 |
| ATOM | 1336 | CB | ASN | A | 321 | 48.133 | 54.715 | −10.176 | 1.00 | 64.86 |
| ATOM | 1337 | CG | ASN | A | 321 | 48.490 | 56.188 | −10.295 | 1.00 | 91.80 |
| ATOM | 1338 | OD1 | ASN | A | 321 | 47.761 | 56.966 | −10.909 | 1.00 | 87.12 |
| ATOM | 1339 | ND2 | ASN | A | 321 | 49.605 | 56.582 | −9.681 | 1.00 | 83.80 |
| ATOM | 1340 | N | ASP | A | 322 | 46.848 | 52.424 | −9.834 | 1.00 | 58.35 |
| ATOM | 1341 | CA | ASP | A | 322 | 45.963 | 51.276 | −9.990 | 1.00 | 56.61 |
| ATOM | 1342 | C | ASP | A | 322 | 46.291 | 50.002 | −9.213 | 1.00 | 55.86 |
| ATOM | 1343 | O | ASP | A | 322 | 47.427 | 49.759 | −8.805 | 1.00 | 56.56 |
| ATOM | 1344 | CB | ASP | A | 322 | 45.721 | 50.964 | −11.470 | 1.00 | 58.47 |
| ATOM | 1345 | CG | ASP | A | 322 | 45.298 | 52.192 | −12.265 | 1.00 | 69.06 |
| ATOM | 1346 | OD1 | ASP | A | 322 | 44.915 | 53.210 | −11.642 | 1.00 | 70.30 |
| ATOM | 1347 | OD2 | ASP | A | 322 | 45.333 | 52.135 | −13.513 | 1.00 | 73.02 |
| ATOM | 1348 | N | TYR | A | 323 | 45.262 | 49.189 | −9.053 | 1.00 | 47.31 |
| ATOM | 1349 | CA | TYR | A | 323 | 45.319 | 47.923 | −8.352 | 1.00 | 44.66 |
| ATOM | 1350 | C | TYR | A | 323 | 43.873 | 47.544 | −8.118 | 1.00 | 41.00 |
| ATOM | 1351 | O | TYR | A | 323 | 42.967 | 48.388 | −8.258 | 1.00 | 39.07 |
| ATOM | 1352 | CB | TYR | A | 323 | 46.086 | 48.039 | −7.022 | 1.00 | 46.37 |
| ATOM | 1353 | CG | TYR | A | 323 | 45.451 | 48.940 | −5.994 | 1.00 | 49.46 |
| ATOM | 1354 | CD1 | TYR | A | 323 | 44.399 | 48.494 | −5.202 | 1.00 | 51.63 |
| ATOM | 1355 | CD2 | TYR | A | 323 | 45.950 | 50.211 | −5.761 | 1.00 | 51.06 |
| ATOM | 1356 | CE1 | TYR | A | 323 | 43.834 | 49.309 | −4.239 | 1.00 | 53.12 |
| ATOM | 1357 | CE2 | TYR | A | 323 | 45.397 | 51.033 | −4.800 | 1.00 | 52.44 |
| ATOM | 1358 | CZ | TYR | A | 323 | 44.337 | 50.582 | −4.045 | 1.00 | 62.34 |
| ATOM | 1359 | OH | TYR | A | 323 | 43.782 | 51.413 | −3.091 | 1.00 | 67.17 |
| ATOM | 1360 | N | GLY | A | 324 | 43.624 | 46.275 | −7.832 | 1.00 | 31.90 |
| ATOM | 1361 | CA | GLY | A | 324 | 42.262 | 45.822 | −7.673 | 1.00 | 29.76 |
| ATOM | 1362 | C | GLY | A | 324 | 42.202 | 44.564 | −6.828 | 1.00 | 27.73 |
| ATOM | 1363 | O | GLY | A | 324 | 42.990 | 44.401 | −5.908 | 1.00 | 26.28 |
| ATOM | 1364 | N | ARG | A | 325 | 41.275 | 43.678 | −7.178 | 1.00 | 23.29 |
| ATOM | 1365 | CA | ARG | A | 325 | 41.064 | 42.438 | −6.405 | 1.00 | 21.77 |
| ATOM | 1366 | C | ARG | A | 325 | 42.323 | 41.580 | −6.268 | 1.00 | 24.12 |
| ATOM | 1367 | O | ARG | A | 325 | 42.477 | 40.872 | −5.272 | 1.00 | 21.95 |
| ATOM | 1368 | CB | ARG | A | 325 | 39.913 | 41.625 | −6.994 | 1.00 | 23.89 |
| ATOM | 1369 | CG | ARG | A | 325 | 40.241 | 41.053 | −8.361 | 1.00 | 30.02 |
| ATOM | 1370 | CD | ARG | A | 325 | 39.009 | 40.527 | −9.094 | 1.00 | 30.11 |
| ATOM | 1371 | NE | ARG | A | 325 | 39.266 | 40.476 | −10.526 | 1.00 | 28.39 |
| ATOM | 1372 | CZ | ARG | A | 325 | 39.962 | 39.523 | −11.142 | 1.00 | 40.06 |
| ATOM | 1373 | NH1 | ARG | A | 325 | 40.444 | 38.479 | −10.459 | 1.00 | 24.79 |
| ATOM | 1374 | NH2 | ARG | A | 325 | 40.170 | 39.610 | −12.451 | 1.00 | 33.83 |
| ATOM | 1375 | N | ALA | A | 326 | 43.225 | 41.620 | −7.257 | 1.00 | 21.23 |
| ATOM | 1376 | CA | ALA | A | 326 | 44.464 | 40.840 | −7.123 | 1.00 | 21.03 |
| ATOM | 1377 | C | ALA | A | 326 | 45.310 | 41.166 | −5.854 | 1.00 | 23.08 |
| ATOM | 1378 | O | ALA | A | 326 | 46.093 | 40.340 | −5.418 | 1.00 | 22.07 |
| ATOM | 1379 | CB | ALA | A | 326 | 45.332 | 40.895 | −8.418 | 1.00 | 22.95 |
| ATOM | 1380 | N | VAL | A | 327 | 45.181 | 42.372 | −5.289 | 1.00 | 21.30 |
| ATOM | 1381 | CA | VAL | A | 327 | 45.965 | 42.701 | −4.086 | 1.00 | 19.84 |
| ATOM | 1382 | C | VAL | A | 327 | 45.583 | 41.760 | −2.934 | 1.00 | 22.30 |
| ATOM | 1383 | O | VAL | A | 327 | 46.408 | 41.443 | −2.074 | 1.00 | 22.23 |
| ATOM | 1384 | CB | VAL | A | 327 | 45.770 | 44.153 | −3.613 | 1.00 | 25.17 |
| ATOM | 1385 | CG1 | VAL | A | 327 | 46.145 | 45.152 | −4.722 | 1.00 | 25.76 |
| ATOM | 1386 | CG2 | VAL | A | 327 | 44.363 | 44.377 | −3.107 | 1.00 | 24.69 |

TABLE 2-continued

| | | | | | | | | | |
|---|---|---|---|---|---|---|---|---|---|
| ATOM | 1387 | N | ASP | A | 328 | 44.346 | 41.292 | −2.957 | 1.00 | 18.01 |
| ATOM | 1388 | CA | ASP | A | 328 | 43.859 | 40.372 | −1.914 | 1.00 | 17.61 |
| ATOM | 1389 | C | ASP | A | 328 | 44.542 | 39.019 | −2.026 | 1.00 | 19.15 |
| ATOM | 1390 | O | ASP | A | 328 | 44.788 | 38.349 | −0.995 | 1.00 | 18.89 |
| ATOM | 1391 | CB | ASP | A | 328 | 42.348 | 40.208 | −1.991 | 1.00 | 19.31 |
| ATOM | 1392 | CG | ASP | A | 328 | 41.585 | 41.438 | −1.428 | 1.00 | 20.11 |
| ATOM | 1393 | OD1 | ASP | A | 328 | 42.177 | 42.257 | −0.669 | 1.00 | 20.17 |
| ATOM | 1394 | OD2 | ASP | A | 328 | 40.423 | 41.566 | −1.757 | 1.00 | 22.34 |
| ATOM | 1395 | N | TRP | A | 329 | 44.848 | 38.589 | −3.259 | 1.00 | 18.29 |
| ATOM | 1396 | CA | TRP | A | 329 | 45.548 | 37.313 | −3.458 | 1.00 | 18.34 |
| ATOM | 1397 | C | TRP | A | 329 | 47.016 | 37.431 | −3.071 | 1.00 | 21.60 |
| ATOM | 1398 | O | TRP | A | 329 | 47.585 | 36.512 | −2.519 | 1.00 | 19.32 |
| ATOM | 1399 | CB | TRP | A | 329 | 45.383 | 36.815 | −4.891 | 1.00 | 18.36 |
| ATOM | 1400 | CG | TRP | A | 329 | 43.924 | 36.663 | −5.258 | 1.00 | 18.28 |
| ATOM | 1401 | CD1 | TRP | A | 329 | 43.289 | 37.208 | −6.335 | 1.00 | 20.68 |
| ATOM | 1402 | CD2 | TRP | A | 329 | 42.916 | 35.965 | −4.508 | 1.00 | 18.43 |
| ATOM | 1403 | NE1 | TRP | A | 329 | 41.966 | 36.907 | −6.303 | 1.00 | 20.01 |
| ATOM | 1404 | CE2 | TRP | A | 329 | 41.702 | 36.136 | −5.194 | 1.00 | 20.43 |
| ATOM | 1405 | CE3 | TRP | A | 329 | 42.931 | 35.193 | −3.340 | 1.00 | 19.84 |
| ATOM | 1406 | CZ2 | TRP | A | 329 | 40.507 | 35.523 | −4.785 | 1.00 | 19.50 |
| ATOM | 1407 | CZ3 | TRP | A | 329 | 41.731 | 34.614 | −2.899 | 1.00 | 21.10 |
| ATOM | 1408 | CH2 | TRP | A | 329 | 40.526 | 34.802 | −3.623 | 1.00 | 21.43 |
| ATOM | 1409 | N | TRP | A | 330 | 47.612 | 38.602 | −3.305 | 1.00 | 20.71 |
| ATOM | 1410 | CA | TRP | A | 330 | 48.970 | 38.861 | −2.843 | 1.00 | 20.80 |
| ATOM | 1411 | C | TRP | A | 330 | 48.950 | 38.748 | −1.296 | 1.00 | 20.84 |
| ATOM | 1412 | O | TRP | A | 330 | 49.776 | 38.052 | −0.701 | 1.00 | 20.13 |
| ATOM | 1413 | CB | TRP | A | 330 | 49.396 | 40.299 | −3.207 | 1.00 | 20.48 |
| ATOM | 1414 | CG | TRP | A | 330 | 50.700 | 40.687 | −2.603 | 1.00 | 21.07 |
| ATOM | 1415 | CD1 | TRP | A | 330 | 50.894 | 41.319 | −1.415 | 1.00 | 23.71 |
| ATOM | 1416 | CD2 | TRP | A | 330 | 51.995 | 40.511 | −3.184 | 1.00 | 21.52 |
| ATOM | 1417 | NE1 | TRP | A | 330 | 52.235 | 41.496 | −1.190 | 1.00 | 23.31 |
| ATOM | 1418 | CE2 | TRP | A | 330 | 52.934 | 40.998 | −2.258 | 1.00 | 25.10 |
| ATOM | 1419 | CE3 | TRP | A | 330 | 52.453 | 39.940 | −4.374 | 1.00 | 23.26 |
| ATOM | 1420 | CZ2 | TRP | A | 330 | 54.330 | 40.949 | −2.497 | 1.00 | 25.22 |
| ATOM | 1421 | CZ3 | TRP | A | 330 | 53.849 | 39.876 | −4.601 | 1.00 | 25.17 |
| ATOM | 1422 | CH2 | TRP | A | 330 | 54.747 | 40.422 | −3.690 | 1.00 | 25.46 |
| ATOM | 1423 | N | GLY | A | 331 | 47.941 | 39.344 | −0.672 | 1.00 | 17.58 |
| ATOM | 1424 | CA | GLY | A | 331 | 47.817 | 39.314 | 0.797 | 1.00 | 17.65 |
| ATOM | 1425 | C | GLY | A | 331 | 47.688 | 37.875 | 1.275 | 1.00 | 20.16 |
| ATOM | 1426 | O | GLY | A | 331 | 48.325 | 37.474 | 2.264 | 1.00 | 19.44 |
| ATOM | 1427 | N | LEU | A | 332 | 46.882 | 37.079 | 0.569 | 1.00 | 17.06 |
| ATOM | 1428 | CA | LEU | A | 332 | 46.745 | 35.654 | 0.931 | 1.00 | 16.31 |
| ATOM | 1429 | C | LEU | A | 332 | 48.097 | 34.948 | 0.848 | 1.00 | 18.64 |
| ATOM | 1430 | O | LEU | A | 332 | 48.453 | 34.147 | 1.732 | 1.00 | 19.28 |
| ATOM | 1431 | CB | LEU | A | 332 | 45.733 | 34.967 | 0.029 | 1.00 | 16.20 |
| ATOM | 1432 | CG | LEU | A | 332 | 45.514 | 33.481 | 0.343 | 1.00 | 17.90 |
| ATOM | 1433 | CD1 | LEU | A | 332 | 44.802 | 33.327 | 1.704 | 1.00 | 20.07 |
| ATOM | 1434 | CD2 | LEU | A | 332 | 44.677 | 32.853 | −0.787 | 1.00 | 16.69 |
| ATOM | 1435 | N | GLY | A | 333 | 48.874 | 35.285 | −0.175 | 1.00 | 16.74 |
| ATOM | 1436 | CA | GLY | A | 333 | 50.191 | 34.713 | −0.361 | 1.00 | 17.89 |
| ATOM | 1437 | C | GLY | A | 333 | 51.069 | 35.047 | 0.832 | 1.00 | 20.27 |
| ATOM | 1438 | O | GLY | A | 333 | 51.738 | 34.176 | 1.356 | 1.00 | 20.68 |
| ATOM | 1439 | N | VAL | A | 334 | 51.059 | 36.309 | 1.271 | 1.00 | 17.63 |
| ATOM | 1440 | CA | VAL | A | 334 | 51.907 | 36.704 | 2.410 | 1.00 | 17.57 |
| ATOM | 1441 | C | VAL | A | 334 | 51.498 | 35.976 | 3.681 | 1.00 | 21.03 |
| ATOM | 1442 | O | VAL | A | 334 | 52.334 | 35.428 | 4.385 | 1.00 | 20.65 |
| ATOM | 1443 | CB | VAL | A | 334 | 51.932 | 38.235 | 2.629 | 1.00 | 21.24 |
| ATOM | 1444 | CG1 | VAL | A | 334 | 52.777 | 38.605 | 3.894 | 1.00 | 22.77 |
| ATOM | 1445 | CG2 | VAL | A | 334 | 52.507 | 38.942 | 1.343 | 1.00 | 20.83 |
| ATOM | 1446 | N | VAL | A | 335 | 50.198 | 35.932 | 3.954 | 1.00 | 18.48 |
| ATOM | 1447 | CA | VAL | A | 335 | 49.685 | 35.237 | 5.146 | 1.00 | 18.38 |
| ATOM | 1448 | C | VAL | A | 335 | 50.027 | 33.723 | 5.132 | 1.00 | 18.69 |
| ATOM | 1449 | O | VAL | A | 335 | 50.548 | 33.185 | 6.115 | 1.00 | 19.12 |
| ATOM | 1450 | CB | VAL | A | 335 | 48.162 | 35.431 | 5.258 | 1.00 | 22.50 |
| ATOM | 1451 | CG1 | VAL | A | 335 | 47.544 | 34.482 | 6.251 | 1.00 | 23.06 |
| ATOM | 1452 | CG2 | VAL | A | 335 | 47.851 | 36.920 | 5.609 | 1.00 | 22.09 |
| ATOM | 1453 | N | MET | A | 336 | 49.716 | 33.039 | 4.036 | 1.00 | 15.10 |
| ATOM | 1454 | CA | MET | A | 336 | 50.015 | 31.616 | 3.952 | 1.00 | 15.15 |
| ATOM | 1455 | C | MET | A | 336 | 51.485 | 31.338 | 4.019 | 1.00 | 19.86 |
| ATOM | 1456 | O | MET | A | 336 | 51.894 | 30.331 | 4.590 | 1.00 | 20.38 |
| ATOM | 1457 | CB | MET | A | 336 | 49.387 | 31.003 | 2.734 | 1.00 | 15.51 |
| ATOM | 1458 | CG | MET | A | 336 | 47.824 | 31.022 | 2.846 | 1.00 | 16.88 |
| ATOM | 1459 | SD | MET | A | 336 | 47.021 | 30.140 | 1.466 | 1.00 | 18.54 |
| ATOM | 1460 | CE | MET | A | 336 | 47.375 | 28.396 | 1.913 | 1.00 | 18.05 |
| ATOM | 1461 | N | TYR | A | 337 | 52.290 | 32.231 | 3.433 | 1.00 | 17.59 |
| ATOM | 1462 | CA | TYR | A | 337 | 53.753 | 32.079 | 3.498 | 1.00 | 17.40 |
| ATOM | 1463 | C | TYR | A | 337 | 54.192 | 32.131 | 4.962 | 1.00 | 22.10 |
| ATOM | 1464 | O | TYR | A | 337 | 54.959 | 31.278 | 5.422 | 1.00 | 20.97 |
| ATOM | 1465 | CB | TYR | A | 337 | 54.446 | 33.195 | 2.716 | 1.00 | 18.75 |
| ATOM | 1466 | CG | TYR | A | 337 | 55.984 | 33.059 | 2.659 | 1.00 | 20.32 |

TABLE 2-continued

| | | | | | | | | | |
|---|---|---|---|---|---|---|---|---|---|
| ATOM | 1467 | CD1 | TYR | A | 337 | 56.763 | 33.374 | 3.761 | 1.00 | 23.67 |
| ATOM | 1468 | CD2 | TYR | A | 337 | 56.615 | 32.529 | 1.528 | 1.00 | 21.22 |
| ATOM | 1469 | CE1 | TYR | A | 337 | 58.175 | 33.264 | 3.714 | 1.00 | 24.08 |
| ATOM | 1470 | CE2 | TYR | A | 337 | 58.028 | 32.398 | 1.473 | 1.00 | 22.61 |
| ATOM | 1471 | CZ | TYR | A | 337 | 58.783 | 32.770 | 2.580 | 1.00 | 28.22 |
| ATOM | 1472 | OH | TYR | A | 337 | 60.173 | 32.625 | 2.576 | 1.00 | 31.88 |
| ATOM | 1473 | N | GLU | A | 338 | 53.712 | 33.142 | 5.689 | 1.00 | 20.92 |
| ATOM | 1474 | CA | GLU | A | 338 | 54.070 | 33.309 | 7.106 | 1.00 | 20.68 |
| ATOM | 1475 | C | GLU | A | 338 | 53.678 | 32.077 | 7.903 | 1.00 | 23.00 |
| ATOM | 1476 | O | GLU | A | 338 | 54.411 | 31.612 | 8.745 | 1.00 | 23.89 |
| ATOM | 1477 | CB | GLU | A | 338 | 53.327 | 34.481 | 7.671 | 1.00 | 22.18 |
| ATOM | 1478 | CG | GLU | A | 338 | 53.762 | 35.806 | 7.195 | 1.00 | 31.80 |
| ATOM | 1479 | CD | GLU | A | 338 | 53.030 | 36.887 | 7.931 | 1.00 | 49.39 |
| ATOM | 1480 | OE1 | GLU | A | 338 | 53.407 | 37.151 | 9.094 | 1.00 | 36.10 |
| ATOM | 1481 | OE2 | GLU | A | 338 | 51.952 | 37.297 | 7.447 | 1.00 | 34.62 |
| ATOM | 1482 | N | MET | A | 339 | 52.483 | 31.558 | 7.639 | 1.00 | 19.27 |
| ATOM | 1483 | CA | MET | A | 339 | 52.010 | 30.394 | 8.336 | 1.00 | 17.99 |
| ATOM | 1484 | C | MET | A | 339 | 52.870 | 29.174 | 8.119 | 1.00 | 22.75 |
| ATOM | 1485 | O | MET | A | 339 | 53.208 | 28.465 | 9.080 | 1.00 | 23.28 |
| ATOM | 1486 | CB | MET | A | 339 | 50.557 | 30.098 | 7.960 | 1.00 | 19.40 |
| ATOM | 1487 | CG | MET | A | 339 | 49.603 | 31.110 | 8.526 | 1.00 | 20.78 |
| ATOM | 1488 | SD | MET | A | 339 | 47.890 | 30.684 | 8.019 | 1.00 | 23.10 |
| ATOM | 1489 | CE | MET | A | 339 | 47.013 | 31.954 | 8.871 | 1.00 | 22.29 |
| ATOM | 1490 | N | MET | A | 340 | 53.218 | 28.909 | 6.862 | 1.00 | 19.71 |
| ATOM | 1491 | CA | MET | A | 340 | 53.962 | 27.698 | 6.518 | 1.00 | 20.52 |
| ATOM | 1492 | C | MET | A | 340 | 55.468 | 27.811 | 6.719 | 1.00 | 26.71 |
| ATOM | 1493 | O | MET | A | 340 | 56.155 | 26.797 | 6.881 | 1.00 | 28.02 |
| ATOM | 1494 | CB | MET | A | 340 | 53.669 | 27.293 | 5.070 | 1.00 | 22.93 |
| ATOM | 1495 | CG | MET | A | 340 | 52.425 | 26.539 | 4.939 | 1.00 | 24.70 |
| ATOM | 1496 | SD | MET | A | 340 | 52.221 | 25.869 | 3.271 | 1.00 | 25.76 |
| ATOM | 1497 | CE | MET | A | 340 | 51.299 | 27.259 | 2.433 | 1.00 | 22.85 |
| ATOM | 1498 | N | CYS | A | 341 | 55.976 | 29.030 | 6.670 | 1.00 | 24.70 |
| ATOM | 1499 | CA | CYS | A | 341 | 57.416 | 29.271 | 6.746 | 1.00 | 24.93 |
| ATOM | 1500 | C | CYS | A | 341 | 57.880 | 29.869 | 8.064 | 1.00 | 30.82 |
| ATOM | 1501 | O | CYS | A | 341 | 59.068 | 29.766 | 8.414 | 1.00 | 31.80 |
| ATOM | 1502 | CB | CYS | A | 341 | 57.868 | 30.124 | 5.564 | 1.00 | 24.76 |
| ATOM | 1503 | SG | CYS | A | 341 | 57.430 | 29.419 | 3.943 | 1.00 | 28.45 |
| ATOM | 1504 | N | GLY | A | 342 | 56.963 | 30.475 | 8.807 | 1.00 | 27.76 |
| ATOM | 1505 | CA | GLY | A | 342 | 57.300 | 31.063 | 10.117 | 1.00 | 28.22 |
| ATOM | 1506 | C | GLY | A | 342 | 58.007 | 32.425 | 10.063 | 1.00 | 33.69 |
| ATOM | 1507 | O | GLY | A | 342 | 58.608 | 32.869 | 11.064 | 1.00 | 33.48 |
| ATOM | 1508 | N | ARG | A | 343 | 57.905 | 33.110 | 8.925 | 1.00 | 30.43 |
| ATOM | 1509 | CA | ARG | A | 343 | 58.500 | 34.431 | 8.777 | 1.00 | 29.98 |
| ATOM | 1510 | C | ARG | A | 343 | 57.878 | 35.128 | 7.564 | 1.00 | 32.08 |
| ATOM | 1511 | O | ARG | A | 343 | 57.291 | 34.472 | 6.706 | 1.00 | 29.69 |
| ATOM | 1512 | CB | ARG | A | 343 | 60.015 | 34.307 | 8.575 | 1.00 | 32.36 |
| ATOM | 1513 | CG | ARG | A | 343 | 60.404 | 33.912 | 7.176 | 1.00 | 40.29 |
| ATOM | 1514 | CD | ARG | A | 343 | 61.897 | 33.650 | 7.053 | 1.00 | 53.16 |
| ATOM | 1515 | NE | ARG | A | 343 | 62.387 | 33.976 | 5.716 | 1.00 | 67.12 |
| ATOM | 1516 | CZ | ARG | A | 343 | 63.513 | 34.639 | 5.475 | 1.00 | 85.19 |
| ATOM | 1517 | NH1 | ARG | A | 343 | 64.270 | 35.057 | 6.484 | 1.00 | 72.86 |
| ATOM | 1518 | NH2 | ARG | A | 343 | 63.885 | 34.890 | 4.224 | 1.00 | 73.09 |
| ATOM | 1519 | N | LEU | A | 344 | 58.037 | 36.447 | 7.481 | 1.00 | 28.39 |
| ATOM | 1520 | CA | LEU | A | 344 | 57.516 | 37.206 | 6.341 | 1.00 | 29.20 |
| ATOM | 1521 | C | LEU | A | 344 | 58.382 | 36.914 | 5.114 | 1.00 | 32.81 |
| ATOM | 1522 | O | LEU | A | 344 | 59.571 | 36.647 | 5.247 | 1.00 | 32.99 |
| ATOM | 1523 | CB | LEU | A | 344 | 57.506 | 38.715 | 6.646 | 1.00 | 29.72 |
| ATOM | 1524 | CG | LEU | A | 344 | 56.335 | 39.288 | 7.475 | 1.00 | 35.60 |
| ATOM | 1525 | CD1 | LEU | A | 344 | 54.998 | 39.016 | 6.836 | 1.00 | 35.86 |
| ATOM | 1526 | CD2 | LEU | A | 344 | 56.356 | 38.778 | 8.906 | 1.00 | 40.72 |
| ATOM | 1527 | N | PRO | A | 345 | 57.773 | 36.916 | 3.928 | 1.00 | 28.71 |
| ATOM | 1528 | CA | PRO | A | 345 | 58.498 | 36.631 | 2.689 | 1.00 | 29.03 |
| ATOM | 1529 | C | PRO | A | 345 | 59.492 | 37.742 | 2.338 | 1.00 | 35.69 |
| ATOM | 1530 | O | PRO | A | 345 | 60.526 | 37.486 | 1.676 | 1.00 | 34.96 |
| ATOM | 1531 | CB | PRO | A | 345 | 57.387 | 36.561 | 1.632 | 1.00 | 29.93 |
| ATOM | 1532 | CG | PRO | A | 345 | 56.220 | 37.296 | 2.226 | 1.00 | 33.14 |
| ATOM | 1533 | CD | PRO | A | 345 | 56.322 | 37.078 | 3.704 | 1.00 | 28.46 |
| ATOM | 1534 | N | PHE | A | 346 | 59.160 | 38.969 | 2.750 | 1.00 | 34.05 |
| ATOM | 1535 | CA | PHE | A | 346 | 60.001 | 40.144 | 2.502 | 1.00 | 34.67 |
| ATOM | 1536 | C | PHE | A | 346 | 60.117 | 40.975 | 3.773 | 1.00 | 41.88 |
| ATOM | 1537 | O | PHE | A | 346 | 59.108 | 41.409 | 4.343 | 1.00 | 40.03 |
| ATOM | 1538 | CB | PHE | A | 346 | 59.394 | 41.023 | 1.395 | 1.00 | 35.64 |
| ATOM | 1539 | CG | PHE | A | 346 | 59.017 | 40.266 | 0.154 | 1.00 | 35.77 |
| ATOM | 1540 | CD1 | PHE | A | 346 | 59.992 | 39.847 | −0.739 | 1.00 | 37.84 |
| ATOM | 1541 | CD2 | PHE | A | 346 | 57.682 | 39.996 | −0.128 | 1.00 | 36.22 |
| ATOM | 1542 | CE1 | PHE | A | 346 | 59.647 | 39.168 | −1.888 | 1.00 | 38.48 |
| ATOM | 1543 | CE2 | PHE | A | 346 | 57.328 | 39.313 | −1.269 | 1.00 | 38.03 |
| ATOM | 1544 | CZ | PHE | A | 346 | 58.308 | 38.890 | −2.151 | 1.00 | 36.59 |
| ATOM | 1545 | N | TYR | A | 347 | 61.347 | 41.223 | 4.201 | 1.00 | 43.80 |
| ATOM | 1546 | CA | TYR | A | 347 | 61.570 | 42.039 | 5.378 | 1.00 | 46.13 |

TABLE 2-continued

| | | | | | | | | | |
|---|---|---|---|---|---|---|---|---|---|
| ATOM | 1547 | C | TYR | A | 347 | 62.859 | 42.857 | 5.366 | 1.00 | 52.07 |
| ATOM | 1548 | O | TYR | A | 347 | 63.888 | 42.432 | 4.833 | 1.00 | 50.91 |
| ATOM | 1549 | CB | TYR | A | 347 | 61.480 | 41.222 | 6.654 | 1.00 | 48.84 |
| ATOM | 1550 | CG | TYR | A | 347 | 61.767 | 42.040 | 7.891 | 1.00 | 53.15 |
| ATOM | 1551 | CD1 | TYR | A | 347 | 61.043 | 43.199 | 8.164 | 1.00 | 55.69 |
| ATOM | 1552 | CD2 | TYR | A | 347 | 62.789 | 41.688 | 8.760 | 1.00 | 54.55 |
| ATOM | 1553 | CE1 | TYR | A | 347 | 61.315 | 43.967 | 9.286 | 1.00 | 56.98 |
| ATOM | 1554 | CE2 | TYR | A | 347 | 63.064 | 42.446 | 9.885 | 1.00 | 55.88 |
| ATOM | 1555 | CZ | TYR | A | 347 | 62.322 | 43.584 | 10.141 | 1.00 | 64.34 |
| ATOM | 1556 | OH | TYR | A | 347 | 62.597 | 44.338 | 11.259 | 1.00 | 67.26 |
| ATOM | 1557 | N | ASN | A | 348 | 62.786 | 44.024 | 5.993 | 1.00 | 51.19 |
| ATOM | 1558 | CA | ASN | A | 348 | 63.929 | 44.922 | 6.124 | 1.00 | 51.81 |
| ATOM | 1559 | C | ASN | A | 348 | 63.510 | 46.148 | 6.919 | 1.00 | 56.90 |
| ATOM | 1560 | O | ASN | A | 348 | 62.386 | 46.636 | 6.777 | 1.00 | 56.10 |
| ATOM | 1561 | CB | ASN | A | 348 | 64.459 | 45.342 | 4.756 | 1.00 | 53.71 |
| ATOM | 1562 | CG | ASN | A | 348 | 65.293 | 46.606 | 4.819 | 1.00 | 80.68 |
| ATOM | 1563 | OD1 | ASN | A | 348 | 66.307 | 46.661 | 5.512 | 1.00 | 75.53 |
| ATOM | 1564 | ND2 | ASN | A | 348 | 64.853 | 47.637 | 4.115 | 1.00 | 73.86 |
| ATOM | 1565 | N | GLN | A | 349 | 64.411 | 46.629 | 7.769 | 1.00 | 54.65 |
| ATOM | 1566 | CA | GLN | A | 349 | 64.144 | 47.794 | 8.606 | 1.00 | 55.13 |
| ATOM | 1567 | C | GLN | A | 349 | 63.993 | 49.058 | 7.757 | 1.00 | 60.06 |
| ATOM | 1568 | O | GLN | A | 349 | 63.085 | 49.867 | 7.977 | 1.00 | 59.33 |
| ATOM | 1569 | CB | GLN | A | 349 | 65.258 | 47.969 | 9.641 | 1.00 | 56.64 |
| ATOM | 1570 | CG | GLN | A | 349 | 65.726 | 46.659 | 10.279 | 1.00 | 74.15 |
| ATOM | 1571 | CD | GLN | A | 349 | 66.573 | 45.814 | 9.337 | 1.00 | 96.03 |
| ATOM | 1572 | OE1 | GLN | A | 349 | 66.220 | 44.675 | 9.015 | 1.00 | 90.84 |
| ATOM | 1573 | NE2 | GLN | A | 349 | 67.685 | 46.377 | 8.876 | 1.00 | 89.30 |
| ATOM | 1574 | N | ASP | A | 350 | 64.871 | 49.211 | 6.773 | 1.00 | 58.08 |
| ATOM | 1575 | CA | ASP | A | 350 | 64.800 | 50.347 | 5.866 | 1.00 | 58.61 |
| ATOM | 1576 | C | ASP | A | 350 | 63.574 | 50.158 | 4.995 | 1.00 | 63.42 |
| ATOM | 1577 | O | ASP | A | 350 | 63.650 | 49.573 | 3.911 | 1.00 | 62.92 |
| ATOM | 1578 | CB | ASP | A | 350 | 66.061 | 50.419 | 4.990 | 1.00 | 60.70 |
| ATOM | 1579 | CG | ASP | A | 350 | 66.109 | 51.680 | 4.136 | 1.00 | 71.79 |
| ATOM | 1580 | OD1 | ASP | A | 350 | 67.223 | 52.098 | 3.754 | 1.00 | 73.04 |
| ATOM | 1581 | OD2 | ASP | A | 350 | 65.036 | 52.256 | 3.853 | 1.00 | 76.75 |
| ATOM | 1582 | N | HIS | A | 351 | 62.434 | 50.641 | 5.471 | 1.00 | 61.03 |
| ATOM | 1583 | CA | HIS | A | 351 | 61.179 | 50.486 | 4.740 | 1.00 | 61.22 |
| ATOM | 1584 | C | HIS | A | 351 | 61.173 | 51.139 | 3.354 | 1.00 | 63.92 |
| ATOM | 1585 | O | HIS | A | 351 | 60.126 | 51.542 | 2.845 | 1.00 | 64.28 |
| ATOM | 1586 | CB | HIS | A | 351 | 59.983 | 50.919 | 5.601 | 1.00 | 62.32 |
| ATOM | 1587 | CG | HIS | A | 351 | 59.663 | 49.956 | 6.706 | 1.00 | 66.08 |
| ATOM | 1588 | ND1 | HIS | A | 351 | 58.747 | 50.233 | 7.700 | 1.00 | 67.94 |
| ATOM | 1589 | CD2 | HIS | A | 351 | 60.143 | 48.715 | 6.974 | 1.00 | 68.01 |
| ATOM | 1590 | CE1 | HIS | A | 351 | 58.673 | 49.203 | 8.528 | 1.00 | 67.49 |
| ATOM | 1591 | NE2 | HIS | A | 351 | 59.509 | 48.269 | 8.109 | 1.00 | 67.82 |
| ATOM | 1592 | N | GLU | A | 352 | 62.358 | 51.196 | 2.747 | 1.00 | 58.23 |
| ATOM | 1593 | CA | GLU | A | 352 | 62.564 | 51.721 | 1.404 | 1.00 | 56.79 |
| ATOM | 1594 | C | GLU | A | 352 | 63.278 | 50.606 | 0.639 | 1.00 | 57.03 |
| ATOM | 1595 | O | GLU | A | 352 | 63.036 | 50.392 | −0.548 | 1.00 | 57.17 |
| ATOM | 1596 | CB | GLU | A | 352 | 63.447 | 52.977 | 1.454 | 1.00 | 58.30 |
| ATOM | 1597 | CG | GLU | A | 352 | 63.381 | 53.848 | 0.205 | 1.00 | 68.31 |
| ATOM | 1598 | CD | GLU | A | 352 | 64.511 | 54.873 | 0.143 | 1.00 | 89.19 |
| ATOM | 1599 | OE1 | GLU | A | 352 | 64.729 | 55.456 | −0.941 | 1.00 | 81.56 |
| ATOM | 1600 | OE2 | GLU | A | 352 | 65.182 | 55.089 | 1.179 | 1.00 | 83.35 |
| ATOM | 1601 | N | LYS | A | 353 | 64.129 | 49.870 | 1.355 | 1.00 | 50.10 |
| ATOM | 1602 | CA | LYS | A | 353 | 64.822 | 48.719 | 0.793 | 1.00 | 48.22 |
| ATOM | 1603 | C | LYS | A | 353 | 63.818 | 47.570 | 0.764 | 1.00 | 50.02 |
| ATOM | 1604 | O | LYS | A | 353 | 63.865 | 46.702 | −0.114 | 1.00 | 49.51 |
| ATOM | 1605 | CB | LYS | A | 353 | 66.012 | 48.330 | 1.671 | 1.00 | 50.69 |
| ATOM | 1606 | CG | LYS | A | 353 | 67.308 | 49.071 | 1.337 | 1.00 | 69.66 |
| ATOM | 1607 | CD | LYS | A | 353 | 68.341 | 48.938 | 2.460 | 1.00 | 80.25 |
| ATOM | 1608 | CE | LYS | A | 353 | 69.597 | 49.754 | 2.160 | 1.00 | 88.75 |
| ATOM | 1609 | NZ | LYS | A | 353 | 70.824 | 49.121 | 2.722 | 1.00 | 95.95 |
| ATOM | 1610 | N | LEU | A | 354 | 62.912 | 47.571 | 1.740 | 1.00 | 45.11 |
| ATOM | 1611 | CA | LEU | A | 354 | 61.863 | 46.556 | 1.816 | 1.00 | 44.32 |
| ATOM | 1612 | C | LEU | A | 354 | 61.030 | 46.622 | 0.546 | 1.00 | 45.10 |
| ATOM | 1613 | O | LEU | A | 354 | 60.692 | 45.599 | −0.047 | 1.00 | 43.47 |
| ATOM | 1614 | CB | LEU | A | 354 | 60.963 | 46.799 | 3.031 | 1.00 | 44.48 |
| ATOM | 1615 | CG | LEU | A | 354 | 59.568 | 46.176 | 2.940 | 1.00 | 49.27 |
| ATOM | 1616 | CD1 | LEU | A | 354 | 59.658 | 44.646 | 2.878 | 1.00 | 48.98 |
| ATOM | 1617 | CD2 | LEU | A | 354 | 58.669 | 46.632 | 4.100 | 1.00 | 51.80 |
| ATOM | 1618 | N | PHE | A | 355 | 60.713 | 47.838 | 0.123 | 1.00 | 40.42 |
| ATOM | 1619 | CA | PHE | A | 355 | 59.921 | 48.038 | −1.076 | 1.00 | 39.68 |
| ATOM | 1620 | C | PHE | A | 355 | 60.629 | 47.484 | −2.311 | 1.00 | 41.32 |
| ATOM | 1621 | O | PHE | A | 355 | 59.981 | 47.031 | −3.270 | 1.00 | 38.39 |
| ATOM | 1622 | CB | PHE | A | 355 | 59.588 | 49.516 | −1.245 | 1.00 | 41.95 |
| ATOM | 1623 | CG | PHE | A | 355 | 58.584 | 50.023 | −0.250 | 1.00 | 44.21 |
| ATOM | 1624 | CD1 | PHE | A | 355 | 57.888 | 49.139 | 0.561 | 1.00 | 47.75 |
| ATOM | 1625 | CD2 | PHE | A | 355 | 58.325 | 51.377 | −0.124 | 1.00 | 47.21 |
| ATOM | 1626 | CE1 | PHE | A | 355 | 56.959 | 49.592 | 1.469 | 1.00 | 49.02 |

TABLE 2-continued

| | | | | | | | | | |
|---|---|---|---|---|---|---|---|---|---|
| ATOM | 1627 | CE2 | PHE | A | 355 | 57.398 | 51.837 | 0.793 | 1.00 | 50.39 |
| ATOM | 1628 | CZ | PHE | A | 355 | 56.710 | 50.940 | 1.588 | 1.00 | 48.46 |
| ATOM | 1629 | N | GLU | A | 356 | 61.958 | 47.498 | −2.277 | 1.00 | 38.32 |
| ATOM | 1630 | CA | GLU | A | 356 | 62.751 | 46.987 | −3.387 | 1.00 | 38.36 |
| ATOM | 1631 | C | GLU | A | 356 | 62.673 | 45.463 | −3.450 | 1.00 | 39.92 |
| ATOM | 1632 | O | GLU | A | 356 | 62.634 | 44.872 | −4.528 | 1.00 | 38.98 |
| ATOM | 1633 | CB | GLU | A | 356 | 64.209 | 47.432 | −3.256 | 1.00 | 40.21 |
| ATOM | 1634 | CG | GLU | A | 356 | 64.756 | 48.092 | −4.499 | 1.00 | 51.50 |
| ATOM | 1635 | CD | GLU | A | 356 | 65.382 | 49.447 | −4.220 | 1.00 | 74.23 |
| ATOM | 1636 | OE1 | GLU | A | 356 | 65.419 | 49.859 | −3.037 | 1.00 | 77.52 |
| ATOM | 1637 | OE2 | GLU | A | 356 | 65.840 | 50.099 | −5.185 | 1.00 | 62.18 |
| ATOM | 1638 | N | LEU | A | 357 | 62.676 | 44.834 | −2.287 | 1.00 | 35.58 |
| ATOM | 1639 | CA | LEU | A | 357 | 62.576 | 43.381 | −2.220 | 1.00 | 35.21 |
| ATOM | 1640 | C | LEU | A | 357 | 61.207 | 42.963 | −2.739 | 1.00 | 34.88 |
| ATOM | 1641 | O | LEU | A | 357 | 61.094 | 42.055 | −3.558 | 1.00 | 34.11 |
| ATOM | 1642 | CB | LEU | A | 357 | 62.753 | 42.908 | −0.778 | 1.00 | 35.65 |
| ATOM | 1643 | CG | LEU | A | 357 | 64.143 | 43.150 | −0.179 | 1.00 | 40.98 |
| ATOM | 1644 | CD1 | LEU | A | 357 | 64.050 | 43.248 | 1.332 | 1.00 | 41.45 |
| ATOM | 1645 | CD2 | LEU | A | 357 | 65.096 | 42.040 | −0.593 | 1.00 | 44.57 |
| ATOM | 1646 | N | ILE | A | 358 | 60.179 | 43.680 | −2.303 | 1.00 | 31.35 |
| ATOM | 1647 | CA | ILE | A | 358 | 58.812 | 43.391 | −2.714 | 1.00 | 30.67 |
| ATOM | 1648 | C | ILE | A | 358 | 58.641 | 43.527 | −4.217 | 1.00 | 35.05 |
| ATOM | 1649 | O | ILE | A | 358 | 57.932 | 42.757 | −4.842 | 1.00 | 33.53 |
| ATOM | 1650 | CB | ILE | A | 358 | 57.793 | 44.287 | −1.986 | 1.00 | 32.79 |
| ATOM | 1651 | CG1 | ILE | A | 358 | 57.801 | 43.991 | −0.483 | 1.00 | 32.39 |
| ATOM | 1652 | CG2 | ILE | A | 358 | 56.389 | 44.109 | −2.575 | 1.00 | 33.34 |
| ATOM | 1653 | CD1 | ILE | A | 358 | 56.842 | 44.851 | 0.322 | 1.00 | 36.35 |
| ATOM | 1654 | N | LEU | A | 359 | 59.302 | 44.520 | −4.793 | 1.00 | 33.48 |
| ATOM | 1655 | CA | LEU | A | 359 | 59.207 | 44.751 | −6.220 | 1.00 | 34.51 |
| ATOM | 1656 | C | LEU | A | 359 | 60.083 | 43.822 | −7.047 | 1.00 | 40.61 |
| ATOM | 1657 | O | LEU | A | 359 | 59.676 | 43.370 | −8.113 | 1.00 | 41.10 |
| ATOM | 1658 | CB | LEU | A | 359 | 59.577 | 46.210 | −6.539 | 1.00 | 34.67 |
| ATOM | 1659 | CG | LEU | A | 359 | 58.509 | 47.251 | −6.230 | 1.00 | 39.48 |
| ATOM | 1660 | CD1 | LEU | A | 359 | 59.054 | 48.679 | −6.435 | 1.00 | 39.83 |
| ATOM | 1661 | CD2 | LEU | A | 359 | 57.284 | 47.018 | −7.090 | 1.00 | 42.43 |
| ATOM | 1662 | N | MET | A | 360 | 61.289 | 43.545 | −6.557 | 1.00 | 39.06 |
| ATOM | 1663 | CA | MET | A | 360 | 62.289 | 42.808 | −7.334 | 1.00 | 40.41 |
| ATOM | 1664 | C | MET | A | 360 | 62.702 | 41.404 | −6.926 | 1.00 | 42.94 |
| ATOM | 1665 | O | MET | A | 360 | 63.140 | 40.627 | −7.773 | 1.00 | 42.71 |
| ATOM | 1666 | CB | MET | A | 360 | 63.564 | 43.648 | −7.446 | 1.00 | 43.55 |
| ATOM | 1667 | CG | MET | A | 360 | 63.325 | 45.106 | −7.711 | 1.00 | 48.66 |
| ATOM | 1668 | SD | MET | A | 360 | 63.590 | 45.468 | −9.431 | 1.00 | 54.03 |
| ATOM | 1669 | CE | MET | A | 360 | 61.881 | 45.339 | −10.053 | 1.00 | 50.56 |
| ATOM | 1670 | N | GLU | A | 361 | 62.689 | 41.112 | −5.634 | 1.00 | 38.50 |
| ATOM | 1671 | CA | GLU | A | 361 | 63.213 | 39.842 | −5.165 | 1.00 | 37.94 |
| ATOM | 1672 | C | GLU | A | 361 | 62.306 | 38.630 | −5.321 | 1.00 | 40.09 |
| ATOM | 1673 | O | GLU | A | 361 | 61.130 | 38.680 | −5.011 | 1.00 | 38.05 |
| ATOM | 1674 | CB | GLU | A | 361 | 63.702 | 39.952 | −3.728 | 1.00 | 39.64 |
| ATOM | 1675 | CG | GLU | A | 361 | 64.539 | 38.767 | −3.273 | 1.00 | 52.10 |
| ATOM | 1676 | CD | GLU | A | 361 | 65.727 | 39.183 | −2.426 | 1.00 | 79.32 |
| ATOM | 1677 | OE1 | GLU | A | 361 | 65.556 | 39.347 | −1.199 | 1.00 | 78.19 |
| ATOM | 1678 | OE2 | GLU | A | 361 | 66.831 | 39.367 | −2.990 | 1.00 | 76.59 |
| ATOM | 1679 | N | ASP | A | 362 | 62.889 | 37.526 | −5.760 | 1.00 | 37.24 |
| ATOM | 1680 | CA | ASP | A | 362 | 62.158 | 36.274 | −5.844 | 1.00 | 37.13 |
| ATOM | 1681 | C | ASP | A | 362 | 62.056 | 35.732 | −4.433 | 1.00 | 39.52 |
| ATOM | 1682 | O | ASP | A | 362 | 62.987 | 35.858 | −3.640 | 1.00 | 37.53 |
| ATOM | 1683 | CB | ASP | A | 362 | 62.902 | 35.272 | −6.725 | 1.00 | 39.59 |
| ATOM | 1684 | CG | ASP | A | 362 | 62.600 | 35.460 | −8.197 | 1.00 | 55.88 |
| ATOM | 1685 | OD1 | ASP | A | 362 | 61.564 | 36.085 | −8.514 | 1.00 | 58.51 |
| ATOM | 1686 | OD2 | ASP | A | 362 | 63.409 | 35.005 | −9.039 | 1.00 | 63.29 |
| ATOM | 1687 | N | ILE | A | 363 | 60.909 | 35.150 | −4.102 | 1.00 | 36.77 |
| ATOM | 1688 | CA | ILE | A | 363 | 60.723 | 34.580 | −2.796 | 1.00 | 36.82 |
| ATOM | 1689 | C | ILE | A | 363 | 61.505 | 33.271 | −2.719 | 1.00 | 39.34 |
| ATOM | 1690 | O | ILE | A | 363 | 61.706 | 32.605 | −3.733 | 1.00 | 38.76 |
| ATOM | 1691 | CB | ILE | A | 363 | 59.219 | 34.300 | −2.529 | 1.00 | 40.94 |
| ATOM | 1692 | CG1 | ILE | A | 363 | 58.843 | 34.727 | −1.126 | 1.00 | 42.03 |
| ATOM | 1693 | CG2 | ILE | A | 363 | 58.884 | 32.849 | −2.775 | 1.00 | 42.35 |
| ATOM | 1694 | CD1 | ILE | A | 363 | 58.881 | 36.214 | −0.936 | 1.00 | 53.04 |
| ATOM | 1695 | N | LYS | A | 364 | 61.967 | 32.932 | −1.521 | 1.00 | 36.01 |
| ATOM | 1696 | CA | LYS | A | 364 | 62.683 | 31.678 | −1.287 | 1.00 | 36.14 |
| ATOM | 1697 | C | LYS | A | 364 | 61.902 | 30.842 | −0.261 | 1.00 | 37.50 |
| ATOM | 1698 | O | LYS | A | 364 | 61.168 | 31.383 | 0.567 | 1.00 | 36.73 |
| ATOM | 1699 | CB | LYS | A | 364 | 64.113 | 31.947 | −0.804 | 1.00 | 39.30 |
| ATOM | 1700 | CG | LYS | A | 364 | 65.075 | 32.361 | −1.914 | 1.00 | 54.76 |
| ATOM | 1701 | CD | LYS | A | 364 | 64.777 | 31.613 | −3.207 | 1.00 | 66.99 |
| ATOM | 1702 | CE | LYS | A | 364 | 65.795 | 31.950 | −4.291 | 1.00 | 80.90 |
| ATOM | 1703 | NZ | LYS | A | 364 | 65.585 | 31.139 | −5.524 | 1.00 | 91.52 |
| ATOM | 1704 | N | PHE | A | 365 | 62.026 | 29.526 | −0.353 | 1.00 | 33.34 |
| ATOM | 1705 | CA | PHE | A | 365 | 61.256 | 28.628 | 0.512 | 1.00 | 32.09 |
| ATOM | 1706 | C | PHE | A | 365 | 62.119 | 27.728 | 1.359 | 1.00 | 37.19 |

TABLE 2-continued

| ATOM | 1707 | O   | PHE | A | 365 | 63.260 | 27.433 | 1.005  | 1.00 | 38.55 |
| ATOM | 1708 | CB  | PHE | A | 365 | 60.363 | 27.709 | −0.345 | 1.00 | 33.16 |
| ATOM | 1709 | CG  | PHE | A | 365 | 59.460 | 28.433 | −1.282 | 1.00 | 33.51 |
| ATOM | 1710 | CD1 | PHE | A | 365 | 58.365 | 29.126 | −0.807 | 1.00 | 35.33 |
| ATOM | 1711 | CD2 | PHE | A | 365 | 59.676 | 28.386 | −2.651 | 1.00 | 34.75 |
| ATOM | 1712 | CE1 | PHE | A | 365 | 57.527 | 29.794 | −1.670 | 1.00 | 36.00 |
| ATOM | 1713 | CE2 | PHE | A | 365 | 58.839 | 29.044 | −3.518 | 1.00 | 36.86 |
| ATOM | 1714 | CZ  | PHE | A | 365 | 57.767 | 29.755 | −3.029 | 1.00 | 35.14 |
| ATOM | 1715 | N   | PRO | A | 366 | 61.542 | 27.200 | 2.428  | 1.00 | 33.39 |
| ATOM | 1716 | CA  | PRO | A | 366 | 62.230 | 26.161 | 3.189  | 1.00 | 33.23 |
| ATOM | 1717 | C   | PRO | A | 366 | 62.298 | 25.005 | 2.168  | 1.00 | 35.92 |
| ATOM | 1718 | O   | PRO | A | 366 | 61.371 | 24.807 | 1.397  | 1.00 | 35.12 |
| ATOM | 1719 | CB  | PRO | A | 366 | 61.244 | 25.826 | 4.314  | 1.00 | 34.38 |
| ATOM | 1720 | CG  | PRO | A | 366 | 60.369 | 27.039 | 4.441  | 1.00 | 38.52 |
| ATOM | 1721 | CD  | PRO | A | 366 | 60.281 | 27.624 | 3.065  | 1.00 | 33.76 |
| ATOM | 1722 | N   | ARG | A | 367 | 63.434 | 24.322 | 2.085  | 1.00 | 32.74 |
| ATOM | 1723 | CA  | ARG | A | 367 | 63.610 | 23.259 | 1.097  | 1.00 | 31.05 |
| ATOM | 1724 | C   | ARG | A | 367 | 62.561 | 22.108 | 1.167  | 1.00 | 32.95 |
| ATOM | 1725 | O   | ARG | A | 367 | 62.130 | 21.558 | 0.129  | 1.00 | 33.52 |
| ATOM | 1726 | CB  | ARG | A | 367 | 65.038 | 22.677 | 1.203  | 1.00 | 29.37 |
| ATOM | 1727 | CG  | ARG | A | 367 | 65.965 | 23.089 | 0.065  | 1.00 | 39.89 |
| ATOM | 1728 | CD  | ARG | A | 367 | 67.403 | 22.594 | 0.309  | 1.00 | 40.34 |
| ATOM | 1729 | NE  | ARG | A | 367 | 67.678 | 22.359 | 1.724  | 1.00 | 39.71 |
| ATOM | 1730 | CZ  | ARG | A | 367 | 68.509 | 21.419 | 2.182  | 1.00 | 55.00 |
| ATOM | 1731 | NH1 | ARG | A | 367 | 69.165 | 20.635 | 1.334  | 1.00 | 43.55 |
| ATOM | 1732 | NH2 | ARG | A | 367 | 68.682 | 21.261 | 3.486  | 1.00 | 42.52 |
| ATOM | 1733 | N   | THR | A | 368 | 62.145 | 21.775 | 2.376  | 1.00 | 27.78 |
| ATOM | 1734 | CA  | THR | A | 368 | 61.209 | 20.668 | 2.595  | 1.00 | 24.23 |
| ATOM | 1735 | C   | THR | A | 368 | 59.751 | 21.029 | 2.391  | 1.00 | 25.27 |
| ATOM | 1736 | O   | THR | A | 368 | 58.904 | 20.179 | 2.535  | 1.00 | 23.68 |
| ATOM | 1737 | CB  | THR | A | 368 | 61.321 | 20.119 | 3.997  | 1.00 | 31.27 |
| ATOM | 1738 | OG1 | THR | A | 368 | 61.212 | 21.207 | 4.928  | 1.00 | 37.05 |
| ATOM | 1739 | CG2 | THR | A | 368 | 62.688 | 19.366 | 4.206  | 1.00 | 31.89 |
| ATOM | 1740 | N   | LEU | A | 369 | 59.454 | 22.288 | 2.069  | 1.00 | 23.74 |
| ATOM | 1741 | CA  | LEU | A | 369 | 58.054 | 22.647 | 1.798  | 1.00 | 23.18 |
| ATOM | 1742 | C   | LEU | A | 369 | 57.604 | 21.822 | 0.563  | 1.00 | 23.90 |
| ATOM | 1743 | O   | LEU | A | 369 | 58.401 | 21.550 | −0.356 | 1.00 | 24.75 |
| ATOM | 1744 | CB  | LEU | A | 369 | 57.925 | 24.150 | 1.534  | 1.00 | 24.19 |
| ATOM | 1745 | CG  | LEU | A | 369 | 56.506 | 24.705 | 1.556  | 1.00 | 29.34 |
| ATOM | 1746 | CD1 | LEU | A | 369 | 55.968 | 24.665 | 2.980  | 1.00 | 29.25 |
| ATOM | 1747 | CD2 | LEU | A | 369 | 56.522 | 26.145 | 1.022  | 1.00 | 29.99 |
| ATOM | 1748 | N   | SER | A | 370 | 56.360 | 21.370 | 0.551  | 1.00 | 20.57 |
| ATOM | 1749 | CA  | SER | A | 370 | 55.895 | 20.571 | −0.572 | 1.00 | 19.20 |
| ATOM | 1750 | C   | SER | A | 370 | 55.876 | 21.330 | −1.884 | 1.00 | 23.35 |
| ATOM | 1751 | O   | SER | A | 370 | 55.746 | 22.571 | −1.917 | 1.00 | 22.58 |
| ATOM | 1752 | CB  | SER | A | 370 | 54.510 | 19.971 | −0.313 | 1.00 | 21.47 |
| ATOM | 1753 | OG  | SER | A | 370 | 53.497 | 20.953 | −0.554 | 1.00 | 20.20 |
| ATOM | 1754 | N   | SER | A | 371 | 55.952 | 20.576 | −2.977 | 1.00 | 20.26 |
| ATOM | 1755 | CA  | SER | A | 371 | 55.940 | 21.141 | −4.302 | 1.00 | 18.89 |
| ATOM | 1756 | C   | SER | A | 371 | 54.683 | 21.980 | −4.561 | 1.00 | 22.04 |
| ATOM | 1757 | O   | SER | A | 371 | 54.761 | 23.115 | −5.070 | 1.00 | 20.14 |
| ATOM | 1758 | CB  | SER | A | 371 | 56.034 | 20.025 | −5.345 | 1.00 | 22.46 |
| ATOM | 1759 | OG  | SER | A | 371 | 55.964 | 20.551 | −6.664 | 1.00 | 26.76 |
| ATOM | 1760 | N   | ASP | A | 372 | 53.531 | 21.435 | −4.175 | 1.00 | 20.32 |
| ATOM | 1761 | CA  | ASP | A | 372 | 52.244 | 22.149 | −4.385 | 1.00 | 19.18 |
| ATOM | 1762 | C   | ASP | A | 372 | 52.196 | 23.454 | −3.552 | 1.00 | 21.30 |
| ATOM | 1763 | O   | ASP | A | 372 | 51.670 | 24.480 | −4.010 | 1.00 | 19.35 |
| ATOM | 1764 | CB  | ASP | A | 372 | 51.070 | 21.240 | −3.990 | 1.00 | 19.54 |
| ATOM | 1765 | CG  | ASP | A | 372 | 50.797 | 20.133 | −4.987 | 1.00 | 23.99 |
| ATOM | 1766 | OD1 | ASP | A | 372 | 51.393 | 20.099 | −6.098 | 1.00 | 27.08 |
| ATOM | 1767 | OD2 | ASP | A | 372 | 49.971 | 19.268 | −4.646 | 1.00 | 27.02 |
| ATOM | 1768 | N   | ALA | A | 373 | 52.743 | 23.414 | −2.338 | 1.00 | 18.09 |
| ATOM | 1769 | CA  | ALA | A | 373 | 52.800 | 24.606 | −1.466 | 1.00 | 19.17 |
| ATOM | 1770 | C   | ALA | A | 373 | 53.692 | 25.653 | −2.137 | 1.00 | 21.43 |
| ATOM | 1771 | O   | ALA | A | 373 | 53.318 | 26.828 | −2.243 | 1.00 | 20.43 |
| ATOM | 1772 | CB  | ALA | A | 373 | 53.367 | 24.235 | −0.067 | 1.00 | 20.21 |
| ATOM | 1773 | N   | LYS | A | 374 | 54.860 | 25.226 | −2.641 | 1.00 | 18.10 |
| ATOM | 1774 | CA  | LYS | A | 374 | 55.750 | 26.178 | −3.322 | 1.00 | 18.06 |
| ATOM | 1775 | C   | LYS | A | 374 | 55.077 | 26.776 | −4.537 | 1.00 | 21.52 |
| ATOM | 1776 | O   | LYS | A | 374 | 55.166 | 28.000 | −4.774 | 1.00 | 22.23 |
| ATOM | 1777 | CB  | LYS | A | 374 | 57.065 | 25.487 | −3.729 | 1.00 | 19.45 |
| ATOM | 1778 | CG  | LYS | A | 374 | 57.894 | 25.079 | −2.574 | 1.00 | 19.67 |
| ATOM | 1779 | CD  | LYS | A | 374 | 59.169 | 24.340 | −3.065 | 1.00 | 24.99 |
| ATOM | 1780 | CE  | LYS | A | 374 | 59.902 | 23.699 | −1.920 | 1.00 | 25.86 |
| ATOM | 1781 | NZ  | LYS | A | 374 | 61.239 | 23.094 | −2.363 | 1.00 | 30.72 |
| ATOM | 1782 | N   | SER | A | 375 | 54.368 | 25.941 | −5.290 | 1.00 | 18.18 |
| ATOM | 1783 | CA  | SER | A | 375 | 53.646 | 26.392 | −6.477 | 1.00 | 18.18 |
| ATOM | 1784 | C   | SER | A | 375 | 52.565 | 27.436 | −6.092 | 1.00 | 21.84 |
| ATOM | 1785 | O   | SER | A | 375 | 52.420 | 28.478 | −6.742 | 1.00 | 21.14 |
| ATOM | 1786 | CB  | SER | A | 375 | 52.970 | 25.215 | −7.150 | 1.00 | 19.55 |

TABLE 2-continued

| | | | | | | | | | |
|---|---|---|---|---|---|---|---|---|---|
| ATOM | 1787 | OG | SER | A | 375 | 52.243 | 25.652 | −8.279 | 1.00 | 23.15 |
| ATOM | 1788 | N | LEU | A | 376 | 51.794 | 27.128 | −5.061 | 1.00 | 18.50 |
| ATOM | 1789 | CA | LEU | A | 376 | 50.736 | 28.040 | −4.624 | 1.00 | 17.60 |
| ATOM | 1790 | C | LEU | A | 376 | 51.298 | 29.394 | −4.191 | 1.00 | 20.87 |
| ATOM | 1791 | O | LEU | A | 376 | 50.839 | 30.425 | −4.639 | 1.00 | 19.68 |
| ATOM | 1792 | CB | LEU | A | 376 | 49.914 | 27.415 | −3.471 | 1.00 | 17.92 |
| ATOM | 1793 | CG | LEU | A | 376 | 48.838 | 28.353 | −2.909 | 1.00 | 19.45 |
| ATOM | 1794 | CD1 | LEU | A | 376 | 47.579 | 28.327 | −3.827 | 1.00 | 21.00 |
| ATOM | 1795 | CD2 | LEU | A | 376 | 48.455 | 27.937 | −1.486 | 1.00 | 20.37 |
| ATOM | 1796 | N | LEU | A | 377 | 52.250 | 29.375 | −3.282 | 1.00 | 19.20 |
| ATOM | 1797 | CA | LEU | A | 377 | 52.824 | 30.615 | −2.743 | 1.00 | 18.88 |
| ATOM | 1798 | C | LEU | A | 377 | 53.485 | 31.415 | −3.838 | 1.00 | 21.61 |
| ATOM | 1799 | O | LEU | A | 377 | 53.315 | 32.639 | −3.914 | 1.00 | 20.35 |
| ATOM | 1800 | CB | LEU | A | 377 | 53.804 | 30.307 | −1.638 | 1.00 | 18.18 |
| ATOM | 1801 | CG | LEU | A | 377 | 53.242 | 29.570 | −0.415 | 1.00 | 19.93 |
| ATOM | 1802 | CD1 | LEU | A | 377 | 54.362 | 29.420 | 0.590 | 1.00 | 19.67 |
| ATOM | 1803 | CD2 | LEU | A | 377 | 52.105 | 30.450 | 0.187 | 1.00 | 22.94 |
| ATOM | 1804 | N | SER | A | 378 | 54.208 | 30.735 | −4.722 | 1.00 | 20.31 |
| ATOM | 1805 | CA | SER | A | 378 | 54.848 | 31.444 | −5.855 | 1.00 | 20.14 |
| ATOM | 1806 | C | SER | A | 378 | 53.789 | 32.119 | −6.721 | 1.00 | 24.97 |
| ATOM | 1807 | O | SER | A | 378 | 53.972 | 33.255 | −7.184 | 1.00 | 25.16 |
| ATOM | 1808 | CB | SER | A | 378 | 55.647 | 30.474 | −6.731 | 1.00 | 22.62 |
| ATOM | 1809 | OG | SER | A | 378 | 56.740 | 29.912 | −6.023 | 1.00 | 28.44 |
| ATOM | 1810 | N | GLY | A | 379 | 52.713 | 31.402 | −6.997 | 1.00 | 20.02 |
| ATOM | 1811 | CA | GLY | A | 379 | 51.663 | 31.929 | −7.869 | 1.00 | 19.49 |
| ATOM | 1812 | C | GLY | A | 379 | 50.953 | 33.139 | −7.245 | 1.00 | 21.98 |
| ATOM | 1813 | O | GLY | A | 379 | 50.640 | 34.111 | −7.936 | 1.00 | 21.24 |
| ATOM | 1814 | N | LEU | A | 380 | 50.705 | 33.085 | −5.936 | 1.00 | 18.17 |
| ATOM | 1815 | CA | LEU | A | 380 | 50.018 | 34.208 | −5.235 | 1.00 | 16.96 |
| ATOM | 1816 | C | LEU | A | 380 | 50.929 | 35.429 | −5.141 | 1.00 | 21.47 |
| ATOM | 1817 | O | LEU | A | 380 | 50.451 | 36.567 | −5.012 | 1.00 | 20.54 |
| ATOM | 1818 | CB | LEU | A | 380 | 49.571 | 33.787 | −3.817 | 1.00 | 17.01 |
| ATOM | 1819 | CG | LEU | A | 380 | 48.494 | 32.688 | −3.786 | 1.00 | 18.41 |
| ATOM | 1820 | CD1 | LEU | A | 380 | 48.296 | 32.203 | −2.344 | 1.00 | 17.45 |
| ATOM | 1821 | CD2 | LEU | A | 380 | 47.151 | 33.233 | −4.341 | 1.00 | 18.97 |
| ATOM | 1822 | N | LEU | A | 381 | 52.241 | 35.171 | −5.171 | 1.00 | 19.92 |
| ATOM | 1823 | CA | LEU | A | 381 | 53.237 | 36.224 | −5.003 | 1.00 | 19.56 |
| ATOM | 1824 | C | LEU | A | 381 | 53.907 | 36.664 | −6.294 | 1.00 | 23.06 |
| ATOM | 1825 | O | LEU | A | 381 | 54.956 | 37.345 | −6.269 | 1.00 | 22.66 |
| ATOM | 1826 | CB | LEU | A | 381 | 54.264 | 35.871 | −3.901 | 1.00 | 20.08 |
| ATOM | 1827 | CG | LEU | A | 381 | 53.628 | 35.722 | −2.501 | 1.00 | 22.95 |
| ATOM | 1828 | CD1 | LEU | A | 381 | 54.649 | 35.218 | −1.457 | 1.00 | 24.97 |
| ATOM | 1829 | CD2 | LEU | A | 381 | 52.959 | 36.994 | −2.011 | 1.00 | 24.88 |
| ATOM | 1830 | N | ILE | A | 382 | 53.290 | 36.317 | −7.410 | 1.00 | 21.21 |
| ATOM | 1831 | CA | ILE | A | 382 | 53.759 | 36.783 | −8.721 | 1.00 | 21.34 |
| ATOM | 1832 | C | ILE | A | 382 | 53.642 | 38.313 | −8.671 | 1.00 | 25.37 |
| ATOM | 1833 | O | ILE | A | 382 | 52.677 | 38.859 | −8.127 | 1.00 | 24.61 |
| ATOM | 1834 | CB | ILE | A | 382 | 52.926 | 36.160 | −9.874 | 1.00 | 24.30 |
| ATOM | 1835 | CG1 | ILE | A | 382 | 53.455 | 34.741 | −10.204 | 1.00 | 24.74 |
| ATOM | 1836 | CG2 | ILE | A | 382 | 52.967 | 37.059 | −11.129 | 1.00 | 26.21 |
| ATOM | 1837 | CD1 | ILE | A | 382 | 52.461 | 33.854 | −10.989 | 1.00 | 25.51 |
| ATOM | 1838 | N | LYS | A | 383 | 54.681 | 39.010 | −9.142 | 1.00 | 23.86 |
| ATOM | 1839 | CA | LYS | A | 383 | 54.727 | 40.465 | −9.027 | 1.00 | 24.71 |
| ATOM | 1840 | C | LYS | A | 383 | 53.651 | 41.191 | −9.855 | 1.00 | 27.50 |
| ATOM | 1841 | O | LYS | A | 383 | 53.072 | 42.187 | −9.403 | 1.00 | 26.84 |
| ATOM | 1842 | CB | LYS | A | 383 | 56.119 | 40.960 | −9.449 | 1.00 | 27.36 |
| ATOM | 1843 | CG | LYS | A | 383 | 57.082 | 41.229 | −8.289 | 1.00 | 43.23 |
| ATOM | 1844 | CD | LYS | A | 383 | 57.396 | 40.001 | −7.488 | 1.00 | 40.21 |
| ATOM | 1845 | CE | LYS | A | 383 | 58.823 | 40.076 | −6.904 | 1.00 | 32.26 |
| ATOM | 1846 | NZ | LYS | A | 383 | 58.825 | 40.056 | −5.398 | 1.00 | 32.19 |
| ATOM | 1847 | N | ASP | A | 384 | 53.441 | 40.718 | −11.082 | 1.00 | 26.53 |
| ATOM | 1848 | CA | ASP | A | 384 | 52.471 | 41.331 | −12.011 | 1.00 | 25.32 |
| ATOM | 1849 | C | ASP | A | 384 | 51.065 | 40.804 | −11.702 | 1.00 | 27.95 |
| ATOM | 1850 | O | ASP | A | 384 | 50.800 | 39.600 | −11.855 | 1.00 | 26.27 |
| ATOM | 1851 | CB | ASP | A | 384 | 52.867 | 40.979 | −13.455 | 1.00 | 26.76 |
| ATOM | 1852 | CG | ASP | A | 384 | 51.923 | 41.581 | −14.488 | 1.00 | 31.50 |
| ATOM | 1853 | OD1 | ASP | A | 384 | 50.929 | 42.237 | −14.096 | 1.00 | 28.14 |
| ATOM | 1854 | OD2 | ASP | A | 384 | 52.193 | 41.398 | −15.701 | 1.00 | 35.19 |
| ATOM | 1855 | N | PRO | A | 385 | 50.167 | 41.682 | −11.268 | 1.00 | 24.77 |
| ATOM | 1856 | CA | PRO | A | 385 | 48.822 | 41.218 | −10.848 | 1.00 | 24.95 |
| ATOM | 1857 | C | PRO | A | 385 | 48.010 | 40.549 | −11.943 | 1.00 | 29.24 |
| ATOM | 1858 | O | PRO | A | 385 | 47.133 | 39.719 | −11.658 | 1.00 | 28.03 |
| ATOM | 1859 | CB | PRO | A | 385 | 48.137 | 42.486 | −10.343 | 1.00 | 26.54 |
| ATOM | 1860 | CG | PRO | A | 385 | 48.931 | 43.633 | −10.973 | 1.00 | 31.13 |
| ATOM | 1861 | CD | PRO | A | 385 | 50.339 | 43.139 | −11.081 | 1.00 | 26.63 |
| ATOM | 1862 | N | ASN | A | 386 | 48.285 | 40.904 | −13.202 | 1.00 | 27.11 |
| ATOM | 1863 | CA | ASN | A | 386 | 47.577 | 40.274 | −14.321 | 1.00 | 27.34 |
| ATOM | 1864 | C | ASN | A | 386 | 47.964 | 38.814 | −14.483 | 1.00 | 30.72 |
| ATOM | 1865 | O | ASN | A | 386 | 47.205 | 38.024 | −15.042 | 1.00 | 32.48 |
| ATOM | 1866 | CB | ASN | A | 386 | 47.889 | 41.014 | −15.626 | 1.00 | 29.32 |

TABLE 2-continued

| | | | | | | | | | |
|---|---|---|---|---|---|---|---|---|---|
| ATOM | 1867 | CG | ASN | A | 386 | 47.571 | 42.473 | −15.542 | 1.00 | 49.58 |
| ATOM | 1868 | OD1 | ASN | A | 386 | 46.435 | 42.851 | −15.257 | 1.00 | 41.53 |
| ATOM | 1869 | ND2 | ASN | A | 386 | 48.584 | 43.310 | −15.724 | 1.00 | 46.81 |
| ATOM | 1870 | N | LYS | A | 387 | 49.172 | 38.478 | −14.038 | 1.00 | 25.69 |
| ATOM | 1871 | CA | LYS | A | 387 | 49.721 | 37.138 | −14.180 | 1.00 | 24.50 |
| ATOM | 1872 | C | LYS | A | 387 | 49.622 | 36.317 | −12.885 | 1.00 | 27.03 |
| ATOM | 1873 | O | LYS | A | 387 | 49.901 | 35.118 | −12.878 | 1.00 | 26.33 |
| ATOM | 1874 | CB | LYS | A | 387 | 51.200 | 37.236 | −14.600 | 1.00 | 26.45 |
| ATOM | 1875 | CG | LYS | A | 387 | 51.403 | 37.872 | −16.001 | 1.00 | 35.45 |
| ATOM | 1876 | CD | LYS | A | 387 | 52.798 | 37.619 | −16.521 | 1.00 | 45.26 |
| ATOM | 1877 | CE | LYS | A | 387 | 52.948 | 38.103 | −17.952 | 1.00 | 56.91 |
| ATOM | 1878 | NZ | LYS | A | 387 | 53.644 | 37.094 | −18.798 | 1.00 | 71.26 |
| ATOM | 1879 | N | ARG | A | 388 | 49.256 | 36.986 | −11.798 | 1.00 | 22.12 |
| ATOM | 1880 | CA | ARG | A | 388 | 49.179 | 36.366 | −10.463 | 1.00 | 20.01 |
| ATOM | 1881 | C | ARG | A | 388 | 48.069 | 35.345 | −10.387 | 1.00 | 21.19 |
| ATOM | 1882 | O | ARG | A | 388 | 47.032 | 35.475 | −11.044 | 1.00 | 21.68 |
| ATOM | 1883 | CB | ARG | A | 388 | 48.918 | 37.460 | −9.433 | 1.00 | 19.76 |
| ATOM | 1884 | CG | ARG | A | 388 | 49.040 | 37.034 | −7.955 | 1.00 | 20.54 |
| ATOM | 1885 | CD | ARG | A | 388 | 48.903 | 38.264 | −7.039 | 1.00 | 20.83 |
| ATOM | 1886 | NE | ARG | A | 388 | 49.983 | 39.236 | −7.291 | 1.00 | 21.72 |
| ATOM | 1887 | CZ | ARG | A | 388 | 49.851 | 40.554 | −7.186 | 1.00 | 26.76 |
| ATOM | 1888 | NH1 | ARG | A | 388 | 48.683 | 41.082 | −6.810 | 1.00 | 22.43 |
| ATOM | 1889 | NH2 | ARG | A | 388 | 50.889 | 41.353 | −7.476 | 1.00 | 23.93 |
| ATOM | 1890 | N | LEU | A | 389 | 48.266 | 34.335 | −9.542 | 1.00 | 18.17 |
| ATOM | 1891 | CA | LEU | A | 389 | 47.217 | 33.337 | −9.323 | 1.00 | 18.33 |
| ATOM | 1892 | C | LEU | A | 389 | 46.024 | 34.068 | −8.668 | 1.00 | 21.38 |
| ATOM | 1893 | O | LEU | A | 389 | 46.183 | 34.732 | −7.604 | 1.00 | 21.90 |
| ATOM | 1894 | CB | LEU | A | 389 | 47.756 | 32.242 | −8.380 | 1.00 | 17.62 |
| ATOM | 1895 | CG | LEU | A | 389 | 46.841 | 31.040 | −8.127 | 1.00 | 20.98 |
| ATOM | 1896 | CD1 | LEU | A | 389 | 46.643 | 30.248 | −9.413 | 1.00 | 20.97 |
| ATOM | 1897 | CD2 | LEU | A | 389 | 47.460 | 30.165 | −7.028 | 1.00 | 21.44 |
| ATOM | 1898 | N | GLY | A | 390 | 44.843 | 33.919 | −9.274 | 1.00 | 18.99 |
| ATOM | 1899 | CA | GLY | A | 390 | 43.623 | 34.586 | −8.800 | 1.00 | 20.05 |
| ATOM | 1900 | C | GLY | A | 390 | 43.399 | 35.926 | −9.526 | 1.00 | 24.20 |
| ATOM | 1901 | O | GLY | A | 390 | 42.345 | 36.528 | −9.408 | 1.00 | 21.87 |
| ATOM | 1902 | N | GLY | A | 391 | 44.386 | 36.343 | −10.308 | 1.00 | 23.94 |
| ATOM | 1903 | CA | GLY | A | 391 | 44.320 | 37.622 | −11.031 | 1.00 | 24.35 |
| ATOM | 1904 | C | GLY | A | 391 | 43.539 | 37.591 | −12.354 | 1.00 | 27.95 |
| ATOM | 1905 | O | GLY | A | 391 | 43.232 | 38.649 | −12.905 | 1.00 | 27.70 |
| ATOM | 1906 | N | GLY | A | 392 | 43.242 | 36.385 | −12.860 | 1.00 | 24.91 |
| ATOM | 1907 | CA | GLY | A | 392 | 42.491 | 36.206 | −14.108 | 1.00 | 24.45 |
| ATOM | 1908 | C | GLY | A | 392 | 40.999 | 36.434 | −13.858 | 1.00 | 25.89 |
| ATOM | 1909 | O | GLY | A | 392 | 40.587 | 36.739 | −12.717 | 1.00 | 23.73 |
| ATOM | 1910 | N | PRO | A | 393 | 40.184 | 36.330 | −14.914 | 1.00 | 23.61 |
| ATOM | 1911 | CA | PRO | A | 393 | 38.767 | 36.619 | −14.805 | 1.00 | 23.90 |
| ATOM | 1912 | C | PRO | A | 393 | 37.971 | 35.679 | −13.911 | 1.00 | 26.63 |
| ATOM | 1913 | O | PRO | A | 393 | 36.882 | 36.037 | −13.463 | 1.00 | 27.63 |
| ATOM | 1914 | CB | PRO | A | 393 | 38.272 | 36.546 | −16.263 | 1.00 | 25.85 |
| ATOM | 1915 | CG | PRO | A | 393 | 39.232 | 35.607 | −16.917 | 1.00 | 28.99 |
| ATOM | 1916 | CD | PRO | A | 393 | 40.564 | 35.978 | −16.302 | 1.00 | 24.51 |
| ATOM | 1917 | N | ASP | A | 394 | 38.506 | 34.476 | −13.639 | 1.00 | 20.88 |
| ATOM | 1918 | CA | ASP | A | 394 | 37.787 | 33.534 | −12.741 | 1.00 | 18.41 |
| ATOM | 1919 | C | ASP | A | 394 | 38.134 | 33.778 | −11.258 | 1.00 | 21.41 |
| ATOM | 1920 | O | ASP | A | 394 | 37.588 | 33.116 | −10.376 | 1.00 | 21.23 |
| ATOM | 1921 | CB | ASP | A | 394 | 38.057 | 32.083 | −13.097 | 1.00 | 19.97 |
| ATOM | 1922 | CG | ASP | A | 394 | 36.769 | 31.247 | −13.200 | 1.00 | 24.89 |
| ATOM | 1923 | OD1 | ASP | A | 394 | 36.877 | 30.031 | −13.448 | 1.00 | 25.68 |
| ATOM | 1924 | OD2 | ASP | A | 394 | 35.643 | 31.800 | −12.994 | 1.00 | 29.60 |
| ATOM | 1925 | N | ASP | A | 395 | 39.054 | 34.707 | −11.014 | 1.00 | 18.91 |
| ATOM | 1926 | CA | ASP | A | 395 | 39.361 | 35.151 | −9.645 | 1.00 | 17.72 |
| ATOM | 1927 | C | ASP | A | 395 | 39.616 | 33.985 | −8.711 | 1.00 | 18.58 |
| ATOM | 1928 | O | ASP | A | 395 | 40.483 | 33.167 | −8.959 | 1.00 | 18.22 |
| ATOM | 1929 | CB | ASP | A | 395 | 38.217 | 35.998 | −9.124 | 1.00 | 18.51 |
| ATOM | 1930 | CG | ASP | A | 395 | 38.577 | 36.769 | −7.845 | 1.00 | 19.54 |
| ATOM | 1931 | OD1 | ASP | A | 395 | 39.555 | 37.547 | −7.867 | 1.00 | 20.30 |
| ATOM | 1932 | OD2 | ASP | A | 395 | 37.836 | 36.596 | −6.872 | 1.00 | 23.19 |
| ATOM | 1933 | N | ALA | A | 396 | 38.887 | 33.936 | −7.611 | 1.00 | 16.73 |
| ATOM | 1934 | CA | ALA | A | 396 | 39.146 | 32.884 | −6.586 | 1.00 | 16.13 |
| ATOM | 1935 | C | ALA | A | 396 | 39.123 | 31.465 | −7.136 | 1.00 | 18.91 |
| ATOM | 1936 | O | ALA | A | 396 | 39.724 | 30.572 | −6.551 | 1.00 | 18.11 |
| ATOM | 1937 | CB | ALA | A | 396 | 38.134 | 33.014 | −5.396 | 1.00 | 17.36 |
| ATOM | 1938 | N | LYS | A | 397 | 38.346 | 31.215 | −8.203 | 1.00 | 18.28 |
| ATOM | 1939 | CA | LYS | A | 397 | 38.284 | 29.849 | −8.732 | 1.00 | 18.32 |
| ATOM | 1940 | C | LYS | A | 397 | 39.635 | 29.330 | −9.211 | 1.00 | 19.51 |
| ATOM | 1941 | O | LYS | A | 397 | 39.896 | 28.120 | −9.158 | 1.00 | 18.87 |
| ATOM | 1942 | CB | LYS | A | 397 | 37.208 | 29.710 | −9.813 | 1.00 | 21.45 |
| ATOM | 1943 | CG | LYS | A | 397 | 35.796 | 29.832 | −9.270 | 1.00 | 27.61 |
| ATOM | 1944 | CD | LYS | A | 397 | 35.512 | 31.199 | −8.715 | 1.00 | 38.09 |
| ATOM | 1945 | CE | LYS | A | 397 | 34.231 | 31.192 | −7.875 | 1.00 | 49.53 |
| ATOM | 1946 | NZ | LYS | A | 397 | 33.392 | 32.397 | −8.136 | 1.00 | 55.46 |

TABLE 2-continued

| | | | | | | | | | |
|---|---|---|---|---|---|---|---|---|---|
| ATOM | 1947 | N | GLU | A | 398 | 40.514 | 30.239 | −9.607 | 1.00 | 17.82 |
| ATOM | 1948 | CA | GLU | A | 398 | 41.880 | 29.863 | −10.001 | 1.00 | 18.17 |
| ATOM | 1949 | C | GLU | A | 398 | 42.597 | 29.201 | −8.825 | 1.00 | 20.19 |
| ATOM | 1950 | O | GLU | A | 398 | 43.372 | 28.219 | −8.996 | 1.00 | 19.84 |
| ATOM | 1951 | CB | GLU | A | 398 | 42.673 | 31.095 | −10.424 | 1.00 | 20.89 |
| ATOM | 1952 | CG | GLU | A | 398 | 42.260 | 31.681 | −11.716 | 1.00 | 26.39 |
| ATOM | 1953 | CD | GLU | A | 398 | 43.314 | 32.630 | −12.281 | 1.00 | 33.11 |
| ATOM | 1954 | OE1 | GLU | A | 398 | 44.491 | 32.554 | −11.867 | 1.00 | 26.42 |
| ATOM | 1955 | OE2 | GLU | A | 398 | 42.980 | 33.411 | −13.176 | 1.00 | 35.12 |
| ATOM | 1956 | N | ILE | A | 399 | 42.419 | 29.792 | −7.650 | 1.00 | 16.52 |
| ATOM | 1957 | CA | ILE | A | 399 | 43.033 | 29.268 | −6.452 | 1.00 | 15.42 |
| ATOM | 1958 | C | ILE | A | 399 | 42.328 | 27.990 | −5.997 | 1.00 | 17.69 |
| ATOM | 1959 | O | ILE | A | 399 | 42.967 | 27.034 | −5.598 | 1.00 | 18.01 |
| ATOM | 1960 | CB | ILE | A | 399 | 43.034 | 30.302 | −5.312 | 1.00 | 18.23 |
| ATOM | 1961 | CG1 | ILE | A | 399 | 43.955 | 31.459 | −5.697 | 1.00 | 20.60 |
| ATOM | 1962 | CG2 | ILE | A | 399 | 43.493 | 29.639 | −3.992 | 1.00 | 18.02 |
| ATOM | 1963 | CD1 | ILE | A | 399 | 43.354 | 32.782 | −5.497 | 1.00 | 32.21 |
| ATOM | 1964 | N | MET | A | 400 | 41.002 | 27.980 | −6.046 | 1.00 | 14.36 |
| ATOM | 1965 | CA | MET | A | 400 | 40.246 | 26.807 | −5.632 | 1.00 | 14.02 |
| ATOM | 1966 | C | MET | A | 400 | 40.628 | 25.572 | −6.472 | 1.00 | 17.45 |
| ATOM | 1967 | O | MET | A | 400 | 40.566 | 24.437 | −5.973 | 1.00 | 19.70 |
| ATOM | 1968 | CB | MET | A | 400 | 38.751 | 27.074 | −5.738 | 1.00 | 17.02 |
| ATOM | 1969 | CG | MET | A | 400 | 38.317 | 28.134 | −4.783 | 1.00 | 19.72 |
| ATOM | 1970 | SD | MET | A | 400 | 36.607 | 28.632 | −5.162 | 1.00 | 25.33 |
| ATOM | 1971 | CE | MET | A | 400 | 36.231 | 29.666 | −3.680 | 1.00 | 24.54 |
| ATOM | 1972 | N | ARG | A | 401 | 41.016 | 25.807 | −7.735 | 1.00 | 16.01 |
| ATOM | 1973 | CA | ARG | A | 401 | 41.421 | 24.723 | −8.636 | 1.00 | 17.36 |
| ATOM | 1974 | C | ARG | A | 401 | 42.893 | 24.337 | −8.498 | 1.00 | 21.48 |
| ATOM | 1975 | O | ARG | A | 401 | 43.353 | 23.381 | −9.156 | 1.00 | 20.58 |
| ATOM | 1976 | CB | ARG | A | 401 | 41.126 | 25.093 | −10.102 | 1.00 | 16.88 |
| ATOM | 1977 | CG | ARG | A | 401 | 39.652 | 25.144 | −10.413 | 1.00 | 24.15 |
| ATOM | 1978 | CD | ARG | A | 401 | 39.451 | 25.231 | −11.925 | 1.00 | 26.40 |
| ATOM | 1979 | NE | ARG | A | 401 | 40.017 | 26.446 | −12.501 | 1.00 | 22.46 |
| ATOM | 1980 | CZ | ARG | A | 401 | 39.296 | 27.531 | −12.786 | 1.00 | 24.41 |
| ATOM | 1981 | NH1 | ARG | A | 401 | 38.011 | 27.555 | −12.501 | 1.00 | 24.23 |
| ATOM | 1982 | NH2 | ARG | A | 401 | 39.871 | 28.579 | −13.333 | 1.00 | 24.74 |
| ATOM | 1983 | N | HIS | A | 402 | 43.651 | 25.092 | −7.708 | 1.00 | 18.16 |
| ATOM | 1984 | CA | HIS | A | 402 | 45.079 | 24.813 | −7.580 | 1.00 | 16.42 |
| ATOM | 1985 | C | HIS | A | 402 | 45.382 | 23.466 | −6.929 | 1.00 | 18.33 |
| ATOM | 1986 | O | HIS | A | 402 | 44.657 | 23.013 | −6.009 | 1.00 | 16.58 |
| ATOM | 1987 | CB | HIS | A | 402 | 45.817 | 25.977 | −6.825 | 1.00 | 16.75 |
| ATOM | 1988 | CG | HIS | A | 402 | 47.319 | 25.879 | −6.881 | 1.00 | 19.22 |
| ATOM | 1989 | ND1 | HIS | A | 402 | 48.046 | 25.072 | −6.029 | 1.00 | 20.99 |
| ATOM | 1990 | CD2 | HIS | A | 402 | 48.220 | 26.455 | −7.718 | 1.00 | 20.69 |
| ATOM | 1991 | CE1 | HIS | A | 402 | 49.333 | 25.158 | −6.332 | 1.00 | 20.52 |
| ATOM | 1992 | NE2 | HIS | A | 402 | 49.467 | 25.984 | −7.363 | 1.00 | 20.53 |
| ATOM | 1993 | N | SER | A | 403 | 46.458 | 22.795 | −7.396 | 1.00 | 17.66 |
| ATOM | 1994 | CA | SER | A | 403 | 46.828 | 21.504 | −6.805 | 1.00 | 17.45 |
| ATOM | 1995 | C | SER | A | 403 | 46.910 | 21.473 | −5.271 | 1.00 | 17.73 |
| ATOM | 1996 | O | SER | A | 403 | 46.602 | 20.463 | −4.653 | 1.00 | 19.65 |
| ATOM | 1997 | CB | SER | A | 403 | 48.153 | 20.978 | −7.389 | 1.00 | 23.50 |
| ATOM | 1998 | OG | SER | A | 403 | 49.240 | 21.814 | −7.012 | 1.00 | 31.49 |
| ATOM | 1999 | N | PHE | A | 404 | 47.380 | 22.563 | −4.658 | 1.00 | 15.27 |
| ATOM | 2000 | CA | PHE | A | 404 | 47.490 | 22.615 | −3.202 | 1.00 | 14.69 |
| ATOM | 2001 | C | PHE | A | 404 | 46.162 | 22.375 | −2.499 | 1.00 | 17.72 |
| ATOM | 2002 | O | PHE | A | 404 | 46.126 | 21.881 | −1.369 | 1.00 | 17.74 |
| ATOM | 2003 | CB | PHE | A | 404 | 48.113 | 23.942 | −2.738 | 1.00 | 16.12 |
| ATOM | 2004 | CG | PHE | A | 404 | 48.332 | 24.025 | −1.246 | 1.00 | 16.19 |
| ATOM | 2005 | CD1 | PHE | A | 404 | 49.441 | 23.402 | −0.648 | 1.00 | 18.28 |
| ATOM | 2006 | CD2 | PHE | A | 404 | 47.426 | 24.695 | −0.422 | 1.00 | 15.43 |
| ATOM | 2007 | CE1 | PHE | A | 404 | 49.645 | 23.460 | 0.724 | 1.00 | 19.19 |
| ATOM | 2008 | CE2 | PHE | A | 404 | 47.639 | 24.776 | 0.970 | 1.00 | 18.23 |
| ATOM | 2009 | CZ | PHE | A | 404 | 48.746 | 24.136 | 1.544 | 1.00 | 18.13 |
| ATOM | 2010 | N | PHE | A | 405 | 45.067 | 22.705 | −3.166 | 1.00 | 15.02 |
| ATOM | 2011 | CA | PHE | A | 405 | 43.708 | 22.540 | −2.544 | 1.00 | 14.93 |
| ATOM | 2012 | C | PHE | A | 405 | 42.932 | 21.367 | −3.180 | 1.00 | 20.24 |
| ATOM | 2013 | O | PHE | A | 405 | 41.694 | 21.302 | −3.102 | 1.00 | 18.70 |
| ATOM | 2014 | CB | PHE | A | 405 | 42.906 | 23.837 | −2.734 | 1.00 | 15.04 |
| ATOM | 2015 | CG | PHE | A | 405 | 43.397 | 24.983 | −1.873 | 1.00 | 14.66 |
| ATOM | 2016 | CD1 | PHE | A | 405 | 43.256 | 24.943 | −0.477 | 1.00 | 15.37 |
| ATOM | 2017 | CD2 | PHE | A | 405 | 44.014 | 26.087 | −2.452 | 1.00 | 15.44 |
| ATOM | 2018 | CE1 | PHE | A | 405 | 43.707 | 26.029 | 0.320 | 1.00 | 16.35 |
| ATOM | 2019 | CE2 | PHE | A | 405 | 44.468 | 27.155 | −1.662 | 1.00 | 17.15 |
| ATOM | 2020 | CZ | PHE | A | 405 | 44.307 | 27.118 | −0.279 | 1.00 | 15.70 |
| ATOM | 2021 | N | SER | A | 406 | 43.637 | 20.480 | −3.869 | 1.00 | 19.86 |
| ATOM | 2022 | CA | SER | A | 406 | 42.983 | 19.411 | −4.612 | 1.00 | 20.40 |
| ATOM | 2023 | C | SER | A | 406 | 42.045 | 18.488 | −3.857 | 1.00 | 23.73 |
| ATOM | 2024 | O | SER | A | 406 | 41.217 | 17.795 | −4.478 | 1.00 | 25.12 |
| ATOM | 2025 | CB | SER | A | 406 | 44.018 | 18.588 | −5.415 | 1.00 | 22.81 |
| ATOM | 2026 | OG | SER | A | 406 | 44.874 | 17.913 | −4.538 | 1.00 | 25.19 |

TABLE 2-continued

| | | | | | | | | | |
|---|---|---|---|---|---|---|---|---|---|
| ATOM | 2027 | N | GLY | A | 407 | 42.164 | 18.431 | −2.548 | 1.00 | 20.77 |
| ATOM | 2028 | CA | GLY | A | 407 | 41.289 | 17.525 | −1.768 | 1.00 | 21.30 |
| ATOM | 2029 | C | GLY | A | 407 | 40.134 | 18.249 | −1.114 | 1.00 | 23.29 |
| ATOM | 2030 | O | GLY | A | 407 | 39.382 | 17.652 | −0.329 | 1.00 | 25.09 |
| ATOM | 2031 | N | VAL | A | 408 | 40.022 | 19.550 | −1.390 | 1.00 | 16.69 |
| ATOM | 2032 | CA | VAL | A | 408 | 39.053 | 20.390 | −0.699 | 1.00 | 15.22 |
| ATOM | 2033 | C | VAL | A | 408 | 37.703 | 20.500 | −1.405 | 1.00 | 18.60 |
| ATOM | 2034 | O | VAL | A | 408 | 37.637 | 20.796 | −2.599 | 1.00 | 18.05 |
| ATOM | 2035 | CB | VAL | A | 408 | 39.606 | 21.819 | −0.489 | 1.00 | 17.81 |
| ATOM | 2036 | CG1 | VAL | A | 408 | 38.498 | 22.728 | 0.071 | 1.00 | 17.81 |
| ATOM | 2037 | CG2 | VAL | A | 408 | 40.825 | 21.790 | 0.458 | 1.00 | 18.48 |
| ATOM | 2038 | N | ASN | A | 409 | 36.628 | 20.248 | −0.628 | 1.00 | 17.67 |
| ATOM | 2039 | CA | ASN | A | 409 | 35.261 | 20.428 | −1.107 | 1.00 | 17.19 |
| ATOM | 2040 | C | ASN | A | 409 | 34.853 | 21.853 | −0.689 | 1.00 | 18.14 |
| ATOM | 2041 | O | ASN | A | 409 | 34.790 | 22.151 | 0.487 | 1.00 | 18.23 |
| ATOM | 2042 | CB | ASN | A | 409 | 34.330 | 19.390 | −0.470 | 1.00 | 19.65 |
| ATOM | 2043 | CG | ASN | A | 409 | 32.890 | 19.569 | −0.917 | 1.00 | 25.94 |
| ATOM | 2044 | OD1 | ASN | A | 409 | 32.289 | 20.624 | −0.680 | 1.00 | 23.14 |
| ATOM | 2045 | ND2 | ASN | A | 409 | 32.383 | 18.612 | −1.711 | 1.00 | 21.56 |
| ATOM | 2046 | N | TRP | A | 410 | 34.707 | 22.763 | −1.672 | 1.00 | 17.26 |
| ATOM | 2047 | CA | TRP | A | 410 | 34.509 | 24.181 | −1.351 | 1.00 | 17.30 |
| ATOM | 2048 | C | TRP | A | 410 | 33.167 | 24.540 | −0.735 | 1.00 | 21.55 |
| ATOM | 2049 | O | TRP | A | 410 | 33.051 | 25.530 | −0.007 | 1.00 | 21.00 |
| ATOM | 2050 | CB | TRP | A | 410 | 34.840 | 25.054 | −2.551 | 1.00 | 16.16 |
| ATOM | 2051 | CG | TRP | A | 410 | 36.282 | 24.990 | −2.842 | 1.00 | 16.89 |
| ATOM | 2052 | CD1 | TRP | A | 410 | 36.924 | 24.075 | −3.649 | 1.00 | 20.04 |
| ATOM | 2053 | CD2 | TRP | A | 410 | 37.305 | 25.743 | −2.194 | 1.00 | 16.51 |
| ATOM | 2054 | NE1 | TRP | A | 410 | 38.288 | 24.249 | −3.569 | 1.00 | 19.27 |
| ATOM | 2055 | CE2 | TRP | A | 410 | 38.547 | 25.298 | −2.711 | 1.00 | 19.45 |
| ATOM | 2056 | CE3 | TRP | A | 410 | 37.298 | 26.805 | −1.277 | 1.00 | 17.11 |
| ATOM | 2057 | CZ2 | TRP | A | 410 | 39.760 | 25.808 | −2.262 | 1.00 | 17.89 |
| ATOM | 2058 | CZ3 | TRP | A | 410 | 38.510 | 27.347 | −0.861 | 1.00 | 18.54 |
| ATOM | 2059 | CH2 | TRP | A | 410 | 39.720 | 26.865 | −1.361 | 1.00 | 19.24 |
| ATOM | 2060 | N | GLN | A | 411 | 32.159 | 23.737 | −1.012 | 1.00 | 20.67 |
| ATOM | 2061 | CA | GLN | A | 411 | 30.884 | 24.001 | −0.371 | 1.00 | 20.81 |
| ATOM | 2062 | C | GLN | A | 411 | 30.986 | 23.638 | 1.100 | 1.00 | 21.59 |
| ATOM | 2063 | O | GLN | A | 411 | 30.514 | 24.374 | 1.931 | 1.00 | 21.86 |
| ATOM | 2064 | CB | GLN | A | 411 | 29.744 | 23.254 | −1.041 | 1.00 | 22.98 |
| ATOM | 2065 | CG | GLN | A | 411 | 28.355 | 23.565 | −0.379 | 1.00 | 26.59 |
| ATOM | 2066 | CD | GLN | A | 411 | 27.933 | 25.042 | −0.521 | 1.00 | 32.47 |
| ATOM | 2067 | OE1 | GLN | A | 411 | 27.429 | 25.661 | 0.432 | 1.00 | 34.09 |
| ATOM | 2068 | NE2 | GLN | A | 411 | 28.109 | 25.587 | −1.700 | 1.00 | 27.00 |
| ATOM | 2069 | N | ASP | A | 412 | 31.712 | 22.557 | 1.424 | 1.00 | 18.12 |
| ATOM | 2070 | CA | ASP | A | 412 | 31.946 | 22.190 | 2.824 | 1.00 | 17.22 |
| ATOM | 2071 | C | ASP | A | 412 | 32.750 | 23.295 | 3.523 | 1.00 | 21.14 |
| ATOM | 2072 | O | ASP | A | 412 | 32.578 | 23.552 | 4.695 | 1.00 | 20.57 |
| ATOM | 2073 | CB | ASP | A | 412 | 32.738 | 20.879 | 2.953 | 1.00 | 17.74 |
| ATOM | 2074 | CG | ASP | A | 412 | 31.876 | 19.643 | 2.764 | 1.00 | 23.95 |
| ATOM | 2075 | OD1 | ASP | A | 412 | 30.625 | 19.771 | 2.685 | 1.00 | 23.73 |
| ATOM | 2076 | OD2 | ASP | A | 412 | 32.465 | 18.546 | 2.649 | 1.00 | 22.68 |
| ATOM | 2077 | N | VAL | A | 413 | 33.663 | 23.927 | 2.799 | 1.00 | 17.57 |
| ATOM | 2078 | CA | VAL | A | 413 | 34.424 | 25.001 | 3.421 | 1.00 | 15.70 |
| ATOM | 2079 | C | VAL | A | 413 | 33.447 | 26.091 | 3.914 | 1.00 | 18.64 |
| ATOM | 2080 | O | VAL | A | 413 | 33.490 | 26.500 | 5.075 | 1.00 | 19.83 |
| ATOM | 2081 | CB | VAL | A | 413 | 35.405 | 25.661 | 2.395 | 1.00 | 18.07 |
| ATOM | 2082 | CG1 | VAL | A | 413 | 36.015 | 27.013 | 2.998 | 1.00 | 17.60 |
| ATOM | 2083 | CG2 | VAL | A | 413 | 36.535 | 24.686 | 2.028 | 1.00 | 17.46 |
| ATOM | 2084 | N | TYR | A | 414 | 32.601 | 26.571 | 3.014 | 1.00 | 18.72 |
| ATOM | 2085 | CA | TYR | A | 414 | 31.618 | 27.628 | 3.356 | 1.00 | 19.64 |
| ATOM | 2086 | C | TYR | A | 414 | 30.688 | 27.187 | 4.520 | 1.00 | 24.17 |
| ATOM | 2087 | O | TYR | A | 414 | 30.369 | 27.972 | 5.415 | 1.00 | 24.96 |
| ATOM | 2088 | CB | TYR | A | 414 | 30.771 | 27.942 | 2.135 | 1.00 | 20.64 |
| ATOM | 2089 | CG | TYR | A | 414 | 29.776 | 29.045 | 2.385 | 1.00 | 22.46 |
| ATOM | 2090 | CD1 | TYR | A | 414 | 28.517 | 28.762 | 2.876 | 1.00 | 24.55 |
| ATOM | 2091 | CD2 | TYR | A | 414 | 30.114 | 30.371 | 2.160 | 1.00 | 23.89 |
| ATOM | 2092 | CE1 | TYR | A | 414 | 27.616 | 29.792 | 3.161 | 1.00 | 25.66 |
| ATOM | 2093 | CE2 | TYR | A | 414 | 29.216 | 31.413 | 2.445 | 1.00 | 24.89 |
| ATOM | 2094 | CZ | TYR | A | 414 | 27.962 | 31.101 | 2.899 | 1.00 | 30.84 |
| ATOM | 2095 | OH | TYR | A | 414 | 27.069 | 32.112 | 3.174 | 1.00 | 32.51 |
| ATOM | 2096 | N | ASP | A | 415 | 30.251 | 25.932 | 4.476 | 1.00 | 20.31 |
| ATOM | 2097 | CA | ASP | A | 415 | 29.318 | 25.383 | 5.474 | 1.00 | 20.77 |
| ATOM | 2098 | C | ASP | A | 415 | 29.983 | 24.991 | 6.814 | 1.00 | 25.10 |
| ATOM | 2099 | O | ASP | A | 415 | 29.334 | 24.407 | 7.722 | 1.00 | 23.85 |
| ATOM | 2100 | CB | ASP | A | 415 | 28.543 | 24.202 | 4.868 | 1.00 | 22.34 |
| ATOM | 2101 | CG | ASP | A | 415 | 27.609 | 24.626 | 3.727 | 1.00 | 27.24 |
| ATOM | 2102 | OD1 | ASP | A | 415 | 27.121 | 25.773 | 3.742 | 1.00 | 31.03 |
| ATOM | 2103 | OD2 | ASP | A | 415 | 27.323 | 23.799 | 2.848 | 1.00 | 27.43 |
| ATOM | 2104 | N | LYS | A | 416 | 31.260 | 25.345 | 6.961 | 1.00 | 21.78 |
| ATOM | 2105 | CA | LYS | A | 416 | 32.040 | 25.035 | 8.171 | 1.00 | 22.39 |
| ATOM | 2106 | C | LYS | A | 416 | 32.028 | 23.550 | 8.503 | 1.00 | 26.48 |

TABLE 2-continued

| | | | | | | | | | |
|---|---|---|---|---|---|---|---|---|---|
| ATOM | 2107 | O | LYS | A | 416 | 31.927 | 23.162 | 9.665 | 1.00 | 27.15 |
| ATOM | 2108 | CB | LYS | A | 416 | 31.542 | 25.874 | 9.368 | 1.00 | 24.11 |
| ATOM | 2109 | CG | LYS | A | 416 | 31.861 | 27.337 | 9.213 | 1.00 | 28.95 |
| ATOM | 2110 | CD | LYS | A | 416 | 31.041 | 28.231 | 10.166 | 1.00 | 32.95 |
| ATOM | 2111 | CE | LYS | A | 416 | 31.472 | 28.119 | 11.611 | 1.00 | 39.83 |
| ATOM | 2112 | NZ | LYS | A | 416 | 30.648 | 29.066 | 12.490 | 1.00 | 33.68 |
| ATOM | 2113 | N | LYS | A | 417 | 32.192 | 22.722 | 7.471 | 1.00 | 23.03 |
| ATOM | 2114 | CA | LYS | A | 417 | 32.189 | 21.276 | 7.649 | 1.00 | 23.26 |
| ATOM | 2115 | C | LYS | A | 417 | 33.625 | 20.713 | 7.596 | 1.00 | 29.02 |
| ATOM | 2116 | O | LYS | A | 417 | 33.841 | 19.522 | 7.855 | 1.00 | 31.21 |
| ATOM | 2117 | CB | LYS | A | 417 | 31.310 | 20.605 | 6.607 | 1.00 | 24.83 |
| ATOM | 2118 | CG | LYS | A | 417 | 29.816 | 20.913 | 6.772 | 1.00 | 33.11 |
| ATOM | 2119 | CD | LYS | A | 417 | 29.001 | 20.047 | 5.840 | 1.00 | 36.15 |
| ATOM | 2120 | CE | LYS | A | 417 | 27.541 | 20.471 | 5.802 | 1.00 | 43.52 |
| ATOM | 2121 | NZ | LYS | A | 417 | 26.869 | 20.028 | 4.532 | 1.00 | 39.87 |
| ATOM | 2122 | N | LEU | A | 418 | 34.600 | 21.557 | 7.285 | 1.00 | 26.47 |
| ATOM | 2123 | CA | LEU | A | 418 | 36.004 | 21.098 | 7.372 | 1.00 | 26.76 |
| ATOM | 2124 | C | LEU | A | 418 | 36.328 | 21.021 | 8.891 | 1.00 | 29.01 |
| ATOM | 2125 | O | LEU | A | 418 | 35.898 | 21.868 | 9.678 | 1.00 | 26.14 |
| ATOM | 2126 | CB | LEU | A | 418 | 36.975 | 22.074 | 6.671 | 1.00 | 27.64 |
| ATOM | 2127 | CG | LEU | A | 418 | 37.020 | 22.171 | 5.133 | 1.00 | 32.99 |
| ATOM | 2128 | CD1 | LEU | A | 418 | 38.305 | 22.878 | 4.688 | 1.00 | 33.43 |
| ATOM | 2129 | CD2 | LEU | A | 418 | 36.898 | 20.850 | 4.470 | 1.00 | 35.72 |
| ATOM | 2130 | N | VAL | A | 419 | 37.051 | 19.981 | 9.304 | 1.00 | 26.64 |
| ATOM | 2131 | CA | VAL | A | 419 | 37.394 | 19.827 | 10.710 | 1.00 | 26.11 |
| ATOM | 2132 | C | VAL | A | 419 | 38.591 | 20.685 | 11.051 | 1.00 | 26.22 |
| ATOM | 2133 | O | VAL | A | 419 | 39.662 | 20.528 | 10.462 | 1.00 | 25.53 |
| ATOM | 2134 | CB | VAL | A | 419 | 37.759 | 18.373 | 11.054 | 1.00 | 30.89 |
| ATOM | 2135 | CG1 | VAL | A | 419 | 38.081 | 18.282 | 12.538 | 1.00 | 30.29 |
| ATOM | 2136 | CG2 | VAL | A | 419 | 36.635 | 17.435 | 10.674 | 1.00 | 31.80 |
| ATOM | 2137 | N | PRO | A | 420 | 38.412 | 21.650 | 11.952 | 1.00 | 23.32 |
| ATOM | 2138 | CA | PRO | A | 420 | 39.537 | 22.524 | 12.294 | 1.00 | 22.48 |
| ATOM | 2139 | C | PRO | A | 420 | 40.676 | 21.726 | 12.898 | 1.00 | 27.31 |
| ATOM | 2140 | O | PRO | A | 420 | 40.458 | 20.896 | 13.769 | 1.00 | 26.78 |
| ATOM | 2141 | CB | PRO | A | 420 | 38.948 | 23.491 | 13.319 | 1.00 | 24.68 |
| ATOM | 2142 | CG | PRO | A | 420 | 37.454 | 23.449 | 13.084 | 1.00 | 29.37 |
| ATOM | 2143 | CD | PRO | A | 420 | 37.180 | 22.020 | 12.667 | 1.00 | 24.66 |
| ATOM | 2144 | N | PRO | A | 421 | 41.895 | 21.997 | 12.455 | 1.00 | 26.51 |
| ATOM | 2145 | CA | PRO | A | 421 | 43.071 | 21.248 | 12.931 | 1.00 | 27.39 |
| ATOM | 2146 | C | PRO | A | 421 | 43.465 | 21.542 | 14.371 | 1.00 | 30.13 |
| ATOM | 2147 | O | PRO | A | 421 | 44.100 | 20.703 | 15.039 | 1.00 | 31.80 |
| ATOM | 2148 | CB | PRO | A | 421 | 44.182 | 21.695 | 11.972 | 1.00 | 29.87 |
| ATOM | 2149 | CG | PRO | A | 421 | 43.589 | 22.859 | 11.176 | 1.00 | 35.02 |
| ATOM | 2150 | CD | PRO | A | 421 | 42.137 | 22.567 | 11.124 | 1.00 | 29.25 |
| ATOM | 2151 | N | PHE | A | 422 | 43.128 | 22.740 | 14.831 | 1.00 | 24.54 |
| ATOM | 2152 | CA | PHE | A | 422 | 43.387 | 23.171 | 16.197 | 1.00 | 24.46 |
| ATOM | 2153 | C | PHE | A | 422 | 42.098 | 23.714 | 16.802 | 1.00 | 27.25 |
| ATOM | 2154 | O | PHE | A | 422 | 41.442 | 24.581 | 16.214 | 1.00 | 24.53 |
| ATOM | 2155 | CB | PHE | A | 422 | 44.467 | 24.270 | 16.226 | 1.00 | 26.56 |
| ATOM | 2156 | CG | PHE | A | 422 | 44.542 | 25.016 | 17.540 | 1.00 | 28.88 |
| ATOM | 2157 | CD1 | PHE | A | 422 | 45.173 | 24.452 | 18.636 | 1.00 | 32.36 |
| ATOM | 2158 | CD2 | PHE | A | 422 | 43.977 | 26.274 | 17.671 | 1.00 | 30.88 |
| ATOM | 2159 | CE1 | PHE | A | 422 | 45.231 | 25.129 | 19.862 | 1.00 | 34.41 |
| ATOM | 2160 | CE2 | PHE | A | 422 | 44.036 | 26.964 | 18.891 | 1.00 | 34.48 |
| ATOM | 2161 | CZ | PHE | A | 422 | 44.661 | 26.375 | 19.989 | 1.00 | 33.30 |
| ATOM | 2162 | N | LYS | A | 423 | 41.719 | 23.183 | 17.967 | 1.00 | 24.80 |
| ATOM | 2163 | CA | LYS | A | 423 | 40.537 | 23.641 | 18.678 | 1.00 | 25.91 |
| ATOM | 2164 | C | LYS | A | 423 | 40.959 | 24.518 | 19.885 | 1.00 | 32.50 |
| ATOM | 2165 | O | LYS | A | 423 | 41.620 | 24.031 | 20.827 | 1.00 | 32.07 |
| ATOM | 2166 | CB | LYS | A | 423 | 39.716 | 22.438 | 19.169 | 1.00 | 28.94 |
| ATOM | 2167 | CG | LYS | A | 423 | 39.437 | 21.395 | 18.089 | 1.00 | 38.50 |
| ATOM | 2168 | CD | LYS | A | 423 | 38.519 | 21.950 | 17.010 | 1.00 | 42.19 |
| ATOM | 2169 | CE | LYS | A | 423 | 37.057 | 21.897 | 17.451 | 1.00 | 43.22 |
| ATOM | 2170 | NZ | LYS | A | 423 | 36.111 | 22.337 | 16.384 | 1.00 | 42.96 |
| ATOM | 2171 | N | PRO | A | 424 | 40.614 | 25.806 | 19.851 | 1.00 | 28.91 |
| ATOM | 2172 | CA | PRO | A | 424 | 40.963 | 26.695 | 20.965 | 1.00 | 29.08 |
| ATOM | 2173 | C | PRO | A | 424 | 40.431 | 26.116 | 22.278 | 1.00 | 34.95 |
| ATOM | 2174 | O | PRO | A | 424 | 39.322 | 25.568 | 22.332 | 1.00 | 33.87 |
| ATOM | 2175 | CB | PRO | A | 424 | 40.225 | 27.994 | 20.619 | 1.00 | 30.14 |
| ATOM | 2176 | CG | PRO | A | 424 | 40.170 | 27.991 | 19.108 | 1.00 | 33.00 |
| ATOM | 2177 | CD | PRO | A | 424 | 39.914 | 26.532 | 18.764 | 1.00 | 29.40 |
| ATOM | 2178 | N | GLN | A | 425 | 41.221 | 26.245 | 23.332 | 1.00 | 35.98 |
| ATOM | 2179 | CA | GLN | A | 425 | 40.836 | 25.686 | 24.619 | 1.00 | 37.69 |
| ATOM | 2180 | C | GLN | A | 425 | 40.049 | 26.663 | 25.481 | 1.00 | 44.09 |
| ATOM | 2181 | O | GLN | A | 425 | 40.516 | 27.093 | 26.533 | 1.00 | 44.59 |
| ATOM | 2182 | CB | GLN | A | 425 | 42.062 | 25.158 | 25.362 | 1.00 | 39.49 |
| ATOM | 2183 | CG | GLN | A | 425 | 42.639 | 23.884 | 24.748 | 1.00 | 56.76 |
| ATOM | 2184 | CD | GLN | A | 425 | 41.585 | 22.810 | 24.542 | 1.00 | 78.98 |
| ATOM | 2185 | OE1 | GLN | A | 425 | 40.684 | 22.954 | 23.713 | 1.00 | 74.46 |
| ATOM | 2186 | NE2 | GLN | A | 425 | 41.687 | 21.727 | 25.306 | 1.00 | 73.56 |

TABLE 2-continued

| | | | | | | | | | |
|---|---|---|---|---|---|---|---|---|---|
| ATOM | 2187 | N | VAL | A | 426 | 38.846 | 26.993 | 25.026 | 1.00 | 41.18 |
| ATOM | 2188 | CA | VAL | A | 426 | 37.970 | 27.913 | 25.740 | 1.00 | 41.81 |
| ATOM | 2189 | C | VAL | A | 426 | 36.888 | 27.121 | 26.440 | 1.00 | 47.63 |
| ATOM | 2190 | O | VAL | A | 426 | 36.337 | 26.179 | 25.885 | 1.00 | 47.94 |
| ATOM | 2191 | CB | VAL | A | 426 | 37.303 | 28.922 | 24.781 | 1.00 | 45.42 |
| ATOM | 2192 | CG1 | VAL | A | 426 | 38.310 | 29.938 | 24.293 | 1.00 | 45.17 |
| ATOM | 2193 | CG2 | VAL | A | 426 | 36.652 | 28.194 | 23.608 | 1.00 | 45.27 |
| ATOM | 2194 | N | THR | A | 427 | 36.588 | 27.514 | 27.666 | 1.00 | 45.47 |
| ATOM | 2195 | CA | THR | A | 427 | 35.581 | 26.841 | 28.466 | 1.00 | 45.89 |
| ATOM | 2196 | C | THR | A | 427 | 34.174 | 27.222 | 28.025 | 1.00 | 50.12 |
| ATOM | 2197 | O | THR | A | 427 | 33.231 | 26.444 | 28.177 | 1.00 | 49.85 |
| ATOM | 2198 | CB | THR | A | 427 | 35.740 | 27.212 | 29.942 | 1.00 | 56.62 |
| ATOM | 2199 | OG1 | THR | A | 427 | 36.562 | 26.239 | 30.594 | 1.00 | 59.56 |
| ATOM | 2200 | CG2 | THR | A | 427 | 34.384 | 27.292 | 30.622 | 1.00 | 55.08 |
| ATOM | 2201 | N | SER | A | 428 | 34.032 | 28.434 | 27.502 | 1.00 | 46.29 |
| ATOM | 2202 | CA | SER | A | 428 | 32.729 | 28.935 | 27.086 | 1.00 | 45.86 |
| ATOM | 2203 | C | SER | A | 428 | 32.857 | 30.018 | 26.021 | 1.00 | 48.95 |
| ATOM | 2204 | O | SER | A | 428 | 33.960 | 30.425 | 25.670 | 1.00 | 48.11 |
| ATOM | 2205 | CB | SER | A | 428 | 31.979 | 29.495 | 28.290 | 1.00 | 49.10 |
| ATOM | 2206 | OG | SER | A | 428 | 32.572 | 30.698 | 28.740 | 1.00 | 56.29 |
| ATOM | 2207 | N | GLU | A | 429 | 31.711 | 30.491 | 25.536 | 1.00 | 45.47 |
| ATOM | 2208 | CA | GLU | A | 429 | 31.656 | 31.529 | 24.506 | 1.00 | 44.69 |
| ATOM | 2209 | C | GLU | A | 429 | 32.122 | 32.891 | 25.031 | 1.00 | 46.41 |
| ATOM | 2210 | O | GLU | A | 429 | 32.465 | 33.777 | 24.248 | 1.00 | 45.81 |
| ATOM | 2211 | CB | GLU | A | 429 | 30.227 | 31.655 | 23.961 | 1.00 | 46.20 |
| ATOM | 2212 | CG | GLU | A | 429 | 29.329 | 32.586 | 24.803 | 1.00 | 58.97 |
| ATOM | 2213 | CD | GLU | A | 429 | 27.848 | 32.239 | 24.707 | 1.00 | 80.51 |
| ATOM | 2214 | OE1 | GLU | A | 429 | 27.182 | 32.727 | 23.769 | 1.00 | 75.53 |
| ATOM | 2215 | OE2 | GLU | A | 429 | 27.343 | 31.520 | 25.596 | 1.00 | 74.88 |
| ATOM | 2216 | N | THR | A | 430 | 32.118 | 33.063 | 26.353 | 1.00 | 40.95 |
| ATOM | 2217 | CA | THR | A | 430 | 32.535 | 34.328 | 26.955 | 1.00 | 39.33 |
| ATOM | 2218 | C | THR | A | 430 | 33.964 | 34.295 | 27.494 | 1.00 | 39.86 |
| ATOM | 2219 | O | THR | A | 430 | 34.555 | 35.342 | 27.767 | 1.00 | 39.84 |
| ATOM | 2220 | CB | THR | A | 430 | 31.573 | 34.780 | 28.065 | 1.00 | 49.85 |
| ATOM | 2221 | OG1 | THR | A | 430 | 31.608 | 33.838 | 29.150 | 1.00 | 50.34 |
| ATOM | 2222 | CG2 | THR | A | 430 | 30.158 | 34.884 | 27.526 | 1.00 | 48.76 |
| ATOM | 2223 | N | ASP | A | 431 | 34.509 | 33.088 | 27.634 | 1.00 | 33.33 |
| ATOM | 2224 | CA | ASP | A | 431 | 35.880 | 32.879 | 28.103 | 1.00 | 32.29 |
| ATOM | 2225 | C | ASP | A | 431 | 36.853 | 33.847 | 27.430 | 1.00 | 35.23 |
| ATOM | 2226 | O | ASP | A | 431 | 36.954 | 33.890 | 26.196 | 1.00 | 35.11 |
| ATOM | 2227 | CB | ASP | A | 431 | 36.291 | 31.435 | 27.787 | 1.00 | 33.62 |
| ATOM | 2228 | CG | ASP | A | 431 | 37.545 | 31.004 | 28.511 | 1.00 | 38.97 |
| ATOM | 2229 | OD1 | ASP | A | 431 | 38.327 | 31.868 | 28.947 | 1.00 | 39.68 |
| ATOM | 2230 | OD2 | ASP | A | 431 | 37.786 | 29.775 | 28.568 | 1.00 | 46.60 |
| ATOM | 2231 | N | THR | A | 432 | 37.558 | 34.630 | 28.237 | 1.00 | 29.56 |
| ATOM | 2232 | CA | THR | A | 432 | 38.504 | 35.617 | 27.729 | 1.00 | 28.40 |
| ATOM | 2233 | C | THR | A | 432 | 39.945 | 35.134 | 27.799 | 1.00 | 32.07 |
| ATOM | 2234 | O | THR | A | 432 | 40.876 | 35.927 | 27.660 | 1.00 | 31.52 |
| ATOM | 2235 | CB | THR | A | 432 | 38.372 | 36.942 | 28.479 | 1.00 | 33.64 |
| ATOM | 2236 | OG1 | THR | A | 432 | 38.560 | 36.706 | 29.884 | 1.00 | 33.17 |
| ATOM | 2237 | CG2 | THR | A | 432 | 36.996 | 37.553 | 28.240 | 1.00 | 28.50 |
| ATOM | 2238 | N | ARG | A | 433 | 40.101 | 33.816 | 27.975 | 1.00 | 31.09 |
| ATOM | 2239 | CA | ARG | A | 433 | 41.388 | 33.133 | 28.056 | 1.00 | 32.69 |
| ATOM | 2240 | C | ARG | A | 433 | 42.432 | 33.698 | 27.093 | 1.00 | 35.99 |
| ATOM | 2241 | O | ARG | A | 433 | 43.501 | 34.139 | 27.496 | 1.00 | 35.67 |
| ATOM | 2242 | CB | ARG | A | 433 | 41.181 | 31.628 | 27.775 | 1.00 | 35.19 |
| ATOM | 2243 | CG | ARG | A | 433 | 42.446 | 30.796 | 27.795 | 1.00 | 49.56 |
| ATOM | 2244 | CD | ARG | A | 433 | 42.323 | 29.635 | 28.781 | 1.00 | 61.26 |
| ATOM | 2245 | NE | ARG | A | 433 | 40.965 | 29.089 | 28.833 | 1.00 | 68.25 |
| ATOM | 2246 | CZ | ARG | A | 433 | 40.587 | 28.098 | 29.637 | 1.00 | 82.33 |
| ATOM | 2247 | NH1 | ARG | A | 433 | 41.463 | 27.536 | 30.461 | 1.00 | 69.05 |
| ATOM | 2248 | NH2 | ARG | A | 433 | 39.331 | 27.675 | 29.623 | 1.00 | 71.18 |
| ATOM | 2249 | N | TYR | A | 434 | 42.104 | 33.718 | 25.812 | 1.00 | 31.97 |
| ATOM | 2250 | CA | TYR | A | 434 | 43.058 | 34.201 | 24.823 | 1.00 | 31.98 |
| ATOM | 2251 | C | TYR | A | 434 | 43.369 | 35.697 | 24.811 | 1.00 | 37.97 |
| ATOM | 2252 | O | TYR | A | 434 | 44.378 | 36.117 | 24.260 | 1.00 | 40.88 |
| ATOM | 2253 | CB | TYR | A | 434 | 42.723 | 33.652 | 23.440 | 1.00 | 31.80 |
| ATOM | 2254 | CG | TYR | A | 434 | 42.898 | 32.157 | 23.371 | 1.00 | 31.20 |
| ATOM | 2255 | CD1 | TYR | A | 434 | 41.809 | 31.309 | 23.401 | 1.00 | 32.53 |
| ATOM | 2256 | CD2 | TYR | A | 434 | 44.170 | 31.590 | 23.352 | 1.00 | 32.08 |
| ATOM | 2257 | CE1 | TYR | A | 434 | 41.971 | 29.928 | 23.342 | 1.00 | 32.62 |
| ATOM | 2258 | CE2 | TYR | A | 434 | 44.343 | 30.229 | 23.305 | 1.00 | 32.88 |
| ATOM | 2259 | CZ | TYR | A | 434 | 43.253 | 29.404 | 23.336 | 1.00 | 38.28 |
| ATOM | 2260 | OH | TYR | A | 434 | 43.435 | 28.044 | 23.282 | 1.00 | 36.98 |
| ATOM | 2261 | N | PHE | A | 435 | 42.514 | 36.499 | 25.436 | 1.00 | 33.49 |
| ATOM | 2262 | CA | PHE | A | 435 | 42.744 | 37.936 | 25.507 | 1.00 | 33.91 |
| ATOM | 2263 | C | PHE | A | 435 | 43.647 | 38.272 | 26.704 | 1.00 | 43.48 |
| ATOM | 2264 | O | PHE | A | 435 | 44.396 | 39.234 | 26.669 | 1.00 | 42.68 |
| ATOM | 2265 | CB | PHE | A | 435 | 41.422 | 38.683 | 25.642 | 1.00 | 34.65 |
| ATOM | 2266 | CG | PHE | A | 435 | 40.587 | 38.647 | 24.414 | 1.00 | 35.21 |

TABLE 2-continued

| | | | | | | | | | |
|---|---|---|---|---|---|---|---|---|---|
| ATOM | 2267 | CD1 | PHE | A | 435 | 39.572 | 37.715 | 24.279 | 1.00 | 37.28 |
| ATOM | 2268 | CD2 | PHE | A | 435 | 40.833 | 39.521 | 23.372 | 1.00 | 37.37 |
| ATOM | 2269 | CE1 | PHE | A | 435 | 38.805 | 37.667 | 23.144 | 1.00 | 38.59 |
| ATOM | 2270 | CE2 | PHE | A | 435 | 40.071 | 39.473 | 22.225 | 1.00 | 40.14 |
| ATOM | 2271 | CZ | PHE | A | 435 | 39.044 | 38.557 | 22.118 | 1.00 | 38.28 |
| ATOM | 2272 | N | ASP | A | 436 | 43.548 | 37.465 | 27.749 | 1.00 | 45.05 |
| ATOM | 2273 | CA | ASP | A | 436 | 44.327 | 37.694 | 28.975 | 1.00 | 47.38 |
| ATOM | 2274 | C | ASP | A | 436 | 45.802 | 38.130 | 28.799 | 1.00 | 57.89 |
| ATOM | 2275 | O | ASP | A | 436 | 46.725 | 37.331 | 28.975 | 1.00 | 58.03 |
| ATOM | 2276 | CB | ASP | A | 436 | 44.212 | 36.497 | 29.914 | 1.00 | 49.07 |
| ATOM | 2277 | CG | ASP | A | 436 | 42.838 | 36.365 | 30.516 | 1.00 | 55.76 |
| ATOM | 2278 | OD1 | ASP | A | 436 | 42.593 | 35.374 | 31.262 | 1.00 | 57.56 |
| ATOM | 2279 | OD2 | ASP | A | 436 | 41.993 | 37.246 | 30.268 | 1.00 | 56.75 |
| ATOM | 2280 | N | GLU | A | 437 | 46.002 | 39.416 | 28.508 | 1.00 | 58.62 |
| ATOM | 2281 | CA | GLU | A | 437 | 47.334 | 39.987 | 28.316 | 1.00 | 60.04 |
| ATOM | 2282 | C | GLU | A | 437 | 47.456 | 41.279 | 29.132 | 1.00 | 66.00 |
| ATOM | 2283 | O | GLU | A | 437 | 47.346 | 41.242 | 30.370 | 1.00 | 65.85 |
| ATOM | 2284 | CB | GLU | A | 437 | 47.557 | 40.282 | 26.831 | 1.00 | 61.53 |
| ATOM | 2285 | CG | GLU | A | 437 | 47.347 | 39.067 | 25.924 | 1.00 | 72.22 |
| ATOM | 2286 | CD | GLU | A | 437 | 48.651 | 38.385 | 25.564 | 1.00 | 92.05 |
| ATOM | 2287 | OE1 | GLU | A | 437 | 48.609 | 37.222 | 25.114 | 1.00 | 84.52 |
| ATOM | 2288 | OE2 | GLU | A | 437 | 49.715 | 39.020 | 25.720 | 1.00 | 88.39 |
| ATOM | 2289 | N | GLU | A | 438 | 47.946 | 42.336 | 28.487 | 1.00 | 63.40 |
| TER | 2290 | | ??? | A | 459 | | | | | |
| ATOM | 2291 | OW | WAT | W | 1 | 44.052 | 42.452 | 1.409 | 1.00 | 23.38 |
| ATOM | 2292 | OW | WAT | W | 2 | 28.598 | 18.064 | 3.193 | 1.00 | 22.98 |
| ATOM | 2293 | OW | WAT | W | 3 | 41.906 | 26.157 | 14.119 | 1.00 | 22.39 |
| ATOM | 2294 | OW | WAT | W | 4 | 37.085 | 18.485 | 1.711 | 1.00 | 24.01 |
| ATOM | 2295 | OW | WAT | W | 5 | 35.096 | 24.828 | 6.780 | 1.00 | 22.99 |
| ATOM | 2296 | OW | WAT | W | 6 | 34.140 | 31.642 | 11.915 | 1.00 | 28.82 |
| ATOM | 2297 | OW | WAT | W | 7 | 28.314 | 28.434 | 7.188 | 1.00 | 32.34 |
| ATOM | 2298 | OW | WAT | W | 8 | 34.273 | 32.690 | 19.197 | 1.00 | 30.42 |
| ATOM | 2299 | OW | WAT | W | 9 | 29.785 | 38.421 | 8.259 | 1.00 | 23.78 |
| ATOM | 2300 | OW | WAT | W | 10 | 30.693 | 41.164 | 7.879 | 1.00 | 29.57 |
| ATOM | 2301 | OW | WAT | W | 11 | 47.935 | 19.414 | 10.793 | 1.00 | 32.13 |
| ATOM | 2302 | OW | WAT | W | 12 | 37.894 | 18.107 | 7.315 | 1.00 | 31.64 |
| ATOM | 2303 | OW | WAT | W | 13 | 27.999 | 34.550 | 2.531 | 1.00 | 33.55 |
| ATOM | 2304 | OW | WAT | W | 14 | 46.041 | 37.872 | 14.691 | 1.00 | 30.23 |
| ATOM | 2305 | OW | WAT | W | 15 | 28.326 | 21.302 | 2.339 | 1.00 | 31.34 |
| ATOM | 2306 | OW | WAT | W | 16 | 43.339 | 20.961 | 18.871 | 1.00 | 40.78 |
| ATOM | 2307 | OW | WAT | W | 17 | 28.831 | 38.138 | 19.269 | 1.00 | 39.03 |
| ATOM | 2308 | OW | WAT | W | 18 | 31.012 | 31.559 | 11.394 | 1.00 | 42.13 |
| ATOM | 2309 | OW | WAT | W | 19 | 37.501 | 47.796 | 1.041 | 1.00 | 39.91 |
| ATOM | 2310 | OW | WAT | W | 20 | 34.812 | 18.237 | 3.569 | 1.00 | 34.50 |
| ATOM | 2311 | OW | WAT | W | 21 | 40.155 | 35.865 | 20.551 | 1.00 | 39.65 |
| ATOM | 2312 | OW | WAT | W | 22 | 40.906 | 46.113 | 8.800 | 1.00 | 37.14 |
| ATOM | 2313 | OW | WAT | W | 23 | 47.014 | 42.830 | 0.226 | 1.00 | 40.50 |
| ATOM | 2314 | OW | WAT | W | 24 | 45.073 | 35.997 | 21.310 | 1.00 | 38.32 |
| ATOM | 2315 | OW | WAT | W | 25 | 31.976 | 32.013 | 14.635 | 1.00 | 36.33 |
| ATOM | 2316 | OW | WAT | W | 26 | 47.799 | 27.128 | 17.921 | 1.00 | 44.70 |
| ATOM | 2317 | OW | WAT | W | 27 | 43.836 | 19.650 | −0.683 | 1.00 | 24.46 |
| ATOM | 2318 | OW | WAT | W | 28 | 32.860 | 23.120 | 13.255 | 1.00 | 45.99 |
| ATOM | 2319 | OW | WAT | W | 29 | 24.993 | 26.870 | 2.600 | 1.00 | 44.10 |
| ATOM | 2320 | OW | WAT | W | 30 | 46.481 | 27.557 | 23.120 | 1.00 | 43.79 |
| ATOM | 2321 | OW | WAT | W | 31 | 25.545 | 35.884 | 22.470 | 1.00 | 46.03 |
| ATOM | 2322 | OW | WAT | W | 32 | 27.761 | 42.389 | 9.141 | 1.00 | 39.69 |
| ATOM | 2323 | OW | WAT | W | 33 | 48.386 | 28.958 | 21.074 | 1.00 | 45.76 |
| ATOM | 2324 | OW | WAT | W | 34 | 32.308 | 33.450 | 21.248 | 1.00 | 44.50 |
| ATOM | 2325 | OW | WAT | W | 35 | 41.346 | 18.321 | 10.848 | 1.00 | 40.25 |
| ATOM | 2326 | OW | WAT | W | 36 | 25.805 | 27.129 | 5.844 | 1.00 | 42.75 |
| ATOM | 2327 | OW | WAT | W | 37 | 35.273 | 17.756 | 6.286 | 1.00 | 35.09 |
| ATOM | 2328 | OW | WAT | W | 38 | 51.254 | 18.885 | −0.870 | 1.00 | 28.15 |
| ATOM | 2329 | OW | WAT | W | 39 | 60.050 | 21.097 | −4.044 | 1.00 | 35.87 |
| ATOM | 2330 | OW | WAT | W | 40 | 27.286 | 38.066 | 16.950 | 1.00 | 46.23 |
| ATOM | 2331 | OW | WAT | W | 41 | 25.183 | 44.675 | 10.160 | 1.00 | 52.14 |
| ATOM | 2332 | OW | WAT | W | 42 | 43.362 | 18.307 | 1.575 | 1.00 | 40.38 |

Example 15

Photomicrograph of Crystals of AKT3 Constructs Expressed in *Escherichia coli*

Photomicrographic analyses of the crystals of the four constructs I in Example 11 (supra) were performed. The AKT3lkd (pT305,pS472) crystal was photographed and determined to have the following dimensions: 21 μm×21 μm. The AKT3lkd (pT305,S472D) crystal was photographed and determined to have the following dimensions: 65 μm×65 μm. The AKT3lkd (T305D,S472D) crystal was photographed and determined to have the following dimensions: 540 μm×325 μm. The AKT3lkd(T305D) crystal was photographed and determined to have the following dimensions: 540 μm×165 μm.

Example 16

Crystallographic Analysis of AKT3 Long Kinase Domain Constructs

|  | *E. coli* expressed AKT3lkd (pT305, pS472) Long Kinase Domain | *E. coli* expressed AKT3lkd (T305D, S472D) Long Kinase Domain | *E. coli* expressed AKT3lkd (pT305, S472D) Long Kinase Domain |
|---|---|---|---|
| Resolution Å | 50-2.40 | 50-1.65 | 50-1.90 |
| Resolution of Last Shell Å | 2.44-2.40 | 1.66-1.65 | 1.92-1.90 |
| Total Reflections | 65141 | 186697 | 185474 |
| Unique Reflections | 13845 | 40002 | 27350 |
| I/σ Overall | 13.8 | 38.8 | 35.1 |
| I/σ Last Shell | 2.8 | 3.3 | 3.3 |
| Rsym Overall | 0.109 | 0.033 | 0.035 |
| Rsym in Last Shell | 0.562 | 0.452 | 0.565 |
| % Completeness Overall | 99.5 | 96.2 | 99.1 |
| % Completeness Last Shell | 98.6 | 93.3 | 97.2 |
| Unit Cell | a = 48.763 b = 73.080 c = 95.115 α = β = γ = 90.0 | a = 48.678 b = 72.894 c = 95.208 α = β = γ = 90.0 | a = 48.828 b = 72.972 c = 95.225 α = β = γ = 90.0 |
| Spacegroup | $P2_12_12_1$ | $P2_12_12_1$ | $P2_12_12_1$ |
| #C, O, N, S Atoms in ASU | 2417 | 2431 | 2262 |
| Rcryst | 21.6 | 20.9 | 25.2 |
| Rfree | 26.5 | 23.2 | 26.8 |
| r.m.s.d Bond Length | 0.007 | 0.011 | 0.008 |
| r.m.s.d Bond Angles | 0.767 | 1.000 | 0.781 |

These structures were solved by difference Fourier calculations. The structural coordinates obtained as set forth below in Tables 3-5.

TABLE 3

Structural coordinates for AKT3lkd(pT305, pS472) (SEQ ID NO:2).

```
REMARK Rfree = 26.5  Rwork = 21.6  Resolution = 2.40
REMARK This is the long kinase domain with S305 and T472
REMARK phosphorylated: AKT3lkd(pT305, pS472)
REMARK SSBOND   1 CYS A  293      CYS A  307
CRYST1 Unit Cell Dimensions:  a = 48.760   b = 73.080   c = 95.110
α = 90.00  β = 90.00   γ = 90.00    Space group: P2₁2₁2₁
ORIGX1          1.000000  0.000000   0.000000       0.00000
ORIGX2          0.000000  1.000000   0.000000       0.00000
ORIGX3          0.000000  0.000000   1.000000       0.00000
SCALE1          0.020509  0.000000   0.000000       0.00000
SCALE2          0.000000  0.013684   0.000000       0.00000
SCALE3          0.000000  0.000000   0.010514       0.00000
ATOM     1  N    ARG  A   142    19.622   55.320   16.563  1.00   67.75
ATOM     2  CA   ARG  A   142    20.711   54.358   16.681  1.00   67.43
ATOM     3  C    ARG  A   142    20.895   53.918   18.126  1.00   69.92
ATOM     4  O    ARG  A   142    20.327   54.510   19.043  1.00   69.45
ATOM     5  CB   ARG  A   142    22.018   54.964   16.170  1.00   68.95
ATOM     6  CG   ARG  A   142    21.968   55.441   14.735  1.00   83.88
ATOM     7  CD   ARG  A   142    22.999   56.534   14.484  1.00   97.99
ATOM     8  NE   ARG  A   142    22.378   57.854   14.386  1.00  110.36
ATOM     9  CZ   ARG  A   142    22.965   58.919   13.850  1.00  125.58
ATOM    10  NH1  ARG  A   142    24.195   58.829   13.362  1.00  113.34
ATOM    11  NH2  ARG  A   142    22.318   60.077   13.796  1.00  112.25
ATOM    12  N    LYS  A   143    21.712   52.887   18.320  1.00   65.04
ATOM    13  CA   LYS  A   143    22.019   52.388   19.655  1.00   63.81
ATOM    14  C    LYS  A   143    23.075   53.295   20.292  1.00   65.63
ATOM    15  O    LYS  A   143    23.923   53.855   19.594  1.00   64.91
ATOM    16  CB   LYS  A   143    22.528   50.948   19.582  1.00   65.59
ATOM    17  CG   LYS  A   143    21.710   50.055   18.667  1.00   75.28
ATOM    18  CD   LYS  A   143    20.271   49.946   19.143  1.00   84.02
ATOM    19  CE   LYS  A   143    19.952   48.539   19.624  1.00   95.86
ATOM    20  NZ   LYS  A   143    18.670   48.030   19.058  1.00  105.83
ATOM    21  N    THR  A   144    22.997   53.464   21.609  1.00   61.01
ATOM    22  CA   THR  A   144    23.935   54.326   22.321  1.00   60.47
ATOM    23  C    THR  A   144    24.857   53.531   23.234  1.00   62.46
```

TABLE 3-continued

Structural coordinates for AKT3lkd(pT305, pS472) (SEQ ID NO:2).

| ATOM | 24 | O | THR | A | 144 | 24.725 | 52.317 | 23.359 | 1.00 | 61.43 |
|---|---|---|---|---|---|---|---|---|---|---|
| ATOM | 25 | CB | THR | A | 144 | 23.198 | 55.384 | 23.180 | 1.00 | 69.77 |
| ATOM | 26 | OG1 | THR | A | 144 | 22.076 | 54.777 | 23.835 | 1.00 | 70.20 |
| ATOM | 27 | CG2 | THR | A | 144 | 22.717 | 56.535 | 22.313 | 1.00 | 68.93 |
| ATOM | 28 | N | MET | A | 145 | 25.774 | 54.232 | 23.890 | 1.00 | 58.43 |
| ATOM | 29 | CA | MET | A | 145 | 26.694 | 53.598 | 24.820 | 1.00 | 58.09 |
| ATOM | 30 | C | MET | A | 145 | 25.917 | 53.067 | 26.020 | 1.00 | 60.88 |
| ATOM | 31 | O | MET | A | 145 | 26.306 | 52.079 | 26.634 | 1.00 | 60.63 |
| ATOM | 32 | CB | MET | A | 145 | 27.757 | 54.590 | 25.284 | 1.00 | 60.53 |
| ATOM | 33 | CG | MET | A | 145 | 29.089 | 53.949 | 25.614 | 1.00 | 64.51 |
| ATOM | 34 | SD | MET | A | 145 | 30.283 | 54.059 | 24.241 | 1.00 | 69.01 |
| ATOM | 35 | CE | MET | A | 145 | 31.634 | 54.883 | 25.013 | 1.00 | 65.83 |
| ATOM | 36 | N | ASN | A | 146 | 24.807 | 53.724 | 26.336 | 1.00 | 56.65 |
| ATOM | 37 | CA | ASN | A | 146 | 23.976 | 53.327 | 27.463 | 1.00 | 56.11 |
| ATOM | 38 | C | ASN | A | 146 | 23.071 | 52.157 | 27.110 | 1.00 | 58.79 |
| ATOM | 39 | O | ASN | A | 146 | 22.260 | 51.725 | 27.921 | 1.00 | 58.46 |
| ATOM | 40 | CB | ASN | A | 146 | 23.139 | 54.511 | 27.963 | 1.00 | 57.69 |
| ATOM | 41 | CG | ASN | A | 146 | 23.837 | 55.837 | 27.774 | 1.00 | 85.28 |
| ATOM | 42 | OD1 | ASN | A | 146 | 24.309 | 56.445 | 28.734 | 1.00 | 80.31 |
| ATOM | 43 | ND2 | ASN | A | 146 | 23.917 | 56.292 | 26.527 | 1.00 | 79.42 |
| ATOM | 44 | N | ASP | A | 147 | 23.223 | 51.639 | 25.897 | 1.00 | 54.53 |
| ATOM | 45 | CA | ASP | A | 147 | 22.419 | 50.508 | 25.444 | 1.00 | 53.67 |
| ATOM | 46 | C | ASP | A | 147 | 23.075 | 49.179 | 25.809 | 1.00 | 55.68 |
| ATOM | 47 | O | ASP | A | 147 | 22.465 | 48.111 | 25.674 | 1.00 | 55.13 |
| ATOM | 48 | CB | ASP | A | 147 | 22.214 | 50.581 | 23.927 | 1.00 | 55.65 |
| ATOM | 49 | CG | ASP | A | 147 | 20.976 | 51.375 | 23.542 | 1.00 | 65.75 |
| ATOM | 50 | OD1 | ASP | A | 147 | 19.869 | 50.799 | 23.579 | 1.00 | 66.59 |
| ATOM | 51 | OD2 | ASP | A | 147 | 21.113 | 52.572 | 23.202 | 1.00 | 70.03 |
| ATOM | 52 | N | PHE | A | 148 | 24.321 | 49.242 | 26.263 | 1.00 | 50.69 |
| ATOM | 53 | CA | PHE | A | 148 | 25.059 | 48.027 | 26.581 | 1.00 | 49.59 |
| ATOM | 54 | C | PHE | A | 148 | 25.662 | 48.008 | 27.974 | 1.00 | 50.98 |
| ATOM | 55 | O | PHE | A | 148 | 25.980 | 49.053 | 28.541 | 1.00 | 50.61 |
| ATOM | 56 | CB | PHE | A | 148 | 26.166 | 47.803 | 25.548 | 1.00 | 51.26 |
| ATOM | 57 | CG | PHE | A | 148 | 25.737 | 48.071 | 24.138 | 1.00 | 52.88 |
| ATOM | 58 | CD1 | PHE | A | 148 | 25.123 | 47.081 | 23.386 | 1.00 | 56.05 |
| ATOM | 59 | CD2 | PHE | A | 148 | 25.954 | 49.310 | 23.559 | 1.00 | 55.01 |
| ATOM | 60 | CE1 | PHE | A | 148 | 24.726 | 47.324 | 22.094 | 1.00 | 56.93 |
| ATOM | 61 | CE2 | PHE | A | 148 | 25.557 | 49.558 | 22.270 | 1.00 | 57.96 |
| ATOM | 62 | CZ | PHE | A | 148 | 24.940 | 48.563 | 21.534 | 1.00 | 56.15 |
| ATOM | 63 | N | ASP | A | 149 | 25.873 | 46.799 | 28.487 | 1.00 | 45.25 |
| ATOM | 64 | CA | ASP | A | 149 | 26.527 | 46.598 | 29.774 | 1.00 | 43.99 |
| ATOM | 65 | C | ASP | A | 149 | 28.009 | 46.334 | 29.520 | 1.00 | 45.24 |
| ATOM | 66 | O | ASP | A | 149 | 28.367 | 45.455 | 28.736 | 1.00 | 44.31 |
| ATOM | 67 | CB | ASP | A | 149 | 25.940 | 45.381 | 30.498 | 1.00 | 45.76 |
| ATOM | 68 | CG | ASP | A | 149 | 24.465 | 45.516 | 30.767 | 1.00 | 55.94 |
| ATOM | 69 | OD1 | ASP | A | 149 | 24.044 | 46.578 | 31.267 | 1.00 | 55.74 |
| ATOM | 70 | OD2 | ASP | A | 149 | 23.729 | 44.543 | 30.507 | 1.00 | 63.78 |
| ATOM | 71 | N | TYR | A | 150 | 28.864 | 47.092 | 30.184 | 1.00 | 40.59 |
| ATOM | 72 | CA | TYR | A | 150 | 30.292 | 46.902 | 30.057 | 1.00 | 39.98 |
| ATOM | 73 | C | TYR | A | 150 | 30.652 | 45.659 | 30.886 | 1.00 | 41.25 |
| ATOM | 74 | O | TYR | A | 150 | 30.398 | 45.618 | 32.084 | 1.00 | 41.34 |
| ATOM | 75 | CB | TYR | A | 150 | 31.022 | 48.147 | 30.568 | 1.00 | 41.92 |
| ATOM | 76 | CG | TYR | A | 150 | 32.512 | 47.984 | 30.741 | 1.00 | 44.66 |
| ATOM | 77 | CD1 | TYR | A | 150 | 33.366 | 48.061 | 29.657 | 1.00 | 46.87 |
| ATOM | 78 | CD2 | TYR | A | 150 | 33.064 | 47.763 | 31.993 | 1.00 | 45.57 |
| ATOM | 79 | CE1 | TYR | A | 150 | 34.721 | 47.911 | 29.809 | 1.00 | 47.65 |
| ATOM | 80 | CE2 | TYR | A | 150 | 34.424 | 47.617 | 32.152 | 1.00 | 46.56 |
| ATOM | 81 | CZ | TYR | A | 150 | 35.247 | 47.697 | 31.056 | 1.00 | 53.90 |
| ATOM | 82 | OH | TYR | A | 150 | 36.603 | 47.550 | 31.203 | 1.00 | 55.91 |
| ATOM | 83 | N | LEU | A | 151 | 31.158 | 44.618 | 30.228 | 1.00 | 35.03 |
| ATOM | 84 | CA | LEU | A | 151 | 31.483 | 43.371 | 30.920 | 1.00 | 33.78 |
| ATOM | 85 | C | LEU | A | 151 | 32.965 | 43.243 | 31.258 | 1.00 | 35.49 |
| ATOM | 86 | O | LEU | A | 151 | 33.326 | 42.926 | 32.396 | 1.00 | 35.39 |
| ATOM | 87 | CB | LEU | A | 151 | 31.035 | 42.157 | 30.096 | 1.00 | 33.78 |
| ATOM | 88 | CG | LEU | A | 151 | 29.534 | 41.901 | 29.922 | 1.00 | 38.26 |
| ATOM | 89 | CD1 | LEU | A | 151 | 29.282 | 40.411 | 29.734 | 1.00 | 38.20 |
| ATOM | 90 | CD2 | LEU | A | 151 | 28.743 | 42.438 | 31.123 | 1.00 | 40.36 |
| ATOM | 91 | N | LYS | A | 152 | 33.824 | 43.469 | 30.265 | 1.00 | 29.65 |
| ATOM | 92 | CA | LYS | A | 152 | 35.249 | 43.332 | 30.471 | 1.00 | 28.48 |
| ATOM | 93 | C | LYS | A | 152 | 36.076 | 43.981 | 29.378 | 1.00 | 31.91 |
| ATOM | 94 | O | LYS | A | 152 | 35.690 | 43.990 | 28.212 | 1.00 | 31.22 |
| ATOM | 95 | CB | LYS | A | 152 | 35.614 | 41.844 | 30.586 | 1.00 | 30.31 |
| ATOM | 96 | CG | LYS | A | 152 | 37.061 | 41.580 | 30.973 | 1.00 | 28.82 |
| ATOM | 97 | CD | LYS | A | 152 | 37.368 | 40.098 | 30.945 | 1.00 | 33.14 |
| ATOM | 98 | CE | LYS | A | 152 | 38.608 | 39.768 | 31.746 | 1.00 | 28.85 |
| ATOM | 99 | NZ | LYS | A | 152 | 38.567 | 38.354 | 32.217 | 1.00 | 35.52 |
| ATOM | 100 | N | LEU | A | 153 | 37.239 | 44.492 | 29.755 | 1.00 | 29.02 |
| ATOM | 101 | CA | LEU | A | 153 | 38.157 | 45.081 | 28.792 | 1.00 | 29.64 |

TABLE 3-continued

Structural coordinates for AKT3lkd(pT305, pS472) (SEQ ID NO:2).

| ATOM | 102 | C | LEU | A | 153 | 38.909 | 43.949 | 28.103 | 1.00 | 35.21 |
|---|---|---|---|---|---|---|---|---|---|---|
| ATOM | 103 | O | LEU | A | 153 | 39.607 | 43.177 | 28.757 | 1.00 | 34.82 |
| ATOM | 104 | CB | LEU | A | 153 | 39.148 | 46.011 | 29.488 | 1.00 | 29.66 |
| ATOM | 105 | CG | LEU | A | 153 | 40.236 | 46.636 | 28.604 | 1.00 | 34.35 |
| ATOM | 106 | CD1 | LEU | A | 153 | 39.647 | 47.732 | 27.710 | 1.00 | 34.27 |
| ATOM | 107 | CD2 | LEU | A | 153 | 41.391 | 47.187 | 29.460 | 1.00 | 35.29 |
| ATOM | 108 | N | LEU | A | 154 | 38.735 | 43.828 | 26.790 | 1.00 | 32.96 |
| ATOM | 109 | CA | LEU | A | 154 | 39.388 | 42.763 | 26.040 | 1.00 | 33.72 |
| ATOM | 110 | C | LEU | A | 154 | 40.768 | 43.140 | 25.527 | 1.00 | 39.94 |
| ATOM | 111 | O | LEU | A | 154 | 41.645 | 42.283 | 25.418 | 1.00 | 40.38 |
| ATOM | 112 | CB | LEU | A | 154 | 38.503 | 42.277 | 24.898 | 1.00 | 33.85 |
| ATOM | 113 | CG | LEU | A | 154 | 37.198 | 41.656 | 25.380 | 1.00 | 38.57 |
| ATOM | 114 | CD1 | LEU | A | 154 | 36.313 | 41.321 | 24.219 | 1.00 | 38.53 |
| ATOM | 115 | CD2 | LEU | A | 154 | 37.493 | 40.415 | 26.229 | 1.00 | 41.53 |
| ATOM | 116 | N | GLY | A | 155 | 40.964 | 44.420 | 25.206 | 1.00 | 37.07 |
| ATOM | 117 | CA | GLY | A | 155 | 42.255 | 44.868 | 24.698 | 1.00 | 36.86 |
| ATOM | 118 | C | GLY | A | 155 | 42.382 | 46.379 | 24.541 | 1.00 | 41.09 |
| ATOM | 119 | O | GLY | A | 155 | 41.386 | 47.091 | 24.395 | 1.00 | 40.17 |
| ATOM | 120 | N | LYS | A | 156 | 43.627 | 46.852 | 24.565 | 1.00 | 38.67 |
| ATOM | 121 | CA | LYS | A | 156 | 43.932 | 48.267 | 24.417 | 1.00 | 39.67 |
| ATOM | 122 | C | LYS | A | 156 | 45.033 | 48.473 | 23.380 | 1.00 | 45.44 |
| ATOM | 123 | O | LYS | A | 156 | 45.946 | 47.663 | 23.263 | 1.00 | 44.87 |
| ATOM | 124 | CB | LYS | A | 156 | 44.368 | 48.871 | 25.759 | 1.00 | 42.41 |
| ATOM | 125 | CG | LYS | A | 156 | 43.280 | 49.653 | 26.469 | 1.00 | 59.28 |
| ATOM | 126 | CD | LYS | A | 156 | 43.859 | 50.831 | 27.244 | 1.00 | 70.65 |
| ATOM | 127 | CE | LYS | A | 156 | 42.781 | 51.849 | 27.593 | 1.00 | 82.48 |
| ATOM | 128 | NZ | LYS | A | 156 | 42.811 | 52.221 | 29.039 | 1.00 | 92.96 |
| ATOM | 129 | N | GLY | A | 157 | 44.936 | 49.566 | 22.632 | 1.00 | 43.67 |
| ATOM | 130 | CA | GLY | A | 157 | 45.922 | 49.899 | 21.613 | 1.00 | 44.00 |
| ATOM | 131 | C | GLY | A | 157 | 45.907 | 51.402 | 21.388 | 1.00 | 49.69 |
| ATOM | 132 | O | GLY | A | 157 | 45.055 | 52.107 | 21.839 | 1.00 | 49.28 |
| ATOM | 133 | N | THR | A | 158 | 46.846 | 51.890 | 20.576 | 1.00 | 47.13 |
| ATOM | 134 | CA | THR | A | 158 | 46.934 | 53.323 | 20.273 | 1.00 | 46.86 |
| ATOM | 135 | C | THR | A | 158 | 45.625 | 53.848 | 19.696 | 1.00 | 50.01 |
| ATOM | 136 | O | THR | A | 158 | 45.172 | 54.946 | 20.049 | 1.00 | 50.13 |
| ATOM | 137 | CB | THR | A | 158 | 48.059 | 53.621 | 19.256 | 1.00 | 57.20 |
| ATOM | 138 | OG1 | THR | A | 158 | 49.118 | 52.666 | 19.412 | 1.00 | 55.77 |
| ATOM | 139 | CG2 | THR | A | 158 | 48.605 | 55.026 | 19.466 | 1.00 | 57.52 |
| ATOM | 140 | N | PHE | A | 159 | 45.030 | 53.069 | 18.795 | 1.00 | 44.94 |
| ATOM | 141 | CA | PHE | A | 159 | 43.787 | 53.459 | 18.139 | 1.00 | 44.51 |
| ATOM | 142 | C | PHE | A | 159 | 42.604 | 53.488 | 19.090 | 1.00 | 46.45 |
| ATOM | 143 | O | PHE | A | 159 | 41.567 | 54.088 | 18.787 | 1.00 | 46.19 |
| ATOM | 144 | CB | PHE | A | 159 | 43.485 | 52.528 | 16.964 | 1.00 | 46.79 |
| ATOM | 145 | CG | PHE | A | 159 | 44.197 | 52.903 | 15.701 | 1.00 | 48.95 |
| ATOM | 146 | CD1 | PHE | A | 159 | 45.308 | 52.192 | 15.278 | 1.00 | 52.35 |
| ATOM | 147 | CD2 | PHE | A | 159 | 43.774 | 53.991 | 14.947 | 1.00 | 51.69 |
| ATOM | 148 | CE1 | PHE | A | 159 | 45.977 | 52.547 | 14.113 | 1.00 | 53.49 |
| ATOM | 149 | CE2 | PHE | A | 159 | 44.437 | 54.346 | 13.785 | 1.00 | 54.48 |
| ATOM | 150 | CZ | PHE | A | 159 | 45.540 | 53.620 | 13.369 | 1.00 | 52.39 |
| ATOM | 151 | N | GLY | A | 160 | 42.752 | 52.828 | 20.233 | 1.00 | 41.31 |
| ATOM | 152 | CA | GLY | A | 160 | 41.680 | 52.763 | 21.218 | 1.00 | 40.30 |
| ATOM | 153 | C | GLY | A | 160 | 41.661 | 51.406 | 21.925 | 1.00 | 42.26 |
| ATOM | 154 | O | GLY | A | 160 | 42.696 | 50.923 | 22.399 | 1.00 | 41.22 |
| ATOM | 155 | N | LYS | A | 161 | 40.486 | 50.795 | 21.998 | 1.00 | 38.30 |
| ATOM | 156 | CA | LYS | A | 161 | 40.354 | 49.520 | 22.681 | 1.00 | 38.09 |
| ATOM | 157 | C | LYS | A | 161 | 39.057 | 48.777 | 22.354 | 1.00 | 40.57 |
| ATOM | 158 | O | LYS | A | 161 | 38.129 | 49.329 | 21.750 | 1.00 | 39.48 |
| ATOM | 159 | CB | LYS | A | 161 | 40.457 | 49.728 | 24.196 | 1.00 | 40.87 |
| ATOM | 160 | CG | LYS | A | 161 | 39.123 | 50.049 | 24.863 | 1.00 | 51.62 |
| ATOM | 161 | CD | LYS | A | 161 | 39.255 | 51.192 | 25.852 | 1.00 | 59.30 |
| ATOM | 162 | CE | LYS | A | 161 | 37.911 | 51.855 | 26.101 | 1.00 | 67.32 |
| ATOM | 163 | NZ | LYS | A | 161 | 36.987 | 51.661 | 24.947 | 1.00 | 76.85 |
| ATOM | 164 | N | VAL | A | 162 | 39.003 | 47.521 | 22.787 | 1.00 | 36.04 |
| ATOM | 165 | CA | VAL | A | 162 | 37.844 | 46.672 | 22.587 | 1.00 | 35.47 |
| ATOM | 166 | C | VAL | A | 162 | 37.398 | 46.151 | 23.948 | 1.00 | 38.64 |
| ATOM | 167 | O | VAL | A | 162 | 38.221 | 45.799 | 24.797 | 1.00 | 38.63 |
| ATOM | 168 | CB | VAL | A | 162 | 38.189 | 45.446 | 21.675 | 1.00 | 39.45 |
| ATOM | 169 | CG1 | VAL | A | 162 | 36.952 | 44.591 | 21.432 | 1.00 | 38.71 |
| ATOM | 170 | CG2 | VAL | A | 162 | 38.798 | 45.906 | 20.353 | 1.00 | 39.35 |
| ATOM | 171 | N | ILE | A | 163 | 36.098 | 46.113 | 24.162 | 1.00 | 34.46 |
| ATOM | 172 | CA | ILE | A | 163 | 35.570 | 45.620 | 25.410 | 1.00 | 33.76 |
| ATOM | 173 | C | ILE | A | 163 | 34.404 | 44.706 | 25.132 | 1.00 | 36.19 |
| ATOM | 174 | O | ILE | A | 163 | 33.632 | 44.948 | 24.217 | 1.00 | 36.25 |
| ATOM | 175 | CB | ILE | A | 163 | 35.100 | 46.777 | 26.312 | 1.00 | 36.90 |
| ATOM | 176 | CG1 | ILE | A | 163 | 33.796 | 47.366 | 25.777 | 1.00 | 37.53 |
| ATOM | 177 | CG2 | ILE | A | 163 | 36.188 | 47.852 | 26.415 | 1.00 | 36.80 |
| ATOM | 178 | CD1 | ILE | A | 163 | 33.553 | 48.808 | 26.189 | 1.00 | 42.85 |
| ATOM | 179 | N | LEU | A | 164 | 34.289 | 43.638 | 25.908 | 1.00 | 31.64 |

TABLE 3-continued

Structural coordinates for AKT3lkd(pT305, pS472) (SEQ ID NO:2).

| ATOM | 180 | CA | LEU | A | 164 | 33.169 | 42.732 | 25.755 | 1.00 | 31.34 |
|------|-----|-----|-----|---|-----|--------|--------|--------|------|-------|
| ATOM | 181 | C | LEU | A | 164 | 31.958 | 43.408 | 26.378 | 1.00 | 35.85 |
| ATOM | 182 | O | LEU | A | 164 | 32.013 | 43.878 | 27.512 | 1.00 | 34.71 |
| ATOM | 183 | CB | LEU | A | 164 | 33.447 | 41.396 | 26.448 | 1.00 | 31.23 |
| ATOM | 184 | CG | LEU | A | 164 | 32.284 | 40.402 | 26.500 | 1.00 | 35.44 |
| ATOM | 185 | CD1 | LEU | A | 164 | 31.979 | 39.817 | 25.124 | 1.00 | 35.23 |
| ATOM | 186 | CD2 | LEU | A | 164 | 32.573 | 39.301 | 27.505 | 1.00 | 37.41 |
| ATOM | 187 | N | VAL | A | 165 | 30.884 | 43.509 | 25.610 | 1.00 | 34.01 |
| ATOM | 188 | CA | VAL | A | 165 | 29.672 | 44.155 | 26.087 | 1.00 | 34.32 |
| ATOM | 189 | C | VAL | A | 165 | 28.460 | 43.258 | 25.927 | 1.00 | 40.41 |
| ATOM | 190 | O | VAL | A | 165 | 28.510 | 42.230 | 25.258 | 1.00 | 39.73 |
| ATOM | 191 | CB | VAL | A | 165 | 29.402 | 45.496 | 25.354 | 1.00 | 37.34 |
| ATOM | 192 | CG1 | VAL | A | 165 | 30.547 | 46.464 | 25.561 | 1.00 | 36.79 |
| ATOM | 193 | CG2 | VAL | A | 165 | 29.135 | 45.260 | 23.884 | 1.00 | 36.93 |
| ATOM | 194 | N | ARG | A | 166 | 27.371 | 43.652 | 26.556 | 1.00 | 39.62 |
| ATOM | 195 | CA | ARG | A | 166 | 26.137 | 42.899 | 26.476 | 1.00 | 40.52 |
| ATOM | 196 | C | ARG | A | 166 | 25.022 | 43.846 | 26.118 | 1.00 | 46.59 |
| ATOM | 197 | O | ARG | A | 166 | 24.897 | 44.924 | 26.704 | 1.00 | 45.83 |
| ATOM | 198 | CB | ARG | A | 166 | 25.839 | 42.217 | 27.809 | 1.00 | 41.57 |
| ATOM | 199 | CG | ARG | A | 166 | 24.638 | 41.282 | 27.777 | 1.00 | 54.51 |
| ATOM | 200 | CD | ARG | A | 166 | 24.132 | 40.986 | 29.185 | 1.00 | 65.54 |
| ATOM | 201 | NE | ARG | A | 166 | 24.743 | 39.785 | 29.753 | 1.00 | 75.62 |
| ATOM | 202 | CZ | ARG | A | 166 | 25.214 | 39.699 | 30.996 | 1.00 | 88.50 |
| ATOM | 203 | NH1 | ARG | A | 166 | 25.149 | 40.749 | 31.805 | 1.00 | 74.43 |
| ATOM | 204 | NH2 | ARG | A | 166 | 25.753 | 38.563 | 31.430 | 1.00 | 73.47 |
| ATOM | 205 | N | GLU | A | 167 | 24.246 | 43.476 | 25.110 | 1.00 | 45.79 |
| ATOM | 206 | CA | GLU | A | 167 | 23.121 | 44.295 | 24.687 | 1.00 | 46.63 |
| ATOM | 207 | C | GLU | A | 167 | 21.992 | 44.089 | 25.682 | 1.00 | 52.01 |
| ATOM | 208 | O | GLU | A | 167 | 21.450 | 42.980 | 25.805 | 1.00 | 51.72 |
| ATOM | 209 | CB | GLU | A | 167 | 22.665 | 43.907 | 23.275 | 1.00 | 48.19 |
| ATOM | 210 | CG | GLU | A | 167 | 21.322 | 44.503 | 22.869 | 1.00 | 59.67 |
| ATOM | 211 | CD | GLU | A | 167 | 21.090 | 44.466 | 21.367 | 1.00 | 77.19 |
| ATOM | 212 | OE1 | GLU | A | 167 | 20.713 | 45.512 | 20.801 | 1.00 | 68.20 |
| ATOM | 213 | OE2 | GLU | A | 167 | 21.272 | 43.390 | 20.758 | 1.00 | 70.28 |
| ATOM | 214 | N | LYS | A | 168 | 21.683 | 45.149 | 26.422 | 1.00 | 49.88 |
| ATOM | 215 | CA | LYS | A | 168 | 20.636 | 45.135 | 27.444 | 1.00 | 50.60 |
| ATOM | 216 | C | LYS | A | 168 | 19.379 | 44.338 | 27.056 | 1.00 | 57.17 |
| ATOM | 217 | O | LYS | A | 168 | 18.984 | 43.404 | 27.761 | 1.00 | 57.09 |
| ATOM | 218 | CB | LYS | A | 168 | 20.257 | 46.569 | 27.829 | 1.00 | 52.46 |
| ATOM | 219 | CG | LYS | A | 168 | 21.278 | 47.262 | 28.723 | 1.00 | 57.64 |
| ATOM | 220 | CD | LYS | A | 168 | 21.286 | 48.767 | 28.492 | 1.00 | 65.26 |
| ATOM | 221 | CE | LYS | A | 168 | 22.049 | 49.484 | 29.585 | 1.00 | 73.94 |
| ATOM | 222 | NZ | LYS | A | 168 | 22.205 | 48.625 | 30.790 | 1.00 | 85.18 |
| ATOM | 223 | N | ALA | A | 169 | 18.774 | 44.694 | 25.927 | 1.00 | 55.14 |
| ATOM | 224 | CA | ALA | A | 169 | 17.559 | 44.021 | 25.465 | 1.00 | 55.36 |
| ATOM | 225 | C | ALA | A | 169 | 17.733 | 42.522 | 25.198 | 1.00 | 60.28 |
| ATOM | 226 | O | ALA | A | 169 | 17.316 | 41.679 | 26.003 | 1.00 | 60.55 |
| ATOM | 227 | CB | ALA | A | 169 | 17.004 | 44.715 | 24.236 | 1.00 | 56.08 |
| ATOM | 228 | N | SER | A | 170 | 18.314 | 42.199 | 24.050 | 1.00 | 56.25 |
| ATOM | 229 | CA | SER | A | 170 | 18.489 | 40.814 | 23.628 | 1.00 | 55.60 |
| ATOM | 230 | C | SER | A | 170 | 19.264 | 39.936 | 24.606 | 1.00 | 57.96 |
| ATOM | 231 | O | SER | A | 170 | 19.000 | 38.731 | 24.716 | 1.00 | 57.29 |
| ATOM | 232 | CB | SER | A | 170 | 19.152 | 40.763 | 22.251 | 1.00 | 59.97 |
| ATOM | 233 | OG | SER | A | 170 | 20.518 | 41.139 | 22.331 | 1.00 | 71.37 |
| ATOM | 234 | N | GLY | A | 171 | 20.246 | 40.526 | 25.285 | 1.00 | 53.32 |
| ATOM | 235 | CA | GLY | A | 171 | 21.101 | 39.769 | 26.184 | 1.00 | 52.46 |
| ATOM | 236 | C | GLY | A | 171 | 22.165 | 39.081 | 25.331 | 1.00 | 54.85 |
| ATOM | 237 | O | GLY | A | 171 | 22.651 | 37.994 | 25.659 | 1.00 | 54.64 |
| ATOM | 238 | N | LYS | A | 172 | 22.493 | 39.715 | 24.209 | 1.00 | 49.71 |
| ATOM | 239 | CA | LYS | A | 172 | 23.485 | 39.190 | 23.285 | 1.00 | 48.29 |
| ATOM | 240 | C | LYS | A | 172 | 24.852 | 39.779 | 23.600 | 1.00 | 48.68 |
| ATOM | 241 | O | LYS | A | 172 | 24.967 | 40.963 | 23.923 | 1.00 | 47.94 |
| ATOM | 242 | CB | LYS | A | 172 | 23.089 | 39.527 | 21.842 | 1.00 | 50.96 |
| ATOM | 243 | CG | LYS | A | 172 | 22.663 | 38.322 | 21.024 | 1.00 | 66.85 |
| ATOM | 244 | CD | LYS | A | 172 | 21.430 | 38.620 | 20.185 | 1.00 | 76.51 |
| ATOM | 245 | CE | LYS | A | 172 | 20.642 | 37.345 | 19.899 | 1.00 | 88.11 |
| ATOM | 246 | NZ | LYS | A | 172 | 19.411 | 37.608 | 19.100 | 1.00 | 97.93 |
| ATOM | 247 | N | TYR | A | 173 | 25.885 | 38.948 | 23.511 | 1.00 | 43.16 |
| ATOM | 248 | CA | TYR | A | 173 | 27.249 | 39.390 | 23.770 | 1.00 | 42.32 |
| ATOM | 249 | C | TYR | A | 173 | 27.917 | 39.852 | 22.484 | 1.00 | 42.91 |
| ATOM | 250 | O | TYR | A | 173 | 27.834 | 39.184 | 21.454 | 1.00 | 41.93 |
| ATOM | 251 | CB | TYR | A | 173 | 28.064 | 38.272 | 24.421 | 1.00 | 44.20 |
| ATOM | 252 | CG | TYR | A | 173 | 27.455 | 37.775 | 25.706 | 1.00 | 47.35 |
| ATOM | 253 | CD1 | TYR | A | 173 | 27.573 | 38.507 | 26.881 | 1.00 | 49.14 |
| ATOM | 254 | CD2 | TYR | A | 173 | 26.692 | 36.617 | 25.729 | 1.00 | 48.81 |
| ATOM | 255 | CE1 | TYR | A | 173 | 26.990 | 38.074 | 28.049 | 1.00 | 49.66 |
| ATOM | 256 | CE2 | TYR | A | 173 | 26.102 | 36.180 | 26.890 | 1.00 | 50.06 |
| ATOM | 257 | CZ | TYR | A | 173 | 26.252 | 36.912 | 28.050 | 1.00 | 57.45 |

TABLE 3-continued

Structural coordinates for AKT3lkd(pT305, pS472) (SEQ ID NO:2).

| ATOM | 258 | OH | TYR | A | 173 | 25.668 | 36.469 | 29.215 | 1.00 | 59.37 |
|---|---|---|---|---|---|---|---|---|---|---|
| ATOM | 259 | N | TYR | A | 174 | 28.561 | 41.009 | 22.548 | 1.00 | 37.41 |
| ATOM | 260 | CA | TYR | A | 174 | 29.250 | 41.570 | 21.399 | 1.00 | 36.58 |
| ATOM | 261 | C | TYR | A | 174 | 30.599 | 42.090 | 21.823 | 1.00 | 38.31 |
| ATOM | 262 | O | TYR | A | 174 | 30.906 | 42.185 | 23.015 | 1.00 | 37.56 |
| ATOM | 263 | CB | TYR | A | 174 | 28.453 | 42.739 | 20.802 | 1.00 | 38.30 |
| ATOM | 264 | CG | TYR | A | 174 | 27.127 | 42.356 | 20.201 | 1.00 | 41.03 |
| ATOM | 265 | CD1 | TYR | A | 174 | 27.060 | 41.675 | 18.988 | 1.00 | 43.16 |
| ATOM | 266 | CD2 | TYR | A | 174 | 25.936 | 42.682 | 20.840 | 1.00 | 41.89 |
| ATOM | 267 | CE1 | TYR | A | 174 | 25.848 | 41.314 | 18.443 | 1.00 | 43.88 |
| ATOM | 268 | CE2 | TYR | A | 174 | 24.721 | 42.332 | 20.299 | 1.00 | 43.00 |
| ATOM | 269 | CZ | TYR | A | 174 | 24.678 | 41.641 | 19.106 | 1.00 | 51.80 |
| ATOM | 270 | OH | TYR | A | 174 | 23.459 | 41.289 | 18.571 | 1.00 | 55.02 |
| ATOM | 271 | N | ALA | A | 175 | 31.402 | 42.448 | 20.839 | 1.00 | 33.23 |
| ATOM | 272 | CA | ALA | A | 175 | 32.676 | 43.070 | 21.088 | 1.00 | 32.15 |
| ATOM | 273 | C | ALA | A | 175 | 32.503 | 44.477 | 20.568 | 1.00 | 35.33 |
| ATOM | 274 | O | ALA | A | 175 | 32.057 | 44.667 | 19.431 | 1.00 | 34.30 |
| ATOM | 275 | CB | ALA | A | 175 | 33.778 | 42.356 | 20.320 | 1.00 | 32.64 |
| ATOM | 276 | N | MET | A | 176 | 32.779 | 45.470 | 21.409 | 1.00 | 31.68 |
| ATOM | 277 | CA | MET | A | 176 | 32.650 | 46.856 | 20.974 | 1.00 | 31.03 |
| ATOM | 278 | C | MET | A | 176 | 34.007 | 47.500 | 20.790 | 1.00 | 36.62 |
| ATOM | 279 | O | MET | A | 176 | 34.794 | 47.580 | 21.728 | 1.00 | 35.28 |
| ATOM | 280 | CB | MET | A | 176 | 31.798 | 47.686 | 21.943 | 1.00 | 32.73 |
| ATOM | 281 | CG | MET | A | 176 | 31.763 | 49.194 | 21.579 | 1.00 | 35.60 |
| ATOM | 282 | SD | MET | A | 176 | 30.835 | 50.265 | 22.758 | 1.00 | 38.78 |
| ATOM | 283 | CE | MET | A | 176 | 29.282 | 49.440 | 22.793 | 1.00 | 34.98 |
| ATOM | 284 | N | LYS | A | 177 | 34.281 | 47.953 | 19.569 | 1.00 | 35.45 |
| ATOM | 285 | CA | LYS | A | 177 | 35.536 | 48.618 | 19.276 | 1.00 | 36.14 |
| ATOM | 286 | C | LYS | A | 177 | 35.362 | 50.120 | 19.439 | 1.00 | 42.65 |
| ATOM | 287 | O | LYS | A | 177 | 34.488 | 50.728 | 18.813 | 1.00 | 42.83 |
| ATOM | 288 | CB | LYS | A | 177 | 36.018 | 48.283 | 17.858 | 1.00 | 38.88 |
| ATOM | 289 | CG | LYS | A | 177 | 37.483 | 47.821 | 17.798 | 1.00 | 53.46 |
| ATOM | 290 | CD | LYS | A | 177 | 37.741 | 46.903 | 16.611 | 1.00 | 61.41 |
| ATOM | 291 | CE | LYS | A | 177 | 38.238 | 45.537 | 17.064 | 1.00 | 67.28 |
| ATOM | 292 | NZ | LYS | A | 177 | 39.172 | 44.914 | 16.082 | 1.00 | 70.56 |
| ATOM | 293 | N | ILE | A | 178 | 36.150 | 50.702 | 20.338 | 1.00 | 39.66 |
| ATOM | 294 | CA | ILE | A | 178 | 36.086 | 52.128 | 20.598 | 1.00 | 38.92 |
| ATOM | 295 | C | ILE | A | 178 | 37.368 | 52.777 | 20.137 | 1.00 | 42.36 |
| ATOM | 296 | O | ILE | A | 178 | 38.437 | 52.574 | 20.731 | 1.00 | 40.79 |
| ATOM | 297 | CB | ILE | A | 178 | 35.885 | 52.438 | 22.083 | 1.00 | 41.90 |
| ATOM | 298 | CG1 | ILE | A | 178 | 34.420 | 52.206 | 22.478 | 1.00 | 42.48 |
| ATOM | 299 | CG2 | ILE | A | 178 | 36.303 | 53.894 | 22.379 | 1.00 | 41.38 |
| ATOM | 300 | CD1 | ILE | A | 178 | 34.231 | 51.181 | 23.557 | 1.00 | 46.64 |
| ATOM | 301 | N | LEU | A | 179 | 37.264 | 53.539 | 19.059 | 1.00 | 39.77 |
| ATOM | 302 | CA | LEU | A | 179 | 38.407 | 54.203 | 18.486 | 1.00 | 40.08 |
| ATOM | 303 | C | LEU | A | 179 | 38.328 | 55.696 | 18.730 | 1.00 | 45.76 |
| ATOM | 304 | O | LEU | A | 179 | 37.238 | 56.277 | 18.797 | 1.00 | 44.91 |
| ATOM | 305 | CB | LEU | A | 179 | 38.495 | 53.910 | 16.985 | 1.00 | 40.06 |
| ATOM | 306 | CG | LEU | A | 179 | 38.253 | 52.456 | 16.576 | 1.00 | 44.08 |
| ATOM | 307 | CD1 | LEU | A | 179 | 38.244 | 52.312 | 15.062 | 1.00 | 44.15 |
| ATOM | 308 | CD2 | LEU | A | 179 | 39.300 | 51.553 | 17.199 | 1.00 | 45.22 |
| ATOM | 309 | N | LYS | A | 180 | 39.492 | 56.311 | 18.884 | 1.00 | 44.14 |
| ATOM | 310 | CA | LYS | A | 180 | 39.577 | 57.738 | 19.113 | 1.00 | 44.55 |
| ATOM | 311 | C | LYS | A | 180 | 39.669 | 58.453 | 17.773 | 1.00 | 49.18 |
| ATOM | 312 | O | LYS | A | 180 | 40.615 | 58.238 | 17.014 | 1.00 | 48.44 |
| ATOM | 313 | CB | LYS | A | 180 | 40.800 | 58.056 | 19.976 | 1.00 | 47.70 |
| ATOM | 314 | CG | LYS | A | 180 | 40.649 | 57.654 | 21.439 | 1.00 | 67.27 |
| ATOM | 315 | CD | LYS | A | 180 | 40.207 | 56.204 | 21.581 | 1.00 | 77.81 |
| ATOM | 316 | CE | LYS | A | 180 | 39.606 | 55.939 | 22.958 | 1.00 | 88.40 |
| ATOM | 317 | NZ | LYS | A | 180 | 39.492 | 54.477 | 23.254 | 1.00 | 95.45 |
| ATOM | 318 | N | LYS | A | 181 | 38.660 | 59.262 | 17.465 | 1.00 | 47.19 |
| ATOM | 319 | CA | LYS | A | 181 | 38.619 | 60.000 | 16.200 | 1.00 | 47.82 |
| ATOM | 320 | C | LYS | A | 181 | 39.929 | 60.730 | 15.980 | 1.00 | 53.89 |
| ATOM | 321 | O | LYS | A | 181 | 40.563 | 60.594 | 14.928 | 1.00 | 53.34 |
| ATOM | 322 | CB | LYS | A | 181 | 37.469 | 61.012 | 16.205 | 1.00 | 49.82 |
| ATOM | 323 | CG | LYS | A | 181 | 36.257 | 60.566 | 16.995 | 1.00 | 57.52 |
| ATOM | 324 | CD | LYS | A | 181 | 34.983 | 60.818 | 16.225 | 1.00 | 64.28 |
| ATOM | 325 | CE | LYS | A | 181 | 33.769 | 60.672 | 17.117 | 1.00 | 73.73 |
| ATOM | 326 | NZ | LYS | A | 181 | 33.377 | 61.971 | 17.706 | 1.00 | 82.65 |
| ATOM | 327 | N | GLU | A | 182 | 40.338 | 61.487 | 16.995 | 1.00 | 51.95 |
| ATOM | 328 | CA | GLU | A | 182 | 41.568 | 62.267 | 16.953 | 1.00 | 52.18 |
| ATOM | 329 | C | GLU | A | 182 | 42.738 | 61.443 | 16.452 | 1.00 | 56.02 |
| ATOM | 330 | O | GLU | A | 182 | 43.631 | 61.958 | 15.785 | 1.00 | 55.70 |
| ATOM | 331 | CB | GLU | A | 182 | 41.877 | 62.834 | 18.337 | 1.00 | 53.79 |
| ATOM | 332 | CG | GLU | A | 182 | 40.633 | 63.134 | 19.176 | 1.00 | 66.13 |
| ATOM | 333 | CD | GLU | A | 182 | 40.188 | 61.939 | 20.011 | 1.00 | 89.01 |
| ATOM | 334 | OE1 | GLU | A | 182 | 41.035 | 61.367 | 20.733 | 1.00 | 83.37 |
| ATOM | 335 | OE2 | GLU | A | 182 | 38.993 | 61.569 | 19.938 | 1.00 | 81.44 |

TABLE 3-continued

Structural coordinates for AKT3lkd(pT305, pS472) (SEQ ID NO:2).

| ATOM | 336 | N | VAL | A | 183 | 42.721 | 60.155 | 16.764 | 1.00 | 53.02 |
|---|---|---|---|---|---|---|---|---|---|---|
| ATOM | 337 | CA | VAL | A | 183 | 43.786 | 59.251 | 16.339 | 1.00 | 52.74 |
| ATOM | 338 | C | VAL | A | 183 | 43.598 | 58.847 | 14.886 | 1.00 | 56.20 |
| ATOM | 339 | O | VAL | A | 183 | 44.546 | 58.863 | 14.103 | 1.00 | 56.03 |
| ATOM | 340 | CB | VAL | A | 183 | 43.866 | 57.986 | 17.242 | 1.00 | 56.63 |
| ATOM | 341 | CG1 | VAL | A | 183 | 43.023 | 56.862 | 16.675 | 1.00 | 56.54 |
| ATOM | 342 | CG2 | VAL | A | 183 | 45.305 | 57.537 | 17.411 | 1.00 | 56.39 |
| ATOM | 343 | N | ILE | A | 184 | 42.362 | 58.512 | 14.522 | 1.00 | 52.64 |
| ATOM | 344 | CA | ILE | A | 184 | 42.048 | 58.124 | 13.152 | 1.00 | 52.46 |
| ATOM | 345 | C | ILE | A | 184 | 42.425 | 59.246 | 12.187 | 1.00 | 56.99 |
| ATOM | 346 | O | ILE | A | 184 | 43.132 | 59.019 | 11.204 | 1.00 | 56.45 |
| ATOM | 347 | CB | ILE | A | 184 | 40.548 | 57.785 | 12.982 | 1.00 | 55.30 |
| ATOM | 348 | CG1 | ILE | A | 184 | 40.138 | 56.689 | 13.962 | 1.00 | 55.36 |
| ATOM | 349 | CG2 | ILE | A | 184 | 40.259 | 57.352 | 11.549 | 1.00 | 55.98 |
| ATOM | 350 | CD1 | ILE | A | 184 | 40.936 | 55.420 | 13.819 | 1.00 | 60.07 |
| ATOM | 351 | N | ILE | A | 185 | 41.962 | 60.459 | 12.478 | 1.00 | 54.13 |
| ATOM | 352 | CA | ILE | A | 185 | 42.292 | 61.608 | 11.645 | 1.00 | 54.32 |
| ATOM | 353 | C | ILE | A | 185 | 43.812 | 61.793 | 11.593 | 1.00 | 58.50 |
| ATOM | 354 | O | ILE | A | 185 | 44.404 | 61.826 | 10.519 | 1.00 | 57.94 |
| ATOM | 355 | CB | ILE | A | 185 | 41.614 | 62.915 | 12.155 | 1.00 | 57.61 |
| ATOM | 356 | CG1 | ILE | A | 185 | 42.215 | 63.359 | 13.488 | 1.00 | 58.62 |
| ATOM | 357 | CG2 | ILE | A | 185 | 40.115 | 62.712 | 12.312 | 1.00 | 58.05 |
| ATOM | 358 | CD1 | ILE | A | 185 | 43.347 | 64.364 | 13.354 | 1.00 | 68.30 |
| ATOM | 359 | N | ALA | A | 186 | 44.441 | 61.863 | 12.762 | 1.00 | 55.74 |
| ATOM | 360 | CA | ALA | A | 186 | 45.883 | 62.041 | 12.845 | 1.00 | 55.76 |
| ATOM | 361 | C | ALA | A | 186 | 46.594 | 60.929 | 12.087 | 1.00 | 60.51 |
| ATOM | 362 | O | ALA | A | 186 | 47.529 | 61.179 | 11.326 | 1.00 | 60.04 |
| ATOM | 363 | CB | ALA | A | 186 | 46.331 | 62.076 | 14.295 | 1.00 | 56.49 |
| ATOM | 364 | N | LYS | A | 187 | 46.134 | 59.701 | 12.289 | 1.00 | 57.80 |
| ATOM | 365 | CA | LYS | A | 187 | 46.709 | 58.553 | 11.601 | 1.00 | 58.09 |
| ATOM | 366 | C | LYS | A | 187 | 46.305 | 58.573 | 10.125 | 1.00 | 62.31 |
| ATOM | 367 | O | LYS | A | 187 | 46.847 | 57.823 | 9.309 | 1.00 | 61.82 |
| ATOM | 368 | CB | LYS | A | 187 | 46.251 | 57.247 | 12.262 | 1.00 | 60.78 |
| ATOM | 369 | CG | LYS | A | 187 | 46.863 | 57.004 | 13.637 | 1.00 | 73.61 |
| ATOM | 370 | CD | LYS | A | 187 | 48.331 | 57.411 | 13.670 | 1.00 | 80.38 |
| ATOM | 371 | CE | LYS | A | 187 | 48.831 | 57.569 | 15.096 | 1.00 | 87.34 |
| ATOM | 372 | NZ | LYS | A | 187 | 50.042 | 56.743 | 15.350 | 1.00 | 95.04 |
| ATOM | 373 | N | ASP | A | 188 | 45.353 | 59.445 | 9.797 | 1.00 | 59.16 |
| ATOM | 374 | CA | ASP | A | 188 | 44.861 | 59.588 | 8.429 | 1.00 | 59.22 |
| ATOM | 375 | C | ASP | A | 188 | 44.137 | 58.327 | 7.961 | 1.00 | 62.36 |
| ATOM | 376 | O | ASP | A | 188 | 44.445 | 57.783 | 6.901 | 1.00 | 62.18 |
| ATOM | 377 | CB | ASP | A | 188 | 46.017 | 59.922 | 7.480 | 1.00 | 61.52 |
| ATOM | 378 | CG | ASP | A | 188 | 46.712 | 61.237 | 7.838 | 1.00 | 74.88 |
| ATOM | 379 | OD1 | ASP | A | 188 | 46.009 | 62.189 | 8.248 | 1.00 | 76.32 |
| ATOM | 380 | OD2 | ASP | A | 188 | 47.955 | 61.319 | 7.693 | 1.00 | 80.04 |
| ATOM | 381 | N | GLU | A | 189 | 43.173 | 57.866 | 8.754 | 1.00 | 57.91 |
| ATOM | 382 | CA | GLU | A | 189 | 42.430 | 56.650 | 8.429 | 1.00 | 57.25 |
| ATOM | 383 | C | GLU | A | 189 | 40.921 | 56.861 | 8.482 | 1.00 | 58.83 |
| ATOM | 384 | O | GLU | A | 189 | 40.178 | 55.959 | 8.851 | 1.00 | 58.77 |
| ATOM | 385 | CB | GLU | A | 189 | 42.813 | 55.522 | 9.395 | 1.00 | 58.81 |
| ATOM | 386 | CG | GLU | A | 189 | 44.252 | 55.561 | 9.876 | 1.00 | 68.86 |
| ATOM | 387 | CD | GLU | A | 189 | 44.977 | 54.251 | 9.630 | 1.00 | 88.61 |
| ATOM | 388 | OE1 | GLU | A | 189 | 45.734 | 53.809 | 10.523 | 1.00 | 89.26 |
| ATOM | 389 | OE2 | GLU | A | 189 | 44.780 | 53.659 | 8.546 | 1.00 | 75.51 |
| ATOM | 390 | N | VAL | A | 190 | 40.473 | 58.054 | 8.122 | 1.00 | 53.38 |
| ATOM | 391 | CA | VAL | A | 190 | 39.054 | 58.374 | 8.180 | 1.00 | 52.15 |
| ATOM | 392 | C | VAL | A | 190 | 38.246 | 57.682 | 7.089 | 1.00 | 53.23 |
| ATOM | 393 | O | VAL | A | 190 | 37.268 | 56.996 | 7.370 | 1.00 | 52.08 |
| ATOM | 394 | CB | VAL | A | 190 | 38.811 | 59.895 | 8.139 | 1.00 | 55.91 |
| ATOM | 395 | CG1 | VAL | A | 190 | 37.324 | 60.197 | 8.165 | 1.00 | 55.61 |
| ATOM | 396 | CG2 | VAL | A | 190 | 39.520 | 60.569 | 9.311 | 1.00 | 55.78 |
| ATOM | 397 | N | ALA | A | 191 | 38.654 | 57.870 | 5.844 | 1.00 | 48.97 |
| ATOM | 398 | CA | ALA | A | 191 | 37.962 | 57.254 | 4.723 | 1.00 | 48.39 |
| ATOM | 399 | C | ALA | A | 191 | 38.132 | 55.739 | 4.774 | 1.00 | 51.30 |
| ATOM | 400 | O | ALA | A | 191 | 37.197 | 54.990 | 4.494 | 1.00 | 50.01 |
| ATOM | 401 | CB | ALA | A | 191 | 38.477 | 57.812 | 3.407 | 1.00 | 49.06 |
| ATOM | 402 | N | HIS | A | 192 | 39.324 | 55.298 | 5.163 | 1.00 | 48.51 |
| ATOM | 403 | CA | HIS | A | 192 | 39.620 | 53.873 | 5.283 | 1.00 | 48.62 |
| ATOM | 404 | C | HIS | A | 192 | 38.656 | 53.244 | 6.277 | 1.00 | 50.26 |
| ATOM | 405 | O | HIS | A | 192 | 37.929 | 52.308 | 5.947 | 1.00 | 49.74 |
| ATOM | 406 | CB | HIS | A | 192 | 41.104 | 53.659 | 5.744 | 1.00 | 50.08 |
| ATOM | 407 | CG | HIS | A | 192 | 41.324 | 52.407 | 6.548 | 1.00 | 54.01 |
| ATOM | 408 | ND1 | HIS | A | 192 | 42.037 | 52.396 | 7.732 | 1.00 | 56.03 |
| ATOM | 409 | CD2 | HIS | A | 192 | 40.955 | 51.122 | 6.323 | 1.00 | 56.20 |
| ATOM | 410 | CE1 | HIS | A | 192 | 42.080 | 51.164 | 8.209 | 1.00 | 55.65 |
| ATOM | 411 | NE2 | HIS | A | 192 | 41.432 | 50.371 | 7.373 | 1.00 | 56.10 |
| ATOM | 412 | N | THR | A | 193 | 38.625 | 53.802 | 7.480 | 1.00 | 45.40 |
| ATOM | 413 | CA | THR | A | 193 | 37.769 | 53.312 | 8.550 | 1.00 | 44.73 |

TABLE 3-continued

Structural coordinates for AKT3lkd(pT305, pS472) (SEQ ID NO:2).

| ATOM | 414 | C | THR | A | 193 | 36.275 | 53.260 | 8.202 | 1.00 | 48.03 |
|---|---|---|---|---|---|---|---|---|---|---|
| ATOM | 415 | O | THR | A | 193 | 35.581 | 52.312 | 8.576 | 1.00 | 47.70 |
| ATOM | 416 | CB | THR | A | 193 | 37.985 | 54.114 | 9.831 | 1.00 | 50.20 |
| ATOM | 417 | OG1 | THR | A | 193 | 39.382 | 54.122 | 10.149 | 1.00 | 49.50 |
| ATOM | 418 | CG2 | THR | A | 193 | 37.207 | 53.504 | 10.990 | 1.00 | 47.68 |
| ATOM | 419 | N | LEU | A | 194 | 35.783 | 54.271 | 7.492 | 1.00 | 43.75 |
| ATOM | 420 | CA | LEU | A | 194 | 34.364 | 54.305 | 7.108 | 1.00 | 43.14 |
| ATOM | 421 | C | LEU | A | 194 | 34.031 | 53.234 | 6.060 | 1.00 | 45.05 |
| ATOM | 422 | O | LEU | A | 194 | 32.986 | 52.595 | 6.118 | 1.00 | 43.85 |
| ATOM | 423 | CB | LEU | A | 194 | 33.969 | 55.699 | 6.606 | 1.00 | 43.25 |
| ATOM | 424 | CG | LEU | A | 194 | 33.166 | 56.564 | 7.588 | 1.00 | 48.40 |
| ATOM | 425 | CD1 | LEU | A | 194 | 33.643 | 56.378 | 9.021 | 1.00 | 48.65 |
| ATOM | 426 | CD2 | LEU | A | 194 | 33.200 | 58.038 | 7.193 | 1.00 | 50.66 |
| ATOM | 427 | N | THR | A | 195 | 34.942 | 53.041 | 5.117 | 1.00 | 41.56 |
| ATOM | 428 | CA | THR | A | 195 | 34.782 | 52.041 | 4.078 | 1.00 | 41.38 |
| ATOM | 429 | C | THR | A | 195 | 34.685 | 50.636 | 4.681 | 1.00 | 45.36 |
| ATOM | 430 | O | THR | A | 195 | 33.740 | 49.893 | 4.404 | 1.00 | 45.01 |
| ATOM | 431 | CB | THR | A | 195 | 35.965 | 52.064 | 3.108 | 1.00 | 50.18 |
| ATOM | 432 | OG1 | THR | A | 195 | 36.071 | 53.359 | 2.506 | 1.00 | 48.97 |
| ATOM | 433 | CG2 | THR | A | 195 | 35.783 | 51.011 | 2.023 | 1.00 | 50.15 |
| ATOM | 434 | N | GLU | A | 196 | 35.667 | 50.274 | 5.498 | 1.00 | 41.97 |
| ATOM | 435 | CA | GLU | A | 196 | 35.682 | 48.955 | 6.111 | 1.00 | 42.29 |
| ATOM | 436 | C | GLU | A | 196 | 34.431 | 48.708 | 6.952 | 1.00 | 45.65 |
| ATOM | 437 | O | GLU | A | 196 | 33.932 | 47.584 | 7.026 | 1.00 | 44.89 |
| ATOM | 438 | CB | GLU | A | 196 | 36.954 | 48.747 | 6.936 | 1.00 | 43.90 |
| ATOM | 439 | CG | GLU | A | 196 | 37.258 | 49.857 | 7.919 | 1.00 | 58.76 |
| ATOM | 440 | CD | GLU | A | 196 | 38.621 | 49.691 | 8.572 | 1.00 | 86.31 |
| ATOM | 441 | OE1 | GLU | A | 196 | 39.297 | 48.682 | 8.284 | 1.00 | 88.34 |
| ATOM | 442 | OE2 | GLU | A | 196 | 39.018 | 50.569 | 9.362 | 1.00 | 82.00 |
| ATOM | 443 | N | SER | A | 197 | 33.911 | 49.771 | 7.554 | 1.00 | 42.05 |
| ATOM | 444 | CA | SER | A | 197 | 32.706 | 49.678 | 8.362 | 1.00 | 42.04 |
| ATOM | 445 | C | SER | A | 197 | 31.503 | 49.299 | 7.503 | 1.00 | 46.06 |
| ATOM | 446 | O | SER | A | 197 | 30.712 | 48.415 | 7.869 | 1.00 | 46.19 |
| ATOM | 447 | CB | SER | A | 197 | 32.438 | 51.004 | 9.072 | 1.00 | 45.83 |
| ATOM | 448 | OG | SER | A | 197 | 31.124 | 51.035 | 9.604 | 1.00 | 54.99 |
| ATOM | 449 | N | ARG | A | 198 | 31.353 | 49.977 | 6.370 | 1.00 | 41.72 |
| ATOM | 450 | CA | ARG | A | 198 | 30.236 | 49.697 | 5.466 | 1.00 | 41.40 |
| ATOM | 451 | C | ARG | A | 198 | 30.276 | 48.248 | 5.005 | 1.00 | 43.85 |
| ATOM | 452 | O | ARG | A | 198 | 29.249 | 47.577 | 4.934 | 1.00 | 43.41 |
| ATOM | 453 | CB | ARG | A | 198 | 30.276 | 50.627 | 4.254 | 1.00 | 42.64 |
| ATOM | 454 | CG | ARG | A | 198 | 29.366 | 51.836 | 4.375 | 1.00 | 57.59 |
| ATOM | 455 | CD | ARG | A | 198 | 30.036 | 53.080 | 3.813 | 1.00 | 71.46 |
| ATOM | 456 | NE | ARG | A | 198 | 30.811 | 52.776 | 2.613 | 1.00 | 79.94 |
| ATOM | 457 | CZ | ARG | A | 198 | 31.657 | 53.621 | 2.036 | 1.00 | 91.64 |
| ATOM | 458 | NH1 | ARG | A | 198 | 31.834 | 54.835 | 2.545 | 1.00 | 77.82 |
| ATOM | 459 | NH2 | ARG | A | 198 | 32.322 | 53.254 | 0.947 | 1.00 | 77.09 |
| ATOM | 460 | N | VAL | A | 199 | 31.475 | 47.770 | 4.701 | 1.00 | 39.20 |
| ATOM | 461 | CA | VAL | A | 199 | 31.656 | 46.409 | 4.234 | 1.00 | 38.35 |
| ATOM | 462 | C | VAL | A | 199 | 31.216 | 45.370 | 5.276 | 1.00 | 40.18 |
| ATOM | 463 | O | VAL | A | 199 | 30.416 | 44.488 | 4.977 | 1.00 | 39.76 |
| ATOM | 464 | CB | VAL | A | 199 | 33.122 | 46.154 | 3.806 | 1.00 | 42.01 |
| ATOM | 465 | CG1 | VAL | A | 199 | 33.367 | 44.661 | 3.555 | 1.00 | 41.48 |
| ATOM | 466 | CG2 | VAL | A | 199 | 33.461 | 46.988 | 2.564 | 1.00 | 41.73 |
| ATOM | 467 | N | LEU | A | 200 | 31.740 | 45.479 | 6.493 | 1.00 | 35.30 |
| ATOM | 468 | CA | LEU | A | 200 | 31.395 | 44.532 | 7.558 | 1.00 | 35.14 |
| ATOM | 469 | C | LEU | A | 200 | 29.930 | 44.665 | 7.983 | 1.00 | 38.82 |
| ATOM | 470 | O | LEU | A | 200 | 29.341 | 43.730 | 8.540 | 1.00 | 37.88 |
| ATOM | 471 | CB | LEU | A | 200 | 32.317 | 44.701 | 8.763 | 1.00 | 34.92 |
| ATOM | 472 | CG | LEU | A | 200 | 33.678 | 43.996 | 8.681 | 1.00 | 39.20 |
| ATOM | 473 | CD1 | LEU | A | 200 | 33.758 | 43.115 | 7.437 | 1.00 | 39.01 |
| ATOM | 474 | CD2 | LEU | A | 200 | 34.805 | 45.016 | 8.702 | 1.00 | 41.29 |
| ATOM | 475 | N | LYS | A | 201 | 29.346 | 45.822 | 7.689 | 1.00 | 34.75 |
| ATOM | 476 | CA | LYS | A | 201 | 27.957 | 46.077 | 8.014 | 1.00 | 34.18 |
| ATOM | 477 | C | LYS | A | 201 | 27.027 | 45.453 | 6.992 | 1.00 | 38.25 |
| ATOM | 478 | O | LYS | A | 201 | 26.013 | 44.865 | 7.351 | 1.00 | 38.46 |
| ATOM | 479 | CB | LYS | A | 201 | 27.695 | 47.583 | 8.104 | 1.00 | 35.90 |
| ATOM | 480 | CG | LYS | A | 201 | 27.359 | 48.060 | 9.493 | 1.00 | 41.82 |
| ATOM | 481 | CD | LYS | A | 201 | 26.958 | 49.521 | 9.494 | 1.00 | 50.50 |
| ATOM | 482 | CE | LYS | A | 201 | 25.981 | 49.822 | 10.619 | 1.00 | 55.93 |
| ATOM | 483 | NZ | LYS | A | 201 | 24.843 | 48.854 | 10.642 | 1.00 | 62.40 |
| ATOM | 484 | N | ASN | A | 202 | 27.376 | 45.580 | 5.715 | 1.00 | 34.37 |
| ATOM | 485 | CA | ASN | A | 202 | 26.533 | 45.063 | 4.642 | 1.00 | 34.06 |
| ATOM | 486 | C | ASN | A | 202 | 26.929 | 43.711 | 4.069 | 1.00 | 37.70 |
| ATOM | 487 | O | ASN | A | 202 | 26.470 | 43.333 | 2.985 | 1.00 | 38.54 |
| ATOM | 488 | CB | ASN | A | 202 | 26.387 | 46.099 | 3.528 | 1.00 | 35.66 |
| ATOM | 489 | CG | ASN | A | 202 | 25.472 | 47.243 | 3.923 | 1.00 | 59.25 |
| ATOM | 490 | OD1 | ASN | A | 202 | 25.769 | 47.989 | 4.858 | 1.00 | 48.45 |
| ATOM | 491 | ND2 | ASN | A | 202 | 24.305 | 47.325 | 3.276 | 1.00 | 52.77 |

TABLE 3-continued

Structural coordinates for AKT3lkd(pT305, pS472) (SEQ ID NO:2).

| ATOM | 492 | N | THR | A | 203 | 27.741 | 42.965 | 4.800 | 1.00 | 32.56 |
|------|-----|-----|-----|---|-----|--------|--------|-------|------|-------|
| ATOM | 493 | CA | THR | A | 203 | 28.156 | 41.656 | 4.344 | 1.00 | 31.99 |
| ATOM | 494 | C | THR | A | 203 | 27.856 | 40.610 | 5.392 | 1.00 | 35.95 |
| ATOM | 495 | O | THR | A | 203 | 27.973 | 40.858 | 6.588 | 1.00 | 35.55 |
| ATOM | 496 | CB | THR | A | 203 | 29.666 | 41.609 | 4.026 | 1.00 | 40.67 |
| ATOM | 497 | OG1 | THR | A | 203 | 30.401 | 42.159 | 5.123 | 1.00 | 41.01 |
| ATOM | 498 | CG2 | THR | A | 203 | 29.977 | 42.397 | 2.762 | 1.00 | 37.36 |
| ATOM | 499 | N | ARG | A | 204 | 27.465 | 39.431 | 4.938 | 1.00 | 32.17 |
| ATOM | 500 | CA | ARG | A | 204 | 27.187 | 38.331 | 5.836 | 1.00 | 31.26 |
| ATOM | 501 | C | ARG | A | 204 | 27.888 | 37.112 | 5.290 | 1.00 | 31.71 |
| ATOM | 502 | O | ARG | A | 204 | 27.631 | 36.700 | 4.160 | 1.00 | 30.76 |
| ATOM | 503 | CB | ARG | A | 204 | 25.677 | 38.083 | 5.936 | 1.00 | 34.12 |
| ATOM | 504 | CG | ARG | A | 204 | 25.298 | 36.656 | 6.306 | 1.00 | 51.24 |
| ATOM | 505 | CD | ARG | A | 204 | 23.773 | 36.471 | 6.362 | 1.00 | 65.51 |
| ATOM | 506 | NE | ARG | A | 204 | 23.218 | 36.899 | 7.645 | 1.00 | 77.47 |
| ATOM | 507 | CZ | ARG | A | 204 | 23.031 | 36.093 | 8.687 | 1.00 | 92.12 |
| ATOM | 508 | NH1 | ARG | A | 204 | 23.349 | 34.807 | 8.601 | 1.00 | 78.47 |
| ATOM | 509 | NH2 | ARG | A | 204 | 22.525 | 36.573 | 9.816 | 1.00 | 79.33 |
| ATOM | 510 | N | HIS | A | 205 | 28.820 | 36.571 | 6.072 | 1.00 | 26.03 |
| ATOM | 511 | CA | HIS | A | 205 | 29.581 | 35.396 | 5.669 | 1.00 | 23.76 |
| ATOM | 512 | C | HIS | A | 205 | 30.171 | 34.685 | 6.884 | 1.00 | 24.46 |
| ATOM | 513 | O | HIS | A | 205 | 30.702 | 35.327 | 7.794 | 1.00 | 22.57 |
| ATOM | 514 | CB | HIS | A | 205 | 30.723 | 35.802 | 4.694 | 1.00 | 24.32 |
| ATOM | 515 | CG | HIS | A | 205 | 31.393 | 34.635 | 4.037 | 1.00 | 27.21 |
| ATOM | 516 | ND1 | HIS | A | 205 | 31.063 | 34.206 | 2.770 | 1.00 | 28.99 |
| ATOM | 517 | CD2 | HIS | A | 205 | 32.329 | 33.775 | 4.493 | 1.00 | 28.21 |
| ATOM | 518 | CE1 | HIS | A | 205 | 31.779 | 33.140 | 2.465 | 1.00 | 27.86 |
| ATOM | 519 | NE2 | HIS | A | 205 | 32.561 | 32.862 | 3.492 | 1.00 | 28.21 |
| ATOM | 520 | N | PRO | A | 206 | 30.131 | 33.353 | 6.861 | 1.00 | 20.64 |
| ATOM | 521 | CA | PRO | A | 206 | 30.668 | 32.529 | 7.940 | 1.00 | 19.55 |
| ATOM | 522 | C | PRO | A | 206 | 32.032 | 32.969 | 8.463 | 1.00 | 22.69 |
| ATOM | 523 | O | PRO | A | 206 | 32.295 | 32.905 | 9.663 | 1.00 | 22.56 |
| ATOM | 524 | CB | PRO | A | 206 | 30.812 | 31.147 | 7.280 | 1.00 | 21.21 |
| ATOM | 525 | CG | PRO | A | 206 | 29.812 | 31.144 | 6.201 | 1.00 | 26.20 |
| ATOM | 526 | CD | PRO | A | 206 | 29.768 | 32.546 | 5.681 | 1.00 | 21.68 |
| ATOM | 527 | N | PHE | A | 207 | 32.920 | 33.356 | 7.559 | 1.00 | 18.55 |
| ATOM | 528 | CA | PHE | A | 207 | 34.270 | 33.697 | 7.947 | 1.00 | 18.34 |
| ATOM | 529 | C | PHE | A | 207 | 34.583 | 35.179 | 8.026 | 1.00 | 25.06 |
| ATOM | 530 | O | PHE | A | 207 | 35.722 | 35.576 | 8.231 | 1.00 | 25.05 |
| ATOM | 531 | CB | PHE | A | 207 | 35.269 | 32.916 | 7.121 | 1.00 | 19.55 |
| ATOM | 532 | CG | PHE | A | 207 | 34.899 | 31.465 | 6.963 | 1.00 | 20.20 |
| ATOM | 533 | CD1 | PHE | A | 207 | 34.625 | 30.683 | 8.083 | 1.00 | 22.53 |
| ATOM | 534 | CD2 | PHE | A | 207 | 34.740 | 30.902 | 5.697 | 1.00 | 21.25 |
| ATOM | 535 | CE1 | PHE | A | 207 | 34.260 | 29.343 | 7.949 | 1.00 | 23.31 |
| ATOM | 536 | CE2 | PHE | A | 207 | 34.380 | 29.570 | 5.556 | 1.00 | 23.64 |
| ATOM | 537 | CZ | PHE | A | 207 | 34.125 | 28.788 | 6.689 | 1.00 | 21.74 |
| ATOM | 538 | N | LEU | A | 208 | 33.547 | 35.992 | 7.957 | 1.00 | 23.81 |
| ATOM | 539 | CA | LEU | A | 208 | 33.715 | 37.421 | 8.103 | 1.00 | 24.40 |
| ATOM | 540 | C | LEU | A | 208 | 33.101 | 37.849 | 9.435 | 1.00 | 28.71 |
| ATOM | 541 | O | LEU | A | 208 | 31.998 | 37.431 | 9.773 | 1.00 | 27.65 |
| ATOM | 542 | CB | LEU | A | 208 | 33.027 | 38.154 | 6.956 | 1.00 | 24.57 |
| ATOM | 543 | CG | LEU | A | 208 | 33.862 | 38.348 | 5.690 | 1.00 | 29.87 |
| ATOM | 544 | CD1 | LEU | A | 208 | 33.039 | 39.084 | 4.632 | 1.00 | 30.33 |
| ATOM | 545 | CD2 | LEU | A | 208 | 35.163 | 39.115 | 6.010 | 1.00 | 30.98 |
| ATOM | 546 | N | THR | A | 209 | 33.835 | 38.640 | 10.208 | 1.00 | 26.50 |
| ATOM | 547 | CA | THR | A | 209 | 33.300 | 39.147 | 11.465 | 1.00 | 27.54 |
| ATOM | 548 | C | THR | A | 209 | 32.189 | 40.142 | 11.117 | 1.00 | 33.46 |
| ATOM | 549 | O | THR | A | 209 | 32.398 | 41.065 | 10.326 | 1.00 | 32.90 |
| ATOM | 550 | CB | THR | A | 209 | 34.385 | 39.866 | 12.308 | 1.00 | 37.13 |
| ATOM | 551 | OG1 | THR | A | 209 | 35.450 | 38.953 | 12.613 | 1.00 | 39.04 |
| ATOM | 552 | CG2 | THR | A | 209 | 33.791 | 40.383 | 13.604 | 1.00 | 34.65 |
| ATOM | 553 | N | SER | A | 210 | 31.000 | 39.922 | 11.666 | 1.00 | 31.73 |
| ATOM | 554 | CA | SER | A | 210 | 29.861 | 40.799 | 11.396 | 1.00 | 32.47 |
| ATOM | 555 | C | SER | A | 210 | 29.835 | 42.050 | 12.271 | 1.00 | 37.61 |
| ATOM | 556 | O | SER | A | 210 | 30.079 | 41.991 | 13.472 | 1.00 | 36.25 |
| ATOM | 557 | CB | SER | A | 210 | 28.556 | 40.037 | 11.545 | 1.00 | 36.99 |
| ATOM | 558 | OG | SER | A | 210 | 28.809 | 38.660 | 11.779 | 1.00 | 49.51 |
| ATOM | 559 | N | LEU | A | 211 | 29.522 | 43.176 | 11.647 | 1.00 | 36.44 |
| ATOM | 560 | CA | LEU | A | 211 | 29.419 | 44.455 | 12.334 | 1.00 | 37.27 |
| ATOM | 561 | C | LEU | A | 211 | 27.936 | 44.782 | 12.493 | 1.00 | 43.62 |
| ATOM | 562 | O | LEU | A | 211 | 27.259 | 45.116 | 11.516 | 1.00 | 43.33 |
| ATOM | 563 | CB | LEU | A | 211 | 30.113 | 45.545 | 11.514 | 1.00 | 37.30 |
| ATOM | 564 | CG | LEU | A | 211 | 30.176 | 46.937 | 12.126 | 1.00 | 41.81 |
| ATOM | 565 | CD1 | LEU | A | 211 | 29.807 | 46.858 | 13.589 | 1.00 | 42.21 |
| ATOM | 566 | CD2 | LEU | A | 211 | 31.558 | 47.521 | 11.950 | 1.00 | 43.56 |
| ATOM | 567 | N | LYS | A | 212 | 27.432 | 44.643 | 13.719 | 1.00 | 41.82 |
| ATOM | 568 | CA | LYS | A | 212 | 26.018 | 44.856 | 14.016 | 1.00 | 42.35 |
| ATOM | 569 | C | LYS | A | 212 | 25.623 | 46.320 | 14.179 | 1.00 | 47.70 |

TABLE 3-continued

Structural coordinates for AKT3lkd(pT305, pS472) (SEQ ID NO:2).

| ATOM | 570 | O | LYS | A | 212 | 24.601 | 46.751 | 13.652 | 1.00 | 48.11 |
|------|-----|------|-----|---|-----|--------|--------|--------|------|-------|
| ATOM | 571 | CB | LYS | A | 212 | 25.593 | 44.045 | 15.240 | 1.00 | 44.94 |
| ATOM | 572 | CG | LYS | A | 212 | 24.083 | 43.932 | 15.410 | 1.00 | 59.02 |
| ATOM | 573 | CD | LYS | A | 212 | 23.697 | 42.634 | 16.110 | 1.00 | 68.40 |
| ATOM | 574 | CE | LYS | A | 212 | 22.211 | 42.600 | 16.438 | 1.00 | 78.75 |
| ATOM | 575 | NZ | LYS | A | 212 | 21.638 | 41.229 | 16.302 | 1.00 | 87.23 |
| ATOM | 576 | N | TYR | A | 213 | 26.425 | 47.083 | 14.909 | 1.00 | 44.53 |
| ATOM | 577 | CA | TYR | A | 213 | 26.139 | 48.503 | 15.095 | 1.00 | 44.43 |
| ATOM | 578 | C | TYR | A | 213 | 27.387 | 49.356 | 14.963 | 1.00 | 49.01 |
| ATOM | 579 | O | TYR | A | 213 | 28.509 | 48.863 | 15.042 | 1.00 | 48.30 |
| ATOM | 580 | CB | TYR | A | 213 | 25.487 | 48.773 | 16.452 | 1.00 | 45.53 |
| ATOM | 581 | CG | TYR | A | 213 | 24.277 | 47.921 | 16.751 | 1.00 | 46.97 |
| ATOM | 582 | CD1 | TYR | A | 213 | 23.182 | 47.910 | 15.901 | 1.00 | 48.71 |
| ATOM | 583 | CD2 | TYR | A | 213 | 24.217 | 47.156 | 17.906 | 1.00 | 47.57 |
| ATOM | 584 | CE1 | TYR | A | 213 | 22.077 | 47.134 | 16.180 | 1.00 | 49.21 |
| ATOM | 585 | CE2 | TYR | A | 213 | 23.118 | 46.385 | 18.192 | 1.00 | 48.39 |
| ATOM | 586 | CZ | TYR | A | 213 | 22.052 | 46.379 | 17.330 | 1.00 | 56.25 |
| ATOM | 587 | OH | TYR | A | 213 | 20.957 | 45.608 | 17.622 | 1.00 | 60.00 |
| ATOM | 588 | N | SER | A | 214 | 27.169 | 50.649 | 14.792 | 1.00 | 46.44 |
| ATOM | 589 | CA | SER | A | 214 | 28.241 | 51.623 | 14.692 | 1.00 | 46.86 |
| ATOM | 590 | C | SER | A | 214 | 27.646 | 52.956 | 15.106 | 1.00 | 51.90 |
| ATOM | 591 | O | SER | A | 214 | 26.675 | 53.414 | 14.513 | 1.00 | 51.28 |
| ATOM | 592 | CB | SER | A | 214 | 28.761 | 51.709 | 13.258 | 1.00 | 50.46 |
| ATOM | 593 | OG | SER | A | 214 | 28.562 | 53.004 | 12.718 | 1.00 | 58.51 |
| ATOM | 594 | N | PHE | A | 215 | 28.171 | 53.539 | 16.174 | 1.00 | 50.06 |
| ATOM | 595 | CA | PHE | A | 215 | 27.633 | 54.794 | 16.655 | 1.00 | 50.60 |
| ATOM | 596 | C | PHE | A | 215 | 28.654 | 55.876 | 16.903 | 1.00 | 57.11 |
| ATOM | 597 | O | PHE | A | 215 | 29.865 | 55.633 | 16.910 | 1.00 | 55.93 |
| ATOM | 598 | CB | PHE | A | 215 | 26.680 | 54.608 | 17.844 | 1.00 | 52.14 |
| ATOM | 599 | CG | PHE | A | 215 | 27.334 | 54.055 | 19.073 | 1.00 | 53.61 |
| ATOM | 600 | CD1 | PHE | A | 215 | 27.120 | 52.743 | 19.454 | 1.00 | 56.38 |
| ATOM | 601 | CD2 | PHE | A | 215 | 28.118 | 54.863 | 19.884 | 1.00 | 55.94 |
| ATOM | 602 | CE1 | PHE | A | 215 | 27.701 | 52.238 | 20.599 | 1.00 | 57.16 |
| ATOM | 603 | CE2 | PHE | A | 215 | 28.707 | 54.359 | 21.026 | 1.00 | 58.53 |
| ATOM | 604 | CZ | PHE | A | 215 | 28.495 | 53.045 | 21.383 | 1.00 | 56.48 |
| ATOM | 605 | N | GLN | A | 216 | 28.145 | 57.083 | 17.085 | 1.00 | 56.44 |
| ATOM | 606 | CA | GLN | A | 216 | 28.958 | 58.267 | 17.231 | 1.00 | 57.55 |
| ATOM | 607 | C | GLN | A | 216 | 29.136 | 58.745 | 18.670 | 1.00 | 62.90 |
| ATOM | 608 | O | GLN | A | 216 | 28.167 | 58.877 | 19.429 | 1.00 | 62.42 |
| ATOM | 609 | CB | GLN | A | 216 | 28.357 | 59.401 | 16.383 | 1.00 | 59.31 |
| ATOM | 610 | CG | GLN | A | 216 | 27.102 | 58.995 | 15.573 | 1.00 | 77.93 |
| ATOM | 611 | CD | GLN | A | 216 | 25.916 | 58.611 | 16.456 | 1.00 | 102.45 |
| ATOM | 612 | OE1 | GLN | A | 216 | 26.021 | 58.593 | 17.683 | 1.00 | 99.72 |
| ATOM | 613 | NE2 | GLN | A | 216 | 24.817 | 58.217 | 15.827 | 1.00 | 96.02 |
| ATOM | 614 | N | THR | A | 217 | 30.380 | 59.061 | 19.013 | 1.00 | 60.47 |
| ATOM | 615 | CA | THR | A | 217 | 30.714 | 59.615 | 20.315 | 1.00 | 61.03 |
| ATOM | 616 | C | THR | A | 217 | 31.289 | 61.001 | 20.076 | 1.00 | 65.98 |
| ATOM | 617 | O | THR | A | 217 | 31.522 | 61.393 | 18.932 | 1.00 | 65.50 |
| ATOM | 618 | CB | THR | A | 217 | 31.787 | 58.771 | 21.037 | 1.00 | 70.55 |
| ATOM | 619 | OG1 | THR | A | 217 | 31.820 | 57.452 | 20.475 | 1.00 | 72.70 |
| ATOM | 620 | CG2 | THR | A | 217 | 31.483 | 58.686 | 22.522 | 1.00 | 67.43 |
| ATOM | 621 | N | LYS | A | 218 | 31.529 | 61.740 | 21.150 | 1.00 | 63.05 |
| ATOM | 622 | CA | LYS | A | 218 | 32.084 | 63.075 | 21.023 | 1.00 | 63.13 |
| ATOM | 623 | C | LYS | A | 218 | 33.428 | 63.008 | 20.305 | 1.00 | 66.77 |
| ATOM | 624 | O | LYS | A | 218 | 33.657 | 63.722 | 19.322 | 1.00 | 66.65 |
| ATOM | 625 | CB | LYS | A | 218 | 32.245 | 63.729 | 22.397 | 1.00 | 65.83 |
| ATOM | 626 | CG | LYS | A | 218 | 30.965 | 64.375 | 22.939 | 1.00 | 81.04 |
| ATOM | 627 | CD | LYS | A | 218 | 31.107 | 65.895 | 23.046 | 1.00 | 90.89 |
| ATOM | 628 | CE | LYS | A | 218 | 29.983 | 66.506 | 23.876 | 1.00 | 100.16 |
| ATOM | 629 | NZ | LYS | A | 218 | 30.298 | 67.897 | 24.317 | 1.00 | 107.95 |
| ATOM | 630 | N | ASP | A | 219 | 34.301 | 62.124 | 20.780 | 1.00 | 62.33 |
| ATOM | 631 | CA | ASP | A | 219 | 35.630 | 61.965 | 20.199 | 1.00 | 61.41 |
| ATOM | 632 | C | ASP | A | 219 | 35.983 | 60.491 | 19.987 | 1.00 | 62.82 |
| ATOM | 633 | O | ASP | A | 219 | 37.159 | 60.127 | 19.916 | 1.00 | 62.26 |
| ATOM | 634 | CB | ASP | A | 219 | 36.673 | 62.619 | 21.099 | 1.00 | 63.58 |
| ATOM | 635 | CG | ASP | A | 219 | 36.239 | 62.664 | 22.555 | 1.00 | 76.55 |
| ATOM | 636 | OD1 | ASP | A | 219 | 35.577 | 61.701 | 23.011 | 1.00 | 77.33 |
| ATOM | 637 | OD2 | ASP | A | 219 | 36.543 | 63.668 | 23.237 | 1.00 | 83.21 |
| ATOM | 638 | N | ARG | A | 220 | 34.962 | 59.649 | 19.887 | 1.00 | 57.21 |
| ATOM | 639 | CA | ARG | A | 220 | 35.179 | 58.221 | 19.696 | 1.00 | 55.79 |
| ATOM | 640 | C | ARG | A | 220 | 34.265 | 57.623 | 18.634 | 1.00 | 55.52 |
| ATOM | 641 | O | ARG | A | 220 | 33.112 | 58.022 | 18.491 | 1.00 | 54.94 |
| ATOM | 642 | CB | ARG | A | 220 | 34.968 | 57.469 | 21.019 | 1.00 | 56.58 |
| ATOM | 643 | CG | ARG | A | 220 | 35.693 | 58.080 | 22.207 | 1.00 | 70.14 |
| ATOM | 644 | CD | ARG | A | 220 | 37.057 | 57.439 | 22.411 | 1.00 | 83.37 |
| ATOM | 645 | NE | ARG | A | 220 | 37.665 | 57.830 | 23.681 | 1.00 | 95.89 |
| ATOM | 646 | CZ | ARG | A | 220 | 37.565 | 57.127 | 24.807 | 1.00 | 112.68 |
| ATOM | 647 | NH1 | ARG | A | 220 | 36.884 | 55.989 | 24.828 | 1.00 | 99.39 |

TABLE 3-continued

Structural coordinates for AKT3lkd(pT305, pS472) (SEQ ID NO:2).

| ATOM | 648 | NH2 | ARG | A | 220 | 38.157 | 57.559 | 25.914 | 1.00 | 102.01 |
|---|---|---|---|---|---|---|---|---|---|---|
| ATOM | 649 | N | LEU | A | 221 | 34.785 | 56.636 | 17.918 | 1.00 | 49.52 |
| ATOM | 650 | CA | LEU | A | 221 | 34.001 | 55.883 | 16.948 | 1.00 | 47.99 |
| ATOM | 651 | C | LEU | A | 221 | 33.733 | 54.527 | 17.603 | 1.00 | 48.42 |
| ATOM | 652 | O | LEU | A | 221 | 34.649 | 53.900 | 18.130 | 1.00 | 46.98 |
| ATOM | 653 | CB | LEU | A | 221 | 34.789 | 55.693 | 15.653 | 1.00 | 48.06 |
| ATOM | 654 | CG | LEU | A | 221 | 34.468 | 56.649 | 14.496 | 1.00 | 52.71 |
| ATOM | 655 | CD1 | LEU | A | 221 | 33.688 | 57.877 | 14.977 | 1.00 | 52.72 |
| ATOM | 656 | CD2 | LEU | A | 221 | 35.743 | 57.060 | 13.781 | 1.00 | 54.34 |
| ATOM | 657 | N | CYS | A | 222 | 32.474 | 54.111 | 17.630 | 1.00 | 43.49 |
| ATOM | 658 | CA | CYS | A | 222 | 32.118 | 52.864 | 18.289 | 1.00 | 42.84 |
| ATOM | 659 | C | CYS | A | 222 | 31.448 | 51.832 | 17.387 | 1.00 | 44.34 |
| ATOM | 660 | O | CYS | A | 222 | 30.342 | 52.042 | 16.894 | 1.00 | 42.93 |
| ATOM | 661 | CB | CYS | A | 222 | 31.274 | 53.143 | 19.534 | 1.00 | 43.28 |
| ATOM | 662 | SG | CYS | A | 222 | 31.993 | 54.431 | 20.615 | 1.00 | 47.26 |
| ATOM | 663 | N | PHE | A | 223 | 32.132 | 50.704 | 17.198 | 1.00 | 40.20 |
| ATOM | 664 | CA | PHE | A | 223 | 31.623 | 49.607 | 16.377 | 1.00 | 39.35 |
| ATOM | 665 | C | PHE | A | 223 | 31.322 | 48.396 | 17.229 | 1.00 | 40.72 |
| ATOM | 666 | O | PHE | A | 223 | 32.191 | 47.896 | 17.940 | 1.00 | 39.82 |
| ATOM | 667 | CB | PHE | A | 223 | 32.636 | 49.232 | 15.293 | 1.00 | 41.31 |
| ATOM | 668 | CG | PHE | A | 223 | 33.118 | 50.402 | 14.488 | 1.00 | 43.04 |
| ATOM | 669 | CD1 | PHE | A | 223 | 32.284 | 51.015 | 13.562 | 1.00 | 46.11 |
| ATOM | 670 | CD2 | PHE | A | 223 | 34.398 | 50.899 | 14.664 | 1.00 | 45.47 |
| ATOM | 671 | CE1 | PHE | A | 223 | 32.723 | 52.091 | 12.817 | 1.00 | 47.07 |
| ATOM | 672 | CE2 | PHE | A | 223 | 34.843 | 51.979 | 13.923 | 1.00 | 48.60 |
| ATOM | 673 | CZ | PHE | A | 223 | 34.000 | 52.579 | 13.000 | 1.00 | 46.51 |
| ATOM | 674 | N | VAL | A | 224 | 30.082 | 47.932 | 17.154 | 1.00 | 36.75 |
| ATOM | 675 | CA | VAL | A | 224 | 29.636 | 46.764 | 17.902 | 1.00 | 36.41 |
| ATOM | 676 | C | VAL | A | 224 | 29.628 | 45.533 | 16.971 | 1.00 | 40.47 |
| ATOM | 677 | O | VAL | A | 224 | 28.745 | 45.384 | 16.136 | 1.00 | 39.44 |
| ATOM | 678 | CB | VAL | A | 224 | 28.218 | 46.997 | 18.486 | 1.00 | 39.86 |
| ATOM | 679 | CG1 | VAL | A | 224 | 27.648 | 45.720 | 19.062 | 1.00 | 39.60 |
| ATOM | 680 | CG2 | VAL | A | 224 | 28.250 | 48.090 | 19.535 | 1.00 | 39.55 |
| ATOM | 681 | N | MET | A | 225 | 30.638 | 44.677 | 17.113 | 1.00 | 37.95 |
| ATOM | 682 | CA | MET | A | 225 | 30.770 | 43.485 | 16.264 | 1.00 | 37.75 |
| ATOM | 683 | C | MET | A | 225 | 30.594 | 42.189 | 17.041 | 1.00 | 38.88 |
| ATOM | 684 | O | MET | A | 225 | 30.585 | 42.188 | 18.271 | 1.00 | 38.19 |
| ATOM | 685 | CB | MET | A | 225 | 32.121 | 43.491 | 15.551 | 1.00 | 40.54 |
| ATOM | 686 | CG | MET | A | 225 | 32.483 | 44.849 | 14.937 | 1.00 | 44.74 |
| ATOM | 687 | SD | MET | A | 225 | 34.250 | 45.174 | 14.978 | 1.00 | 49.50 |
| ATOM | 688 | CE | MET | A | 225 | 34.776 | 44.357 | 13.406 | 1.00 | 46.18 |
| ATOM | 689 | N | GLU | A | 226 | 30.453 | 41.081 | 16.317 | 1.00 | 33.69 |
| ATOM | 690 | CA | GLU | A | 226 | 30.255 | 39.790 | 16.953 | 1.00 | 32.41 |
| ATOM | 691 | C | GLU | A | 226 | 31.455 | 39.370 | 17.781 | 1.00 | 34.82 |
| ATOM | 692 | O | GLU | A | 226 | 32.598 | 39.645 | 17.425 | 1.00 | 33.81 |
| ATOM | 693 | CB | GLU | A | 226 | 29.881 | 38.717 | 15.943 | 1.00 | 33.64 |
| ATOM | 694 | CG | GLU | A | 226 | 31.049 | 38.113 | 15.205 | 1.00 | 42.22 |
| ATOM | 695 | CD | GLU | A | 226 | 30.615 | 37.045 | 14.229 | 1.00 | 50.19 |
| ATOM | 696 | OE1 | GLU | A | 226 | 30.423 | 37.372 | 13.046 | 1.00 | 31.52 |
| ATOM | 697 | OE2 | GLU | A | 226 | 30.416 | 35.889 | 14.655 | 1.00 | 45.47 |
| ATOM | 698 | N | TYR | A | 227 | 31.180 | 38.751 | 18.922 | 1.00 | 30.64 |
| ATOM | 699 | CA | TYR | A | 227 | 32.225 | 38.348 | 19.830 | 1.00 | 30.02 |
| ATOM | 700 | C | TYR | A | 227 | 32.881 | 37.054 | 19.381 | 1.00 | 33.49 |
| ATOM | 701 | O | TYR | A | 227 | 32.239 | 36.017 | 19.299 | 1.00 | 33.18 |
| ATOM | 702 | CB | TYR | A | 227 | 31.683 | 38.220 | 21.254 | 1.00 | 30.52 |
| ATOM | 703 | CG | TYR | A | 227 | 32.725 | 37.817 | 22.262 | 1.00 | 30.51 |
| ATOM | 704 | CD1 | TYR | A | 227 | 33.872 | 38.571 | 22.433 | 1.00 | 31.76 |
| ATOM | 705 | CD2 | TYR | A | 227 | 32.570 | 36.673 | 23.029 | 1.00 | 30.91 |
| ATOM | 706 | CE1 | TYR | A | 227 | 34.837 | 38.208 | 23.350 | 1.00 | 31.30 |
| ATOM | 707 | CE2 | TYR | A | 227 | 33.532 | 36.301 | 23.955 | 1.00 | 31.64 |
| ATOM | 708 | CZ | TYR | A | 227 | 34.665 | 37.078 | 24.106 | 1.00 | 35.18 |
| ATOM | 709 | OH | TYR | A | 227 | 35.627 | 36.720 | 25.011 | 1.00 | 33.31 |
| ATOM | 710 | N | VAL | A | 228 | 34.165 | 37.143 | 19.072 | 1.00 | 30.17 |
| ATOM | 711 | CA | VAL | A | 228 | 34.946 | 36.005 | 18.612 | 1.00 | 30.20 |
| ATOM | 712 | C | VAL | A | 228 | 35.993 | 35.722 | 19.685 | 1.00 | 32.06 |
| ATOM | 713 | O | VAL | A | 228 | 36.798 | 36.588 | 20.012 | 1.00 | 29.94 |
| ATOM | 714 | CB | VAL | A | 228 | 35.652 | 36.337 | 17.260 | 1.00 | 34.26 |
| ATOM | 715 | CG1 | VAL | A | 228 | 36.233 | 35.094 | 16.636 | 1.00 | 33.93 |
| ATOM | 716 | CG2 | VAL | A | 228 | 34.670 | 37.010 | 16.307 | 1.00 | 34.27 |
| ATOM | 717 | N | ASN | A | 229 | 35.956 | 34.524 | 20.264 | 1.00 | 29.13 |
| ATOM | 718 | CA | ASN | A | 229 | 36.863 | 34.210 | 21.374 | 1.00 | 28.91 |
| ATOM | 719 | C | ASN | A | 229 | 37.806 | 33.015 | 21.227 | 1.00 | 32.04 |
| ATOM | 720 | O | ASN | A | 229 | 38.293 | 32.491 | 22.222 | 1.00 | 32.59 |
| ATOM | 721 | CB | ASN | A | 229 | 36.092 | 34.137 | 22.692 | 1.00 | 28.22 |
| ATOM | 722 | CG | ASN | A | 229 | 35.296 | 32.843 | 22.837 | 1.00 | 43.75 |
| ATOM | 723 | OD1 | ASN | A | 229 | 34.858 | 32.245 | 21.846 | 1.00 | 33.37 |
| ATOM | 724 | ND2 | ASN | A | 229 | 35.087 | 32.420 | 24.079 | 1.00 | 33.01 |
| ATOM | 725 | N | GLY | A | 230 | 38.108 | 32.622 | 19.997 | 1.00 | 27.18 |

TABLE 3-continued

Structural coordinates for AKT3lkd(pT305, pS472) (SEQ ID NO:2).

| ATOM | 726 | CA  | GLY | A | 230 | 39.032 | 31.504 | 19.761 | 1.00 | 26.70 |
|------|-----|-----|-----|---|-----|--------|--------|--------|------|-------|
| ATOM | 727 | C   | GLY | A | 230 | 40.494 | 31.973 | 19.768 | 1.00 | 30.61 |
| ATOM | 728 | O   | GLY | A | 230 | 41.430 | 31.164 | 19.704 | 1.00 | 29.49 |
| ATOM | 729 | N   | GLY | A | 231 | 40.686 | 33.283 | 19.857 | 1.00 | 27.91 |
| ATOM | 730 | CA  | GLY | A | 231 | 42.024 | 33.849 | 19.894 | 1.00 | 28.27 |
| ATOM | 731 | C   | GLY | A | 231 | 42.519 | 34.374 | 18.545 | 1.00 | 33.13 |
| ATOM | 732 | O   | GLY | A | 231 | 42.092 | 33.909 | 17.476 | 1.00 | 32.60 |
| ATOM | 733 | N   | GLU | A | 232 | 43.443 | 35.329 | 18.615 | 1.00 | 30.32 |
| ATOM | 734 | CA  | GLU | A | 232 | 44.051 | 35.933 | 17.434 | 1.00 | 30.33 |
| ATOM | 735 | C   | GLU | A | 232 | 45.079 | 34.992 | 16.821 | 1.00 | 35.44 |
| ATOM | 736 | O   | GLU | A | 232 | 45.942 | 34.465 | 17.520 | 1.00 | 35.11 |
| ATOM | 737 | CB  | GLU | A | 232 | 44.730 | 37.246 | 17.821 | 1.00 | 31.50 |
| ATOM | 738 | CG  | GLU | A | 232 | 43.763 | 38.339 | 18.242 | 1.00 | 41.26 |
| ATOM | 739 | CD  | GLU | A | 232 | 44.440 | 39.697 | 18.402 | 1.00 | 64.42 |
| ATOM | 740 | OE1 | GLU | A | 232 | 45.692 | 39.752 | 18.396 | 1.00 | 61.08 |
| ATOM | 741 | OE2 | GLU | A | 232 | 43.717 | 40.706 | 18.569 | 1.00 | 56.22 |
| ATOM | 742 | N   | LEU | A | 233 | 44.988 | 34.783 | 15.513 | 1.00 | 33.46 |
| ATOM | 743 | CA  | LEU | A | 233 | 45.922 | 33.888 | 14.818 | 1.00 | 33.97 |
| ATOM | 744 | C   | LEU | A | 233 | 47.379 | 34.332 | 14.971 | 1.00 | 39.43 |
| ATOM | 745 | O   | LEU | A | 233 | 48.293 | 33.509 | 14.964 | 1.00 | 37.91 |
| ATOM | 746 | CB  | LEU | A | 233 | 45.546 | 33.743 | 13.343 | 1.00 | 34.07 |
| ATOM | 747 | CG  | LEU | A | 233 | 44.839 | 32.442 | 12.922 | 1.00 | 38.82 |
| ATOM | 748 | CD1 | LEU | A | 233 | 45.179 | 32.099 | 11.481 | 1.00 | 39.03 |
| ATOM | 749 | CD2 | LEU | A | 233 | 45.181 | 31.280 | 13.844 | 1.00 | 39.86 |
| ATOM | 750 | N   | PHE | A | 234 | 47.590 | 35.632 | 15.137 | 1.00 | 38.97 |
| ATOM | 751 | CA  | PHE | A | 234 | 48.939 | 36.151 | 15.343 | 1.00 | 40.06 |
| ATOM | 752 | C   | PHE | A | 234 | 49.533 | 35.548 | 16.622 | 1.00 | 43.27 |
| ATOM | 753 | O   | PHE | A | 234 | 50.727 | 35.293 | 16.702 | 1.00 | 42.90 |
| ATOM | 754 | CB  | PHE | A | 234 | 48.923 | 37.683 | 15.430 | 1.00 | 42.71 |
| ATOM | 755 | CG  | PHE | A | 234 | 50.270 | 38.290 | 15.727 | 1.00 | 45.44 |
| ATOM | 756 | CD1 | PHE | A | 234 | 50.816 | 38.220 | 17.007 | 1.00 | 49.40 |
| ATOM | 757 | CD2 | PHE | A | 234 | 50.983 | 38.953 | 14.735 | 1.00 | 48.49 |
| ATOM | 758 | CE1 | PHE | A | 234 | 52.057 | 38.783 | 17.286 | 1.00 | 50.84 |
| ATOM | 759 | CE2 | PHE | A | 234 | 52.231 | 39.522 | 15.007 | 1.00 | 51.68 |
| ATOM | 760 | CZ  | PHE | A | 234 | 52.765 | 39.442 | 16.277 | 1.00 | 50.01 |
| ATOM | 761 | N   | PHE | A | 235 | 48.685 | 35.304 | 17.610 | 1.00 | 40.00 |
| ATOM | 762 | CA  | PHE | A | 235 | 49.148 | 34.739 | 18.874 | 1.00 | 39.88 |
| ATOM | 763 | C   | PHE | A | 235 | 49.334 | 33.238 | 18.820 | 1.00 | 40.96 |
| ATOM | 764 | O   | PHE | A | 235 | 50.282 | 32.701 | 19.400 | 1.00 | 41.04 |
| ATOM | 765 | CB  | PHE | A | 235 | 48.243 | 35.155 | 20.027 | 1.00 | 42.40 |
| ATOM | 766 | CG  | PHE | A | 235 | 48.522 | 36.538 | 20.530 | 1.00 | 44.97 |
| ATOM | 767 | CD1 | PHE | A | 235 | 49.803 | 36.891 | 20.952 | 1.00 | 49.04 |
| ATOM | 768 | CD2 | PHE | A | 235 | 47.530 | 37.511 | 20.518 | 1.00 | 47.89 |
| ATOM | 769 | CE1 | PHE | A | 235 | 50.077 | 38.179 | 21.393 | 1.00 | 50.27 |
| ATOM | 770 | CE2 | PHE | A | 235 | 47.793 | 38.796 | 20.960 | 1.00 | 51.12 |
| ATOM | 771 | CZ  | PHE | A | 235 | 49.073 | 39.134 | 21.392 | 1.00 | 49.50 |
| ATOM | 772 | N   | HIS | A | 236 | 48.458 | 32.557 | 18.091 | 1.00 | 35.08 |
| ATOM | 773 | CA  | HIS | A | 236 | 48.589 | 31.112 | 17.936 | 1.00 | 33.84 |
| ATOM | 774 | C   | HIS | A | 236 | 49.863 | 30.785 | 17.151 | 1.00 | 37.87 |
| ATOM | 775 | O   | HIS | A | 236 | 50.585 | 29.853 | 17.491 | 1.00 | 37.94 |
| ATOM | 776 | CB  | HIS | A | 236 | 47.350 | 30.514 | 17.240 | 1.00 | 33.62 |
| ATOM | 777 | CG  | HIS | A | 236 | 46.089 | 30.639 | 18.039 | 1.00 | 36.21 |
| ATOM | 778 | ND1 | HIS | A | 236 | 45.917 | 30.022 | 19.257 | 1.00 | 37.51 |
| ATOM | 779 | CD2 | HIS | A | 236 | 44.941 | 31.316 | 17.796 | 1.00 | 37.33 |
| ATOM | 780 | CE1 | HIS | A | 236 | 44.720 | 30.317 | 19.733 | 1.00 | 36.63 |
| ATOM | 781 | NE2 | HIS | A | 236 | 44.108 | 31.099 | 18.865 | 1.00 | 36.80 |
| ATOM | 782 | N   | LEU | A | 237 | 50.152 | 31.589 | 16.128 | 1.00 | 34.11 |
| ATOM | 783 | CA  | LEU | A | 237 | 51.344 | 31.384 | 15.299 | 1.00 | 33.93 |
| ATOM | 784 | C   | LEU | A | 237 | 52.634 | 31.800 | 16.008 | 1.00 | 40.39 |
| ATOM | 785 | O   | LEU | A | 237 | 53.699 | 31.241 | 15.751 | 1.00 | 39.62 |
| ATOM | 786 | CB  | LEU | A | 237 | 51.215 | 32.130 | 13.966 | 1.00 | 33.25 |
| ATOM | 787 | CG  | LEU | A | 237 | 52.277 | 31.811 | 12.902 | 1.00 | 36.51 |
| ATOM | 788 | CD1 | LEU | A | 237 | 52.186 | 30.340 | 12.426 | 1.00 | 35.69 |
| ATOM | 789 | CD2 | LEU | A | 237 | 52.181 | 32.779 | 11.722 | 1.00 | 36.56 |
| ATOM | 790 | N   | SER | A | 238 | 52.537 | 32.794 | 16.884 | 1.00 | 39.50 |
| ATOM | 791 | CA  | SER | A | 238 | 53.698 | 33.271 | 17.624 | 1.00 | 40.53 |
| ATOM | 792 | C   | SER | A | 238 | 54.097 | 32.251 | 18.674 | 1.00 | 47.16 |
| ATOM | 793 | O   | SER | A | 238 | 55.258 | 32.176 | 19.071 | 1.00 | 47.91 |
| ATOM | 794 | CB  | SER | A | 238 | 53.402 | 34.614 | 18.288 | 1.00 | 44.65 |
| ATOM | 795 | OG  | SER | A | 238 | 52.343 | 34.488 | 19.221 | 1.00 | 56.44 |
| ATOM | 796 | N   | ARG | A | 239 | 53.128 | 31.457 | 19.118 | 1.00 | 44.09 |
| ATOM | 797 | CA  | ARG | A | 239 | 53.390 | 30.420 | 20.110 | 1.00 | 43.39 |
| ATOM | 798 | C   | ARG | A | 239 | 53.862 | 29.145 | 19.438 | 1.00 | 44.92 |
| ATOM | 799 | O   | ARG | A | 239 | 54.803 | 28.507 | 19.894 | 1.00 | 44.59 |
| ATOM | 800 | CB  | ARG | A | 239 | 52.132 | 30.135 | 20.939 | 1.00 | 44.44 |
| ATOM | 801 | CG  | ARG | A | 239 | 51.743 | 31.268 | 21.876 | 1.00 | 58.93 |
| ATOM | 802 | CD  | ARG | A | 239 | 50.586 | 30.872 | 22.772 | 1.00 | 73.30 |
| ATOM | 803 | NE  | ARG | A | 239 | 50.915 | 31.020 | 24.187 | 1.00 | 85.53 |

TABLE 3-continued

Structural coordinates for AKT3lkd(pT305, pS472) (SEQ ID NO:2).

| ATOM | 804 | CZ | ARG | A | 239 | 50.393 | 30.274 | 25.157 | 1.00 | 102.69 |
|------|-----|-----|-----|---|-----|--------|--------|--------|------|--------|
| ATOM | 805 | NH1 | ARG | A | 239 | 49.516 | 29.323 | 24.866 | 1.00 | 92.29 |
| ATOM | 806 | NH2 | ARG | A | 239 | 50.748 | 30.478 | 26.418 | 1.00 | 89.92 |
| ATOM | 807 | N | GLU | A | 240 | 53.193 | 28.770 | 18.353 | 1.00 | 39.56 |
| ATOM | 808 | CA | GLU | A | 240 | 53.529 | 27.548 | 17.638 | 1.00 | 38.22 |
| ATOM | 809 | C | GLU | A | 240 | 54.698 | 27.718 | 16.687 | 1.00 | 39.09 |
| ATOM | 810 | O | GLU | A | 240 | 55.300 | 26.733 | 16.251 | 1.00 | 38.35 |
| ATOM | 811 | CB | GLU | A | 240 | 52.310 | 27.015 | 16.894 | 1.00 | 39.89 |
| ATOM | 812 | CG | GLU | A | 240 | 51.616 | 25.864 | 17.612 | 1.00 | 54.37 |
| ATOM | 813 | CD | GLU | A | 240 | 50.164 | 25.715 | 17.211 | 1.00 | 75.18 |
| ATOM | 814 | OE1 | GLU | A | 240 | 49.299 | 25.745 | 18.113 | 1.00 | 70.76 |
| ATOM | 815 | OE2 | GLU | A | 240 | 49.894 | 25.560 | 15.999 | 1.00 | 67.23 |
| ATOM | 816 | N | ARG | A | 241 | 55.020 | 28.971 | 16.376 | 1.00 | 34.39 |
| ATOM | 817 | CA | ARG | A | 241 | 56.120 | 29.310 | 15.464 | 1.00 | 33.45 |
| ATOM | 818 | C | ARG | A | 241 | 55.736 | 29.114 | 14.001 | 1.00 | 34.71 |
| ATOM | 819 | O | ARG | A | 241 | 55.997 | 29.969 | 13.156 | 1.00 | 33.92 |
| ATOM | 820 | CB | ARG | A | 241 | 57.386 | 28.518 | 15.795 | 1.00 | 35.11 |
| ATOM | 821 | CG | ARG | A | 241 | 57.973 | 28.814 | 17.176 | 1.00 | 51.29 |
| ATOM | 822 | CD | ARG | A | 241 | 58.980 | 27.745 | 17.575 | 1.00 | 69.04 |
| ATOM | 823 | NE | ARG | A | 241 | 59.779 | 28.136 | 18.734 | 1.00 | 86.53 |
| ATOM | 824 | CZ | ARG | A | 241 | 60.907 | 27.532 | 19.101 | 1.00 | 105.47 |
| ATOM | 825 | NH1 | ARG | A | 241 | 61.381 | 26.515 | 18.389 | 1.00 | 93.52 |
| ATOM | 826 | NH2 | ARG | A | 241 | 61.571 | 27.952 | 20.174 | 1.00 | 94.15 |
| ATOM | 827 | N | VAL | A | 242 | 55.094 | 27.994 | 13.714 | 1.00 | 29.73 |
| ATOM | 828 | CA | VAL | A | 242 | 54.683 | 27.685 | 12.362 | 1.00 | 28.96 |
| ATOM | 829 | C | VAL | A | 242 | 53.539 | 26.690 | 12.404 | 1.00 | 31.76 |
| ATOM | 830 | O | VAL | A | 242 | 53.382 | 25.960 | 13.385 | 1.00 | 32.37 |
| ATOM | 831 | CB | VAL | A | 242 | 55.873 | 27.107 | 11.539 | 1.00 | 32.66 |
| ATOM | 832 | CG1 | VAL | A | 242 | 56.238 | 25.726 | 12.015 | 1.00 | 32.41 |
| ATOM | 833 | CG2 | VAL | A | 242 | 55.560 | 27.101 | 10.069 | 1.00 | 32.61 |
| ATOM | 834 | N | PHE | A | 243 | 52.704 | 26.698 | 11.368 | 1.00 | 26.11 |
| ATOM | 835 | CA | PHE | A | 243 | 51.594 | 25.751 | 11.279 | 1.00 | 24.16 |
| ATOM | 836 | C | PHE | A | 243 | 51.953 | 24.734 | 10.194 | 1.00 | 28.22 |
| ATOM | 837 | O | PHE | A | 243 | 52.724 | 25.036 | 9.277 | 1.00 | 27.88 |
| ATOM | 838 | CB | PHE | A | 243 | 50.294 | 26.457 | 10.880 | 1.00 | 24.65 |
| ATOM | 839 | CG | PHE | A | 243 | 49.783 | 27.439 | 11.896 | 1.00 | 24.99 |
| ATOM | 840 | CD1 | PHE | A | 243 | 50.070 | 27.289 | 13.245 | 1.00 | 27.03 |
| ATOM | 841 | CD2 | PHE | A | 243 | 48.992 | 28.518 | 11.496 | 1.00 | 26.15 |
| ATOM | 842 | CE1 | PHE | A | 243 | 49.596 | 28.198 | 14.177 | 1.00 | 27.21 |
| ATOM | 843 | CE2 | PHE | A | 243 | 48.517 | 29.432 | 12.417 | 1.00 | 28.65 |
| ATOM | 844 | CZ | PHE | A | 243 | 48.814 | 29.274 | 13.763 | 1.00 | 26.74 |
| ATOM | 845 | N | SER | A | 244 | 51.385 | 23.541 | 10.286 | 1.00 | 24.58 |
| ATOM | 846 | CA | SER | A | 244 | 51.607 | 22.512 | 9.268 | 1.00 | 23.94 |
| ATOM | 847 | C | SER | A | 244 | 50.951 | 23.019 | 7.974 | 1.00 | 27.15 |
| ATOM | 848 | O | SER | A | 244 | 50.146 | 23.948 | 8.011 | 1.00 | 26.67 |
| ATOM | 849 | CB | SER | A | 244 | 50.925 | 21.210 | 9.695 | 1.00 | 26.04 |
| ATOM | 850 | OG | SER | A | 244 | 49.514 | 21.397 | 9.789 | 1.00 | 32.03 |
| ATOM | 851 | N | GLU | A | 245 | 51.282 | 22.397 | 6.845 | 1.00 | 22.90 |
| ATOM | 852 | CA | GLU | A | 245 | 50.690 | 22.769 | 5.562 | 1.00 | 22.20 |
| ATOM | 853 | C | GLU | A | 245 | 49.182 | 22.540 | 5.586 | 1.00 | 26.48 |
| ATOM | 854 | O | GLU | A | 245 | 48.418 | 23.367 | 5.097 | 1.00 | 25.95 |
| ATOM | 855 | CB | GLU | A | 245 | 51.325 | 21.978 | 4.404 | 1.00 | 22.98 |
| ATOM | 856 | CG | GLU | A | 245 | 52.853 | 22.083 | 4.322 | 1.00 | 25.59 |
| ATOM | 857 | CD | GLU | A | 245 | 53.381 | 21.755 | 2.947 | 1.00 | 35.08 |
| ATOM | 858 | OE1 | GLU | A | 245 | 52.567 | 21.602 | 2.026 | 1.00 | 32.64 |
| ATOM | 859 | OE2 | GLU | A | 245 | 54.607 | 21.620 | 2.784 | 1.00 | 31.48 |
| ATOM | 860 | N | ASP | A | 246 | 48.754 | 21.427 | 6.174 | 1.00 | 24.03 |
| ATOM | 861 | CA | ASP | A | 246 | 47.312 | 21.124 | 6.261 | 1.00 | 24.29 |
| ATOM | 862 | C | ASP | A | 246 | 46.516 | 22.101 | 7.139 | 1.00 | 25.51 |
| ATOM | 863 | O | ASP | A | 246 | 45.389 | 22.458 | 6.822 | 1.00 | 25.60 |
| ATOM | 864 | CB | ASP | A | 246 | 47.055 | 19.693 | 6.715 | 1.00 | 26.38 |
| ATOM | 865 | CG | ASP | A | 246 | 45.636 | 19.247 | 6.410 | 1.00 | 36.57 |
| ATOM | 866 | OD1 | ASP | A | 246 | 45.247 | 19.313 | 5.226 | 1.00 | 36.84 |
| ATOM | 867 | OD2 | ASP | A | 246 | 44.877 | 18.944 | 7.359 | 1.00 | 43.79 |
| ATOM | 868 | N | ARG | A | 247 | 47.104 | 22.518 | 8.240 | 1.00 | 19.91 |
| ATOM | 869 | CA | ARG | A | 247 | 46.453 | 23.476 | 9.114 | 1.00 | 19.19 |
| ATOM | 870 | C | ARG | A | 247 | 46.393 | 24.823 | 8.377 | 1.00 | 21.86 |
| ATOM | 871 | O | ARG | A | 247 | 45.383 | 25.545 | 8.426 | 1.00 | 21.14 |
| ATOM | 872 | CB | ARG | A | 247 | 47.234 | 23.601 | 10.425 | 1.00 | 19.46 |
| ATOM | 873 | CG | ARG | A | 247 | 47.002 | 24.866 | 11.168 | 1.00 | 24.34 |
| ATOM | 874 | CD | ARG | A | 247 | 47.115 | 24.628 | 12.643 | 1.00 | 21.95 |
| ATOM | 875 | NE | ARG | A | 247 | 46.358 | 25.622 | 13.407 | 1.00 | 29.20 |
| ATOM | 876 | CZ | ARG | A | 247 | 46.670 | 26.009 | 14.638 | 1.00 | 40.42 |
| ATOM | 877 | NH1 | ARG | A | 247 | 47.727 | 25.489 | 15.233 | 1.00 | 28.39 |
| ATOM | 878 | NH2 | ARG | A | 247 | 45.927 | 26.911 | 15.273 | 1.00 | 23.01 |
| ATOM | 879 | N | THR | A | 248 | 47.451 | 25.124 | 7.637 | 1.00 | 17.93 |
| ATOM | 880 | CA | THR | A | 248 | 47.479 | 26.345 | 6.846 | 1.00 | 17.35 |
| ATOM | 881 | C | THR | A | 248 | 46.438 | 26.238 | 5.725 | 1.00 | 20.93 |

TABLE 3-continued

Structural coordinates for AKT3lkd(pT305, pS472) (SEQ ID NO:2).

| ATOM | 882 | O | THR | A | 248 | 45.702 | 27.185 | 5.465 | 1.00 | 21.71 |
|---|---|---|---|---|---|---|---|---|---|---|
| ATOM | 883 | CB | THR | A | 248 | 48.865 | 26.604 | 6.263 | 1.00 | 20.44 |
| ATOM | 884 | OG1 | THR | A | 248 | 49.803 | 26.759 | 7.335 | 1.00 | 18.45 |
| ATOM | 885 | CG2 | THR | A | 248 | 48.856 | 27.886 | 5.407 | 1.00 | 17.61 |
| ATOM | 886 | N | ARG | A | 249 | 46.347 | 25.054 | 5.119 | 1.00 | 16.24 |
| ATOM | 887 | CA | ARG | A | 249 | 45.365 | 24.779 | 4.080 | 1.00 | 16.03 |
| ATOM | 888 | C | ARG | A | 249 | 43.952 | 25.043 | 4.573 | 1.00 | 20.18 |
| ATOM | 889 | O | ARG | A | 249 | 43.128 | 25.570 | 3.841 | 1.00 | 19.61 |
| ATOM | 890 | CB | ARG | A | 249 | 45.453 | 23.320 | 3.637 | 1.00 | 16.34 |
| ATOM | 891 | CG | ARG | A | 249 | 44.248 | 22.866 | 2.803 | 1.00 | 23.97 |
| ATOM | 892 | CD | ARG | A | 249 | 44.423 | 21.441 | 2.292 | 1.00 | 21.51 |
| ATOM | 893 | NE | ARG | A | 249 | 45.599 | 21.312 | 1.440 | 1.00 | 22.80 |
| ATOM | 894 | CZ | ARG | A | 249 | 46.702 | 20.659 | 1.791 | 1.00 | 30.74 |
| ATOM | 895 | NH1 | ARG | A | 249 | 46.787 | 20.090 | 2.977 | 1.00 | 12.12 |
| ATOM | 896 | NH2 | ARG | A | 249 | 47.717 | 20.572 | 0.950 | 1.00 | 20.90 |
| ATOM | 897 | N | PHE | A | 250 | 43.667 | 24.622 | 5.811 | 1.00 | 17.35 |
| ATOM | 898 | CA | PHE | A | 250 | 42.347 | 24.804 | 6.406 | 1.00 | 16.63 |
| ATOM | 899 | C | PHE | A | 250 | 42.000 | 26.291 | 6.525 | 1.00 | 21.98 |
| ATOM | 900 | O | PHE | A | 250 | 40.914 | 26.712 | 6.126 | 1.00 | 23.01 |
| ATOM | 901 | CB | PHE | A | 250 | 42.271 | 24.119 | 7.779 | 1.00 | 18.17 |
| ATOM | 902 | CG | PHE | A | 250 | 41.015 | 24.451 | 8.561 | 1.00 | 19.11 |
| ATOM | 903 | CD1 | PHE | A | 250 | 39.866 | 23.669 | 8.425 | 1.00 | 21.47 |
| ATOM | 904 | CD2 | PHE | A | 250 | 40.982 | 25.546 | 9.418 | 1.00 | 20.92 |
| ATOM | 905 | CE1 | PHE | A | 250 | 38.707 | 23.972 | 9.128 | 1.00 | 22.76 |
| ATOM | 906 | CE2 | PHE | A | 250 | 39.815 | 25.878 | 10.114 | 1.00 | 24.10 |
| ATOM | 907 | CZ | PHE | A | 250 | 38.671 | 25.081 | 9.972 | 1.00 | 22.44 |
| ATOM | 908 | N | TYR | A | 251 | 42.930 | 27.089 | 7.054 | 1.00 | 17.84 |
| ATOM | 909 | CA | TYR | A | 251 | 42.697 | 28.527 | 7.204 | 1.00 | 17.26 |
| ATOM | 910 | C | TYR | A | 251 | 42.575 | 29.242 | 5.845 | 1.00 | 20.52 |
| ATOM | 911 | O | TYR | A | 251 | 41.627 | 29.984 | 5.621 | 1.00 | 19.86 |
| ATOM | 912 | CB | TYR | A | 251 | 43.783 | 29.184 | 8.063 | 1.00 | 17.85 |
| ATOM | 913 | CG | TYR | A | 251 | 43.806 | 28.683 | 9.480 | 1.00 | 19.71 |
| ATOM | 914 | CD1 | TYR | A | 251 | 42.626 | 28.371 | 10.143 | 1.00 | 21.29 |
| ATOM | 915 | CD2 | TYR | A | 251 | 45.015 | 28.516 | 10.166 | 1.00 | 20.33 |
| ATOM | 916 | CE1 | TYR | A | 251 | 42.643 | 27.878 | 11.443 | 1.00 | 21.50 |
| ATOM | 917 | CE2 | TYR | A | 251 | 45.036 | 28.050 | 11.460 | 1.00 | 20.98 |
| ATOM | 918 | CZ | TYR | A | 251 | 43.841 | 27.725 | 12.095 | 1.00 | 25.94 |
| ATOM | 919 | OH | TYR | A | 251 | 43.856 | 27.243 | 13.384 | 1.00 | 23.29 |
| ATOM | 920 | N | GLY | A | 252 | 43.541 | 29.003 | 4.948 | 1.00 | 16.56 |
| ATOM | 921 | CA | GLY | A | 252 | 43.534 | 29.604 | 3.609 | 1.00 | 15.90 |
| ATOM | 922 | C | GLY | A | 252 | 42.236 | 29.306 | 2.839 | 1.00 | 19.87 |
| ATOM | 923 | O | GLY | A | 252 | 41.682 | 30.187 | 2.165 | 1.00 | 19.54 |
| ATOM | 924 | N | ALA | A | 253 | 41.757 | 28.071 | 2.937 | 1.00 | 16.19 |
| ATOM | 925 | CA | ALA | A | 253 | 40.503 | 27.690 | 2.276 | 1.00 | 16.37 |
| ATOM | 926 | C | ALA | A | 253 | 39.335 | 28.564 | 2.767 | 1.00 | 20.68 |
| ATOM | 927 | O | ALA | A | 253 | 38.522 | 29.043 | 1.977 | 1.00 | 19.80 |
| ATOM | 928 | CB | ALA | A | 253 | 40.203 | 26.220 | 2.509 | 1.00 | 16.98 |
| ATOM | 929 | N | GLU | A | 254 | 39.268 | 28.776 | 4.073 | 1.00 | 18.10 |
| ATOM | 930 | CA | GLU | A | 254 | 38.189 | 29.577 | 4.656 | 1.00 | 17.37 |
| ATOM | 931 | C | GLU | A | 254 | 38.279 | 31.024 | 4.243 | 1.00 | 20.35 |
| ATOM | 932 | O | GLU | A | 254 | 37.270 | 31.654 | 3.924 | 1.00 | 20.47 |
| ATOM | 933 | CB | GLU | A | 254 | 38.151 | 29.414 | 6.172 | 1.00 | 18.31 |
| ATOM | 934 | CG | GLU | A | 254 | 38.065 | 27.967 | 6.591 | 1.00 | 21.31 |
| ATOM | 935 | CD | GLU | A | 254 | 37.453 | 27.778 | 7.965 | 1.00 | 28.80 |
| ATOM | 936 | OE1 | GLU | A | 254 | 36.699 | 26.796 | 8.155 | 1.00 | 21.49 |
| ATOM | 937 | OE2 | GLU | A | 254 | 37.799 | 28.548 | 8.879 | 1.00 | 18.42 |
| ATOM | 938 | N | ILE | A | 255 | 39.502 | 31.527 | 4.171 | 1.00 | 16.60 |
| ATOM | 939 | CA | ILE | A | 255 | 39.753 | 32.892 | 3.718 | 1.00 | 15.08 |
| ATOM | 940 | C | ILE | A | 255 | 39.420 | 33.002 | 2.236 | 1.00 | 21.56 |
| ATOM | 941 | O | ILE | A | 255 | 38.858 | 33.992 | 1.789 | 1.00 | 22.63 |
| ATOM | 942 | CB | ILE | A | 255 | 41.220 | 33.269 | 3.914 | 1.00 | 16.85 |
| ATOM | 943 | CG1 | ILE | A | 255 | 41.604 | 33.220 | 5.400 | 1.00 | 16.07 |
| ATOM | 944 | CG2 | ILE | A | 255 | 41.518 | 34.628 | 3.284 | 1.00 | 15.64 |
| ATOM | 945 | CD1 | ILE | A | 255 | 43.105 | 33.405 | 5.652 | 1.00 | 13.53 |
| ATOM | 946 | N | VAL | A | 256 | 39.764 | 31.976 | 1.471 | 1.00 | 19.17 |
| ATOM | 947 | CA | VAL | A | 256 | 39.442 | 31.974 | 0.049 | 1.00 | 19.40 |
| ATOM | 948 | C | VAL | A | 256 | 37.917 | 32.065 | −0.137 | 1.00 | 23.92 |
| ATOM | 949 | O | VAL | A | 256 | 37.420 | 32.846 | −0.955 | 1.00 | 24.23 |
| ATOM | 950 | CB | VAL | A | 256 | 39.992 | 30.717 | −0.652 | 1.00 | 22.59 |
| ATOM | 951 | CG1 | VAL | A | 256 | 39.386 | 30.568 | −2.025 | 1.00 | 21.83 |
| ATOM | 952 | CG2 | VAL | A | 256 | 41.519 | 30.793 | −0.742 | 1.00 | 22.49 |
| ATOM | 953 | N | SER | A | 257 | 37.189 | 31.275 | 0.644 | 1.00 | 19.78 |
| ATOM | 954 | CA | SER | A | 257 | 35.717 | 31.264 | 0.613 | 1.00 | 19.01 |
| ATOM | 955 | C | SER | A | 257 | 35.150 | 32.680 | 0.859 | 1.00 | 23.34 |
| ATOM | 956 | O | SER | A | 257 | 34.294 | 33.145 | 0.117 | 1.00 | 22.91 |
| ATOM | 957 | CB | SER | A | 257 | 35.177 | 30.290 | 1.664 | 1.00 | 20.31 |
| ATOM | 958 | OG | SER | A | 257 | 33.767 | 30.213 | 1.612 | 1.00 | 26.09 |
| ATOM | 959 | N | ALA | A | 258 | 35.639 | 33.347 | 1.898 | 1.00 | 20.21 |

TABLE 3-continued

Structural coordinates for AKT3lkd(pT305, pS472) (SEQ ID NO:2).

| ATOM | 960 | CA | ALA | A | 258 | 35.200 | 34.717 | 2.215 | 1.00 | 20.19 |
|---|---|---|---|---|---|---|---|---|---|---|
| ATOM | 961 | C | ALA | A | 258 | 35.526 | 35.681 | 1.068 | 1.00 | 24.73 |
| ATOM | 962 | O | ALA | A | 258 | 34.692 | 36.504 | 0.690 | 1.00 | 24.83 |
| ATOM | 963 | CB | ALA | A | 258 | 35.861 | 35.204 | 3.504 | 1.00 | 20.64 |
| ATOM | 964 | N | LEU | A | 259 | 36.747 | 35.585 | 0.532 | 1.00 | 20.57 |
| ATOM | 965 | CA | LEU | A | 259 | 37.188 | 36.480 | −0.548 | 1.00 | 20.35 |
| ATOM | 966 | C | LEU | A | 259 | 36.395 | 36.261 | −1.846 | 1.00 | 24.01 |
| ATOM | 967 | O | LEU | A | 259 | 36.051 | 37.217 | −2.550 | 1.00 | 24.72 |
| ATOM | 968 | CB | LEU | A | 259 | 38.684 | 36.329 | −0.799 | 1.00 | 20.23 |
| ATOM | 969 | CG | LEU | A | 259 | 39.597 | 36.858 | 0.306 | 1.00 | 24.91 |
| ATOM | 970 | CD1 | LEU | A | 259 | 41.071 | 36.534 | 0.015 | 1.00 | 24.70 |
| ATOM | 971 | CD2 | LEU | A | 259 | 39.398 | 38.341 | 0.479 | 1.00 | 26.84 |
| ATOM | 972 | N | ASP | A | 260 | 36.108 | 35.002 | −2.145 | 1.00 | 19.03 |
| ATOM | 973 | CA | ASP | A | 260 | 35.316 | 34.638 | −3.313 | 1.00 | 18.48 |
| ATOM | 974 | C | ASP | A | 260 | 33.973 | 35.355 | −3.209 | 1.00 | 24.58 |
| ATOM | 975 | O | ASP | A | 260 | 33.483 | 35.938 | −4.173 | 1.00 | 23.71 |
| ATOM | 976 | CB | ASP | A | 260 | 35.071 | 33.123 | −3.310 | 1.00 | 19.40 |
| ATOM | 977 | CG | ASP | A | 260 | 34.260 | 32.659 | −4.502 | 1.00 | 21.92 |
| ATOM | 978 | OD1 | ASP | A | 260 | 34.413 | 33.243 | −5.585 | 1.00 | 21.27 |
| ATOM | 979 | OD2 | ASP | A | 260 | 33.443 | 31.729 | −4.345 | 1.00 | 26.90 |
| ATOM | 980 | N | TYR | A | 261 | 33.395 | 35.310 | −2.016 | 1.00 | 23.03 |
| ATOM | 981 | CA | TYR | A | 261 | 32.117 | 35.933 | −1.748 | 1.00 | 23.45 |
| ATOM | 982 | C | TYR | A | 261 | 32.170 | 37.459 | −1.924 | 1.00 | 26.95 |
| ATOM | 983 | O | TYR | A | 261 | 31.304 | 38.047 | −2.568 | 1.00 | 27.55 |
| ATOM | 984 | CB | TYR | A | 261 | 31.664 | 35.576 | −0.335 | 1.00 | 25.23 |
| ATOM | 985 | CG | TYR | A | 261 | 30.637 | 36.522 | 0.228 | 1.00 | 28.07 |
| ATOM | 986 | CD1 | TYR | A | 261 | 29.303 | 36.452 | −0.169 | 1.00 | 30.62 |
| ATOM | 987 | CD2 | TYR | A | 261 | 30.991 | 37.481 | 1.150 | 1.00 | 28.44 |
| ATOM | 988 | CE1 | TYR | A | 261 | 28.360 | 37.302 | 0.368 | 1.00 | 31.70 |
| ATOM | 989 | CE2 | TYR | A | 261 | 30.057 | 38.332 | 1.686 | 1.00 | 29.18 |
| ATOM | 990 | CZ | TYR | A | 261 | 28.751 | 38.247 | 1.294 | 1.00 | 36.46 |
| ATOM | 991 | OH | TYR | A | 261 | 27.831 | 39.129 | 1.825 | 1.00 | 38.25 |
| ATOM | 992 | N | LEU | A | 262 | 33.199 | 38.083 | −1.360 | 1.00 | 22.58 |
| ATOM | 993 | CA | LEU | A | 262 | 33.382 | 39.533 | −1.450 | 1.00 | 22.05 |
| ATOM | 994 | C | LEU | A | 262 | 33.601 | 40.004 | −2.890 | 1.00 | 26.35 |
| ATOM | 995 | O | LEU | A | 262 | 32.950 | 40.948 | −3.337 | 1.00 | 25.56 |
| ATOM | 996 | CB | LEU | A | 262 | 34.544 | 39.995 | −0.552 | 1.00 | 21.90 |
| ATOM | 997 | CG | LEU | A | 262 | 34.314 | 39.949 | 0.980 | 1.00 | 26.34 |
| ATOM | 998 | CD1 | LEU | A | 262 | 35.617 | 40.071 | 1.726 | 1.00 | 25.85 |
| ATOM | 999 | CD2 | LEU | A | 262 | 33.329 | 41.031 | 1.448 | 1.00 | 27.91 |
| ATOM | 1000 | N | HIS | A | 263 | 34.533 | 39.354 | −3.604 | 1.00 | 22.99 |
| ATOM | 1001 | CA | HIS | A | 263 | 34.846 | 39.708 | −5.004 | 1.00 | 22.47 |
| ATOM | 1002 | C | HIS | A | 263 | 33.593 | 39.614 | −5.878 | 1.00 | 28.26 |
| ATOM | 1003 | O | HIS | A | 263 | 33.352 | 40.465 | −6.738 | 1.00 | 28.53 |
| ATOM | 1004 | CB | HIS | A | 263 | 35.952 | 38.780 | −5.576 | 1.00 | 22.17 |
| ATOM | 1005 | CG | HIS | A | 263 | 37.294 | 38.969 | −4.935 | 1.00 | 24.50 |
| ATOM | 1006 | ND1 | HIS | A | 263 | 37.561 | 39.996 | −4.053 | 1.00 | 25.66 |
| ATOM | 1007 | CD2 | HIS | A | 263 | 38.450 | 38.277 | −5.065 | 1.00 | 24.75 |
| ATOM | 1008 | CE1 | HIS | A | 263 | 38.823 | 39.928 | −3.674 | 1.00 | 24.19 |
| ATOM | 1009 | NE2 | HIS | A | 263 | 39.387 | 38.901 | −4.283 | 1.00 | 24.17 |
| ATOM | 1010 | N | SER | A | 264 | 32.788 | 38.596 | −5.635 | 1.00 | 25.96 |
| ATOM | 1011 | CA | SER | A | 264 | 31.546 | 38.431 | −6.373 | 1.00 | 26.79 |
| ATOM | 1012 | C | SER | A | 264 | 30.649 | 39.639 | −6.151 | 1.00 | 32.29 |
| ATOM | 1013 | O | SER | A | 264 | 29.857 | 39.996 | −7.015 | 1.00 | 33.39 |
| ATOM | 1014 | CB | SER | A | 264 | 30.819 | 37.164 | −5.930 | 1.00 | 29.91 |
| ATOM | 1015 | OG | SER | A | 264 | 31.462 | 36.027 | −6.453 | 1.00 | 42.12 |
| ATOM | 1016 | N | GLY | A | 265 | 30.768 | 40.252 | −4.978 | 1.00 | 28.25 |
| ATOM | 1017 | CA | GLY | A | 265 | 29.975 | 41.421 | −4.644 | 1.00 | 27.72 |
| ATOM | 1018 | C | GLY | A | 265 | 30.707 | 42.675 | −5.088 | 1.00 | 31.89 |
| ATOM | 1019 | O | GLY | A | 265 | 30.335 | 43.785 | −4.716 | 1.00 | 31.40 |
| ATOM | 1020 | N | LYS | A | 266 | 31.771 | 42.494 | −5.865 | 1.00 | 28.62 |
| ATOM | 1021 | CA | LYS | A | 266 | 32.550 | 43.625 | −6.350 | 1.00 | 28.52 |
| ATOM | 1022 | C | LYS | A | 266 | 33.239 | 44.368 | −5.207 | 1.00 | 31.13 |
| ATOM | 1023 | O | LYS | A | 266 | 33.464 | 45.567 | −5.283 | 1.00 | 30.73 |
| ATOM | 1024 | CB | LYS | A | 266 | 31.654 | 44.589 | −7.129 | 1.00 | 31.56 |
| ATOM | 1025 | CG | LYS | A | 266 | 31.105 | 44.005 | −8.431 | 1.00 | 45.42 |
| ATOM | 1026 | CD | LYS | A | 266 | 32.197 | 43.889 | −9.486 | 1.00 | 55.57 |
| ATOM | 1027 | CE | LYS | A | 266 | 32.392 | 42.437 | −9.931 | 1.00 | 65.94 |
| ATOM | 1028 | NZ | LYS | A | 266 | 33.595 | 42.272 | −10.796 | 1.00 | 72.37 |
| ATOM | 1029 | N | ILE | A | 267 | 33.582 | 43.642 | −4.155 | 1.00 | 26.90 |
| ATOM | 1030 | CA | ILE | A | 267 | 34.266 | 44.231 | −3.022 | 1.00 | 26.05 |
| ATOM | 1031 | C | ILE | A | 267 | 35.688 | 43.706 | −2.902 | 1.00 | 27.75 |
| ATOM | 1032 | O | ILE | A | 267 | 35.912 | 42.507 | −2.890 | 1.00 | 27.33 |
| ATOM | 1033 | CB | ILE | A | 267 | 33.538 | 43.925 | −1.707 | 1.00 | 29.34 |
| ATOM | 1034 | CG1 | ILE | A | 267 | 32.116 | 44.520 | −1.725 | 1.00 | 30.38 |
| ATOM | 1035 | CG2 | ILE | A | 267 | 34.338 | 44.446 | −0.526 | 1.00 | 29.00 |
| ATOM | 1036 | CD1 | ILE | A | 267 | 31.329 | 44.271 | −0.434 | 1.00 | 36.21 |
| ATOM | 1037 | N | VAL | A | 268 | 36.644 | 44.619 | −2.805 | 1.00 | 23.48 |

TABLE 3-continued

Structural coordinates for AKT3lkd(pT305, pS472) (SEQ ID NO:2).

| ATOM | 1038 | CA  | VAL | A | 268 | 38.035 | 44.260 | −2.577 | 1.00 | 22.40 |
|------|------|-----|-----|---|-----|--------|--------|--------|------|-------|
| ATOM | 1039 | C   | VAL | A | 268 | 38.280 | 44.476 | −1.078 | 1.00 | 25.45 |
| ATOM | 1040 | O   | VAL | A | 268 | 38.054 | 45.570 | −0.576 | 1.00 | 24.88 |
| ATOM | 1041 | CB  | VAL | A | 268 | 38.990 | 45.172 | −3.371 | 1.00 | 25.24 |
| ATOM | 1042 | CG1 | VAL | A | 268 | 40.428 | 44.819 | −3.073 | 1.00 | 24.89 |
| ATOM | 1043 | CG2 | VAL | A | 268 | 38.714 | 45.066 | −4.854 | 1.00 | 25.05 |
| ATOM | 1044 | N   | TYR | A | 269 | 38.698 | 43.431 | −0.361 | 1.00 | 21.12 |
| ATOM | 1045 | CA  | TYR | A | 269 | 38.918 | 43.552 | 1.090  | 1.00 | 20.61 |
| ATOM | 1046 | C   | TYR | A | 269 | 40.068 | 44.489 | 1.483  | 1.00 | 25.60 |
| ATOM | 1047 | O   | TYR | A | 269 | 39.895 | 45.353 | 2.335  | 1.00 | 24.34 |
| ATOM | 1048 | CB  | TYR | A | 269 | 39.032 | 42.182 | 1.782  | 1.00 | 21.21 |
| ATOM | 1049 | CG  | TYR | A | 269 | 38.889 | 42.279 | 3.280  | 1.00 | 22.09 |
| ATOM | 1050 | CD1 | TYR | A | 269 | 37.712 | 42.759 | 3.852  | 1.00 | 24.02 |
| ATOM | 1051 | CD2 | TYR | A | 269 | 39.955 | 41.998 | 4.121  | 1.00 | 22.11 |
| ATOM | 1052 | CE1 | TYR | A | 269 | 37.593 | 42.921 | 5.220  | 1.00 | 22.72 |
| ATOM | 1053 | CE2 | TYR | A | 269 | 39.836 | 42.139 | 5.484  | 1.00 | 22.78 |
| ATOM | 1054 | CZ  | TYR | A | 269 | 38.652 | 42.628 | 6.025  | 1.00 | 30.15 |
| ATOM | 1055 | OH  | TYR | A | 269 | 38.526 | 42.793 | 7.393  | 1.00 | 32.46 |
| ATOM | 1056 | N   | ARG | A | 270 | 41.238 | 44.310 | 0.860  | 1.00 | 23.34 |
| ATOM | 1057 | CA  | ARG | A | 270 | 42.400 | 45.193 | 1.098  | 1.00 | 23.05 |
| ATOM | 1058 | C   | ARG | A | 270 | 43.129 | 44.981 | 2.424  | 1.00 | 25.89 |
| ATOM | 1059 | O   | ARG | A | 270 | 44.336 | 45.177 | 2.512  | 1.00 | 25.21 |
| ATOM | 1060 | CB  | ARG | A | 270 | 41.977 | 46.667 | 1.026  | 1.00 | 23.62 |
| ATOM | 1061 | CG  | ARG | A | 270 | 41.480 | 47.150 | −0.320 | 1.00 | 32.31 |
| ATOM | 1062 | CD  | ARG | A | 270 | 40.905 | 48.553 | −0.187 | 1.00 | 39.48 |
| ATOM | 1063 | NE  | ARG | A | 270 | 40.880 | 49.269 | −1.457 | 1.00 | 53.61 |
| ATOM | 1064 | CZ  | ARG | A | 270 | 40.583 | 50.563 | −1.585 | 1.00 | 67.12 |
| ATOM | 1065 | NH1 | ARG | A | 270 | 40.309 | 51.295 | −0.512 | 1.00 | 50.15 |
| ATOM | 1066 | NH2 | ARG | A | 270 | 40.591 | 51.133 | −2.788 | 1.00 | 51.84 |
| ATOM | 1067 | N   | ASP | A | 271 | 42.384 | 44.670 | 3.469  | 1.00 | 21.65 |
| ATOM | 1068 | CA  | ASP | A | 271 | 42.970 | 44.558 | 4.791  | 1.00 | 21.18 |
| ATOM | 1069 | C   | ASP | A | 271 | 43.354 | 43.161 | 5.249  | 1.00 | 24.69 |
| ATOM | 1070 | O   | ASP | A | 271 | 43.587 | 42.939 | 6.437  | 1.00 | 23.31 |
| ATOM | 1071 | CB  | ASP | A | 271 | 42.086 | 45.260 | 5.823  | 1.00 | 22.34 |
| ATOM | 1072 | CG  | ASP | A | 271 | 41.897 | 46.738 | 5.507  | 1.00 | 29.06 |
| ATOM | 1073 | OD1 | ASP | A | 271 | 42.648 | 47.257 | 4.653  | 1.00 | 29.58 |
| ATOM | 1074 | OD2 | ASP | A | 271 | 40.960 | 47.362 | 6.051  | 1.00 | 33.24 |
| ATOM | 1075 | N   | LEU | A | 272 | 43.459 | 42.230 | 4.308  | 1.00 | 21.07 |
| ATOM | 1076 | CA  | LEU | A | 272 | 43.836 | 40.870 | 4.660  | 1.00 | 21.43 |
| ATOM | 1077 | C   | LEU | A | 272 | 45.268 | 40.811 | 5.203  | 1.00 | 26.07 |
| ATOM | 1078 | O   | LEU | A | 272 | 46.231 | 41.117 | 4.494  | 1.00 | 26.11 |
| ATOM | 1079 | CB  | LEU | A | 272 | 43.668 | 39.914 | 3.472  | 1.00 | 21.27 |
| ATOM | 1080 | CG  | LEU | A | 272 | 44.254 | 38.526 | 3.725  | 1.00 | 25.48 |
| ATOM | 1081 | CD1 | LEU | A | 272 | 43.922 | 38.065 | 5.121  | 1.00 | 25.46 |
| ATOM | 1082 | CD2 | LEU | A | 272 | 43.763 | 37.520 | 2.690  | 1.00 | 27.30 |
| ATOM | 1083 | N   | LYS | A | 273 | 45.392 | 40.442 | 6.471  | 1.00 | 22.57 |
| ATOM | 1084 | CA  | LYS | A | 273 | 46.687 | 40.340 | 7.126  | 1.00 | 22.12 |
| ATOM | 1085 | C   | LYS | A | 273 | 46.536 | 39.520 | 8.404  | 1.00 | 26.45 |
| ATOM | 1086 | O   | LYS | A | 273 | 45.450 | 39.469 | 8.999  | 1.00 | 26.58 |
| ATOM | 1087 | CB  | LYS | A | 273 | 47.227 | 41.735 | 7.463  | 1.00 | 23.92 |
| ATOM | 1088 | CG  | LYS | A | 273 | 46.351 | 42.510 | 8.413  | 1.00 | 31.07 |
| ATOM | 1089 | CD  | LYS | A | 273 | 46.825 | 43.953 | 8.557  | 1.00 | 40.82 |
| ATOM | 1090 | CE  | LYS | A | 273 | 46.209 | 44.849 | 7.483  | 1.00 | 50.23 |
| ATOM | 1091 | NZ  | LYS | A | 273 | 47.041 | 46.062 | 7.220  | 1.00 | 58.70 |
| ATOM | 1092 | N   | LEU | A | 274 | 47.628 | 38.899 | 8.826  | 1.00 | 22.42 |
| ATOM | 1093 | CA  | LEU | A | 274 | 47.642 | 38.043 | 10.006 | 1.00 | 22.00 |
| ATOM | 1094 | C   | LEU | A | 274 | 46.939 | 38.666 | 11.219 | 1.00 | 26.30 |
| ATOM | 1095 | O   | LEU | A | 274 | 46.066 | 38.054 | 11.819 | 1.00 | 25.73 |
| ATOM | 1096 | CB  | LEU | A | 274 | 49.080 | 37.633 | 10.349 | 1.00 | 21.97 |
| ATOM | 1097 | CG  | LEU | A | 274 | 49.224 | 36.476 | 11.341 | 1.00 | 27.16 |
| ATOM | 1098 | CD1 | LEU | A | 274 | 48.488 | 35.245 | 10.826 | 1.00 | 27.20 |
| ATOM | 1099 | CD2 | LEU | A | 274 | 50.699 | 36.156 | 11.607 | 1.00 | 29.75 |
| ATOM | 1100 | N   | GLU | A | 275 | 47.314 | 39.892 | 11.552 | 1.00 | 23.41 |
| ATOM | 1101 | CA  | GLU | A | 275 | 46.710 | 40.598 | 12.671 | 1.00 | 23.49 |
| ATOM | 1102 | C   | GLU | A | 275 | 45.193 | 40.742 | 12.527 | 1.00 | 27.14 |
| ATOM | 1103 | O   | GLU | A | 275 | 44.520 | 41.093 | 13.480 | 1.00 | 26.62 |
| ATOM | 1104 | CB  | GLU | A | 275 | 47.349 | 41.984 | 12.838 | 1.00 | 24.87 |
| ATOM | 1105 | CG  | GLU | A | 275 | 48.868 | 41.955 | 13.078 | 1.00 | 39.33 |
| ATOM | 1106 | CD  | GLU | A | 275 | 49.669 | 41.578 | 11.826 | 1.00 | 59.94 |
| ATOM | 1107 | OE1 | GLU | A | 275 | 49.407 | 42.143 | 10.748 | 1.00 | 42.84 |
| ATOM | 1108 | OE2 | GLU | A | 275 | 50.578 | 40.731 | 11.934 | 1.00 | 60.45 |
| ATOM | 1109 | N   | ASN | A | 276 | 44.661 | 40.485 | 11.332 | 1.00 | 23.93 |
| ATOM | 1110 | CA  | ASN | A | 276 | 43.208 | 40.605 | 11.110 | 1.00 | 23.52 |
| ATOM | 1111 | C   | ASN | A | 276 | 42.497 | 39.266 | 11.093 | 1.00 | 26.77 |
| ATOM | 1112 | O   | ASN | A | 276 | 41.311 | 39.182 | 10.749 | 1.00 | 27.19 |
| ATOM | 1113 | CB  | ASN | A | 276 | 42.902 | 41.399 | 9.833  | 1.00 | 22.43 |
| ATOM | 1114 | CG  | ASN | A | 276 | 43.017 | 42.903 | 10.051 | 1.00 | 40.10 |
| ATOM | 1115 | OD1 | ASN | A | 276 | 42.840 | 43.388 | 11.163 | 1.00 | 34.39 |

TABLE 3-continued

Structural coordinates for AKT3lkd(pT305, pS472) (SEQ ID NO:2).

| ATOM | 1116 | ND2 | ASN | A | 276 | 43.349 | 43.629 | 9.006 | 1.00 | 26.00 |
|---|---|---|---|---|---|---|---|---|---|---|
| ATOM | 1117 | N | LEU | A | 277 | 43.213 | 38.226 | 11.490 | 1.00 | 21.82 |
| ATOM | 1118 | CA | LEU | A | 277 | 42.649 | 36.889 | 11.528 | 1.00 | 21.61 |
| ATOM | 1119 | C | LEU | A | 277 | 42.495 | 36.424 | 12.942 | 1.00 | 28.12 |
| ATOM | 1120 | O | LEU | A | 277 | 43.414 | 36.538 | 13.751 | 1.00 | 29.09 |
| ATOM | 1121 | CB | LEU | A | 277 | 43.521 | 35.896 | 10.733 | 1.00 | 20.90 |
| ATOM | 1122 | CG | LEU | A | 277 | 43.738 | 36.267 | 9.260 | 1.00 | 23.64 |
| ATOM | 1123 | CD1 | LEU | A | 277 | 44.784 | 35.392 | 8.616 | 1.00 | 22.69 |
| ATOM | 1124 | CD2 | LEU | A | 277 | 42.416 | 36.199 | 8.496 | 1.00 | 24.67 |
| ATOM | 1125 | N | MET | A | 278 | 41.325 | 35.900 | 13.242 | 1.00 | 25.70 |
| ATOM | 1126 | CA | MET | A | 278 | 41.034 | 35.377 | 14.549 | 1.00 | 26.49 |
| ATOM | 1127 | C | MET | A | 278 | 40.355 | 34.045 | 14.379 | 1.00 | 29.80 |
| ATOM | 1128 | O | MET | A | 278 | 40.018 | 33.658 | 13.268 | 1.00 | 28.52 |
| ATOM | 1129 | CB | MET | A | 278 | 40.094 | 36.320 | 15.284 | 1.00 | 29.37 |
| ATOM | 1130 | CG | MET | A | 278 | 40.738 | 37.627 | 15.674 | 1.00 | 34.08 |
| ATOM | 1131 | SD | MET | A | 278 | 39.701 | 38.530 | 16.781 | 1.00 | 39.25 |
| ATOM | 1132 | CE | MET | A | 278 | 40.068 | 37.716 | 18.331 | 1.00 | 36.13 |
| ATOM | 1133 | N | LEU | A | 279 | 40.110 | 33.366 | 15.490 | 1.00 | 27.22 |
| ATOM | 1134 | CA | LEU | A | 279 | 39.392 | 32.099 | 15.455 | 1.00 | 26.98 |
| ATOM | 1135 | C | LEU | A | 279 | 38.156 | 32.217 | 16.307 | 1.00 | 31.34 |
| ATOM | 1136 | O | LEU | A | 279 | 38.152 | 32.937 | 17.291 | 1.00 | 32.38 |
| ATOM | 1137 | CB | LEU | A | 279 | 40.264 | 30.961 | 16.000 | 1.00 | 26.42 |
| ATOM | 1138 | CG | LEU | A | 279 | 41.602 | 30.686 | 15.319 | 1.00 | 29.75 |
| ATOM | 1139 | CD1 | LEU | A | 279 | 42.326 | 29.531 | 16.050 | 1.00 | 29.55 |
| ATOM | 1140 | CD2 | LEU | A | 279 | 41.395 | 30.360 | 13.847 | 1.00 | 29.50 |
| ATOM | 1141 | N | ASP | A | 280 | 37.098 | 31.514 | 15.928 | 1.00 | 27.19 |
| ATOM | 1142 | CA | ASP | A | 280 | 35.900 | 31.486 | 16.744 | 1.00 | 26.13 |
| ATOM | 1143 | C | ASP | A | 280 | 36.053 | 30.339 | 17.766 | 1.00 | 30.35 |
| ATOM | 1144 | O | ASP | A | 280 | 37.050 | 29.605 | 17.746 | 1.00 | 28.81 |
| ATOM | 1145 | CB | ASP | A | 280 | 34.635 | 31.323 | 15.888 | 1.00 | 27.23 |
| ATOM | 1146 | CG | ASP | A | 280 | 34.623 | 30.023 | 15.063 | 1.00 | 34.86 |
| ATOM | 1147 | OD1 | ASP | A | 280 | 35.351 | 29.061 | 15.402 | 1.00 | 35.33 |
| ATOM | 1148 | OD2 | ASP | A | 280 | 33.831 | 29.956 | 14.099 | 1.00 | 36.81 |
| ATOM | 1149 | N | LYS | A | 281 | 35.079 | 30.195 | 18.654 | 1.00 | 27.71 |
| ATOM | 1150 | CA | LYS | A | 281 | 35.132 | 29.158 | 19.685 | 1.00 | 27.60 |
| ATOM | 1151 | C | LYS | A | 281 | 35.485 | 27.770 | 19.145 | 1.00 | 30.98 |
| ATOM | 1152 | O | LYS | A | 281 | 36.128 | 26.977 | 19.830 | 1.00 | 30.94 |
| ATOM | 1153 | CB | LYS | A | 281 | 33.793 | 29.087 | 20.435 | 1.00 | 30.19 |
| ATOM | 1154 | CG | LYS | A | 281 | 32.655 | 28.488 | 19.624 | 1.00 | 37.92 |
| ATOM | 1155 | CD | LYS | A | 281 | 31.311 | 28.820 | 20.240 | 1.00 | 47.66 |
| ATOM | 1156 | CE | LYS | A | 281 | 30.217 | 28.878 | 19.185 | 1.00 | 55.64 |
| ATOM | 1157 | NZ | LYS | A | 281 | 29.174 | 27.837 | 19.414 | 1.00 | 65.16 |
| ATOM | 1158 | N | ASP | A | 282 | 35.043 | 27.476 | 17.926 | 1.00 | 27.08 |
| ATOM | 1159 | CA | ASP | A | 282 | 35.234 | 26.147 | 17.329 | 1.00 | 26.53 |
| ATOM | 1160 | C | ASP | A | 282 | 36.541 | 25.934 | 16.570 | 1.00 | 29.49 |
| ATOM | 1161 | O | ASP | A | 282 | 36.863 | 24.801 | 16.190 | 1.00 | 29.45 |
| ATOM | 1162 | CB | ASP | A | 282 | 34.051 | 25.802 | 16.424 | 1.00 | 28.10 |
| ATOM | 1163 | CG | ASP | A | 282 | 32.735 | 25.814 | 17.164 | 1.00 | 36.54 |
| ATOM | 1164 | OD1 | ASP | A | 282 | 32.579 | 24.990 | 18.088 | 1.00 | 37.94 |
| ATOM | 1165 | OD2 | ASP | A | 282 | 31.861 | 26.655 | 16.831 | 1.00 | 37.95 |
| ATOM | 1166 | N | GLY | A | 283 | 37.265 | 27.012 | 16.297 | 1.00 | 23.97 |
| ATOM | 1167 | CA | GLY | A | 283 | 38.521 | 26.896 | 15.562 | 1.00 | 23.07 |
| ATOM | 1168 | C | GLY | A | 283 | 38.363 | 27.295 | 14.098 | 1.00 | 26.08 |
| ATOM | 1169 | O | GLY | A | 283 | 39.242 | 27.033 | 13.273 | 1.00 | 26.07 |
| ATOM | 1170 | N | HIS | A | 284 | 37.254 | 27.939 | 13.778 | 1.00 | 21.49 |
| ATOM | 1171 | CA | HIS | A | 284 | 37.039 | 28.409 | 12.418 | 1.00 | 20.85 |
| ATOM | 1172 | C | HIS | A | 284 | 37.534 | 29.809 | 12.310 | 1.00 | 26.53 |
| ATOM | 1173 | O | HIS | A | 284 | 37.503 | 30.560 | 13.287 | 1.00 | 27.62 |
| ATOM | 1174 | CB | HIS | A | 284 | 35.570 | 28.337 | 12.018 | 1.00 | 20.44 |
| ATOM | 1175 | CG | HIS | A | 284 | 35.126 | 26.964 | 11.639 | 1.00 | 23.00 |
| ATOM | 1176 | ND1 | HIS | A | 284 | 35.486 | 26.369 | 10.446 | 1.00 | 24.40 |
| ATOM | 1177 | CD2 | HIS | A | 284 | 34.389 | 26.049 | 12.312 | 1.00 | 24.00 |
| ATOM | 1178 | CE1 | HIS | A | 284 | 34.980 | 25.148 | 10.400 | 1.00 | 23.77 |
| ATOM | 1179 | NE2 | HIS | A | 284 | 34.324 | 24.925 | 11.526 | 1.00 | 23.94 |
| ATOM | 1180 | N | ILE | A | 285 | 38.018 | 30.162 | 11.127 | 1.00 | 22.75 |
| ATOM | 1181 | CA | ILE | A | 285 | 38.561 | 31.491 | 10.889 | 1.00 | 22.64 |
| ATOM | 1182 | C | ILE | A | 285 | 37.505 | 32.563 | 10.954 | 1.00 | 25.65 |
| ATOM | 1183 | O | ILE | A | 285 | 36.336 | 32.334 | 10.642 | 1.00 | 24.98 |
| ATOM | 1184 | CB | ILE | A | 285 | 39.236 | 31.583 | 9.472 | 1.00 | 26.04 |
| ATOM | 1185 | CG1 | ILE | A | 285 | 40.741 | 31.293 | 9.564 | 1.00 | 26.68 |
| ATOM | 1186 | CG2 | ILE | A | 285 | 39.005 | 32.960 | 8.859 | 1.00 | 26.42 |
| ATOM | 1187 | CD1 | ILE | A | 285 | 41.600 | 32.528 | 9.511 | 1.00 | 33.55 |
| ATOM | 1188 | N | LYS | A | 286 | 37.940 | 33.758 | 11.311 | 1.00 | 22.98 |
| ATOM | 1189 | CA | LYS | A | 286 | 37.098 | 34.935 | 11.276 | 1.00 | 22.77 |
| ATOM | 1190 | C | LYS | A | 286 | 37.976 | 36.131 | 10.909 | 1.00 | 28.00 |
| ATOM | 1191 | O | LYS | A | 286 | 38.977 | 36.406 | 11.567 | 1.00 | 26.44 |
| ATOM | 1192 | CB | LYS | A | 286 | 36.389 | 35.163 | 12.610 | 1.00 | 24.81 |
| ATOM | 1193 | CG | LYS | A | 286 | 34.893 | 35.480 | 12.464 | 1.00 | 30.89 |

TABLE 3-continued

Structural coordinates for AKT3lkd(pT305, pS472) (SEQ ID NO:2).

| ATOM | 1194 | CD  | LYS | A | 286 | 34.063 | 34.219 | 12.443 | 1.00 | 37.12 |
| ---- | ---- | --- | --- | - | --- | ------ | ------ | ------ | ---- | ----- |
| ATOM | 1195 | CE  | LYS | A | 286 | 32.614 | 34.496 | 12.808 | 1.00 | 42.64 |
| ATOM | 1196 | NZ  | LYS | A | 286 | 31.723 | 34.517 | 11.612 | 1.00 | 47.63 |
| ATOM | 1197 | N   | ILE | A | 287 | 37.657 | 36.757 | 9.784  | 1.00 | 26.72 |
| ATOM | 1198 | CA  | ILE | A | 287 | 38.363 | 37.939 | 9.331  | 1.00 | 27.21 |
| ATOM | 1199 | C   | ILE | A | 287 | 37.655 | 39.171 | 9.895  | 1.00 | 34.11 |
| ATOM | 1200 | O   | ILE | A | 287 | 36.426 | 39.210 | 9.977  | 1.00 | 33.07 |
| ATOM | 1201 | CB  | ILE | A | 287 | 38.331 | 38.049 | 7.804  | 1.00 | 30.00 |
| ATOM | 1202 | CG1 | ILE | A | 287 | 38.824 | 36.749 | 7.160  | 1.00 | 29.88 |
| ATOM | 1203 | CG2 | ILE | A | 287 | 39.131 | 39.290 | 7.332  | 1.00 | 29.78 |
| ATOM | 1204 | CD1 | ILE | A | 287 | 38.628 | 36.700 | 5.654  | 1.00 | 29.75 |
| ATOM | 1205 | N   | THR | A | 288 | 38.426 | 40.183 | 10.253 | 1.00 | 34.45 |
| ATOM | 1206 | CA  | THR | A | 288 | 37.854 | 41.411 | 10.789 | 1.00 | 36.26 |
| ATOM | 1207 | C   | THR | A | 288 | 38.899 | 42.487 | 10.785 | 1.00 | 44.53 |
| ATOM | 1208 | O   | THR | A | 288 | 39.661 | 42.652 | 9.825  | 1.00 | 43.54 |
| ATOM | 1209 | CB  | THR | A | 288 | 37.421 | 41.213 | 12.277 | 1.00 | 46.69 |
| ATOM | 1210 | OG1 | THR | A | 288 | 36.889 | 42.441 | 12.796 | 1.00 | 51.16 |
| ATOM | 1211 | CG2 | THR | A | 288 | 38.624 | 40.781 | 13.140 | 1.00 | 42.36 |
| ATOM | 1212 | N   | ASP | A | 289 | 38.913 | 43.228 | 11.877 | 1.00 | 45.66 |
| ATOM | 1213 | CA  | ASP | A | 289 | 39.948 | 44.172 | 12.176 | 1.00 | 46.96 |
| ATOM | 1214 | C   | ASP | A | 289 | 39.678 | 45.609 | 11.894 | 1.00 | 53.03 |
| ATOM | 1215 | O   | ASP | A | 289 | 39.587 | 46.062 | 10.753 | 1.00 | 53.14 |
| ATOM | 1216 | CB  | ASP | A | 289 | 40.305 | 44.063 | 13.670 | 1.00 | 48.88 |
| ATOM | 1217 | CG  | ASP | A | 289 | 41.619 | 43.349 | 13.915 | 1.00 | 59.89 |
| ATOM | 1218 | OD1 | ASP | A | 289 | 42.661 | 43.858 | 13.470 | 1.00 | 60.65 |
| ATOM | 1219 | OD2 | ASP | A | 289 | 41.619 | 42.327 | 14.641 | 1.00 | 66.96 |
| ATOM | 1220 | N   | PHE | A | 290 | 39.592 | 46.319 | 12.997 | 1.00 | 50.85 |
| ATOM | 1221 | CA  | PHE | A | 290 | 39.610 | 47.748 | 13.084 | 1.00 | 50.80 |
| ATOM | 1222 | C   | PHE | A | 290 | 40.768 | 47.777 | 14.064 | 1.00 | 55.20 |
| ATOM | 1223 | O   | PHE | A | 290 | 40.576 | 47.995 | 15.258 | 1.00 | 55.02 |
| ATOM | 1224 | CB  | PHE | A | 290 | 38.333 | 48.269 | 13.757 | 1.00 | 52.33 |
| ATOM | 1225 | CG  | PHE | A | 290 | 37.203 | 48.522 | 12.798 | 1.00 | 53.86 |
| ATOM | 1226 | CD1 | PHE | A | 290 | 36.192 | 47.585 | 12.634 | 1.00 | 56.92 |
| ATOM | 1227 | CD2 | PHE | A | 290 | 37.150 | 49.696 | 12.060 | 1.00 | 55.82 |
| ATOM | 1228 | CE1 | PHE | A | 290 | 35.151 | 47.816 | 11.751 | 1.00 | 57.82 |
| ATOM | 1229 | CE2 | PHE | A | 290 | 36.116 | 49.928 | 11.175 | 1.00 | 58.61 |
| ATOM | 1230 | CZ  | PHE | A | 290 | 35.117 | 48.985 | 11.018 | 1.00 | 56.89 |
| ATOM | 1231 | N   | GLY | A | 291 | 41.914 | 47.296 | 13.582 | 1.00 | 51.93 |
| ATOM | 1232 | CA  | GLY | A | 291 | 43.125 | 47.136 | 14.387 | 1.00 | 52.01 |
| ATOM | 1233 | C   | GLY | A | 291 | 43.354 | 48.222 | 15.427 | 1.00 | 56.50 |
| ATOM | 1234 | O   | GLY | A | 291 | 43.251 | 49.409 | 15.136 | 1.00 | 55.67 |
| ATOM | 1235 | N   | LEU | A | 292 | 43.701 | 47.796 | 16.635 | 1.00 | 54.44 |
| ATOM | 1236 | CA  | LEU | A | 292 | 43.951 | 48.712 | 17.741 | 1.00 | 55.07 |
| ATOM | 1237 | C   | LEU | A | 292 | 45.371 | 49.267 | 17.725 | 1.00 | 61.49 |
| ATOM | 1238 | O   | LEU | A | 292 | 45.637 | 50.326 | 18.295 | 1.00 | 60.35 |
| ATOM | 1239 | CB  | LEU | A | 292 | 43.700 | 48.012 | 19.074 | 1.00 | 54.99 |
| ATOM | 1240 | CG  | LEU | A | 292 | 42.249 | 47.889 | 19.541 | 1.00 | 59.95 |
| ATOM | 1241 | CD1 | LEU | A | 292 | 42.199 | 47.807 | 21.056 | 1.00 | 60.26 |
| ATOM | 1242 | CD2 | LEU | A | 292 | 41.411 | 49.051 | 19.034 | 1.00 | 62.45 |
| ATOM | 1243 | N   | CYS | A | 293 | 46.285 | 48.529 | 17.102 | 1.00 | 60.55 |
| ATOM | 1244 | CA  | CYS | A | 293 | 47.684 | 48.928 | 17.070 | 1.00 | 60.70 |
| ATOM | 1245 | C   | CYS | A | 293 | 48.206 | 48.985 | 18.502 | 1.00 | 63.50 |
| ATOM | 1246 | O   | CYS | A | 293 | 48.102 | 50.013 | 19.169 | 1.00 | 63.28 |
| ATOM | 1247 | CB  | CYS | A | 293 | 47.854 | 50.301 | 16.399 | 1.00 | 61.48 |
| ATOM | 1248 | SG  | CYS | A | 293 | 49.457 | 51.095 | 16.763 | 1.00 | 65.86 |
| ATOM | 1249 | N   | LYS | A | 294 | 48.726 | 47.862 | 18.989 | 1.00 | 58.80 |
| ATOM | 1250 | CA  | LYS | A | 294 | 49.254 | 47.792 | 20.349 | 1.00 | 58.17 |
| ATOM | 1251 | CA  | PHE | A | 306 | 53.197 | 54.491 | 12.556 | 1.00 | 62.94 |
| ATOM | 1252 | C   | PHE | A | 306 | 52.629 | 53.084 | 12.777 | 1.00 | 66.01 |
| ATOM | 1253 | O   | PHE | A | 306 | 53.375 | 52.109 | 12.866 | 1.00 | 65.72 |
| ATOM | 1254 | N   | CYS | A | 307 | 51.297 | 52.992 | 12.814 | 1.00 | 62.13 |
| ATOM | 1255 | CA  | CYS | A | 307 | 50.626 | 51.703 | 12.990 | 1.00 | 61.65 |
| ATOM | 1256 | C   | CYS | A | 307 | 50.254 | 51.103 | 11.659 | 1.00 | 63.81 |
| ATOM | 1257 | O   | CYS | A | 307 | 49.136 | 50.627 | 11.475 | 1.00 | 63.25 |
| ATOM | 1258 | CB  | CYS | A | 307 | 49.354 | 51.868 | 13.823 | 1.00 | 61.97 |
| ATOM | 1259 | SG  | CYS | A | 307 | 49.589 | 52.638 | 15.447 | 1.00 | 66.03 |
| ATOM | 1260 | N   | GLY | A | 308 | 51.180 | 51.145 | 10.717 | 1.00 | 59.17 |
| ATOM | 1261 | CA  | GLY | A | 308 | 50.906 | 50.605 | 9.401  | 1.00 | 58.08 |
| ATOM | 1262 | C   | GLY | A | 308 | 51.384 | 49.173 | 9.291  | 1.00 | 59.27 |
| ATOM | 1263 | O   | GLY | A | 308 | 51.917 | 48.606 | 10.244 | 1.00 | 59.29 |
| ATOM | 1264 | N   | THR | A | 309 | 51.177 | 48.589 | 8.118  | 1.00 | 52.37 |
| ATOM | 1265 | CA  | THR | A | 309 | 51.623 | 47.230 | 7.846  | 1.00 | 50.31 |
| ATOM | 1266 | C   | THR | A | 309 | 52.141 | 47.163 | 6.420  | 1.00 | 50.59 |
| ATOM | 1267 | O   | THR | A | 309 | 51.711 | 46.330 | 5.623  | 1.00 | 49.85 |
| ATOM | 1268 | CB  | THR | A | 309 | 50.501 | 46.203 | 8.040  | 1.00 | 57.53 |
| ATOM | 1269 | OG1 | THR | A | 309 | 49.781 | 46.498 | 9.242  | 1.00 | 56.74 |
| ATOM | 1270 | CG2 | THR | A | 309 | 51.088 | 44.820 | 8.154  | 1.00 | 58.06 |
| ATOM | 1271 | N   | PRO | A | 310 | 53.042 | 48.084 | 6.100  | 1.00 | 44.89 |

TABLE 3-continued

Structural coordinates for AKT3lkd(pT305, pS472) (SEQ ID NO:2).

| ATOM | 1272 | CA | PRO | A | 310 | 53.627 | 48.180 | 4.764 | 1.00 | 43.25 |
|---|---|---|---|---|---|---|---|---|---|---|
| ATOM | 1273 | C | PRO | A | 310 | 54.128 | 46.839 | 4.240 | 1.00 | 43.20 |
| ATOM | 1274 | O | PRO | A | 310 | 54.188 | 46.630 | 3.034 | 1.00 | 41.71 |
| ATOM | 1275 | CB | PRO | A | 310 | 54.811 | 49.136 | 4.970 | 1.00 | 44.99 |
| ATOM | 1276 | CG | PRO | A | 310 | 55.141 | 49.015 | 6.434 | 1.00 | 49.70 |
| ATOM | 1277 | CD | PRO | A | 310 | 53.811 | 48.849 | 7.098 | 1.00 | 45.23 |
| ATOM | 1278 | N | GLU | A | 311 | 54.498 | 45.938 | 5.150 | 1.00 | 37.98 |
| ATOM | 1279 | CA | GLU | A | 311 | 55.015 | 44.613 | 4.757 | 1.00 | 36.51 |
| ATOM | 1280 | C | GLU | A | 311 | 53.996 | 43.818 | 3.943 | 1.00 | 36.40 |
| ATOM | 1281 | O | GLU | A | 311 | 54.346 | 42.850 | 3.249 | 1.00 | 35.27 |
| ATOM | 1282 | CB | GLU | A | 311 | 55.439 | 43.802 | 5.990 | 1.00 | 37.78 |
| ATOM | 1283 | CG | GLU | A | 311 | 55.999 | 44.649 | 7.133 | 1.00 | 46.74 |
| ATOM | 1284 | CD | GLU | A | 311 | 54.912 | 45.227 | 8.020 | 1.00 | 60.25 |
| ATOM | 1285 | OE1 | GLU | A | 311 | 54.978 | 46.429 | 8.320 | 1.00 | 53.06 |
| ATOM | 1286 | OE2 | GLU | A | 311 | 54.001 | 44.475 | 8.438 | 1.00 | 51.82 |
| ATOM | 1287 | N | TYR | A | 312 | 52.737 | 44.230 | 4.024 | 1.00 | 30.85 |
| ATOM | 1288 | CA | TYR | A | 312 | 51.674 | 43.549 | 3.311 | 1.00 | 30.17 |
| ATOM | 1289 | C | TYR | A | 312 | 51.389 | 44.183 | 1.962 | 1.00 | 33.71 |
| ATOM | 1290 | O | TYR | A | 312 | 50.673 | 43.620 | 1.141 | 1.00 | 33.86 |
| ATOM | 1291 | CB | TYR | A | 312 | 50.403 | 43.502 | 4.166 | 1.00 | 30.86 |
| ATOM | 1292 | CG | TYR | A | 312 | 50.371 | 42.322 | 5.099 | 1.00 | 31.93 |
| ATOM | 1293 | CD1 | TYR | A | 312 | 50.893 | 42.415 | 6.385 | 1.00 | 34.34 |
| ATOM | 1294 | CD2 | TYR | A | 312 | 49.891 | 41.089 | 4.672 | 1.00 | 32.03 |
| ATOM | 1295 | CE1 | TYR | A | 312 | 50.902 | 41.329 | 7.229 | 1.00 | 35.27 |
| ATOM | 1296 | CE2 | TYR | A | 312 | 49.908 | 40.001 | 5.496 | 1.00 | 32.83 |
| ATOM | 1297 | CZ | TYR | A | 312 | 50.423 | 40.119 | 6.776 | 1.00 | 40.45 |
| ATOM | 1298 | OH | TYR | A | 312 | 50.412 | 39.042 | 7.614 | 1.00 | 40.46 |
| ATOM | 1299 | N | LEU | A | 313 | 51.972 | 45.352 | 1.735 | 1.00 | 29.22 |
| ATOM | 1300 | CA | LEU | A | 313 | 51.764 | 46.110 | 0.505 | 1.00 | 28.25 |
| ATOM | 1301 | C | LEU | A | 313 | 52.052 | 45.349 | −0.789 | 1.00 | 31.03 |
| ATOM | 1302 | O | LEU | A | 313 | 53.169 | 44.901 | −1.023 | 1.00 | 31.19 |
| ATOM | 1303 | CB | LEU | A | 313 | 52.569 | 47.413 | 0.549 | 1.00 | 28.15 |
| ATOM | 1304 | CG | LEU | A | 313 | 52.074 | 48.406 | 1.596 | 1.00 | 32.67 |
| ATOM | 1305 | CD1 | LEU | A | 313 | 52.977 | 49.645 | 1.668 | 1.00 | 32.57 |
| ATOM | 1306 | CD2 | LEU | A | 313 | 50.628 | 48.789 | 1.298 | 1.00 | 34.43 |
| ATOM | 1307 | N | ALA | A | 314 | 51.045 | 45.255 | −1.650 | 1.00 | 26.63 |
| ATOM | 1308 | CA | ALA | A | 314 | 51.199 | 44.584 | −2.941 | 1.00 | 26.26 |
| ATOM | 1309 | C | ALA | A | 314 | 52.021 | 45.467 | −3.906 | 1.00 | 30.75 |
| ATOM | 1310 | O | ALA | A | 314 | 51.973 | 46.702 | −3.823 | 1.00 | 29.76 |
| ATOM | 1311 | CB | ALA | A | 314 | 49.831 | 44.259 | −3.537 | 1.00 | 26.69 |
| ATOM | 1312 | N | PRO | A | 315 | 52.763 | 44.825 | −4.814 | 1.00 | 27.78 |
| ATOM | 1313 | CA | PRO | A | 315 | 53.620 | 45.535 | −5.758 | 1.00 | 27.57 |
| ATOM | 1314 | C | PRO | A | 315 | 52.896 | 46.572 | −6.607 | 1.00 | 32.34 |
| ATOM | 1315 | O | PRO | A | 315 | 53.441 | 47.629 | −6.878 | 1.00 | 32.19 |
| ATOM | 1316 | CB | PRO | A | 315 | 54.179 | 44.407 | −6.641 | 1.00 | 28.84 |
| ATOM | 1317 | CG | PRO | A | 315 | 54.087 | 43.198 | −5.794 | 1.00 | 33.09 |
| ATOM | 1318 | CD | PRO | A | 315 | 52.809 | 43.371 | −5.037 | 1.00 | 28.29 |
| ATOM | 1319 | N | GLU | A | 316 | 51.669 | 46.266 | −7.023 | 1.00 | 29.50 |
| ATOM | 1320 | CA | GLU | A | 316 | 50.878 | 47.206 | −7.825 | 1.00 | 29.50 |
| ATOM | 1321 | C | GLU | A | 316 | 50.408 | 48.429 | −7.014 | 1.00 | 34.97 |
| ATOM | 1322 | O | GLU | A | 316 | 50.041 | 49.454 | −7.580 | 1.00 | 34.64 |
| ATOM | 1323 | CB | GLU | A | 316 | 49.680 | 46.504 | −8.461 | 1.00 | 30.29 |
| ATOM | 1324 | CG | GLU | A | 316 | 48.655 | 46.030 | −7.452 | 1.00 | 37.63 |
| ATOM | 1325 | CD | GLU | A | 316 | 48.733 | 44.532 | −7.200 | 1.00 | 40.97 |
| ATOM | 1326 | OE1 | GLU | A | 316 | 49.849 | 43.982 | −7.156 | 1.00 | 24.67 |
| ATOM | 1327 | OE2 | GLU | A | 316 | 47.673 | 43.904 | −7.095 | 1.00 | 27.32 |
| ATOM | 1328 | N | VAL | A | 317 | 50.372 | 48.300 | −5.696 | 1.00 | 32.86 |
| ATOM | 1329 | CA | VAL | A | 317 | 49.939 | 49.413 | −4.854 | 1.00 | 32.79 |
| ATOM | 1330 | C | VAL | A | 317 | 51.093 | 50.376 | −4.694 | 1.00 | 37.22 |
| ATOM | 1331 | O | VAL | A | 317 | 50.923 | 51.597 | −4.803 | 1.00 | 36.69 |
| ATOM | 1332 | CB | VAL | A | 317 | 49.442 | 48.941 | −3.478 | 1.00 | 36.72 |
| ATOM | 1333 | CG1 | VAL | A | 317 | 49.263 | 50.140 | −2.531 | 1.00 | 36.27 |
| ATOM | 1334 | CG2 | VAL | A | 317 | 48.139 | 48.166 | −3.622 | 1.00 | 36.30 |
| ATOM | 1335 | N | LEU | A | 318 | 52.288 | 49.816 | −4.529 | 1.00 | 34.94 |
| ATOM | 1336 | CA | LEU | A | 318 | 53.509 | 50.608 | −4.442 | 1.00 | 35.37 |
| ATOM | 1337 | C | LEU | A | 318 | 53.765 | 51.333 | −5.772 | 1.00 | 42.98 |
| ATOM | 1338 | O | LEU | A | 318 | 54.022 | 52.539 | −5.798 | 1.00 | 42.08 |
| ATOM | 1339 | CB | LEU | A | 318 | 54.705 | 49.701 | −4.130 | 1.00 | 34.87 |
| ATOM | 1340 | CG | LEU | A | 318 | 54.659 | 48.895 | −2.832 | 1.00 | 38.34 |
| ATOM | 1341 | CD1 | LEU | A | 318 | 55.884 | 47.992 | −2.717 | 1.00 | 37.79 |
| ATOM | 1342 | CD2 | LEU | A | 318 | 54.544 | 49.820 | −1.631 | 1.00 | 39.53 |
| ATOM | 1343 | N | GLU | A | 319 | 53.717 | 50.581 | −6.871 | 1.00 | 42.89 |
| ATOM | 1344 | CA | GLU | A | 319 | 53.972 | 51.145 | −8.191 | 1.00 | 44.75 |
| ATOM | 1345 | C | GLU | A | 319 | 53.002 | 52.258 | −8.527 | 1.00 | 54.52 |
| ATOM | 1346 | O | GLU | A | 319 | 53.266 | 53.435 | −8.272 | 1.00 | 54.84 |
| ATOM | 1347 | CB | GLU | A | 319 | 53.905 | 50.061 | −9.262 | 1.00 | 46.05 |
| ATOM | 1348 | CG | GLU | A | 319 | 54.993 | 49.020 | −9.146 | 1.00 | 57.51 |
| ATOM | 1349 | CD | GLU | A | 319 | 56.002 | 49.110 | −10.268 | 1.00 | 81.33 |

TABLE 3-continued

Structural coordinates for AKT3lkd(pT305, pS472) (SEQ ID NO:2).

| ATOM | 1350 | OE1 | GLU | A | 319 | 56.541 | 50.214 | −10.500 | 1.00 | 75.84 |
|------|------|-----|-----|---|-----|--------|--------|---------|------|-------|
| ATOM | 1351 | OE2 | GLU | A | 319 | 56.264 | 48.074 | −10.914 | 1.00 | 78.31 |
| ATOM | 1352 | N   | ASP | A | 320 | 51.884 | 51.879 | −9.127  | 1.00 | 54.55 |
| ATOM | 1353 | CA  | ASP | A | 320 | 50.858 | 52.825 | −9.512  | 1.00 | 55.75 |
| ATOM | 1354 | C   | ASP | A | 320 | 49.937 | 53.028 | −8.336  | 1.00 | 61.90 |
| ATOM | 1355 | O   | ASP | A | 320 | 50.134 | 53.918 | −7.510  | 1.00 | 62.47 |
| ATOM | 1356 | CB  | ASP | A | 320 | 50.056 | 52.260 | −10.687 | 1.00 | 57.61 |
| ATOM | 1357 | CG  | ASP | A | 320 | 50.591 | 50.917 | −11.166 | 1.00 | 68.18 |
| ATOM | 1358 | OD1 | ASP | A | 320 | 50.115 | 49.877 | −10.669 | 1.00 | 69.57 |
| ATOM | 1359 | OD2 | ASP | A | 320 | 51.495 | 50.901 | −12.031 | 1.00 | 72.68 |
| ATOM | 1360 | N   | ASN | A | 321 | 48.954 | 52.151 | −8.253  | 1.00 | 59.17 |
| ATOM | 1361 | CA  | ASN | A | 321 | 47.957 | 52.153 | −7.196  | 1.00 | 58.95 |
| ATOM | 1362 | C   | ASN | A | 321 | 46.842 | 51.299 | −7.743  | 1.00 | 61.96 |
| ATOM | 1363 | O   | ASN | A | 321 | 46.218 | 50.539 | −7.019  | 1.00 | 61.84 |
| ATOM | 1364 | CB  | ASN | A | 321 | 47.434 | 53.569 | −6.941  | 1.00 | 61.13 |
| ATOM | 1365 | CG  | ASN | A | 321 | 48.019 | 54.192 | −5.682  | 1.00 | 89.17 |
| ATOM | 1366 | OD1 | ASN | A | 321 | 47.614 | 53.865 | −4.564  | 1.00 | 84.93 |
| ATOM | 1367 | ND2 | ASN | A | 321 | 48.962 | 55.114 | −5.860  | 1.00 | 80.88 |
| ATOM | 1368 | N   | ASP | A | 322 | 46.640 | 51.406 | −9.058  | 1.00 | 57.53 |
| ATOM | 1369 | CA  | ASP | A | 322 | 45.606 | 50.661 | −9.774  | 1.00 | 56.64 |
| ATOM | 1370 | C   | ASP | A | 322 | 45.546 | 49.205 | −9.346  | 1.00 | 57.31 |
| ATOM | 1371 | O   | ASP | A | 322 | 46.017 | 48.310 | −10.049 | 1.00 | 56.93 |
| ATOM | 1372 | CB  | ASP | A | 322 | 45.816 | 50.764 | −11.288 | 1.00 | 58.67 |
| ATOM | 1373 | CG  | ASP | A | 322 | 44.506 | 50.903 | −12.053 | 1.00 | 71.23 |
| ATOM | 1374 | OD1 | ASP | A | 322 | 43.456 | 51.122 | −11.412 | 1.00 | 71.78 |
| ATOM | 1375 | OD2 | ASP | A | 322 | 44.532 | 50.803 | −13.301 | 1.00 | 78.83 |
| ATOM | 1376 | N   | TYR | A | 323 | 44.983 | 48.982 | −8.169  | 1.00 | 51.42 |
| ATOM | 1377 | CA  | TYR | A | 323 | 44.838 | 47.643 | −7.646  | 1.00 | 49.95 |
| ATOM | 1378 | C   | TYR | A | 323 | 43.392 | 47.202 | −7.799  | 1.00 | 48.46 |
| ATOM | 1379 | O   | TYR | A | 323 | 42.526 | 47.992 | −8.191  | 1.00 | 48.17 |
| ATOM | 1380 | CB  | TYR | A | 323 | 45.260 | 47.594 | −6.175  | 1.00 | 51.57 |
| ATOM | 1381 | CG  | TYR | A | 323 | 44.602 | 48.639 | −5.306  | 1.00 | 53.86 |
| ATOM | 1382 | CD1 | TYR | A | 323 | 43.228 | 48.679 | −5.152  | 1.00 | 55.87 |
| ATOM | 1383 | CD2 | TYR | A | 323 | 45.365 | 49.544 | −4.588  | 1.00 | 55.23 |
| ATOM | 1384 | CE1 | TYR | A | 323 | 42.628 | 49.638 | −4.351  | 1.00 | 57.58 |
| ATOM | 1385 | CE2 | TYR | A | 323 | 44.782 | 50.518 | −3.804  | 1.00 | 56.49 |
| ATOM | 1386 | CZ  | TYR | A | 323 | 43.419 | 50.556 | −3.678  | 1.00 | 65.93 |
| ATOM | 1387 | OH  | TYR | A | 323 | 42.850 | 51.524 | −2.880  | 1.00 | 69.56 |
| ATOM | 1388 | N   | GLY | A | 324 | 43.136 | 45.941 | −7.491  | 1.00 | 40.22 |
| ATOM | 1389 | CA  | GLY | A | 324 | 41.801 | 45.387 | −7.575  | 1.00 | 37.64 |
| ATOM | 1390 | C   | GLY | A | 324 | 41.726 | 44.169 | −6.693  | 1.00 | 36.14 |
| ATOM | 1391 | O   | GLY | A | 324 | 42.478 | 44.051 | −5.729  | 1.00 | 35.17 |
| ATOM | 1392 | N   | ARG | A | 325 | 40.831 | 43.249 | −7.040  | 1.00 | 29.03 |
| ATOM | 1393 | CA  | ARG | A | 325 | 40.648 | 42.026 | −6.277  | 1.00 | 26.53 |
| ATOM | 1394 | C   | ARG | A | 325 | 41.979 | 41.310 | −6.048  | 1.00 | 26.32 |
| ATOM | 1395 | O   | ARG | A | 325 | 42.161 | 40.652 | −5.040  | 1.00 | 25.06 |
| ATOM | 1396 | CB  | ARG | A | 325 | 39.677 | 41.102 | −7.011  | 1.00 | 24.67 |
| ATOM | 1397 | CG  | ARG | A | 325 | 39.728 | 41.258 | −8.515  | 1.00 | 26.78 |
| ATOM | 1398 | CD  | ARG | A | 325 | 38.730 | 40.363 | −9.221  | 1.00 | 28.18 |
| ATOM | 1399 | NE  | ARG | A | 325 | 39.030 | 40.267 | −10.646 | 1.00 | 30.93 |
| ATOM | 1400 | CZ  | ARG | A | 325 | 39.824 | 39.348 | −11.187 | 1.00 | 42.49 |
| ATOM | 1401 | NH1 | ARG | A | 325 | 40.377 | 38.410 | −10.427 | 1.00 | 31.44 |
| ATOM | 1402 | NH2 | ARG | A | 325 | 40.060 | 39.361 | −12.490 | 1.00 | 25.82 |
| ATOM | 1403 | N   | ALA | A | 326 | 42.903 | 41.458 | −6.996  | 1.00 | 21.45 |
| ATOM | 1404 | CA  | ALA | A | 326 | 44.221 | 40.798 | −6.932  | 1.00 | 20.28 |
| ATOM | 1405 | C   | ALA | A | 326 | 45.113 | 41.159 | −5.726  | 1.00 | 23.46 |
| ATOM | 1406 | O   | ALA | A | 326 | 45.976 | 40.363 | −5.327  | 1.00 | 23.05 |
| ATOM | 1407 | CB  | ALA | A | 326 | 44.977 | 40.970 | −8.242  | 1.00 | 20.78 |
| ATOM | 1408 | N   | VAL | A | 327 | 44.932 | 42.347 | −5.154  | 1.00 | 19.71 |
| ATOM | 1409 | CA  | VAL | A | 327 | 45.701 | 42.703 | −3.970  | 1.00 | 19.33 |
| ATOM | 1410 | C   | VAL | A | 327 | 45.315 | 41.711 | −2.868  | 1.00 | 22.74 |
| ATOM | 1411 | O   | VAL | A | 327 | 46.156 | 41.302 | −2.058  | 1.00 | 22.05 |
| ATOM | 1412 | CB  | VAL | A | 327 | 45.424 | 44.140 | −3.486  | 1.00 | 23.72 |
| ATOM | 1413 | CG1 | VAL | A | 327 | 45.853 | 45.157 | −4.546  | 1.00 | 23.99 |
| ATOM | 1414 | CG2 | VAL | A | 327 | 43.946 | 44.324 | −3.109  | 1.00 | 23.14 |
| ATOM | 1415 | N   | ASP | A | 328 | 44.056 | 41.275 | −2.891  | 1.00 | 18.42 |
| ATOM | 1416 | CA  | ASP | A | 328 | 43.562 | 40.321 | −1.897  | 1.00 | 18.35 |
| ATOM | 1417 | C   | ASP | A | 328 | 44.284 | 38.991 | −1.969  | 1.00 | 22.19 |
| ATOM | 1418 | O   | ASP | A | 328 | 44.619 | 38.395 | −0.939  | 1.00 | 20.55 |
| ATOM | 1419 | CB  | ASP | A | 328 | 42.055 | 40.125 | −2.037  | 1.00 | 19.95 |
| ATOM | 1420 | CG  | ASP | A | 328 | 41.268 | 41.265 | −1.415  | 1.00 | 23.70 |
| ATOM | 1421 | OD1 | ASP | A | 328 | 41.890 | 42.086 | −0.714  | 1.00 | 23.46 |
| ATOM | 1422 | OD2 | ASP | A | 328 | 40.043 | 41.335 | −1.617  | 1.00 | 25.34 |
| ATOM | 1423 | N   | TRP | A | 329 | 44.562 | 38.542 | −3.188  | 1.00 | 19.47 |
| ATOM | 1424 | CA  | TRP | A | 329 | 45.252 | 37.285 | −3.372  | 1.00 | 19.82 |
| ATOM | 1425 | C   | TRP | A | 329 | 46.707 | 37.405 | −2.962  | 1.00 | 23.30 |
| ATOM | 1426 | O   | TRP | A | 329 | 47.283 | 36.466 | −2.447  | 1.00 | 22.76 |
| ATOM | 1427 | CB  | TRP | A | 329 | 45.097 | 36.786 | −4.805  | 1.00 | 19.31 |

TABLE 3-continued

Structural coordinates for AKT3lkd(pT305, pS472) (SEQ ID NO:2).

| ATOM | 1428 | CG | TRP | A | 329 | 43.655 | 36.601 | −5.172 | 1.00 | 20.51 |
|---|---|---|---|---|---|---|---|---|---|---|
| ATOM | 1429 | CD1 | TRP | A | 329 | 42.983 | 37.208 | −6.191 | 1.00 | 23.36 |
| ATOM | 1430 | CD2 | TRP | A | 329 | 42.681 | 35.842 | −4.449 | 1.00 | 20.59 |
| ATOM | 1431 | NE1 | TRP | A | 329 | 41.672 | 36.821 | −6.189 | 1.00 | 22.47 |
| ATOM | 1432 | CE2 | TRP | A | 329 | 41.452 | 36.002 | −5.115 | 1.00 | 23.76 |
| ATOM | 1433 | CE3 | TRP | A | 329 | 42.737 | 35.008 | −3.318 | 1.00 | 21.87 |
| ATOM | 1434 | CZ2 | TRP | A | 329 | 40.280 | 35.386 | −4.678 | 1.00 | 22.71 |
| ATOM | 1435 | CZ3 | TRP | A | 329 | 41.568 | 34.383 | −2.897 | 1.00 | 22.73 |
| ATOM | 1436 | CH2 | TRP | A | 329 | 40.359 | 34.581 | −3.575 | 1.00 | 23.01 |
| ATOM | 1437 | N | TRP | A | 330 | 47.284 | 38.591 | −3.146 | 1.00 | 20.91 |
| ATOM | 1438 | CA | TRP | A | 330 | 48.654 | 38.846 | −2.709 | 1.00 | 20.21 |
| ATOM | 1439 | C | TRP | A | 330 | 48.662 | 38.709 | −1.176 | 1.00 | 23.21 |
| ATOM | 1440 | O | TRP | A | 330 | 49.526 | 38.028 | −0.604 | 1.00 | 22.99 |
| ATOM | 1441 | CB | TRP | A | 330 | 49.092 | 40.270 | −3.114 | 1.00 | 18.78 |
| ATOM | 1442 | CG | TRP | A | 330 | 50.414 | 40.681 | −2.515 | 1.00 | 19.33 |
| ATOM | 1443 | CD1 | TRP | A | 330 | 50.621 | 41.241 | −1.279 | 1.00 | 22.05 |
| ATOM | 1444 | CD2 | TRP | A | 330 | 51.713 | 40.490 | −3.093 | 1.00 | 19.01 |
| ATOM | 1445 | NE1 | TRP | A | 330 | 51.967 | 41.418 | −1.068 | 1.00 | 21.60 |
| ATOM | 1446 | CE2 | TRP | A | 330 | 52.657 | 40.971 | −2.167 | 1.00 | 22.89 |
| ATOM | 1447 | CE3 | TRP | A | 330 | 52.165 | 40.011 | −4.329 | 1.00 | 20.54 |
| ATOM | 1448 | CZ2 | TRP | A | 330 | 54.030 | 40.953 | −2.420 | 1.00 | 22.58 |
| ATOM | 1449 | CZ3 | TRP | A | 330 | 53.528 | 40.006 | −4.586 | 1.00 | 22.03 |
| ATOM | 1450 | CH2 | TRP | A | 330 | 54.446 | 40.465 | −3.633 | 1.00 | 22.52 |
| ATOM | 1451 | N | GLY | A | 331 | 47.667 | 39.332 | −0.529 | 1.00 | 18.65 |
| ATOM | 1452 | CA | GLY | A | 331 | 47.511 | 39.274 | 0.930 | 1.00 | 18.65 |
| ATOM | 1453 | C | GLY | A | 331 | 47.398 | 37.832 | 1.446 | 1.00 | 22.38 |
| ATOM | 1454 | O | GLY | A | 331 | 48.001 | 37.475 | 2.446 | 1.00 | 22.17 |
| ATOM | 1455 | N | LEU | A | 332 | 46.638 | 37.008 | 0.743 | 1.00 | 19.56 |
| ATOM | 1456 | CA | LEU | A | 332 | 46.486 | 35.601 | 1.117 | 1.00 | 19.59 |
| ATOM | 1457 | C | LEU | A | 332 | 47.840 | 34.883 | 1.012 | 1.00 | 24.07 |
| ATOM | 1458 | O | LEU | A | 332 | 48.174 | 34.011 | 1.842 | 1.00 | 23.58 |
| ATOM | 1459 | CB | LEU | A | 332 | 45.452 | 34.910 | 0.217 | 1.00 | 19.26 |
| ATOM | 1460 | CG | LEU | A | 332 | 45.291 | 33.399 | 0.460 | 1.00 | 23.14 |
| ATOM | 1461 | CD1 | LEU | A | 332 | 44.555 | 33.153 | 1.759 | 1.00 | 22.99 |
| ATOM | 1462 | CD2 | LEU | A | 332 | 44.574 | 32.734 | −0.705 | 1.00 | 22.71 |
| ATOM | 1463 | N | GLY | A | 333 | 48.622 | 35.266 | 0.002 | 1.00 | 20.09 |
| ATOM | 1464 | CA | GLY | A | 333 | 49.944 | 34.695 | −0.194 | 1.00 | 19.48 |
| ATOM | 1465 | C | GLY | A | 333 | 50.870 | 35.034 | 0.978 | 1.00 | 22.66 |
| ATOM | 1466 | O | GLY | A | 333 | 51.609 | 34.182 | 1.460 | 1.00 | 23.16 |
| ATOM | 1467 | N | VAL | A | 334 | 50.847 | 36.287 | 1.419 | 1.00 | 17.68 |
| ATOM | 1468 | CA | VAL | A | 334 | 51.714 | 36.717 | 2.515 | 1.00 | 17.09 |
| ATOM | 1469 | C | VAL | A | 334 | 51.315 | 36.013 | 3.814 | 1.00 | 21.40 |
| ATOM | 1470 | O | VAL | A | 334 | 52.167 | 35.554 | 4.577 | 1.00 | 21.63 |
| ATOM | 1471 | CB | VAL | A | 334 | 51.634 | 38.265 | 2.731 | 1.00 | 20.71 |
| ATOM | 1472 | CG1 | VAL | A | 334 | 52.554 | 38.697 | 3.840 | 1.00 | 19.35 |
| ATOM | 1473 | CG2 | VAL | A | 334 | 51.944 | 39.029 | 1.407 | 1.00 | 21.10 |
| ATOM | 1474 | N | VAL | A | 335 | 50.008 | 35.927 | 4.041 | 1.00 | 17.19 |
| ATOM | 1475 | CA | VAL | A | 335 | 49.455 | 35.311 | 5.234 | 1.00 | 17.17 |
| ATOM | 1476 | C | VAL | A | 335 | 49.728 | 33.802 | 5.297 | 1.00 | 21.51 |
| ATOM | 1477 | O | VAL | A | 335 | 50.058 | 33.268 | 6.352 | 1.00 | 22.46 |
| ATOM | 1478 | CB | VAL | A | 335 | 47.923 | 35.630 | 5.339 | 1.00 | 21.87 |
| ATOM | 1479 | CG1 | VAL | A | 335 | 47.191 | 34.560 | 6.064 | 1.00 | 21.96 |
| ATOM | 1480 | CG2 | VAL | A | 335 | 47.699 | 37.004 | 6.008 | 1.00 | 21.86 |
| ATOM | 1481 | N | MET | A | 336 | 49.605 | 33.122 | 4.160 | 1.00 | 17.27 |
| ATOM | 1482 | CA | MET | A | 336 | 49.849 | 31.682 | 4.088 | 1.00 | 16.23 |
| ATOM | 1483 | C | MET | A | 336 | 51.344 | 31.382 | 4.108 | 1.00 | 21.81 |
| ATOM | 1484 | O | MET | A | 336 | 51.772 | 30.371 | 4.643 | 1.00 | 21.71 |
| ATOM | 1485 | CB | MET | A | 336 | 49.186 | 31.077 | 2.843 | 1.00 | 17.69 |
| ATOM | 1486 | CG | MET | A | 336 | 47.665 | 30.885 | 2.984 | 1.00 | 19.57 |
| ATOM | 1487 | SD | MET | A | 336 | 46.915 | 30.126 | 1.531 | 1.00 | 21.89 |
| ATOM | 1488 | CE | MET | A | 336 | 47.352 | 28.363 | 1.813 | 1.00 | 18.44 |
| ATOM | 1489 | N | TYR | A | 337 | 52.141 | 32.282 | 3.548 | 1.00 | 19.98 |
| ATOM | 1490 | CA | TYR | A | 337 | 53.586 | 32.134 | 3.605 | 1.00 | 20.22 |
| ATOM | 1491 | C | TYR | A | 337 | 53.989 | 32.144 | 5.084 | 1.00 | 25.08 |
| ATOM | 1492 | O | TYR | A | 337 | 54.673 | 31.239 | 5.569 | 1.00 | 25.01 |
| ATOM | 1493 | CB | TYR | A | 337 | 54.273 | 33.298 | 2.883 | 1.00 | 21.68 |
| ATOM | 1494 | CG | TYR | A | 337 | 55.780 | 33.160 | 2.825 | 1.00 | 23.14 |
| ATOM | 1495 | CD1 | TYR | A | 337 | 56.578 | 33.566 | 3.897 | 1.00 | 24.44 |
| ATOM | 1496 | CD2 | TYR | A | 337 | 56.404 | 32.557 | 1.729 | 1.00 | 23.63 |
| ATOM | 1497 | CE1 | TYR | A | 337 | 57.945 | 33.374 | 3.874 | 1.00 | 24.31 |
| ATOM | 1498 | CE2 | TYR | A | 337 | 57.768 | 32.378 | 1.695 | 1.00 | 23.84 |
| ATOM | 1499 | CZ | TYR | A | 337 | 58.537 | 32.787 | 2.771 | 1.00 | 28.11 |
| ATOM | 1500 | OH | TYR | A | 337 | 59.903 | 32.628 | 2.737 | 1.00 | 24.93 |
| ATOM | 1501 | N | GLU | A | 338 | 53.517 | 33.155 | 5.802 | 1.00 | 22.14 |
| ATOM | 1502 | CA | GLU | A | 338 | 53.810 | 33.307 | 7.229 | 1.00 | 21.95 |
| ATOM | 1503 | C | GLU | A | 338 | 53.448 | 32.074 | 8.034 | 1.00 | 25.78 |
| ATOM | 1504 | O | GLU | A | 338 | 54.170 | 31.676 | 8.947 | 1.00 | 26.42 |
| ATOM | 1505 | CB | GLU | A | 338 | 53.034 | 34.498 | 7.793 | 1.00 | 23.27 |

TABLE 3-continued

Structural coordinates for AKT3lkd(pT305, pS472) (SEQ ID NO:2).

| ATOM | 1506 | CG  | GLU | A | 338 | 53.647 | 35.846 | 7.499  | 1.00 | 33.02 |
|------|------|-----|-----|---|-----|--------|--------|--------|------|-------|
| ATOM | 1507 | CD  | GLU | A | 338 | 52.999 | 36.945 | 8.314  | 1.00 | 46.75 |
| ATOM | 1508 | OE1 | GLU | A | 338 | 53.562 | 37.346 | 9.351  | 1.00 | 44.86 |
| ATOM | 1509 | OE2 | GLU | A | 338 | 51.877 | 37.329 | 7.972  | 1.00 | 37.58 |
| ATOM | 1510 | N   | MET | A | 339 | 52.282 | 31.521 | 7.754  | 1.00 | 21.70 |
| ATOM | 1511 | CA  | MET | A | 339 | 51.799 | 30.367 | 8.493  | 1.00 | 20.66 |
| ATOM | 1512 | C   | MET | A | 339 | 52.671 | 29.133 | 8.295  | 1.00 | 24.48 |
| ATOM | 1513 | O   | MET | A | 339 | 53.026 | 28.456 | 9.255  | 1.00 | 24.91 |
| ATOM | 1514 | CB  | MET | A | 339 | 50.357 | 30.060 | 8.094  | 1.00 | 22.34 |
| ATOM | 1515 | CG  | MET | A | 339 | 49.372 | 31.128 | 8.509  | 1.00 | 24.65 |
| ATOM | 1516 | SD  | MET | A | 339 | 47.690 | 30.713 | 8.033  | 1.00 | 27.42 |
| ATOM | 1517 | CE  | MET | A | 339 | 46.844 | 31.819 | 9.017  | 1.00 | 24.31 |
| ATOM | 1518 | N   | MET | A | 340 | 52.984 | 28.830 | 7.048  | 1.00 | 20.91 |
| ATOM | 1519 | CA  | MET | A | 340 | 53.775 | 27.638 | 6.722  | 1.00 | 22.04 |
| ATOM | 1520 | C   | MET | A | 340 | 55.271 | 27.834 | 6.920  | 1.00 | 26.94 |
| ATOM | 1521 | O   | MET | A | 340 | 56.000 | 26.877 | 7.191  | 1.00 | 25.30 |
| ATOM | 1522 | CB  | MET | A | 340 | 53.527 | 27.217 | 5.261  | 1.00 | 24.21 |
| ATOM | 1523 | CG  | MET | A | 340 | 52.315 | 26.363 | 5.048  | 1.00 | 27.34 |
| ATOM | 1524 | SD  | MET | A | 340 | 52.159 | 25.897 | 3.310  | 1.00 | 31.34 |
| ATOM | 1525 | CE  | MET | A | 340 | 51.270 | 27.284 | 2.657  | 1.00 | 28.17 |
| ATOM | 1526 | N   | CYS | A | 341 | 55.733 | 29.073 | 6.746  | 1.00 | 25.46 |
| ATOM | 1527 | CA  | CYS | A | 341 | 57.162 | 29.375 | 6.830  | 1.00 | 25.29 |
| ATOM | 1528 | C   | CYS | A | 341 | 57.603 | 29.974 | 8.156  | 1.00 | 30.69 |
| ATOM | 1529 | O   | CYS | A | 341 | 58.795 | 29.990 | 8.467  | 1.00 | 29.91 |
| ATOM | 1530 | CB  | CYS | A | 341 | 57.591 | 30.259 | 5.658  | 1.00 | 24.90 |
| ATOM | 1531 | SG  | CYS | A | 341 | 57.262 | 29.504 | 4.037  | 1.00 | 28.50 |
| ATOM | 1532 | N   | GLY | A | 342 | 56.649 | 30.478 | 8.928  | 1.00 | 28.98 |
| ATOM | 1533 | CA  | GLY | A | 342 | 56.956 | 31.049 | 10.249 | 1.00 | 29.50 |
| ATOM | 1534 | C   | GLY | A | 342 | 57.558 | 32.455 | 10.202 | 1.00 | 35.76 |
| ATOM | 1535 | O   | GLY | A | 342 | 58.131 | 32.932 | 11.191 | 1.00 | 36.56 |
| ATOM | 1536 | N   | ARG | A | 343 | 57.420 | 33.127 | 9.067  | 1.00 | 32.38 |
| ATOM | 1537 | CA  | ARG | A | 343 | 57.948 | 34.478 | 8.932  | 1.00 | 31.68 |
| ATOM | 1538 | C   | ARG | A | 343 | 57.419 | 35.152 | 7.684  | 1.00 | 33.95 |
| ATOM | 1539 | O   | ARG | A | 343 | 56.815 | 34.505 | 6.823  | 1.00 | 32.73 |
| ATOM | 1540 | CB  | ARG | A | 343 | 59.482 | 34.457 | 8.900  | 1.00 | 32.75 |
| ATOM | 1541 | CG  | ARG | A | 343 | 60.072 | 33.527 | 7.845  | 1.00 | 41.11 |
| ATOM | 1542 | CD  | ARG | A | 343 | 61.539 | 33.839 | 7.591  | 1.00 | 51.33 |
| ATOM | 1543 | NE  | ARG | A | 343 | 61.806 | 34.081 | 6.176  | 1.00 | 62.30 |
| ATOM | 1544 | CZ  | ARG | A | 343 | 61.990 | 35.285 | 5.643  | 1.00 | 78.59 |
| ATOM | 1545 | NH1 | ARG | A | 343 | 61.950 | 36.372 | 6.412  | 1.00 | 66.87 |
| ATOM | 1546 | NH2 | ARG | A | 343 | 62.212 | 35.406 | 4.339  | 1.00 | 64.13 |
| ATOM | 1547 | N   | LEU | A | 344 | 57.661 | 36.460 | 7.595  | 1.00 | 30.09 |
| ATOM | 1548 | CA  | LEU | A | 344 | 57.244 | 37.268 | 6.452  | 1.00 | 29.54 |
| ATOM | 1549 | C   | LEU | A | 344 | 58.084 | 36.908 | 5.240  | 1.00 | 32.46 |
| ATOM | 1550 | O   | LEU | A | 344 | 59.276 | 36.663 | 5.359  | 1.00 | 32.37 |
| ATOM | 1551 | CB  | LEU | A | 344 | 57.451 | 38.753 | 6.768  | 1.00 | 29.84 |
| ATOM | 1552 | CG  | LEU | A | 344 | 56.252 | 39.693 | 6.962  | 1.00 | 34.57 |
| ATOM | 1553 | CD1 | LEU | A | 344 | 54.977 | 38.950 | 7.293  | 1.00 | 34.26 |
| ATOM | 1554 | CD2 | LEU | A | 344 | 56.566 | 40.734 | 8.023  | 1.00 | 37.21 |
| ATOM | 1555 | N   | PRO | A | 345 | 57.466 | 36.909 | 4.068  | 1.00 | 28.93 |
| ATOM | 1556 | CA  | PRO | A | 345 | 58.194 | 36.620 | 2.833  | 1.00 | 28.45 |
| ATOM | 1557 | C   | PRO | A | 345 | 59.149 | 37.785 | 2.492  | 1.00 | 33.68 |
| ATOM | 1558 | O   | PRO | A | 345 | 60.193 | 37.584 | 1.876  | 1.00 | 33.74 |
| ATOM | 1559 | CB  | PRO | A | 345 | 57.078 | 36.512 | 1.777  | 1.00 | 29.91 |
| ATOM | 1560 | CG  | PRO | A | 345 | 55.928 | 37.272 | 2.338  | 1.00 | 34.06 |
| ATOM | 1561 | CD  | PRO | A | 345 | 56.027 | 37.160 | 3.834  | 1.00 | 29.46 |
| ATOM | 1562 | N   | PHE | A | 346 | 58.767 | 38.996 | 2.894  | 1.00 | 30.51 |
| ATOM | 1563 | CA  | PHE | A | 346 | 59.578 | 40.190 | 2.658  | 1.00 | 30.94 |
| ATOM | 1564 | C   | PHE | A | 346 | 59.621 | 41.026 | 3.937  | 1.00 | 36.62 |
| ATOM | 1565 | O   | PHE | A | 346 | 58.581 | 41.428 | 4.454  | 1.00 | 34.72 |
| ATOM | 1566 | CB  | PHE | A | 346 | 58.983 | 41.047 | 1.527  | 1.00 | 32.42 |
| ATOM | 1567 | CG  | PHE | A | 346 | 58.710 | 40.290 | 0.265  | 1.00 | 33.74 |
| ATOM | 1568 | CD1 | PHE | A | 346 | 59.747 | 39.917 | −0.577 | 1.00 | 36.28 |
| ATOM | 1569 | CD2 | PHE | A | 346 | 57.410 | 39.989 | −0.106 | 1.00 | 35.60 |
| ATOM | 1570 | CE1 | PHE | A | 346 | 59.496 | 39.226 | −1.737 | 1.00 | 36.95 |
| ATOM | 1571 | CE2 | PHE | A | 346 | 57.152 | 39.311 | −1.274 | 1.00 | 38.18 |
| ATOM | 1572 | CZ  | PHE | A | 346 | 58.194 | 38.930 | −2.093 | 1.00 | 36.23 |
| ATOM | 1573 | N   | TYR | A | 347 | 60.823 | 41.291 | 4.435  | 1.00 | 36.79 |
| ATOM | 1574 | CA  | TYR | A | 347 | 60.979 | 42.087 | 5.647  | 1.00 | 38.92 |
| ATOM | 1575 | C   | TYR | A | 347 | 62.218 | 42.998 | 5.645  | 1.00 | 45.38 |
| ATOM | 1576 | O   | TYR | A | 347 | 63.276 | 42.634 | 5.125  | 1.00 | 44.71 |
| ATOM | 1577 | CB  | TYR | A | 347 | 60.998 | 41.195 | 6.878  | 1.00 | 41.29 |
| ATOM | 1578 | CG  | TYR | A | 347 | 61.243 | 41.950 | 8.159  | 1.00 | 45.59 |
| ATOM | 1579 | CD1 | TYR | A | 347 | 60.187 | 42.510 | 8.873  | 1.00 | 48.06 |
| ATOM | 1580 | CD2 | TYR | A | 347 | 62.525 | 42.115 | 8.654  | 1.00 | 46.92 |
| ATOM | 1581 | CE1 | TYR | A | 347 | 60.405 | 43.187 | 10.054 | 1.00 | 49.18 |
| ATOM | 1582 | CE2 | TYR | A | 347 | 62.752 | 42.806 | 9.830  | 1.00 | 48.25 |
| ATOM | 1583 | CZ  | TYR | A | 347 | 61.691 | 43.338 | 10.524 | 1.00 | 57.32 |

TABLE 3-continued

Structural coordinates for AKT3lkd(pT305, pS472) (SEQ ID NO:2).

| ATOM | 1584 | OH | TYR | A | 347 | 61.916 | 44.026 | 11.697 | 1.00 | 61.08 |
|---|---|---|---|---|---|---|---|---|---|---|
| ATOM | 1585 | N | ASN | A | 348 | 62.080 | 44.172 | 6.255 | 1.00 | 43.77 |
| ATOM | 1586 | CA | ASN | A | 348 | 63.191 | 45.113 | 6.353 | 1.00 | 44.32 |
| ATOM | 1587 | C | ASN | A | 348 | 62.885 | 46.284 | 7.273 | 1.00 | 49.03 |
| ATOM | 1588 | O | ASN | A | 348 | 61.809 | 46.875 | 7.209 | 1.00 | 47.92 |
| ATOM | 1589 | CB | ASN | A | 348 | 63.588 | 45.631 | 4.974 | 1.00 | 46.12 |
| ATOM | 1590 | CG | ASN | A | 348 | 64.840 | 46.483 | 5.015 | 1.00 | 73.58 |
| ATOM | 1591 | OD1 | ASN | A | 348 | 65.931 | 45.988 | 5.289 | 1.00 | 64.24 |
| ATOM | 1592 | ND2 | ASN | A | 348 | 64.683 | 47.780 | 4.766 | 1.00 | 70.22 |
| ATOM | 1593 | N | GLN | A | 349 | 63.848 | 46.624 | 8.123 | 1.00 | 47.32 |
| ATOM | 1594 | CA | GLN | A | 349 | 63.698 | 47.758 | 9.033 | 1.00 | 47.88 |
| ATOM | 1595 | C | GLN | A | 349 | 63.507 | 49.028 | 8.217 | 1.00 | 53.03 |
| ATOM | 1596 | O | GLN | A | 349 | 62.592 | 49.812 | 8.473 | 1.00 | 53.20 |
| ATOM | 1597 | CB | GLN | A | 349 | 64.931 | 47.890 | 9.933 | 1.00 | 49.49 |
| ATOM | 1598 | CG | GLN | A | 349 | 65.551 | 46.553 | 10.334 | 1.00 | 68.32 |
| ATOM | 1599 | CD | GLN | A | 349 | 66.331 | 45.907 | 9.198 | 1.00 | 88.49 |
| ATOM | 1600 | OE1 | GLN | A | 349 | 65.950 | 44.852 | 8.685 | 1.00 | 81.92 |
| ATOM | 1601 | NE2 | GLN | A | 349 | 67.421 | 46.548 | 8.791 | 1.00 | 83.88 |
| ATOM | 1602 | N | ASP | A | 350 | 64.357 | 49.214 | 7.212 | 1.00 | 50.06 |
| ATOM | 1603 | CA | ASP | A | 350 | 64.254 | 50.374 | 6.338 | 1.00 | 50.23 |
| ATOM | 1604 | C | ASP | A | 350 | 63.047 | 50.192 | 5.430 | 1.00 | 54.14 |
| ATOM | 1605 | O | ASP | A | 350 | 63.085 | 49.415 | 4.471 | 1.00 | 53.06 |
| ATOM | 1606 | CB | ASP | A | 350 | 65.526 | 50.544 | 5.500 | 1.00 | 52.32 |
| ATOM | 1607 | CG | ASP | A | 350 | 65.460 | 51.749 | 4.581 | 1.00 | 62.71 |
| ATOM | 1608 | OD1 | ASP | A | 350 | 65.664 | 51.585 | 3.362 | 1.00 | 63.96 |
| ATOM | 1609 | OD2 | ASP | A | 350 | 65.189 | 52.860 | 5.079 | 1.00 | 67.61 |
| ATOM | 1610 | N | HIS | A | 351 | 61.967 | 50.893 | 5.750 | 1.00 | 51.40 |
| ATOM | 1611 | CA | HIS | A | 351 | 60.737 | 50.772 | 4.993 | 1.00 | 51.43 |
| ATOM | 1612 | C | HIS | A | 351 | 60.806 | 51.352 | 3.597 | 1.00 | 54.36 |
| ATOM | 1613 | O | HIS | A | 351 | 59.838 | 51.920 | 3.095 | 1.00 | 54.56 |
| ATOM | 1614 | CB | HIS | A | 351 | 59.534 | 51.277 | 5.799 | 1.00 | 52.64 |
| ATOM | 1615 | CG | HIS | A | 351 | 59.191 | 50.396 | 6.964 | 1.00 | 56.42 |
| ATOM | 1616 | ND1 | HIS | A | 351 | 58.404 | 50.816 | 8.015 | 1.00 | 58.44 |
| ATOM | 1617 | CD2 | HIS | A | 351 | 59.556 | 49.122 | 7.252 | 1.00 | 58.56 |
| ATOM | 1618 | CE1 | HIS | A | 351 | 58.289 | 49.834 | 8.894 | 1.00 | 58.07 |
| ATOM | 1619 | NE2 | HIS | A | 351 | 58.976 | 48.794 | 8.453 | 1.00 | 58.43 |
| ATOM | 1620 | N | GLU | A | 352 | 61.958 | 51.157 | 2.962 | 1.00 | 49.33 |
| ATOM | 1621 | CA | GLU | A | 352 | 62.194 | 51.585 | 1.588 | 1.00 | 47.82 |
| ATOM | 1622 | C | GLU | A | 352 | 62.914 | 50.447 | 0.881 | 1.00 | 47.98 |
| ATOM | 1623 | O | GLU | A | 352 | 62.710 | 50.213 | −0.307 | 1.00 | 47.45 |
| ATOM | 1624 | CB | GLU | A | 352 | 63.045 | 52.862 | 1.546 | 1.00 | 49.23 |
| ATOM | 1625 | CG | GLU | A | 352 | 62.856 | 53.698 | 0.277 | 1.00 | 59.39 |
| ATOM | 1626 | CD | GLU | A | 352 | 63.948 | 54.750 | 0.096 | 1.00 | 82.10 |
| ATOM | 1627 | OE1 | GLU | A | 352 | 64.005 | 55.373 | −0.986 | 1.00 | 71.19 |
| ATOM | 1628 | OE2 | GLU | A | 352 | 64.743 | 54.956 | 1.039 | 1.00 | 79.54 |
| ATOM | 1629 | N | LYS | A | 353 | 63.747 | 49.730 | 1.637 | 1.00 | 42.39 |
| ATOM | 1630 | CA | LYS | A | 353 | 64.448 | 48.549 | 1.125 | 1.00 | 41.37 |
| ATOM | 1631 | C | LYS | A | 353 | 63.402 | 47.453 | 1.029 | 1.00 | 43.16 |
| ATOM | 1632 | O | LYS | A | 353 | 63.391 | 46.655 | 0.088 | 1.00 | 42.39 |
| ATOM | 1633 | CB | LYS | A | 353 | 65.527 | 48.104 | 2.117 | 1.00 | 43.99 |
| ATOM | 1634 | CG | LYS | A | 353 | 66.889 | 48.748 | 1.904 | 1.00 | 62.43 |
| ATOM | 1635 | CD | LYS | A | 353 | 67.725 | 48.715 | 3.182 | 1.00 | 71.66 |
| ATOM | 1636 | CE | LYS | A | 353 | 68.660 | 49.918 | 3.268 | 1.00 | 78.20 |
| ATOM | 1637 | NZ | LYS | A | 353 | 70.091 | 49.519 | 3.193 | 1.00 | 82.07 |
| ATOM | 1638 | N | LEU | A | 354 | 62.519 | 47.432 | 2.023 | 1.00 | 38.37 |
| ATOM | 1639 | CA | LEU | A | 354 | 61.436 | 46.475 | 2.084 | 1.00 | 37.62 |
| ATOM | 1640 | C | LEU | A | 354 | 60.609 | 46.587 | 0.813 | 1.00 | 40.84 |
| ATOM | 1641 | O | LEU | A | 354 | 60.235 | 45.580 | 0.210 | 1.00 | 39.70 |
| ATOM | 1642 | CB | LEU | A | 354 | 60.561 | 46.760 | 3.304 | 1.00 | 37.55 |
| ATOM | 1643 | CG | LEU | A | 354 | 59.171 | 46.131 | 3.295 | 1.00 | 41.85 |
| ATOM | 1644 | CD1 | LEU | A | 354 | 59.255 | 44.631 | 3.607 | 1.00 | 41.50 |
| ATOM | 1645 | CD2 | LEU | A | 354 | 58.249 | 46.847 | 4.273 | 1.00 | 44.32 |
| ATOM | 1646 | N | PHE | A | 355 | 60.359 | 47.827 | 0.393 | 1.00 | 37.35 |
| ATOM | 1647 | CA | PHE | A | 355 | 59.593 | 48.094 | −0.821 | 1.00 | 36.85 |
| ATOM | 1648 | C | PHE | A | 355 | 60.301 | 47.522 | −2.035 | 1.00 | 39.04 |
| ATOM | 1649 | O | PHE | A | 355 | 59.662 | 47.017 | −2.964 | 1.00 | 38.36 |
| ATOM | 1650 | CB | PHE | A | 355 | 59.385 | 49.600 | −0.997 | 1.00 | 38.76 |
| ATOM | 1651 | CG | PHE | A | 355 | 58.397 | 50.188 | −0.037 | 1.00 | 40.25 |
| ATOM | 1652 | CD1 | PHE | A | 355 | 57.726 | 49.382 | 0.861 | 1.00 | 42.73 |
| ATOM | 1653 | CD2 | PHE | A | 355 | 58.145 | 51.551 | −0.027 | 1.00 | 42.98 |
| ATOM | 1654 | CE1 | PHE | A | 355 | 56.813 | 49.919 | 1.754 | 1.00 | 43.61 |
| ATOM | 1655 | CE2 | PHE | A | 355 | 57.232 | 52.096 | 0.869 | 1.00 | 45.47 |
| ATOM | 1656 | CZ | PHE | A | 355 | 56.566 | 51.273 | 1.757 | 1.00 | 43.01 |
| ATOM | 1657 | N | GLU | A | 356 | 61.628 | 47.601 | −2.021 | 1.00 | 34.69 |
| ATOM | 1658 | CA | GLU | A | 356 | 62.444 | 47.083 | −3.118 | 1.00 | 33.67 |
| ATOM | 1659 | C | GLU | A | 356 | 62.364 | 45.561 | −3.152 | 1.00 | 36.72 |
| ATOM | 1660 | O | GLU | A | 356 | 62.242 | 44.954 | −4.213 | 1.00 | 36.54 |
| ATOM | 1661 | CB | GLU | A | 356 | 63.899 | 47.541 | −2.956 | 1.00 | 34.78 |

TABLE 3-continued

Structural coordinates for AKT3lkd(pT305, pS472) (SEQ ID NO:2).

| ATOM | 1662 | CG | GLU | A | 356 | 64.580 | 47.919 | −4.246 | 1.00 | 43.71 |
|---|---|---|---|---|---|---|---|---|---|---|
| ATOM | 1663 | CD | GLU | A | 356 | 65.147 | 49.333 | −4.223 | 1.00 | 68.10 |
| ATOM | 1664 | OE1 | GLU | A | 356 | 65.417 | 49.863 | −3.117 | 1.00 | 61.79 |
| ATOM | 1665 | OE2 | GLU | A | 356 | 65.341 | 49.908 | −5.316 | 1.00 | 62.04 |
| ATOM | 1666 | N | LEU | A | 357 | 62.435 | 44.947 | −1.983 | 1.00 | 33.43 |
| ATOM | 1667 | CA | LEU | A | 357 | 62.334 | 43.493 | −1.885 | 1.00 | 33.35 |
| ATOM | 1668 | C | LEU | A | 357 | 60.990 | 43.075 | −2.462 | 1.00 | 35.99 |
| ATOM | 1669 | O | LEU | A | 357 | 60.912 | 42.256 | −3.382 | 1.00 | 35.77 |
| ATOM | 1670 | CB | LEU | A | 357 | 62.422 | 43.055 | −0.417 | 1.00 | 33.42 |
| ATOM | 1671 | CG | LEU | A | 357 | 63.771 | 43.320 | 0.264 | 1.00 | 38.41 |
| ATOM | 1672 | CD1 | LEU | A | 357 | 63.754 | 42.857 | 1.719 | 1.00 | 38.35 |
| ATOM | 1673 | CD2 | LEU | A | 357 | 64.894 | 42.629 | −0.513 | 1.00 | 40.72 |
| ATOM | 1674 | N | ILE | A | 358 | 59.939 | 43.674 | −1.922 | 1.00 | 31.06 |
| ATOM | 1675 | CA | ILE | A | 358 | 58.585 | 43.411 | −2.348 | 1.00 | 30.49 |
| ATOM | 1676 | C | ILE | A | 358 | 58.426 | 43.537 | −3.861 | 1.00 | 35.09 |
| ATOM | 1677 | O | ILE | A | 358 | 57.752 | 42.733 | −4.480 | 1.00 | 34.68 |
| ATOM | 1678 | CB | ILE | A | 358 | 57.594 | 44.363 | −1.633 | 1.00 | 32.85 |
| ATOM | 1679 | CG1 | ILE | A | 358 | 57.425 | 43.950 | −0.166 | 1.00 | 32.47 |
| ATOM | 1680 | CG2 | ILE | A | 358 | 56.253 | 44.413 | −2.366 | 1.00 | 33.41 |
| ATOM | 1681 | CD1 | ILE | A | 358 | 56.550 | 44.885 | 0.646 | 1.00 | 34.08 |
| ATOM | 1682 | N | LEU | A | 359 | 59.092 | 44.528 | −4.445 | 1.00 | 33.06 |
| ATOM | 1683 | CA | LEU | A | 359 | 58.996 | 44.802 | −5.881 | 1.00 | 33.62 |
| ATOM | 1684 | C | LEU | A | 359 | 59.883 | 43.944 | −6.794 | 1.00 | 39.94 |
| ATOM | 1685 | O | LEU | A | 359 | 59.493 | 43.621 | −7.916 | 1.00 | 39.48 |
| ATOM | 1686 | CB | LEU | A | 359 | 59.269 | 46.292 | −6.151 | 1.00 | 33.74 |
| ATOM | 1687 | CG | LEU | A | 359 | 58.105 | 47.259 | −5.899 | 1.00 | 38.63 |
| ATOM | 1688 | CD1 | LEU | A | 359 | 58.603 | 48.697 | −5.766 | 1.00 | 38.69 |
| ATOM | 1689 | CD2 | LEU | A | 359 | 57.074 | 47.145 | −7.023 | 1.00 | 41.60 |
| ATOM | 1690 | N | MET | A | 360 | 61.079 | 43.603 | −6.332 | 1.00 | 38.74 |
| ATOM | 1691 | CA | MET | A | 360 | 62.026 | 42.864 | −7.169 | 1.00 | 39.66 |
| ATOM | 1692 | C | MET | A | 360 | 62.415 | 41.476 | −6.690 | 1.00 | 43.59 |
| ATOM | 1693 | O | MET | A | 360 | 62.729 | 40.608 | −7.497 | 1.00 | 43.53 |
| ATOM | 1694 | CB | MET | A | 360 | 63.297 | 43.688 | −7.362 | 1.00 | 42.63 |
| ATOM | 1695 | CG | MET | A | 360 | 63.043 | 45.175 | −7.625 | 1.00 | 47.26 |
| ATOM | 1696 | SD | MET | A | 360 | 62.890 | 45.517 | −9.383 | 1.00 | 52.38 |
| ATOM | 1697 | CE | MET | A | 360 | 61.449 | 44.523 | −9.811 | 1.00 | 48.98 |
| ATOM | 1698 | N | GLU | A | 361 | 62.469 | 41.291 | −5.381 | 1.00 | 40.01 |
| ATOM | 1699 | CA | GLU | A | 361 | 62.936 | 40.041 | −4.814 | 1.00 | 39.70 |
| ATOM | 1700 | C | GLU | A | 361 | 62.041 | 38.833 | −4.993 | 1.00 | 43.22 |
| ATOM | 1701 | O | GLU | A | 361 | 60.833 | 38.891 | −4.763 | 1.00 | 42.16 |
| ATOM | 1702 | CB | GLU | A | 361 | 63.279 | 40.211 | −3.339 | 1.00 | 41.09 |
| ATOM | 1703 | CG | GLU | A | 361 | 64.356 | 39.253 | −2.848 | 1.00 | 52.49 |
| ATOM | 1704 | CD | GLU | A | 361 | 65.758 | 39.846 | −2.959 | 1.00 | 73.40 |
| ATOM | 1705 | OE1 | GLU | A | 361 | 66.622 | 39.492 | −2.125 | 1.00 | 63.23 |
| ATOM | 1706 | OE2 | GLU | A | 361 | 65.990 | 40.677 | −3.872 | 1.00 | 64.94 |
| ATOM | 1707 | N | ASP | A | 362 | 62.666 | 37.712 | −5.333 | 1.00 | 40.73 |
| ATOM | 1708 | CA | ASP | A | 362 | 61.968 | 36.446 | −5.430 | 1.00 | 40.90 |
| ATOM | 1709 | C | ASP | A | 362 | 61.904 | 35.854 | −4.034 | 1.00 | 43.43 |
| ATOM | 1710 | O | ASP | A | 362 | 62.757 | 36.130 | −3.195 | 1.00 | 42.80 |
| ATOM | 1711 | CB | ASP | A | 362 | 62.686 | 35.497 | −6.388 | 1.00 | 43.28 |
| ATOM | 1712 | CG | ASP | A | 362 | 62.203 | 35.645 | −7.814 | 1.00 | 59.64 |
| ATOM | 1713 | OD1 | ASP | A | 362 | 60.967 | 35.736 | −8.017 | 1.00 | 61.15 |
| ATOM | 1714 | OD2 | ASP | A | 362 | 63.055 | 35.713 | −8.729 | 1.00 | 67.58 |
| ATOM | 1715 | N | ILE | A | 363 | 60.868 | 35.078 | −3.772 | 1.00 | 39.82 |
| ATOM | 1716 | CA | ILE | A | 363 | 60.657 | 34.522 | −2.448 | 1.00 | 39.25 |
| ATOM | 1717 | C | ILE | A | 363 | 61.455 | 33.246 | −2.179 | 1.00 | 41.76 |
| ATOM | 1718 | O | ILE | A | 363 | 61.807 | 32.511 | −3.104 | 1.00 | 40.89 |
| ATOM | 1719 | CB | ILE | A | 363 | 59.144 | 34.320 | −2.159 | 1.00 | 42.40 |
| ATOM | 1720 | CG1 | ILE | A | 363 | 58.832 | 34.649 | −0.710 | 1.00 | 43.27 |
| ATOM | 1721 | CG2 | ILE | A | 363 | 58.686 | 32.927 | −2.538 | 1.00 | 43.07 |
| ATOM | 1722 | CD1 | ILE | A | 363 | 59.146 | 36.089 | −0.338 | 1.00 | 54.45 |
| ATOM | 1723 | N | LYS | A | 364 | 61.759 | 33.010 | −0.903 | 1.00 | 36.87 |
| ATOM | 1724 | CA | LYS | A | 364 | 62.504 | 31.821 | −0.494 | 1.00 | 35.76 |
| ATOM | 1725 | C | LYS | A | 364 | 61.616 | 30.832 | 0.288 | 1.00 | 35.78 |
| ATOM | 1726 | O | LYS | A | 364 | 60.734 | 31.244 | 1.039 | 1.00 | 34.17 |
| ATOM | 1727 | CB | LYS | A | 364 | 63.722 | 32.225 | 0.343 | 1.00 | 38.36 |
| ATOM | 1728 | CG | LYS | A | 364 | 64.987 | 32.432 | −0.478 | 1.00 | 53.38 |
| ATOM | 1729 | CD | LYS | A | 364 | 64.935 | 31.637 | −1.778 | 1.00 | 64.42 |
| ATOM | 1730 | CE | LYS | A | 364 | 65.616 | 32.388 | −2.917 | 1.00 | 77.54 |
| ATOM | 1731 | NZ | LYS | A | 364 | 64.885 | 32.229 | −4.208 | 1.00 | 86.03 |
| ATOM | 1732 | N | PHE | A | 365 | 61.873 | 29.534 | 0.120 | 1.00 | 30.70 |
| ATOM | 1733 | CA | PHE | A | 365 | 61.073 | 28.504 | 0.784 | 1.00 | 29.97 |
| ATOM | 1734 | C | PHE | A | 365 | 61.883 | 27.573 | 1.657 | 1.00 | 36.28 |
| ATOM | 1735 | O | PHE | A | 365 | 62.996 | 27.203 | 1.312 | 1.00 | 36.38 |
| ATOM | 1736 | CB | PHE | A | 365 | 60.334 | 27.661 | −0.258 | 1.00 | 30.93 |
| ATOM | 1737 | CG | PHE | A | 365 | 59.358 | 28.439 | −1.087 | 1.00 | 31.24 |
| ATOM | 1738 | CD1 | PHE | A | 365 | 58.340 | 29.162 | −0.486 | 1.00 | 32.84 |
| ATOM | 1739 | CD2 | PHE | A | 365 | 59.438 | 28.423 | −2.471 | 1.00 | 32.44 |

TABLE 3-continued

| | | | | | | | | | |
|---|---|---|---|---|---|---|---|---|---|
| | Structural coordinates for AKT3lkd(pT305, pS472) (SEQ ID NO:2). |

| ATOM | 1740 | CE1 | PHE | A | 365 | 57.440 | 29.876 | −1.247 | 1.00 | 33.71 |
|---|---|---|---|---|---|---|---|---|---|---|
| ATOM | 1741 | CE2 | PHE | A | 365 | 58.538 | 29.138 | −3.235 | 1.00 | 35.12 |
| ATOM | 1742 | CZ | PHE | A | 365 | 57.539 | 29.872 | −2.617 | 1.00 | 32.83 |
| ATOM | 1743 | N | PRO | A | 366 | 61.294 | 27.133 | 2.765 | 1.00 | 34.14 |
| ATOM | 1744 | CA | PRO | A | 366 | 61.945 | 26.126 | 3.601 | 1.00 | 33.91 |
| ATOM | 1745 | C | PRO | A | 366 | 62.107 | 24.926 | 2.675 | 1.00 | 39.25 |
| ATOM | 1746 | O | PRO | A | 366 | 61.232 | 24.654 | 1.843 | 1.00 | 38.00 |
| ATOM | 1747 | CB | PRO | A | 366 | 60.888 | 25.829 | 4.667 | 1.00 | 35.06 |
| ATOM | 1748 | CG | PRO | A | 366 | 60.122 | 27.090 | 4.788 | 1.00 | 38.56 |
| ATOM | 1749 | CD | PRO | A | 366 | 60.102 | 27.706 | 3.415 | 1.00 | 33.86 |
| ATOM | 1750 | N | ARG | A | 367 | 63.237 | 24.238 | 2.769 | 1.00 | 37.84 |
| ATOM | 1751 | CA | ARG | A | 367 | 63.509 | 23.134 | 1.848 | 1.00 | 37.87 |
| ATOM | 1752 | C | ARG | A | 367 | 62.482 | 21.996 | 1.805 | 1.00 | 39.60 |
| ATOM | 1753 | O | ARG | A | 367 | 62.152 | 21.491 | 0.728 | 1.00 | 40.61 |
| ATOM | 1754 | CB | ARG | A | 367 | 64.935 | 22.615 | 1.994 | 1.00 | 39.63 |
| ATOM | 1755 | CG | ARG | A | 367 | 65.726 | 22.638 | 0.681 | 1.00 | 50.39 |
| ATOM | 1756 | CD | ARG | A | 367 | 67.218 | 22.796 | 0.933 | 1.00 | 58.04 |
| ATOM | 1757 | NE | ARG | A | 367 | 67.561 | 22.592 | 2.338 | 1.00 | 58.70 |
| ATOM | 1758 | CZ | ARG | A | 367 | 68.280 | 21.569 | 2.788 | 1.00 | 67.34 |
| ATOM | 1759 | NH1 | ARG | A | 367 | 68.733 | 20.653 | 1.946 | 1.00 | 50.05 |
| ATOM | 1760 | NH2 | ARG | A | 367 | 68.540 | 21.457 | 4.085 | 1.00 | 52.16 |
| ATOM | 1761 | N | THR | A | 368 | 61.956 | 21.609 | 2.956 | 1.00 | 32.96 |
| ATOM | 1762 | CA | THR | A | 368 | 60.998 | 20.508 | 2.987 | 1.00 | 31.30 |
| ATOM | 1763 | C | THR | A | 368 | 59.543 | 20.886 | 2.658 | 1.00 | 32.57 |
| ATOM | 1764 | O | THR | A | 368 | 58.648 | 20.034 | 2.694 | 1.00 | 31.63 |
| ATOM | 1765 | CB | THR | A | 368 | 61.090 | 19.686 | 4.282 | 1.00 | 36.15 |
| ATOM | 1766 | OG1 | THR | A | 368 | 60.479 | 20.406 | 5.351 | 1.00 | 41.38 |
| ATOM | 1767 | CG2 | THR | A | 368 | 62.561 | 19.386 | 4.637 | 1.00 | 30.21 |
| ATOM | 1768 | N | LEU | A | 369 | 59.313 | 22.147 | 2.304 | 1.00 | 27.73 |
| ATOM | 1769 | CA | LEU | A | 369 | 57.970 | 22.581 | 1.936 | 1.00 | 27.21 |
| ATOM | 1770 | C | LEU | A | 369 | 57.518 | 21.828 | 0.692 | 1.00 | 30.21 |
| ATOM | 1771 | O | LEU | A | 369 | 58.281 | 21.658 | −0.252 | 1.00 | 30.31 |
| ATOM | 1772 | CB | LEU | A | 369 | 57.908 | 24.087 | 1.688 | 1.00 | 27.10 |
| ATOM | 1773 | CG | LEU | A | 369 | 56.484 | 24.647 | 1.803 | 1.00 | 31.52 |
| ATOM | 1774 | CD1 | LEU | A | 369 | 56.008 | 24.680 | 3.274 | 1.00 | 31.07 |
| ATOM | 1775 | CD2 | LEU | A | 369 | 56.359 | 26.015 | 1.151 | 1.00 | 33.55 |
| ATOM | 1776 | N | SER | A | 370 | 56.283 | 21.355 | 0.706 | 1.00 | 24.76 |
| ATOM | 1777 | CA | SER | A | 370 | 55.783 | 20.578 | −0.410 | 1.00 | 23.56 |
| ATOM | 1778 | C | SER | A | 370 | 55.818 | 21.345 | −1.717 | 1.00 | 27.07 |
| ATOM | 1779 | O | SER | A | 370 | 55.772 | 22.579 | −1.739 | 1.00 | 27.67 |
| ATOM | 1780 | CB | SER | A | 370 | 54.374 | 20.034 | −0.121 | 1.00 | 24.86 |
| ATOM | 1781 | OG | SER | A | 370 | 53.392 | 21.023 | −0.338 | 1.00 | 29.41 |
| ATOM | 1782 | N | SER | A | 371 | 55.881 | 20.607 | −2.811 | 1.00 | 22.13 |
| ATOM | 1783 | CA | SER | A | 371 | 55.897 | 21.204 | −4.132 | 1.00 | 21.37 |
| ATOM | 1784 | C | SER | A | 371 | 54.635 | 22.052 | −4.398 | 1.00 | 24.10 |
| ATOM | 1785 | O | SER | A | 371 | 54.730 | 23.138 | −4.944 | 1.00 | 23.41 |
| ATOM | 1786 | CB | SER | A | 371 | 56.033 | 20.120 | −5.200 | 1.00 | 23.38 |
| ATOM | 1787 | OG | SER | A | 371 | 55.828 | 20.672 | −6.490 | 1.00 | 32.66 |
| ATOM | 1788 | N | ASP | A | 372 | 53.460 | 21.524 | −4.034 | 1.00 | 19.26 |
| ATOM | 1789 | CA | ASP | A | 372 | 52.178 | 22.240 | −4.237 | 1.00 | 17.91 |
| ATOM | 1790 | C | ASP | A | 372 | 52.131 | 23.541 | −3.416 | 1.00 | 20.47 |
| ATOM | 1791 | O | ASP | A | 372 | 51.552 | 24.525 | −3.843 | 1.00 | 19.60 |
| ATOM | 1792 | CB | ASP | A | 372 | 50.985 | 21.349 | −3.823 | 1.00 | 19.32 |
| ATOM | 1793 | CG | ASP | A | 372 | 50.701 | 20.232 | −4.816 | 1.00 | 28.47 |
| ATOM | 1794 | OD1 | ASP | A | 372 | 51.241 | 20.256 | −5.938 | 1.00 | 30.26 |
| ATOM | 1795 | OD2 | ASP | A | 372 | 49.920 | 19.335 | −4.472 | 1.00 | 33.40 |
| ATOM | 1796 | N | ALA | A | 373 | 52.701 | 23.513 | −2.215 | 1.00 | 17.42 |
| ATOM | 1797 | CA | ALA | A | 373 | 52.714 | 24.704 | −1.348 | 1.00 | 16.68 |
| ATOM | 1798 | C | ALA | A | 373 | 53.609 | 25.785 | −1.957 | 1.00 | 21.81 |
| ATOM | 1799 | O | ALA | A | 373 | 53.249 | 26.971 | −1.979 | 1.00 | 22.03 |
| ATOM | 1800 | CB | ALA | A | 373 | 53.177 | 24.341 | 0.070 | 1.00 | 16.76 |
| ATOM | 1801 | N | LYS | A | 374 | 54.748 | 25.362 | −2.503 | 1.00 | 18.34 |
| ATOM | 1802 | CA | LYS | A | 374 | 55.672 | 26.289 | −3.157 | 1.00 | 18.12 |
| ATOM | 1803 | C | LYS | A | 374 | 55.008 | 26.876 | −4.377 | 1.00 | 21.55 |
| ATOM | 1804 | O | LYS | A | 374 | 55.088 | 28.079 | −4.621 | 1.00 | 21.28 |
| ATOM | 1805 | CB | LYS | A | 374 | 56.953 | 25.579 | −3.566 | 1.00 | 19.98 |
| ATOM | 1806 | CG | LYS | A | 374 | 57.915 | 25.336 | −2.428 | 1.00 | 27.09 |
| ATOM | 1807 | CD | LYS | A | 374 | 59.206 | 24.733 | −2.949 | 1.00 | 35.46 |
| ATOM | 1808 | CE | LYS | A | 374 | 59.980 | 24.027 | −1.844 | 1.00 | 37.89 |
| ATOM | 1809 | NZ | LYS | A | 374 | 61.084 | 23.198 | −2.399 | 1.00 | 39.91 |
| ATOM | 1810 | N | SER | A | 375 | 54.316 | 26.028 | −5.130 | 1.00 | 17.04 |
| ATOM | 1811 | CA | SER | A | 375 | 53.608 | 26.490 | −6.316 | 1.00 | 16.93 |
| ATOM | 1812 | C | SER | A | 375 | 52.512 | 27.509 | −5.967 | 1.00 | 21.68 |
| ATOM | 1813 | O | SER | A | 375 | 52.387 | 28.539 | −6.610 | 1.00 | 22.44 |
| ATOM | 1814 | CB | SER | A | 375 | 52.996 | 25.319 | −7.061 | 1.00 | 19.95 |
| ATOM | 1815 | OG | SER | A | 375 | 52.207 | 25.787 | −8.125 | 1.00 | 25.77 |
| ATOM | 1816 | N | LEU | A | 376 | 51.737 | 27.217 | −4.935 | 1.00 | 17.77 |
| ATOM | 1817 | CA | LEU | A | 376 | 50.659 | 28.097 | −4.525 | 1.00 | 17.51 |

TABLE 3-continued

| | | | | | | | | | |
|---|---|---|---|---|---|---|---|---|---|
| | Structural coordinates for AKT3lkd(pT305, pS472) (SEQ ID NO:2). |

| ATOM | 1818 | C | LEU | A | 376 | 51.178 | 29.459 | −4.034 | 1.00 | 21.07 |
|---|---|---|---|---|---|---|---|---|---|---|
| ATOM | 1819 | O | LEU | A | 376 | 50.673 | 30.502 | −4.427 | 1.00 | 21.31 |
| ATOM | 1820 | CB | LEU | A | 376 | 49.813 | 27.431 | −3.419 | 1.00 | 17.53 |
| ATOM | 1821 | CG | LEU | A | 376 | 48.740 | 28.369 | −2.841 | 1.00 | 22.09 |
| ATOM | 1822 | CD1 | LEU | A | 376 | 47.443 | 28.281 | −3.659 | 1.00 | 22.32 |
| ATOM | 1823 | CD2 | LEU | A | 376 | 48.496 | 28.093 | −1.384 | 1.00 | 22.98 |
| ATOM | 1824 | N | LEU | A | 377 | 52.148 | 29.427 | −3.133 | 1.00 | 17.22 |
| ATOM | 1825 | CA | LEU | A | 377 | 52.731 | 30.648 | −2.577 | 1.00 | 17.29 |
| ATOM | 1826 | C | LEU | A | 377 | 53.374 | 31.478 | −3.666 | 1.00 | 21.80 |
| ATOM | 1827 | O | LEU | A | 377 | 53.235 | 32.702 | −3.692 | 1.00 | 21.64 |
| ATOM | 1828 | CB | LEU | A | 377 | 53.767 | 30.300 | −1.511 | 1.00 | 17.19 |
| ATOM | 1829 | CG | LEU | A | 377 | 53.185 | 29.601 | −0.293 | 1.00 | 21.25 |
| ATOM | 1830 | CD1 | LEU | A | 377 | 54.306 | 29.246 | 0.674 | 1.00 | 21.48 |
| ATOM | 1831 | CD2 | LEU | A | 377 | 52.177 | 30.542 | 0.358 | 1.00 | 23.66 |
| ATOM | 1832 | N | SER | A | 378 | 54.065 | 30.804 | −4.573 | 1.00 | 19.49 |
| ATOM | 1833 | CA | SER | A | 378 | 54.703 | 31.465 | −5.712 | 1.00 | 20.05 |
| ATOM | 1834 | C | SER | A | 378 | 53.673 | 32.182 | −6.577 | 1.00 | 24.01 |
| ATOM | 1835 | O | SER | A | 378 | 53.873 | 33.326 | −6.960 | 1.00 | 23.85 |
| ATOM | 1836 | CB | SER | A | 378 | 55.450 | 30.445 | −6.573 | 1.00 | 22.91 |
| ATOM | 1837 | OG | SER | A | 378 | 56.534 | 29.890 | −5.863 | 1.00 | 31.49 |
| ATOM | 1838 | N | GLY | A | 379 | 52.590 | 31.485 | −6.911 | 1.00 | 20.76 |
| ATOM | 1839 | CA | GLY | A | 379 | 51.537 | 32.057 | −7.757 | 1.00 | 20.29 |
| ATOM | 1840 | C | GLY | A | 379 | 50.836 | 33.249 | −7.090 | 1.00 | 22.58 |
| ATOM | 1841 | O | GLY | A | 379 | 50.567 | 34.258 | −7.732 | 1.00 | 20.76 |
| ATOM | 1842 | N | LEU | A | 380 | 50.541 | 33.117 | −5.800 | 1.00 | 19.49 |
| ATOM | 1843 | CA | LEU | A | 380 | 49.854 | 34.177 | −5.053 | 1.00 | 19.53 |
| ATOM | 1844 | C | LEU | A | 380 | 50.732 | 35.407 | −4.921 | 1.00 | 23.55 |
| ATOM | 1845 | O | LEU | A | 380 | 50.236 | 36.519 | −4.750 | 1.00 | 22.78 |
| ATOM | 1846 | CB | LEU | A | 380 | 49.488 | 33.678 | −3.641 | 1.00 | 19.60 |
| ATOM | 1847 | CG | LEU | A | 380 | 48.369 | 32.632 | −3.514 | 1.00 | 23.28 |
| ATOM | 1848 | CD1 | LEU | A | 380 | 48.200 | 32.218 | −2.070 | 1.00 | 22.61 |
| ATOM | 1849 | CD2 | LEU | A | 380 | 47.049 | 33.172 | −4.079 | 1.00 | 24.08 |
| ATOM | 1850 | N | LEU | A | 381 | 52.047 | 35.189 | −4.966 | 1.00 | 19.70 |
| ATOM | 1851 | CA | LEU | A | 381 | 53.011 | 36.256 | −4.782 | 1.00 | 19.02 |
| ATOM | 1852 | C | LEU | A | 381 | 53.706 | 36.687 | −6.073 | 1.00 | 23.25 |
| ATOM | 1853 | O | LEU | A | 381 | 54.731 | 37.388 | −6.045 | 1.00 | 22.21 |
| ATOM | 1854 | CB | LEU | A | 381 | 54.023 | 35.886 | −3.681 | 1.00 | 18.72 |
| ATOM | 1855 | CG | LEU | A | 381 | 53.463 | 35.764 | −2.242 | 1.00 | 22.73 |
| ATOM | 1856 | CD1 | LEU | A | 381 | 54.555 | 35.310 | −1.230 | 1.00 | 22.63 |
| ATOM | 1857 | CD2 | LEU | A | 381 | 52.810 | 37.049 | −1.766 | 1.00 | 22.84 |
| ATOM | 1858 | N | ILE | A | 382 | 53.107 | 36.347 | −7.206 | 1.00 | 20.36 |
| ATOM | 1859 | CA | ILE | A | 382 | 53.644 | 36.797 | −8.476 | 1.00 | 19.42 |
| ATOM | 1860 | C | ILE | A | 382 | 53.509 | 38.304 | −8.451 | 1.00 | 24.37 |
| ATOM | 1861 | O | ILE | A | 382 | 52.529 | 38.837 | −7.933 | 1.00 | 23.22 |
| ATOM | 1862 | CB | ILE | A | 382 | 52.882 | 36.190 | −9.675 | 1.00 | 21.63 |
| ATOM | 1863 | CG1 | ILE | A | 382 | 53.586 | 34.906 | −10.156 | 1.00 | 21.37 |
| ATOM | 1864 | CG2 | ILE | A | 382 | 52.760 | 37.199 | −10.805 | 1.00 | 20.91 |
| ATOM | 1865 | CD1 | ILE | A | 382 | 52.648 | 33.911 | −10.819 | 1.00 | 26.06 |
| ATOM | 1866 | N | LYS | A | 383 | 54.528 | 38.997 | −8.939 | 1.00 | 22.93 |
| ATOM | 1867 | CA | LYS | A | 383 | 54.561 | 40.450 | −8.863 | 1.00 | 23.40 |
| ATOM | 1868 | C | LYS | A | 383 | 53.450 | 41.132 | −9.653 | 1.00 | 26.39 |
| ATOM | 1869 | O | LYS | A | 383 | 52.807 | 42.065 | −9.163 | 1.00 | 25.25 |
| ATOM | 1870 | CB | LYS | A | 383 | 55.937 | 40.969 | −9.297 | 1.00 | 26.72 |
| ATOM | 1871 | CG | LYS | A | 383 | 56.883 | 41.284 | −8.140 | 1.00 | 38.64 |
| ATOM | 1872 | CD | LYS | A | 383 | 57.460 | 40.036 | −7.507 | 1.00 | 37.29 |
| ATOM | 1873 | CE | LYS | A | 383 | 58.701 | 40.371 | −6.662 | 1.00 | 29.38 |
| ATOM | 1874 | NZ | LYS | A | 383 | 58.505 | 40.086 | −5.191 | 1.00 | 25.80 |
| ATOM | 1875 | N | ASP | A | 384 | 53.237 | 40.652 | −10.873 | 1.00 | 23.39 |
| ATOM | 1876 | CA | ASP | A | 384 | 52.257 | 41.209 | −11.805 | 1.00 | 22.95 |
| ATOM | 1877 | C | ASP | A | 384 | 50.854 | 40.695 | −11.485 | 1.00 | 27.86 |
| ATOM | 1878 | O | ASP | A | 384 | 50.566 | 39.499 | −11.634 | 1.00 | 28.57 |
| ATOM | 1879 | CB | ASP | A | 384 | 52.665 | 40.832 | −13.243 | 1.00 | 24.53 |
| ATOM | 1880 | CG | ASP | A | 384 | 51.817 | 41.514 | −14.296 | 1.00 | 32.43 |
| ATOM | 1881 | OD1 | ASP | A | 384 | 50.860 | 42.211 | −13.936 | 1.00 | 34.12 |
| ATOM | 1882 | OD2 | ASP | A | 384 | 52.096 | 41.323 | −15.492 | 1.00 | 36.38 |
| ATOM | 1883 | N | PRO | A | 385 | 49.997 | 41.596 | −11.015 | 1.00 | 24.29 |
| ATOM | 1884 | CA | PRO | A | 385 | 48.629 | 41.239 | −10.616 | 1.00 | 24.28 |
| ATOM | 1885 | C | PRO | A | 385 | 47.870 | 40.505 | −11.715 | 1.00 | 29.82 |
| ATOM | 1886 | O | PRO | A | 385 | 47.037 | 39.645 | −11.437 | 1.00 | 29.82 |
| ATOM | 1887 | CB | PRO | A | 385 | 47.967 | 42.608 | −10.342 | 1.00 | 25.57 |
| ATOM | 1888 | CG | PRO | A | 385 | 48.823 | 43.612 | −11.068 | 1.00 | 28.95 |
| ATOM | 1889 | CD | PRO | A | 385 | 50.208 | 43.060 | −11.070 | 1.00 | 24.38 |
| ATOM | 1890 | N | ASN | A | 386 | 48.167 | 40.842 | −12.960 | 1.00 | 27.03 |
| ATOM | 1891 | CA | ASN | A | 386 | 47.492 | 40.218 | −14.095 | 1.00 | 27.38 |
| ATOM | 1892 | C | ASN | A | 386 | 47.879 | 38.773 | −14.283 | 1.00 | 31.65 |
| ATOM | 1893 | O | ASN | A | 386 | 47.088 | 37.977 | −14.780 | 1.00 | 31.96 |
| ATOM | 1894 | CB | ASN | A | 386 | 47.765 | 40.993 | −15.374 | 1.00 | 27.07 |
| ATOM | 1895 | CG | ASN | A | 386 | 47.118 | 42.342 | −15.368 | 1.00 | 41.29 |

TABLE 3-continued

Structural coordinates for AKT3lkd(pT305, pS472) (SEQ ID NO:2).

| ATOM | 1896 | OD1 | ASN | A | 386 | 45.965 | 42.491 | −14.940 | 1.00 | 32.60 |
| ATOM | 1897 | ND2 | ASN | A | 386 | 47.868 | 43.353 | −15.776 | 1.00 | 31.53 |
| ATOM | 1898 | N | LYS | A | 387 | 49.106 | 38.441 | −13.880 | 1.00 | 27.35 |
| ATOM | 1899 | CA | LYS | A | 387 | 49.630 | 37.089 | −14.006 | 1.00 | 26.08 |
| ATOM | 1900 | C | LYS | A | 387 | 49.536 | 36.336 | −12.681 | 1.00 | 27.83 |
| ATOM | 1901 | O | LYS | A | 387 | 49.812 | 35.151 | −12.614 | 1.00 | 27.43 |
| ATOM | 1902 | CB | LYS | A | 387 | 51.092 | 37.140 | −14.462 | 1.00 | 28.24 |
| ATOM | 1903 | CG | LYS | A | 387 | 51.298 | 37.786 | −15.816 | 1.00 | 37.00 |
| ATOM | 1904 | CD | LYS | A | 387 | 52.597 | 37.333 | −16.444 | 1.00 | 46.93 |
| ATOM | 1905 | CE | LYS | A | 387 | 53.073 | 38.324 | −17.497 | 1.00 | 61.29 |
| ATOM | 1906 | NZ | LYS | A | 387 | 53.058 | 37.726 | −18.862 | 1.00 | 73.81 |
| ATOM | 1907 | N | ARG | A | 388 | 49.149 | 37.042 | −11.630 | 1.00 | 23.21 |
| ATOM | 1908 | CA | ARG | A | 388 | 49.063 | 36.458 | −10.293 | 1.00 | 21.28 |
| ATOM | 1909 | C | ARG | A | 388 | 47.956 | 35.425 | −10.191 | 1.00 | 22.89 |
| ATOM | 1910 | O | ARG | A | 388 | 46.912 | 35.566 | −10.811 | 1.00 | 23.12 |
| ATOM | 1911 | CB | ARG | A | 388 | 48.861 | 37.568 | −9.258 | 1.00 | 17.91 |
| ATOM | 1912 | CG | ARG | A | 388 | 48.946 | 37.128 | −7.815 | 1.00 | 18.70 |
| ATOM | 1913 | CD | ARG | A | 388 | 48.915 | 38.331 | −6.864 | 1.00 | 19.61 |
| ATOM | 1914 | NE | ARG | A | 388 | 49.925 | 39.323 | −7.226 | 1.00 | 24.63 |
| ATOM | 1915 | CZ | ARG | A | 388 | 49.760 | 40.637 | −7.134 | 1.00 | 33.54 |
| ATOM | 1916 | NH1 | ARG | A | 388 | 48.620 | 41.148 | −6.685 | 1.00 | 17.97 |
| ATOM | 1917 | NH2 | ARG | A | 388 | 50.737 | 41.443 | −7.500 | 1.00 | 23.43 |
| ATOM | 1918 | N | LEU | A | 389 | 48.181 | 34.390 | −9.393 | 1.00 | 18.03 |
| ATOM | 1919 | CA | LEU | A | 389 | 47.158 | 33.377 | −9.172 | 1.00 | 17.50 |
| ATOM | 1920 | C | LEU | A | 389 | 45.940 | 34.020 | −8.525 | 1.00 | 22.30 |
| ATOM | 1921 | O | LEU | A | 389 | 46.036 | 34.638 | −7.457 | 1.00 | 20.36 |
| ATOM | 1922 | CB | LEU | A | 389 | 47.679 | 32.253 | −8.283 | 1.00 | 16.95 |
| ATOM | 1923 | CG | LEU | A | 389 | 46.713 | 31.087 | −8.117 | 1.00 | 20.64 |
| ATOM | 1924 | CD1 | LEU | A | 389 | 46.643 | 30.259 | −9.405 | 1.00 | 20.82 |
| ATOM | 1925 | CD2 | LEU | A | 389 | 47.111 | 30.218 | −6.931 | 1.00 | 22.35 |
| ATOM | 1926 | N | GLY | A | 390 | 44.795 | 33.870 | −9.172 | 1.00 | 20.28 |
| ATOM | 1927 | CA | GLY | A | 390 | 43.564 | 34.459 | −8.681 | 1.00 | 20.71 |
| ATOM | 1928 | C | GLY | A | 390 | 43.277 | 35.755 | −9.434 | 1.00 | 26.84 |
| ATOM | 1929 | O | GLY | A | 390 | 42.158 | 36.266 | −9.399 | 1.00 | 27.25 |
| ATOM | 1930 | N | GLY | A | 391 | 44.287 | 36.257 | −10.143 | 1.00 | 24.17 |
| ATOM | 1931 | CA | GLY | A | 391 | 44.165 | 37.504 | −10.915 | 1.00 | 24.32 |
| ATOM | 1932 | C | GLY | A | 391 | 43.377 | 37.356 | −12.232 | 1.00 | 28.25 |
| ATOM | 1933 | O | GLY | A | 391 | 42.875 | 38.348 | −12.778 | 1.00 | 28.39 |
| ATOM | 1934 | N | GLY | A | 392 | 43.273 | 36.125 | −12.730 | 1.00 | 23.40 |
| ATOM | 1935 | CA | GLY | A | 392 | 42.533 | 35.846 | −13.963 | 1.00 | 22.30 |
| ATOM | 1936 | C | GLY | A | 392 | 41.040 | 36.119 | −13.775 | 1.00 | 26.07 |
| ATOM | 1937 | O | GLY | A | 392 | 40.585 | 36.413 | −12.667 | 1.00 | 25.06 |
| ATOM | 1938 | N | PRO | A | 393 | 40.275 | 36.020 | −14.857 | 1.00 | 23.04 |
| ATOM | 1939 | CA | PRO | A | 393 | 38.845 | 36.318 | −14.803 | 1.00 | 22.78 |
| ATOM | 1940 | C | PRO | A | 393 | 38.004 | 35.385 | −13.911 | 1.00 | 25.63 |
| ATOM | 1941 | O | PRO | A | 393 | 36.912 | 35.748 | −13.494 | 1.00 | 25.41 |
| ATOM | 1942 | CB | PRO | A | 393 | 38.408 | 36.227 | −16.276 | 1.00 | 24.34 |
| ATOM | 1943 | CG | PRO | A | 393 | 39.554 | 35.525 | −16.979 | 1.00 | 28.41 |
| ATOM | 1944 | CD | PRO | A | 393 | 40.762 | 35.922 | −16.239 | 1.00 | 23.45 |
| ATOM | 1945 | N | ASP | A | 394 | 38.507 | 34.189 | −13.627 | 1.00 | 21.62 |
| ATOM | 1946 | CA | ASP | A | 394 | 37.772 | 33.256 | −12.761 | 1.00 | 20.94 |
| ATOM | 1947 | C | ASP | A | 394 | 38.020 | 33.533 | −11.271 | 1.00 | 24.08 |
| ATOM | 1948 | O | ASP | A | 394 | 37.434 | 32.882 | −10.403 | 1.00 | 23.84 |
| ATOM | 1949 | CB | ASP | A | 394 | 38.079 | 31.801 | −13.107 | 1.00 | 22.69 |
| ATOM | 1950 | CG | ASP | A | 394 | 36.816 | 30.936 | −13.167 | 1.00 | 30.64 |
| ATOM | 1951 | OD1 | ASP | A | 394 | 36.929 | 29.717 | −13.449 | 1.00 | 30.07 |
| ATOM | 1952 | OD2 | ASP | A | 394 | 35.714 | 31.482 | −12.944 | 1.00 | 32.64 |
| ATOM | 1953 | N | ASP | A | 395 | 38.882 | 34.513 | −10.993 | 1.00 | 19.77 |
| ATOM | 1954 | CA | ASP | A | 395 | 39.164 | 34.957 | −9.619 | 1.00 | 19.11 |
| ATOM | 1955 | C | ASP | A | 395 | 39.512 | 33.810 | −8.647 | 1.00 | 23.16 |
| ATOM | 1956 | O | ASP | A | 395 | 40.453 | 33.049 | −8.878 | 1.00 | 23.87 |
| ATOM | 1957 | CB | ASP | A | 395 | 37.970 | 35.756 | −9.092 | 1.00 | 20.40 |
| ATOM | 1958 | CG | ASP | A | 395 | 38.288 | 36.521 | −7.826 | 1.00 | 25.56 |
| ATOM | 1959 | OD1 | ASP | A | 395 | 39.258 | 37.325 | −7.824 | 1.00 | 23.87 |
| ATOM | 1960 | OD2 | ASP | A | 395 | 37.538 | 36.351 | −6.845 | 1.00 | 30.02 |
| ATOM | 1961 | N | ALA | A | 396 | 38.749 | 33.713 | −7.560 | 1.00 | 19.35 |
| ATOM | 1962 | CA | ALA | A | 396 | 38.946 | 32.671 | −6.533 | 1.00 | 19.36 |
| ATOM | 1963 | C | ALA | A | 396 | 38.984 | 31.224 | −7.058 | 1.00 | 23.21 |
| ATOM | 1964 | O | ALA | A | 396 | 39.585 | 30.359 | −6.432 | 1.00 | 23.48 |
| ATOM | 1965 | CB | ALA | A | 396 | 37.886 | 32.797 | −5.437 | 1.00 | 20.04 |
| ATOM | 1966 | N | LYS | A | 397 | 38.316 | 30.953 | −8.175 | 1.00 | 19.59 |
| ATOM | 1967 | CA | LYS | A | 397 | 38.285 | 29.583 | −8.713 | 1.00 | 19.87 |
| ATOM | 1968 | C | LYS | A | 397 | 39.657 | 29.077 | −9.148 | 1.00 | 23.20 |
| ATOM | 1969 | O | LYS | A | 397 | 39.876 | 27.878 | −9.217 | 1.00 | 22.19 |
| ATOM | 1970 | CB | LYS | A | 397 | 37.275 | 29.454 | −9.875 | 1.00 | 22.33 |
| ATOM | 1971 | CG | LYS | A | 397 | 35.828 | 29.258 | −9.433 | 1.00 | 29.99 |
| ATOM | 1972 | CD | LYS | A | 397 | 35.172 | 30.573 | −9.164 | 1.00 | 37.38 |
| ATOM | 1973 | CE | LYS | A | 397 | 34.056 | 30.442 | −8.154 | 1.00 | 49.14 |

TABLE 3-continued

Structural coordinates for AKT3lkd(pT305, pS472) (SEQ ID NO:2).

| ATOM | 1974 | NZ | LYS | A | 397 | 33.389 | 31.756 | −7.923 | 1.00 | 55.01 |
|---|---|---|---|---|---|---|---|---|---|---|
| ATOM | 1975 | N | GLU | A | 398 | 40.557 | 29.998 | −9.491 | 1.00 | 20.53 |
| ATOM | 1976 | CA | GLU | A | 398 | 41.908 | 29.625 | −9.907 | 1.00 | 20.88 |
| ATOM | 1977 | C | GLU | A | 398 | 42.612 | 29.009 | −8.705 | 1.00 | 25.02 |
| ATOM | 1978 | O | GLU | A | 398 | 43.312 | 28.008 | −8.831 | 1.00 | 25.28 |
| ATOM | 1979 | CB | GLU | A | 398 | 42.698 | 30.857 | −10.388 | 1.00 | 22.43 |
| ATOM | 1980 | CG | GLU | A | 398 | 42.040 | 31.635 | −11.506 | 1.00 | 33.85 |
| ATOM | 1981 | CD | GLU | A | 398 | 43.023 | 32.544 | −12.249 | 1.00 | 47.11 |
| ATOM | 1982 | OE1 | GLU | A | 398 | 44.010 | 32.990 | −11.631 | 1.00 | 37.08 |
| ATOM | 1983 | OE2 | GLU | A | 398 | 42.793 | 32.831 | −13.440 | 1.00 | 34.41 |
| ATOM | 1984 | N | ILE | A | 399 | 42.415 | 29.624 | −7.537 | 1.00 | 20.60 |
| ATOM | 1985 | CA | ILE | A | 399 | 42.989 | 29.124 | −6.296 | 1.00 | 19.48 |
| ATOM | 1986 | C | ILE | A | 399 | 42.266 | 27.852 | −5.856 | 1.00 | 22.88 |
| ATOM | 1987 | O | ILE | A | 399 | 42.897 | 26.869 | −5.491 | 1.00 | 23.86 |
| ATOM | 1988 | CB | ILE | A | 399 | 42.946 | 30.195 | −5.162 | 1.00 | 21.82 |
| ATOM | 1989 | CG1 | ILE | A | 399 | 43.943 | 31.325 | −5.455 | 1.00 | 22.12 |
| ATOM | 1990 | CG2 | ILE | A | 399 | 43.270 | 29.555 | −3.818 | 1.00 | 21.08 |
| ATOM | 1991 | CD1 | ILE | A | 399 | 43.312 | 32.634 | −5.848 | 1.00 | 25.42 |
| ATOM | 1992 | N | MET | A | 400 | 40.944 | 27.859 | −5.912 | 1.00 | 18.62 |
| ATOM | 1993 | CA | MET | A | 400 | 40.173 | 26.654 | −5.530 | 1.00 | 17.82 |
| ATOM | 1994 | C | MET | A | 400 | 40.592 | 25.423 | −6.348 | 1.00 | 21.08 |
| ATOM | 1995 | O | MET | A | 400 | 40.551 | 24.298 | −5.855 | 1.00 | 20.92 |
| ATOM | 1996 | CB | MET | A | 400 | 38.665 | 26.891 | −5.663 | 1.00 | 19.30 |
| ATOM | 1997 | CG | MET | A | 400 | 38.175 | 28.184 | −5.030 | 1.00 | 22.31 |
| ATOM | 1998 | SD | MET | A | 400 | 36.367 | 28.358 | −5.073 | 1.00 | 26.17 |
| ATOM | 1999 | CE | MET | A | 400 | 36.119 | 29.706 | −3.904 | 1.00 | 23.16 |
| ATOM | 2000 | N | ARG | A | 401 | 40.978 | 25.640 | −7.597 | 1.00 | 18.25 |
| ATOM | 2001 | CA | ARG | A | 401 | 41.399 | 24.532 | −8.476 | 1.00 | 19.00 |
| ATOM | 2002 | C | ARG | A | 401 | 42.892 | 24.189 | −8.356 | 1.00 | 23.58 |
| ATOM | 2003 | O | ARG | A | 401 | 43.344 | 23.202 | −8.938 | 1.00 | 23.95 |
| ATOM | 2004 | CB | ARG | A | 401 | 41.070 | 24.837 | −9.939 | 1.00 | 20.04 |
| ATOM | 2005 | CG | ARG | A | 401 | 39.589 | 24.819 | −10.273 | 1.00 | 27.04 |
| ATOM | 2006 | CD | ARG | A | 401 | 39.375 | 24.929 | −11.777 | 1.00 | 29.73 |
| ATOM | 2007 | NE | ARG | A | 401 | 39.860 | 26.196 | −12.324 | 1.00 | 24.17 |
| ATOM | 2008 | CZ | ARG | A | 401 | 39.079 | 27.234 | −12.604 | 1.00 | 33.67 |
| ATOM | 2009 | NH1 | ARG | A | 401 | 37.777 | 27.161 | −12.403 | 1.00 | 23.07 |
| ATOM | 2010 | NH2 | ARG | A | 401 | 39.597 | 28.334 | −13.106 | 1.00 | 22.89 |
| ATOM | 2011 | N | HIS | A | 402 | 43.656 | 25.007 | −7.623 | 1.00 | 18.92 |
| ATOM | 2012 | CA | HIS | A | 402 | 45.089 | 24.751 | −7.448 | 1.00 | 17.87 |
| ATOM | 2013 | C | HIS | A | 402 | 45.319 | 23.418 | −6.745 | 1.00 | 21.81 |
| ATOM | 2014 | O | HIS | A | 402 | 44.536 | 23.020 | −5.879 | 1.00 | 20.68 |
| ATOM | 2015 | CB | HIS | A | 402 | 45.788 | 25.905 | −6.675 | 1.00 | 17.79 |
| ATOM | 2016 | CG | HIS | A | 402 | 47.289 | 25.863 | −6.758 | 1.00 | 19.99 |
| ATOM | 2017 | ND1 | HIS | A | 402 | 48.067 | 25.107 | −5.898 | 1.00 | 20.85 |
| ATOM | 2018 | CD2 | HIS | A | 402 | 48.150 | 26.449 | −7.625 | 1.00 | 20.31 |
| ATOM | 2019 | CE1 | HIS | A | 402 | 49.341 | 25.256 | −6.215 | 1.00 | 19.47 |
| ATOM | 2020 | NE2 | HIS | A | 402 | 49.419 | 26.058 | −7.263 | 1.00 | 19.81 |
| ATOM | 2021 | N | SER | A | 403 | 46.385 | 22.720 | −7.130 | 1.00 | 19.82 |
| ATOM | 2022 | CA | SER | A | 403 | 46.676 | 21.387 | −6.555 | 1.00 | 20.00 |
| ATOM | 2023 | C | SER | A | 403 | 46.863 | 21.365 | −5.038 | 1.00 | 22.70 |
| ATOM | 2024 | O | SER | A | 403 | 46.604 | 20.353 | −4.391 | 1.00 | 23.85 |
| ATOM | 2025 | CB | SER | A | 403 | 47.860 | 20.724 | −7.263 | 1.00 | 24.59 |
| ATOM | 2026 | OG | SER | A | 403 | 48.869 | 21.672 | −7.536 | 1.00 | 37.92 |
| ATOM | 2027 | N | PHE | A | 404 | 47.301 | 22.476 | −4.462 | 1.00 | 17.65 |
| ATOM | 2028 | CA | PHE | A | 404 | 47.452 | 22.546 | −3.016 | 1.00 | 16.64 |
| ATOM | 2029 | C | PHE | A | 404 | 46.093 | 22.302 | −2.304 | 1.00 | 20.73 |
| ATOM | 2030 | O | PHE | A | 404 | 46.060 | 21.906 | −1.129 | 1.00 | 21.04 |
| ATOM | 2031 | CB | PHE | A | 404 | 48.042 | 23.895 | −2.583 | 1.00 | 18.10 |
| ATOM | 2032 | CG | PHE | A | 404 | 48.225 | 24.028 | −1.075 | 1.00 | 19.14 |
| ATOM | 2033 | CD1 | PHE | A | 404 | 49.358 | 23.511 | −0.443 | 1.00 | 22.08 |
| ATOM | 2034 | CD2 | PHE | A | 404 | 47.259 | 24.636 | −0.297 | 1.00 | 20.14 |
| ATOM | 2035 | CE1 | PHE | A | 404 | 49.524 | 23.629 | 0.935 | 1.00 | 22.45 |
| ATOM | 2036 | CE2 | PHE | A | 404 | 47.417 | 24.749 | 1.079 | 1.00 | 22.75 |
| ATOM | 2037 | CZ | PHE | A | 404 | 48.547 | 24.235 | 1.694 | 1.00 | 20.80 |
| ATOM | 2038 | N | PHE | A | 405 | 44.987 | 22.556 | −3.010 | 1.00 | 16.61 |
| ATOM | 2039 | CA | PHE | A | 405 | 43.635 | 22.358 | −2.441 | 1.00 | 16.31 |
| ATOM | 2040 | C | PHE | A | 405 | 42.903 | 21.223 | −3.148 | 1.00 | 20.87 |
| ATOM | 2041 | O | PHE | A | 405 | 41.671 | 21.145 | −3.114 | 1.00 | 21.22 |
| ATOM | 2042 | CB | PHE | A | 405 | 42.788 | 23.633 | −2.574 | 1.00 | 17.75 |
| ATOM | 2043 | CG | PHE | A | 405 | 43.315 | 24.808 | −1.793 | 1.00 | 18.71 |
| ATOM | 2044 | CD1 | PHE | A | 405 | 43.132 | 24.883 | −0.410 | 1.00 | 21.06 |
| ATOM | 2045 | CD2 | PHE | A | 405 | 43.935 | 25.874 | −2.450 | 1.00 | 19.71 |
| ATOM | 2046 | CE1 | PHE | A | 405 | 43.588 | 25.991 | 0.314 | 1.00 | 21.69 |
| ATOM | 2047 | CE2 | PHE | A | 405 | 44.393 | 26.978 | −1.740 | 1.00 | 22.37 |
| ATOM | 2048 | CZ | PHE | A | 405 | 44.205 | 27.046 | −0.349 | 1.00 | 20.30 |
| ATOM | 2049 | N | SER | A | 406 | 43.656 | 20.357 | −3.806 | 1.00 | 17.77 |
| ATOM | 2050 | CA | SER | A | 406 | 43.066 | 19.245 | −4.553 | 1.00 | 18.27 |
| ATOM | 2051 | C | SER | A | 406 | 42.136 | 18.305 | −3.753 | 1.00 | 22.95 |

TABLE 3-continued

Structural coordinates for AKT3lkd(pT305, pS472) (SEQ ID NO:2).

| ATOM | 2052 | O   | SER | A | 406 | 41.318 | 17.622 | −4.334 | 1.00 | 24.03 |
| ATOM | 2053 | CB  | SER | A | 406 | 44.138 | 18.447 | −5.291 | 1.00 | 20.59 |
| ATOM | 2054 | OG  | SER | A | 406 | 44.805 | 17.594 | −4.404 | 1.00 | 31.28 |
| ATOM | 2055 | N   | GLY | A | 407 | 42.245 | 18.287 | −2.436 | 1.00 | 19.09 |
| ATOM | 2056 | CA  | GLY | A | 407 | 41.370 | 17.415 | −1.644 | 1.00 | 19.28 |
| ATOM | 2057 | C   | GLY | A | 407 | 40.206 | 18.172 | −0.979 | 1.00 | 23.69 |
| ATOM | 2058 | O   | GLY | A | 407 | 39.494 | 17.620 | −0.142 | 1.00 | 23.93 |
| ATOM | 2059 | N   | VAL | A | 408 | 40.012 | 19.430 | −1.359 | 1.00 | 19.36 |
| ATOM | 2060 | CA  | VAL | A | 408 | 38.996 | 20.251 | −0.729 | 1.00 | 18.25 |
| ATOM | 2061 | C   | VAL | A | 408 | 37.653 | 20.364 | −1.437 | 1.00 | 21.39 |
| ATOM | 2062 | O   | VAL | A | 408 | 37.588 | 20.685 | −2.611 | 1.00 | 20.52 |
| ATOM | 2063 | CB  | VAL | A | 408 | 39.537 | 21.657 | −0.409 | 1.00 | 21.79 |
| ATOM | 2064 | CG1 | VAL | A | 408 | 38.426 | 22.546 | 0.147  | 1.00 | 21.39 |
| ATOM | 2065 | CG2 | VAL | A | 408 | 40.707 | 21.566 | 0.570  | 1.00 | 21.46 |
| ATOM | 2066 | N   | ASN | A | 409 | 36.577 | 20.129 | −0.687 | 1.00 | 18.99 |
| ATOM | 2067 | CA  | ASN | A | 409 | 35.223 | 20.331 | −1.191 | 1.00 | 18.97 |
| ATOM | 2068 | C   | ASN | A | 409 | 34.836 | 21.734 | −0.739 | 1.00 | 21.95 |
| ATOM | 2069 | O   | ASN | A | 409 | 34.764 | 22.015 | 0.458  | 1.00 | 21.19 |
| ATOM | 2070 | CB  | ASN | A | 409 | 34.244 | 19.297 | −0.615 | 1.00 | 20.47 |
| ATOM | 2071 | CG  | ASN | A | 409 | 32.804 | 19.504 | −1.120 | 1.00 | 31.89 |
| ATOM | 2072 | OD1 | ASN | A | 409 | 32.181 | 20.521 | −0.843 | 1.00 | 20.89 |
| ATOM | 2073 | ND2 | ASN | A | 409 | 32.299 | 18.546 | −1.884 | 1.00 | 23.48 |
| ATOM | 2074 | N   | TRP | A | 410 | 34.648 | 22.619 | −1.702 | 1.00 | 18.92 |
| ATOM | 2075 | CA  | TRP | A | 410 | 34.385 | 24.022 | −1.431 | 1.00 | 18.67 |
| ATOM | 2076 | C   | TRP | A | 410 | 33.011 | 24.392 | −0.863 | 1.00 | 25.15 |
| ATOM | 2077 | O   | TRP | A | 410 | 32.860 | 25.441 | −0.231 | 1.00 | 24.00 |
| ATOM | 2078 | CB  | TRP | A | 410 | 34.771 | 24.865 | −2.628 | 1.00 | 16.68 |
| ATOM | 2079 | CG  | TRP | A | 410 | 36.248 | 24.832 | −2.866 | 1.00 | 17.40 |
| ATOM | 2080 | CD1 | TRP | A | 410 | 36.921 | 24.005 | −3.722 | 1.00 | 20.26 |
| ATOM | 2081 | CD2 | TRP | A | 410 | 37.248 | 25.566 | −2.147 | 1.00 | 17.29 |
| ATOM | 2082 | NE1 | TRP | A | 410 | 38.276 | 24.204 | −3.610 | 1.00 | 19.81 |
| ATOM | 2083 | CE2 | TRP | A | 410 | 38.507 | 25.164 | −2.655 | 1.00 | 21.07 |
| ATOM | 2084 | CE3 | TRP | A | 410 | 37.202 | 26.562 | −1.154 | 1.00 | 18.58 |
| ATOM | 2085 | CZ2 | TRP | A | 410 | 39.711 | 25.723 | −2.208 | 1.00 | 19.97 |
| ATOM | 2086 | CZ3 | TRP | A | 410 | 38.399 | 27.094 | −0.690 | 1.00 | 20.00 |
| ATOM | 2087 | CH2 | TRP | A | 410 | 39.641 | 26.668 | −1.216 | 1.00 | 20.44 |
| ATOM | 2088 | N   | GLN | A | 411 | 32.027 | 23.513 | −1.045 | 1.00 | 23.66 |
| ATOM | 2089 | CA  | GLN | A | 411 | 30.702 | 23.733 | −0.464 | 1.00 | 23.18 |
| ATOM | 2090 | C   | GLN | A | 411 | 30.840 | 23.432 | 1.023  | 1.00 | 24.99 |
| ATOM | 2091 | O   | GLN | A | 411 | 30.339 | 24.168 | 1.872  | 1.00 | 24.61 |
| ATOM | 2092 | CB  | GLN | A | 411 | 29.669 | 22.787 | −1.108 | 1.00 | 24.71 |
| ATOM | 2093 | CG  | GLN | A | 411 | 28.213 | 22.985 | −0.610 | 1.00 | 37.69 |
| ATOM | 2094 | CD  | GLN | A | 411 | 27.803 | 24.454 | −0.519 | 1.00 | 52.75 |
| ATOM | 2095 | OE1 | GLN | A | 411 | 27.277 | 24.902 | 0.504  | 1.00 | 50.33 |
| ATOM | 2096 | NE2 | GLN | A | 411 | 28.039 | 25.207 | −1.589 | 1.00 | 36.48 |
| ATOM | 2097 | N   | ASP | A | 412 | 31.596 | 22.378 | 1.325  | 1.00 | 20.47 |
| ATOM | 2098 | CA  | ASP | A | 412 | 31.865 | 21.967 | 2.701  | 1.00 | 20.00 |
| ATOM | 2099 | C   | ASP | A | 412 | 32.633 | 23.046 | 3.486  | 1.00 | 24.15 |
| ATOM | 2100 | O   | ASP | A | 412 | 32.499 | 23.147 | 4.712  | 1.00 | 22.96 |
| ATOM | 2101 | CB  | ASP | A | 412 | 32.688 | 20.692 | 2.704  | 1.00 | 21.69 |
| ATOM | 2102 | CG  | ASP | A | 412 | 31.840 | 19.444 | 2.547  | 1.00 | 26.07 |
| ATOM | 2103 | OD1 | ASP | A | 412 | 30.607 | 19.574 | 2.390  | 1.00 | 25.09 |
| ATOM | 2104 | OD2 | ASP | A | 412 | 32.416 | 18.333 | 2.615  | 1.00 | 25.95 |
| ATOM | 2105 | N   | VAL | A | 413 | 33.485 | 23.801 | 2.781  | 1.00 | 20.34 |
| ATOM | 2106 | CA  | VAL | A | 413 | 34.272 | 24.858 | 3.398  | 1.00 | 19.90 |
| ATOM | 2107 | C   | VAL | A | 413 | 33.341 | 25.971 | 3.878  | 1.00 | 24.54 |
| ATOM | 2108 | O   | VAL | A | 413 | 33.452 | 26.456 | 5.010  | 1.00 | 22.82 |
| ATOM | 2109 | CB  | VAL | A | 413 | 35.337 | 25.456 | 2.397  | 1.00 | 22.90 |
| ATOM | 2110 | CG1 | VAL | A | 413 | 35.925 | 26.734 | 2.946  | 1.00 | 21.95 |
| ATOM | 2111 | CG2 | VAL | A | 413 | 36.464 | 24.436 | 2.127  | 1.00 | 22.70 |
| ATOM | 2112 | N   | TYR | A | 414 | 32.424 | 26.363 | 2.998  | 1.00 | 22.54 |
| ATOM | 2113 | CA  | TYR | A | 414 | 31.432 | 27.389 | 3.293  | 1.00 | 22.58 |
| ATOM | 2114 | C   | TYR | A | 414 | 30.516 | 26.960 | 4.469  | 1.00 | 27.48 |
| ATOM | 2115 | O   | TYR | A | 414 | 30.303 | 27.723 | 5.404  | 1.00 | 27.68 |
| ATOM | 2116 | CB  | TYR | A | 414 | 30.592 | 27.666 | 2.033  | 1.00 | 23.70 |
| ATOM | 2117 | CG  | TYR | A | 414 | 29.597 | 28.786 | 2.203  | 1.00 | 25.18 |
| ATOM | 2118 | CD1 | TYR | A | 414 | 28.290 | 28.526 | 2.612  | 1.00 | 27.64 |
| ATOM | 2119 | CD2 | TYR | A | 414 | 29.971 | 30.106 | 2.007  | 1.00 | 25.71 |
| ATOM | 2120 | CE1 | TYR | A | 414 | 27.375 | 29.564 | 2.802  | 1.00 | 29.40 |
| ATOM | 2121 | CE2 | TYR | A | 414 | 29.063 | 31.155 | 2.195  | 1.00 | 26.56 |
| ATOM | 2122 | CZ  | TYR | A | 414 | 27.775 | 30.872 | 2.597  | 1.00 | 34.61 |
| ATOM | 2123 | OH  | TYR | A | 414 | 26.886 | 31.887 | 2.788  | 1.00 | 36.78 |
| ATOM | 2124 | N   | ASP | A | 415 | 30.018 | 25.722 | 4.416  | 1.00 | 23.95 |
| ATOM | 2125 | CA  | ASP | A | 415 | 29.117 | 25.178 | 5.449  | 1.00 | 23.40 |
| ATOM | 2126 | C   | ASP | A | 415 | 29.858 | 24.789 | 6.725  | 1.00 | 28.99 |
| ATOM | 2127 | O   | ASP | A | 415 | 29.285 | 24.153 | 7.625  | 1.00 | 28.88 |
| ATOM | 2128 | CB  | ASP | A | 415 | 28.363 | 23.951 | 4.906  | 1.00 | 24.72 |
| ATOM | 2129 | CG  | ASP | A | 415 | 27.554 | 24.265 | 3.653  | 1.00 | 27.81 |

TABLE 3-continued

Structural coordinates for AKT3lkd(pT305, pS472) (SEQ ID NO:2).

| ATOM | 2130 | OD1 | ASP | A | 415 | 26.888 | 25.305 | 3.624 | 1.00 | 28.85 |
|---|---|---|---|---|---|---|---|---|---|---|
| ATOM | 2131 | OD2 | ASP | A | 415 | 27.594 | 23.478 | 2.703 | 1.00 | 32.25 |
| ATOM | 2132 | N | LYS | A | 416 | 31.138 | 25.140 | 6.796 | 1.00 | 25.82 |
| ATOM | 2133 | CA | LYS | A | 416 | 31.932 | 24.857 | 7.984 | 1.00 | 25.78 |
| ATOM | 2134 | C | LYS | A | 416 | 31.910 | 23.369 | 8.326 | 1.00 | 30.59 |
| ATOM | 2135 | O | LYS | A | 416 | 31.668 | 22.980 | 9.478 | 1.00 | 28.99 |
| ATOM | 2136 | CB | LYS | A | 416 | 31.422 | 25.693 | 9.170 | 1.00 | 27.91 |
| ATOM | 2137 | CG | LYS | A | 416 | 31.708 | 27.194 | 9.040 | 1.00 | 40.01 |
| ATOM | 2138 | CD | LYS | A | 416 | 30.790 | 28.033 | 9.923 | 1.00 | 46.22 |
| ATOM | 2139 | CE | LYS | A | 416 | 31.340 | 28.158 | 11.330 | 1.00 | 55.89 |
| ATOM | 2140 | NZ | LYS | A | 416 | 30.409 | 28.897 | 12.238 | 1.00 | 63.84 |
| ATOM | 2141 | N | LYS | A | 417 | 32.193 | 22.541 | 7.322 | 1.00 | 28.76 |
| ATOM | 2142 | CA | LYS | A | 417 | 32.188 | 21.097 | 7.495 | 1.00 | 28.59 |
| ATOM | 2143 | C | LYS | A | 417 | 33.567 | 20.446 | 7.534 | 1.00 | 34.43 |
| ATOM | 2144 | O | LYS | A | 417 | 33.680 | 19.243 | 7.738 | 1.00 | 35.92 |
| ATOM | 2145 | CB | LYS | A | 417 | 31.289 | 20.435 | 6.464 | 1.00 | 30.12 |
| ATOM | 2146 | CG | LYS | A | 417 | 29.804 | 20.716 | 6.691 | 1.00 | 26.57 |
| ATOM | 2147 | CD | LYS | A | 417 | 28.938 | 19.651 | 6.055 | 1.00 | 30.94 |
| ATOM | 2148 | CE | LYS | A | 417 | 27.507 | 20.129 | 5.862 | 1.00 | 41.38 |
| ATOM | 2149 | NZ | LYS | A | 417 | 26.895 | 19.537 | 4.634 | 1.00 | 52.18 |
| ATOM | 2150 | N | LEU | A | 418 | 34.617 | 21.235 | 7.370 | 1.00 | 30.81 |
| ATOM | 2151 | CA | LEU | A | 418 | 35.971 | 20.698 | 7.516 | 1.00 | 30.40 |
| ATOM | 2152 | C | LEU | A | 418 | 36.263 | 20.721 | 9.009 | 1.00 | 32.57 |
| ATOM | 2153 | O | LEU | A | 418 | 35.903 | 21.673 | 9.700 | 1.00 | 30.49 |
| ATOM | 2154 | CB | LEU | A | 418 | 37.013 | 21.590 | 6.817 | 1.00 | 30.56 |
| ATOM | 2155 | CG | LEU | A | 418 | 36.943 | 21.919 | 5.325 | 1.00 | 34.75 |
| ATOM | 2156 | CD1 | LEU | A | 418 | 38.198 | 22.702 | 4.931 | 1.00 | 34.75 |
| ATOM | 2157 | CD2 | LEU | A | 418 | 36.802 | 20.680 | 4.476 | 1.00 | 35.45 |
| ATOM | 2158 | N | VAL | A | 419 | 36.932 | 19.693 | 9.503 | 1.00 | 29.95 |
| ATOM | 2159 | CA | VAL | A | 419 | 37.292 | 19.652 | 10.908 | 1.00 | 30.10 |
| ATOM | 2160 | C | VAL | A | 419 | 38.493 | 20.552 | 11.156 | 1.00 | 33.89 |
| ATOM | 2161 | O | VAL | A | 419 | 39.543 | 20.376 | 10.540 | 1.00 | 33.52 |
| ATOM | 2162 | CB | VAL | A | 419 | 37.637 | 18.217 | 11.361 | 1.00 | 34.21 |
| ATOM | 2163 | CG1 | VAL | A | 419 | 37.752 | 18.153 | 12.900 | 1.00 | 33.78 |
| ATOM | 2164 | CG2 | VAL | A | 419 | 36.590 | 17.232 | 10.841 | 1.00 | 33.91 |
| ATOM | 2165 | N | PRO | A | 420 | 38.335 | 21.521 | 12.051 | 1.00 | 31.13 |
| ATOM | 2166 | CA | PRO | A | 420 | 39.423 | 22.442 | 12.371 | 1.00 | 30.61 |
| ATOM | 2167 | C | PRO | A | 420 | 40.572 | 21.676 | 12.993 | 1.00 | 34.77 |
| ATOM | 2168 | O | PRO | A | 420 | 40.375 | 20.893 | 13.903 | 1.00 | 34.32 |
| ATOM | 2169 | CB | PRO | A | 420 | 38.794 | 23.386 | 13.398 | 1.00 | 31.74 |
| ATOM | 2170 | CG | PRO | A | 420 | 37.345 | 23.346 | 13.089 | 1.00 | 36.44 |
| ATOM | 2171 | CD | PRO | A | 420 | 37.071 | 21.930 | 12.686 | 1.00 | 31.80 |
| ATOM | 2172 | N | PRO | A | 421 | 41.775 | 21.896 | 12.481 | 1.00 | 32.00 |
| ATOM | 2173 | CA | PRO | A | 421 | 42.953 | 21.197 | 12.985 | 1.00 | 30.89 |
| ATOM | 2174 | C | PRO | A | 421 | 43.264 | 21.596 | 14.427 | 1.00 | 34.29 |
| ATOM | 2175 | O | PRO | A | 421 | 43.860 | 20.827 | 15.172 | 1.00 | 33.60 |
| ATOM | 2176 | CB | PRO | A | 421 | 44.065 | 21.639 | 12.027 | 1.00 | 32.37 |
| ATOM | 2177 | CG | PRO | A | 421 | 43.583 | 22.919 | 11.446 | 1.00 | 37.27 |
| ATOM | 2178 | CD | PRO | A | 421 | 42.097 | 22.790 | 11.357 | 1.00 | 32.59 |
| ATOM | 2179 | N | PHE | A | 422 | 42.817 | 22.781 | 14.830 | 1.00 | 30.80 |
| ATOM | 2180 | CA | PHE | A | 422 | 43.031 | 23.243 | 16.199 | 1.00 | 30.38 |
| ATOM | 2181 | C | PHE | A | 422 | 41.757 | 23.819 | 16.819 | 1.00 | 35.19 |
| ATOM | 2182 | O | PHE | A | 422 | 41.120 | 24.704 | 16.251 | 1.00 | 34.70 |
| ATOM | 2183 | CB | PHE | A | 422 | 44.161 | 24.278 | 16.260 | 1.00 | 31.89 |
| ATOM | 2184 | CG | PHE | A | 422 | 44.266 | 24.979 | 17.588 | 1.00 | 33.06 |
| ATOM | 2185 | CD1 | PHE | A | 422 | 44.965 | 24.396 | 18.646 | 1.00 | 35.78 |
| ATOM | 2186 | CD2 | PHE | A | 422 | 43.642 | 26.208 | 17.792 | 1.00 | 34.77 |
| ATOM | 2187 | CE1 | PHE | A | 422 | 45.049 | 25.033 | 19.881 | 1.00 | 36.48 |
| ATOM | 2188 | CE2 | PHE | A | 422 | 43.726 | 26.857 | 19.021 | 1.00 | 37.55 |
| ATOM | 2189 | CZ | PHE | A | 422 | 44.424 | 26.265 | 20.071 | 1.00 | 35.87 |
| ATOM | 2190 | N | LYS | A | 423 | 41.392 | 23.316 | 17.991 | 1.00 | 32.61 |
| ATOM | 2191 | CA | LYS | A | 423 | 40.209 | 23.808 | 18.678 | 1.00 | 33.21 |
| ATOM | 2192 | C | LYS | A | 423 | 40.628 | 24.612 | 19.903 | 1.00 | 38.13 |
| ATOM | 2193 | O | LYS | A | 423 | 41.217 | 24.068 | 20.830 | 1.00 | 37.85 |
| ATOM | 2194 | CB | LYS | A | 423 | 39.303 | 22.643 | 19.087 | 1.00 | 35.86 |
| ATOM | 2195 | CG | LYS | A | 423 | 39.111 | 21.600 | 17.993 | 1.00 | 46.84 |
| ATOM | 2196 | CD | LYS | A | 423 | 38.103 | 22.068 | 16.948 | 1.00 | 51.59 |
| ATOM | 2197 | CE | LYS | A | 423 | 36.755 | 22.381 | 17.585 | 1.00 | 50.52 |
| ATOM | 2198 | NZ | LYS | A | 423 | 35.632 | 22.200 | 16.636 | 1.00 | 49.46 |
| ATOM | 2199 | N | PRO | A | 424 | 40.370 | 25.918 | 19.879 | 1.00 | 35.59 |
| ATOM | 2200 | CA | PRO | A | 424 | 40.746 | 26.781 | 21.004 | 1.00 | 35.54 |
| ATOM | 2201 | C | PRO | A | 424 | 40.204 | 26.200 | 22.320 | 1.00 | 41.14 |
| ATOM | 2202 | O | PRO | A | 424 | 39.065 | 25.718 | 22.387 | 1.00 | 38.95 |
| ATOM | 2203 | CB | PRO | A | 424 | 40.053 | 28.115 | 20.675 | 1.00 | 36.77 |
| ATOM | 2204 | CG | PRO | A | 424 | 39.790 | 28.058 | 19.195 | 1.00 | 40.44 |
| ATOM | 2205 | CD | PRO | A | 424 | 39.525 | 26.624 | 18.899 | 1.00 | 35.77 |
| ATOM | 2206 | N | GLN | A | 425 | 41.038 | 26.234 | 23.355 | 1.00 | 40.66 |
| ATOM | 2207 | CA | GLN | A | 425 | 40.667 | 25.688 | 24.658 | 1.00 | 41.84 |

TABLE 3-continued

Structural coordinates for AKT3lkd(pT305, pS472) (SEQ ID NO:2).

| ATOM | 2208 | C   | GLN | A | 425 | 39.820 | 26.656 | 25.492 | 1.00 | 46.99 |
|------|------|-----|-----|---|-----|--------|--------|--------|------|-------|
| ATOM | 2209 | O   | GLN | A | 425 | 40.255 | 27.119 | 26.542 | 1.00 | 46.88 |
| ATOM | 2210 | CB  | GLN | A | 425 | 41.925 | 25.289 | 25.431 | 1.00 | 43.49 |
| ATOM | 2211 | CG  | GLN | A | 425 | 42.612 | 24.040 | 24.890 | 1.00 | 58.09 |
| ATOM | 2212 | CD  | GLN | A | 425 | 41.635 | 22.910 | 24.623 | 1.00 | 79.52 |
| ATOM | 2213 | OE1 | GLN | A | 425 | 40.735 | 23.032 | 23.791 | 1.00 | 73.68 |
| ATOM | 2214 | NE2 | GLN | A | 425 | 41.803 | 21.802 | 25.341 | 1.00 | 75.05 |
| ATOM | 2215 | N   | VAL | A | 426 | 38.610 | 26.943 | 25.026 | 1.00 | 44.06 |
| ATOM | 2216 | CA  | VAL | A | 426 | 37.723 | 27.853 | 25.732 | 1.00 | 44.46 |
| ATOM | 2217 | C   | VAL | A | 426 | 36.537 | 27.121 | 26.337 | 1.00 | 50.21 |
| ATOM | 2218 | O   | VAL | A | 426 | 35.943 | 26.247 | 25.708 | 1.00 | 49.82 |
| ATOM | 2219 | CB  | VAL | A | 426 | 37.221 | 29.005 | 24.826 | 1.00 | 48.12 |
| ATOM | 2220 | CG1 | VAL | A | 426 | 38.332 | 30.018 | 24.588 | 1.00 | 47.61 |
| ATOM | 2221 | CG2 | VAL | A | 426 | 36.689 | 28.459 | 23.508 | 1.00 | 47.93 |
| ATOM | 2222 | N   | THR | A | 427 | 36.190 | 27.509 | 27.557 | 1.00 | 48.03 |
| ATOM | 2223 | CA  | THR | A | 427 | 35.109 | 26.888 | 28.310 | 1.00 | 48.27 |
| ATOM | 2224 | C   | THR | A | 427 | 33.707 | 27.312 | 27.860 | 1.00 | 52.09 |
| ATOM | 2225 | O   | THR | A | 427 | 32.734 | 26.579 | 28.058 | 1.00 | 51.94 |
| ATOM | 2226 | CB  | THR | A | 427 | 35.270 | 27.183 | 29.811 | 1.00 | 57.86 |
| ATOM | 2227 | OG1 | THR | A | 427 | 36.147 | 26.211 | 30.395 | 1.00 | 58.06 |
| ATOM | 2228 | CG2 | THR | A | 427 | 33.925 | 27.149 | 30.513 | 1.00 | 56.57 |
| ATOM | 2229 | N   | SER | A | 428 | 33.602 | 28.495 | 27.268 | 1.00 | 47.93 |
| ATOM | 2230 | CA  | SER | A | 428 | 32.312 | 28.990 | 26.811 | 1.00 | 47.43 |
| ATOM | 2231 | C   | SER | A | 428 | 32.455 | 29.926 | 25.624 | 1.00 | 51.01 |
| ATOM | 2232 | O   | SER | A | 428 | 33.563 | 30.182 | 25.148 | 1.00 | 51.18 |
| ATOM | 2233 | CB  | SER | A | 428 | 31.588 | 29.710 | 27.944 | 1.00 | 50.83 |
| ATOM | 2234 | OG  | SER | A | 428 | 32.369 | 30.782 | 28.443 | 1.00 | 59.82 |
| ATOM | 2235 | N   | GLU | A | 429 | 31.323 | 30.439 | 25.155 | 1.00 | 46.41 |
| ATOM | 2236 | CA  | GLU | A | 429 | 31.301 | 31.375 | 24.043 | 1.00 | 45.40 |
| ATOM | 2237 | C   | GLU | A | 429 | 31.699 | 32.761 | 24.534 | 1.00 | 46.63 |
| ATOM | 2238 | O   | GLU | A | 429 | 31.971 | 33.658 | 23.738 | 1.00 | 46.78 |
| ATOM | 2239 | CB  | GLU | A | 429 | 29.905 | 31.433 | 23.432 | 1.00 | 46.73 |
| ATOM | 2240 | CG  | GLU | A | 429 | 28.893 | 32.161 | 24.303 | 1.00 | 59.21 |
| ATOM | 2241 | CD  | GLU | A | 429 | 27.472 | 31.679 | 24.079 | 1.00 | 86.31 |
| ATOM | 2242 | OE1 | GLU | A | 429 | 27.100 | 31.445 | 22.908 | 1.00 | 81.70 |
| ATOM | 2243 | OE2 | GLU | A | 429 | 26.724 | 31.545 | 25.075 | 1.00 | 83.17 |
| ATOM | 2244 | N   | THR | A | 430 | 31.704 | 32.943 | 25.849 | 1.00 | 40.62 |
| ATOM | 2245 | CA  | THR | A | 430 | 32.076 | 34.231 | 26.425 | 1.00 | 39.30 |
| ATOM | 2246 | C   | THR | A | 430 | 33.414 | 34.154 | 27.141 | 1.00 | 39.89 |
| ATOM | 2247 | O   | THR | A | 430 | 33.958 | 35.170 | 27.572 | 1.00 | 40.41 |
| ATOM | 2248 | CB  | THR | A | 430 | 30.984 | 34.794 | 27.353 | 1.00 | 47.81 |
| ATOM | 2249 | OG1 | THR | A | 430 | 31.026 | 34.121 | 28.618 | 1.00 | 48.25 |
| ATOM | 2250 | CG2 | THR | A | 430 | 29.610 | 34.608 | 26.725 | 1.00 | 45.57 |
| ATOM | 2251 | N   | ASP | A | 431 | 33.951 | 32.944 | 27.234 | 1.00 | 33.48 |
| ATOM | 2252 | CA  | ASP | A | 431 | 35.251 | 32.718 | 27.835 | 1.00 | 32.54 |
| ATOM | 2253 | C   | ASP | A | 431 | 36.262 | 33.669 | 27.176 | 1.00 | 35.67 |
| ATOM | 2254 | O   | ASP | A | 431 | 36.396 | 33.700 | 25.942 | 1.00 | 35.73 |
| ATOM | 2255 | CB  | ASP | A | 431 | 35.666 | 31.268 | 27.620 | 1.00 | 33.90 |
| ATOM | 2256 | CG  | ASP | A | 431 | 36.893 | 30.887 | 28.412 | 1.00 | 40.44 |
| ATOM | 2257 | OD1 | ASP | A | 431 | 37.597 | 31.792 | 28.889 | 1.00 | 41.85 |
| ATOM | 2258 | OD2 | ASP | A | 431 | 37.177 | 29.673 | 28.521 | 1.00 | 44.02 |
| ATOM | 2259 | N   | THR | A | 432 | 36.923 | 34.476 | 28.000 | 1.00 | 30.24 |
| ATOM | 2260 | CA  | THR | A | 432 | 37.857 | 35.490 | 27.531 | 1.00 | 29.39 |
| ATOM | 2261 | C   | THR | A | 432 | 39.308 | 35.054 | 27.681 | 1.00 | 33.24 |
| ATOM | 2262 | O   | THR | A | 432 | 40.231 | 35.860 | 27.530 | 1.00 | 32.59 |
| ATOM | 2263 | CB  | THR | A | 432 | 37.664 | 36.792 | 28.318 | 1.00 | 34.24 |
| ATOM | 2264 | OG1 | THR | A | 432 | 37.842 | 36.525 | 29.716 | 1.00 | 32.75 |
| ATOM | 2265 | CG2 | THR | A | 432 | 36.264 | 37.349 | 28.085 | 1.00 | 29.64 |
| ATOM | 2266 | N   | ARG | A | 433 | 39.491 | 33.778 | 27.988 | 1.00 | 31.04 |
| ATOM | 2267 | CA  | ARG | A | 433 | 40.808 | 33.173 | 28.184 | 1.00 | 31.48 |
| ATOM | 2268 | C   | ARG | A | 433 | 41.938 | 33.690 | 27.253 | 1.00 | 36.85 |
| ATOM | 2269 | O   | ARG | A | 433 | 42.979 | 34.139 | 27.726 | 1.00 | 37.26 |
| ATOM | 2270 | CB  | ARG | A | 433 | 40.686 | 31.649 | 28.103 | 1.00 | 32.37 |
| ATOM | 2271 | CG  | ARG | A | 433 | 41.917 | 30.950 | 27.546 | 1.00 | 46.51 |
| ATOM | 2272 | CD  | ARG | A | 433 | 41.857 | 29.446 | 27.783 | 1.00 | 57.16 |
| ATOM | 2273 | NE  | ARG | A | 433 | 43.164 | 28.813 | 27.580 | 1.00 | 66.21 |
| ATOM | 2274 | CZ  | ARG | A | 433 | 43.377 | 27.499 | 27.626 | 1.00 | 78.03 |
| ATOM | 2275 | NH1 | ARG | A | 433 | 42.372 | 26.667 | 27.866 | 1.00 | 60.34 |
| ATOM | 2276 | NH2 | ARG | A | 433 | 44.596 | 27.017 | 27.423 | 1.00 | 66.57 |
| ATOM | 2277 | N   | TYR | A | 434 | 41.720 | 33.640 | 25.945 | 1.00 | 33.43 |
| ATOM | 2278 | CA  | TYR | A | 434 | 42.727 | 34.099 | 24.989 | 1.00 | 33.15 |
| ATOM | 2279 | C   | TYR | A | 434 | 43.025 | 35.591 | 25.000 | 1.00 | 37.89 |
| ATOM | 2280 | O   | TYR | A | 434 | 44.147 | 35.989 | 24.737 | 1.00 | 37.82 |
| ATOM | 2281 | CB  | TYR | A | 434 | 42.450 | 33.571 | 23.600 | 1.00 | 33.89 |
| ATOM | 2282 | CG  | TYR | A | 434 | 42.582 | 32.078 | 23.492 | 1.00 | 35.02 |
| ATOM | 2283 | CD1 | TYR | A | 434 | 41.468 | 31.276 | 23.384 | 1.00 | 36.82 |
| ATOM | 2284 | CD2 | TYR | A | 434 | 43.828 | 31.476 | 23.518 | 1.00 | 35.80 |
| ATOM | 2285 | CE1 | TYR | A | 434 | 41.594 | 29.887 | 23.319 | 1.00 | 38.18 |

TABLE 3-continued

Structural coordinates for AKT3lkd(pT305, pS472) (SEQ ID NO:2).

| ATOM | 2286 | CE2 | TYR | A | 434 | 43.965 | 30.104 | 23.465 | 1.00 | 36.79 |
|---|---|---|---|---|---|---|---|---|---|---|
| ATOM | 2287 | CZ | TYR | A | 434 | 42.852 | 29.307 | 23.354 | 1.00 | 44.47 |
| ATOM | 2288 | OH | TYR | A | 434 | 42.989 | 27.943 | 23.281 | 1.00 | 47.47 |
| ATOM | 2289 | N | PHE | A | 435 | 42.041 | 36.414 | 25.366 | 1.00 | 34.37 |
| ATOM | 2290 | CA | PHE | A | 435 | 42.279 | 37.859 | 25.478 | 1.00 | 34.26 |
| ATOM | 2291 | C | PHE | A | 435 | 43.085 | 38.130 | 26.753 | 1.00 | 41.54 |
| ATOM | 2292 | O | PHE | A | 435 | 43.939 | 39.030 | 26.793 | 1.00 | 40.33 |
| ATOM | 2293 | CB | PHE | A | 435 | 40.960 | 38.644 | 25.536 | 1.00 | 35.27 |
| ATOM | 2294 | CG | PHE | A | 435 | 40.117 | 38.498 | 24.317 | 1.00 | 36.39 |
| ATOM | 2295 | CD1 | PHE | A | 435 | 39.135 | 37.519 | 24.253 | 1.00 | 39.28 |
| ATOM | 2296 | CD2 | PHE | A | 435 | 40.314 | 39.315 | 23.224 | 1.00 | 38.21 |
| ATOM | 2297 | CE1 | PHE | A | 435 | 38.373 | 37.366 | 23.133 | 1.00 | 40.14 |
| ATOM | 2298 | CE2 | PHE | A | 435 | 39.548 | 39.164 | 22.092 | 1.00 | 41.19 |
| ATOM | 2299 | CZ | PHE | A | 435 | 38.574 | 38.189 | 22.047 | 1.00 | 39.42 |
| ATOM | 2300 | N | ASP | A | 436 | 42.780 | 37.367 | 27.802 | 1.00 | 41.32 |
| ATOM | 2301 | CA | ASP | A | 436 | 43.461 | 37.508 | 29.076 | 1.00 | 42.93 |
| ATOM | 2302 | C | ASP | A | 436 | 44.879 | 36.972 | 28.952 | 1.00 | 50.92 |
| ATOM | 2303 | O | ASP | A | 436 | 45.838 | 37.613 | 29.378 | 1.00 | 50.50 |
| ATOM | 2304 | CB | ASP | A | 436 | 42.714 | 36.733 | 30.163 | 1.00 | 44.69 |
| ATOM | 2305 | CG | ASP | A | 436 | 41.273 | 37.159 | 30.291 | 1.00 | 55.62 |
| ATOM | 2306 | OD1 | ASP | A | 436 | 40.416 | 36.293 | 30.573 | 1.00 | 55.74 |
| ATOM | 2307 | OD2 | ASP | A | 436 | 40.993 | 38.361 | 30.096 | 1.00 | 63.83 |
| ATOM | 2308 | N | GLU | A | 437 | 44.998 | 35.785 | 28.369 | 1.00 | 50.88 |
| ATOM | 2309 | CA | GLU | A | 437 | 46.287 | 35.128 | 28.193 | 1.00 | 52.47 |
| ATOM | 2310 | C | GLU | A | 437 | 46.889 | 35.483 | 26.832 | 1.00 | 59.47 |
| ATOM | 2311 | O | GLU | A | 437 | 47.204 | 34.603 | 26.025 | 1.00 | 59.34 |
| ATOM | 2312 | CB | GLU | A | 437 | 46.116 | 33.612 | 28.325 | 1.00 | 53.96 |
| ATOM | 2313 | CG | GLU | A | 437 | 47.385 | 32.806 | 28.142 | 1.00 | 66.37 |
| ATOM | 2314 | CD | GLU | A | 437 | 47.210 | 31.693 | 27.124 | 1.00 | 88.92 |
| ATOM | 2315 | OE1 | GLU | A | 437 | 48.108 | 31.519 | 26.272 | 1.00 | 85.70 |
| ATOM | 2316 | OE2 | GLU | A | 437 | 46.152 | 31.027 | 27.145 | 1.00 | 80.68 |
| ATOM | 2317 | N | GLU | A | 438 | 47.010 | 36.784 | 26.576 | 1.00 | 57.61 |
| ATOM | 2318 | CA | GLU | A | 438 | 47.573 | 37.305 | 25.330 | 1.00 | 58.31 |
| ATOM | 2319 | C | GLU | A | 438 | 48.031 | 38.719 | 25.619 | 1.00 | 64.05 |
| ATOM | 2320 | O | GLU | A | 438 | 49.020 | 39.193 | 25.062 | 1.00 | 63.87 |
| ATOM | 2321 | CB | GLU | A | 438 | 46.511 | 37.348 | 24.224 | 1.00 | 59.81 |
| ATOM | 2322 | CG | GLU | A | 438 | 46.508 | 36.143 | 23.267 | 1.00 | 71.89 |
| ATOM | 2323 | CD | GLU | A | 438 | 45.401 | 36.230 | 22.202 | 1.00 | 89.37 |
| ATOM | 2324 | OE1 | GLU | A | 438 | 44.772 | 37.302 | 22.077 | 1.00 | 78.55 |
| ATOM | 2325 | OE2 | GLU | A | 438 | 45.177 | 35.231 | 21.483 | 1.00 | 82.08 |
| ATOM | 2326 | N | PHE | A | 439 | 47.298 | 39.385 | 26.507 | 1.00 | 61.75 |
| ATOM | 2327 | CA | PHE | A | 439 | 47.582 | 40.763 | 26.890 | 1.00 | 62.15 |
| ATOM | 2328 | C | PHE | A | 439 | 48.688 | 40.856 | 27.929 | 1.00 | 66.56 |
| ATOM | 2329 | O | PHE | A | 439 | 48.965 | 41.937 | 28.446 | 1.00 | 66.46 |
| ATOM | 2330 | CB | PHE | A | 439 | 46.317 | 41.434 | 27.427 | 1.00 | 64.11 |
| TER | 2331 | | GLU | A | 479 | | | | | |
| ATOM | 2332 | OW | WAT | W | 1 | 43.679 | 42.223 | 1.497 | 1.00 | 18.63 |
| ATOM | 2333 | OW | WAT | W | 3 | 41.626 | 25.902 | 14.026 | 1.00 | 25.37 |
| ATOM | 2334 | OW | WAT | W | 4 | 37.386 | 18.280 | 1.990 | 1.00 | 36.56 |
| ATOM | 2335 | OW | WAT | W | 5 | 34.964 | 24.969 | 6.737 | 1.00 | 28.39 |
| ATOM | 2336 | OW | WAT | W | 6 | 33.981 | 31.470 | 11.792 | 1.00 | 38.58 |
| ATOM | 2337 | OW | WAT | W | 7 | 28.078 | 28.258 | 6.982 | 1.00 | 38.70 |
| ATOM | 2338 | OW | WAT | W | 8 | 33.938 | 32.667 | 19.190 | 1.00 | 39.16 |
| ATOM | 2339 | OW | WAT | W | 10 | 30.581 | 40.854 | 7.663 | 1.00 | 28.84 |
| ATOM | 2340 | OW | WAT | W | 11 | 48.052 | 19.709 | 11.242 | 1.00 | 38.37 |
| ATOM | 2341 | OW | WAT | W | 12 | 38.319 | 18.232 | 7.350 | 1.00 | 51.56 |
| ATOM | 2342 | OW | WAT | W | 13 | 27.456 | 34.299 | 2.526 | 1.00 | 33.00 |
| ATOM | 2343 | OW | WAT | W | 14 | 31.768 | 32.045 | −0.168 | 1.00 | 25.13 |
| ATOM | 2344 | OW | WAT | W | 15 | 28.586 | 20.986 | 2.477 | 1.00 | 36.62 |
| ATOM | 2345 | OW | WAT | W | 16 | 43.082 | 20.822 | 19.106 | 1.00 | 47.08 |
| ATOM | 2346 | OW | WAT | W | 19 | 37.669 | 46.113 | 4.661 | 1.00 | 40.48 |
| ATOM | 2347 | OW | WAT | W | 22 | 36.413 | 24.620 | 21.062 | 1.00 | 38.63 |
| ATOM | 2348 | OW | WAT | W | 23 | 46.787 | 42.550 | 1.003 | 1.00 | 43.43 |
| ATOM | 2349 | OW | WAT | W | 25 | 31.151 | 31.674 | 14.536 | 1.00 | 37.27 |
| ATOM | 2350 | OW | WAT | W | 28 | 32.684 | 23.502 | 13.260 | 1.00 | 50.21 |
| ATOM | 2351 | OW | WAT | W | 29 | 24.862 | 26.487 | 2.489 | 1.00 | 45.18 |
| ATOM | 2352 | OW | WAT | W | 30 | 47.058 | 27.504 | 22.687 | 1.00 | 49.11 |
| ATOM | 2353 | OW | WAT | W | 32 | 27.245 | 41.743 | 8.915 | 1.00 | 47.66 |
| ATOM | 2354 | OW | WAT | W | 33 | 48.373 | 28.927 | 20.645 | 1.00 | 51.95 |
| ATOM | 2355 | OW | WAT | W | 34 | 29.001 | 35.557 | 21.034 | 1.00 | 43.90 |
| ATOM | 2356 | OW | WAT | W | 38 | 53.069 | 18.679 | −3.147 | 1.00 | 25.74 |
| ATOM | 2357 | OW | WAT | W | 39 | 62.738 | 24.996 | −3.998 | 1.00 | 49.49 |
| ATOM | 2358 | OW | WAT | W | 41 | 23.447 | 52.129 | 15.519 | 1.00 | 47.33 |
| ATOM | 2359 | OW | WAT | W | 42 | 42.935 | 17.749 | 1.725 | 1.00 | 32.40 |
| ATOM | 2360 | OW | WAT | W | 43 | 29.469 | 56.066 | 13.120 | 1.00 | 44.52 |
| ATOM | 2361 | OW | WAT | W | 44 | 42.187 | 20.834 | 5.300 | 1.00 | 40.27 |
| ATOM | 2362 | OW | WAT | W | 46 | 39.507 | 21.451 | −4.505 | 1.00 | 18.79 |
| ATOM | 2363 | OW | WAT | W | 47 | 42.047 | 21.998 | −6.147 | 1.00 | 14.97 |

TABLE 3-continued

Structural coordinates for AKT3lkd(pT305, pS472) (SEQ ID NO:2).

| ATOM | 2364 | OW | WAT | W | 48 | 50.515 | 18.810 | 6.819 | 1.00 | 28.42 |
|---|---|---|---|---|---|---|---|---|---|---|
| ATOM | 2365 | OW | WAT | W | 49 | 33.502 | 28.403 | −0.311 | 1.00 | 26.42 |
| ATOM | 2366 | OW | WAT | W | 50 | 54.233 | 17.556 | 3.482 | 1.00 | 53.33 |
| ATOM | 2367 | OW | WAT | W | 51 | 38.001 | 44.472 | 32.620 | 1.00 | 34.95 |
| ATOM | 2368 | OW | WAT | W | 52 | 47.628 | 23.485 | −9.842 | 1.00 | 25.54 |
| ATOM | 2369 | OW | WAT | W | 53 | 56.890 | 37.500 | −10.177 | 1.00 | 36.15 |
| ATOM | 2370 | OW | WAT | W | 54 | 56.249 | 40.566 | 3.797 | 1.00 | 43.24 |
| ATOM | 2371 | OW | WAT | W | 55 | 48.447 | 19.138 | −2.080 | 1.00 | 39.09 |
| ATOM | 2372 | OW | WAT | W | 56 | 40.511 | 32.673 | −14.341 | 1.00 | 25.28 |
| ATOM | 2373 | OW | WAT | W | 57 | 57.170 | 37.732 | −4.901 | 1.00 | 20.69 |
| ATOM | 2374 | OW | WAT | W | 58 | 56.803 | 26.554 | −8.494 | 1.00 | 46.51 |
| ATOM | 2375 | OW | WAT | W | 59 | 43.060 | 42.870 | −9.492 | 1.00 | 27.99 |
| ATOM | 2376 | OW | WAT | W | 60 | 44.687 | 26.963 | −10.900 | 1.00 | 25.67 |
| ATOM | 2377 | OW | WAT | W | 61 | 34.408 | 21.155 | −4.782 | 1.00 | 36.92 |
| ATOM | 2378 | OW | WAT | W | 62 | 50.621 | 19.801 | 1.811 | 1.00 | 37.09 |
| ATOM | 2379 | OW | WAT | W | 63 | 35.325 | 35.414 | −6.788 | 1.00 | 32.81 |
| ATOM | 2380 | OW | WAT | W | 64 | 54.358 | 24.417 | 7.504 | 1.00 | 23.29 |
| ATOM | 2381 | OW | WAT | W | 65 | 54.011 | 42.637 | 0.770 | 1.00 | 29.09 |
| ATOM | 2382 | OW | WAT | W | 66 | 55.558 | 38.912 | −12.308 | 1.00 | 36.79 |
| ATOM | 2383 | OW | WAT | W | 67 | 53.476 | 20.174 | 7.158 | 1.00 | 45.86 |
| ATOM | 2384 | OW | WAT | W | 68 | 45.415 | 44.550 | −8.195 | 1.00 | 29.46 |
| ATOM | 2385 | OW | WAT | W | 69 | 32.565 | 30.030 | −1.964 | 1.00 | 32.63 |
| ATOM | 2386 | OW | WAT | W | 70 | 50.383 | 23.080 | 13.678 | 1.00 | 36.19 |
| ATOM | 2387 | OW | WAT | W | 71 | 56.247 | 34.103 | −7.749 | 1.00 | 39.48 |
| ATOM | 2388 | OW | WAT | W | 72 | 46.506 | 34.021 | −13.473 | 1.00 | 37.17 |
| ATOM | 2389 | OW | WAT | W | 73 | 38.996 | 44.501 | −9.146 | 1.00 | 35.06 |
| ATOM | 2390 | OW | WAT | W | 74 | 31.906 | 27.893 | 14.333 | 1.00 | 28.49 |
| ATOM | 2391 | OW | WAT | W | 75 | 70.674 | 18.174 | 1.822 | 1.00 | 39.59 |
| ATOM | 2392 | OW | WAT | W | 76 | 53.225 | 20.775 | −7.562 | 1.00 | 30.86 |
| ATOM | 2393 | OW | WAT | W | 77 | 35.706 | 47.752 | −2.633 | 1.00 | 33.85 |
| ATOM | 2394 | OW | WAT | W | 79 | 58.464 | 25.053 | 7.538 | 1.00 | 40.72 |
| ATOM | 2395 | OW | WAT | W | 81 | 41.462 | 20.397 | −8.209 | 1.00 | 27.19 |
| ATOM | 2396 | OW | WAT | W | 83 | 48.487 | 31.853 | −12.309 | 1.00 | 52.00 |
| ATOM | 2397 | OW | WAT | W | 84 | 44.203 | 41.662 | −11.944 | 1.00 | 54.69 |
| ATOM | 2398 | OW | WAT | W | 85 | 51.101 | 29.290 | −8.750 | 1.00 | 46.89 |
| ATOM | 2399 | OW | WAT | W | 86 | 36.410 | 33.709 | 30.932 | 1.00 | 36.55 |
| ATOM | 2400 | OW | WAT | W | 87 | 61.184 | 35.041 | 1.256 | 1.00 | 41.24 |
| ATOM | 2401 | OW | WAT | W | 88 | 33.417 | 30.336 | −12.839 | 1.00 | 41.72 |
| ATOM | 2402 | OW | WAT | W | 90 | 64.560 | 28.647 | −1.651 | 1.00 | 45.61 |
| ATOM | 2403 | OW | WAT | W | 91 | 62.967 | 39.411 | 2.679 | 1.00 | 49.56 |
| ATOM | 2404 | OW | WAT | W | 93 | 58.325 | 35.634 | −5.783 | 1.00 | 51.85 |
| ATOM | 2405 | OW | WAT | W | 94 | 65.279 | 37.223 | −6.997 | 1.00 | 55.72 |
| ATOM | 2406 | OW | WAT | W | 95 | 36.101 | 43.172 | −8.011 | 1.00 | 56.42 |
| ATOM | 2407 | OW | WAT | W | 96 | 59.493 | 38.015 | 9.604 | 1.00 | 41.97 |
| ATOM | 2408 | OW | WAT | W | 97 | 48.239 | 45.587 | −0.336 | 1.00 | 40.93 |
| ATOM | 2409 | OW | WAT | W | 99 | 27.545 | 48.073 | 32.756 | 1.00 | 39.45 |
| ATOM | 2410 | OW | WAT | W | 100 | 27.595 | 28.137 | −1.590 | 1.00 | 40.50 |
| ATOM | 2411 | OW | WAT | W | 101 | 42.268 | 41.409 | 29.275 | 1.00 | 47.50 |
| ATOM | 2412 | OW | WAT | W | 106 | 52.739 | 39.629 | 11.095 | 1.00 | 50.83 |
| ATOM | 2413 | OW | WAT | W | 110 | 59.318 | 22.508 | −6.513 | 1.00 | 41.36 |
| ATOM | 2414 | OW | WAT | W | 112 | 46.612 | 44.383 | 3.790 | 1.00 | 46.04 |
| ATOM | 2415 | OW | WAT | W | 114 | 54.730 | 41.677 | −16.114 | 1.00 | 52.45 |
| ATOM | 2416 | OW | WAT | W | 115 | 37.897 | 43.199 | −11.667 | 1.00 | 52.49 |
| ATOM | 2417 | OW | WAT | W | 116 | 43.518 | 39.204 | −16.289 | 1.00 | 54.69 |
| END | | | | | | | | | | |

TABLE 4

Structural coordinates for AKT3lkd(T305D, S472D) (SEQ ID NO:2).

REMARK Rfree = 23.2 Rwork = 20.9 Resolution = 1.65
REMARK This is the long kinase domain with S305D and T472D
REMARK mutations: AKT3lkd(T305D, S472D)
REMARK
CRYST1 Unit Cell Dimensions: a = 48.680    b = 72.890    c = 95.210
$\alpha$ = 90.00 $\beta$ = 90.00 $\gamma$ = 90.00 Space group: $P2_12_12_1$

| ORIGX1 | 1.000000 | 0.000000 | 0.000000 | 0.00000 |
|---|---|---|---|---|
| ORIGX2 | 0.000000 | 1.000000 | 0.000000 | 0.00000 |
| ORIGX3 | 0.000000 | 0.000000 | 1.000000 | 0.00000 |
| SCALE1 | 0.020542 | 0.000000 | 0.000000 | 0.00000 |
| SCALE2 | 0.000000 | 0.013719 | 0.000000 | 0.00000 |
| SCALE3 | 0.000000 | 0.000000 | 0.010503 | 0.00000 |

| ATOM | 1 | N | ARG | A | 142 | 18.900 | 54.550 | 16.946 | 1.00 | 57.12 |
|---|---|---|---|---|---|---|---|---|---|---|
| ATOM | 2 | CA | ARG | A | 142 | 20.303 | 54.151 | 16.989 | 1.00 | 56.63 |
| ATOM | 3 | C | ARG | A | 142 | 20.686 | 53.579 | 18.351 | 1.00 | 58.20 |

TABLE 4-continued

Structural coordinates for AKT3lkd(T305D, S472D) (SEQ ID NO:2).

| ATOM | 4 | O | ARG | A | 142 | 19.852 | 53.482 | 19.257 | 1.00 | 57.62 |
|---|---|---|---|---|---|---|---|---|---|---|
| ATOM | 5 | CB | ARG | A | 142 | 21.206 | 55.333 | 16.646 | 1.00 | 58.26 |
| ATOM | 6 | CG | ARG | A | 142 | 20.696 | 56.180 | 15.498 | 1.00 | 74.26 |
| ATOM | 7 | CD | ARG | A | 142 | 19.545 | 57.081 | 15.940 | 1.00 | 90.63 |
| ATOM | 8 | NE | ARG | A | 142 | 18.983 | 57.836 | 14.823 | 1.00 | 103.50 |
| ATOM | 9 | CZ | ARG | A | 142 | 17.997 | 57.398 | 14.045 | 1.00 | 118.80 |
| ATOM | 10 | NH1 | ARG | A | 142 | 17.458 | 56.205 | 14.261 | 1.00 | 105.97 |
| ATOM | 11 | NH2 | ARG | A | 142 | 17.553 | 58.151 | 13.047 | 1.00 | 105.77 |
| ATOM | 12 | N | LYS | A | 143 | 21.951 | 53.183 | 18.480 | 1.00 | 52.59 |
| ATOM | 13 | CA | LYS | A | 143 | 22.456 | 52.614 | 19.724 | 1.00 | 50.91 |
| ATOM | 14 | C | LYS | A | 143 | 23.387 | 53.597 | 20.417 | 1.00 | 53.28 |
| ATOM | 15 | O | LYS | A | 143 | 24.023 | 54.436 | 19.768 | 1.00 | 52.44 |
| ATOM | 16 | CB | LYS | A | 143 | 23.206 | 51.306 | 19.451 | 1.00 | 52.23 |
| ATOM | 17 | CG | LYS | A | 143 | 22.314 | 50.153 | 19.031 | 1.00 | 61.40 |
| ATOM | 18 | CD | LYS | A | 143 | 21.004 | 50.154 | 19.798 | 1.00 | 69.59 |
| ATOM | 19 | CE | LYS | A | 143 | 20.683 | 48.770 | 20.337 | 1.00 | 81.41 |
| ATOM | 20 | NZ | LYS | A | 143 | 19.883 | 47.967 | 19.369 | 1.00 | 91.92 |
| ATOM | 21 | N | THR | A | 144 | 23.477 | 53.478 | 21.737 | 1.00 | 49.19 |
| ATOM | 22 | CA | THR | A | 144 | 24.350 | 54.342 | 22.525 | 1.00 | 49.04 |
| ATOM | 23 | C | THR | A | 144 | 25.158 | 53.519 | 23.516 | 1.00 | 51.89 |
| ATOM | 24 | O | THR | A | 144 | 24.901 | 52.329 | 23.705 | 1.00 | 51.07 |
| ATOM | 25 | CB | THR | A | 144 | 23.546 | 55.397 | 23.318 | 1.00 | 58.57 |
| ATOM | 26 | OG1 | THR | A | 144 | 22.527 | 54.746 | 24.089 | 1.00 | 61.11 |
| ATOM | 27 | CG2 | THR | A | 144 | 22.903 | 56.398 | 22.369 | 1.00 | 58.09 |
| ATOM | 28 | N | MET | A | 145 | 26.123 | 54.166 | 24.159 | 1.00 | 48.89 |
| ATOM | 29 | CA | MET | A | 145 | 26.940 | 53.506 | 25.168 | 1.00 | 49.00 |
| ATOM | 30 | C | MET | A | 145 | 26.019 | 52.912 | 26.223 | 1.00 | 51.08 |
| ATOM | 31 | O | MET | A | 145 | 26.316 | 51.875 | 26.809 | 1.00 | 50.72 |
| ATOM | 32 | CB | MET | A | 145 | 27.869 | 54.515 | 25.837 | 1.00 | 51.62 |
| ATOM | 33 | CG | MET | A | 145 | 29.095 | 54.857 | 25.050 | 1.00 | 56.02 |
| ATOM | 34 | SD | MET | A | 145 | 29.859 | 53.410 | 24.355 | 1.00 | 60.99 |
| ATOM | 35 | CE | MET | A | 145 | 29.612 | 52.191 | 25.724 | 1.00 | 57.71 |
| ATOM | 36 | N | ASN | A | 146 | 24.901 | 53.598 | 26.465 | 1.00 | 46.79 |
| ATOM | 37 | CA | ASN | A | 146 | 23.924 | 53.199 | 27.482 | 1.00 | 45.72 |
| ATOM | 38 | C | ASN | A | 146 | 23.093 | 51.991 | 27.093 | 1.00 | 46.48 |
| ATOM | 39 | O | ASN | A | 146 | 22.377 | 51.424 | 27.923 | 1.00 | 45.13 |
| ATOM | 40 | CB | ASN | A | 146 | 22.994 | 54.373 | 27.817 | 1.00 | 48.37 |
| ATOM | 41 | CG | ASN | A | 146 | 23.745 | 55.671 | 28.021 | 1.00 | 77.54 |
| ATOM | 42 | OD1 | ASN | A | 146 | 24.160 | 55.991 | 29.134 | 1.00 | 74.36 |
| ATOM | 43 | ND2 | ASN | A | 146 | 23.932 | 56.424 | 26.940 | 1.00 | 71.01 |
| ATOM | 44 | N | ASP | A | 147 | 23.171 | 51.602 | 25.828 | 1.00 | 41.63 |
| ATOM | 45 | CA | ASP | A | 147 | 22.427 | 50.451 | 25.358 | 1.00 | 40.73 |
| ATOM | 46 | C | ASP | A | 147 | 23.139 | 49.147 | 25.734 | 1.00 | 42.68 |
| ATOM | 47 | O | ASP | A | 147 | 22.586 | 48.058 | 25.583 | 1.00 | 42.84 |
| ATOM | 48 | CB | ASP | A | 147 | 22.213 | 50.537 | 23.846 | 1.00 | 42.78 |
| ATOM | 49 | CG | ASP | A | 147 | 21.282 | 51.680 | 23.455 | 1.00 | 52.76 |
| ATOM | 50 | OD1 | ASP | A | 147 | 20.295 | 51.910 | 24.188 | 1.00 | 53.81 |
| ATOM | 51 | OD2 | ASP | A | 147 | 21.590 | 52.398 | 22.475 | 1.00 | 54.02 |
| ATOM | 52 | N | PHE | A | 148 | 24.337 | 49.264 | 26.290 | 1.00 | 37.77 |
| ATOM | 53 | CA | PHE | A | 148 | 25.103 | 48.069 | 26.658 | 1.00 | 36.54 |
| ATOM | 54 | C | PHE | A | 148 | 25.646 | 48.035 | 28.081 | 1.00 | 41.40 |
| ATOM | 55 | O | PHE | A | 148 | 26.014 | 49.066 | 28.641 | 1.00 | 41.37 |
| ATOM | 56 | CB | PHE | A | 148 | 26.273 | 47.883 | 25.684 | 1.00 | 37.34 |
| ATOM | 57 | CG | PHE | A | 148 | 25.899 | 48.086 | 24.246 | 1.00 | 37.36 |
| ATOM | 58 | CD1 | PHE | A | 148 | 25.572 | 47.008 | 23.448 | 1.00 | 40.42 |
| ATOM | 59 | CD2 | PHE | A | 148 | 25.882 | 49.360 | 23.694 | 1.00 | 39.32 |
| ATOM | 60 | CE1 | PHE | A | 148 | 25.198 | 47.189 | 22.127 | 1.00 | 40.19 |
| ATOM | 61 | CE2 | PHE | A | 148 | 25.517 | 49.555 | 22.379 | 1.00 | 41.46 |
| ATOM | 62 | CZ | PHE | A | 148 | 25.177 | 48.462 | 21.589 | 1.00 | 39.32 |
| ATOM | 63 | N | ASP | A | 149 | 25.790 | 46.814 | 28.603 | 1.00 | 38.26 |
| ATOM | 64 | CA | ASP | A | 149 | 26.437 | 46.564 | 29.888 | 1.00 | 37.59 |
| ATOM | 65 | C | ASP | A | 149 | 27.920 | 46.298 | 29.571 | 1.00 | 40.27 |
| ATOM | 66 | O | ASP | A | 149 | 28.231 | 45.571 | 28.622 | 1.00 | 39.87 |
| ATOM | 67 | CB | ASP | A | 149 | 25.868 | 45.297 | 30.535 | 1.00 | 39.12 |
| ATOM | 68 | CG | ASP | A | 149 | 24.470 | 45.498 | 31.122 | 1.00 | 49.62 |
| ATOM | 69 | OD1 | ASP | A | 149 | 24.124 | 46.641 | 31.490 | 1.00 | 50.87 |
| ATOM | 70 | OD2 | ASP | A | 149 | 23.754 | 44.486 | 31.277 | 1.00 | 54.44 |
| ATOM | 71 | N | TYR | A | 150 | 28.812 | 46.856 | 30.390 | 1.00 | 35.24 |
| ATOM | 72 | CA | TYR | A | 150 | 30.263 | 46.668 | 30.256 | 1.00 | 33.44 |
| ATOM | 73 | C | TYR | A | 150 | 30.687 | 45.395 | 31.035 | 1.00 | 31.80 |
| ATOM | 74 | O | TYR | A | 150 | 30.613 | 45.369 | 32.280 | 1.00 | 30.95 |
| ATOM | 75 | CB | TYR | A | 150 | 30.962 | 47.903 | 30.849 | 1.00 | 35.91 |
| ATOM | 76 | CG | TYR | A | 150 | 32.467 | 47.854 | 30.902 | 1.00 | 38.98 |
| ATOM | 77 | CD1 | TYR | A | 150 | 33.230 | 48.687 | 30.099 | 1.00 | 41.40 |
| ATOM | 78 | CD2 | TYR | A | 150 | 33.126 | 47.055 | 31.816 | 1.00 | 39.88 |
| ATOM | 79 | CE1 | TYR | A | 150 | 34.601 | 48.667 | 30.153 | 1.00 | 42.78 |
| ATOM | 80 | CE2 | TYR | A | 150 | 34.516 | 47.035 | 31.877 | 1.00 | 40.07 |
| ATOM | 81 | CZ | TYR | A | 150 | 35.237 | 47.833 | 31.045 | 1.00 | 44.19 |

TABLE 4-continued

Structural coordinates for AKT3lkd(T305D, S472D) (SEQ ID NO:2).

| ATOM | 82 | OH | TYR | A | 150 | 36.601 | 47.828 | 31.108 | 1.00 | 42.48 |
|---|---|---|---|---|---|---|---|---|---|---|
| ATOM | 83 | N | LEU | A | 151 | 31.118 | 44.337 | 30.334 | 1.00 | 25.07 |
| ATOM | 84 | CA | LEU | A | 151 | 31.490 | 43.098 | 31.028 | 1.00 | 24.95 |
| ATOM | 85 | C | LEU | A | 151 | 32.981 | 42.966 | 31.362 | 1.00 | 27.20 |
| ATOM | 86 | O | LEU | A | 151 | 33.355 | 42.587 | 32.475 | 1.00 | 23.90 |
| ATOM | 87 | CB | LEU | A | 151 | 30.993 | 41.844 | 30.277 | 1.00 | 25.95 |
| ATOM | 88 | CG | LEU | A | 151 | 29.463 | 41.606 | 30.208 | 1.00 | 30.17 |
| ATOM | 89 | CD1 | LEU | A | 151 | 29.183 | 40.213 | 29.714 | 1.00 | 30.45 |
| ATOM | 90 | CD2 | LEU | A | 151 | 28.831 | 41.803 | 31.585 | 1.00 | 33.61 |
| ATOM | 91 | N | LYS | A | 152 | 33.846 | 43.246 | 30.389 | 1.00 | 23.05 |
| ATOM | 92 | CA | LYS | A | 152 | 35.277 | 43.107 | 30.637 | 1.00 | 22.96 |
| ATOM | 93 | C | LYS | A | 152 | 36.107 | 43.814 | 29.585 | 1.00 | 25.64 |
| ATOM | 94 | O | LYS | A | 152 | 35.730 | 43.831 | 28.407 | 1.00 | 27.00 |
| ATOM | 95 | CB | LYS | A | 152 | 35.651 | 41.630 | 30.625 | 1.00 | 23.53 |
| ATOM | 96 | CG | LYS | A | 152 | 37.099 | 41.329 | 31.012 | 1.00 | 27.05 |
| ATOM | 97 | CD | LYS | A | 152 | 37.273 | 39.858 | 31.279 | 1.00 | 24.56 |
| ATOM | 98 | CE | LYS | A | 152 | 38.521 | 39.606 | 32.096 | 1.00 | 27.96 |
| ATOM | 99 | NZ | LYS | A | 152 | 38.768 | 38.154 | 32.210 | 1.00 | 33.58 |
| ATOM | 100 | N | LEU | A | 153 | 37.254 | 44.341 | 30.003 | 1.00 | 22.86 |
| ATOM | 101 | CA | LEU | A | 153 | 38.211 | 44.965 | 29.058 | 1.00 | 22.82 |
| ATOM | 102 | C | LEU | A | 153 | 38.922 | 43.804 | 28.358 | 1.00 | 27.10 |
| ATOM | 103 | O | LEU | A | 153 | 39.510 | 42.928 | 29.025 | 1.00 | 27.86 |
| ATOM | 104 | CB | LEU | A | 153 | 39.252 | 45.819 | 29.807 | 1.00 | 22.76 |
| ATOM | 105 | CG | LEU | A | 153 | 40.344 | 46.420 | 28.898 | 1.00 | 27.91 |
| ATOM | 106 | CD1 | LEU | A | 153 | 39.674 | 47.333 | 27.875 | 1.00 | 27.72 |
| ATOM | 107 | CD2 | LEU | A | 153 | 41.368 | 47.195 | 29.749 | 1.00 | 32.12 |
| ATOM | 108 | N | LEU | A | 154 | 38.860 | 43.778 | 27.022 | 1.00 | 24.24 |
| ATOM | 109 | CA | LEU | A | 154 | 39.475 | 42.711 | 26.235 | 1.00 | 24.22 |
| ATOM | 110 | C | LEU | A | 154 | 40.860 | 43.076 | 25.708 | 1.00 | 31.60 |
| ATOM | 111 | O | LEU | A | 154 | 41.713 | 42.207 | 25.549 | 1.00 | 32.82 |
| ATOM | 112 | CB | LEU | A | 154 | 38.572 | 42.311 | 25.080 | 1.00 | 23.29 |
| ATOM | 113 | CG | LEU | A | 154 | 37.284 | 41.590 | 25.532 | 1.00 | 26.17 |
| ATOM | 114 | CD1 | LEU | A | 154 | 36.429 | 41.276 | 24.332 | 1.00 | 25.85 |
| ATOM | 115 | CD2 | LEU | A | 154 | 37.595 | 40.307 | 26.373 | 1.00 | 28.58 |
| ATOM | 116 | N | GLY | A | 155 | 41.076 | 44.353 | 25.422 | 1.00 | 28.71 |
| ATOM | 117 | CA | GLY | A | 155 | 42.392 | 44.790 | 24.916 | 1.00 | 29.97 |
| ATOM | 118 | C | GLY | A | 155 | 42.465 | 46.285 | 24.823 | 1.00 | 36.60 |
| ATOM | 119 | O | GLY | A | 155 | 41.443 | 46.969 | 24.795 | 1.00 | 35.19 |
| ATOM | 120 | N | LYS | A | 156 | 43.692 | 46.799 | 24.806 | 1.00 | 37.81 |
| ATOM | 121 | CA | LYS | A | 156 | 43.920 | 48.220 | 24.742 | 1.00 | 39.32 |
| ATOM | 122 | C | LYS | A | 156 | 45.126 | 48.512 | 23.853 | 1.00 | 46.71 |
| ATOM | 123 | O | LYS | A | 156 | 46.128 | 47.790 | 23.886 | 1.00 | 47.31 |
| ATOM | 124 | CB | LYS | A | 156 | 44.146 | 48.785 | 26.144 | 1.00 | 42.54 |
| ATOM | 125 | CG | LYS | A | 156 | 43.098 | 49.795 | 26.579 | 1.00 | 61.01 |
| ATOM | 126 | CD | LYS | A | 156 | 43.739 | 51.016 | 27.233 | 1.00 | 73.78 |
| ATOM | 127 | CE | LYS | A | 156 | 42.699 | 52.090 | 27.551 | 1.00 | 84.87 |
| ATOM | 128 | NZ | LYS | A | 156 | 42.409 | 52.182 | 29.014 | 1.00 | 92.74 |
| ATOM | 129 | N | GLY | A | 157 | 45.013 | 49.558 | 23.051 | 1.00 | 45.96 |
| ATOM | 130 | CA | GLY | A | 157 | 46.086 | 49.959 | 22.146 | 1.00 | 46.87 |
| ATOM | 131 | C | GLY | A | 157 | 45.976 | 51.443 | 21.810 | 1.00 | 52.61 |
| ATOM | 132 | O | GLY | A | 157 | 45.004 | 52.112 | 22.195 | 1.00 | 51.63 |
| ATOM | 133 | N | THR | A | 158 | 46.970 | 51.959 | 21.088 | 1.00 | 50.45 |
| ATOM | 134 | CA | THR | A | 158 | 46.992 | 53.378 | 20.738 | 1.00 | 50.35 |
| ATOM | 135 | C | THR | A | 158 | 45.707 | 53.842 | 20.070 | 1.00 | 53.23 |
| ATOM | 136 | O | THR | A | 158 | 45.234 | 54.952 | 20.327 | 1.00 | 51.74 |
| ATOM | 137 | CB | THR | A | 158 | 48.200 | 53.735 | 19.855 | 1.00 | 61.29 |
| ATOM | 138 | OG1 | THR | A | 158 | 48.388 | 52.717 | 18.859 | 1.00 | 64.00 |
| ATOM | 139 | CG2 | THR | A | 158 | 49.463 | 53.853 | 20.708 | 1.00 | 59.99 |
| ATOM | 140 | N | PHE | A | 159 | 45.142 | 52.985 | 19.218 | 1.00 | 49.60 |
| ATOM | 141 | CA | PHE | A | 159 | 43.909 | 53.309 | 18.504 | 1.00 | 49.28 |
| ATOM | 142 | C | PHE | A | 159 | 42.691 | 53.321 | 19.409 | 1.00 | 49.16 |
| ATOM | 143 | O | PHE | A | 159 | 41.636 | 53.814 | 19.027 | 1.00 | 49.18 |
| ATOM | 144 | CB | PHE | A | 159 | 43.681 | 52.328 | 17.353 | 1.00 | 51.82 |
| ATOM | 145 | CG | PHE | A | 159 | 44.236 | 52.797 | 16.043 | 1.00 | 54.18 |
| ATOM | 146 | CD1 | PHE | A | 159 | 45.402 | 52.245 | 15.530 | 1.00 | 58.09 |
| ATOM | 147 | CD2 | PHE | A | 159 | 43.605 | 53.809 | 15.329 | 1.00 | 56.71 |
| ATOM | 148 | CE1 | PHE | A | 159 | 45.925 | 52.690 | 14.317 | 1.00 | 59.03 |
| ATOM | 149 | CE2 | PHE | A | 159 | 44.122 | 54.256 | 14.123 | 1.00 | 59.66 |
| ATOM | 150 | CZ | PHE | A | 159 | 45.277 | 53.694 | 13.615 | 1.00 | 57.82 |
| ATOM | 151 | N | GLY | A | 160 | 42.820 | 52.732 | 20.592 | 1.00 | 42.95 |
| ATOM | 152 | CA | GLY | A | 160 | 41.693 | 52.667 | 21.522 | 1.00 | 41.17 |
| ATOM | 153 | C | GLY | A | 160 | 41.665 | 51.335 | 22.279 | 1.00 | 41.01 |
| ATOM | 154 | O | GLY | A | 160 | 42.718 | 50.809 | 22.659 | 1.00 | 40.12 |
| ATOM | 155 | N | LYS | A | 161 | 40.458 | 50.790 | 22.469 | 1.00 | 34.92 |
| ATOM | 156 | CA | LYS | A | 161 | 40.282 | 49.537 | 23.227 | 1.00 | 32.72 |
| ATOM | 157 | C | LYS | A | 161 | 39.112 | 48.684 | 22.727 | 1.00 | 35.13 |
| ATOM | 158 | O | LYS | A | 161 | 38.264 | 49.143 | 21.935 | 1.00 | 33.83 |
| ATOM | 159 | CB | LYS | A | 161 | 40.057 | 49.875 | 24.703 | 1.00 | 34.64 |

TABLE 4-continued

Structural coordinates for AKT3lkd(T305D, S472D) (SEQ ID NO:2).

| ATOM | 160 | CG | LYS | A | 161 | 38.701 | 50.508 | 24.975 | 1.00 | 34.42 |
|---|---|---|---|---|---|---|---|---|---|---|
| ATOM | 161 | CD | LYS | A | 161 | 38.604 | 51.045 | 26.415 | 1.00 | 42.55 |
| ATOM | 162 | CE | LYS | A | 161 | 37.293 | 51.787 | 26.644 | 1.00 | 48.84 |
| ATOM | 163 | NZ | LYS | A | 161 | 37.235 | 52.459 | 27.993 | 1.00 | 60.24 |
| ATOM | 164 | N | VAL | A | 162 | 39.049 | 47.443 | 23.216 | 1.00 | 29.07 |
| ATOM | 165 | CA | VAL | A | 162 | 37.969 | 46.544 | 22.859 | 1.00 | 27.37 |
| ATOM | 166 | C | VAL | A | 162 | 37.436 | 45.977 | 24.159 | 1.00 | 28.55 |
| ATOM | 167 | O | VAL | A | 162 | 38.215 | 45.541 | 25.009 | 1.00 | 26.88 |
| ATOM | 168 | CB | VAL | A | 162 | 38.466 | 45.362 | 21.999 | 1.00 | 31.34 |
| ATOM | 169 | CG1 | VAL | A | 162 | 37.270 | 44.515 | 21.518 | 1.00 | 30.47 |
| ATOM | 170 | CG2 | VAL | A | 162 | 39.290 | 45.861 | 20.812 | 1.00 | 32.62 |
| ATOM | 171 | N | ILE | A | 163 | 36.126 | 46.031 | 24.324 | 1.00 | 25.48 |
| ATOM | 172 | CA | ILE | A | 163 | 35.482 | 45.548 | 25.546 | 1.00 | 25.51 |
| ATOM | 173 | C | ILE | A | 163 | 34.403 | 44.535 | 25.239 | 1.00 | 27.24 |
| ATOM | 174 | O | ILE | A | 163 | 33.729 | 44.616 | 24.222 | 1.00 | 26.67 |
| ATOM | 175 | CB | ILE | A | 163 | 34.843 | 46.739 | 26.345 | 1.00 | 29.02 |
| ATOM | 176 | CG1 | ILE | A | 163 | 33.779 | 47.441 | 25.491 | 1.00 | 30.11 |
| ATOM | 177 | CG2 | ILE | A | 163 | 35.905 | 47.731 | 26.743 | 1.00 | 30.59 |
| ATOM | 178 | CD1 | ILE | A | 163 | 32.956 | 48.523 | 26.256 | 1.00 | 33.65 |
| ATOM | 179 | N | LEU | A | 164 | 34.199 | 43.592 | 26.149 | 1.00 | 21.92 |
| ATOM | 180 | CA | LEU | A | 164 | 33.149 | 42.606 | 25.992 | 1.00 | 22.65 |
| ATOM | 181 | C | LEU | A | 164 | 31.897 | 43.244 | 26.584 | 1.00 | 28.04 |
| ATOM | 182 | O | LEU | A | 164 | 31.955 | 43.768 | 27.709 | 1.00 | 26.93 |
| ATOM | 183 | CB | LEU | A | 164 | 33.494 | 41.336 | 26.801 | 1.00 | 23.40 |
| ATOM | 184 | CG | LEU | A | 164 | 32.411 | 40.273 | 26.836 | 1.00 | 26.46 |
| ATOM | 185 | CD1 | LEU | A | 164 | 32.092 | 39.724 | 25.457 | 1.00 | 28.18 |
| ATOM | 186 | CD2 | LEU | A | 164 | 32.743 | 39.140 | 27.802 | 1.00 | 25.31 |
| ATOM | 187 | N | VAL | A | 165 | 30.789 | 43.238 | 25.831 | 1.00 | 26.05 |
| ATOM | 188 | CA | VAL | A | 165 | 29.524 | 43.865 | 26.331 | 1.00 | 26.33 |
| ATOM | 189 | C | VAL | A | 165 | 28.328 | 42.945 | 26.164 | 1.00 | 33.32 |
| ATOM | 190 | O | VAL | A | 165 | 28.393 | 41.917 | 25.487 | 1.00 | 32.64 |
| ATOM | 191 | CB | VAL | A | 165 | 29.218 | 45.235 | 25.639 | 1.00 | 28.27 |
| ATOM | 192 | CG1 | VAL | A | 165 | 30.377 | 46.217 | 25.793 | 1.00 | 28.34 |
| ATOM | 193 | CG2 | VAL | A | 165 | 28.870 | 45.016 | 24.127 | 1.00 | 27.92 |
| ATOM | 194 | N | ARG | A | 166 | 27.229 | 43.306 | 26.823 | 1.00 | 33.33 |
| ATOM | 195 | CA | ARG | A | 166 | 25.982 | 42.552 | 26.718 | 1.00 | 34.00 |
| ATOM | 196 | C | ARG | A | 166 | 24.941 | 43.565 | 26.264 | 1.00 | 38.11 |
| ATOM | 197 | O | ARG | A | 166 | 24.856 | 44.648 | 26.817 | 1.00 | 34.96 |
| ATOM | 198 | CB | ARG | A | 166 | 25.574 | 41.969 | 28.095 | 1.00 | 36.30 |
| ATOM | 199 | CG | ARG | A | 166 | 24.659 | 40.730 | 28.020 | 1.00 | 43.60 |
| ATOM | 200 | CD | ARG | A | 166 | 24.116 | 40.318 | 29.407 | 1.00 | 51.19 |
| ATOM | 201 | NE | ARG | A | 166 | 24.848 | 39.178 | 29.981 | 1.00 | 56.20 |
| ATOM | 202 | CZ | ARG | A | 166 | 25.386 | 39.167 | 31.202 | 1.00 | 60.31 |
| ATOM | 203 | NH1 | ARG | A | 166 | 25.261 | 40.231 | 31.995 | 1.00 | 45.63 |
| ATOM | 204 | NH2 | ARG | A | 166 | 26.054 | 38.094 | 31.633 | 1.00 | 41.98 |
| ATOM | 205 | N | GLU | A | 167 | 24.220 | 43.247 | 25.193 | 1.00 | 36.97 |
| ATOM | 206 | CA | GLU | A | 167 | 23.184 | 44.140 | 24.698 | 1.00 | 38.74 |
| ATOM | 207 | C | GLU | A | 167 | 22.074 | 44.091 | 25.738 | 1.00 | 45.99 |
| ATOM | 208 | O | GLU | A | 167 | 21.588 | 43.013 | 26.067 | 1.00 | 45.75 |
| ATOM | 209 | CB | GLU | A | 167 | 22.642 | 43.632 | 23.352 | 1.00 | 40.46 |
| ATOM | 210 | CG | GLU | A | 167 | 21.511 | 44.475 | 22.787 | 1.00 | 52.70 |
| ATOM | 211 | CD | GLU | A | 167 | 21.361 | 44.337 | 21.278 | 1.00 | 70.05 |
| ATOM | 212 | OE1 | GLU | A | 167 | 21.004 | 45.340 | 20.627 | 1.00 | 64.77 |
| ATOM | 213 | OE2 | GLU | A | 167 | 21.587 | 43.226 | 20.747 | 1.00 | 63.87 |
| ATOM | 214 | N | LYS | A | 168 | 21.706 | 45.245 | 26.288 | 1.00 | 45.36 |
| ATOM | 215 | CA | LYS | A | 168 | 20.665 | 45.276 | 27.307 | 1.00 | 46.45 |
| ATOM | 216 | C | LYS | A | 168 | 19.389 | 44.561 | 26.842 | 1.00 | 53.75 |
| ATOM | 217 | O | LYS | A | 168 | 18.926 | 43.613 | 27.483 | 1.00 | 53.93 |
| ATOM | 218 | CB | LYS | A | 168 | 20.368 | 46.709 | 27.747 | 1.00 | 48.59 |
| ATOM | 219 | CG | LYS | A | 168 | 21.291 | 47.219 | 28.846 | 1.00 | 56.46 |
| ATOM | 220 | CD | LYS | A | 168 | 21.323 | 48.742 | 28.886 | 1.00 | 63.10 |
| ATOM | 221 | CE | LYS | A | 168 | 21.643 | 49.246 | 30.278 | 1.00 | 72.14 |
| ATOM | 222 | NZ | LYS | A | 168 | 22.704 | 50.291 | 30.259 | 1.00 | 81.45 |
| ATOM | 223 | N | ALA | A | 169 | 18.849 | 44.990 | 25.708 | 1.00 | 51.90 |
| ATOM | 224 | CA | ALA | A | 169 | 17.610 | 44.404 | 25.192 | 1.00 | 52.65 |
| ATOM | 225 | C | ALA | A | 169 | 17.623 | 42.872 | 25.047 | 1.00 | 57.49 |
| ATOM | 226 | O | ALA | A | 169 | 16.829 | 42.173 | 25.677 | 1.00 | 57.74 |
| ATOM | 227 | CB | ALA | A | 169 | 17.213 | 45.065 | 23.890 | 1.00 | 53.56 |
| ATOM | 228 | N | SER | A | 170 | 18.515 | 42.363 | 24.206 | 1.00 | 53.81 |
| ATOM | 229 | CA | SER | A | 170 | 18.590 | 40.926 | 23.928 | 1.00 | 53.24 |
| ATOM | 230 | C | SER | A | 170 | 19.406 | 40.132 | 24.931 | 1.00 | 56.00 |
| ATOM | 231 | O | SER | A | 170 | 19.275 | 38.904 | 25.012 | 1.00 | 55.64 |
| ATOM | 232 | CB | SER | A | 170 | 19.181 | 40.700 | 22.540 | 1.00 | 56.78 |
| ATOM | 233 | OG | SER | A | 170 | 20.568 | 41.001 | 22.535 | 1.00 | 65.05 |
| ATOM | 234 | N | GLY | A | 171 | 20.303 | 40.812 | 25.636 | 1.00 | 51.37 |
| ATOM | 235 | CA | GLY | A | 171 | 21.197 | 40.143 | 26.568 | 1.00 | 50.62 |
| ATOM | 236 | C | GLY | A | 171 | 22.255 | 39.345 | 25.784 | 1.00 | 52.94 |
| ATOM | 237 | O | GLY | A | 171 | 22.863 | 38.406 | 26.311 | 1.00 | 53.48 |

TABLE 4-continued

Structural coordinates for AKT3lkd(T305D, S472D) (SEQ ID NO:2).

| ATOM | 238 | N | LYS | A | 172 | 22.461 | 39.722 | 24.519 | 1.00 | 46.64 |
|------|-----|-----|-----|---|-----|--------|--------|--------|------|-------|
| ATOM | 239 | CA | LYS | A | 172 | 23.448 | 39.042 | 23.665 | 1.00 | 44.68 |
| ATOM | 240 | C | LYS | A | 172 | 24.855 | 39.611 | 23.880 | 1.00 | 43.05 |
| ATOM | 241 | O | LYS | A | 172 | 25.019 | 40.820 | 24.094 | 1.00 | 41.86 |
| ATOM | 242 | CB | LYS | A | 172 | 23.056 | 39.174 | 22.189 | 1.00 | 46.78 |
| ATOM | 243 | CG | LYS | A | 172 | 22.277 | 37.985 | 21.651 | 1.00 | 58.71 |
| ATOM | 244 | CD | LYS | A | 172 | 21.207 | 38.426 | 20.657 | 1.00 | 69.60 |
| ATOM | 245 | CE | LYS | A | 172 | 20.872 | 37.311 | 19.670 | 1.00 | 81.27 |
| ATOM | 246 | NZ | LYS | A | 172 | 19.411 | 37.020 | 19.618 | 1.00 | 90.00 |
| ATOM | 247 | N | TYR | A | 173 | 25.863 | 38.745 | 23.772 | 1.00 | 37.47 |
| ATOM | 248 | CA | TYR | A | 173 | 27.265 | 39.153 | 23.945 | 1.00 | 35.54 |
| ATOM | 249 | C | TYR | A | 173 | 27.888 | 39.645 | 22.646 | 1.00 | 35.94 |
| ATOM | 250 | O | TYR | A | 173 | 27.768 | 39.002 | 21.607 | 1.00 | 35.77 |
| ATOM | 251 | CB | TYR | A | 173 | 28.108 | 37.987 | 24.456 | 1.00 | 36.72 |
| ATOM | 252 | CG | TYR | A | 173 | 27.624 | 37.395 | 25.759 | 1.00 | 39.15 |
| ATOM | 253 | CD1 | TYR | A | 173 | 27.878 | 38.027 | 26.964 | 1.00 | 40.02 |
| ATOM | 254 | CD2 | TYR | A | 173 | 26.897 | 36.209 | 25.777 | 1.00 | 40.71 |
| ATOM | 255 | CE1 | TYR | A | 173 | 27.440 | 37.486 | 28.166 | 1.00 | 40.19 |
| ATOM | 256 | CE2 | TYR | A | 173 | 26.455 | 35.652 | 26.974 | 1.00 | 42.03 |
| ATOM | 257 | CZ | TYR | A | 173 | 26.721 | 36.295 | 28.161 | 1.00 | 49.53 |
| ATOM | 258 | OH | TYR | A | 173 | 26.279 | 35.736 | 29.347 | 1.00 | 51.65 |
| ATOM | 259 | N | TYR | A | 174 | 28.626 | 40.739 | 22.736 | 1.00 | 30.94 |
| ATOM | 260 | CA | TYR | A | 174 | 29.345 | 41.292 | 21.578 | 1.00 | 29.53 |
| ATOM | 261 | C | TYR | A | 174 | 30.673 | 41.876 | 22.031 | 1.00 | 30.50 |
| ATOM | 262 | O | TYR | A | 174 | 30.917 | 42.080 | 23.218 | 1.00 | 29.32 |
| ATOM | 263 | CB | TYR | A | 174 | 28.526 | 42.428 | 20.917 | 1.00 | 31.52 |
| ATOM | 264 | CG | TYR | A | 174 | 27.197 | 41.983 | 20.352 | 1.00 | 35.21 |
| ATOM | 265 | CD1 | TYR | A | 174 | 27.138 | 41.191 | 19.210 | 1.00 | 37.44 |
| ATOM | 266 | CD2 | TYR | A | 174 | 25.996 | 42.343 | 20.967 | 1.00 | 36.70 |
| ATOM | 267 | CE1 | TYR | A | 174 | 25.922 | 40.756 | 18.698 | 1.00 | 38.93 |
| ATOM | 268 | CE2 | TYR | A | 174 | 24.769 | 41.916 | 20.453 | 1.00 | 38.36 |
| ATOM | 269 | CZ | TYR | A | 174 | 24.742 | 41.133 | 19.316 | 1.00 | 45.92 |
| ATOM | 270 | OH | TYR | A | 174 | 23.537 | 40.697 | 18.809 | 1.00 | 47.91 |
| ATOM | 271 | N | ALA | A | 175 | 31.527 | 42.181 | 21.074 | 1.00 | 24.63 |
| ATOM | 272 | CA | ALA | A | 175 | 32.742 | 42.870 | 21.380 | 1.00 | 24.18 |
| ATOM | 273 | C | ALA | A | 175 | 32.550 | 44.298 | 20.863 | 1.00 | 30.18 |
| ATOM | 274 | O | ALA | A | 175 | 32.199 | 44.488 | 19.709 | 1.00 | 31.38 |
| ATOM | 275 | CB | ALA | A | 175 | 33.927 | 42.220 | 20.630 | 1.00 | 25.20 |
| ATOM | 276 | N | MET | A | 176 | 32.803 | 45.294 | 21.702 | 1.00 | 25.47 |
| ATOM | 277 | CA | MET | A | 176 | 32.736 | 46.692 | 21.237 | 1.00 | 24.45 |
| ATOM | 278 | C | MET | A | 176 | 34.116 | 47.291 | 21.058 | 1.00 | 29.15 |
| ATOM | 279 | O | MET | A | 176 | 34.891 | 47.404 | 22.020 | 1.00 | 29.17 |
| ATOM | 280 | CB | MET | A | 176 | 31.912 | 47.590 | 22.176 | 1.00 | 25.93 |
| ATOM | 281 | CG | MET | A | 176 | 31.829 | 49.020 | 21.642 | 1.00 | 28.24 |
| ATOM | 282 | SD | MET | A | 176 | 31.116 | 50.174 | 22.852 | 1.00 | 31.73 |
| ATOM | 283 | CE | MET | A | 176 | 29.619 | 49.506 | 23.021 | 1.00 | 25.84 |
| ATOM | 284 | N | LYS | A | 177 | 34.455 | 47.663 | 19.824 | 1.00 | 26.57 |
| ATOM | 285 | CA | LYS | A | 177 | 35.747 | 48.280 | 19.571 | 1.00 | 27.07 |
| ATOM | 286 | C | LYS | A | 177 | 35.554 | 49.779 | 19.663 | 1.00 | 32.72 |
| ATOM | 287 | O | LYS | A | 177 | 34.648 | 50.327 | 19.043 | 1.00 | 32.40 |
| ATOM | 288 | CB | LYS | A | 177 | 36.286 | 47.884 | 18.194 | 1.00 | 28.96 |
| ATOM | 289 | CG | LYS | A | 177 | 36.671 | 46.388 | 18.105 | 1.00 | 38.10 |
| ATOM | 290 | CD | LYS | A | 177 | 37.515 | 46.092 | 16.865 | 1.00 | 51.19 |
| ATOM | 291 | CE | LYS | A | 177 | 38.084 | 44.676 | 16.903 | 1.00 | 56.43 |
| ATOM | 292 | NZ | LYS | A | 177 | 39.456 | 44.619 | 16.313 | 1.00 | 57.01 |
| ATOM | 293 | N | ILE | A | 178 | 36.322 | 50.414 | 20.549 | 1.00 | 31.98 |
| ATOM | 294 | CA | ILE | A | 178 | 36.180 | 51.850 | 20.832 | 1.00 | 32.63 |
| ATOM | 295 | C | ILE | A | 178 | 37.420 | 52.551 | 20.359 | 1.00 | 38.35 |
| ATOM | 296 | O | ILE | A | 178 | 38.448 | 52.516 | 21.020 | 1.00 | 37.35 |
| ATOM | 297 | CB | ILE | A | 178 | 35.998 | 52.095 | 22.345 | 1.00 | 35.59 |
| ATOM | 298 | CG1 | ILE | A | 178 | 34.625 | 51.568 | 22.814 | 1.00 | 35.64 |
| ATOM | 299 | CG2 | ILE | A | 178 | 36.172 | 53.595 | 22.672 | 1.00 | 35.83 |
| ATOM | 300 | CD1 | ILE | A | 178 | 34.572 | 51.231 | 24.307 | 1.00 | 45.13 |
| ATOM | 301 | N | LEU | A | 179 | 37.332 | 53.151 | 19.173 | 1.00 | 36.49 |
| ATOM | 302 | CA | LEU | A | 179 | 38.474 | 53.791 | 18.537 | 1.00 | 37.11 |
| ATOM | 303 | C | LEU | A | 179 | 38.554 | 55.309 | 18.772 | 1.00 | 42.01 |
| ATOM | 304 | O | LEU | A | 179 | 37.543 | 56.024 | 18.729 | 1.00 | 40.93 |
| ATOM | 305 | CB | LEU | A | 179 | 38.474 | 53.497 | 17.027 | 1.00 | 37.24 |
| ATOM | 306 | CG | LEU | A | 179 | 38.234 | 52.043 | 16.625 | 1.00 | 41.27 |
| ATOM | 307 | CD1 | LEU | A | 179 | 38.299 | 51.885 | 15.114 | 1.00 | 40.73 |
| ATOM | 308 | CD2 | LEU | A | 179 | 39.260 | 51.144 | 17.304 | 1.00 | 44.09 |
| ATOM | 309 | N | LYS | A | 180 | 39.778 | 55.775 | 18.994 | 1.00 | 39.98 |
| ATOM | 310 | CA | LYS | A | 180 | 40.067 | 57.182 | 19.227 | 1.00 | 40.07 |
| ATOM | 311 | C | LYS | A | 180 | 39.979 | 57.941 | 17.921 | 1.00 | 44.50 |
| ATOM | 312 | O | LYS | A | 180 | 40.796 | 57.726 | 17.031 | 1.00 | 43.50 |
| ATOM | 313 | CB | LYS | A | 180 | 41.495 | 57.334 | 19.759 | 1.00 | 42.31 |
| ATOM | 314 | CG | LYS | A | 180 | 41.687 | 56.928 | 21.206 | 1.00 | 53.89 |
| ATOM | 315 | CD | LYS | A | 180 | 43.090 | 56.375 | 21.420 | 1.00 | 62.01 |

TABLE 4-continued

Structural coordinates for AKT3lkd(T305D, S472D) (SEQ ID NO:2).

| ATOM | 316 | CE | LYS | A | 180 | 43.598 | 56.663 | 22.826 | 1.00 | 72.87 |
| ATOM | 317 | NZ | LYS | A | 180 | 44.987 | 56.151 | 23.022 | 1.00 | 82.75 |
| ATOM | 318 | N | LYS | A | 181 | 39.000 | 58.830 | 17.810 | 1.00 | 42.93 |
| ATOM | 319 | CA | LYS | A | 181 | 38.846 | 59.643 | 16.599 | 1.00 | 44.05 |
| ATOM | 320 | C | LYS | A | 181 | 40.175 | 60.315 | 16.246 | 1.00 | 50.60 |
| ATOM | 321 | O | LYS | A | 181 | 40.719 | 60.116 | 15.153 | 1.00 | 50.15 |
| ATOM | 322 | CB | LYS | A | 181 | 37.767 | 60.718 | 16.811 | 1.00 | 46.23 |
| ATOM | 323 | CG | LYS | A | 181 | 36.386 | 60.329 | 16.318 | 1.00 | 57.29 |
| ATOM | 324 | CD | LYS | A | 181 | 35.312 | 61.176 | 16.972 | 1.00 | 67.92 |
| ATOM | 325 | CE | LYS | A | 181 | 33.997 | 60.424 | 17.067 | 1.00 | 79.31 |
| ATOM | 326 | NZ | LYS | A | 181 | 32.826 | 61.322 | 16.863 | 1.00 | 88.23 |
| ATOM | 327 | N | GLU | A | 182 | 40.709 | 61.084 | 17.197 | 1.00 | 49.01 |
| ATOM | 328 | CA | GLU | A | 182 | 41.953 | 61.818 | 16.987 | 1.00 | 49.86 |
| ATOM | 329 | C | GLU | A | 182 | 43.066 | 60.951 | 16.404 | 1.00 | 54.99 |
| ATOM | 330 | O | GLU | A | 182 | 43.886 | 61.423 | 15.616 | 1.00 | 54.37 |
| ATOM | 331 | CB | GLU | A | 182 | 42.414 | 62.485 | 18.288 | 1.00 | 51.39 |
| ATOM | 332 | CG | GLU | A | 182 | 43.454 | 61.691 | 19.058 | 1.00 | 62.60 |
| ATOM | 333 | CD | GLU | A | 182 | 44.681 | 62.512 | 19.384 | 1.00 | 86.77 |
| ATOM | 334 | OE1 | GLU | A | 182 | 44.539 | 63.740 | 19.582 | 1.00 | 81.39 |
| ATOM | 335 | OE2 | GLU | A | 182 | 45.790 | 61.935 | 19.438 | 1.00 | 83.19 |
| ATOM | 336 | N | VAL | A | 183 | 43.082 | 59.677 | 16.783 | 1.00 | 52.66 |
| ATOM | 337 | CA | VAL | A | 183 | 44.111 | 58.759 | 16.303 | 1.00 | 52.49 |
| ATOM | 338 | C | VAL | A | 183 | 43.936 | 58.373 | 14.838 | 1.00 | 55.93 |
| ATOM | 339 | O | VAL | A | 183 | 44.894 | 58.404 | 14.068 | 1.00 | 55.52 |
| ATOM | 340 | CB | VAL | A | 183 | 44.229 | 57.495 | 17.194 | 1.00 | 56.59 |
| ATOM | 341 | CG1 | VAL | A | 183 | 43.247 | 56.426 | 16.746 | 1.00 | 56.61 |
| ATOM | 342 | CG2 | VAL | A | 183 | 45.655 | 56.955 | 17.173 | 1.00 | 56.30 |
| ATOM | 343 | N | ILE | A | 184 | 42.710 | 58.013 | 14.451 | 1.00 | 52.52 |
| ATOM | 344 | CA | ILE | A | 184 | 42.431 | 57.630 | 13.058 | 1.00 | 51.98 |
| ATOM | 345 | C | ILE | A | 184 | 42.726 | 58.804 | 12.116 | 1.00 | 57.67 |
| ATOM | 346 | O | ILE | A | 184 | 43.305 | 58.624 | 11.041 | 1.00 | 56.90 |
| ATOM | 347 | CB | ILE | A | 184 | 40.961 | 57.197 | 12.864 | 1.00 | 54.44 |
| ATOM | 348 | CG1 | ILE | A | 184 | 40.655 | 55.948 | 13.693 | 1.00 | 54.27 |
| ATOM | 349 | CG2 | ILE | A | 184 | 40.669 | 56.943 | 11.384 | 1.00 | 54.45 |
| ATOM | 350 | CD1 | ILE | A | 184 | 39.583 | 56.164 | 14.718 | 1.00 | 61.71 |
| ATOM | 351 | N | ILE | A | 185 | 42.308 | 60.000 | 12.526 | 1.00 | 55.43 |
| ATOM | 352 | CA | ILE | A | 185 | 42.565 | 61.211 | 11.748 | 1.00 | 55.77 |
| ATOM | 353 | C | ILE | A | 185 | 44.064 | 61.448 | 11.705 | 1.00 | 61.70 |
| ATOM | 354 | O | ILE | A | 185 | 44.650 | 61.570 | 10.633 | 1.00 | 61.40 |
| ATOM | 355 | CB | ILE | A | 185 | 41.913 | 62.444 | 12.387 | 1.00 | 58.49 |
| ATOM | 356 | CG1 | ILE | A | 185 | 40.396 | 62.374 | 12.268 | 1.00 | 58.47 |
| ATOM | 357 | CG2 | ILE | A | 185 | 42.444 | 63.712 | 11.742 | 1.00 | 59.48 |
| ATOM | 358 | CD1 | ILE | A | 185 | 39.672 | 63.091 | 13.375 | 1.00 | 62.47 |
| ATOM | 359 | N | ALA | A | 186 | 44.683 | 61.501 | 12.884 | 1.00 | 59.86 |
| ATOM | 360 | CA | ALA | A | 186 | 46.123 | 61.709 | 12.981 | 1.00 | 60.50 |
| ATOM | 361 | C | ALA | A | 186 | 46.860 | 60.699 | 12.103 | 1.00 | 65.98 |
| ATOM | 362 | O | ALA | A | 186 | 47.648 | 61.078 | 11.236 | 1.00 | 66.01 |
| ATOM | 363 | CB | ALA | A | 186 | 46.585 | 61.598 | 14.438 | 1.00 | 61.28 |
| ATOM | 364 | N | LYS | A | 187 | 46.578 | 59.414 | 12.315 | 1.00 | 63.29 |
| ATOM | 365 | CA | LYS | A | 187 | 47.184 | 58.352 | 11.510 | 1.00 | 63.15 |
| ATOM | 366 | C | LYS | A | 187 | 46.501 | 58.336 | 10.146 | 1.00 | 66.08 |
| ATOM | 367 | O | LYS | A | 187 | 46.793 | 57.491 | 9.299 | 1.00 | 65.76 |
| ATOM | 368 | CB | LYS | A | 187 | 47.012 | 56.989 | 12.196 | 1.00 | 65.90 |
| ATOM | 369 | CG | LYS | A | 187 | 47.289 | 57.004 | 13.701 | 1.00 | 80.86 |
| ATOM | 370 | CD | LYS | A | 187 | 48.684 | 57.531 | 14.000 | 1.00 | 90.00 |
| ATOM | 371 | CE | LYS | A | 187 | 49.221 | 56.967 | 15.302 | 1.00 | 101.35 |
| ATOM | 372 | NZ | LYS | A | 187 | 50.706 | 56.860 | 15.286 | 1.00 | 110.73 |
| ATOM | 373 | N | ASP | A | 188 | 45.590 | 59.286 | 9.957 | 1.00 | 61.72 |
| ATOM | 374 | CA | ASP | A | 188 | 44.809 | 59.426 | 8.722 | 1.00 | 61.25 |
| ATOM | 375 | C | ASP | A | 188 | 44.353 | 58.117 | 8.102 | 1.00 | 62.99 |
| ATOM | 376 | O | ASP | A | 188 | 45.161 | 57.345 | 7.582 | 1.00 | 63.49 |
| ATOM | 377 | CB | ASP | A | 188 | 45.527 | 60.283 | 7.684 | 1.00 | 63.40 |
| ATOM | 378 | CG | ASP | A | 188 | 44.575 | 60.840 | 6.632 | 1.00 | 73.97 |
| ATOM | 379 | OD1 | ASP | A | 188 | 44.986 | 60.974 | 5.456 | 1.00 | 73.66 |
| ATOM | 380 | OD2 | ASP | A | 188 | 43.407 | 61.126 | 6.983 | 1.00 | 80.71 |
| ATOM | 381 | N | GLU | A | 189 | 43.043 | 57.902 | 8.117 | 1.00 | 56.45 |
| ATOM | 382 | CA | GLU | A | 189 | 42.442 | 56.709 | 7.539 | 1.00 | 54.36 |
| ATOM | 383 | C | GLU | A | 189 | 40.964 | 56.713 | 7.882 | 1.00 | 52.02 |
| ATOM | 384 | O | GLU | A | 189 | 40.355 | 55.664 | 8.078 | 1.00 | 50.81 |
| ATOM | 385 | CB | GLU | A | 189 | 43.115 | 55.442 | 8.082 | 1.00 | 56.02 |
| ATOM | 386 | CG | GLU | A | 189 | 43.632 | 55.569 | 9.518 | 1.00 | 69.29 |
| ATOM | 387 | CD | GLU | A | 189 | 44.639 | 54.493 | 9.873 | 1.00 | 93.42 |
| ATOM | 388 | OE1 | GLU | A | 189 | 45.396 | 54.685 | 10.848 | 1.00 | 90.60 |
| ATOM | 389 | OE2 | GLU | A | 189 | 44.679 | 53.460 | 9.169 | 1.00 | 90.55 |
| ATOM | 390 | N | VAL | A | 190 | 40.400 | 57.917 | 7.975 | 1.00 | 44.08 |
| ATOM | 391 | CA | VAL | A | 190 | 38.992 | 58.089 | 8.303 | 1.00 | 41.86 |
| ATOM | 392 | C | VAL | A | 190 | 38.106 | 57.427 | 7.258 | 1.00 | 41.38 |
| ATOM | 393 | O | VAL | A | 190 | 37.167 | 56.714 | 7.589 | 1.00 | 40.04 |

TABLE 4-continued

Structural coordinates for AKT3lkd(T305D, S472D) (SEQ ID NO:2).

| ATOM | 394 | CB | VAL | A | 190 | 38.616 | 59.594 | 8.401 | 1.00 | 45.15 |
|---|---|---|---|---|---|---|---|---|---|---|
| ATOM | 395 | CG1 | VAL | A | 190 | 37.171 | 59.745 | 8.858 | 1.00 | 44.76 |
| ATOM | 396 | CG2 | VAL | A | 190 | 39.576 | 60.326 | 9.346 | 1.00 | 44.92 |
| ATOM | 397 | N | ALA | A | 191 | 38.406 | 57.682 | 5.990 | 1.00 | 38.52 |
| ATOM | 398 | CA | ALA | A | 191 | 37.638 | 57.108 | 4.898 | 1.00 | 38.88 |
| ATOM | 399 | C | ALA | A | 191 | 37.843 | 55.588 | 4.841 | 1.00 | 43.69 |
| ATOM | 400 | O | ALA | A | 191 | 36.886 | 54.843 | 4.664 | 1.00 | 43.05 |
| ATOM | 401 | CB | ALA | A | 191 | 38.027 | 57.740 | 3.581 | 1.00 | 39.66 |
| ATOM | 402 | N | HIS | A | 192 | 39.094 | 55.148 | 4.987 | 1.00 | 42.98 |
| ATOM | 403 | CA | HIS | A | 192 | 39.407 | 53.707 | 4.979 | 1.00 | 44.10 |
| ATOM | 404 | C | HIS | A | 192 | 38.504 | 53.029 | 5.992 | 1.00 | 43.39 |
| ATOM | 405 | O | HIS | A | 192 | 37.811 | 52.051 | 5.690 | 1.00 | 42.68 |
| ATOM | 406 | CB | HIS | A | 192 | 40.897 | 53.452 | 5.413 | 1.00 | 46.74 |
| ATOM | 407 | CG | HIS | A | 192 | 41.066 | 52.277 | 6.351 | 1.00 | 51.95 |
| ATOM | 408 | ND1 | HIS | A | 192 | 41.456 | 52.418 | 7.670 | 1.00 | 54.54 |
| ATOM | 409 | CD2 | HIS | A | 192 | 40.873 | 50.947 | 6.159 | 1.00 | 54.58 |
| ATOM | 410 | CE1 | HIS | A | 192 | 41.513 | 51.227 | 8.244 | 1.00 | 54.31 |
| ATOM | 411 | NE2 | HIS | A | 192 | 41.155 | 50.318 | 7.352 | 1.00 | 54.72 |
| ATOM | 412 | N | THR | A | 193 | 38.505 | 53.583 | 7.189 | 1.00 | 37.40 |
| ATOM | 413 | CA | THR | A | 193 | 37.742 | 53.043 | 8.298 | 1.00 | 36.29 |
| ATOM | 414 | C | THR | A | 193 | 36.242 | 52.926 | 8.075 | 1.00 | 39.45 |
| ATOM | 415 | O | THR | A | 193 | 35.653 | 51.879 | 8.313 | 1.00 | 38.28 |
| ATOM | 416 | CB | THR | A | 193 | 38.019 | 53.807 | 9.540 | 1.00 | 43.15 |
| ATOM | 417 | OG1 | THR | A | 193 | 39.441 | 53.859 | 9.743 | 1.00 | 39.45 |
| ATOM | 418 | CG2 | THR | A | 193 | 37.329 | 53.153 | 10.736 | 1.00 | 40.56 |
| ATOM | 419 | N | LEU | A | 194 | 35.616 | 54.009 | 7.638 | 1.00 | 34.24 |
| ATOM | 420 | CA | LEU | A | 194 | 34.177 | 53.986 | 7.380 | 1.00 | 33.51 |
| ATOM | 421 | C | LEU | A | 194 | 33.825 | 52.943 | 6.307 | 1.00 | 34.74 |
| ATOM | 422 | O | LEU | A | 194 | 32.763 | 52.313 | 6.344 | 1.00 | 33.92 |
| ATOM | 423 | CB | LEU | A | 194 | 33.710 | 55.367 | 6.919 | 1.00 | 33.61 |
| ATOM | 424 | CG | LEU | A | 194 | 33.267 | 56.307 | 8.047 | 1.00 | 39.29 |
| ATOM | 425 | CD1 | LEU | A | 194 | 34.170 | 56.217 | 9.248 | 1.00 | 40.34 |
| ATOM | 426 | CD2 | LEU | A | 194 | 33.192 | 57.734 | 7.540 | 1.00 | 42.18 |
| ATOM | 427 | N | THR | A | 195 | 34.717 | 52.787 | 5.352 | 1.00 | 31.19 |
| ATOM | 428 | CA | THR | A | 195 | 34.518 | 51.838 | 4.279 | 1.00 | 32.36 |
| ATOM | 429 | C | THR | A | 195 | 34.568 | 50.422 | 4.800 | 1.00 | 36.45 |
| ATOM | 430 | O | THR | A | 195 | 33.707 | 49.606 | 4.474 | 1.00 | 33.91 |
| ATOM | 431 | CB | THR | A | 195 | 35.570 | 52.012 | 3.200 | 1.00 | 42.11 |
| ATOM | 432 | OG1 | THR | A | 195 | 35.264 | 53.179 | 2.433 | 1.00 | 43.48 |
| ATOM | 433 | CG2 | THR | A | 195 | 35.593 | 50.805 | 2.275 | 1.00 | 43.19 |
| ATOM | 434 | N | GLU | A | 196 | 35.581 | 50.116 | 5.600 | 1.00 | 35.12 |
| ATOM | 435 | CA | GLU | A | 196 | 35.687 | 48.752 | 6.130 | 1.00 | 35.33 |
| ATOM | 436 | C | GLU | A | 196 | 34.500 | 48.447 | 7.068 | 1.00 | 38.77 |
| ATOM | 437 | O | GLU | A | 196 | 33.975 | 47.333 | 7.076 | 1.00 | 36.71 |
| ATOM | 438 | CB | GLU | A | 196 | 37.056 | 48.498 | 6.783 | 1.00 | 36.99 |
| ATOM | 439 | CG | GLU | A | 196 | 38.277 | 48.673 | 5.819 | 1.00 | 46.56 |
| ATOM | 440 | CD | GLU | A | 196 | 38.231 | 47.775 | 4.549 | 1.00 | 63.05 |
| ATOM | 441 | OE1 | GLU | A | 196 | 37.994 | 46.542 | 4.658 | 1.00 | 47.32 |
| ATOM | 442 | OE2 | GLU | A | 196 | 38.561 | 48.290 | 3.458 | 1.00 | 53.25 |
| ATOM | 443 | N | SER | A | 197 | 34.005 | 49.474 | 7.756 | 1.00 | 34.76 |
| ATOM | 444 | CA | SER | A | 197 | 32.848 | 49.319 | 8.628 | 1.00 | 34.46 |
| ATOM | 445 | C | SER | A | 197 | 31.642 | 48.905 | 7.797 | 1.00 | 36.61 |
| ATOM | 446 | O | SER | A | 197 | 30.914 | 47.965 | 8.148 | 1.00 | 34.63 |
| ATOM | 447 | CB | SER | A | 197 | 32.551 | 50.645 | 9.350 | 1.00 | 39.30 |
| ATOM | 448 | OG | SER | A | 197 | 31.183 | 50.737 | 9.700 | 1.00 | 48.59 |
| ATOM | 449 | N | ARG | A | 198 | 31.417 | 49.630 | 6.706 | 1.00 | 31.99 |
| ATOM | 450 | CA | ARG | A | 198 | 30.319 | 49.330 | 5.794 | 1.00 | 32.94 |
| ATOM | 451 | C | ARG | A | 198 | 30.379 | 47.872 | 5.303 | 1.00 | 35.05 |
| ATOM | 452 | O | ARG | A | 198 | 29.353 | 47.170 | 5.247 | 1.00 | 35.77 |
| ATOM | 453 | CB | ARG | A | 198 | 30.383 | 50.278 | 4.585 | 1.00 | 35.23 |
| ATOM | 454 | CG | ARG | A | 198 | 29.986 | 51.716 | 4.886 | 1.00 | 49.54 |
| ATOM | 455 | CD | ARG | A | 198 | 29.974 | 52.565 | 3.609 | 1.00 | 63.96 |
| ATOM | 456 | NE | ARG | A | 198 | 31.249 | 53.246 | 3.381 | 1.00 | 75.40 |
| ATOM | 457 | CZ | ARG | A | 198 | 31.405 | 54.567 | 3.399 | 1.00 | 90.89 |
| ATOM | 458 | NH1 | ARG | A | 198 | 30.364 | 55.356 | 3.625 | 1.00 | 80.68 |
| ATOM | 459 | NH2 | ARG | A | 198 | 32.603 | 55.098 | 3.188 | 1.00 | 77.14 |
| ATOM | 460 | N | VAL | A | 199 | 31.576 | 47.412 | 4.961 | 1.00 | 30.87 |
| ATOM | 461 | CA | VAL | A | 199 | 31.736 | 46.040 | 4.468 | 1.00 | 30.42 |
| ATOM | 462 | C | VAL | A | 199 | 31.285 | 45.002 | 5.489 | 1.00 | 32.96 |
| ATOM | 463 | O | VAL | A | 199 | 30.483 | 44.128 | 5.176 | 1.00 | 33.43 |
| ATOM | 464 | CB | VAL | A | 199 | 33.200 | 45.745 | 4.038 | 1.00 | 33.56 |
| ATOM | 465 | CG1 | VAL | A | 199 | 33.371 | 44.228 | 3.723 | 1.00 | 33.02 |
| ATOM | 466 | CG2 | VAL | A | 199 | 33.569 | 46.597 | 2.823 | 1.00 | 33.46 |
| ATOM | 467 | N | LEU | A | 200 | 31.811 | 45.091 | 6.712 | 1.00 | 30.51 |
| ATOM | 468 | CA | LEU | A | 200 | 31.490 | 44.100 | 7.750 | 1.00 | 29.13 |
| ATOM | 469 | C | LEU | A | 200 | 30.030 | 44.205 | 8.233 | 1.00 | 32.00 |
| ATOM | 470 | O | LEU | A | 200 | 29.458 | 43.248 | 8.753 | 1.00 | 31.78 |
| ATOM | 471 | CB | LEU | A | 200 | 32.467 | 44.222 | 8.932 | 1.00 | 28.76 |

TABLE 4-continued

Structural coordinates for AKT3lkd(T305D, S472D) (SEQ ID NO:2).

| ATOM | 472 | CG | LEU | A | 200 | 33.930 | 43.899 | 8.554 | 1.00 | 32.44 |
|---|---|---|---|---|---|---|---|---|---|---|
| ATOM | 473 | CD1 | LEU | A | 200 | 34.886 | 44.096 | 9.730 | 1.00 | 32.70 |
| ATOM | 474 | CD2 | LEU | A | 200 | 34.029 | 42.479 | 8.017 | 1.00 | 34.09 |
| ATOM | 475 | N | LYS | A | 201 | 29.447 | 45.381 | 8.046 | 1.00 | 29.97 |
| ATOM | 476 | CA | LYS | A | 201 | 28.065 | 45.636 | 8.439 | 1.00 | 30.53 |
| ATOM | 477 | C | LYS | A | 201 | 27.073 | 45.066 | 7.440 | 1.00 | 34.20 |
| ATOM | 478 | O | LYS | A | 201 | 26.024 | 44.550 | 7.829 | 1.00 | 33.54 |
| ATOM | 479 | CB | LYS | A | 201 | 27.831 | 47.141 | 8.531 | 1.00 | 34.67 |
| ATOM | 480 | CG | LYS | A | 201 | 26.665 | 47.541 | 9.394 | 1.00 | 44.83 |
| ATOM | 481 | CD | LYS | A | 201 | 26.795 | 49.003 | 9.800 | 1.00 | 54.74 |
| ATOM | 482 | CE | LYS | A | 201 | 25.765 | 49.389 | 10.848 | 1.00 | 64.48 |
| ATOM | 483 | NZ | LYS | A | 201 | 25.827 | 50.842 | 11.153 | 1.00 | 72.31 |
| ATOM | 484 | N | ASN | A | 202 | 27.404 | 45.194 | 6.149 | 1.00 | 31.69 |
| ATOM | 485 | CA | ASN | A | 202 | 26.506 | 44.832 | 5.049 | 1.00 | 31.17 |
| ATOM | 486 | C | ASN | A | 202 | 26.759 | 43.484 | 4.403 | 1.00 | 34.18 |
| ATOM | 487 | O | ASN | A | 202 | 26.118 | 43.144 | 3.413 | 1.00 | 34.67 |
| ATOM | 488 | CB | ASN | A | 202 | 26.563 | 45.907 | 3.957 | 1.00 | 32.53 |
| ATOM | 489 | CG | ASN | A | 202 | 25.783 | 47.148 | 4.324 | 1.00 | 62.80 |
| ATOM | 490 | OD1 | ASN | A | 202 | 24.918 | 47.596 | 3.573 | 1.00 | 64.85 |
| ATOM | 491 | ND2 | ASN | A | 202 | 26.075 | 47.702 | 5.489 | 1.00 | 54.23 |
| ATOM | 492 | N | THR | A | 203 | 27.725 | 42.741 | 4.920 | 1.00 | 27.80 |
| ATOM | 493 | CA | THR | A | 203 | 28.018 | 41.418 | 4.392 | 1.00 | 27.49 |
| ATOM | 494 | C | THR | A | 203 | 27.720 | 40.379 | 5.452 | 1.00 | 31.97 |
| ATOM | 495 | O | THR | A | 203 | 27.713 | 40.680 | 6.657 | 1.00 | 32.53 |
| ATOM | 496 | CB | THR | A | 203 | 29.494 | 41.290 | 3.999 | 1.00 | 31.45 |
| ATOM | 497 | OG1 | THR | A | 203 | 30.308 | 41.540 | 5.147 | 1.00 | 34.38 |
| ATOM | 498 | CG2 | THR | A | 203 | 29.847 | 42.277 | 2.907 | 1.00 | 30.95 |
| ATOM | 499 | N | ARG | A | 204 | 27.505 | 39.146 | 5.014 | 1.00 | 28.09 |
| ATOM | 500 | CA | ARG | A | 204 | 27.251 | 38.033 | 5.926 | 1.00 | 27.37 |
| ATOM | 501 | C | ARG | A | 204 | 27.944 | 36.806 | 5.373 | 1.00 | 27.86 |
| ATOM | 502 | O | ARG | A | 204 | 27.587 | 36.322 | 4.304 | 1.00 | 28.16 |
| ATOM | 503 | CB | ARG | A | 204 | 25.753 | 37.760 | 6.028 | 1.00 | 31.61 |
| ATOM | 504 | CG | ARG | A | 204 | 25.391 | 36.524 | 6.828 | 1.00 | 49.17 |
| ATOM | 505 | CD | ARG | A | 204 | 23.917 | 36.146 | 6.643 | 1.00 | 66.78 |
| ATOM | 506 | NE | ARG | A | 204 | 23.088 | 36.629 | 7.747 | 1.00 | 81.26 |
| ATOM | 507 | CZ | ARG | A | 204 | 22.956 | 36.003 | 8.912 | 1.00 | 98.48 |
| ATOM | 508 | NH1 | ARG | A | 204 | 23.591 | 34.858 | 9.127 | 1.00 | 86.57 |
| ATOM | 509 | NH2 | ARG | A | 204 | 22.186 | 36.518 | 9.863 | 1.00 | 87.43 |
| ATOM | 510 | N | HIS | A | 205 | 28.938 | 36.316 | 6.102 | 1.00 | 22.04 |
| ATOM | 511 | CA | HIS | A | 205 | 29.671 | 35.129 | 5.655 | 1.00 | 20.60 |
| ATOM | 512 | C | HIS | A | 205 | 30.194 | 34.401 | 6.891 | 1.00 | 22.38 |
| ATOM | 513 | O | HIS | A | 205 | 30.549 | 35.034 | 7.904 | 1.00 | 23.80 |
| ATOM | 514 | CB | HIS | A | 205 | 30.849 | 35.560 | 4.775 | 1.00 | 20.39 |
| ATOM | 515 | CG | HIS | A | 205 | 31.460 | 34.425 | 4.017 | 1.00 | 21.42 |
| ATOM | 516 | ND1 | HIS | A | 205 | 32.438 | 33.609 | 4.550 | 1.00 | 22.77 |
| ATOM | 517 | CD2 | HIS | A | 205 | 31.151 | 33.912 | 2.805 | 1.00 | 21.30 |
| ATOM | 518 | CE1 | HIS | A | 205 | 32.729 | 32.659 | 3.669 | 1.00 | 20.84 |
| ATOM | 519 | NE2 | HIS | A | 205 | 31.970 | 32.834 | 2.600 | 1.00 | 21.01 |
| ATOM | 520 | N | PRO | A | 206 | 30.255 | 33.076 | 6.818 | 1.00 | 21.28 |
| ATOM | 521 | CA | PRO | A | 206 | 30.710 | 32.299 | 7.943 | 1.00 | 21.23 |
| ATOM | 522 | C | PRO | A | 206 | 32.044 | 32.730 | 8.498 | 1.00 | 22.16 |
| ATOM | 523 | O | PRO | A | 206 | 32.291 | 32.565 | 9.695 | 1.00 | 23.28 |
| ATOM | 524 | CB | PRO | A | 206 | 30.819 | 30.861 | 7.381 | 1.00 | 23.44 |
| ATOM | 525 | CG | PRO | A | 206 | 29.926 | 30.815 | 6.233 | 1.00 | 28.41 |
| ATOM | 526 | CD | PRO | A | 206 | 29.758 | 32.240 | 5.712 | 1.00 | 23.10 |
| ATOM | 527 | N | PHE | A | 207 | 32.936 | 33.233 | 7.629 | 1.00 | 18.38 |
| ATOM | 528 | CA | PHE | A | 207 | 34.278 | 33.549 | 8.050 | 1.00 | 16.96 |
| ATOM | 529 | C | PHE | A | 207 | 34.614 | 35.023 | 8.143 | 1.00 | 18.43 |
| ATOM | 530 | O | PHE | A | 207 | 35.764 | 35.377 | 8.320 | 1.00 | 19.40 |
| ATOM | 531 | CB | PHE | A | 207 | 35.346 | 32.759 | 7.196 | 1.00 | 17.61 |
| ATOM | 532 | CG | PHE | A | 207 | 35.053 | 31.266 | 7.118 | 1.00 | 17.46 |
| ATOM | 533 | CD1 | PHE | A | 207 | 34.879 | 30.530 | 8.268 | 1.00 | 19.14 |
| ATOM | 534 | CD2 | PHE | A | 207 | 34.742 | 30.671 | 5.896 | 1.00 | 17.91 |
| ATOM | 535 | CE1 | PHE | A | 207 | 34.496 | 29.171 | 8.203 | 1.00 | 19.50 |
| ATOM | 536 | CE2 | PHE | A | 207 | 34.370 | 29.325 | 5.825 | 1.00 | 19.27 |
| ATOM | 537 | CZ | PHE | A | 207 | 34.281 | 28.574 | 6.978 | 1.00 | 18.36 |
| ATOM | 538 | N | LEU | A | 208 | 33.584 | 35.865 | 8.118 | 1.00 | 18.44 |
| ATOM | 539 | CA | LEU | A | 208 | 33.764 | 37.316 | 8.265 | 1.00 | 19.22 |
| ATOM | 540 | C | LEU | A | 208 | 33.090 | 37.709 | 9.581 | 1.00 | 22.18 |
| ATOM | 541 | O | LEU | A | 208 | 31.985 | 37.249 | 9.849 | 1.00 | 23.35 |
| ATOM | 542 | CB | LEU | A | 208 | 33.038 | 38.044 | 7.143 | 1.00 | 19.63 |
| ATOM | 543 | CG | LEU | A | 208 | 33.712 | 38.073 | 5.765 | 1.00 | 24.84 |
| ATOM | 544 | CD1 | LEU | A | 208 | 32.832 | 38.826 | 4.748 | 1.00 | 25.97 |
| ATOM | 545 | CD2 | LEU | A | 208 | 35.114 | 38.707 | 5.838 | 1.00 | 27.32 |
| ATOM | 546 | N | THR | A | 209 | 33.746 | 38.556 | 10.382 | 1.00 | 20.31 |
| ATOM | 547 | CA | THR | A | 209 | 33.160 | 39.013 | 11.653 | 1.00 | 20.45 |
| ATOM | 548 | C | THR | A | 209 | 32.027 | 39.960 | 11.358 | 1.00 | 27.39 |
| ATOM | 549 | O | THR | A | 209 | 32.206 | 40.920 | 10.630 | 1.00 | 27.71 |

TABLE 4-continued

Structural coordinates for AKT3lkd(T305D, S472D) (SEQ ID NO:2).

| ATOM | 550 | CB | THR | A | 209 | 34.221 | 39.732 | 12.497 | 1.00 | 30.38 |
|---|---|---|---|---|---|---|---|---|---|---|
| ATOM | 551 | OG1 | THR | A | 209 | 35.305 | 38.824 | 12.751 | 1.00 | 31.52 |
| ATOM | 552 | CG2 | THR | A | 209 | 33.630 | 40.177 | 13.811 | 1.00 | 32.83 |
| ATOM | 553 | N | SER | A | 210 | 30.833 | 39.662 | 11.861 | 1.00 | 23.92 |
| ATOM | 554 | CA | SER | A | 210 | 29.724 | 40.541 | 11.579 | 1.00 | 25.09 |
| ATOM | 555 | C | SER | A | 210 | 29.745 | 41.770 | 12.478 | 1.00 | 29.83 |
| ATOM | 556 | O | SER | A | 210 | 29.963 | 41.661 | 13.694 | 1.00 | 29.35 |
| ATOM | 557 | CB | SER | A | 210 | 28.392 | 39.813 | 11.688 | 1.00 | 30.30 |
| ATOM | 558 | OG | SER | A | 210 | 28.321 | 39.021 | 12.857 | 1.00 | 43.73 |
| ATOM | 559 | N | LEU | A | 211 | 29.523 | 42.926 | 11.868 | 1.00 | 26.86 |
| ATOM | 560 | CA | LEU | A | 211 | 29.441 | 44.206 | 12.587 | 1.00 | 28.45 |
| ATOM | 561 | C | LEU | A | 211 | 27.945 | 44.498 | 12.706 | 1.00 | 32.91 |
| ATOM | 562 | O | LEU | A | 211 | 27.233 | 44.551 | 11.709 | 1.00 | 31.21 |
| ATOM | 563 | CB | LEU | A | 211 | 30.166 | 45.295 | 11.797 | 1.00 | 29.84 |
| ATOM | 564 | CG | LEU | A | 211 | 30.116 | 46.763 | 12.228 | 1.00 | 36.89 |
| ATOM | 565 | CD1 | LEU | A | 211 | 29.782 | 46.897 | 13.691 | 1.00 | 38.71 |
| ATOM | 566 | CD2 | LEU | A | 211 | 31.453 | 47.416 | 11.907 | 1.00 | 40.48 |
| ATOM | 567 | N | LYS | A | 212 | 27.451 | 44.554 | 13.941 | 1.00 | 31.55 |
| ATOM | 568 | CA | LYS | A | 212 | 26.025 | 44.714 | 14.186 | 1.00 | 32.25 |
| ATOM | 569 | C | LYS | A | 212 | 25.604 | 46.186 | 14.269 | 1.00 | 37.28 |
| ATOM | 570 | O | LYS | A | 212 | 24.640 | 46.591 | 13.622 | 1.00 | 38.26 |
| ATOM | 571 | CB | LYS | A | 212 | 25.620 | 43.958 | 15.456 | 1.00 | 35.47 |
| ATOM | 572 | CG | LYS | A | 212 | 24.914 | 42.625 | 15.201 | 1.00 | 52.68 |
| ATOM | 573 | CD | LYS | A | 212 | 25.656 | 41.795 | 14.158 | 1.00 | 60.97 |
| ATOM | 574 | CE | LYS | A | 212 | 25.374 | 40.303 | 14.320 | 1.00 | 70.06 |
| ATOM | 575 | NZ | LYS | A | 212 | 26.559 | 39.562 | 14.854 | 1.00 | 77.69 |
| ATOM | 576 | N | TYR | A | 213 | 26.345 | 46.980 | 15.039 | 1.00 | 33.99 |
| ATOM | 577 | CA | TYR | A | 213 | 26.050 | 48.418 | 15.200 | 1.00 | 33.42 |
| ATOM | 578 | C | TYR | A | 213 | 27.309 | 49.286 | 15.115 | 1.00 | 36.85 |
| ATOM | 579 | O | TYR | A | 213 | 28.403 | 48.859 | 15.463 | 1.00 | 34.71 |
| ATOM | 580 | CB | TYR | A | 213 | 25.337 | 48.705 | 16.549 | 1.00 | 34.45 |
| ATOM | 581 | CG | TYR | A | 213 | 24.217 | 47.754 | 16.907 | 1.00 | 35.73 |
| ATOM | 582 | CD1 | TYR | A | 213 | 23.039 | 47.723 | 16.170 | 1.00 | 37.99 |
| ATOM | 583 | CD2 | TYR | A | 213 | 24.302 | 46.951 | 18.030 | 1.00 | 36.09 |
| ATOM | 584 | CE1 | TYR | A | 213 | 22.011 | 46.859 | 16.514 | 1.00 | 39.53 |
| ATOM | 585 | CE2 | TYR | A | 213 | 23.290 | 46.093 | 18.377 | 1.00 | 36.72 |
| ATOM | 586 | CZ | TYR | A | 213 | 22.137 | 46.057 | 17.623 | 1.00 | 46.40 |
| ATOM | 587 | OH | TYR | A | 213 | 21.113 | 45.203 | 17.981 | 1.00 | 49.08 |
| ATOM | 588 | N | SER | A | 214 | 27.133 | 50.542 | 14.719 | 1.00 | 34.09 |
| ATOM | 589 | CA | SER | A | 214 | 28.227 | 51.488 | 14.711 | 1.00 | 34.89 |
| ATOM | 590 | C | SER | A | 214 | 27.659 | 52.789 | 15.220 | 1.00 | 41.60 |
| ATOM | 591 | O | SER | A | 214 | 26.501 | 53.117 | 14.939 | 1.00 | 41.30 |
| ATOM | 592 | CB | SER | A | 214 | 28.819 | 51.662 | 13.316 | 1.00 | 40.86 |
| ATOM | 593 | OG | SER | A | 214 | 28.031 | 52.542 | 12.536 | 1.00 | 50.61 |
| ATOM | 594 | N | PHE | A | 215 | 28.419 | 53.480 | 16.051 | 1.00 | 39.73 |
| ATOM | 595 | CA | PHE | A | 215 | 27.934 | 54.724 | 16.608 | 1.00 | 40.13 |
| ATOM | 596 | C | PHE | A | 215 | 29.003 | 55.704 | 16.986 | 1.00 | 46.28 |
| ATOM | 597 | O | PHE | A | 215 | 30.197 | 55.369 | 17.061 | 1.00 | 43.90 |
| ATOM | 598 | CB | PHE | A | 215 | 26.869 | 54.526 | 17.696 | 1.00 | 41.35 |
| ATOM | 599 | CG | PHE | A | 215 | 27.386 | 53.894 | 18.957 | 1.00 | 42.31 |
| ATOM | 600 | CD1 | PHE | A | 215 | 27.164 | 52.545 | 19.214 | 1.00 | 44.66 |
| ATOM | 601 | CD2 | PHE | A | 215 | 28.033 | 54.656 | 19.918 | 1.00 | 44.12 |
| ATOM | 602 | CE1 | PHE | A | 215 | 27.632 | 51.962 | 20.373 | 1.00 | 45.05 |
| ATOM | 603 | CE2 | PHE | A | 215 | 28.508 | 54.072 | 21.087 | 1.00 | 46.76 |
| ATOM | 604 | CZ | PHE | A | 215 | 28.301 | 52.726 | 21.313 | 1.00 | 44.74 |
| ATOM | 605 | N | GLN | A | 216 | 28.571 | 56.942 | 17.159 | 1.00 | 46.12 |
| ATOM | 606 | CA | GLN | A | 216 | 29.458 | 58.051 | 17.376 | 1.00 | 47.54 |
| ATOM | 607 | C | GLN | A | 216 | 29.493 | 58.563 | 18.813 | 1.00 | 52.31 |
| ATOM | 608 | O | GLN | A | 216 | 28.460 | 58.677 | 19.475 | 1.00 | 51.30 |
| ATOM | 609 | CB | GLN | A | 216 | 29.010 | 59.203 | 16.457 | 1.00 | 49.49 |
| ATOM | 610 | CG | GLN | A | 216 | 27.476 | 59.222 | 16.208 | 1.00 | 73.10 |
| ATOM | 611 | CD | GLN | A | 216 | 26.950 | 60.592 | 15.793 | 1.00 | 100.92 |
| ATOM | 612 | OE1 | GLN | A | 216 | 27.545 | 61.268 | 14.955 | 1.00 | 98.67 |
| ATOM | 613 | NE2 | GLN | A | 216 | 25.822 | 60.998 | 16.372 | 1.00 | 95.00 |
| ATOM | 614 | N | THR | A | 217 | 30.691 | 58.931 | 19.256 | 1.00 | 50.50 |
| ATOM | 615 | CA | THR | A | 217 | 30.888 | 59.574 | 20.545 | 1.00 | 51.56 |
| ATOM | 616 | C | THR | A | 217 | 31.667 | 60.843 | 20.225 | 1.00 | 56.51 |
| ATOM | 617 | O | THR | A | 217 | 32.145 | 61.012 | 19.100 | 1.00 | 55.75 |
| ATOM | 618 | CB | THR | A | 217 | 31.693 | 58.689 | 21.540 | 1.00 | 62.47 |
| ATOM | 619 | OG1 | THR | A | 217 | 32.888 | 59.372 | 21.936 | 1.00 | 61.25 |
| ATOM | 620 | CG2 | THR | A | 217 | 32.064 | 57.351 | 20.902 | 1.00 | 63.21 |
| ATOM | 621 | N | LYS | A | 218 | 31.762 | 61.754 | 21.183 | 1.00 | 53.96 |
| ATOM | 622 | CA | LYS | A | 218 | 32.468 | 63.002 | 20.941 | 1.00 | 53.57 |
| ATOM | 623 | C | LYS | A | 218 | 33.888 | 62.760 | 20.419 | 1.00 | 56.46 |
| ATOM | 624 | O | LYS | A | 218 | 34.304 | 63.357 | 19.417 | 1.00 | 56.57 |
| ATOM | 625 | CB | LYS | A | 218 | 32.492 | 63.871 | 22.203 | 1.00 | 56.48 |
| ATOM | 626 | CG | LYS | A | 218 | 31.105 | 64.241 | 22.726 | 1.00 | 72.86 |
| ATOM | 627 | CD | LYS | A | 218 | 30.899 | 65.758 | 22.741 | 1.00 | 82.49 |

TABLE 4-continued

Structural coordinates for AKT3lkd(T305D, S472D) (SEQ ID NO:2).

| ATOM | 628 | CE  | LYS | A | 218 | 30.066 | 66.196 | 23.942 | 1.00 | 91.13  |
|------|-----|-----|-----|---|-----|--------|--------|--------|------|--------|
| ATOM | 629 | NZ  | LYS | A | 218 | 30.151 | 67.667 | 24.182 | 1.00 | 98.47  |
| ATOM | 630 | N   | ASP | A | 219 | 34.617 | 61.860 | 21.072 | 1.00 | 51.29  |
| ATOM | 631 | CA  | ASP | A | 219 | 35.993 | 61.585 | 20.682 | 1.00 | 50.43  |
| ATOM | 632 | C   | ASP | A | 219 | 36.258 | 60.128 | 20.283 | 1.00 | 51.16  |
| ATOM | 633 | O   | ASP | A | 219 | 37.406 | 59.744 | 20.055 | 1.00 | 49.51  |
| ATOM | 634 | CB  | ASP | A | 219 | 36.944 | 61.992 | 21.807 | 1.00 | 53.09  |
| ATOM | 635 | CG  | ASP | A | 219 | 36.337 | 61.774 | 23.196 | 1.00 | 68.97  |
| ATOM | 636 | OD1 | ASP | A | 219 | 35.850 | 60.652 | 23.466 | 1.00 | 70.23  |
| ATOM | 637 | OD2 | ASP | A | 219 | 36.333 | 62.733 | 24.006 | 1.00 | 76.33  |
| ATOM | 638 | N   | ARG | A | 220 | 35.207 | 59.322 | 20.209 | 1.00 | 46.61  |
| ATOM | 639 | CA  | ARG | A | 220 | 35.378 | 57.911 | 19.860 | 1.00 | 45.78  |
| ATOM | 640 | C   | ARG | A | 220 | 34.483 | 57.421 | 18.729 | 1.00 | 47.92  |
| ATOM | 641 | O   | ARG | A | 220 | 33.388 | 57.949 | 18.499 | 1.00 | 47.25  |
| ATOM | 642 | CB  | ARG | A | 220 | 35.166 | 57.020 | 21.093 | 1.00 | 46.64  |
| ATOM | 643 | CG  | ARG | A | 220 | 35.605 | 57.649 | 22.408 | 1.00 | 59.29  |
| ATOM | 644 | CD  | ARG | A | 220 | 37.013 | 57.205 | 22.788 | 1.00 | 77.01  |
| ATOM | 645 | NE  | ARG | A | 220 | 37.389 | 57.652 | 24.129 | 1.00 | 92.03  |
| ATOM | 646 | CZ  | ARG | A | 220 | 37.544 | 56.843 | 25.174 | 1.00 | 108.52 |
| ATOM | 647 | NH1 | ARG | A | 220 | 37.347 | 55.536 | 25.042 | 1.00 | 94.49  |
| ATOM | 648 | NH2 | ARG | A | 220 | 37.891 | 57.341 | 26.356 | 1.00 | 97.04  |
| ATOM | 649 | N   | LEU | A | 221 | 34.939 | 56.363 | 18.064 | 1.00 | 43.36  |
| ATOM | 650 | CA  | LEU | A | 221 | 34.163 | 55.696 | 17.023 | 1.00 | 42.02  |
| ATOM | 651 | C   | LEU | A | 221 | 33.930 | 54.291 | 17.569 | 1.00 | 41.50  |
| ATOM | 652 | O   | LEU | A | 221 | 34.884 | 53.600 | 17.894 | 1.00 | 40.05  |
| ATOM | 653 | CB  | LEU | A | 221 | 34.967 | 55.624 | 15.721 | 1.00 | 42.15  |
| ATOM | 654 | CG  | LEU | A | 221 | 34.374 | 56.368 | 14.525 | 1.00 | 47.28  |
| ATOM | 655 | CD1 | LEU | A | 221 | 35.439 | 56.547 | 13.443 | 1.00 | 47.18  |
| ATOM | 656 | CD2 | LEU | A | 221 | 33.171 | 55.584 | 13.985 | 1.00 | 50.42  |
| ATOM | 657 | N   | CYS | A | 222 | 32.667 | 53.910 | 17.742 | 1.00 | 36.46  |
| ATOM | 658 | CA  | CYS | A | 222 | 32.341 | 52.610 | 18.332 | 1.00 | 36.57  |
| ATOM | 659 | C   | CYS | A | 222 | 31.697 | 51.609 | 17.369 | 1.00 | 38.15  |
| ATOM | 660 | O   | CYS | A | 222 | 30.692 | 51.908 | 16.716 | 1.00 | 37.77  |
| ATOM | 661 | CB  | CYS | A | 222 | 31.464 | 52.809 | 19.555 | 1.00 | 37.16  |
| ATOM | 662 | SG  | CYS | A | 222 | 32.151 | 54.070 | 20.684 | 1.00 | 40.93  |
| ATOM | 663 | N   | PHE | A | 223 | 32.261 | 50.398 | 17.340 | 1.00 | 33.04  |
| ATOM | 664 | CA  | PHE | A | 223 | 31.775 | 49.313 | 16.478 | 1.00 | 31.56  |
| ATOM | 665 | C   | PHE | A | 223 | 31.400 | 48.102 | 17.323 | 1.00 | 32.73  |
| ATOM | 666 | O   | PHE | A | 223 | 32.245 | 47.540 | 18.010 | 1.00 | 32.05  |
| ATOM | 667 | CB  | PHE | A | 223 | 32.893 | 48.895 | 15.513 | 1.00 | 33.79  |
| ATOM | 668 | CG  | PHE | A | 223 | 33.313 | 49.979 | 14.574 | 1.00 | 36.33  |
| ATOM | 669 | CD1 | PHE | A | 223 | 32.368 | 50.808 | 13.996 | 1.00 | 39.67  |
| ATOM | 670 | CD2 | PHE | A | 223 | 34.641 | 50.141 | 14.232 | 1.00 | 39.68  |
| ATOM | 671 | CE1 | PHE | A | 223 | 32.744 | 51.794 | 13.109 | 1.00 | 40.61  |
| ATOM | 672 | CE2 | PHE | A | 223 | 35.022 | 51.115 | 13.318 | 1.00 | 42.71  |
| ATOM | 673 | CZ  | PHE | A | 223 | 34.069 | 51.955 | 12.781 | 1.00 | 40.73  |
| ATOM | 674 | N   | VAL | A | 224 | 30.137 | 47.712 | 17.275 | 1.00 | 27.48  |
| ATOM | 675 | CA  | VAL | A | 224 | 29.671 | 46.570 | 18.028 | 1.00 | 27.02  |
| ATOM | 676 | C   | VAL | A | 224 | 29.688 | 45.356 | 17.127 | 1.00 | 30.10  |
| ATOM | 677 | O   | VAL | A | 224 | 28.902 | 45.257 | 16.191 | 1.00 | 28.39  |
| ATOM | 678 | CB  | VAL | A | 224 | 28.268 | 46.785 | 18.576 | 1.00 | 31.24  |
| ATOM | 679 | CG1 | VAL | A | 224 | 27.839 | 45.580 | 19.400 | 1.00 | 31.61  |
| ATOM | 680 | CG2 | VAL | A | 224 | 28.227 | 48.068 | 19.418 | 1.00 | 31.21  |
| ATOM | 681 | N   | MET | A | 225 | 30.593 | 44.433 | 17.425 | 1.00 | 26.26  |
| ATOM | 682 | CA  | MET | A | 225 | 30.803 | 43.276 | 16.564 | 1.00 | 27.14  |
| ATOM | 683 | C   | MET | A | 225 | 30.595 | 41.935 | 17.230 | 1.00 | 28.60  |
| ATOM | 684 | O   | MET | A | 225 | 30.622 | 41.813 | 18.452 | 1.00 | 26.23  |
| ATOM | 685 | CB  | MET | A | 225 | 32.231 | 43.362 | 16.027 | 1.00 | 30.34  |
| ATOM | 686 | CG  | MET | A | 225 | 32.545 | 44.758 | 15.436 | 1.00 | 35.95  |
| ATOM | 687 | SD  | MET | A | 225 | 34.242 | 45.008 | 14.969 | 1.00 | 42.76  |
| ATOM | 688 | CE  | MET | A | 225 | 34.314 | 43.910 | 13.430 | 1.00 | 39.30  |
| ATOM | 689 | N   | GLU | A | 226 | 30.462 | 40.910 | 16.394 | 1.00 | 25.99  |
| ATOM | 690 | CA  | GLU | A | 226 | 30.393 | 39.537 | 16.825 | 1.00 | 25.43  |
| ATOM | 691 | C   | GLU | A | 226 | 31.542 | 39.262 | 17.813 | 1.00 | 28.16  |
| ATOM | 692 | O   | GLU | A | 226 | 32.678 | 39.676 | 17.572 | 1.00 | 27.66  |
| ATOM | 693 | CB  | GLU | A | 226 | 30.635 | 38.663 | 15.570 | 1.00 | 26.94  |
| ATOM | 694 | CG  | GLU | A | 226 | 30.600 | 37.209 | 15.803 | 1.00 | 37.91  |
| ATOM | 695 | CD  | GLU | A | 226 | 30.499 | 36.440 | 14.507 | 1.00 | 40.29  |
| ATOM | 696 | OE1 | GLU | A | 226 | 30.731 | 37.039 | 13.418 | 1.00 | 28.43  |
| ATOM | 697 | OE2 | GLU | A | 226 | 30.209 | 35.234 | 14.571 | 1.00 | 43.30  |
| ATOM | 698 | N   | TYR | A | 227 | 31.248 | 38.578 | 18.928 | 1.00 | 25.68  |
| ATOM | 699 | CA  | TYR | A | 227 | 32.297 | 38.231 | 19.905 | 1.00 | 24.71  |
| ATOM | 700 | C   | TYR | A | 227 | 32.909 | 36.889 | 19.532 | 1.00 | 28.25  |
| ATOM | 701 | O   | TYR | A | 227 | 32.215 | 35.876 | 19.515 | 1.00 | 29.35  |
| ATOM | 702 | CB  | TYR | A | 227 | 31.726 | 38.146 | 21.332 | 1.00 | 24.91  |
| ATOM | 703 | CG  | TYR | A | 227 | 32.742 | 37.692 | 22.346 | 1.00 | 25.71  |
| ATOM | 704 | CD1 | TYR | A | 227 | 33.890 | 38.414 | 22.557 | 1.00 | 26.72  |
| ATOM | 705 | CD2 | TYR | A | 227 | 32.545 | 36.522 | 23.097 | 1.00 | 26.90  |

TABLE 4-continued

Structural coordinates for AKT3lkd(T305D, S472D) (SEQ ID NO:2).

| ATOM | 706 | CE1 | TYR | A | 227 | 34.833 | 38.006 | 23.470 | 1.00 | 27.42 |
|------|-----|-----|-----|---|-----|--------|--------|--------|------|-------|
| ATOM | 707 | CE2 | TYR | A | 227 | 33.495 | 36.101 | 24.012 | 1.00 | 27.21 |
| ATOM | 708 | CZ | TYR | A | 227 | 34.632 | 36.864 | 24.201 | 1.00 | 26.59 |
| ATOM | 709 | OH | TYR | A | 227 | 35.616 | 36.474 | 25.082 | 1.00 | 28.30 |
| ATOM | 710 | N | VAL | A | 228 | 34.208 | 36.908 | 19.250 | 1.00 | 24.81 |
| ATOM | 711 | CA | VAL | A | 228 | 34.975 | 35.732 | 18.801 | 1.00 | 25.95 |
| ATOM | 712 | C | VAL | A | 228 | 36.072 | 35.459 | 19.836 | 1.00 | 26.21 |
| ATOM | 713 | O | VAL | A | 228 | 36.924 | 36.305 | 20.059 | 1.00 | 25.42 |
| ATOM | 714 | CB | VAL | A | 228 | 35.686 | 36.095 | 17.450 | 1.00 | 31.05 |
| ATOM | 715 | CG1 | VAL | A | 228 | 36.437 | 34.904 | 16.903 | 1.00 | 31.86 |
| ATOM | 716 | CG2 | VAL | A | 228 | 34.674 | 36.618 | 16.443 | 1.00 | 31.06 |
| ATOM | 717 | N | ASN | A | 229 | 36.097 | 34.253 | 20.424 | 1.00 | 24.70 |
| ATOM | 718 | CA | ASN | A | 229 | 37.013 | 34.025 | 21.540 | 1.00 | 24.38 |
| ATOM | 719 | C | ASN | A | 229 | 38.006 | 32.879 | 21.440 | 1.00 | 27.13 |
| ATOM | 720 | O | ASN | A | 229 | 38.505 | 32.396 | 22.457 | 1.00 | 25.37 |
| ATOM | 721 | CB | ASN | A | 229 | 36.210 | 33.898 | 22.846 | 1.00 | 25.72 |
| ATOM | 722 | CG | ASN | A | 229 | 35.457 | 32.575 | 22.935 | 1.00 | 35.49 |
| ATOM | 723 | OD1 | ASN | A | 229 | 35.068 | 31.984 | 21.910 | 1.00 | 26.21 |
| ATOM | 724 | ND2 | ASN | A | 229 | 35.294 | 32.074 | 24.150 | 1.00 | 28.99 |
| ATOM | 725 | N | GLY | A | 230 | 38.361 | 32.496 | 20.214 | 1.00 | 22.75 |
| ATOM | 726 | CA | GLY | A | 230 | 39.358 | 31.432 | 20.017 | 1.00 | 22.57 |
| ATOM | 727 | C | GLY | A | 230 | 40.794 | 31.942 | 19.954 | 1.00 | 24.21 |
| ATOM | 728 | O | GLY | A | 230 | 41.738 | 31.153 | 19.797 | 1.00 | 24.51 |
| ATOM | 729 | N | GLY | A | 231 | 40.980 | 33.260 | 20.074 | 1.00 | 23.12 |
| ATOM | 730 | CA | GLY | A | 231 | 42.314 | 33.837 | 20.090 | 1.00 | 23.49 |
| ATOM | 731 | C | GLY | A | 231 | 42.776 | 34.402 | 18.750 | 1.00 | 27.87 |
| ATOM | 732 | O | GLY | A | 231 | 42.320 | 33.965 | 17.677 | 1.00 | 25.69 |
| ATOM | 733 | N | GLU | A | 232 | 43.724 | 35.331 | 18.818 | 1.00 | 25.99 |
| ATOM | 734 | CA | GLU | A | 232 | 44.290 | 35.945 | 17.610 | 1.00 | 25.13 |
| ATOM | 735 | C | GLU | A | 232 | 45.232 | 34.952 | 16.926 | 1.00 | 25.05 |
| ATOM | 736 | O | GLU | A | 232 | 46.071 | 34.327 | 17.581 | 1.00 | 25.20 |
| ATOM | 737 | CB | GLU | A | 232 | 45.089 | 37.187 | 17.982 | 1.00 | 26.84 |
| ATOM | 738 | CG | GLU | A | 232 | 44.256 | 38.291 | 18.589 | 1.00 | 38.59 |
| ATOM | 739 | CD | GLU | A | 232 | 44.920 | 39.650 | 18.455 | 1.00 | 68.94 |
| ATOM | 740 | OE1 | GLU | A | 232 | 46.083 | 39.704 | 17.990 | 1.00 | 68.07 |
| ATOM | 741 | OE2 | GLU | A | 232 | 44.273 | 40.663 | 18.790 | 1.00 | 62.74 |
| ATOM | 742 | N | LEU | A | 233 | 45.137 | 34.817 | 15.602 | 1.00 | 22.97 |
| ATOM | 743 | CA | LEU | A | 233 | 46.041 | 33.889 | 14.912 | 1.00 | 23.26 |
| ATOM | 744 | C | LEU | A | 233 | 47.502 | 34.349 | 15.039 | 1.00 | 27.78 |
| ATOM | 745 | O | LEU | A | 233 | 48.414 | 33.535 | 15.052 | 1.00 | 27.79 |
| ATOM | 746 | CB | LEU | A | 233 | 45.641 | 33.725 | 13.412 | 1.00 | 23.89 |
| ATOM | 747 | CG | LEU | A | 233 | 45.578 | 32.329 | 12.810 | 1.00 | 30.16 |
| ATOM | 748 | CD1 | LEU | A | 233 | 45.334 | 31.224 | 13.848 | 1.00 | 29.73 |
| ATOM | 749 | CD2 | LEU | A | 233 | 44.494 | 32.284 | 11.703 | 1.00 | 32.30 |
| ATOM | 750 | N | PHE | A | 234 | 47.715 | 35.659 | 15.169 | 1.00 | 27.56 |
| ATOM | 751 | CA | PHE | A | 234 | 49.060 | 36.179 | 15.318 | 1.00 | 29.94 |
| ATOM | 752 | C | PHE | A | 234 | 49.665 | 35.555 | 16.572 | 1.00 | 32.68 |
| ATOM | 753 | O | PHE | A | 234 | 50.797 | 35.110 | 16.569 | 1.00 | 32.02 |
| ATOM | 754 | CB | PHE | A | 234 | 49.054 | 37.718 | 15.412 | 1.00 | 33.18 |
| ATOM | 755 | CG | PHE | A | 234 | 50.404 | 38.314 | 15.713 | 1.00 | 37.34 |
| ATOM | 756 | CD1 | PHE | A | 234 | 50.951 | 38.225 | 16.994 | 1.00 | 42.68 |
| ATOM | 757 | CD2 | PHE | A | 234 | 51.125 | 38.972 | 14.726 | 1.00 | 41.95 |
| ATOM | 758 | CE1 | PHE | A | 234 | 52.201 | 38.781 | 17.286 | 1.00 | 44.70 |
| ATOM | 759 | CE2 | PHE | A | 234 | 52.383 | 39.534 | 15.006 | 1.00 | 45.42 |
| ATOM | 760 | CZ | PHE | A | 234 | 52.919 | 39.430 | 16.287 | 1.00 | 44.10 |
| ATOM | 761 | N | PHE | A | 235 | 48.864 | 35.451 | 17.620 | 1.00 | 31.08 |
| ATOM | 762 | CA | PHE | A | 235 | 49.352 | 34.864 | 18.854 | 1.00 | 32.03 |
| ATOM | 763 | C | PHE | A | 235 | 49.531 | 33.363 | 18.801 | 1.00 | 31.49 |
| ATOM | 764 | O | PHE | A | 235 | 50.555 | 32.844 | 19.233 | 1.00 | 28.92 |
| ATOM | 765 | CB | PHE | A | 235 | 48.562 | 35.348 | 20.060 | 1.00 | 35.63 |
| ATOM | 766 | CG | PHE | A | 235 | 48.837 | 36.789 | 20.397 | 1.00 | 39.70 |
| ATOM | 767 | CD1 | PHE | A | 235 | 50.143 | 37.236 | 20.550 | 1.00 | 44.73 |
| ATOM | 768 | CD2 | PHE | A | 235 | 47.803 | 37.715 | 20.483 | 1.00 | 43.55 |
| ATOM | 769 | CE1 | PHE | A | 235 | 50.413 | 38.581 | 20.817 | 1.00 | 46.26 |
| ATOM | 770 | CE2 | PHE | A | 235 | 48.065 | 39.055 | 20.744 | 1.00 | 46.89 |
| ATOM | 771 | CZ | PHE | A | 235 | 49.369 | 39.487 | 20.893 | 1.00 | 45.45 |
| ATOM | 772 | N | HIS | A | 236 | 48.592 | 32.658 | 18.172 | 1.00 | 26.44 |
| ATOM | 773 | CA | HIS | A | 236 | 48.782 | 31.235 | 18.031 | 1.00 | 25.15 |
| ATOM | 774 | C | HIS | A | 236 | 50.042 | 30.957 | 17.216 | 1.00 | 29.18 |
| ATOM | 775 | O | HIS | A | 236 | 50.786 | 30.041 | 17.538 | 1.00 | 28.66 |
| ATOM | 776 | CB | HIS | A | 236 | 47.574 | 30.559 | 17.373 | 1.00 | 25.66 |
| ATOM | 777 | CG | HIS | A | 236 | 46.350 | 30.557 | 18.233 | 1.00 | 28.27 |
| ATOM | 778 | ND1 | HIS | A | 236 | 46.299 | 29.906 | 19.452 | 1.00 | 30.18 |
| ATOM | 779 | CD2 | HIS | A | 236 | 45.142 | 31.150 | 18.069 | 1.00 | 28.54 |
| ATOM | 780 | CE1 | HIS | A | 236 | 45.108 | 30.096 | 19.992 | 1.00 | 29.25 |
| ATOM | 781 | NE2 | HIS | A | 236 | 44.381 | 30.829 | 19.162 | 1.00 | 28.75 |
| ATOM | 782 | N | LEU | A | 237 | 50.255 | 31.714 | 16.126 | 1.00 | 25.31 |
| ATOM | 783 | CA | LEU | A | 237 | 51.426 | 31.461 | 15.281 | 1.00 | 24.08 |

TABLE 4-continued

Structural coordinates for AKT3lkd(T305D, S472D) (SEQ ID NO:2).

| ATOM | 784 | C | LEU | A | 237 | 52.712 | 31.795 | 16.032 | 1.00 | 32.17 |
|---|---|---|---|---|---|---|---|---|---|---|
| ATOM | 785 | O | LEU | A | 237 | 53.687 | 31.062 | 15.943 | 1.00 | 31.02 |
| ATOM | 786 | CB | LEU | A | 237 | 51.354 | 32.228 | 13.961 | 1.00 | 23.13 |
| ATOM | 787 | CG | LEU | A | 237 | 52.446 | 31.903 | 12.944 | 1.00 | 24.64 |
| ATOM | 788 | CD1 | LEU | A | 237 | 52.485 | 30.393 | 12.604 | 1.00 | 24.13 |
| ATOM | 789 | CD2 | LEU | A | 237 | 52.231 | 32.719 | 11.687 | 1.00 | 23.00 |
| ATOM | 790 | N | SER | A | 238 | 52.680 | 32.885 | 16.792 | 1.00 | 32.63 |
| ATOM | 791 | CA | SER | A | 238 | 53.840 | 33.304 | 17.575 | 1.00 | 34.36 |
| ATOM | 792 | C | SER | A | 238 | 54.251 | 32.181 | 18.516 | 1.00 | 41.05 |
| ATOM | 793 | O | SER | A | 238 | 55.432 | 31.836 | 18.614 | 1.00 | 43.05 |
| ATOM | 794 | CB | SER | A | 238 | 53.529 | 34.582 | 18.360 | 1.00 | 39.02 |
| ATOM | 795 | OG | SER | A | 238 | 52.761 | 34.302 | 19.521 | 1.00 | 51.20 |
| ATOM | 796 | N | ARG | A | 239 | 53.267 | 31.571 | 19.161 | 1.00 | 38.04 |
| ATOM | 797 | CA | ARG | A | 239 | 53.528 | 30.459 | 20.080 | 1.00 | 38.48 |
| ATOM | 798 | C | ARG | A | 239 | 53.982 | 29.163 | 19.402 | 1.00 | 41.01 |
| ATOM | 799 | O | ARG | A | 239 | 54.879 | 28.490 | 19.888 | 1.00 | 41.13 |
| ATOM | 800 | CB | ARG | A | 239 | 52.315 | 30.201 | 20.983 | 1.00 | 39.58 |
| ATOM | 801 | CG | ARG | A | 239 | 51.904 | 31.403 | 21.808 | 1.00 | 49.53 |
| ATOM | 802 | CD | ARG | A | 239 | 50.668 | 31.104 | 22.639 | 1.00 | 63.77 |
| ATOM | 803 | NE | ARG | A | 239 | 50.984 | 30.990 | 24.059 | 1.00 | 76.42 |
| ATOM | 804 | CZ | ARG | A | 239 | 50.221 | 30.359 | 24.945 | 1.00 | 93.79 |
| ATOM | 805 | NH1 | ARG | A | 239 | 49.087 | 29.788 | 24.560 | 1.00 | 82.34 |
| ATOM | 806 | NH2 | ARG | A | 239 | 50.587 | 30.303 | 26.218 | 1.00 | 82.70 |
| ATOM | 807 | N | GLU | A | 240 | 53.368 | 28.813 | 18.275 | 1.00 | 35.13 |
| ATOM | 808 | CA | GLU | A | 240 | 53.712 | 27.576 | 17.580 | 1.00 | 32.67 |
| ATOM | 809 | C | GLU | A | 240 | 54.916 | 27.715 | 16.640 | 1.00 | 32.59 |
| ATOM | 810 | O | GLU | A | 240 | 55.494 | 26.719 | 16.218 | 1.00 | 31.66 |
| ATOM | 811 | CB | GLU | A | 240 | 52.503 | 27.049 | 16.799 | 1.00 | 34.19 |
| ATOM | 812 | CG | GLU | A | 240 | 51.265 | 26.837 | 17.648 | 1.00 | 46.63 |
| ATOM | 813 | CD | GLU | A | 240 | 50.884 | 25.377 | 17.754 | 1.00 | 71.29 |
| ATOM | 814 | OE1 | GLU | A | 240 | 51.793 | 24.515 | 17.670 | 1.00 | 59.40 |
| ATOM | 815 | OE2 | GLU | A | 240 | 49.680 | 25.089 | 17.940 | 1.00 | 69.46 |
| ATOM | 816 | N | ARG | A | 241 | 55.249 | 28.960 | 16.293 | 1.00 | 30.07 |
| ATOM | 817 | CA | ARG | A | 241 | 56.353 | 29.294 | 15.380 | 1.00 | 29.71 |
| ATOM | 818 | C | ARG | A | 241 | 55.939 | 29.084 | 13.923 | 1.00 | 29.63 |
| ATOM | 819 | O | ARG | A | 241 | 56.098 | 29.976 | 13.084 | 1.00 | 28.11 |
| ATOM | 820 | CB | ARG | A | 241 | 57.620 | 28.493 | 15.696 | 1.00 | 33.58 |
| ATOM | 821 | CG | ARG | A | 241 | 57.862 | 28.291 | 17.189 | 1.00 | 50.80 |
| ATOM | 822 | CD | ARG | A | 241 | 59.347 | 28.393 | 17.533 | 1.00 | 72.40 |
| ATOM | 823 | NE | ARG | A | 241 | 59.675 | 27.686 | 18.772 | 1.00 | 89.34 |
| ATOM | 824 | CZ | ARG | A | 241 | 60.891 | 27.237 | 19.078 | 1.00 | 107.99 |
| ATOM | 825 | NH1 | ARG | A | 241 | 61.902 | 27.416 | 18.233 | 1.00 | 95.42 |
| ATOM | 826 | NH2 | ARG | A | 241 | 61.096 | 26.597 | 20.226 | 1.00 | 96.72 |
| ATOM | 827 | N | VAL | A | 242 | 55.434 | 27.895 | 13.630 | 1.00 | 26.20 |
| ATOM | 828 | CA | VAL | A | 242 | 54.946 | 27.570 | 12.282 | 1.00 | 25.29 |
| ATOM | 829 | C | VAL | A | 242 | 53.730 | 26.651 | 12.382 | 1.00 | 27.65 |
| ATOM | 830 | O | VAL | A | 242 | 53.587 | 25.887 | 13.343 | 1.00 | 26.45 |
| ATOM | 831 | CB | VAL | A | 242 | 56.039 | 26.869 | 11.377 | 1.00 | 29.38 |
| ATOM | 832 | CG1 | VAL | A | 242 | 57.207 | 27.812 | 11.116 | 1.00 | 30.56 |
| ATOM | 833 | CG2 | VAL | A | 242 | 56.545 | 25.558 | 12.016 | 1.00 | 29.35 |
| ATOM | 834 | N | PHE | A | 243 | 52.840 | 26.738 | 11.390 | 1.00 | 21.01 |
| ATOM | 835 | CA | PHE | A | 243 | 51.695 | 25.818 | 11.309 | 1.00 | 19.51 |
| ATOM | 836 | C | PHE | A | 243 | 52.032 | 24.739 | 10.247 | 1.00 | 20.95 |
| ATOM | 837 | O | PHE | A | 243 | 52.800 | 25.002 | 9.306 | 1.00 | 20.54 |
| ATOM | 838 | CB | PHE | A | 243 | 50.458 | 26.571 | 10.804 | 1.00 | 19.38 |
| ATOM | 839 | CG | PHE | A | 243 | 49.864 | 27.501 | 11.799 | 1.00 | 19.05 |
| ATOM | 840 | CD1 | PHE | A | 243 | 50.163 | 27.408 | 13.162 | 1.00 | 21.63 |
| ATOM | 841 | CD2 | PHE | A | 243 | 49.075 | 28.561 | 11.368 | 1.00 | 19.62 |
| ATOM | 842 | CE1 | PHE | A | 243 | 49.590 | 28.285 | 14.072 | 1.00 | 22.71 |
| ATOM | 843 | CE2 | PHE | A | 243 | 48.515 | 29.450 | 12.267 | 1.00 | 21.18 |
| ATOM | 844 | CZ | PHE | A | 243 | 48.779 | 29.336 | 13.623 | 1.00 | 21.26 |
| ATOM | 845 | N | SER | A | 244 | 51.446 | 23.537 | 10.363 | 1.00 | 17.81 |
| ATOM | 846 | CA | SER | A | 244 | 51.708 | 22.521 | 9.352 | 1.00 | 18.94 |
| ATOM | 847 | C | SER | A | 244 | 51.104 | 23.013 | 8.027 | 1.00 | 20.97 |
| ATOM | 848 | O | SER | A | 244 | 50.253 | 23.916 | 8.024 | 1.00 | 19.66 |
| ATOM | 849 | CB | SER | A | 244 | 51.020 | 21.205 | 9.722 | 1.00 | 21.37 |
| ATOM | 850 | OG | SER | A | 244 | 49.605 | 21.396 | 9.827 | 1.00 | 20.31 |
| ATOM | 851 | N | GLU | A | 245 | 51.460 | 22.358 | 6.930 | 1.00 | 18.26 |
| ATOM | 852 | CA | GLU | A | 245 | 50.836 | 22.693 | 5.653 | 1.00 | 16.48 |
| ATOM | 853 | C | GLU | A | 245 | 49.331 | 22.445 | 5.725 | 1.00 | 19.66 |
| ATOM | 854 | O | GLU | A | 245 | 48.522 | 23.237 | 5.163 | 1.00 | 17.43 |
| ATOM | 855 | CB | GLU | A | 245 | 51.453 | 21.891 | 4.515 | 1.00 | 17.14 |
| ATOM | 856 | CG | GLU | A | 245 | 52.894 | 22.350 | 4.223 | 1.00 | 19.29 |
| ATOM | 857 | CD | GLU | A | 245 | 53.422 | 21.822 | 2.944 | 1.00 | 24.64 |
| ATOM | 858 | OE1 | GLU | A | 245 | 52.613 | 21.590 | 2.014 | 1.00 | 20.16 |
| ATOM | 859 | OE2 | GLU | A | 245 | 54.659 | 21.537 | 2.891 | 1.00 | 20.65 |
| ATOM | 860 | N | ASP | A | 246 | 48.920 | 21.352 | 6.371 | 1.00 | 18.79 |
| ATOM | 861 | CA | ASP | A | 246 | 47.482 | 21.064 | 6.392 | 1.00 | 18.16 |

TABLE 4-continued

Structural coordinates for AKT3lkd(T305D, S472D) (SEQ ID NO:2).

| ATOM | 862 | C | ASP | A | 246 | 46.679 | 22.029 | 7.265 | 1.00 | 19.47 |
|---|---|---|---|---|---|---|---|---|---|---|
| ATOM | 863 | O | ASP | A | 246 | 45.561 | 22.372 | 6.931 | 1.00 | 19.09 |
| ATOM | 864 | CB | ASP | A | 246 | 47.165 | 19.614 | 6.731 | 1.00 | 20.18 |
| ATOM | 865 | CG | ASP | A | 246 | 45.728 | 19.262 | 6.398 | 1.00 | 25.07 |
| ATOM | 866 | OD1 | ASP | A | 246 | 45.337 | 19.424 | 5.217 | 1.00 | 22.85 |
| ATOM | 867 | OD2 | ASP | A | 246 | 44.946 | 18.985 | 7.347 | 1.00 | 29.02 |
| ATOM | 868 | N | ARG | A | 247 | 47.260 | 22.476 | 8.379 | 1.00 | 17.80 |
| ATOM | 869 | CA | ARG | A | 247 | 46.592 | 23.477 | 9.211 | 1.00 | 17.18 |
| ATOM | 870 | C | ARG | A | 247 | 46.475 | 24.786 | 8.412 | 1.00 | 18.02 |
| ATOM | 871 | O | ARG | A | 247 | 45.433 | 25.473 | 8.420 | 1.00 | 18.12 |
| ATOM | 872 | CB | ARG | A | 247 | 47.387 | 23.729 | 10.485 | 1.00 | 18.04 |
| ATOM | 873 | CG | ARG | A | 247 | 46.752 | 24.741 | 11.379 | 1.00 | 22.27 |
| ATOM | 874 | CD | ARG | A | 247 | 47.153 | 24.540 | 12.837 | 1.00 | 23.31 |
| ATOM | 875 | NE | ARG | A | 247 | 46.593 | 25.594 | 13.656 | 1.00 | 21.53 |
| ATOM | 876 | CZ | ARG | A | 247 | 47.048 | 25.914 | 14.863 | 1.00 | 31.13 |
| ATOM | 877 | NH1 | ARG | A | 247 | 48.062 | 25.244 | 15.383 | 1.00 | 30.15 |
| ATOM | 878 | NH2 | ARG | A | 247 | 46.472 | 26.875 | 15.550 | 1.00 | 24.60 |
| ATOM | 879 | N | THR | A | 248 | 47.547 | 25.126 | 7.703 | 1.00 | 15.58 |
| ATOM | 880 | CA | THR | A | 248 | 47.548 | 26.336 | 6.872 | 1.00 | 14.92 |
| ATOM | 881 | C | THR | A | 248 | 46.514 | 26.224 | 5.727 | 1.00 | 17.28 |
| ATOM | 882 | O | THR | A | 248 | 45.859 | 27.197 | 5.391 | 1.00 | 17.32 |
| ATOM | 883 | CB | THR | A | 248 | 48.956 | 26.649 | 6.338 | 1.00 | 18.93 |
| ATOM | 884 | OG1 | THR | A | 248 | 49.839 | 26.765 | 7.461 | 1.00 | 15.92 |
| ATOM | 885 | CG2 | THR | A | 248 | 48.963 | 27.984 | 5.532 | 1.00 | 18.85 |
| ATOM | 886 | N | ARG | A | 249 | 46.385 | 25.018 | 5.159 | 1.00 | 15.04 |
| ATOM | 887 | CA | ARG | A | 249 | 45.398 | 24.747 | 4.100 | 1.00 | 14.88 |
| ATOM | 888 | C | ARG | A | 249 | 43.995 | 24.985 | 4.651 | 1.00 | 15.16 |
| ATOM | 889 | O | ARG | A | 249 | 43.154 | 25.579 | 3.981 | 1.00 | 16.23 |
| ATOM | 890 | CB | ARG | A | 249 | 45.535 | 23.299 | 3.676 | 1.00 | 14.34 |
| ATOM | 891 | CG | ARG | A | 249 | 44.468 | 22.837 | 2.684 | 1.00 | 16.59 |
| ATOM | 892 | CD | ARG | A | 249 | 44.660 | 21.375 | 2.409 | 1.00 | 19.18 |
| ATOM | 893 | NE | ARG | A | 249 | 45.774 | 21.187 | 1.505 | 1.00 | 19.53 |
| ATOM | 894 | CZ | ARG | A | 249 | 46.932 | 20.622 | 1.824 | 1.00 | 17.31 |
| ATOM | 895 | NH1 | ARG | A | 249 | 47.152 | 20.093 | 3.047 | 1.00 | 20.14 |
| ATOM | 896 | NH2 | ARG | A | 249 | 47.890 | 20.537 | 0.892 | 1.00 | 17.64 |
| ATOM | 897 | N | PHE | A | 250 | 43.749 | 24.538 | 5.892 | 1.00 | 14.75 |
| ATOM | 898 | CA | PHE | A | 250 | 42.434 | 24.745 | 6.517 | 1.00 | 14.76 |
| ATOM | 899 | C | PHE | A | 250 | 42.105 | 26.246 | 6.621 | 1.00 | 15.82 |
| ATOM | 900 | O | PHE | A | 250 | 41.053 | 26.726 | 6.143 | 1.00 | 15.93 |
| ATOM | 901 | CB | PHE | A | 250 | 42.423 | 24.125 | 7.905 | 1.00 | 14.83 |
| ATOM | 902 | CG | PHE | A | 250 | 41.160 | 24.432 | 8.704 | 1.00 | 15.84 |
| ATOM | 903 | CD1 | PHE | A | 250 | 39.980 | 23.709 | 8.495 | 1.00 | 19.52 |
| ATOM | 904 | CD2 | PHE | A | 250 | 41.177 | 25.440 | 9.656 | 1.00 | 19.20 |
| ATOM | 905 | CE1 | PHE | A | 250 | 38.826 | 24.039 | 9.218 | 1.00 | 19.75 |
| ATOM | 906 | CE2 | PHE | A | 250 | 40.035 | 25.779 | 10.365 | 1.00 | 22.07 |
| ATOM | 907 | CZ | PHE | A | 250 | 38.869 | 25.075 | 10.155 | 1.00 | 20.65 |
| ATOM | 908 | N | TYR | A | 251 | 43.019 | 27.003 | 7.183 | 1.00 | 14.83 |
| ATOM | 909 | CA | TYR | A | 251 | 42.768 | 28.456 | 7.360 | 1.00 | 14.63 |
| ATOM | 910 | C | TYR | A | 251 | 42.691 | 29.132 | 5.990 | 1.00 | 17.32 |
| ATOM | 911 | O | TYR | A | 251 | 41.808 | 29.969 | 5.735 | 1.00 | 15.44 |
| ATOM | 912 | CB | TYR | A | 251 | 43.888 | 29.090 | 8.172 | 1.00 | 15.15 |
| ATOM | 913 | CG | TYR | A | 251 | 43.937 | 28.627 | 9.619 | 1.00 | 15.60 |
| ATOM | 914 | CD1 | TYR | A | 251 | 42.749 | 28.312 | 10.334 | 1.00 | 18.33 |
| ATOM | 915 | CD2 | TYR | A | 251 | 45.166 | 28.421 | 10.245 | 1.00 | 17.91 |
| ATOM | 916 | CE1 | TYR | A | 251 | 42.804 | 27.853 | 11.662 | 1.00 | 18.43 |
| ATOM | 917 | CE2 | TYR | A | 251 | 45.227 | 27.957 | 11.555 | 1.00 | 19.01 |
| ATOM | 918 | CZ | TYR | A | 251 | 44.043 | 27.687 | 12.255 | 1.00 | 22.04 |
| ATOM | 919 | OH | TYR | A | 251 | 44.129 | 27.196 | 13.560 | 1.00 | 21.68 |
| ATOM | 920 | N | GLY | A | 252 | 43.603 | 28.768 | 5.092 | 1.00 | 14.75 |
| ATOM | 921 | CA | GLY | A | 252 | 43.599 | 29.390 | 3.759 | 1.00 | 14.25 |
| ATOM | 922 | C | GLY | A | 252 | 42.285 | 29.123 | 3.008 | 1.00 | 15.97 |
| ATOM | 923 | O | GLY | A | 252 | 41.767 | 29.995 | 2.311 | 1.00 | 15.33 |
| ATOM | 924 | N | ALA | A | 253 | 41.770 | 27.898 | 3.107 | 1.00 | 15.18 |
| ATOM | 925 | CA | ALA | A | 253 | 40.541 | 27.560 | 2.394 | 1.00 | 14.13 |
| ATOM | 926 | C | ALA | A | 253 | 39.389 | 28.437 | 2.923 | 1.00 | 16.10 |
| ATOM | 927 | O | ALA | A | 253 | 38.590 | 28.949 | 2.153 | 1.00 | 15.71 |
| ATOM | 928 | CB | ALA | A | 253 | 40.230 | 26.080 | 2.574 | 1.00 | 14.56 |
| ATOM | 929 | N | GLU | A | 254 | 39.311 | 28.612 | 4.224 | 1.00 | 15.33 |
| ATOM | 930 | CA | GLU | A | 254 | 38.237 | 29.445 | 4.787 | 1.00 | 14.00 |
| ATOM | 931 | C | GLU | A | 254 | 38.396 | 30.894 | 4.381 | 1.00 | 16.35 |
| ATOM | 932 | O | GLU | A | 254 | 37.409 | 31.579 | 4.052 | 1.00 | 16.72 |
| ATOM | 933 | CB | GLU | A | 254 | 38.183 | 29.258 | 6.303 | 1.00 | 14.71 |
| ATOM | 934 | CG | GLU | A | 254 | 37.873 | 27.751 | 6.656 | 1.00 | 16.18 |
| ATOM | 935 | CD | GLU | A | 254 | 37.428 | 27.542 | 8.097 | 1.00 | 20.74 |
| ATOM | 936 | OE1 | GLU | A | 254 | 36.651 | 26.571 | 8.375 | 1.00 | 18.03 |
| ATOM | 937 | OE2 | GLU | A | 254 | 37.878 | 28.304 | 8.939 | 1.00 | 19.16 |
| ATOM | 938 | N | ILE | A | 255 | 39.644 | 31.371 | 4.322 | 1.00 | 14.02 |
| ATOM | 939 | CA | ILE | A | 255 | 39.876 | 32.732 | 3.837 | 1.00 | 13.81 |

TABLE 4-continued

Structural coordinates for AKT3lkd(T305D, S472D) (SEQ ID NO:2).

| ATOM | 940 | C | ILE | A | 255 | 39.449 | 32.851 | 2.360 | 1.00 | 16.53 |
|------|-----|----|-----|---|-----|--------|--------|--------|------|-------|
| ATOM | 941 | O | ILE | A | 255 | 38.784 | 33.816 | 1.976 | 1.00 | 16.98 |
| ATOM | 942 | CB | ILE | A | 255 | 41.330 | 33.130 | 4.008 | 1.00 | 15.51 |
| ATOM | 943 | CG1 | ILE | A | 255 | 41.663 | 33.159 | 5.539 | 1.00 | 15.52 |
| ATOM | 944 | CG2 | ILE | A | 255 | 41.611 | 34.531 | 3.360 | 1.00 | 15.82 |
| ATOM | 945 | CD1 | ILE | A | 255 | 43.139 | 33.276 | 5.829 | 1.00 | 16.96 |
| ATOM | 946 | N | VAL | A | 256 | 39.801 | 31.861 | 1.554 | 1.00 | 13.81 |
| ATOM | 947 | CA | VAL | A | 256 | 39.434 | 31.856 | 0.143 | 1.00 | 14.24 |
| ATOM | 948 | C | VAL | A | 256 | 37.927 | 31.900 | −0.023 | 1.00 | 17.02 |
| ATOM | 949 | O | VAL | A | 256 | 37.404 | 32.647 | −0.841 | 1.00 | 17.26 |
| ATOM | 950 | CB | VAL | A | 256 | 40.009 | 30.639 | −0.579 | 1.00 | 16.12 |
| ATOM | 951 | CG1 | VAL | A | 256 | 39.360 | 30.485 | −2.032 | 1.00 | 15.06 |
| ATOM | 952 | CG2 | VAL | A | 256 | 41.556 | 30.805 | −0.730 | 1.00 | 15.73 |
| ATOM | 953 | N | SER | A | 257 | 37.224 | 31.139 | 0.793 | 1.00 | 15.54 |
| ATOM | 954 | CA | SER | A | 257 | 35.754 | 31.135 | 0.739 | 1.00 | 16.48 |
| ATOM | 955 | C | SER | A | 257 | 35.193 | 32.564 | 0.960 | 1.00 | 19.19 |
| ATOM | 956 | O | SER | A | 257 | 34.309 | 33.046 | 0.194 | 1.00 | 18.89 |
| ATOM | 957 | CB | SER | A | 257 | 35.195 | 30.159 | 1.777 | 1.00 | 19.64 |
| ATOM | 958 | OG | SER | A | 257 | 33.759 | 30.128 | 1.725 | 1.00 | 18.50 |
| ATOM | 959 | N | ALA | A | 258 | 35.711 | 33.249 | 1.976 | 1.00 | 16.13 |
| ATOM | 960 | CA | ALA | A | 258 | 35.220 | 34.606 | 2.283 | 1.00 | 16.60 |
| ATOM | 961 | C | ALA | A | 258 | 35.547 | 35.583 | 1.146 | 1.00 | 18.38 |
| ATOM | 962 | O | ALA | A | 258 | 34.705 | 36.375 | 0.745 | 1.00 | 18.69 |
| ATOM | 963 | CB | ALA | A | 258 | 35.785 | 35.097 | 3.594 | 1.00 | 17.55 |
| ATOM | 964 | N | LEU | A | 259 | 36.768 | 35.510 | 0.621 | 1.00 | 17.04 |
| ATOM | 965 | CA | LEU | A | 259 | 37.185 | 36.418 | −0.452 | 1.00 | 16.25 |
| ATOM | 966 | C | LEU | A | 259 | 36.383 | 36.138 | −1.742 | 1.00 | 18.54 |
| ATOM | 967 | O | LEU | A | 259 | 36.049 | 37.084 | −2.496 | 1.00 | 19.17 |
| ATOM | 968 | CB | LEU | A | 259 | 38.685 | 36.281 | −0.724 | 1.00 | 16.25 |
| ATOM | 969 | CG | LEU | A | 259 | 39.599 | 36.781 | 0.400 | 1.00 | 18.76 |
| ATOM | 970 | CD1 | LEU | A | 259 | 41.100 | 36.524 | 0.071 | 1.00 | 20.56 |
| ATOM | 971 | CD2 | LEU | A | 259 | 39.343 | 38.292 | 0.679 | 1.00 | 21.95 |
| ATOM | 972 | N | ASP | A | 260 | 36.078 | 34.867 | −2.004 | 1.00 | 17.81 |
| ATOM | 973 | CA | ASP | A | 260 | 35.247 | 34.508 | −3.176 | 1.00 | 17.64 |
| ATOM | 974 | C | ASP | A | 260 | 33.906 | 35.251 | −3.034 | 1.00 | 21.64 |
| ATOM | 975 | O | ASP | A | 260 | 33.445 | 35.945 | −3.972 | 1.00 | 22.02 |
| ATOM | 976 | CB | ASP | A | 260 | 35.025 | 33.001 | −3.217 | 1.00 | 19.11 |
| ATOM | 977 | CG | ASP | A | 260 | 34.187 | 32.554 | −4.400 | 1.00 | 22.44 |
| ATOM | 978 | OD1 | ASP | A | 260 | 34.309 | 33.138 | −5.503 | 1.00 | 23.10 |
| ATOM | 979 | OD2 | ASP | A | 260 | 33.551 | 31.486 | −4.258 | 1.00 | 26.48 |
| ATOM | 980 | N | TYR | A | 261 | 33.312 | 35.155 | −1.849 | 1.00 | 19.22 |
| ATOM | 981 | CA | TYR | A | 261 | 32.032 | 35.835 | −1.576 | 1.00 | 18.95 |
| ATOM | 982 | C | TYR | A | 261 | 32.152 | 37.359 | −1.738 | 1.00 | 22.04 |
| ATOM | 983 | O | TYR | A | 261 | 31.317 | 38.005 | −2.416 | 1.00 | 22.54 |
| ATOM | 984 | CB | TYR | A | 261 | 31.587 | 35.483 | −0.149 | 1.00 | 20.38 |
| ATOM | 985 | CG | TYR | A | 261 | 30.508 | 36.392 | 0.404 | 1.00 | 23.64 |
| ATOM | 986 | CD1 | TYR | A | 261 | 29.194 | 36.229 | 0.039 | 1.00 | 27.40 |
| ATOM | 987 | CD2 | TYR | A | 261 | 30.818 | 37.361 | 1.337 | 1.00 | 24.59 |
| ATOM | 988 | CE1 | TYR | A | 261 | 28.183 | 37.053 | 0.595 | 1.00 | 28.64 |
| ATOM | 989 | CE2 | TYR | A | 261 | 29.823 | 38.180 | 1.897 | 1.00 | 24.81 |
| ATOM | 990 | CZ | TYR | A | 261 | 28.525 | 38.012 | 1.511 | 1.00 | 30.56 |
| ATOM | 991 | OH | TYR | A | 261 | 27.573 | 38.847 | 2.060 | 1.00 | 30.20 |
| ATOM | 992 | N | LEU | A | 262 | 33.177 | 37.954 | −1.139 | 1.00 | 17.35 |
| ATOM | 993 | CA | LEU | A | 262 | 33.359 | 39.406 | −1.242 | 1.00 | 18.62 |
| ATOM | 994 | C | LEU | A | 262 | 33.551 | 39.863 | −2.668 | 1.00 | 22.96 |
| ATOM | 995 | O | LEU | A | 262 | 32.914 | 40.818 | −3.113 | 1.00 | 23.20 |
| ATOM | 996 | CB | LEU | A | 262 | 34.510 | 39.869 | −0.394 | 1.00 | 19.17 |
| ATOM | 997 | CG | LEU | A | 262 | 34.243 | 39.797 | 1.122 | 1.00 | 22.63 |
| ATOM | 998 | CD1 | LEU | A | 262 | 35.502 | 40.139 | 1.847 | 1.00 | 24.49 |
| ATOM | 999 | CD2 | LEU | A | 262 | 33.119 | 40.803 | 1.523 | 1.00 | 25.32 |
| ATOM | 1000 | N | HIS | A | 263 | 34.407 | 39.166 | −3.401 | 1.00 | 20.26 |
| ATOM | 1001 | CA | HIS | A | 263 | 34.693 | 39.546 | −4.772 | 1.00 | 19.31 |
| ATOM | 1002 | C | HIS | A | 263 | 33.469 | 39.363 | −5.644 | 1.00 | 24.41 |
| ATOM | 1003 | O | HIS | A | 263 | 33.251 | 40.155 | −6.563 | 1.00 | 26.29 |
| ATOM | 1004 | CB | HIS | A | 263 | 35.851 | 38.714 | −5.318 | 1.00 | 18.21 |
| ATOM | 1005 | CG | HIS | A | 263 | 37.151 | 39.003 | −4.646 | 1.00 | 18.46 |
| ATOM | 1006 | ND1 | HIS | A | 263 | 38.307 | 38.319 | −4.947 | 1.00 | 19.27 |
| ATOM | 1007 | CD2 | HIS | A | 263 | 37.492 | 39.935 | −3.723 | 1.00 | 18.20 |
| ATOM | 1008 | CE1 | HIS | A | 263 | 39.306 | 38.805 | −4.224 | 1.00 | 18.28 |
| ATOM | 1009 | NE2 | HIS | A | 263 | 38.834 | 39.777 | −3.464 | 1.00 | 18.28 |
| ATOM | 1010 | N | SER | A | 264 | 32.649 | 38.367 | −5.335 | 1.00 | 23.00 |
| ATOM | 1011 | CA | SER | A | 264 | 31.405 | 38.138 | −6.132 | 1.00 | 23.09 |
| ATOM | 1012 | C | SER | A | 264 | 30.448 | 39.329 | −5.975 | 1.00 | 29.81 |
| ATOM | 1013 | O | SER | A | 264 | 29.598 | 39.561 | −6.841 | 1.00 | 30.66 |
| ATOM | 1014 | CB | SER | A | 264 | 30.699 | 36.850 | −5.734 | 1.00 | 25.69 |
| ATOM | 1015 | OG | SER | A | 264 | 30.086 | 36.956 | −4.457 | 1.00 | 33.02 |
| ATOM | 1016 | N | GLY | A | 265 | 30.573 | 40.049 | −4.859 | 1.00 | 26.12 |
| ATOM | 1017 | CA | GLY | A | 265 | 29.780 | 41.249 | −4.596 | 1.00 | 26.62 |

TABLE 4-continued

Structural coordinates for AKT3lkd(T305D, S472D) (SEQ ID NO:2).

| ATOM | 1018 | C   | GLY | A | 265 | 30.550 | 42.519 | −4.965  | 1.00 | 29.92 |
|------|------|-----|-----|---|-----|--------|--------|---------|------|-------|
| ATOM | 1019 | O   | GLY | A | 265 | 30.170 | 43.634 | −4.557  | 1.00 | 31.59 |
| ATOM | 1020 | N   | LYS | A | 266 | 31.634 | 42.353 | −5.724  | 1.00 | 25.51 |
| ATOM | 1021 | CA  | LYS | A | 266 | 32.472 | 43.453 | −6.152  | 1.00 | 25.83 |
| ATOM | 1022 | C   | LYS | A | 266 | 33.088 | 44.261 | −4.994  | 1.00 | 29.58 |
| ATOM | 1023 | O   | LYS | A | 266 | 33.169 | 45.489 | −5.052  | 1.00 | 30.78 |
| ATOM | 1024 | CB  | LYS | A | 266 | 31.683 | 44.400 | −7.100  | 1.00 | 29.23 |
| ATOM | 1025 | CG  | LYS | A | 266 | 30.862 | 43.656 | −8.146  | 1.00 | 36.25 |
| ATOM | 1026 | CD  | LYS | A | 266 | 31.734 | 42.853 | −9.081  | 1.00 | 45.43 |
| ATOM | 1027 | CE  | LYS | A | 266 | 30.984 | 41.618 | −9.609  | 1.00 | 60.82 |
| ATOM | 1028 | NZ  | LYS | A | 266 | 31.907 | 40.574 | −10.153 | 1.00 | 69.59 |
| ATOM | 1029 | N   | ILE | A | 267 | 33.523 | 43.556 | −3.944  | 1.00 | 22.11 |
| ATOM | 1030 | CA  | ILE | A | 267 | 34.141 | 44.172 | −2.827  | 1.00 | 20.65 |
| ATOM | 1031 | C   | ILE | A | 267 | 35.537 | 43.631 | −2.732  | 1.00 | 24.05 |
| ATOM | 1032 | O   | ILE | A | 267 | 35.726 | 42.421 | −2.810  | 1.00 | 24.23 |
| ATOM | 1033 | CB  | ILE | A | 267 | 33.426 | 43.803 | −1.526  | 1.00 | 23.45 |
| ATOM | 1034 | CG1 | ILE | A | 267 | 31.994 | 44.403 | −1.517  | 1.00 | 24.66 |
| ATOM | 1035 | CG2 | ILE | A | 267 | 34.242 | 44.283 | −0.347  | 1.00 | 24.62 |
| ATOM | 1036 | CD1 | ILE | A | 267 | 31.112 | 43.857 | −0.409  | 1.00 | 30.66 |
| ATOM | 1037 | N   | VAL | A | 268 | 36.498 | 44.524 | −2.598  | 1.00 | 20.85 |
| ATOM | 1038 | CA  | VAL | A | 268 | 37.897 | 44.150 | −2.398  | 1.00 | 21.03 |
| ATOM | 1039 | C   | VAL | A | 268 | 38.162 | 44.375 | −0.914  | 1.00 | 24.03 |
| ATOM | 1040 | O   | VAL | A | 268 | 37.904 | 45.487 | −0.393  | 1.00 | 23.98 |
| ATOM | 1041 | CB  | VAL | A | 268 | 38.840 | 45.040 | −3.218  | 1.00 | 24.16 |
| ATOM | 1042 | CG1 | VAL | A | 268 | 40.296 | 44.655 | −2.962  | 1.00 | 23.84 |
| ATOM | 1043 | CG2 | VAL | A | 268 | 38.503 | 44.919 | −4.745  | 1.00 | 24.60 |
| ATOM | 1044 | N   | TYR | A | 269 | 38.631 | 43.346 | −0.197  | 1.00 | 18.99 |
| ATOM | 1045 | CA  | TYR | A | 269 | 38.819 | 43.519 | 1.249   | 1.00 | 18.16 |
| ATOM | 1046 | C   | TYR | A | 269 | 39.920 | 44.482 | 1.661   | 1.00 | 21.76 |
| ATOM | 1047 | O   | TYR | A | 269 | 39.750 | 45.265 | 2.634   | 1.00 | 21.87 |
| ATOM | 1048 | CB  | TYR | A | 269 | 38.992 | 42.157 | 1.934   | 1.00 | 19.55 |
| ATOM | 1049 | CG  | TYR | A | 269 | 38.736 | 42.231 | 3.403   | 1.00 | 21.49 |
| ATOM | 1050 | CD1 | TYR | A | 269 | 37.459 | 42.562 | 3.893   | 1.00 | 22.94 |
| ATOM | 1051 | CD2 | TYR | A | 269 | 39.759 | 42.067 | 4.291   | 1.00 | 21.62 |
| ATOM | 1052 | CE1 | TYR | A | 269 | 37.237 | 42.729 | 5.272   | 1.00 | 21.45 |
| ATOM | 1053 | CE2 | TYR | A | 269 | 39.557 | 42.230 | 5.664   | 1.00 | 23.06 |
| ATOM | 1054 | CZ  | TYR | A | 269 | 38.281 | 42.521 | 6.138   | 1.00 | 23.93 |
| ATOM | 1055 | OH  | TYR | A | 269 | 38.078 | 42.665 | 7.510   | 1.00 | 23.87 |
| ATOM | 1056 | N   | ARG | A | 270 | 41.074 | 44.362 | 0.992   | 1.00 | 18.88 |
| ATOM | 1057 | CA  | ARG | A | 270 | 42.243 | 45.202 | 1.223   | 1.00 | 18.41 |
| ATOM | 1058 | C   | ARG | A | 270 | 43.012 | 44.976 | 2.512   | 1.00 | 21.70 |
| ATOM | 1059 | O   | ARG | A | 270 | 44.228 | 45.221 | 2.567   | 1.00 | 23.10 |
| ATOM | 1060 | CB  | ARG | A | 270 | 41.884 | 46.703 | 1.099   | 1.00 | 21.15 |
| ATOM | 1061 | CG  | ARG | A | 270 | 41.171 | 47.071 | −0.162  | 1.00 | 29.06 |
| ATOM | 1062 | CD  | ARG | A | 270 | 40.824 | 48.569 | −0.079  | 1.00 | 36.08 |
| ATOM | 1063 | NE  | ARG | A | 270 | 40.726 | 49.228 | −1.372  | 1.00 | 53.43 |
| ATOM | 1064 | CZ  | ARG | A | 270 | 40.612 | 50.546 | −1.509  | 1.00 | 63.89 |
| ATOM | 1065 | NH1 | ARG | A | 270 | 40.605 | 51.313 | −0.427  | 1.00 | 41.31 |
| ATOM | 1066 | NH2 | ARG | A | 270 | 40.530 | 51.097 | −2.716  | 1.00 | 52.61 |
| ATOM | 1067 | N   | ASP | A | 271 | 42.296 | 44.584 | 3.554   | 1.00 | 20.42 |
| ATOM | 1068 | CA  | ASP | A | 271 | 42.856 | 44.547 | 4.906   | 1.00 | 20.48 |
| ATOM | 1069 | C   | ASP | A | 271 | 43.202 | 43.167 | 5.424   | 1.00 | 24.07 |
| ATOM | 1070 | O   | ASP | A | 271 | 43.394 | 42.991 | 6.655   | 1.00 | 23.21 |
| ATOM | 1071 | CB  | ASP | A | 271 | 41.909 | 45.232 | 5.900   | 1.00 | 21.82 |
| ATOM | 1072 | CG  | ASP | A | 271 | 41.800 | 46.738 | 5.678   | 1.00 | 28.89 |
| ATOM | 1073 | OD1 | ASP | A | 271 | 42.568 | 47.283 | 4.855   | 1.00 | 28.97 |
| ATOM | 1074 | OD2 | ASP | A | 271 | 41.023 | 47.377 | 6.414   | 1.00 | 32.58 |
| ATOM | 1075 | N   | LEU | A | 272 | 43.383 | 42.211 | 4.512   | 1.00 | 19.30 |
| ATOM | 1076 | CA  | LEU | A | 272 | 43.780 | 40.871 | 4.956   | 1.00 | 19.18 |
| ATOM | 1077 | C   | LEU | A | 272 | 45.246 | 40.871 | 5.432   | 1.00 | 24.02 |
| ATOM | 1078 | O   | LEU | A | 272 | 46.165 | 41.189 | 4.677   | 1.00 | 26.42 |
| ATOM | 1079 | CB  | LEU | A | 272 | 43.576 | 39.861 | 3.819   | 1.00 | 19.82 |
| ATOM | 1080 | CG  | LEU | A | 272 | 44.015 | 38.426 | 4.129   | 1.00 | 23.20 |
| ATOM | 1081 | CD1 | LEU | A | 272 | 43.284 | 37.878 | 5.319   | 1.00 | 24.24 |
| ATOM | 1082 | CD2 | LEU | A | 272 | 43.743 | 37.582 | 2.885   | 1.00 | 24.17 |
| ATOM | 1083 | N   | LYS | A | 273 | 45.432 | 40.541 | 6.705   | 1.00 | 20.52 |
| ATOM | 1084 | CA  | LYS | A | 273 | 46.750 | 40.384 | 7.292   | 1.00 | 20.63 |
| ATOM | 1085 | C   | LYS | A | 273 | 46.594 | 39.477 | 8.499   | 1.00 | 21.10 |
| ATOM | 1086 | O   | LYS | A | 273 | 45.485 | 39.250 | 8.975   | 1.00 | 20.62 |
| ATOM | 1087 | CB  | LYS | A | 273 | 47.338 | 41.748 | 7.722   | 1.00 | 23.77 |
| ATOM | 1088 | CG  | LYS | A | 273 | 46.528 | 42.481 | 8.772   | 1.00 | 29.43 |
| ATOM | 1089 | CD  | LYS | A | 273 | 46.919 | 43.994 | 8.819   | 1.00 | 38.07 |
| ATOM | 1090 | CE  | LYS | A | 273 | 46.320 | 44.741 | 7.619   | 1.00 | 48.63 |
| ATOM | 1091 | NZ  | LYS | A | 273 | 46.721 | 46.185 | 7.496   | 1.00 | 56.56 |
| ATOM | 1092 | N   | LEU | A | 274 | 47.710 | 38.939 | 8.983   | 1.00 | 20.61 |
| ATOM | 1093 | CA  | LEU | A | 274 | 47.670 | 37.991 | 10.090  | 1.00 | 20.75 |
| ATOM | 1094 | C   | LEU | A | 274 | 46.997 | 38.584 | 11.312  | 1.00 | 24.28 |
| ATOM | 1095 | O   | LEU | A | 274 | 46.183 | 37.926 | 11.966  | 1.00 | 23.13 |

TABLE 4-continued

Structural coordinates for AKT3lkd(T305D, S472D) (SEQ ID NO:2).

| ATOM | 1096 | CB  | LEU | A | 274 | 49.076 | 37.497 | 10.415 | 1.00 | 21.41 |
|------|------|-----|-----|---|-----|--------|--------|--------|------|-------|
| ATOM | 1097 | CG  | LEU | A | 274 | 49.151 | 36.499 | 11.545 | 1.00 | 26.21 |
| ATOM | 1098 | CD1 | LEU | A | 274 | 48.424 | 35.234 | 11.136 | 1.00 | 26.10 |
| ATOM | 1099 | CD2 | LEU | A | 274 | 50.639 | 36.219 | 11.834 | 1.00 | 28.76 |
| ATOM | 1100 | N   | GLU | A | 275 | 47.305 | 39.854 | 11.592 | 1.00 | 23.51 |
| ATOM | 1101 | CA  | GLU | A | 275 | 46.724 | 40.537 | 12.739 | 1.00 | 24.48 |
| ATOM | 1102 | C   | GLU | A | 275 | 45.203 | 40.671 | 12.668 | 1.00 | 26.27 |
| ATOM | 1103 | O   | GLU | A | 275 | 44.567 | 40.989 | 13.667 | 1.00 | 26.39 |
| ATOM | 1104 | CB  | GLU | A | 275 | 47.365 | 41.924 | 12.895 | 1.00 | 26.62 |
| ATOM | 1105 | CG  | GLU | A | 275 | 48.891 | 41.872 | 13.194 | 1.00 | 39.83 |
| ATOM | 1106 | CD  | GLU | A | 275 | 49.792 | 41.927 | 11.926 | 1.00 | 57.62 |
| ATOM | 1107 | OE1 | GLU | A | 275 | 50.868 | 42.559 | 12.007 | 1.00 | 46.21 |
| ATOM | 1108 | OE2 | GLU | A | 275 | 49.472 | 41.284 | 10.884 | 1.00 | 35.57 |
| ATOM | 1109 | N   | ASN | A | 276 | 44.630 | 40.494 | 11.466 | 1.00 | 21.60 |
| ATOM | 1110 | CA  | ASN | A | 276 | 43.176 | 40.608 | 11.291 | 1.00 | 20.98 |
| ATOM | 1111 | C   | ASN | A | 276 | 42.486 | 39.236 | 11.188 | 1.00 | 22.59 |
| ATOM | 1112 | O   | ASN | A | 276 | 41.344 | 39.142 | 10.750 | 1.00 | 21.98 |
| ATOM | 1113 | CB  | ASN | A | 276 | 42.831 | 41.451 | 10.087 | 1.00 | 20.13 |
| ATOM | 1114 | CG  | ASN | A | 276 | 42.965 | 42.945 | 10.364 | 1.00 | 30.14 |
| ATOM | 1115 | OD1 | ASN | A | 276 | 42.873 | 43.384 | 11.527 | 1.00 | 28.32 |
| ATOM | 1116 | ND2 | ASN | A | 276 | 43.231 | 43.734 | 9.309  | 1.00 | 24.17 |
| ATOM | 1117 | N   | LEU | A | 277 | 43.174 | 38.184 | 11.647 | 1.00 | 19.49 |
| ATOM | 1118 | CA  | LEU | A | 277 | 42.608 | 36.847 | 11.622 | 1.00 | 18.95 |
| ATOM | 1119 | C   | LEU | A | 277 | 42.505 | 36.351 | 13.042 | 1.00 | 22.76 |
| ATOM | 1120 | O   | LEU | A | 277 | 43.477 | 36.368 | 13.768 | 1.00 | 22.18 |
| ATOM | 1121 | CB  | LEU | A | 277 | 43.531 | 35.866 | 10.853 | 1.00 | 18.68 |
| ATOM | 1122 | CG  | LEU | A | 277 | 43.686 | 36.223 | 9.376  | 1.00 | 20.05 |
| ATOM | 1123 | CD1 | LEU | A | 277 | 44.753 | 35.326 | 8.675  | 1.00 | 19.36 |
| ATOM | 1124 | CD2 | LEU | A | 277 | 42.315 | 36.133 | 8.646  | 1.00 | 18.86 |
| ATOM | 1125 | N   | MET | A | 278 | 41.326 | 35.889 | 13.408 | 1.00 | 21.58 |
| ATOM | 1126 | CA  | MET | A | 278 | 41.120 | 35.291 | 14.725 | 1.00 | 23.06 |
| ATOM | 1127 | C   | MET | A | 278 | 40.483 | 33.922 | 14.544 | 1.00 | 24.59 |
| ATOM | 1128 | O   | MET | A | 278 | 39.983 | 33.606 | 13.454 | 1.00 | 21.46 |
| ATOM | 1129 | CB  | MET | A | 278 | 40.164 | 36.151 | 15.531 | 1.00 | 26.85 |
| ATOM | 1130 | CG  | MET | A | 278 | 40.613 | 37.601 | 15.670 | 1.00 | 32.49 |
| ATOM | 1131 | SD  | MET | A | 278 | 39.395 | 38.438 | 16.619 | 1.00 | 38.94 |
| ATOM | 1132 | CE  | MET | A | 278 | 39.782 | 37.776 | 18.181 | 1.00 | 34.99 |
| ATOM | 1133 | N   | LEU | A | 279 | 40.447 | 33.132 | 15.622 | 1.00 | 21.99 |
| ATOM | 1134 | CA  | LEU | A | 279 | 39.710 | 31.863 | 15.600 | 1.00 | 21.24 |
| ATOM | 1135 | C   | LEU | A | 279 | 38.455 | 32.028 | 16.443 | 1.00 | 22.94 |
| ATOM | 1136 | O   | LEU | A | 279 | 38.480 | 32.716 | 17.480 | 1.00 | 23.50 |
| ATOM | 1137 | CB  | LEU | A | 279 | 40.539 | 30.741 | 16.217 | 1.00 | 20.74 |
| ATOM | 1138 | CG  | LEU | A | 279 | 41.851 | 30.424 | 15.512 | 1.00 | 22.50 |
| ATOM | 1139 | CD1 | LEU | A | 279 | 42.498 | 29.159 | 16.158 | 1.00 | 23.67 |
| ATOM | 1140 | CD2 | LEU | A | 279 | 41.556 | 30.195 | 13.994 | 1.00 | 21.15 |
| ATOM | 1141 | N   | ASP | A | 280 | 37.383 | 31.370 | 16.054 | 1.00 | 20.87 |
| ATOM | 1142 | CA  | ASP | A | 280 | 36.205 | 31.326 | 16.899 | 1.00 | 20.53 |
| ATOM | 1143 | C   | ASP | A | 280 | 36.372 | 30.183 | 17.900 | 1.00 | 24.38 |
| ATOM | 1144 | O   | ASP | A | 280 | 37.395 | 29.476 | 17.891 | 1.00 | 21.88 |
| ATOM | 1145 | CB  | ASP | A | 280 | 34.902 | 31.251 | 16.112 | 1.00 | 21.93 |
| ATOM | 1146 | CG  | ASP | A | 280 | 34.736 | 29.930 | 15.285 | 1.00 | 20.57 |
| ATOM | 1147 | OD1 | ASP | A | 280 | 35.313 | 28.881 | 15.661 | 1.00 | 21.76 |
| ATOM | 1148 | OD2 | ASP | A | 280 | 33.874 | 29.936 | 14.378 | 1.00 | 23.09 |
| ATOM | 1149 | N   | LYS | A | 281 | 35.373 | 30.004 | 18.763 | 1.00 | 24.49 |
| ATOM | 1150 | CA  | LYS | A | 281 | 35.428 | 28.985 | 19.810 | 1.00 | 24.20 |
| ATOM | 1151 | C   | LYS | A | 281 | 35.724 | 27.578 | 19.310 | 1.00 | 27.78 |
| ATOM | 1152 | O   | LYS | A | 281 | 36.344 | 26.760 | 20.028 | 1.00 | 29.42 |
| ATOM | 1153 | CB  | LYS | A | 281 | 34.102 | 28.980 | 20.606 | 1.00 | 26.16 |
| ATOM | 1154 | CG  | LYS | A | 281 | 32.956 | 28.319 | 19.896 | 1.00 | 35.78 |
| ATOM | 1155 | CD  | LYS | A | 281 | 31.640 | 28.618 | 20.599 | 1.00 | 45.18 |
| ATOM | 1156 | CE  | LYS | A | 281 | 30.477 | 28.520 | 19.651 | 1.00 | 53.19 |
| ATOM | 1157 | NZ  | LYS | A | 281 | 29.880 | 27.159 | 19.677 | 1.00 | 64.55 |
| ATOM | 1158 | N   | ASP | A | 282 | 35.307 | 27.297 | 18.074 | 1.00 | 23.60 |
| ATOM | 1159 | CA  | ASP | A | 282 | 35.448 | 25.969 | 17.485 | 1.00 | 23.27 |
| ATOM | 1160 | C   | ASP | A | 282 | 36.741 | 25.794 | 16.668 | 1.00 | 26.29 |
| ATOM | 1161 | O   | ASP | A | 282 | 37.106 | 24.659 | 16.302 | 1.00 | 25.67 |
| ATOM | 1162 | CB  | ASP | A | 282 | 34.251 | 25.683 | 16.603 | 1.00 | 24.04 |
| ATOM | 1163 | CG  | ASP | A | 282 | 32.960 | 25.657 | 17.371 | 1.00 | 31.78 |
| ATOM | 1164 | OD1 | ASP | A | 282 | 32.906 | 24.936 | 18.385 | 1.00 | 32.49 |
| ATOM | 1165 | OD2 | ASP | A | 282 | 32.014 | 26.386 | 16.982 | 1.00 | 35.20 |
| ATOM | 1166 | N   | GLY | A | 283 | 37.428 | 26.905 | 16.395 | 1.00 | 21.93 |
| ATOM | 1167 | CA  | GLY | A | 283 | 38.696 | 26.855 | 15.662 | 1.00 | 20.78 |
| ATOM | 1168 | C   | GLY | A | 283 | 38.526 | 27.245 | 14.191 | 1.00 | 22.27 |
| ATOM | 1169 | O   | GLY | A | 283 | 39.464 | 27.103 | 13.424 | 1.00 | 21.06 |
| ATOM | 1170 | N   | HIS | A | 284 | 37.360 | 27.757 | 13.813 | 1.00 | 20.12 |
| ATOM | 1171 | CA  | HIS | A | 284 | 37.190 | 28.223 | 12.416 | 1.00 | 19.61 |
| ATOM | 1172 | C   | HIS | A | 284 | 37.697 | 29.653 | 12.348 | 1.00 | 22.62 |
| ATOM | 1173 | O   | HIS | A | 284 | 37.744 | 30.371 | 13.366 | 1.00 | 23.09 |

TABLE 4-continued

Structural coordinates for AKT3lkd(T305D, S472D) (SEQ ID NO:2).

| ATOM | 1174 | CB | HIS | A | 284 | 35.732 | 28.157 | 11.960 | 1.00 | 19.94 |
|---|---|---|---|---|---|---|---|---|---|---|
| ATOM | 1175 | CG | HIS | A | 284 | 35.238 | 26.765 | 11.759 | 1.00 | 21.56 |
| ATOM | 1176 | ND1 | HIS | A | 284 | 35.564 | 26.012 | 10.643 | 1.00 | 22.36 |
| ATOM | 1177 | CD2 | HIS | A | 284 | 34.529 | 25.946 | 12.576 | 1.00 | 22.48 |
| ATOM | 1178 | CE1 | HIS | A | 284 | 35.037 | 24.801 | 10.766 | 1.00 | 22.42 |
| ATOM | 1179 | NE2 | HIS | A | 284 | 34.381 | 24.743 | 11.923 | 1.00 | 22.33 |
| ATOM | 1180 | N | ILE | A | 285 | 38.073 | 30.087 | 11.156 | 1.00 | 19.30 |
| ATOM | 1181 | CA | ILE | A | 285 | 38.575 | 31.477 | 10.963 | 1.00 | 20.44 |
| ATOM | 1182 | C | ILE | A | 285 | 37.525 | 32.541 | 11.086 | 1.00 | 22.54 |
| ATOM | 1183 | O | ILE | A | 285 | 36.361 | 32.341 | 10.693 | 1.00 | 20.91 |
| ATOM | 1184 | CB | ILE | A | 285 | 39.128 | 31.607 | 9.465 | 1.00 | 25.13 |
| ATOM | 1185 | CG1 | ILE | A | 285 | 40.526 | 31.016 | 9.382 | 1.00 | 27.79 |
| ATOM | 1186 | CG2 | ILE | A | 285 | 39.070 | 33.076 | 8.938 | 1.00 | 28.79 |
| ATOM | 1187 | CD1 | ILE | A | 285 | 41.617 | 31.931 | 9.960 | 1.00 | 33.50 |
| ATOM | 1188 | N | LYS | A | 286 | 37.946 | 33.730 | 11.564 | 1.00 | 20.05 |
| ATOM | 1189 | CA | LYS | A | 286 | 37.105 | 34.904 | 11.515 | 1.00 | 19.83 |
| ATOM | 1190 | C | LYS | A | 286 | 38.012 | 36.039 | 11.068 | 1.00 | 21.63 |
| ATOM | 1191 | O | LYS | A | 286 | 39.064 | 36.301 | 11.693 | 1.00 | 22.44 |
| ATOM | 1192 | CB | LYS | A | 286 | 36.505 | 35.237 | 12.896 | 1.00 | 21.67 |
| ATOM | 1193 | CG | LYS | A | 286 | 35.242 | 34.415 | 13.212 | 1.00 | 28.06 |
| ATOM | 1194 | CD | LYS | A | 286 | 34.036 | 34.916 | 12.392 | 1.00 | 28.46 |
| ATOM | 1195 | CE | LYS | A | 286 | 32.771 | 34.074 | 12.665 | 1.00 | 27.04 |
| ATOM | 1196 | NZ | LYS | A | 286 | 31.622 | 34.509 | 11.799 | 1.00 | 36.89 |
| ATOM | 1197 | N | ILE | A | 287 | 37.688 | 36.619 | 9.928 | 1.00 | 18.05 |
| ATOM | 1198 | CA | ILE | A | 287 | 38.425 | 37.765 | 9.411 | 1.00 | 16.94 |
| ATOM | 1199 | C | ILE | A | 287 | 37.768 | 38.985 | 10.027 | 1.00 | 24.17 |
| ATOM | 1200 | O | ILE | A | 287 | 36.536 | 39.132 | 9.978 | 1.00 | 23.61 |
| ATOM | 1201 | CB | ILE | A | 287 | 38.234 | 37.861 | 7.882 | 1.00 | 19.07 |
| ATOM | 1202 | CG1 | ILE | A | 287 | 38.910 | 36.679 | 7.184 | 1.00 | 19.37 |
| ATOM | 1203 | CG2 | ILE | A | 287 | 38.794 | 39.208 | 7.360 | 1.00 | 21.22 |
| ATOM | 1204 | CD1 | ILE | A | 287 | 38.394 | 36.450 | 5.775 | 1.00 | 22.83 |
| ATOM | 1205 | N | THR | A | 288 | 38.572 | 39.851 | 10.601 | 1.00 | 23.53 |
| ATOM | 1206 | CA | THR | A | 288 | 38.026 | 41.064 | 11.196 | 1.00 | 25.17 |
| ATOM | 1207 | C | THR | A | 288 | 38.825 | 42.290 | 10.749 | 1.00 | 29.87 |
| ATOM | 1208 | O | THR | A | 288 | 39.525 | 42.261 | 9.723 | 1.00 | 28.59 |
| ATOM | 1209 | CB | THR | A | 288 | 37.959 | 40.933 | 12.729 | 1.00 | 30.04 |
| ATOM | 1210 | OG1 | THR | A | 288 | 37.341 | 42.102 | 13.299 | 1.00 | 31.35 |
| ATOM | 1211 | CG2 | THR | A | 288 | 39.343 | 40.705 | 13.342 | 1.00 | 26.22 |
| ATOM | 1212 | N | ASP | A | 289 | 38.672 | 43.387 | 11.464 | 1.00 | 27.94 |
| ATOM | 1213 | CA | ASP | A | 289 | 39.416 | 44.586 | 11.116 | 1.00 | 28.47 |
| ATOM | 1214 | C | ASP | A | 289 | 39.474 | 45.471 | 12.339 | 1.00 | 36.02 |
| ATOM | 1215 | O | ASP | A | 289 | 39.031 | 45.077 | 13.413 | 1.00 | 34.00 |
| ATOM | 1216 | CB | ASP | A | 289 | 38.742 | 45.329 | 9.950 | 1.00 | 29.50 |
| ATOM | 1217 | CG | ASP | A | 289 | 39.746 | 46.009 | 9.030 | 1.00 | 31.82 |
| ATOM | 1218 | OD1 | ASP | A | 289 | 40.910 | 46.210 | 9.445 | 1.00 | 34.88 |
| ATOM | 1219 | OD2 | ASP | A | 289 | 39.397 | 46.260 | 7.862 | 1.00 | 34.11 |
| ATOM | 1220 | N | PHE | A | 290 | 40.007 | 46.677 | 12.160 | 1.00 | 36.49 |
| ATOM | 1221 | CA | PHE | A | 290 | 40.096 | 47.655 | 13.254 | 1.00 | 38.13 |
| ATOM | 1222 | C | PHE | A | 290 | 41.020 | 47.201 | 14.360 | 1.00 | 47.45 |
| ATOM | 1223 | O | PHE | A | 290 | 40.634 | 47.176 | 15.526 | 1.00 | 47.52 |
| ATOM | 1224 | CB | PHE | A | 290 | 38.708 | 47.958 | 13.823 | 1.00 | 39.95 |
| ATOM | 1225 | CG | PHE | A | 290 | 37.662 | 48.155 | 12.774 | 1.00 | 41.94 |
| ATOM | 1226 | CD1 | PHE | A | 290 | 36.491 | 47.403 | 12.785 | 1.00 | 44.77 |
| ATOM | 1227 | CD2 | PHE | A | 290 | 37.862 | 49.061 | 11.743 | 1.00 | 44.57 |
| ATOM | 1228 | CE1 | PHE | A | 290 | 35.532 | 47.566 | 11.800 | 1.00 | 46.04 |
| ATOM | 1229 | CE2 | PHE | A | 290 | 36.909 | 49.217 | 10.743 | 1.00 | 47.42 |
| ATOM | 1230 | CZ | PHE | A | 290 | 35.740 | 48.480 | 10.780 | 1.00 | 45.37 |
| ATOM | 1231 | N | GLY | A | 291 | 42.249 | 46.855 | 14.002 | 1.00 | 47.35 |
| ATOM | 1232 | CA | GLY | A | 291 | 43.218 | 46.446 | 15.005 | 1.00 | 48.70 |
| ATOM | 1233 | C | GLY | A | 291 | 43.477 | 47.619 | 15.949 | 1.00 | 56.08 |
| ATOM | 1234 | O | GLY | A | 291 | 43.351 | 48.783 | 15.557 | 1.00 | 55.58 |
| ATOM | 1235 | N | LEU | A | 292 | 43.840 | 47.314 | 17.186 | 1.00 | 55.38 |
| ATOM | 1236 | CA | LEU | A | 292 | 44.136 | 48.356 | 18.165 | 1.00 | 56.32 |
| ATOM | 1237 | C | LEU | A | 292 | 45.574 | 48.864 | 18.025 | 1.00 | 60.88 |
| ATOM | 1238 | O | LEU | A | 292 | 45.895 | 49.976 | 18.457 | 1.00 | 60.82 |
| ATOM | 1239 | CB | LEU | A | 292 | 43.897 | 47.845 | 19.584 | 1.00 | 56.70 |
| ATOM | 1240 | CG | LEU | A | 292 | 42.452 | 47.871 | 20.086 | 1.00 | 61.69 |
| ATOM | 1241 | CD1 | LEU | A | 292 | 42.414 | 48.205 | 21.567 | 1.00 | 62.05 |
| ATOM | 1242 | CD2 | LEU | A | 292 | 41.614 | 48.859 | 19.286 | 1.00 | 64.18 |
| ATOM | 1243 | N | THR | A | 309 | 51.642 | 46.880 | 8.615 | 1.00 | 46.32 |
| ATOM | 1244 | CA | THR | A | 309 | 50.996 | 46.563 | 7.349 | 1.00 | 45.26 |
| ATOM | 1245 | C | THR | A | 309 | 51.762 | 46.966 | 6.072 | 1.00 | 44.61 |
| ATOM | 1246 | O | THR | A | 309 | 51.344 | 46.603 | 4.977 | 1.00 | 44.32 |
| ATOM | 1247 | CB | THR | A | 309 | 49.561 | 47.103 | 7.277 | 1.00 | 57.87 |
| ATOM | 1248 | OG1 | THR | A | 309 | 49.549 | 48.355 | 6.573 | 1.00 | 59.39 |
| ATOM | 1249 | CG2 | THR | A | 309 | 49.002 | 47.300 | 8.671 | 1.00 | 58.06 |
| ATOM | 1250 | N | PRO | A | 310 | 52.853 | 47.730 | 6.187 | 1.00 | 37.74 |
| ATOM | 1251 | CA | PRO | A | 310 | 53.625 | 48.036 | 4.989 | 1.00 | 35.39 |

TABLE 4-continued

Structural coordinates for AKT3lkd(T305D, S472D) (SEQ ID NO:2).

| ATOM | 1252 | C | PRO | A | 310 | 54.154 | 46.717 | 4.369 | 1.00 | 33.52 |
|---|---|---|---|---|---|---|---|---|---|---|
| ATOM | 1253 | O | PRO | A | 310 | 54.307 | 46.603 | 3.153 | 1.00 | 30.69 |
| ATOM | 1254 | CB | PRO | A | 310 | 54.801 | 48.878 | 5.533 | 1.00 | 37.74 |
| ATOM | 1255 | CG | PRO | A | 310 | 54.391 | 49.275 | 6.980 | 1.00 | 42.66 |
| ATOM | 1256 | CD | PRO | A | 310 | 52.968 | 48.824 | 7.171 | 1.00 | 38.42 |
| ATOM | 1257 | N | GLU | A | 311 | 54.464 | 45.743 | 5.227 | 1.00 | 30.16 |
| ATOM | 1258 | CA | GLU | A | 311 | 54.983 | 44.448 | 4.761 | 1.00 | 29.28 |
| ATOM | 1259 | C | GLU | A | 311 | 53.937 | 43.698 | 3.947 | 1.00 | 30.27 |
| ATOM | 1260 | O | GLU | A | 311 | 54.244 | 42.664 | 3.342 | 1.00 | 28.18 |
| ATOM | 1261 | CB | GLU | A | 311 | 55.406 | 43.554 | 5.934 | 1.00 | 30.65 |
| ATOM | 1262 | CG | GLU | A | 311 | 54.640 | 43.794 | 7.217 | 1.00 | 41.78 |
| ATOM | 1263 | CD | GLU | A | 311 | 55.006 | 45.126 | 7.865 | 1.00 | 56.52 |
| ATOM | 1264 | OE1 | GLU | A | 311 | 54.099 | 45.830 | 8.328 | 1.00 | 48.82 |
| ATOM | 1265 | OE2 | GLU | A | 311 | 56.183 | 45.520 | 7.780 | 1.00 | 54.98 |
| ATOM | 1266 | N | TYR | A | 312 | 52.701 | 44.176 | 3.991 | 1.00 | 26.95 |
| ATOM | 1267 | CA | TYR | A | 312 | 51.616 | 43.523 | 3.259 | 1.00 | 26.55 |
| ATOM | 1268 | C | TYR | A | 312 | 51.271 | 44.250 | 1.967 | 1.00 | 29.30 |
| ATOM | 1269 | O | TYR | A | 312 | 50.391 | 43.806 | 1.225 | 1.00 | 27.52 |
| ATOM | 1270 | CB | TYR | A | 312 | 50.351 | 43.429 | 4.108 | 1.00 | 27.23 |
| ATOM | 1271 | CG | TYR | A | 312 | 50.399 | 42.350 | 5.164 | 1.00 | 28.78 |
| ATOM | 1272 | CD1 | TYR | A | 312 | 50.876 | 42.629 | 6.434 | 1.00 | 30.17 |
| ATOM | 1273 | CD2 | TYR | A | 312 | 49.929 | 41.065 | 4.901 | 1.00 | 29.71 |
| ATOM | 1274 | CE1 | TYR | A | 312 | 50.934 | 41.662 | 7.396 | 1.00 | 31.99 |
| ATOM | 1275 | CE2 | TYR | A | 312 | 50.009 | 40.066 | 5.873 | 1.00 | 31.26 |
| ATOM | 1276 | CZ | TYR | A | 312 | 50.502 | 40.390 | 7.123 | 1.00 | 37.68 |
| ATOM | 1277 | OH | TYR | A | 312 | 50.561 | 39.444 | 8.121 | 1.00 | 40.60 |
| ATOM | 1278 | N | LEU | A | 313 | 51.913 | 45.383 | 1.699 | 1.00 | 25.79 |
| ATOM | 1279 | CA | LEU | A | 313 | 51.551 | 46.127 | 0.482 | 1.00 | 25.61 |
| ATOM | 1280 | C | LEU | A | 313 | 51.898 | 45.362 | −0.792 | 1.00 | 25.83 |
| ATOM | 1281 | O | LEU | A | 313 | 53.041 | 44.910 | −0.963 | 1.00 | 25.11 |
| ATOM | 1282 | CB | LEU | A | 313 | 52.213 | 47.518 | 0.457 | 1.00 | 26.28 |
| ATOM | 1283 | CG | LEU | A | 313 | 51.807 | 48.406 | 1.632 | 1.00 | 31.62 |
| ATOM | 1284 | CD1 | LEU | A | 313 | 52.653 | 49.694 | 1.669 | 1.00 | 33.36 |
| ATOM | 1285 | CD2 | LEU | A | 313 | 50.341 | 48.728 | 1.524 | 1.00 | 34.72 |
| ATOM | 1286 | N | ALA | A | 314 | 50.937 | 45.289 | −1.721 | 1.00 | 22.47 |
| ATOM | 1287 | CA | ALA | A | 314 | 51.151 | 44.591 | −3.001 | 1.00 | 21.83 |
| ATOM | 1288 | C | ALA | A | 314 | 52.006 | 45.440 | −3.960 | 1.00 | 26.02 |
| ATOM | 1289 | O | ALA | A | 314 | 52.001 | 46.659 | −3.873 | 1.00 | 25.89 |
| ATOM | 1290 | CB | ALA | A | 314 | 49.818 | 44.255 | −3.646 | 1.00 | 22.07 |
| ATOM | 1291 | N | PRO | A | 315 | 52.733 | 44.784 | −4.860 | 1.00 | 23.75 |
| ATOM | 1292 | CA | PRO | A | 315 | 53.589 | 45.526 | −5.806 | 1.00 | 23.92 |
| ATOM | 1293 | C | PRO | A | 315 | 52.795 | 46.573 | −6.552 | 1.00 | 28.31 |
| ATOM | 1294 | O | PRO | A | 315 | 53.255 | 47.709 | −6.676 | 1.00 | 27.63 |
| ATOM | 1295 | CB | PRO | A | 315 | 54.091 | 44.454 | −6.761 | 1.00 | 25.94 |
| ATOM | 1296 | CG | PRO | A | 315 | 54.176 | 43.194 | −5.866 | 1.00 | 28.98 |
| ATOM | 1297 | CD | PRO | A | 315 | 52.912 | 43.318 | −4.986 | 1.00 | 24.08 |
| ATOM | 1298 | N | GLU | A | 316 | 51.586 | 46.216 | −7.006 | 1.00 | 24.65 |
| ATOM | 1299 | CA | GLU | A | 316 | 50.748 | 47.153 | −7.786 | 1.00 | 25.47 |
| ATOM | 1300 | C | GLU | A | 316 | 50.258 | 48.341 | −6.986 | 1.00 | 29.25 |
| ATOM | 1301 | O | GLU | A | 316 | 49.989 | 49.418 | −7.545 | 1.00 | 31.49 |
| ATOM | 1302 | CB | GLU | A | 316 | 49.596 | 46.433 | −8.494 | 1.00 | 26.33 |
| ATOM | 1303 | CG | GLU | A | 316 | 48.512 | 45.903 | −7.582 | 1.00 | 26.54 |
| ATOM | 1304 | CD | GLU | A | 316 | 48.753 | 44.452 | −7.186 | 1.00 | 27.42 |
| ATOM | 1305 | OE1 | GLU | A | 316 | 49.913 | 44.036 | −7.179 | 1.00 | 23.38 |
| ATOM | 1306 | OE2 | GLU | A | 316 | 47.765 | 43.738 | −6.923 | 1.00 | 22.61 |
| ATOM | 1307 | N | VAL | A | 317 | 50.169 | 48.179 | −5.675 | 1.00 | 24.84 |
| ATOM | 1308 | CA | VAL | A | 317 | 49.780 | 49.295 | −4.815 | 1.00 | 24.86 |
| ATOM | 1309 | C | VAL | A | 317 | 50.955 | 50.240 | −4.728 | 1.00 | 30.96 |
| ATOM | 1310 | O | VAL | A | 317 | 50.795 | 51.462 | −4.848 | 1.00 | 30.93 |
| ATOM | 1311 | CB | VAL | A | 317 | 49.397 | 48.848 | −3.420 | 1.00 | 28.36 |
| ATOM | 1312 | CG1 | VAL | A | 317 | 49.263 | 50.060 | −2.491 | 1.00 | 28.36 |
| ATOM | 1313 | CG2 | VAL | A | 317 | 48.117 | 48.069 | −3.470 | 1.00 | 28.00 |
| ATOM | 1314 | N | LEU | A | 318 | 52.147 | 49.671 | −4.593 | 1.00 | 27.03 |
| ATOM | 1315 | CA | LEU | A | 318 | 53.381 | 50.473 | −4.535 | 1.00 | 27.66 |
| ATOM | 1316 | C | LEU | A | 318 | 53.625 | 51.223 | −5.848 | 1.00 | 35.17 |
| ATOM | 1317 | O | LEU | A | 318 | 54.036 | 52.389 | −5.835 | 1.00 | 35.20 |
| ATOM | 1318 | CB | LEU | A | 318 | 54.591 | 49.578 | −4.231 | 1.00 | 27.46 |
| ATOM | 1319 | CG | LEU | A | 318 | 54.577 | 48.908 | −2.849 | 1.00 | 30.42 |
| ATOM | 1320 | CD1 | LEU | A | 318 | 55.851 | 48.097 | −2.617 | 1.00 | 30.25 |
| ATOM | 1321 | CD2 | LEU | A | 318 | 54.361 | 49.929 | −1.755 | 1.00 | 33.34 |
| ATOM | 1322 | N | GLU | A | 319 | 53.375 | 50.551 | −6.972 | 1.00 | 34.50 |
| ATOM | 1323 | CA | GLU | A | 319 | 53.647 | 51.113 | −8.302 | 1.00 | 36.31 |
| ATOM | 1324 | C | GLU | A | 319 | 52.657 | 52.117 | −8.860 | 1.00 | 48.03 |
| ATOM | 1325 | O | GLU | A | 319 | 53.036 | 52.994 | −9.648 | 1.00 | 48.00 |
| ATOM | 1326 | CB | GLU | A | 319 | 53.884 | 50.000 | −9.319 | 1.00 | 37.72 |
| ATOM | 1327 | CG | GLU | A | 319 | 55.136 | 49.205 | −9.071 | 1.00 | 50.45 |
| ATOM | 1328 | CD | GLU | A | 319 | 55.883 | 48.901 | −10.350 | 1.00 | 75.12 |
| ATOM | 1329 | OE1 | GLU | A | 319 | 57.030 | 49.373 | −10.500 | 1.00 | 78.33 |

TABLE 4-continued

Structural coordinates for AKT3lkd(T305D, S472D) (SEQ ID NO:2).

| ATOM | 1330 | OE2 | GLU | A | 319 | 55.316 | 48.204 | −11.215 | 1.00 | 68.76 |
|---|---|---|---|---|---|---|---|---|---|---|
| ATOM | 1331 | N | ASP | A | 320 | 51.384 | 51.975 | −8.528 | 1.00 | 49.02 |
| ATOM | 1332 | CA | ASP | A | 320 | 50.401 | 52.899 | −9.077 | 1.00 | 51.06 |
| ATOM | 1333 | C | ASP | A | 320 | 49.277 | 53.228 | −8.142 | 1.00 | 58.76 |
| ATOM | 1334 | O | ASP | A | 320 | 48.460 | 54.103 | −8.440 | 1.00 | 59.91 |
| ATOM | 1335 | CB | ASP | A | 320 | 49.820 | 52.368 | −10.397 | 1.00 | 53.33 |
| ATOM | 1336 | CG | ASP | A | 320 | 50.380 | 51.009 | −10.786 | 1.00 | 64.96 |
| ATOM | 1337 | OD1 | ASP | A | 320 | 51.108 | 50.928 | −11.802 | 1.00 | 64.89 |
| ATOM | 1338 | OD2 | ASP | A | 320 | 50.024 | 50.009 | −10.131 | 1.00 | 74.20 |
| ATOM | 1339 | N | ASN | A | 321 | 49.154 | 52.454 | −7.065 | 1.00 | 56.22 |
| ATOM | 1340 | CA | ASN | A | 321 | 48.018 | 52.580 | −6.152 | 1.00 | 56.63 |
| ATOM | 1341 | C | ASN | A | 321 | 46.824 | 52.060 | −6.957 | 1.00 | 60.78 |
| ATOM | 1342 | O | ASN | A | 321 | 45.668 | 52.156 | −6.542 | 1.00 | 60.39 |
| ATOM | 1343 | CB | ASN | A | 321 | 47.791 | 54.050 | −5.748 | 1.00 | 60.86 |
| ATOM | 1344 | CG | ASN | A | 321 | 48.663 | 54.479 | −4.580 | 1.00 | 91.28 |
| ATOM | 1345 | OD1 | ASN | A | 321 | 48.294 | 55.364 | −3.809 | 1.00 | 87.41 |
| ATOM | 1346 | ND2 | ASN | A | 321 | 49.832 | 53.858 | −4.451 | 1.00 | 85.37 |
| ATOM | 1347 | N | ASP | A | 322 | 47.146 | 51.540 | −8.140 | 1.00 | 56.87 |
| ATOM | 1348 | CA | ASP | A | 322 | 46.191 | 51.021 | −9.088 | 1.00 | 55.83 |
| ATOM | 1349 | C | ASP | A | 322 | 46.078 | 49.562 | −8.783 | 1.00 | 55.38 |
| ATOM | 1350 | O | ASP | A | 322 | 47.045 | 48.813 | −8.904 | 1.00 | 55.10 |
| ATOM | 1351 | CB | ASP | A | 322 | 46.714 | 51.216 | −10.516 | 1.00 | 58.07 |
| ATOM | 1352 | CG | ASP | A | 322 | 45.596 | 51.275 | −11.547 | 1.00 | 70.46 |
| ATOM | 1353 | OD1 | ASP | A | 322 | 45.158 | 52.395 | −11.893 | 1.00 | 71.59 |
| ATOM | 1354 | OD2 | ASP | A | 322 | 45.164 | 50.202 | −12.021 | 1.00 | 76.65 |
| ATOM | 1355 | N | TYR | A | 323 | 44.909 | 49.156 | −8.333 | 1.00 | 47.86 |
| ATOM | 1356 | CA | TYR | A | 323 | 44.752 | 47.796 | −7.921 | 1.00 | 44.48 |
| ATOM | 1357 | C | TYR | A | 323 | 43.299 | 47.402 | −7.818 | 1.00 | 41.09 |
| ATOM | 1358 | O | TYR | A | 323 | 42.381 | 48.214 | −8.046 | 1.00 | 39.56 |
| ATOM | 1359 | CB | TYR | A | 323 | 45.438 | 47.623 | −6.570 | 1.00 | 45.00 |
| ATOM | 1360 | CG | TYR | A | 323 | 44.844 | 48.505 | −5.507 | 1.00 | 46.94 |
| ATOM | 1361 | CD1 | TYR | A | 323 | 43.690 | 48.130 | −4.835 | 1.00 | 47.87 |
| ATOM | 1362 | CD2 | TYR | A | 323 | 45.420 | 49.729 | −5.191 | 1.00 | 48.19 |
| ATOM | 1363 | CE1 | TYR | A | 323 | 43.142 | 48.929 | −3.851 | 1.00 | 48.81 |
| ATOM | 1364 | CE2 | TYR | A | 323 | 44.871 | 50.547 | −4.201 | 1.00 | 49.44 |
| ATOM | 1365 | CZ | TYR | A | 323 | 43.735 | 50.139 | −3.540 | 1.00 | 58.00 |
| ATOM | 1366 | OH | TYR | A | 323 | 43.184 | 50.942 | −2.568 | 1.00 | 63.06 |
| ATOM | 1367 | N | GLY | A | 324 | 43.079 | 46.152 | −7.454 | 1.00 | 31.36 |
| ATOM | 1368 | CA | GLY | A | 324 | 41.749 | 45.629 | −7.384 | 1.00 | 28.01 |
| ATOM | 1369 | C | GLY | A | 324 | 41.762 | 44.345 | −6.611 | 1.00 | 26.03 |
| ATOM | 1370 | O | GLY | A | 324 | 42.543 | 44.180 | −5.693 | 1.00 | 23.26 |
| ATOM | 1371 | N | ARG | A | 325 | 40.862 | 43.454 | −6.975 | 1.00 | 20.60 |
| ATOM | 1372 | CA | ARG | A | 325 | 40.704 | 42.189 | −6.248 | 1.00 | 18.71 |
| ATOM | 1373 | C | ARG | A | 325 | 41.997 | 41.390 | −6.089 | 1.00 | 20.29 |
| ATOM | 1374 | O | ARG | A | 325 | 42.136 | 40.628 | −5.137 | 1.00 | 18.87 |
| ATOM | 1375 | CB | ARG | A | 325 | 39.604 | 41.335 | −6.883 | 1.00 | 21.03 |
| ATOM | 1376 | CG | ARG | A | 325 | 39.942 | 40.868 | −8.272 | 1.00 | 24.49 |
| ATOM | 1377 | CD | ARG | A | 325 | 38.713 | 40.341 | −9.025 | 1.00 | 25.79 |
| ATOM | 1378 | NE | ARG | A | 325 | 38.995 | 40.276 | −10.457 | 1.00 | 26.05 |
| ATOM | 1379 | CZ | ARG | A | 325 | 39.698 | 39.313 | −11.059 | 1.00 | 31.28 |
| ATOM | 1380 | NH1 | ARG | A | 325 | 40.227 | 38.282 | −10.355 | 1.00 | 22.56 |
| ATOM | 1381 | NH2 | ARG | A | 325 | 39.924 | 39.401 | −12.372 | 1.00 | 28.41 |
| ATOM | 1382 | N | ALA | A | 326 | 42.935 | 41.519 | −7.037 | 1.00 | 19.92 |
| ATOM | 1383 | CA | ALA | A | 326 | 44.176 | 40.735 | −6.919 | 1.00 | 19.49 |
| ATOM | 1384 | C | ALA | A | 326 | 44.961 | 41.085 | −5.673 | 1.00 | 19.90 |
| ATOM | 1385 | O | ALA | A | 326 | 45.785 | 40.299 | −5.221 | 1.00 | 19.24 |
| ATOM | 1386 | CB | ALA | A | 326 | 45.055 | 40.874 | −8.153 | 1.00 | 21.45 |
| ATOM | 1387 | N | VAL | A | 327 | 44.780 | 42.290 | −5.133 | 1.00 | 18.39 |
| ATOM | 1388 | CA | VAL | A | 327 | 45.523 | 42.630 | −3.893 | 1.00 | 17.38 |
| ATOM | 1389 | C | VAL | A | 327 | 45.166 | 41.685 | −2.743 | 1.00 | 19.68 |
| ATOM | 1390 | O | VAL | A | 327 | 46.018 | 41.390 | −1.903 | 1.00 | 18.76 |
| ATOM | 1391 | CB | VAL | A | 327 | 45.301 | 44.091 | −3.436 | 1.00 | 22.44 |
| ATOM | 1392 | CG1 | VAL | A | 327 | 45.703 | 45.061 | −4.544 | 1.00 | 23.50 |
| ATOM | 1393 | CG2 | VAL | A | 327 | 43.872 | 44.295 | −2.966 | 1.00 | 21.83 |
| ATOM | 1394 | N | ASP | A | 328 | 43.936 | 41.152 | −2.754 | 1.00 | 16.55 |
| ATOM | 1395 | CA | ASP | A | 328 | 43.514 | 40.226 | −1.688 | 1.00 | 15.31 |
| ATOM | 1396 | C | ASP | A | 328 | 44.231 | 38.897 | −1.833 | 1.00 | 17.16 |
| ATOM | 1397 | O | ASP | A | 328 | 44.519 | 38.239 | −0.835 | 1.00 | 16.85 |
| ATOM | 1398 | CB | ASP | A | 328 | 41.987 | 39.995 | −1.723 | 1.00 | 15.62 |
| ATOM | 1399 | CG | ASP | A | 328 | 41.179 | 41.221 | −1.274 | 1.00 | 16.69 |
| ATOM | 1400 | OD1 | ASP | A | 328 | 41.680 | 42.005 | −0.460 | 1.00 | 18.57 |
| ATOM | 1401 | OD2 | ASP | A | 328 | 39.968 | 41.228 | −1.563 | 1.00 | 19.43 |
| ATOM | 1402 | N | TRP | A | 329 | 44.515 | 38.493 | −3.084 | 1.00 | 16.20 |
| ATOM | 1403 | CA | TRP | A | 329 | 45.244 | 37.245 | −3.320 | 1.00 | 16.19 |
| ATOM | 1404 | C | TRP | A | 329 | 46.717 | 37.406 | −2.910 | 1.00 | 18.92 |
| ATOM | 1405 | O | TRP | A | 329 | 47.318 | 36.478 | −2.342 | 1.00 | 16.78 |
| ATOM | 1406 | CB | TRP | A | 329 | 45.095 | 36.780 | −4.766 | 1.00 | 16.23 |
| ATOM | 1407 | CG | TRP | A | 329 | 43.663 | 36.556 | −5.141 | 1.00 | 16.51 |

TABLE 4-continued

Structural coordinates for AKT3lkd(T305D, S472D) (SEQ ID NO:2).

| ATOM | 1408 | CD1 | TRP | A | 329 | 43.000 | 37.092 | −6.227 | 1.00 | 19.07 |
|---|---|---|---|---|---|---|---|---|---|---|
| ATOM | 1409 | CD2 | TRP | A | 329 | 42.680 | 35.839 | −4.386 | 1.00 | 16.61 |
| ATOM | 1410 | NE1 | TRP | A | 329 | 41.685 | 36.699 | −6.219 | 1.00 | 18.23 |
| ATOM | 1411 | CE2 | TRP | A | 329 | 41.446 | 35.959 | −5.081 | 1.00 | 18.84 |
| ATOM | 1412 | CE3 | TRP | A | 329 | 42.726 | 35.051 | −3.228 | 1.00 | 18.23 |
| ATOM | 1413 | CZ2 | TRP | A | 329 | 40.282 | 35.304 | −4.670 | 1.00 | 19.28 |
| ATOM | 1414 | CZ3 | TRP | A | 329 | 41.543 | 34.451 | −2.766 | 1.00 | 19.07 |
| ATOM | 1415 | CH2 | TRP | A | 329 | 40.323 | 34.572 | −3.515 | 1.00 | 19.26 |
| ATOM | 1416 | N | TRP | A | 330 | 47.287 | 38.600 | −3.141 | 1.00 | 17.85 |
| ATOM | 1417 | CA | TRP | A | 330 | 48.638 | 38.876 | −2.648 | 1.00 | 17.99 |
| ATOM | 1418 | C | TRP | A | 330 | 48.611 | 38.744 | −1.095 | 1.00 | 18.30 |
| ATOM | 1419 | O | TRP | A | 330 | 49.467 | 38.053 | −0.493 | 1.00 | 17.84 |
| ATOM | 1420 | CB | TRP | A | 330 | 49.071 | 40.315 | −3.030 | 1.00 | 16.95 |
| ATOM | 1421 | CG | TRP | A | 330 | 50.363 | 40.700 | −2.435 | 1.00 | 16.84 |
| ATOM | 1422 | CD1 | TRP | A | 330 | 50.560 | 41.305 | −1.236 | 1.00 | 19.36 |
| ATOM | 1423 | CD2 | TRP | A | 330 | 51.665 | 40.510 | −3.014 | 1.00 | 17.43 |
| ATOM | 1424 | NE1 | TRP | A | 330 | 51.919 | 41.479 | −1.012 | 1.00 | 19.59 |
| ATOM | 1425 | CE2 | TRP | A | 330 | 52.611 | 41.002 | −2.089 | 1.00 | 20.54 |
| ATOM | 1426 | CE3 | TRP | A | 330 | 52.120 | 39.943 | −4.201 | 1.00 | 19.19 |
| ATOM | 1427 | CZ2 | TRP | A | 330 | 54.023 | 40.970 | −2.342 | 1.00 | 20.81 |
| ATOM | 1428 | CZ3 | TRP | A | 330 | 53.534 | 39.934 | −4.462 | 1.00 | 21.51 |
| ATOM | 1429 | CH2 | TRP | A | 330 | 54.438 | 40.449 | −3.534 | 1.00 | 22.16 |
| ATOM | 1430 | N | GLY | A | 331 | 47.598 | 39.344 | −0.466 | 1.00 | 16.32 |
| ATOM | 1431 | CA | GLY | A | 331 | 47.456 | 39.289 | 0.999 | 1.00 | 16.72 |
| ATOM | 1432 | C | GLY | A | 331 | 47.389 | 37.823 | 1.479 | 1.00 | 18.64 |
| ATOM | 1433 | O | GLY | A | 331 | 47.995 | 37.447 | 2.500 | 1.00 | 17.98 |
| ATOM | 1434 | N | LEU | A | 332 | 46.612 | 37.002 | 0.768 | 1.00 | 16.76 |
| ATOM | 1435 | CA | LEU | A | 332 | 46.487 | 35.571 | 1.118 | 1.00 | 15.53 |
| ATOM | 1436 | C | LEU | A | 332 | 47.882 | 34.884 | 1.031 | 1.00 | 17.89 |
| ATOM | 1437 | O | LEU | A | 332 | 48.240 | 34.066 | 1.895 | 1.00 | 18.16 |
| ATOM | 1438 | CB | LEU | A | 332 | 45.496 | 34.878 | 0.192 | 1.00 | 15.07 |
| ATOM | 1439 | CG | LEU | A | 332 | 45.330 | 33.373 | 0.469 | 1.00 | 15.20 |
| ATOM | 1440 | CD1 | LEU | A | 332 | 44.636 | 33.170 | 1.815 | 1.00 | 16.87 |
| ATOM | 1441 | CD2 | LEU | A | 332 | 44.538 | 32.679 | −0.638 | 1.00 | 15.76 |
| ATOM | 1442 | N | GLY | A | 333 | 48.641 | 35.201 | −0.020 | 1.00 | 14.45 |
| ATOM | 1443 | CA | GLY | A | 333 | 49.969 | 34.667 | −0.181 | 1.00 | 14.50 |
| ATOM | 1444 | C | GLY | A | 333 | 50.846 | 35.054 | 1.013 | 1.00 | 18.64 |
| ATOM | 1445 | O | GLY | A | 333 | 51.549 | 34.219 | 1.542 | 1.00 | 18.32 |
| ATOM | 1446 | N | VAL | A | 334 | 50.825 | 36.320 | 1.412 | 1.00 | 15.93 |
| ATOM | 1447 | CA | VAL | A | 334 | 51.637 | 36.726 | 2.567 | 1.00 | 15.27 |
| ATOM | 1448 | C | VAL | A | 334 | 51.224 | 35.979 | 3.833 | 1.00 | 17.86 |
| ATOM | 1449 | O | VAL | A | 334 | 52.082 | 35.467 | 4.561 | 1.00 | 17.51 |
| ATOM | 1450 | CB | VAL | A | 334 | 51.571 | 38.270 | 2.826 | 1.00 | 19.12 |
| ATOM | 1451 | CG1 | VAL | A | 334 | 52.450 | 38.638 | 4.053 | 1.00 | 19.24 |
| ATOM | 1452 | CG2 | VAL | A | 334 | 52.076 | 39.046 | 1.566 | 1.00 | 19.34 |
| ATOM | 1453 | N | VAL | A | 335 | 49.917 | 35.899 | 4.105 | 1.00 | 15.88 |
| ATOM | 1454 | CA | VAL | A | 335 | 49.472 | 35.240 | 5.319 | 1.00 | 16.12 |
| ATOM | 1455 | C | VAL | A | 335 | 49.819 | 33.738 | 5.294 | 1.00 | 17.10 |
| ATOM | 1456 | O | VAL | A | 335 | 50.257 | 33.174 | 6.302 | 1.00 | 17.52 |
| ATOM | 1457 | CB | VAL | A | 335 | 47.964 | 35.387 | 5.484 | 1.00 | 21.25 |
| ATOM | 1458 | CG1 | VAL | A | 335 | 47.432 | 34.438 | 6.580 | 1.00 | 24.00 |
| ATOM | 1459 | CG2 | VAL | A | 335 | 47.622 | 36.848 | 5.794 | 1.00 | 20.72 |
| ATOM | 1460 | N | MET | A | 336 | 49.554 | 33.068 | 4.169 | 1.00 | 14.76 |
| ATOM | 1461 | CA | MET | A | 336 | 49.846 | 31.649 | 4.099 | 1.00 | 14.57 |
| ATOM | 1462 | C | MET | A | 336 | 51.332 | 31.369 | 4.134 | 1.00 | 17.97 |
| ATOM | 1463 | O | MET | A | 336 | 51.781 | 30.354 | 4.725 | 1.00 | 18.29 |
| ATOM | 1464 | CB | MET | A | 336 | 49.194 | 31.016 | 2.863 | 1.00 | 15.67 |
| ATOM | 1465 | CG | MET | A | 336 | 47.671 | 30.988 | 3.013 | 1.00 | 15.88 |
| ATOM | 1466 | SD | MET | A | 336 | 46.861 | 30.091 | 1.620 | 1.00 | 16.58 |
| ATOM | 1467 | CE | MET | A | 336 | 47.261 | 28.350 | 2.093 | 1.00 | 16.34 |
| ATOM | 1468 | N | TYR | A | 337 | 52.128 | 32.292 | 3.590 | 1.00 | 15.43 |
| ATOM | 1469 | CA | TYR | A | 337 | 53.582 | 32.124 | 3.635 | 1.00 | 16.32 |
| ATOM | 1470 | C | TYR | A | 337 | 54.007 | 32.218 | 5.127 | 1.00 | 20.33 |
| ATOM | 1471 | O | TYR | A | 337 | 54.801 | 31.377 | 5.631 | 1.00 | 19.84 |
| ATOM | 1472 | CB | TYR | A | 337 | 54.247 | 33.246 | 2.839 | 1.00 | 16.95 |
| ATOM | 1473 | CG | TYR | A | 337 | 55.763 | 33.122 | 2.776 | 1.00 | 17.41 |
| ATOM | 1474 | CD1 | TYR | A | 337 | 56.544 | 33.495 | 3.882 | 1.00 | 20.25 |
| ATOM | 1475 | CD2 | TYR | A | 337 | 56.402 | 32.655 | 1.640 | 1.00 | 19.35 |
| ATOM | 1476 | CE1 | TYR | A | 337 | 57.936 | 33.376 | 3.857 | 1.00 | 21.90 |
| ATOM | 1477 | CE2 | TYR | A | 337 | 57.824 | 32.508 | 1.613 | 1.00 | 19.47 |
| ATOM | 1478 | CZ | TYR | A | 337 | 58.560 | 32.883 | 2.726 | 1.00 | 23.17 |
| ATOM | 1479 | OH | TYR | A | 337 | 59.965 | 32.761 | 2.731 | 1.00 | 25.62 |
| ATOM | 1480 | N | GLU | A | 338 | 53.502 | 33.247 | 5.832 | 1.00 | 17.56 |
| ATOM | 1481 | CA | GLU | A | 338 | 53.854 | 33.415 | 7.260 | 1.00 | 17.68 |
| ATOM | 1482 | C | GLU | A | 338 | 53.485 | 32.142 | 8.028 | 1.00 | 21.54 |
| ATOM | 1483 | O | GLU | A | 338 | 54.247 | 31.641 | 8.862 | 1.00 | 21.77 |
| ATOM | 1484 | CB | GLU | A | 338 | 53.065 | 34.565 | 7.844 | 1.00 | 19.29 |
| ATOM | 1485 | CG | GLU | A | 338 | 53.455 | 35.900 | 7.330 | 1.00 | 26.16 |

TABLE 4-continued

Structural coordinates for AKT3lkd(T305D, S472D) (SEQ ID NO:2).

| ATOM | 1486 | CD | GLU | A | 338 | 52.713 | 37.001 | 8.076 | 1.00 | 37.95 |
|---|---|---|---|---|---|---|---|---|---|---|
| ATOM | 1487 | OE1 | GLU | A | 338 | 53.130 | 37.329 | 9.198 | 1.00 | 33.83 |
| ATOM | 1488 | OE2 | GLU | A | 338 | 51.607 | 37.371 | 7.636 | 1.00 | 35.56 |
| ATOM | 1489 | N | MET | A | 339 | 52.278 | 31.643 | 7.784 | 1.00 | 16.93 |
| ATOM | 1490 | CA | MET | A | 339 | 51.832 | 30.452 | 8.477 | 1.00 | 16.46 |
| ATOM | 1491 | C | MET | A | 339 | 52.714 | 29.252 | 8.266 | 1.00 | 20.73 |
| ATOM | 1492 | O | MET | A | 339 | 53.024 | 28.549 | 9.236 | 1.00 | 21.26 |
| ATOM | 1493 | CB | MET | A | 339 | 50.396 | 30.122 | 8.065 | 1.00 | 17.29 |
| ATOM | 1494 | CG | MET | A | 339 | 49.421 | 31.113 | 8.668 | 1.00 | 18.59 |
| ATOM | 1495 | SD | MET | A | 339 | 47.737 | 30.622 | 8.164 | 1.00 | 20.87 |
| ATOM | 1496 | CE | MET | A | 339 | 46.783 | 31.909 | 9.038 | 1.00 | 21.85 |
| ATOM | 1497 | N | MET | A | 340 | 53.055 | 28.949 | 7.008 | 1.00 | 18.20 |
| ATOM | 1498 | CA | MET | A | 340 | 53.857 | 27.736 | 6.696 | 1.00 | 19.13 |
| ATOM | 1499 | C | MET | A | 340 | 55.343 | 27.876 | 6.892 | 1.00 | 24.73 |
| ATOM | 1500 | O | MET | A | 340 | 56.033 | 26.862 | 7.056 | 1.00 | 24.72 |
| ATOM | 1501 | CB | MET | A | 340 | 53.607 | 27.261 | 5.253 | 1.00 | 21.96 |
| ATOM | 1502 | CG | MET | A | 340 | 52.360 | 26.433 | 5.106 | 1.00 | 24.40 |
| ATOM | 1503 | SD | MET | A | 340 | 52.220 | 25.908 | 3.385 | 1.00 | 25.49 |
| ATOM | 1504 | CE | MET | A | 340 | 51.144 | 27.256 | 2.678 | 1.00 | 22.68 |
| ATOM | 1505 | N | CYS | A | 341 | 55.860 | 29.104 | 6.812 | 1.00 | 22.20 |
| ATOM | 1506 | CA | CYS | A | 341 | 57.304 | 29.319 | 6.888 | 1.00 | 22.90 |
| ATOM | 1507 | C | CYS | A | 341 | 57.756 | 29.975 | 8.187 | 1.00 | 28.22 |
| ATOM | 1508 | O | CYS | A | 341 | 58.958 | 29.997 | 8.489 | 1.00 | 28.49 |
| ATOM | 1509 | CB | CYS | A | 341 | 57.778 | 30.135 | 5.686 | 1.00 | 22.30 |
| ATOM | 1510 | SG | CYS | A | 341 | 57.243 | 29.505 | 4.078 | 1.00 | 25.77 |
| ATOM | 1511 | N | GLY | A | 342 | 56.818 | 30.555 | 8.926 | 1.00 | 24.40 |
| ATOM | 1512 | CA | GLY | A | 342 | 57.126 | 31.152 | 10.227 | 1.00 | 25.16 |
| ATOM | 1513 | C | GLY | A | 342 | 57.753 | 32.558 | 10.192 | 1.00 | 30.72 |
| ATOM | 1514 | O | GLY | A | 342 | 58.230 | 33.064 | 11.223 | 1.00 | 32.18 |
| ATOM | 1515 | N | ARG | A | 343 | 57.719 | 33.197 | 9.028 | 1.00 | 25.66 |
| ATOM | 1516 | CA | ARG | A | 343 | 58.223 | 34.555 | 8.878 | 1.00 | 25.98 |
| ATOM | 1517 | C | ARG | A | 343 | 57.583 | 35.191 | 7.644 | 1.00 | 27.44 |
| ATOM | 1518 | O | ARG | A | 343 | 57.032 | 34.495 | 6.778 | 1.00 | 24.39 |
| ATOM | 1519 | CB | ARG | A | 343 | 59.742 | 34.548 | 8.701 | 1.00 | 28.62 |
| ATOM | 1520 | CG | ARG | A | 343 | 60.247 | 33.640 | 7.614 | 1.00 | 39.03 |
| ATOM | 1521 | CD | ARG | A | 343 | 61.465 | 34.230 | 6.904 | 1.00 | 56.59 |
| ATOM | 1522 | NE | ARG | A | 343 | 61.160 | 34.561 | 5.512 | 1.00 | 70.89 |
| ATOM | 1523 | CZ | ARG | A | 343 | 62.039 | 35.052 | 4.643 | 1.00 | 87.08 |
| ATOM | 1524 | NH1 | ARG | A | 343 | 63.291 | 35.286 | 5.019 | 1.00 | 77.50 |
| ATOM | 1525 | NH2 | ARG | A | 343 | 61.663 | 35.307 | 3.396 | 1.00 | 70.52 |
| ATOM | 1526 | N | LEU | A | 344 | 57.704 | 36.506 | 7.541 | 1.00 | 24.60 |
| ATOM | 1527 | CA | LEU | A | 344 | 57.181 | 37.219 | 6.374 | 1.00 | 24.21 |
| ATOM | 1528 | C | LEU | A | 344 | 58.067 | 36.927 | 5.166 | 1.00 | 26.92 |
| ATOM | 1529 | O | LEU | A | 344 | 59.278 | 36.683 | 5.299 | 1.00 | 26.42 |
| ATOM | 1530 | CB | LEU | A | 344 | 57.160 | 38.728 | 6.643 | 1.00 | 24.72 |
| ATOM | 1531 | CG | LEU | A | 344 | 56.152 | 39.262 | 7.647 | 1.00 | 29.92 |
| ATOM | 1532 | CD1 | LEU | A | 344 | 56.500 | 40.707 | 8.020 | 1.00 | 31.62 |
| ATOM | 1533 | CD2 | LEU | A | 344 | 54.732 | 39.159 | 7.097 | 1.00 | 31.95 |
| ATOM | 1534 | N | PRO | A | 345 | 57.472 | 36.916 | 3.975 | 1.00 | 24.26 |
| ATOM | 1535 | CA | PRO | A | 345 | 58.248 | 36.653 | 2.769 | 1.00 | 24.08 |
| ATOM | 1536 | C | PRO | A | 345 | 59.212 | 37.830 | 2.451 | 1.00 | 28.46 |
| ATOM | 1537 | O | PRO | A | 345 | 60.243 | 37.627 | 1.806 | 1.00 | 28.34 |
| ATOM | 1538 | CB | PRO | A | 345 | 57.182 | 36.525 | 1.666 | 1.00 | 25.61 |
| ATOM | 1539 | CG | PRO | A | 345 | 55.992 | 37.253 | 2.169 | 1.00 | 28.62 |
| ATOM | 1540 | CD | PRO | A | 345 | 56.073 | 37.303 | 3.692 | 1.00 | 24.42 |
| ATOM | 1541 | N | PHE | A | 346 | 58.829 | 39.041 | 2.867 | 1.00 | 26.74 |
| ATOM | 1542 | CA | PHE | A | 346 | 59.645 | 40.251 | 2.621 | 1.00 | 26.84 |
| ATOM | 1543 | C | PHE | A | 346 | 59.746 | 41.039 | 3.904 | 1.00 | 31.96 |
| ATOM | 1544 | O | PHE | A | 346 | 58.727 | 41.404 | 4.498 | 1.00 | 29.22 |
| ATOM | 1545 | CB | PHE | A | 346 | 59.001 | 41.159 | 1.563 | 1.00 | 27.30 |
| ATOM | 1546 | CG | PHE | A | 346 | 58.560 | 40.446 | 0.350 | 1.00 | 27.12 |
| ATOM | 1547 | CD1 | PHE | A | 346 | 59.485 | 40.007 | −0.582 | 1.00 | 27.66 |
| ATOM | 1548 | CD2 | PHE | A | 346 | 57.213 | 40.190 | 0.139 | 1.00 | 27.56 |
| ATOM | 1549 | CE1 | PHE | A | 346 | 59.078 | 39.314 | −1.712 | 1.00 | 28.74 |
| ATOM | 1550 | CE2 | PHE | A | 346 | 56.806 | 39.478 | −0.961 | 1.00 | 28.95 |
| ATOM | 1551 | CZ | PHE | A | 346 | 57.739 | 39.049 | −1.895 | 1.00 | 27.40 |
| ATOM | 1552 | N | TYR | A | 347 | 60.976 | 41.306 | 4.334 | 1.00 | 33.90 |
| ATOM | 1553 | CA | TYR | A | 347 | 61.179 | 42.109 | 5.523 | 1.00 | 36.04 |
| ATOM | 1554 | C | TYR | A | 347 | 62.462 | 42.941 | 5.525 | 1.00 | 40.34 |
| ATOM | 1555 | O | TYR | A | 347 | 63.540 | 42.446 | 5.198 | 1.00 | 39.59 |
| ATOM | 1556 | CB | TYR | A | 347 | 61.117 | 41.275 | 6.801 | 1.00 | 39.11 |
| ATOM | 1557 | CG | TYR | A | 347 | 61.215 | 42.157 | 8.030 | 1.00 | 43.57 |
| ATOM | 1558 | CD1 | TYR | A | 347 | 60.169 | 43.006 | 8.373 | 1.00 | 46.06 |
| ATOM | 1559 | CD2 | TYR | A | 347 | 62.413 | 42.288 | 8.721 | 1.00 | 45.12 |
| ATOM | 1560 | CE1 | TYR | A | 347 | 60.280 | 43.889 | 9.435 | 1.00 | 47.71 |
| ATOM | 1561 | CE2 | TYR | A | 347 | 62.528 | 43.161 | 9.797 | 1.00 | 46.32 |
| ATOM | 1562 | CZ | TYR | A | 347 | 61.455 | 43.956 | 10.144 | 1.00 | 54.92 |
| ATOM | 1563 | OH | TYR | A | 347 | 61.557 | 44.833 | 11.202 | 1.00 | 58.51 |

TABLE 4-continued

Structural coordinates for AKT3lkd(T305D, S472D) (SEQ ID NO:2).

| ATOM | 1564 | N | ASN | A | 348 | 62.318 | 44.194 | 5.950 | 1.00 | 38.31 |
|------|------|-----|-----|---|-----|--------|--------|--------|------|-------|
| ATOM | 1565 | CA | ASN | A | 348 | 63.447 | 45.125 | 6.150 | 1.00 | 38.57 |
| ATOM | 1566 | C | ASN | A | 348 | 62.958 | 46.284 | 7.009 | 1.00 | 43.57 |
| ATOM | 1567 | O | ASN | A | 348 | 61.819 | 46.736 | 6.861 | 1.00 | 41.78 |
| ATOM | 1568 | CB | ASN | A | 348 | 63.997 | 45.648 | 4.828 | 1.00 | 38.84 |
| ATOM | 1569 | CG | ASN | A | 348 | 65.409 | 46.179 | 4.961 | 1.00 | 59.16 |
| ATOM | 1570 | OD1 | ASN | A | 348 | 65.646 | 47.181 | 5.637 | 1.00 | 47.66 |
| ATOM | 1571 | ND2 | ASN | A | 348 | 66.365 | 45.470 | 4.372 | 1.00 | 54.49 |
| ATOM | 1572 | N | GLN | A | 349 | 63.805 | 46.749 | 7.928 | 1.00 | 42.40 |
| ATOM | 1573 | CA | GLN | A | 349 | 63.432 | 47.861 | 8.804 | 1.00 | 43.44 |
| ATOM | 1574 | C | GLN | A | 349 | 63.311 | 49.174 | 8.018 | 1.00 | 47.96 |
| ATOM | 1575 | O | GLN | A | 349 | 62.496 | 50.035 | 8.352 | 1.00 | 48.00 |
| ATOM | 1576 | CB | GLN | A | 349 | 64.424 | 48.002 | 9.971 | 1.00 | 45.17 |
| ATOM | 1577 | CG | GLN | A | 349 | 65.848 | 47.550 | 9.650 | 1.00 | 66.65 |
| ATOM | 1578 | CD | GLN | A | 349 | 66.903 | 48.416 | 10.323 | 1.00 | 90.56 |
| ATOM | 1579 | CE1 | GLN | A | 349 | 66.640 | 49.058 | 11.343 | 1.00 | 87.43 |
| ATOM | 1580 | NE2 | GLN | A | 349 | 68.102 | 48.445 | 9.746 | 1.00 | 82.86 |
| ATOM | 1581 | N | ASP | A | 350 | 64.090 | 49.298 | 6.947 | 1.00 | 45.20 |
| ATOM | 1582 | CA | ASP | A | 350 | 64.017 | 50.472 | 6.068 | 1.00 | 45.04 |
| ATOM | 1583 | C | ASP | A | 350 | 62.872 | 50.232 | 5.088 | 1.00 | 48.86 |
| ATOM | 1584 | O | ASP | A | 350 | 62.954 | 49.343 | 4.235 | 1.00 | 48.45 |
| ATOM | 1585 | CB | ASP | A | 350 | 65.331 | 50.643 | 5.287 | 1.00 | 46.53 |
| ATOM | 1586 | CG | ASP | A | 350 | 65.318 | 51.870 | 4.373 | 1.00 | 55.80 |
| ATOM | 1587 | OD1 | ASP | A | 350 | 66.048 | 52.837 | 4.667 | 1.00 | 57.12 |
| ATOM | 1588 | OD2 | ASP | A | 350 | 64.577 | 51.872 | 3.368 | 1.00 | 58.12 |
| ATOM | 1589 | N | HIS | A | 351 | 61.800 | 50.999 | 5.228 | 1.00 | 46.04 |
| ATOM | 1590 | CA | HIS | A | 351 | 60.628 | 50.816 | 4.378 | 1.00 | 46.24 |
| ATOM | 1591 | C | HIS | A | 351 | 60.937 | 50.885 | 2.883 | 1.00 | 47.93 |
| ATOM | 1592 | O | HIS | A | 351 | 60.381 | 50.128 | 2.087 | 1.00 | 46.55 |
| ATOM | 1593 | CB | HIS | A | 351 | 59.491 | 51.760 | 4.788 | 1.00 | 47.88 |
| ATOM | 1594 | CG | HIS | A | 351 | 58.806 | 51.352 | 6.060 | 1.00 | 52.10 |
| ATOM | 1595 | ND1 | HIS | A | 351 | 57.990 | 52.204 | 6.777 | 1.00 | 54.35 |
| ATOM | 1596 | CD2 | HIS | A | 351 | 58.825 | 50.185 | 6.747 | 1.00 | 54.52 |
| ATOM | 1597 | CE1 | HIS | A | 351 | 57.533 | 51.576 | 7.847 | 1.00 | 53.94 |
| ATOM | 1598 | NE2 | HIS | A | 351 | 58.025 | 50.350 | 7.852 | 1.00 | 54.40 |
| ATOM | 1599 | N | GLU | A | 352 | 61.877 | 51.740 | 2.506 | 1.00 | 42.35 |
| ATOM | 1600 | CA | GLU | A | 352 | 62.262 | 51.825 | 1.108 | 1.00 | 41.09 |
| ATOM | 1601 | C | GLU | A | 352 | 62.934 | 50.530 | 0.622 | 1.00 | 41.83 |
| ATOM | 1602 | O | GLU | A | 352 | 62.691 | 50.090 | −0.489 | 1.00 | 41.97 |
| ATOM | 1603 | CB | GLU | A | 352 | 63.151 | 53.057 | 0.849 | 1.00 | 42.53 |
| ATOM | 1604 | CG | GLU | A | 352 | 62.402 | 54.203 | 0.203 | 1.00 | 48.64 |
| ATOM | 1605 | CD | GLU | A | 352 | 63.294 | 55.112 | −0.635 | 1.00 | 62.36 |
| ATOM | 1606 | OE1 | GLU | A | 352 | 62.748 | 55.828 | −1.505 | 1.00 | 50.55 |
| ATOM | 1607 | OE2 | GLU | A | 352 | 64.530 | 55.130 | −0.409 | 1.00 | 50.32 |
| ATOM | 1608 | N | LYS | A | 353 | 63.762 | 49.922 | 1.469 | 1.00 | 35.22 |
| ATOM | 1609 | CA | LYS | A | 353 | 64.428 | 48.656 | 1.123 | 1.00 | 34.20 |
| ATOM | 1610 | C | LYS | A | 353 | 63.374 | 47.553 | 1.099 | 1.00 | 35.17 |
| ATOM | 1611 | O | LYS | A | 353 | 63.443 | 46.629 | 0.287 | 1.00 | 34.92 |
| ATOM | 1612 | CB | LYS | A | 353 | 65.479 | 48.292 | 2.178 | 1.00 | 37.53 |
| ATOM | 1613 | CG | LYS | A | 353 | 66.870 | 48.868 | 1.909 | 1.00 | 54.86 |
| ATOM | 1614 | CD | LYS | A | 353 | 67.811 | 48.609 | 3.082 | 1.00 | 64.47 |
| ATOM | 1615 | CE | LYS | A | 353 | 69.185 | 49.221 | 2.839 | 1.00 | 75.39 |
| ATOM | 1616 | NZ | LYS | A | 353 | 70.283 | 48.353 | 3.358 | 1.00 | 83.20 |
| ATOM | 1617 | N | LEU | A | 354 | 62.426 | 47.644 | 2.021 | 1.00 | 31.25 |
| ATOM | 1618 | CA | LEU | A | 354 | 61.317 | 46.668 | 2.087 | 1.00 | 30.66 |
| ATOM | 1619 | C | LEU | A | 354 | 60.538 | 46.741 | 0.794 | 1.00 | 34.29 |
| ATOM | 1620 | O | LEU | A | 354 | 60.202 | 45.712 | 0.203 | 1.00 | 33.45 |
| ATOM | 1621 | CB | LEU | A | 354 | 60.395 | 46.977 | 3.265 | 1.00 | 30.67 |
| ATOM | 1622 | CG | LEU | A | 354 | 59.013 | 46.307 | 3.249 | 1.00 | 35.20 |
| ATOM | 1623 | CD1 | LEU | A | 354 | 59.181 | 44.807 | 3.530 | 1.00 | 35.00 |
| ATOM | 1624 | CD2 | LEU | A | 354 | 58.072 | 46.972 | 4.271 | 1.00 | 37.28 |
| ATOM | 1625 | N | PHE | A | 355 | 60.245 | 47.958 | 0.345 | 1.00 | 30.30 |
| ATOM | 1626 | CA | PHE | A | 355 | 59.506 | 48.123 | −0.899 | 1.00 | 30.04 |
| ATOM | 1627 | C | PHE | A | 355 | 60.286 | 47.576 | −2.082 | 1.00 | 31.77 |
| ATOM | 1628 | O | PHE | A | 355 | 59.709 | 47.029 | −3.029 | 1.00 | 31.15 |
| ATOM | 1629 | CB | PHE | A | 355 | 59.101 | 49.593 | −1.092 | 1.00 | 32.31 |
| ATOM | 1630 | CG | PHE | A | 355 | 58.135 | 50.104 | −0.049 | 1.00 | 34.87 |
| ATOM | 1631 | CD1 | PHE | A | 355 | 57.462 | 49.225 | 0.791 | 1.00 | 38.18 |
| ATOM | 1632 | CD2 | PHE | A | 355 | 57.882 | 51.469 | 0.079 | 1.00 | 37.95 |
| ATOM | 1633 | CE1 | PHE | A | 355 | 56.562 | 49.691 | 1.744 | 1.00 | 39.50 |
| ATOM | 1634 | CE2 | PHE | A | 355 | 56.985 | 51.943 | 1.035 | 1.00 | 41.20 |
| ATOM | 1635 | CZ | PHE | A | 355 | 56.318 | 51.052 | 1.865 | 1.00 | 39.77 |
| ATOM | 1636 | N | GLU | A | 356 | 61.609 | 47.736 | −2.055 | 1.00 | 30.68 |
| ATOM | 1637 | CA | GLU | A | 356 | 62.455 | 47.221 | −3.120 | 1.00 | 31.42 |
| ATOM | 1638 | C | GLU | A | 356 | 62.380 | 45.682 | −3.180 | 1.00 | 34.01 |
| ATOM | 1639 | O | GLU | A | 356 | 62.365 | 45.078 | −4.257 | 1.00 | 33.39 |
| ATOM | 1640 | CB | GLU | A | 356 | 63.904 | 47.698 | −2.930 | 1.00 | 33.63 |
| ATOM | 1641 | CG | GLU | A | 356 | 64.759 | 47.615 | −4.182 | 1.00 | 44.77 |

TABLE 4-continued

Structural coordinates for AKT3lkd(T305D, S472D) (SEQ ID NO:2).

| ATOM | 1642 | CD | GLU | A | 356 | 64.771 | 48.915 | −4.975 | 1.00 | 71.77 |
|---|---|---|---|---|---|---|---|---|---|---|
| ATOM | 1643 | OE1 | GLU | A | 356 | 63.901 | 49.083 | −5.856 | 1.00 | 72.94 |
| ATOM | 1644 | OE2 | GLU | A | 356 | 65.662 | 49.759 | −4.732 | 1.00 | 64.67 |
| ATOM | 1645 | N | LEU | A | 357 | 62.293 | 45.061 | −2.015 | 1.00 | 29.89 |
| ATOM | 1646 | CA | LEU | A | 357 | 62.164 | 43.607 | −1.935 | 1.00 | 29.27 |
| ATOM | 1647 | C | LEU | A | 357 | 60.803 | 43.181 | −2.477 | 1.00 | 29.62 |
| ATOM | 1648 | O | LEU | A | 357 | 60.696 | 42.257 | −3.289 | 1.00 | 30.25 |
| ATOM | 1649 | CB | LEU | A | 357 | 62.284 | 43.151 | −0.476 | 1.00 | 29.51 |
| ATOM | 1650 | CG | LEU | A | 357 | 63.637 | 43.411 | 0.220 | 1.00 | 35.97 |
| ATOM | 1651 | CD1 | LEU | A | 357 | 63.595 | 42.988 | 1.663 | 1.00 | 36.60 |
| ATOM | 1652 | CD2 | LEU | A | 357 | 64.743 | 42.678 | −0.519 | 1.00 | 40.30 |
| ATOM | 1653 | N | ILE | A | 358 | 59.766 | 43.863 | −2.028 | 1.00 | 25.18 |
| ATOM | 1654 | CA | ILE | A | 358 | 58.416 | 43.541 | −2.473 | 1.00 | 24.14 |
| ATOM | 1655 | C | ILE | A | 358 | 58.298 | 43.669 | −3.983 | 1.00 | 29.07 |
| ATOM | 1656 | O | ILE | A | 358 | 57.719 | 42.818 | −4.640 | 1.00 | 27.15 |
| ATOM | 1657 | CB | ILE | A | 358 | 57.372 | 44.403 | −1.795 | 1.00 | 26.57 |
| ATOM | 1658 | CG1 | ILE | A | 358 | 57.248 | 44.051 | −0.303 | 1.00 | 26.57 |
| ATOM | 1659 | CG2 | ILE | A | 358 | 56.008 | 44.277 | −2.498 | 1.00 | 26.86 |
| ATOM | 1660 | CD1 | ILE | A | 358 | 56.424 | 45.056 | 0.489 | 1.00 | 28.46 |
| ATOM | 1661 | N | LEU | A | 359 | 58.863 | 44.738 | −4.538 | 1.00 | 27.20 |
| ATOM | 1662 | CA | LEU | A | 359 | 58.788 | 44.932 | −5.973 | 1.00 | 28.25 |
| ATOM | 1663 | C | LEU | A | 359 | 59.654 | 43.996 | −6.803 | 1.00 | 34.03 |
| ATOM | 1664 | O | LEU | A | 359 | 59.246 | 43.564 | −7.883 | 1.00 | 33.34 |
| ATOM | 1665 | CB | LEU | A | 359 | 59.113 | 46.402 | −6.334 | 1.00 | 28.57 |
| ATOM | 1666 | CG | LEU | A | 359 | 58.127 | 47.441 | −5.813 | 1.00 | 33.50 |
| ATOM | 1667 | CD1 | LEU | A | 359 | 58.846 | 48.808 | −5.621 | 1.00 | 34.61 |
| ATOM | 1668 | CD2 | LEU | A | 359 | 56.967 | 47.580 | −6.778 | 1.00 | 34.60 |
| ATOM | 1669 | N | MET | A | 360 | 60.848 | 43.673 | −6.305 | 1.00 | 33.71 |
| ATOM | 1670 | CA | MET | A | 360 | 61.813 | 42.949 | −7.113 | 1.00 | 35.42 |
| ATOM | 1671 | C | MET | A | 360 | 62.329 | 41.577 | −6.718 | 1.00 | 38.67 |
| ATOM | 1672 | O | MET | A | 360 | 62.828 | 40.841 | −7.576 | 1.00 | 38.53 |
| ATOM | 1673 | CB | MET | A | 360 | 63.001 | 43.856 | −7.376 | 1.00 | 38.44 |
| ATOM | 1674 | CG | MET | A | 360 | 62.593 | 45.266 | −7.762 | 1.00 | 43.23 |
| ATOM | 1675 | SD | MET | A | 360 | 62.246 | 45.416 | −9.504 | 1.00 | 48.47 |
| ATOM | 1676 | CE | MET | A | 360 | 61.186 | 44.014 | −9.837 | 1.00 | 45.78 |
| ATOM | 1677 | N | GLU | A | 361 | 62.295 | 41.257 | −5.433 | 1.00 | 34.30 |
| ATOM | 1678 | CA | GLU | A | 361 | 62.902 | 40.020 | −4.964 | 1.00 | 33.28 |
| ATOM | 1679 | C | GLU | A | 361 | 61.996 | 38.826 | −5.048 | 1.00 | 35.17 |
| ATOM | 1680 | O | GLU | A | 361 | 60.813 | 38.925 | −4.770 | 1.00 | 32.91 |
| ATOM | 1681 | CB | GLU | A | 361 | 63.374 | 40.175 | −3.533 | 1.00 | 34.94 |
| ATOM | 1682 | CG | GLU | A | 361 | 63.898 | 38.869 | −2.934 | 1.00 | 48.45 |
| ATOM | 1683 | CD | GLU | A | 361 | 64.463 | 39.050 | −1.540 | 1.00 | 79.14 |
| ATOM | 1684 | OE1 | GLU | A | 361 | 63.688 | 38.914 | −0.559 | 1.00 | 76.08 |
| ATOM | 1685 | OE2 | GLU | A | 361 | 65.685 | 39.311 | −1.426 | 1.00 | 76.80 |
| ATOM | 1686 | N | ASP | A | 362 | 62.572 | 37.673 | −5.368 | 1.00 | 31.67 |
| ATOM | 1687 | CA | ASP | A | 362 | 61.785 | 36.444 | −5.401 | 1.00 | 32.57 |
| ATOM | 1688 | C | ASP | A | 362 | 61.797 | 35.863 | −4.002 | 1.00 | 35.78 |
| ATOM | 1689 | O | ASP | A | 362 | 62.720 | 36.105 | −3.238 | 1.00 | 36.79 |
| ATOM | 1690 | CB | ASP | A | 362 | 62.369 | 35.453 | −6.411 | 1.00 | 35.54 |
| ATOM | 1691 | CG | ASP | A | 362 | 61.758 | 35.608 | −7.795 | 1.00 | 51.73 |
| ATOM | 1692 | OD1 | ASP | A | 362 | 60.504 | 35.694 | −7.897 | 1.00 | 52.19 |
| ATOM | 1693 | OD2 | ASP | A | 362 | 62.532 | 35.687 | −8.778 | 1.00 | 59.33 |
| ATOM | 1694 | N | ILE | A | 363 | 60.748 | 35.144 | −3.627 | 1.00 | 30.95 |
| ATOM | 1695 | CA | ILE | A | 363 | 60.717 | 34.585 | −2.293 | 1.00 | 29.82 |
| ATOM | 1696 | C | ILE | A | 363 | 61.536 | 33.300 | −2.203 | 1.00 | 32.78 |
| ATOM | 1697 | O | ILE | A | 363 | 61.765 | 32.617 | −3.210 | 1.00 | 33.01 |
| ATOM | 1698 | CB | ILE | A | 363 | 59.260 | 34.269 | −1.828 | 1.00 | 32.23 |
| ATOM | 1699 | CG1 | ILE | A | 363 | 58.557 | 33.393 | −2.856 | 1.00 | 32.50 |
| ATOM | 1700 | CG2 | ILE | A | 363 | 58.486 | 35.536 | −1.572 | 1.00 | 33.40 |
| ATOM | 1701 | CD1 | ILE | A | 363 | 57.069 | 33.237 | −2.605 | 1.00 | 33.02 |
| ATOM | 1702 | N | LYS | A | 364 | 61.917 | 32.964 | −0.983 | 1.00 | 30.38 |
| ATOM | 1703 | CA | LYS | A | 364 | 62.627 | 31.718 | −0.692 | 1.00 | 30.58 |
| ATOM | 1704 | C | LYS | A | 364 | 61.696 | 30.838 | 0.165 | 1.00 | 31.92 |
| ATOM | 1705 | O | LYS | A | 364 | 60.827 | 31.349 | 0.878 | 1.00 | 30.56 |
| ATOM | 1706 | CB | LYS | A | 364 | 63.908 | 32.023 | 0.075 | 1.00 | 33.95 |
| ATOM | 1707 | CG | LYS | A | 364 | 64.974 | 32.729 | −0.765 | 1.00 | 47.75 |
| ATOM | 1708 | CD | LYS | A | 364 | 64.852 | 32.364 | −2.246 | 1.00 | 55.44 |
| ATOM | 1709 | CE | LYS | A | 364 | 65.921 | 33.074 | −3.082 | 1.00 | 69.93 |
| ATOM | 1710 | NZ | LYS | A | 364 | 65.551 | 33.157 | −4.526 | 1.00 | 77.97 |
| ATOM | 1711 | N | PHE | A | 365 | 61.921 | 29.527 | 0.128 | 1.00 | 27.05 |
| ATOM | 1712 | CA | PHE | A | 365 | 61.085 | 28.560 | 0.852 | 1.00 | 25.83 |
| ATOM | 1713 | C | PHE | A | 365 | 61.926 | 27.638 | 1.722 | 1.00 | 31.06 |
| ATOM | 1714 | O | PHE | A | 365 | 63.076 | 27.328 | 1.381 | 1.00 | 33.12 |
| ATOM | 1715 | CB | PHE | A | 365 | 60.342 | 27.663 | −0.168 | 1.00 | 26.75 |
| ATOM | 1716 | CG | PHE | A | 365 | 59.376 | 28.400 | −1.050 | 1.00 | 26.49 |
| ATOM | 1717 | CD1 | PHE | A | 365 | 58.262 | 29.016 | −0.510 | 1.00 | 26.37 |
| ATOM | 1718 | CD2 | PHE | A | 365 | 59.566 | 28.463 | −2.432 | 1.00 | 28.75 |
| ATOM | 1719 | CE1 | PHE | A | 365 | 57.388 | 29.732 | −1.317 | 1.00 | 27.17 |

TABLE 4-continued

Structural coordinates for AKT3lkd(T305D, S472D) (SEQ ID NO:2).

| ATOM | 1720 | CE2 | PHE | A | 365 | 58.671 | 29.156 | −3.233 | 1.00 | 30.11 |
|---|---|---|---|---|---|---|---|---|---|---|
| ATOM | 1721 | CZ | PHE | A | 365 | 57.584 | 29.782 | −2.669 | 1.00 | 27.82 |
| ATOM | 1722 | N | PRO | A | 366 | 61.330 | 27.116 | 2.783 | 1.00 | 28.26 |
| ATOM | 1723 | CA | PRO | A | 366 | 61.987 | 26.067 | 3.565 | 1.00 | 28.30 |
| ATOM | 1724 | C | PRO | A | 366 | 62.162 | 24.930 | 2.534 | 1.00 | 33.54 |
| ATOM | 1725 | O | PRO | A | 366 | 61.250 | 24.652 | 1.752 | 1.00 | 33.29 |
| ATOM | 1726 | CB | PRO | A | 366 | 60.935 | 25.688 | 4.591 | 1.00 | 30.03 |
| ATOM | 1727 | CG | PRO | A | 366 | 60.110 | 26.945 | 4.780 | 1.00 | 32.57 |
| ATOM | 1728 | CD | PRO | A | 366 | 60.094 | 27.609 | 3.431 | 1.00 | 28.03 |
| ATOM | 1729 | N | ARG | A | 367 | 63.355 | 24.341 | 2.445 | 1.00 | 34.10 |
| ATOM | 1730 | CA | ARG | A | 367 | 63.567 | 23.312 | 1.433 | 1.00 | 32.42 |
| ATOM | 1731 | C | ARG | A | 367 | 62.524 | 22.172 | 1.467 | 1.00 | 34.35 |
| ATOM | 1732 | O | ARG | A | 367 | 62.138 | 21.667 | 0.406 | 1.00 | 35.93 |
| ATOM | 1733 | CB | ARG | A | 367 | 64.985 | 22.724 | 1.511 | 1.00 | 31.46 |
| ATOM | 1734 | CG | ARG | A | 367 | 65.687 | 22.588 | 0.157 | 1.00 | 46.30 |
| ATOM | 1735 | CD | ARG | A | 367 | 67.211 | 22.507 | 0.342 | 1.00 | 53.23 |
| ATOM | 1736 | NE | ARG | A | 367 | 67.554 | 22.258 | 1.739 | 1.00 | 52.84 |
| ATOM | 1737 | CZ | ARG | A | 367 | 68.394 | 21.314 | 2.155 | 1.00 | 61.23 |
| ATOM | 1738 | NH1 | ARG | A | 367 | 69.016 | 20.533 | 1.276 | 1.00 | 48.93 |
| ATOM | 1739 | NH2 | ARG | A | 367 | 68.615 | 21.155 | 3.453 | 1.00 | 41.97 |
| ATOM | 1740 | N | THR | A | 368 | 62.103 | 21.736 | 2.663 | 1.00 | 27.04 |
| ATOM | 1741 | CA | THR | A | 368 | 61.138 | 20.598 | 2.718 | 1.00 | 23.58 |
| ATOM | 1742 | C | THR | A | 368 | 59.688 | 20.990 | 2.484 | 1.00 | 23.82 |
| ATOM | 1743 | O | THR | A | 368 | 58.808 | 20.136 | 2.511 | 1.00 | 22.10 |
| ATOM | 1744 | CB | THR | A | 368 | 61.193 | 19.785 | 4.013 | 1.00 | 32.98 |
| ATOM | 1745 | OG1 | THR | A | 368 | 60.820 | 20.614 | 5.114 | 1.00 | 37.39 |
| ATOM | 1746 | CG2 | THR | A | 368 | 62.595 | 19.154 | 4.247 | 1.00 | 31.49 |
| ATOM | 1747 | N | LEU | A | 369 | 59.437 | 22.264 | 2.206 | 1.00 | 21.06 |
| ATOM | 1748 | CA | LEU | A | 369 | 58.062 | 22.650 | 1.903 | 1.00 | 19.33 |
| ATOM | 1749 | C | LEU | A | 369 | 57.637 | 21.874 | 0.655 | 1.00 | 20.47 |
| ATOM | 1750 | O | LEU | A | 369 | 58.444 | 21.650 | −0.260 | 1.00 | 20.50 |
| ATOM | 1751 | CB | LEU | A | 369 | 57.969 | 24.150 | 1.650 | 1.00 | 20.19 |
| ATOM | 1752 | CG | LEU | A | 369 | 56.560 | 24.730 | 1.791 | 1.00 | 24.57 |
| ATOM | 1753 | CD1 | LEU | A | 369 | 56.089 | 24.651 | 3.242 | 1.00 | 25.89 |
| ATOM | 1754 | CD2 | LEU | A | 369 | 56.493 | 26.174 | 1.260 | 1.00 | 24.16 |
| ATOM | 1755 | N | SER | A | 370 | 56.374 | 21.438 | 0.617 | 1.00 | 17.25 |
| ATOM | 1756 | CA | SER | A | 370 | 55.899 | 20.657 | −0.499 | 1.00 | 17.14 |
| ATOM | 1757 | C | SER | A | 370 | 55.867 | 21.410 | −1.805 | 1.00 | 19.15 |
| ATOM | 1758 | O | SER | A | 370 | 55.727 | 22.635 | −1.843 | 1.00 | 18.81 |
| ATOM | 1759 | CB | SER | A | 370 | 54.519 | 20.046 | −0.208 | 1.00 | 19.51 |
| ATOM | 1760 | OG | SER | A | 370 | 53.486 | 21.028 | −0.392 | 1.00 | 19.30 |
| ATOM | 1761 | N | SER | A | 371 | 55.991 | 20.665 | −2.893 | 1.00 | 17.66 |
| ATOM | 1762 | CA | SER | A | 371 | 55.972 | 21.233 | −4.208 | 1.00 | 15.98 |
| ATOM | 1763 | C | SER | A | 371 | 54.696 | 22.066 | −4.445 | 1.00 | 17.96 |
| ATOM | 1764 | O | SER | A | 371 | 54.745 | 23.184 | −4.977 | 1.00 | 18.34 |
| ATOM | 1765 | CB | SER | A | 371 | 56.032 | 20.103 | −5.240 | 1.00 | 19.53 |
| ATOM | 1766 | OG | SER | A | 371 | 56.046 | 20.631 | −6.542 | 1.00 | 24.49 |
| ATOM | 1767 | N | ASP | A | 372 | 53.556 | 21.501 | −4.055 | 1.00 | 17.27 |
| ATOM | 1768 | CA | ASP | A | 372 | 52.267 | 22.219 | −4.259 | 1.00 | 16.58 |
| ATOM | 1769 | C | ASP | A | 372 | 52.214 | 23.509 | −3.417 | 1.00 | 18.41 |
| ATOM | 1770 | O | ASP | A | 372 | 51.662 | 24.534 | −3.870 | 1.00 | 18.08 |
| ATOM | 1771 | CB | ASP | A | 372 | 51.091 | 21.313 | −3.882 | 1.00 | 18.58 |
| ATOM | 1772 | CG | ASP | A | 372 | 50.798 | 20.215 | −4.920 | 1.00 | 20.80 |
| ATOM | 1773 | OD1 | ASP | A | 372 | 51.367 | 20.221 | −6.033 | 1.00 | 23.06 |
| ATOM | 1774 | OD2 | ASP | A | 372 | 49.918 | 19.375 | −4.631 | 1.00 | 23.82 |
| ATOM | 1775 | N | ALA | A | 373 | 52.762 | 23.467 | −2.197 | 1.00 | 16.12 |
| ATOM | 1776 | CA | ALA | A | 373 | 52.795 | 24.666 | −1.338 | 1.00 | 15.51 |
| ATOM | 1777 | C | ALA | A | 373 | 53.661 | 25.740 | −1.995 | 1.00 | 19.84 |
| ATOM | 1778 | O | ALA | A | 373 | 53.282 | 26.915 | −2.062 | 1.00 | 17.22 |
| ATOM | 1779 | CB | ALA | A | 373 | 53.326 | 24.337 | 0.013 | 1.00 | 16.70 |
| ATOM | 1780 | N | LYS | A | 374 | 54.817 | 25.320 | −2.490 | 1.00 | 16.75 |
| ATOM | 1781 | CA | LYS | A | 374 | 55.707 | 26.268 | −3.156 | 1.00 | 17.66 |
| ATOM | 1782 | C | LYS | A | 374 | 55.013 | 26.881 | −4.358 | 1.00 | 18.57 |
| ATOM | 1783 | O | LYS | A | 374 | 55.099 | 28.095 | −4.588 | 1.00 | 19.66 |
| ATOM | 1784 | CB | LYS | A | 374 | 56.997 | 25.559 | −3.591 | 1.00 | 19.59 |
| ATOM | 1785 | CG | LYS | A | 374 | 57.854 | 25.160 | −2.413 | 1.00 | 17.97 |
| ATOM | 1786 | CD | LYS | A | 374 | 59.215 | 24.572 | −2.911 | 1.00 | 24.10 |
| ATOM | 1787 | CE | LYS | A | 374 | 59.976 | 23.952 | −1.782 | 1.00 | 28.30 |
| ATOM | 1788 | NZ | LYS | A | 374 | 61.116 | 23.103 | −2.323 | 1.00 | 29.85 |
| ATOM | 1789 | N | SER | A | 375 | 54.291 | 26.059 | −5.121 | 1.00 | 16.53 |
| ATOM | 1790 | CA | SER | A | 375 | 53.587 | 26.526 | −6.311 | 1.00 | 17.04 |
| ATOM | 1791 | C | SER | A | 375 | 52.494 | 27.548 | −5.933 | 1.00 | 19.63 |
| ATOM | 1792 | O | SER | A | 375 | 52.339 | 28.596 | −6.574 | 1.00 | 18.45 |
| ATOM | 1793 | CB | SER | A | 375 | 52.938 | 25.349 | −6.997 | 1.00 | 18.66 |
| ATOM | 1794 | OG | SER | A | 375 | 52.207 | 25.768 | −8.110 | 1.00 | 19.21 |
| ATOM | 1795 | N | LEU | A | 376 | 51.748 | 27.235 | −4.884 | 1.00 | 16.56 |
| ATOM | 1796 | CA | LEU | A | 376 | 50.660 | 28.127 | −4.451 | 1.00 | 15.62 |
| ATOM | 1797 | C | LEU | A | 376 | 51.209 | 29.459 | −3.998 | 1.00 | 18.53 |

TABLE 4-continued

Structural coordinates for AKT3lkd(T305D, S472D) (SEQ ID NO:2).

| ATOM | 1798 | O | LEU | A | 376 | 50.716 | 30.509 | −4.410 | 1.00 | 18.89 |
|------|------|-----|-----|---|-----|--------|--------|--------|------|-------|
| ATOM | 1799 | CB | LEU | A | 376 | 49.891 | 27.461 | −3.292 | 1.00 | 15.41 |
| ATOM | 1800 | CG | LEU | A | 376 | 48.737 | 28.332 | −2.730 | 1.00 | 16.82 |
| ATOM | 1801 | CD1 | LEU | A | 376 | 47.478 | 28.194 | −3.655 | 1.00 | 17.84 |
| ATOM | 1802 | CD2 | LEU | A | 376 | 48.405 | 27.952 | −1.270 | 1.00 | 19.01 |
| ATOM | 1803 | N | LEU | A | 377 | 52.186 | 29.423 | −3.087 | 1.00 | 16.52 |
| ATOM | 1804 | CA | LEU | A | 377 | 52.752 | 30.657 | −2.543 | 1.00 | 16.49 |
| ATOM | 1805 | C | LEU | A | 377 | 53.402 | 31.476 | −3.645 | 1.00 | 20.16 |
| ATOM | 1806 | O | LEU | A | 377 | 53.223 | 32.705 | −3.720 | 1.00 | 19.57 |
| ATOM | 1807 | CB | LEU | A | 377 | 53.726 | 30.340 | −1.414 | 1.00 | 16.03 |
| ATOM | 1808 | CG | LEU | A | 377 | 53.112 | 29.611 | −0.233 | 1.00 | 18.12 |
| ATOM | 1809 | CD1 | LEU | A | 377 | 54.207 | 29.313 | 0.756 | 1.00 | 17.18 |
| ATOM | 1810 | CD2 | LEU | A | 377 | 52.029 | 30.561 | 0.388 | 1.00 | 20.38 |
| ATOM | 1811 | N | SER | A | 378 | 54.110 | 30.795 | −4.537 | 1.00 | 17.73 |
| ATOM | 1812 | CA | SER | A | 378 | 54.711 | 31.486 | −5.673 | 1.00 | 17.36 |
| ATOM | 1813 | C | SER | A | 378 | 53.668 | 32.152 | −6.520 | 1.00 | 20.62 |
| ATOM | 1814 | O | SER | A | 378 | 53.852 | 33.288 | −6.980 | 1.00 | 22.51 |
| ATOM | 1815 | CB | SER | A | 378 | 55.497 | 30.509 | −6.529 | 1.00 | 19.86 |
| ATOM | 1816 | OG | SER | A | 378 | 56.657 | 30.091 | −5.826 | 1.00 | 26.26 |
| ATOM | 1817 | N | GLY | A | 379 | 52.564 | 31.449 | −6.754 | 1.00 | 18.60 |
| ATOM | 1818 | CA | GLY | A | 379 | 51.518 | 31.973 | −7.617 | 1.00 | 18.40 |
| ATOM | 1819 | C | GLY | A | 379 | 50.817 | 33.171 | −7.020 | 1.00 | 20.11 |
| ATOM | 1820 | O | GLY | A | 379 | 50.515 | 34.156 | −7.723 | 1.00 | 19.05 |
| ATOM | 1821 | N | LEU | A | 380 | 50.545 | 33.096 | −5.723 | 1.00 | 16.35 |
| ATOM | 1822 | CA | LEU | A | 380 | 49.843 | 34.190 | −5.043 | 1.00 | 15.34 |
| ATOM | 1823 | C | LEU | A | 380 | 50.724 | 35.428 | −4.960 | 1.00 | 18.01 |
| ATOM | 1824 | O | LEU | A | 380 | 50.234 | 36.522 | −4.800 | 1.00 | 17.89 |
| ATOM | 1825 | CB | LEU | A | 380 | 49.428 | 33.756 | −3.617 | 1.00 | 15.84 |
| ATOM | 1826 | CG | LEU | A | 380 | 48.362 | 32.643 | −3.600 | 1.00 | 16.85 |
| ATOM | 1827 | CD1 | LEU | A | 380 | 48.182 | 32.148 | −2.156 | 1.00 | 15.23 |
| ATOM | 1828 | CD2 | LEU | A | 380 | 47.025 | 33.226 | −4.135 | 1.00 | 17.87 |
| ATOM | 1829 | N | LEU | A | 381 | 52.035 | 35.194 | −4.970 | 1.00 | 16.86 |
| ATOM | 1830 | CA | LEU | A | 381 | 53.009 | 36.278 | −4.789 | 1.00 | 16.56 |
| ATOM | 1831 | C | LEU | A | 381 | 53.680 | 36.706 | −6.098 | 1.00 | 20.60 |
| ATOM | 1832 | O | LEU | A | 381 | 54.679 | 37.446 | −6.085 | 1.00 | 20.10 |
| ATOM | 1833 | CB | LEU | A | 381 | 54.023 | 35.944 | −3.696 | 1.00 | 17.13 |
| ATOM | 1834 | CG | LEU | A | 381 | 53.400 | 35.758 | −2.300 | 1.00 | 19.32 |
| ATOM | 1835 | CD1 | LEU | A | 381 | 54.462 | 35.367 | −1.214 | 1.00 | 20.19 |
| ATOM | 1836 | CD2 | LEU | A | 381 | 52.695 | 37.043 | −1.859 | 1.00 | 20.23 |
| ATOM | 1837 | N | ILE | A | 382 | 53.077 | 36.332 | −7.217 | 1.00 | 17.87 |
| ATOM | 1838 | CA | ILE | A | 382 | 53.544 | 36.841 | −8.525 | 1.00 | 18.10 |
| ATOM | 1839 | C | ILE | A | 382 | 53.365 | 38.367 | −8.497 | 1.00 | 20.77 |
| ATOM | 1840 | O | ILE | A | 382 | 52.376 | 38.884 | −8.005 | 1.00 | 19.57 |
| ATOM | 1841 | CB | ILE | A | 382 | 52.736 | 36.212 | −9.661 | 1.00 | 20.78 |
| ATOM | 1842 | CG1 | ILE | A | 382 | 53.236 | 34.773 | −9.918 | 1.00 | 21.18 |
| ATOM | 1843 | CG2 | ILE | A | 382 | 52.812 | 37.073 | −10.962 | 1.00 | 22.14 |
| ATOM | 1844 | CD1 | ILE | A | 382 | 52.333 | 33.958 | −10.852 | 1.00 | 25.88 |
| ATOM | 1845 | N | LYS | A | 383 | 54.380 | 39.107 | −8.944 | 1.00 | 20.97 |
| ATOM | 1846 | CA | LYS | A | 383 | 54.326 | 40.560 | −8.841 | 1.00 | 21.13 |
| ATOM | 1847 | C | LYS | A | 383 | 53.251 | 41.232 | −9.668 | 1.00 | 22.44 |
| ATOM | 1848 | O | LYS | A | 383 | 52.635 | 42.218 | −9.229 | 1.00 | 22.89 |
| ATOM | 1849 | CB | LYS | A | 383 | 55.690 | 41.173 | −9.194 | 1.00 | 23.45 |
| ATOM | 1850 | CG | LYS | A | 383 | 56.876 | 40.398 | −8.680 | 1.00 | 32.49 |
| ATOM | 1851 | CD | LYS | A | 383 | 57.001 | 40.591 | −7.206 | 1.00 | 31.31 |
| ATOM | 1852 | CE | LYS | A | 383 | 58.458 | 40.296 | −6.710 | 1.00 | 27.15 |
| ATOM | 1853 | NZ | LYS | A | 383 | 58.456 | 40.255 | −5.235 | 1.00 | 25.11 |
| ATOM | 1854 | N | ASP | A | 384 | 53.087 | 40.759 | −10.893 | 1.00 | 21.98 |
| ATOM | 1855 | CA | ASP | A | 384 | 52.120 | 41.331 | −11.823 | 1.00 | 22.23 |
| ATOM | 1856 | C | ASP | A | 384 | 50.724 | 40.800 | −11.486 | 1.00 | 23.86 |
| ATOM | 1857 | O | ASP | A | 384 | 50.477 | 39.596 | −11.637 | 1.00 | 23.20 |
| ATOM | 1858 | CB | ASP | A | 384 | 52.496 | 40.913 | −13.248 | 1.00 | 24.81 |
| ATOM | 1859 | CG | ASP | A | 384 | 51.585 | 41.526 | −14.298 | 1.00 | 29.23 |
| ATOM | 1860 | OD1 | ASP | A | 384 | 50.521 | 42.083 | −13.942 | 1.00 | 27.30 |
| ATOM | 1861 | OD2 | ASP | A | 384 | 51.927 | 41.402 | −15.499 | 1.00 | 31.50 |
| ATOM | 1862 | N | PRO | A | 385 | 49.810 | 41.672 | −11.035 | 1.00 | 22.85 |
| ATOM | 1863 | CA | PRO | A | 385 | 48.466 | 41.171 | −10.641 | 1.00 | 22.82 |
| ATOM | 1864 | C | PRO | A | 385 | 47.720 | 40.502 | −11.759 | 1.00 | 26.02 |
| ATOM | 1865 | O | PRO | A | 385 | 46.869 | 39.642 | −11.499 | 1.00 | 25.06 |
| ATOM | 1866 | CB | PRO | A | 385 | 47.725 | 42.417 | −10.165 | 1.00 | 24.27 |
| ATOM | 1867 | CG | PRO | A | 385 | 48.452 | 43.572 | −10.876 | 1.00 | 27.97 |
| ATOM | 1868 | CD | PRO | A | 385 | 49.900 | 43.142 | −10.905 | 1.00 | 23.84 |
| ATOM | 1869 | N | ASN | A | 386 | 48.023 | 40.882 | −13.016 | 1.00 | 24.84 |
| ATOM | 1870 | CA | ASN | A | 386 | 47.374 | 40.255 | −14.161 | 1.00 | 25.28 |
| ATOM | 1871 | C | ASN | A | 386 | 47.749 | 38.780 | −14.297 | 1.00 | 28.43 |
| ATOM | 1872 | O | ASN | A | 386 | 46.998 | 37.993 | −14.871 | 1.00 | 30.72 |
| ATOM | 1873 | CB | ASN | A | 386 | 47.767 | 40.970 | −15.457 | 1.00 | 26.45 |
| ATOM | 1874 | CG | ASN | A | 386 | 47.198 | 42.343 | −15.535 | 1.00 | 42.53 |
| ATOM | 1875 | OD1 | ASN | A | 386 | 46.118 | 42.589 | −15.031 | 1.00 | 37.15 |

TABLE 4-continued

Structural coordinates for AKT3lkd(T305D, S472D) (SEQ ID NO:2).

| ATOM | 1876 | ND2 | ASN | A | 386 | 47.936 | 43.262 | −16.141 | 1.00 | 44.15 |
|---|---|---|---|---|---|---|---|---|---|---|
| ATOM | 1877 | N | LYS | A | 387 | 48.935 | 38.419 | −13.809 | 1.00 | 22.43 |
| ATOM | 1878 | CA | LYS | A | 387 | 49.428 | 37.061 | −13.968 | 1.00 | 21.62 |
| ATOM | 1879 | C | LYS | A | 387 | 49.372 | 36.269 | −12.673 | 1.00 | 23.06 |
| ATOM | 1880 | O | LYS | A | 387 | 49.700 | 35.088 | −12.646 | 1.00 | 22.42 |
| ATOM | 1881 | CB | LYS | A | 387 | 50.869 | 37.083 | −14.488 | 1.00 | 24.08 |
| ATOM | 1882 | CG | LYS | A | 387 | 50.974 | 37.593 | −15.964 | 1.00 | 32.44 |
| ATOM | 1883 | CD | LYS | A | 387 | 52.405 | 37.633 | −16.429 | 1.00 | 39.48 |
| ATOM | 1884 | CE | LYS | A | 387 | 52.502 | 38.178 | −17.855 | 1.00 | 48.51 |
| ATOM | 1885 | NZ | LYS | A | 387 | 53.827 | 38.823 | −18.123 | 1.00 | 60.20 |
| ATOM | 1886 | N | ARG | A | 388 | 48.993 | 36.948 | −11.597 | 1.00 | 20.16 |
| ATOM | 1887 | CA | ARG | A | 388 | 48.926 | 36.324 | −10.273 | 1.00 | 18.81 |
| ATOM | 1888 | C | ARG | A | 388 | 47.817 | 35.289 | −10.196 | 1.00 | 21.83 |
| ATOM | 1889 | O | ARG | A | 388 | 46.789 | 35.424 | −10.832 | 1.00 | 22.22 |
| ATOM | 1890 | CB | ARG | A | 388 | 48.657 | 37.422 | −9.244 | 1.00 | 19.11 |
| ATOM | 1891 | CG | ARG | A | 388 | 48.689 | 36.964 | −7.781 | 1.00 | 18.50 |
| ATOM | 1892 | CD | ARG | A | 388 | 48.560 | 38.196 | −6.847 | 1.00 | 18.31 |
| ATOM | 1893 | NE | ARG | A | 388 | 49.645 | 39.168 | −7.078 | 1.00 | 18.73 |
| ATOM | 1894 | CZ | ARG | A | 388 | 49.483 | 40.486 | −6.991 | 1.00 | 21.14 |
| ATOM | 1895 | NH1 | ARG | A | 388 | 48.319 | 40.986 | −6.587 | 1.00 | 18.49 |
| ATOM | 1896 | NH2 | ARG | A | 388 | 50.498 | 41.311 | −7.290 | 1.00 | 19.41 |
| ATOM | 1897 | N | LEU | A | 389 | 48.037 | 34.261 | −9.383 | 1.00 | 17.05 |
| ATOM | 1898 | CA | LEU | A | 389 | 47.026 | 33.247 | −9.139 | 1.00 | 15.97 |
| ATOM | 1899 | C | LEU | A | 389 | 45.828 | 33.956 | −8.444 | 1.00 | 19.82 |
| ATOM | 1900 | O | LEU | A | 389 | 45.983 | 34.604 | −7.376 | 1.00 | 18.85 |
| ATOM | 1901 | CB | LEU | A | 389 | 47.626 | 32.152 | −8.224 | 1.00 | 15.31 |
| ATOM | 1902 | CG | LEU | A | 389 | 46.691 | 30.988 | −7.908 | 1.00 | 19.10 |
| ATOM | 1903 | CD1 | LEU | A | 389 | 46.394 | 30.170 | −9.166 | 1.00 | 21.12 |
| ATOM | 1904 | CD2 | LEU | A | 389 | 47.344 | 30.090 | −6.797 | 1.00 | 18.51 |
| ATOM | 1905 | N | GLY | A | 390 | 44.639 | 33.807 | −9.037 | 1.00 | 17.63 |
| ATOM | 1906 | CA | GLY | A | 390 | 43.440 | 34.479 | −8.543 | 1.00 | 18.19 |
| ATOM | 1907 | C | GLY | A | 390 | 43.194 | 35.781 | −9.338 | 1.00 | 23.28 |
| ATOM | 1908 | O | GLY | A | 390 | 42.111 | 36.376 | −9.252 | 1.00 | 21.31 |
| ATOM | 1909 | N | GLY | A | 391 | 44.211 | 36.219 | −10.090 | 1.00 | 21.24 |
| ATOM | 1910 | CA | GLY | A | 391 | 44.141 | 37.489 | −10.862 | 1.00 | 21.52 |
| ATOM | 1911 | C | GLY | A | 391 | 43.318 | 37.391 | −12.191 | 1.00 | 24.54 |
| ATOM | 1912 | O | GLY | A | 391 | 42.921 | 38.425 | −12.772 | 1.00 | 25.06 |
| ATOM | 1913 | N | GLY | A | 392 | 43.087 | 36.164 | −12.659 | 1.00 | 21.46 |
| ATOM | 1914 | CA | GLY | A | 392 | 42.323 | 35.915 | −13.899 | 1.00 | 20.68 |
| ATOM | 1915 | C | GLY | A | 392 | 40.848 | 36.120 | −13.694 | 1.00 | 22.35 |
| ATOM | 1916 | O | GLY | A | 392 | 40.377 | 36.384 | −12.569 | 1.00 | 20.50 |
| ATOM | 1917 | N | PRO | A | 393 | 40.084 | 36.002 | −14.772 | 1.00 | 22.09 |
| ATOM | 1918 | CA | PRO | A | 393 | 38.654 | 36.270 | −14.712 | 1.00 | 22.84 |
| ATOM | 1919 | C | PRO | A | 393 | 37.828 | 35.359 | −13.814 | 1.00 | 24.99 |
| ATOM | 1920 | O | PRO | A | 393 | 36.742 | 35.746 | −13.394 | 1.00 | 24.99 |
| ATOM | 1921 | CB | PRO | A | 393 | 38.200 | 36.143 | −16.192 | 1.00 | 24.73 |
| ATOM | 1922 | CG | PRO | A | 393 | 39.267 | 35.333 | −16.836 | 1.00 | 29.79 |
| ATOM | 1923 | CD | PRO | A | 393 | 40.531 | 35.679 | −16.141 | 1.00 | 25.06 |
| ATOM | 1924 | N | ASP | A | 394 | 38.342 | 34.163 | −13.506 | 1.00 | 20.40 |
| ATOM | 1925 | CA | ASP | A | 394 | 37.634 | 33.228 | −12.591 | 1.00 | 18.71 |
| ATOM | 1926 | C | ASP | A | 394 | 38.000 | 33.478 | −11.115 | 1.00 | 20.22 |
| ATOM | 1927 | O | ASP | A | 394 | 37.494 | 32.791 | −10.224 | 1.00 | 18.55 |
| ATOM | 1928 | CB | ASP | A | 394 | 37.892 | 31.780 | −12.959 | 1.00 | 20.70 |
| ATOM | 1929 | CG | ASP | A | 394 | 36.623 | 30.925 | −12.925 | 1.00 | 22.18 |
| ATOM | 1930 | OD1 | ASP | A | 394 | 36.741 | 29.709 | −13.211 | 1.00 | 22.73 |
| ATOM | 1931 | OD2 | ASP | A | 394 | 35.507 | 31.481 | −12.702 | 1.00 | 24.16 |
| ATOM | 1932 | N | ASP | A | 395 | 38.865 | 34.444 | −10.887 | 1.00 | 17.87 |
| ATOM | 1933 | CA | ASP | A | 395 | 39.166 | 34.909 | −9.519 | 1.00 | 16.96 |
| ATOM | 1934 | C | ASP | A | 395 | 39.462 | 33.780 | −8.565 | 1.00 | 18.41 |
| ATOM | 1935 | O | ASP | A | 395 | 40.390 | 32.989 | −8.808 | 1.00 | 16.77 |
| ATOM | 1936 | CB | ASP | A | 395 | 38.012 | 35.793 | −9.007 | 1.00 | 17.62 |
| ATOM | 1937 | CG | ASP | A | 395 | 38.380 | 36.571 | −7.727 | 1.00 | 17.10 |
| ATOM | 1938 | OD1 | ASP | A | 395 | 39.377 | 37.317 | −7.742 | 1.00 | 18.18 |
| ATOM | 1939 | OD2 | ASP | A | 395 | 37.650 | 36.383 | −6.748 | 1.00 | 21.25 |
| ATOM | 1940 | N | ALA | A | 396 | 38.700 | 33.702 | −7.462 | 1.00 | 16.04 |
| ATOM | 1941 | CA | ALA | A | 396 | 38.939 | 32.665 | −6.424 | 1.00 | 16.11 |
| ATOM | 1942 | C | ALA | A | 396 | 38.978 | 31.235 | −6.970 | 1.00 | 16.25 |
| ATOM | 1943 | O | ALA | A | 396 | 39.621 | 30.350 | −6.381 | 1.00 | 15.92 |
| ATOM | 1944 | CB | ALA | A | 396 | 37.861 | 32.762 | −5.332 | 1.00 | 17.75 |
| ATOM | 1945 | N | LYS | A | 397 | 38.200 | 30.956 | −8.026 | 1.00 | 15.64 |
| ATOM | 1946 | CA | LYS | A | 397 | 38.170 | 29.600 | −8.564 | 1.00 | 15.95 |
| ATOM | 1947 | C | LYS | A | 397 | 39.558 | 29.122 | −9.033 | 1.00 | 18.60 |
| ATOM | 1948 | O | LYS | A | 397 | 39.831 | 27.926 | −9.004 | 1.00 | 19.06 |
| ATOM | 1949 | CB | LYS | A | 397 | 37.118 | 29.465 | −9.655 | 1.00 | 19.41 |
| ATOM | 1950 | CG | LYS | A | 397 | 35.684 | 29.477 | −9.105 | 1.00 | 24.63 |
| ATOM | 1951 | CD | LYS | A | 397 | 35.289 | 30.810 | −8.546 | 1.00 | 34.61 |
| ATOM | 1952 | CE | LYS | A | 397 | 33.801 | 30.830 | −8.137 | 1.00 | 43.81 |
| ATOM | 1953 | NZ | LYS | A | 397 | 33.280 | 32.237 | −8.005 | 1.00 | 41.68 |

TABLE 4-continued

Structural coordinates for AKT3lkd(T305D, S472D) (SEQ ID NO:2).

| ATOM | 1954 | N   | GLU | A | 398 | 40.409 | 30.049 | −9.460  | 1.00 | 16.66 |
|------|------|-----|-----|---|-----|--------|--------|---------|------|-------|
| ATOM | 1955 | CA  | GLU | A | 398 | 41.792 | 29.694 | −9.835  | 1.00 | 16.15 |
| ATOM | 1956 | C   | GLU | A | 398 | 42.502 | 29.061 | −8.641  | 1.00 | 18.30 |
| ATOM | 1957 | O   | GLU | A | 398 | 43.302 | 28.123 | −8.802  | 1.00 | 19.30 |
| ATOM | 1958 | CB  | GLU | A | 398 | 42.600 | 30.930 | −10.269 | 1.00 | 17.91 |
| ATOM | 1959 | CG  | GLU | A | 398 | 42.142 | 31.506 | −11.572 | 1.00 | 20.09 |
| ATOM | 1960 | CD  | GLU | A | 398 | 43.121 | 32.499 | −12.114 | 1.00 | 26.24 |
| ATOM | 1961 | OE1 | GLU | A | 398 | 44.223 | 32.578 | −11.570 | 1.00 | 26.56 |
| ATOM | 1962 | OE2 | GLU | A | 398 | 42.863 | 33.066 | −13.189 | 1.00 | 29.96 |
| ATOM | 1963 | N   | ILE | A | 399 | 42.318 | 29.657 | −7.467  | 1.00 | 15.34 |
| ATOM | 1964 | CA  | ILE | A | 399 | 42.936 | 29.113 | −6.241  | 1.00 | 14.94 |
| ATOM | 1965 | C   | ILE | A | 399 | 42.246 | 27.814 | −5.810  | 1.00 | 17.39 |
| ATOM | 1966 | O   | ILE | A | 399 | 42.888 | 26.851 | −5.437  | 1.00 | 16.56 |
| ATOM | 1967 | CB  | ILE | A | 399 | 42.880 | 30.142 | −5.089  | 1.00 | 16.63 |
| ATOM | 1968 | CG1 | ILE | A | 399 | 43.791 | 31.314 | −5.445  | 1.00 | 18.56 |
| ATOM | 1969 | CG2 | ILE | A | 399 | 43.315 | 29.470 | −3.797  | 1.00 | 18.94 |
| ATOM | 1970 | CD1 | ILE | A | 399 | 43.178 | 32.332 | −6.272  | 1.00 | 29.21 |
| ATOM | 1971 | N   | MET | A | 400 | 40.922 | 27.803 | −5.843  | 1.00 | 15.22 |
| ATOM | 1972 | CA  | MET | A | 400 | 40.179 | 26.584 | −5.478  | 1.00 | 14.66 |
| ATOM | 1973 | C   | MET | A | 400 | 40.595 | 25.375 | −6.301  | 1.00 | 15.89 |
| ATOM | 1974 | O   | MET | A | 400 | 40.606 | 24.260 | −5.787  | 1.00 | 17.49 |
| ATOM | 1975 | CB  | MET | A | 400 | 38.686 | 26.824 | −5.596  | 1.00 | 15.81 |
| ATOM | 1976 | CG  | MET | A | 400 | 38.243 | 27.904 | −4.672  | 1.00 | 17.32 |
| ATOM | 1977 | SD  | MET | A | 400 | 36.447 | 28.227 | −4.976  | 1.00 | 23.67 |
| ATOM | 1978 | CE  | MET | A | 400 | 36.079 | 29.295 | −3.616  | 1.00 | 23.36 |
| ATOM | 1979 | N   | ARG | A | 401 | 40.979 | 25.602 | −7.560  | 1.00 | 16.37 |
| ATOM | 1980 | CA  | ARG | A | 401 | 41.425 | 24.525 | −8.436  | 1.00 | 15.42 |
| ATOM | 1981 | C   | ARG | A | 401 | 42.916 | 24.188 | −8.341  | 1.00 | 18.43 |
| ATOM | 1982 | O   | ARG | A | 401 | 43.396 | 23.263 | −9.043  | 1.00 | 17.92 |
| ATOM | 1983 | CB  | ARG | A | 401 | 41.100 | 24.902 | −9.905  | 1.00 | 15.18 |
| ATOM | 1984 | CG  | ARG | A | 401 | 39.628 | 24.882 | −10.190 | 1.00 | 19.98 |
| ATOM | 1985 | CD  | ARG | A | 401 | 39.357 | 24.956 | −11.699 | 1.00 | 25.37 |
| ATOM | 1986 | NE  | ARG | A | 401 | 39.857 | 26.188 | −12.286 | 1.00 | 22.84 |
| ATOM | 1987 | CZ  | ARG | A | 401 | 39.118 | 27.261 | −12.571 | 1.00 | 23.69 |
| ATOM | 1988 | NH1 | ARG | A | 401 | 37.829 | 27.275 | −12.310 | 1.00 | 24.55 |
| ATOM | 1989 | NH2 | ARG | A | 401 | 39.694 | 28.322 | −13.095 | 1.00 | 24.81 |
| ATOM | 1990 | N   | HIS | A | 402 | 43.668 | 24.946 | −7.536  | 1.00 | 16.64 |
| ATOM | 1991 | CA  | HIS | A | 402 | 45.088 | 24.717 | −7.440  | 1.00 | 15.60 |
| ATOM | 1992 | C   | HIS | A | 402 | 45.399 | 23.387 | −6.765  | 1.00 | 18.74 |
| ATOM | 1993 | O   | HIS | A | 402 | 44.669 | 22.932 | −5.861  | 1.00 | 17.39 |
| ATOM | 1994 | CB  | HIS | A | 402 | 45.786 | 25.896 | −6.687  | 1.00 | 16.09 |
| ATOM | 1995 | CG  | HIS | A | 402 | 47.278 | 25.828 | −6.731  | 1.00 | 17.74 |
| ATOM | 1996 | ND1 | HIS | A | 402 | 48.018 | 25.044 | −5.861  | 1.00 | 18.80 |
| ATOM | 1997 | CD2 | HIS | A | 402 | 48.169 | 26.421 | −7.562  | 1.00 | 19.12 |
| ATOM | 1998 | CE1 | HIS | A | 402 | 49.306 | 25.179 | −6.144  | 1.00 | 18.89 |
| ATOM | 1999 | NE2 | HIS | A | 402 | 49.421 | 26.003 | −7.180  | 1.00 | 19.19 |
| ATOM | 2000 | N   | SER | A | 403 | 46.486 | 22.728 | −7.208  | 1.00 | 16.78 |
| ATOM | 2001 | CA  | SER | A | 403 | 46.835 | 21.427 | −6.647  | 1.00 | 16.64 |
| ATOM | 2002 | C   | SER | A | 403 | 46.939 | 21.394 | −5.120  | 1.00 | 16.81 |
| ATOM | 2003 | O   | SER | A | 403 | 46.677 | 20.370 | −4.497  | 1.00 | 17.29 |
| ATOM | 2004 | CB  | SER | A | 403 | 48.148 | 20.936 | −7.250  | 1.00 | 21.61 |
| ATOM | 2005 | OG  | SER | A | 403 | 49.207 | 21.838 | −6.913  | 1.00 | 32.71 |
| ATOM | 2006 | N   | PHE | A | 404 | 47.372 | 22.514 | −4.508  | 1.00 | 14.26 |
| ATOM | 2007 | CA  | PHE | A | 404 | 47.525 | 22.544 | −3.050  | 1.00 | 13.71 |
| ATOM | 2008 | C   | PHE | A | 404 | 46.187 | 22.285 | −2.364  | 1.00 | 16.46 |
| ATOM | 2009 | O   | PHE | A | 404 | 46.157 | 21.775 | −1.262  | 1.00 | 17.07 |
| ATOM | 2010 | CB  | PHE | A | 404 | 48.092 | 23.892 | −2.597  | 1.00 | 14.94 |
| ATOM | 2011 | CG  | PHE | A | 404 | 48.321 | 23.979 | −1.103  | 1.00 | 15.06 |
| ATOM | 2012 | CD1 | PHE | A | 404 | 49.472 | 23.418 | −0.522  | 1.00 | 16.33 |
| ATOM | 2013 | CD2 | PHE | A | 404 | 47.366 | 24.598 | −0.271  | 1.00 | 16.54 |
| ATOM | 2014 | CE1 | PHE | A | 404 | 49.681 | 23.486 | 0.873   | 1.00 | 17.36 |
| ATOM | 2015 | CE2 | PHE | A | 404 | 47.601 | 24.728 | 1.116   | 1.00 | 17.73 |
| ATOM | 2016 | CZ  | PHE | A | 404 | 48.748 | 24.146 | 1.689   | 1.00 | 17.12 |
| ATOM | 2017 | N   | PHE | A | 405 | 45.090 | 22.630 | −3.035  | 1.00 | 15.91 |
| ATOM | 2018 | CA  | PHE | A | 405 | 43.755 | 22.422 | −2.437  | 1.00 | 14.89 |
| ATOM | 2019 | C   | PHE | A | 405 | 43.002 | 21.254 | −3.099  | 1.00 | 18.15 |
| ATOM | 2020 | O   | PHE | A | 405 | 41.780 | 21.161 | −2.983  | 1.00 | 17.17 |
| ATOM | 2021 | CB  | PHE | A | 405 | 42.914 | 23.693 | −2.615  | 1.00 | 15.66 |
| ATOM | 2022 | CG  | PHE | A | 405 | 43.372 | 24.847 | −1.756  | 1.00 | 14.46 |
| ATOM | 2023 | CD1 | PHE | A | 405 | 43.199 | 24.804 | −0.350  | 1.00 | 15.41 |
| ATOM | 2024 | CD2 | PHE | A | 405 | 44.001 | 25.972 | −2.331  | 1.00 | 14.70 |
| ATOM | 2025 | CE1 | PHE | A | 405 | 43.613 | 25.873 | 0.465   | 1.00 | 15.73 |
| ATOM | 2026 | CE2 | PHE | A | 405 | 44.428 | 27.047 | −1.512  | 1.00 | 17.18 |
| ATOM | 2027 | CZ  | PHE | A | 405 | 44.195 | 27.004 | −0.114  | 1.00 | 14.72 |
| ATOM | 2028 | N   | SER | A | 406 | 43.724 | 20.383 | −3.783  | 1.00 | 16.45 |
| ATOM | 2029 | CA  | SER | A | 406 | 43.080 | 19.267 | −4.513  | 1.00 | 17.40 |
| ATOM | 2030 | C   | SER | A | 406 | 42.172 | 18.295 | −3.721  | 1.00 | 21.71 |
| ATOM | 2031 | O   | SER | A | 406 | 41.377 | 17.554 | −4.331  | 1.00 | 24.03 |

TABLE 4-continued

Structural coordinates for AKT3lkd(T305D, S472D) (SEQ ID NO:2).

| ATOM | 2032 | CB | SER | A | 406 | 44.120 | 18.462 | −5.320 | 1.00 | 21.92 |
|---|---|---|---|---|---|---|---|---|---|---|
| ATOM | 2033 | OG | SER | A | 406 | 45.004 | 17.862 | −4.430 | 1.00 | 23.28 |
| ATOM | 2034 | N | GLY | A | 407 | 42.268 | 18.268 | −2.407 | 1.00 | 19.13 |
| ATOM | 2035 | CA | GLY | A | 407 | 41.383 | 17.342 | −1.655 | 1.00 | 18.49 |
| ATOM | 2036 | C | GLY | A | 407 | 40.239 | 18.067 | −0.961 | 1.00 | 21.68 |
| ATOM | 2037 | O | GLY | A | 407 | 39.492 | 17.471 | −0.162 | 1.00 | 22.11 |
| ATOM | 2038 | N | VAL | A | 408 | 40.129 | 19.357 | −1.230 | 1.00 | 15.73 |
| ATOM | 2039 | CA | VAL | A | 408 | 39.110 | 20.199 | −0.571 | 1.00 | 15.70 |
| ATOM | 2040 | C | VAL | A | 408 | 37.772 | 20.312 | −1.287 | 1.00 | 17.38 |
| ATOM | 2041 | O | VAL | A | 408 | 37.705 | 20.602 | −2.479 | 1.00 | 17.40 |
| ATOM | 2042 | CB | VAL | A | 408 | 39.641 | 21.628 | −0.357 | 1.00 | 17.74 |
| ATOM | 2043 | CG1 | VAL | A | 408 | 38.562 | 22.522 | 0.248 | 1.00 | 17.96 |
| ATOM | 2044 | CG2 | VAL | A | 408 | 40.890 | 21.625 | 0.549 | 1.00 | 17.45 |
| ATOM | 2045 | N | ASN | A | 409 | 36.690 | 20.019 | −0.529 | 1.00 | 16.17 |
| ATOM | 2046 | CA | ASN | A | 409 | 35.342 | 20.197 | −1.039 | 1.00 | 16.65 |
| ATOM | 2047 | C | ASN | A | 409 | 34.901 | 21.614 | −0.600 | 1.00 | 17.87 |
| ATOM | 2048 | O | ASN | A | 409 | 34.780 | 21.894 | 0.597 | 1.00 | 16.54 |
| ATOM | 2049 | CB | ASN | A | 409 | 34.419 | 19.132 | −0.459 | 1.00 | 17.54 |
| ATOM | 2050 | CG | ASN | A | 409 | 33.010 | 19.292 | −0.944 | 1.00 | 24.51 |
| ATOM | 2051 | OD1 | ASN | A | 409 | 32.372 | 20.324 | −0.692 | 1.00 | 21.48 |
| ATOM | 2052 | ND2 | ASN | A | 409 | 32.555 | 18.344 | −1.759 | 1.00 | 20.65 |
| ATOM | 2053 | N | TRP | A | 410 | 34.759 | 22.510 | −1.577 | 1.00 | 17.01 |
| ATOM | 2054 | CA | TRP | A | 410 | 34.494 | 23.914 | −1.309 | 1.00 | 17.34 |
| ATOM | 2055 | C | TRP | A | 410 | 33.154 | 24.252 | −0.719 | 1.00 | 19.98 |
| ATOM | 2056 | O | TRP | A | 410 | 33.036 | 25.224 | 0.038 | 1.00 | 18.99 |
| ATOM | 2057 | CB | TRP | A | 410 | 34.855 | 24.779 | −2.499 | 1.00 | 16.01 |
| ATOM | 2058 | CG | TRP | A | 410 | 36.301 | 24.717 | −2.757 | 1.00 | 15.89 |
| ATOM | 2059 | CD1 | TRP | A | 410 | 36.970 | 23.827 | −3.565 | 1.00 | 18.34 |
| ATOM | 2060 | CD2 | TRP | A | 410 | 37.312 | 25.506 | −2.094 | 1.00 | 15.54 |
| ATOM | 2061 | NE1 | TRP | A | 410 | 38.340 | 24.041 | −3.472 | 1.00 | 17.79 |
| ATOM | 2062 | CE2 | TRP | A | 410 | 38.574 | 25.071 | −2.581 | 1.00 | 18.09 |
| ATOM | 2063 | CE3 | TRP | A | 410 | 37.271 | 26.564 | −1.156 | 1.00 | 15.96 |
| ATOM | 2064 | CZ2 | TRP | A | 410 | 39.784 | 25.605 | −2.103 | 1.00 | 15.73 |
| ATOM | 2065 | CZ3 | TRP | A | 410 | 38.491 | 27.111 | −0.693 | 1.00 | 17.29 |
| ATOM | 2066 | CH2 | TRP | A | 410 | 39.717 | 26.651 | −1.197 | 1.00 | 17.75 |
| ATOM | 2067 | N | GLN | A | 411 | 32.151 | 23.421 | −0.998 | 1.00 | 19.08 |
| ATOM | 2068 | CA | GLN | A | 411 | 30.863 | 23.650 | −0.348 | 1.00 | 19.60 |
| ATOM | 2069 | C | GLN | A | 411 | 30.999 | 23.320 | 1.139 | 1.00 | 19.99 |
| ATOM | 2070 | O | GLN | A | 411 | 30.466 | 24.032 | 1.991 | 1.00 | 20.53 |
| ATOM | 2071 | CB | GLN | A | 411 | 29.740 | 22.821 | −0.997 | 1.00 | 21.32 |
| ATOM | 2072 | CG | GLN | A | 411 | 28.387 | 23.110 | −0.310 | 1.00 | 26.79 |
| ATOM | 2073 | CD | GLN | A | 411 | 27.930 | 24.575 | −0.454 | 1.00 | 35.77 |
| ATOM | 2074 | OE1 | GLN | A | 411 | 27.479 | 25.199 | 0.520 | 1.00 | 35.13 |
| ATOM | 2075 | NE2 | GLN | A | 411 | 28.038 | 25.115 | −1.658 | 1.00 | 27.38 |
| ATOM | 2076 | N | ASP | A | 412 | 31.758 | 22.250 | 1.465 | 1.00 | 17.00 |
| ATOM | 2077 | CA | ASP | A | 412 | 32.007 | 21.862 | 2.865 | 1.00 | 15.65 |
| ATOM | 2078 | C | ASP | A | 412 | 32.801 | 22.959 | 3.582 | 1.00 | 18.75 |
| ATOM | 2079 | O | ASP | A | 412 | 32.574 | 23.242 | 4.748 | 1.00 | 18.60 |
| ATOM | 2080 | CB | ASP | A | 412 | 32.808 | 20.586 | 2.938 | 1.00 | 17.80 |
| ATOM | 2081 | CG | ASP | A | 412 | 31.955 | 19.344 | 2.709 | 1.00 | 22.56 |
| ATOM | 2082 | OD1 | ASP | A | 412 | 30.706 | 19.450 | 2.615 | 1.00 | 21.26 |
| ATOM | 2083 | OD2 | ASP | A | 412 | 32.555 | 18.295 | 2.657 | 1.00 | 19.62 |
| ATOM | 2084 | N | VAL | A | 413 | 33.664 | 23.639 | 2.853 | 1.00 | 16.87 |
| ATOM | 2085 | CA | VAL | A | 413 | 34.392 | 24.728 | 3.479 | 1.00 | 14.72 |
| ATOM | 2086 | C | VAL | A | 413 | 33.397 | 25.792 | 3.960 | 1.00 | 17.77 |
| ATOM | 2087 | O | VAL | A | 413 | 33.435 | 26.218 | 5.118 | 1.00 | 17.65 |
| ATOM | 2088 | CB | VAL | A | 413 | 35.400 | 25.405 | 2.493 | 1.00 | 17.01 |
| ATOM | 2089 | CG1 | VAL | A | 413 | 35.957 | 26.696 | 3.121 | 1.00 | 17.31 |
| ATOM | 2090 | CG2 | VAL | A | 413 | 36.563 | 24.418 | 2.114 | 1.00 | 17.16 |
| ATOM | 2091 | N | TYR | A | 414 | 32.521 | 26.216 | 3.052 | 1.00 | 18.10 |
| ATOM | 2092 | CA | TYR | A | 414 | 31.535 | 27.258 | 3.364 | 1.00 | 18.54 |
| ATOM | 2093 | C | TYR | A | 414 | 30.613 | 26.806 | 4.538 | 1.00 | 21.77 |
| ATOM | 2094 | O | TYR | A | 414 | 30.258 | 27.596 | 5.450 | 1.00 | 21.20 |
| ATOM | 2095 | CB | TYR | A | 414 | 30.710 | 27.574 | 2.128 | 1.00 | 19.47 |
| ATOM | 2096 | CG | TYR | A | 414 | 29.681 | 28.634 | 2.398 | 1.00 | 21.74 |
| ATOM | 2097 | CD1 | TYR | A | 414 | 28.473 | 28.309 | 2.964 | 1.00 | 24.54 |
| ATOM | 2098 | CD2 | TYR | A | 414 | 29.963 | 29.973 | 2.171 | 1.00 | 22.95 |
| ATOM | 2099 | CE1 | TYR | A | 414 | 27.522 | 29.300 | 3.238 | 1.00 | 24.97 |
| ATOM | 2100 | CE2 | TYR | A | 414 | 29.021 | 30.982 | 2.477 | 1.00 | 24.77 |
| ATOM | 2101 | CZ | TYR | A | 414 | 27.809 | 30.619 | 2.980 | 1.00 | 30.44 |
| ATOM | 2102 | OH | TYR | A | 414 | 26.874 | 31.594 | 3.283 | 1.00 | 30.55 |
| ATOM | 2103 | N | ASP | A | 415 | 30.228 | 25.536 | 4.502 | 1.00 | 19.53 |
| ATOM | 2104 | CA | ASP | A | 415 | 29.323 | 24.978 | 5.514 | 1.00 | 19.21 |
| ATOM | 2105 | C | ASP | A | 415 | 29.999 | 24.622 | 6.868 | 1.00 | 22.85 |
| ATOM | 2106 | O | ASP | A | 415 | 29.361 | 24.030 | 7.762 | 1.00 | 22.98 |
| ATOM | 2107 | CB | ASP | A | 415 | 28.574 | 23.766 | 4.908 | 1.00 | 20.48 |
| ATOM | 2108 | CG | ASP | A | 415 | 27.654 | 24.157 | 3.713 | 1.00 | 25.36 |
| ATOM | 2109 | OD1 | ASP | A | 415 | 27.104 | 25.285 | 3.704 | 1.00 | 28.76 |

TABLE 4-continued

Structural coordinates for AKT3lkd(T305D, S472D) (SEQ ID NO:2).

| ATOM | 2110 | OD2 | ASP | A | 415 | 27.406 | 23.301 | 2.844 | 1.00 | 30.38 |
|------|------|-----|-----|---|-----|--------|--------|-------|------|-------|
| ATOM | 2111 | N   | LYS | A | 416 | 31.286 | 24.982 | 7.029 | 1.00 | 19.81 |
| ATOM | 2112 | CA  | LYS | A | 416 | 32.022 | 24.706 | 8.271 | 1.00 | 19.86 |
| ATOM | 2113 | C   | LYS | A | 416 | 32.112 | 23.232 | 8.597 | 1.00 | 24.07 |
| ATOM | 2114 | O   | LYS | A | 416 | 32.101 | 22.823 | 9.787 | 1.00 | 24.61 |
| ATOM | 2115 | CB  | LYS | A | 416 | 31.476 | 25.523 | 9.469 | 1.00 | 21.40 |
| ATOM | 2116 | CG  | LYS | A | 416 | 31.790 | 27.013 | 9.349 | 1.00 | 25.75 |
| ATOM | 2117 | CD  | LYS | A | 416 | 31.024 | 27.875 | 10.376 | 1.00 | 32.08 |
| ATOM | 2118 | CE  | LYS | A | 416 | 31.473 | 27.618 | 11.794 | 1.00 | 42.08 |
| ATOM | 2119 | NZ  | LYS | A | 416 | 30.638 | 28.413 | 12.787 | 1.00 | 44.79 |
| ATOM | 2120 | N   | LYS | A | 417 | 32.262 | 22.425 | 7.535 | 1.00 | 22.89 |
| ATOM | 2121 | CA  | LYS | A | 417 | 32.370 | 20.981 | 7.678 | 1.00 | 23.35 |
| ATOM | 2122 | C   | LYS | A | 417 | 33.827 | 20.478 | 7.631 | 1.00 | 26.65 |
| ATOM | 2123 | O   | LYS | A | 417 | 34.075 | 19.303 | 7.882 | 1.00 | 27.61 |
| ATOM | 2124 | CB  | LYS | A | 417 | 31.487 | 20.252 | 6.662 | 1.00 | 23.53 |
| ATOM | 2125 | CG  | LYS | A | 417 | 29.993 | 20.448 | 6.895 | 1.00 | 24.28 |
| ATOM | 2126 | CD  | LYS | A | 417 | 29.180 | 19.831 | 5.748 | 1.00 | 28.83 |
| ATOM | 2127 | CE  | LYS | A | 417 | 27.653 | 20.038 | 5.938 | 1.00 | 33.62 |
| ATOM | 2128 | NZ  | LYS | A | 417 | 26.891 | 19.587 | 4.711 | 1.00 | 34.10 |
| ATOM | 2129 | N   | LEU | A | 418 | 34.804 | 21.350 | 7.328 | 1.00 | 22.26 |
| ATOM | 2130 | CA  | LEU | A | 418 | 36.186 | 20.892 | 7.466 | 1.00 | 21.62 |
| ATOM | 2131 | C   | LEU | A | 418 | 36.428 | 20.804 | 8.984 | 1.00 | 24.58 |
| ATOM | 2132 | O   | LEU | A | 418 | 35.969 | 21.671 | 9.753 | 1.00 | 22.31 |
| ATOM | 2133 | CB  | LEU | A | 418 | 37.193 | 21.918 | 6.895 | 1.00 | 21.73 |
| ATOM | 2134 | CG  | LEU | A | 418 | 37.197 | 22.180 | 5.384 | 1.00 | 27.86 |
| ATOM | 2135 | CD1 | LEU | A | 418 | 38.507 | 22.873 | 4.988 | 1.00 | 27.95 |
| ATOM | 2136 | CD2 | LEU | A | 418 | 36.986 | 20.940 | 4.567 | 1.00 | 32.14 |
| ATOM | 2137 | N   | VAL | A | 419 | 37.175 | 19.803 | 9.414 | 1.00 | 21.99 |
| ATOM | 2138 | CA  | VAL | A | 419 | 37.459 | 19.660 | 10.854 | 1.00 | 22.38 |
| ATOM | 2139 | C   | VAL | A | 419 | 38.633 | 20.542 | 11.235 | 1.00 | 23.59 |
| ATOM | 2140 | O   | VAL | A | 419 | 39.724 | 20.387 | 10.677 | 1.00 | 24.06 |
| ATOM | 2141 | CB  | VAL | A | 419 | 37.777 | 18.202 | 11.207 | 1.00 | 28.95 |
| ATOM | 2142 | CG1 | VAL | A | 419 | 38.203 | 18.094 | 12.637 | 1.00 | 29.09 |
| ATOM | 2143 | CG2 | VAL | A | 419 | 36.556 | 17.313 | 10.921 | 1.00 | 29.30 |
| ATOM | 2144 | N   | PRO | A | 420 | 38.441 | 21.485 | 12.168 | 1.00 | 21.67 |
| ATOM | 2145 | CA  | PRO | A | 420 | 39.551 | 22.386 | 12.505 | 1.00 | 20.54 |
| ATOM | 2146 | C   | PRO | A | 420 | 40.732 | 21.610 | 13.105 | 1.00 | 24.51 |
| ATOM | 2147 | O   | PRO | A | 420 | 40.537 | 20.740 | 13.968 | 1.00 | 24.22 |
| ATOM | 2148 | CB  | PRO | A | 420 | 38.946 | 23.360 | 13.524 | 1.00 | 22.28 |
| ATOM | 2149 | CG  | PRO | A | 420 | 37.454 | 23.340 | 13.235 | 1.00 | 26.69 |
| ATOM | 2150 | CD  | PRO | A | 420 | 37.188 | 21.875 | 12.846 | 1.00 | 22.18 |
| ATOM | 2151 | N   | PRO | A | 421 | 41.953 | 21.907 | 12.642 | 1.00 | 24.66 |
| ATOM | 2152 | CA  | PRO | A | 421 | 43.140 | 21.182 | 13.119 | 1.00 | 24.90 |
| ATOM | 2153 | C   | PRO | A | 421 | 43.497 | 21.512 | 14.568 | 1.00 | 28.42 |
| ATOM | 2154 | O   | PRO | A | 421 | 44.157 | 20.716 | 15.258 | 1.00 | 29.94 |
| ATOM | 2155 | CB  | PRO | A | 421 | 44.250 | 21.652 | 12.165 | 1.00 | 27.61 |
| ATOM | 2156 | CG  | PRO | A | 421 | 43.709 | 22.961 | 11.547 | 1.00 | 32.84 |
| ATOM | 2157 | CD  | PRO | A | 421 | 42.245 | 22.686 | 11.417 | 1.00 | 27.40 |
| ATOM | 2158 | N   | PHE | A | 422 | 43.104 | 22.695 | 15.009 | 1.00 | 23.38 |
| ATOM | 2159 | CA  | PHE | A | 422 | 43.339 | 23.143 | 16.375 | 1.00 | 23.49 |
| ATOM | 2160 | C   | PHE | A | 422 | 42.021 | 23.614 | 16.988 | 1.00 | 27.67 |
| ATOM | 2161 | O   | PHE | A | 422 | 41.307 | 24.434 | 16.398 | 1.00 | 24.07 |
| ATOM | 2162 | CB  | PHE | A | 422 | 44.362 | 24.289 | 16.380 | 1.00 | 25.25 |
| ATOM | 2163 | CG  | PHE | A | 422 | 44.441 | 25.014 | 17.686 | 1.00 | 27.53 |
| ATOM | 2164 | CD1 | PHE | A | 422 | 45.031 | 24.407 | 18.792 | 1.00 | 31.62 |
| ATOM | 2165 | CD2 | PHE | A | 422 | 43.892 | 26.275 | 17.828 | 1.00 | 29.92 |
| ATOM | 2166 | CE1 | PHE | A | 422 | 45.080 | 25.070 | 20.024 | 1.00 | 33.47 |
| ATOM | 2167 | CE2 | PHE | A | 422 | 43.927 | 26.927 | 19.041 | 1.00 | 33.76 |
| ATOM | 2168 | CZ  | PHE | A | 422 | 44.511 | 26.306 | 20.152 | 1.00 | 32.30 |
| ATOM | 2169 | N   | LYS | A | 423 | 41.670 | 23.069 | 18.151 | 1.00 | 25.32 |
| ATOM | 2170 | CA  | LYS | A | 423 | 40.431 | 23.476 | 18.828 | 1.00 | 27.53 |
| ATOM | 2171 | C   | LYS | A | 423 | 40.799 | 24.372 | 20.042 | 1.00 | 32.98 |
| ATOM | 2172 | O   | LYS | A | 423 | 41.437 | 23.909 | 20.987 | 1.00 | 32.80 |
| ATOM | 2173 | CB  | LYS | A | 423 | 39.641 | 22.234 | 19.305 | 1.00 | 30.41 |
| ATOM | 2174 | CG  | LYS | A | 423 | 39.573 | 21.099 | 18.287 | 1.00 | 37.57 |
| ATOM | 2175 | CD  | LYS | A | 423 | 38.832 | 21.528 | 17.030 | 1.00 | 46.15 |
| ATOM | 2176 | CE  | LYS | A | 423 | 38.693 | 20.371 | 16.036 | 1.00 | 49.95 |
| ATOM | 2177 | NZ  | LYS | A | 423 | 37.752 | 19.326 | 16.519 | 1.00 | 64.68 |
| ATOM | 2178 | N   | PRO | A | 424 | 40.458 | 25.658 | 19.980 | 1.00 | 28.42 |
| ATOM | 2179 | CA  | PRO | A | 424 | 40.774 | 26.566 | 21.084 | 1.00 | 28.36 |
| ATOM | 2180 | C   | PRO | A | 424 | 40.244 | 25.993 | 22.408 | 1.00 | 33.70 |
| ATOM | 2181 | O   | PRO | A | 424 | 39.140 | 25.424 | 22.468 | 1.00 | 33.00 |
| ATOM | 2182 | CB  | PRO | A | 424 | 40.037 | 27.854 | 20.699 | 1.00 | 29.78 |
| ATOM | 2183 | CG  | PRO | A | 424 | 40.073 | 27.850 | 19.188 | 1.00 | 32.31 |
| ATOM | 2184 | CD  | PRO | A | 424 | 39.959 | 26.377 | 18.789 | 1.00 | 28.66 |
| ATOM | 2185 | N   | GLN | A | 425 | 41.049 | 26.123 | 23.445 | 1.00 | 33.37 |
| ATOM | 2186 | CA  | GLN | A | 425 | 40.730 | 25.543 | 24.745 | 1.00 | 34.51 |
| ATOM | 2187 | C   | GLN | A | 425 | 39.943 | 26.477 | 25.638 | 1.00 | 39.38 |

TABLE 4-continued

Structural coordinates for AKT3lkd(T305D, S472D) (SEQ ID NO:2).

| ATOM | 2188 | O   | GLN | A | 425 | 40.420 | 26.868 | 26.699 | 1.00 | 39.40 |
|------|------|-----|-----|---|-----|--------|--------|--------|------|-------|
| ATOM | 2189 | CB  | GLN | A | 425 | 42.022 | 25.109 | 25.439 | 1.00 | 35.87 |
| ATOM | 2190 | CG  | GLN | A | 425 | 42.697 | 23.908 | 24.765 | 1.00 | 49.08 |
| ATOM | 2191 | CD  | GLN | A | 425 | 41.764 | 22.718 | 24.642 | 1.00 | 68.69 |
| ATOM | 2192 | OE1 | GLN | A | 425 | 41.722 | 21.858 | 25.517 | 1.00 | 66.46 |
| ATOM | 2193 | NE2 | GLN | A | 425 | 40.985 | 22.684 | 23.568 | 1.00 | 61.29 |
| ATOM | 2194 | N   | VAL | A | 426 | 38.746 | 26.845 | 25.195 | 1.00 | 35.85 |
| ATOM | 2195 | CA  | VAL | A | 426 | 37.864 | 27.734 | 25.966 | 1.00 | 36.85 |
| ATOM | 2196 | C   | VAL | A | 426 | 36.743 | 26.866 | 26.525 | 1.00 | 43.80 |
| ATOM | 2197 | O   | VAL | A | 426 | 36.362 | 25.886 | 25.903 | 1.00 | 44.79 |
| ATOM | 2198 | CB  | VAL | A | 426 | 37.231 | 28.838 | 25.058 | 1.00 | 40.72 |
| ATOM | 2199 | CG1 | VAL | A | 426 | 38.293 | 29.819 | 24.586 | 1.00 | 40.79 |
| ATOM | 2200 | CG2 | VAL | A | 426 | 36.500 | 28.205 | 23.858 | 1.00 | 40.51 |
| ATOM | 2201 | N   | THR | A | 427 | 36.224 | 27.220 | 27.698 | 1.00 | 41.10 |
| ATOM | 2202 | CA  | THR | A | 427 | 35.175 | 26.425 | 28.334 | 1.00 | 41.68 |
| ATOM | 2203 | C   | THR | A | 427 | 33.762 | 26.865 | 27.958 | 1.00 | 45.11 |
| ATOM | 2204 | O   | THR | A | 427 | 32.785 | 26.245 | 28.369 | 1.00 | 45.97 |
| ATOM | 2205 | CB  | THR | A | 427 | 35.316 | 26.449 | 29.859 | 1.00 | 53.25 |
| ATOM | 2206 | OG1 | THR | A | 427 | 35.361 | 27.810 | 30.318 | 1.00 | 54.18 |
| ATOM | 2207 | CG2 | THR | A | 427 | 36.589 | 25.736 | 30.276 | 1.00 | 52.84 |
| ATOM | 2208 | N   | SER | A | 428 | 33.658 | 27.937 | 27.180 | 1.00 | 39.68 |
| ATOM | 2209 | CA  | SER | A | 428 | 32.363 | 28.464 | 26.775 | 1.00 | 39.19 |
| ATOM | 2210 | C   | SER | A | 428 | 32.543 | 29.527 | 25.704 | 1.00 | 42.68 |
| ATOM | 2211 | O   | SER | A | 428 | 33.662 | 29.891 | 25.373 | 1.00 | 41.66 |
| ATOM | 2212 | CB  | SER | A | 428 | 31.644 | 29.078 | 27.970 | 1.00 | 41.89 |
| ATOM | 2213 | OG  | SER | A | 428 | 32.213 | 30.333 | 28.317 | 1.00 | 45.35 |
| ATOM | 2214 | N   | GLU | A | 429 | 31.429 | 30.032 | 25.193 | 1.00 | 39.05 |
| ATOM | 2215 | CA  | GLU | A | 429 | 31.446 | 31.050 | 24.144 | 1.00 | 38.01 |
| ATOM | 2216 | C   | GLU | A | 429 | 31.819 | 32.439 | 24.667 | 1.00 | 39.49 |
| ATOM | 2217 | O   | GLU | A | 429 | 32.047 | 33.360 | 23.876 | 1.00 | 38.19 |
| ATOM | 2218 | CB  | GLU | A | 429 | 30.088 | 31.107 | 23.428 | 1.00 | 39.47 |
| ATOM | 2219 | CG  | GLU | A | 429 | 29.066 | 31.990 | 24.116 | 1.00 | 51.68 |
| ATOM | 2220 | CD  | GLU | A | 429 | 27.640 | 31.499 | 23.932 | 1.00 | 76.76 |
| ATOM | 2221 | OE1 | GLU | A | 429 | 27.393 | 30.698 | 22.999 | 1.00 | 72.64 |
| ATOM | 2222 | OE2 | GLU | A | 429 | 26.762 | 31.927 | 24.716 | 1.00 | 72.12 |
| ATOM | 2223 | N   | THR | A | 430 | 31.891 | 32.392 | 25.990 | 1.00 | 34.72 |
| ATOM | 2224 | CA  | THR | A | 430 | 32.236 | 33.876 | 26.586 | 1.00 | 33.56 |
| ATOM | 2225 | C   | THR | A | 430 | 33.607 | 33.876 | 27.275 | 1.00 | 35.02 |
| ATOM | 2226 | O   | THR | A | 430 | 34.144 | 34.927 | 27.584 | 1.00 | 36.08 |
| ATOM | 2227 | CB  | THR | A | 430 | 31.158 | 34.368 | 27.564 | 1.00 | 44.50 |
| ATOM | 2228 | OG1 | THR | A | 430 | 31.039 | 33.437 | 28.646 | 1.00 | 46.24 |
| ATOM | 2229 | CG2 | THR | A | 430 | 29.820 | 34.485 | 26.856 | 1.00 | 43.24 |
| ATOM | 2230 | N   | ASP | A | 431 | 34.168 | 32.688 | 27.481 | 1.00 | 29.32 |
| ATOM | 2231 | CA  | ASP | A | 431 | 35.481 | 32.531 | 28.082 | 1.00 | 28.75 |
| ATOM | 2232 | C   | ASP | A | 431 | 36.490 | 33.492 | 27.451 | 1.00 | 33.09 |
| ATOM | 2233 | O   | ASP | A | 431 | 36.686 | 33.492 | 26.239 | 1.00 | 33.73 |
| ATOM | 2234 | CB  | ASP | A | 431 | 35.929 | 31.079 | 27.902 | 1.00 | 29.80 |
| ATOM | 2235 | CG  | ASP | A | 431 | 37.201 | 30.749 | 28.645 | 1.00 | 33.41 |
| ATOM | 2236 | OD1 | ASP | A | 431 | 37.845 | 31.649 | 29.208 | 1.00 | 34.19 |
| ATOM | 2237 | OD2 | ASP | A | 431 | 37.567 | 29.553 | 28.651 | 1.00 | 36.60 |
| ATOM | 2238 | N   | THR | A | 432 | 37.103 | 34.333 | 28.272 | 1.00 | 28.05 |
| ATOM | 2239 | CA  | THR | A | 432 | 38.035 | 35.333 | 27.769 | 1.00 | 26.57 |
| ATOM | 2240 | C   | THR | A | 432 | 39.476 | 34.897 | 27.832 | 1.00 | 29.98 |
| ATOM | 2241 | O   | THR | A | 432 | 40.373 | 35.706 | 27.644 | 1.00 | 31.01 |
| ATOM | 2242 | CB  | THR | A | 432 | 37.882 | 36.659 | 28.529 | 1.00 | 30.23 |
| ATOM | 2243 | OG1 | THR | A | 432 | 38.063 | 36.409 | 29.934 | 1.00 | 31.05 |
| ATOM | 2244 | CG2 | THR | A | 432 | 36.502 | 37.272 | 28.275 | 1.00 | 24.82 |
| ATOM | 2245 | N   | ARG | A | 433 | 39.697 | 33.599 | 28.042 | 1.00 | 29.09 |
| ATOM | 2246 | CA  | ARG | A | 433 | 41.039 | 33.042 | 28.161 | 1.00 | 30.19 |
| ATOM | 2247 | C   | ARG | A | 433 | 42.136 | 33.614 | 27.243 | 1.00 | 33.69 |
| ATOM | 2248 | O   | ARG | A | 433 | 43.215 | 34.015 | 27.704 | 1.00 | 32.75 |
| ATOM | 2249 | CB  | ARG | A | 433 | 40.992 | 31.515 | 28.006 | 1.00 | 31.35 |
| ATOM | 2250 | CG  | ARG | A | 433 | 42.339 | 30.915 | 27.713 | 1.00 | 42.59 |
| ATOM | 2251 | CD  | ARG | A | 433 | 42.307 | 29.407 | 27.746 | 1.00 | 46.98 |
| ATOM | 2252 | NE  | ARG | A | 433 | 43.658 | 28.854 | 27.644 | 1.00 | 56.66 |
| ATOM | 2253 | CZ  | ARG | A | 433 | 43.955 | 27.570 | 27.807 | 1.00 | 71.50 |
| ATOM | 2254 | NH1 | ARG | A | 433 | 42.998 | 26.691 | 28.079 | 1.00 | 56.52 |
| ATOM | 2255 | NH2 | ARG | A | 433 | 45.211 | 27.165 | 27.692 | 1.00 | 62.35 |
| ATOM | 2256 | N   | TYR | A | 434 | 41.889 | 33.595 | 25.938 | 1.00 | 30.09 |
| ATOM | 2257 | CA  | TYR | A | 434 | 42.905 | 34.043 | 24.993 | 1.00 | 29.19 |
| ATOM | 2258 | C   | TYR | A | 434 | 43.137 | 35.546 | 25.026 | 1.00 | 32.74 |
| ATOM | 2259 | O   | TYR | A | 434 | 44.260 | 36.021 | 24.830 | 1.00 | 34.56 |
| ATOM | 2260 | CB  | TYR | A | 434 | 42.609 | 33.503 | 23.590 | 1.00 | 29.85 |
| ATOM | 2261 | CG  | TYR | A | 434 | 42.770 | 31.995 | 23.517 | 1.00 | 29.86 |
| ATOM | 2262 | CD1 | TYR | A | 434 | 41.670 | 31.151 | 23.520 | 1.00 | 31.33 |
| ATOM | 2263 | CD2 | TYR | A | 434 | 44.026 | 31.421 | 23.570 | 1.00 | 31.20 |
| ATOM | 2264 | CE1 | TYR | A | 434 | 41.829 | 29.758 | 23.474 | 1.00 | 31.74 |
| ATOM | 2265 | CE2 | TYR | A | 434 | 44.190 | 30.045 | 23.529 | 1.00 | 31.79 |

TABLE 4-continued

Structural coordinates for AKT3lkd(T305D, S472D) (SEQ ID NO:2).

| | | | | | | | | | |
|---|---|---|---|---|---|---|---|---|---|
| ATOM | 2266 | CZ | TYR | A | 434 | 43.102 | 29.228 | 23.491 | 1.00 | 36.47 |
| ATOM | 2267 | OH | TYR | A | 434 | 43.283 | 27.865 | 23.461 | 1.00 | 38.69 |
| ATOM | 2268 | N | PHE | A | 435 | 42.103 | 36.310 | 25.348 | 1.00 | 29.02 |
| ATOM | 2269 | CA | PHE | A | 435 | 42.292 | 37.735 | 25.458 | 1.00 | 28.73 |
| ATOM | 2270 | C | PHE | A | 435 | 43.163 | 38.008 | 26.681 | 1.00 | 34.96 |
| ATOM | 2271 | O | PHE | A | 435 | 44.046 | 38.855 | 26.642 | 1.00 | 33.90 |
| ATOM | 2272 | CB | PHE | A | 435 | 40.957 | 38.435 | 25.628 | 1.00 | 30.01 |
| ATOM | 2273 | CG | PHE | A | 435 | 40.121 | 38.423 | 24.404 | 1.00 | 30.52 |
| ATOM | 2274 | CD1 | PHE | A | 435 | 39.102 | 37.497 | 24.251 | 1.00 | 32.52 |
| ATOM | 2275 | CD2 | PHE | A | 435 | 40.353 | 39.341 | 23.391 | 1.00 | 32.94 |
| ATOM | 2276 | CE1 | PHE | A | 435 | 38.331 | 37.489 | 23.120 | 1.00 | 33.28 |
| ATOM | 2277 | CE2 | PHE | A | 435 | 39.575 | 39.336 | 22.245 | 1.00 | 35.53 |
| ATOM | 2278 | CZ | PHE | A | 435 | 38.557 | 38.425 | 22.115 | 1.00 | 33.67 |
| ATOM | 2279 | N | ASP | A | 436 | 42.895 | 37.272 | 27.766 | 1.00 | 34.76 |
| ATOM | 2280 | CA | ASP | A | 436 | 43.641 | 37.437 | 29.019 | 1.00 | 36.02 |
| ATOM | 2281 | C | ASP | A | 436 | 45.100 | 37.051 | 28.811 | 1.00 | 43.86 |
| ATOM | 2282 | O | ASP | A | 436 | 46.011 | 37.804 | 29.163 | 1.00 | 44.24 |
| ATOM | 2283 | CB | ASP | A | 436 | 43.013 | 36.594 | 30.149 | 1.00 | 37.70 |
| ATOM | 2284 | CG | ASP | A | 436 | 41.541 | 36.926 | 30.381 | 1.00 | 42.73 |
| ATOM | 2285 | OD1 | ASP | A | 436 | 40.785 | 36.044 | 30.859 | 1.00 | 43.11 |
| ATOM | 2286 | OD2 | ASP | A | 436 | 41.138 | 38.065 | 30.070 | 1.00 | 47.09 |
| ATOM | 2287 | N | GLU | A | 437 | 45.315 | 35.880 | 28.216 | 1.00 | 42.59 |
| ATOM | 2288 | CA | GLU | A | 437 | 46.665 | 35.395 | 27.932 | 1.00 | 43.13 |
| ATOM | 2289 | C | GLU | A | 437 | 47.434 | 36.359 | 27.025 | 1.00 | 46.91 |
| ATOM | 2290 | O | GLU | A | 437 | 48.605 | 36.632 | 27.258 | 1.00 | 47.08 |
| ATOM | 2291 | CB | GLU | A | 437 | 46.617 | 34.005 | 27.297 | 1.00 | 44.68 |
| ATOM | 2292 | CG | GLU | A | 437 | 46.290 | 32.883 | 28.275 | 1.00 | 55.50 |
| ATOM | 2293 | CD | GLU | A | 437 | 46.212 | 31.529 | 27.600 | 1.00 | 76.67 |
| ATOM | 2294 | OE1 | GLU | A | 437 | 45.698 | 30.580 | 28.226 | 1.00 | 73.71 |
| ATOM | 2295 | OE2 | GLU | A | 437 | 46.659 | 31.417 | 26.439 | 1.00 | 69.71 |
| ATOM | 2296 | N | GLU | A | 438 | 46.771 | 36.855 | 25.981 | 1.00 | 43.69 |
| ATOM | 2297 | CA | GLU | A | 438 | 47.399 | 37.782 | 25.036 | 1.00 | 43.30 |
| ATOM | 2298 | C | GLU | A | 438 | 47.743 | 39.110 | 25.706 | 1.00 | 49.94 |
| ATOM | 2299 | O | GLU | A | 438 | 48.765 | 39.723 | 25.398 | 1.00 | 49.97 |
| ATOM | 2300 | CB | GLU | A | 438 | 46.491 | 38.027 | 23.825 | 1.00 | 44.03 |
| ATOM | 2301 | CG | GLU | A | 438 | 46.221 | 36.775 | 22.992 | 1.00 | 49.49 |
| ATOM | 2302 | CD | GLU | A | 438 | 45.011 | 36.916 | 22.063 | 1.00 | 57.48 |
| ATOM | 2303 | OE1 | GLU | A | 438 | 44.408 | 38.013 | 22.009 | 1.00 | 49.97 |
| ATOM | 2304 | OE2 | GLU | A | 438 | 44.661 | 35.918 | 21.394 | 1.00 | 36.46 |
| ATOM | 2305 | N | PHE | A | 439 | 46.874 | 39.560 | 26.609 | 1.00 | 47.61 |
| ATOM | 2306 | CA | PHE | A | 439 | 47.090 | 40.822 | 27.317 | 1.00 | 47.80 |
| TER | 2307 | | GLU | A | 479 | | | | | |
| ATOM | 2308 | OW | WAT | W | 1 | 43.468 | 42.232 | 1.602 | 1.00 | 20.77 |
| ATOM | 2309 | OW | WAT | W | 2 | 28.678 | 17.636 | 3.196 | 1.00 | 22.50 |
| ATOM | 2310 | OW | WAT | W | 3 | 41.819 | 25.901 | 14.194 | 1.00 | 24.13 |
| ATOM | 2311 | OW | WAT | W | 4 | 37.157 | 18.378 | 1.831 | 1.00 | 24.58 |
| ATOM | 2312 | OW | WAT | W | 5 | 35.069 | 24.559 | 6.875 | 1.00 | 21.29 |
| ATOM | 2313 | OW | WAT | W | 6 | 34.026 | 31.235 | 11.924 | 1.00 | 27.32 |
| ATOM | 2314 | OW | WAT | W | 7 | 28.182 | 27.973 | 7.200 | 1.00 | 37.04 |
| ATOM | 2315 | OW | WAT | W | 8 | 33.793 | 32.329 | 19.210 | 1.00 | 33.17 |
| ATOM | 2316 | OW | WAT | W | 9 | 29.610 | 37.982 | 8.456 | 1.00 | 24.27 |
| ATOM | 2317 | OW | WAT | W | 10 | 30.480 | 40.583 | 7.919 | 1.00 | 26.59 |
| ATOM | 2318 | OW | WAT | W | 11 | 48.194 | 19.515 | 11.040 | 1.00 | 30.98 |
| ATOM | 2319 | OW | WAT | W | 12 | 38.175 | 17.929 | 7.349 | 1.00 | 32.14 |
| ATOM | 2320 | OW | WAT | W | 13 | 27.718 | 34.086 | 2.542 | 1.00 | 32.52 |
| ATOM | 2321 | OW | WAT | W | 14 | 31.803 | 31.871 | −0.184 | 1.00 | 24.33 |
| ATOM | 2322 | OW | WAT | W | 15 | 28.388 | 20.983 | 2.420 | 1.00 | 30.34 |
| ATOM | 2323 | OW | WAT | W | 16 | 43.518 | 20.976 | 19.191 | 1.00 | 37.86 |
| ATOM | 2324 | OW | WAT | W | 17 | 28.541 | 38.091 | 19.466 | 1.00 | 35.47 |
| ATOM | 2325 | OW | WAT | W | 18 | 31.170 | 30.735 | 11.377 | 1.00 | 44.23 |
| ATOM | 2326 | OW | WAT | W | 19 | 37.299 | 47.685 | 0.963 | 1.00 | 37.60 |
| ATOM | 2327 | OW | WAT | W | 20 | 35.054 | 17.946 | 3.640 | 1.00 | 28.92 |
| ATOM | 2328 | OW | WAT | W | 21 | 39.394 | 18.351 | 3.007 | 1.00 | 33.77 |
| ATOM | 2329 | OW | WAT | W | 22 | 36.551 | 24.625 | 21.742 | 1.00 | 43.08 |
| ATOM | 2330 | OW | WAT | W | 23 | 46.354 | 42.494 | 0.575 | 1.00 | 41.49 |
| ATOM | 2331 | OW | WAT | W | 24 | 45.808 | 18.746 | 9.888 | 1.00 | 44.21 |
| ATOM | 2332 | OW | WAT | W | 25 | 31.730 | 31.508 | 14.885 | 1.00 | 33.28 |
| ATOM | 2333 | OW | WAT | W | 26 | 47.511 | 27.277 | 18.028 | 1.00 | 36.58 |
| ATOM | 2334 | OW | WAT | W | 27 | 43.953 | 19.565 | −0.499 | 1.00 | 22.57 |
| ATOM | 2335 | OW | WAT | W | 28 | 32.178 | 23.253 | 12.847 | 1.00 | 43.82 |
| ATOM | 2336 | OW | WAT | W | 29 | 24.757 | 26.241 | 2.990 | 1.00 | 53.39 |
| ATOM | 2337 | OW | WAT | W | 30 | 46.389 | 27.359 | 23.280 | 1.00 | 47.84 |
| ATOM | 2338 | OW | WAT | W | 31 | 32.963 | 16.958 | 8.593 | 1.00 | 38.64 |
| ATOM | 2339 | OW | WAT | W | 32 | 27.005 | 41.647 | 9.189 | 1.00 | 36.60 |
| ATOM | 2340 | OW | WAT | W | 33 | 48.414 | 29.405 | 21.271 | 1.00 | 46.52 |
| ATOM | 2341 | OW | WAT | W | 34 | 32.077 | 33.332 | 21.113 | 1.00 | 39.88 |
| ATOM | 2342 | OW | WAT | W | 35 | 41.441 | 18.309 | 11.013 | 1.00 | 43.19 |
| ATOM | 2343 | OW | WAT | W | 36 | 25.923 | 26.547 | 5.801 | 1.00 | 44.50 |

TABLE 4-continued

Structural coordinates for AKT3lkd(T305D, S472D) (SEQ ID NO:2).

| ATOM | 2344 | OW | WAT | W | 37 | 35.464 | 17.443 | 6.283 | 1.00 | 37.28 |
|---|---|---|---|---|---|---|---|---|---|---|
| ATOM | 2345 | OW | WAT | W | 38 | 51.296 | 18.943 | −0.801 | 1.00 | 28.66 |
| ATOM | 2346 | OW | WAT | W | 39 | 60.012 | 21.050 | −4.389 | 1.00 | 40.43 |
| ATOM | 2347 | OW | WAT | W | 40 | 26.783 | 37.564 | 17.221 | 1.00 | 54.10 |
| ATOM | 2348 | OW | WAT | W | 41 | 24.670 | 51.000 | 13.233 | 1.00 | 40.80 |
| ATOM | 2349 | OW | WAT | W | 42 | 42.815 | 18.185 | 1.663 | 1.00 | 38.72 |
| ATOM | 2350 | OW | WAT | W | 43 | 28.925 | 55.150 | 12.710 | 1.00 | 47.85 |
| ATOM | 2351 | OW | WAT | W | 44 | 42.589 | 16.798 | 6.022 | 1.00 | 42.59 |
| ATOM | 2352 | OW | WAT | W | 45 | 47.669 | 17.606 | −5.335 | 1.00 | 36.58 |
| ATOM | 2353 | OW | WAT | W | 46 | 39.368 | 21.411 | −4.530 | 1.00 | 17.32 |
| ATOM | 2354 | OW | WAT | W | 47 | 42.110 | 22.021 | −6.120 | 1.00 | 17.41 |
| ATOM | 2355 | OW | WAT | W | 48 | 50.611 | 18.994 | 6.791 | 1.00 | 22.42 |
| ATOM | 2356 | OW | WAT | W | 49 | 33.725 | 28.046 | −0.229 | 1.00 | 22.47 |
| ATOM | 2357 | OW | WAT | W | 50 | 50.566 | 19.821 | 1.783 | 1.00 | 23.64 |
| ATOM | 2358 | OW | WAT | W | 51 | 38.018 | 44.367 | 32.839 | 1.00 | 24.69 |
| ATOM | 2359 | OW | WAT | W | 52 | 47.815 | 23.515 | −9.723 | 1.00 | 25.70 |
| ATOM | 2360 | OW | WAT | W | 53 | 56.706 | 37.579 | −10.201 | 1.00 | 27.74 |
| ATOM | 2361 | OW | WAT | W | 54 | 56.242 | 40.661 | 3.790 | 1.00 | 27.99 |
| ATOM | 2362 | OW | WAT | W | 55 | 48.787 | 19.380 | −2.043 | 1.00 | 24.58 |
| ATOM | 2363 | OW | WAT | W | 56 | 40.669 | 32.903 | −14.359 | 1.00 | 22.30 |
| ATOM | 2364 | OW | WAT | W | 57 | 57.097 | 37.816 | −4.941 | 1.00 | 25.07 |
| ATOM | 2365 | OW | WAT | W | 58 | 56.719 | 23.911 | −6.937 | 1.00 | 26.68 |
| ATOM | 2366 | OW | WAT | W | 59 | 42.761 | 42.797 | −9.679 | 1.00 | 28.88 |
| ATOM | 2367 | OW | WAT | W | 60 | 44.323 | 26.949 | −11.046 | 1.00 | 26.61 |
| ATOM | 2368 | OW | WAT | W | 61 | 34.423 | 21.557 | −4.404 | 1.00 | 25.07 |
| ATOM | 2369 | OW | WAT | W | 62 | 49.598 | 18.452 | 4.023 | 1.00 | 26.59 |
| ATOM | 2370 | OW | WAT | W | 63 | 35.170 | 35.301 | −6.987 | 1.00 | 31.58 |
| ATOM | 2371 | OW | WAT | W | 64 | 54.677 | 24.401 | 7.382 | 1.00 | 28.10 |
| ATOM | 2372 | OW | WAT | W | 65 | 53.835 | 42.672 | 0.703 | 1.00 | 26.25 |
| ATOM | 2373 | OW | WAT | W | 66 | 55.315 | 39.266 | −12.262 | 1.00 | 27.34 |
| ATOM | 2374 | OW | WAT | W | 67 | 53.557 | 20.316 | 7.279 | 1.00 | 27.39 |
| ATOM | 2375 | OW | WAT | W | 68 | 45.269 | 44.433 | −7.889 | 1.00 | 29.08 |
| ATOM | 2376 | OW | WAT | W | 69 | 32.765 | 29.982 | −2.017 | 1.00 | 29.29 |
| ATOM | 2377 | OW | WAT | W | 70 | 50.306 | 22.932 | 13.020 | 1.00 | 32.45 |
| ATOM | 2378 | OW | WAT | W | 71 | 56.184 | 34.129 | −7.896 | 1.00 | 34.44 |
| ATOM | 2379 | OW | WAT | W | 72 | 46.051 | 34.099 | −13.325 | 1.00 | 35.09 |
| ATOM | 2380 | OW | WAT | W | 73 | 38.980 | 44.437 | −9.022 | 1.00 | 32.61 |
| ATOM | 2381 | OW | WAT | W | 74 | 32.154 | 27.629 | 14.505 | 1.00 | 30.93 |
| ATOM | 2382 | OW | WAT | W | 75 | 70.611 | 17.966 | 1.633 | 1.00 | 30.56 |
| ATOM | 2383 | OW | WAT | W | 76 | 53.354 | 20.850 | −7.496 | 1.00 | 35.40 |
| ATOM | 2384 | OW | WAT | W | 77 | 35.728 | 47.448 | −2.661 | 1.00 | 33.90 |
| ATOM | 2385 | OW | WAT | W | 78 | 31.577 | 21.519 | −3.410 | 1.00 | 27.82 |
| ATOM | 2386 | OW | WAT | W | 79 | 56.103 | 21.027 | 4.961 | 1.00 | 33.64 |
| ATOM | 2387 | OW | WAT | W | 80 | 36.117 | 22.097 | 16.675 | 1.00 | 36.97 |
| ATOM | 2388 | OW | WAT | W | 81 | 41.565 | 20.139 | −7.873 | 1.00 | 33.83 |
| ATOM | 2389 | OW | WAT | W | 82 | 40.801 | 17.869 | −7.044 | 1.00 | 34.94 |
| ATOM | 2390 | OW | WAT | W | 83 | 48.983 | 32.074 | −11.867 | 1.00 | 40.52 |
| ATOM | 2391 | OW | WAT | W | 84 | 43.677 | 41.023 | −11.773 | 1.00 | 35.78 |
| ATOM | 2392 | OW | WAT | W | 85 | 50.541 | 28.632 | −8.931 | 1.00 | 37.08 |
| ATOM | 2393 | OW | WAT | W | 86 | 36.808 | 33.758 | 31.225 | 1.00 | 35.10 |
| ATOM | 2394 | OW | WAT | W | 87 | 61.431 | 34.955 | 1.137 | 1.00 | 35.87 |
| ATOM | 2395 | OW | WAT | W | 88 | 33.187 | 30.345 | −12.430 | 1.00 | 45.96 |
| ATOM | 2396 | OW | WAT | W | 89 | 53.881 | 26.777 | −9.947 | 1.00 | 44.73 |
| ATOM | 2397 | OW | WAT | W | 90 | 64.203 | 28.712 | −1.574 | 1.00 | 43.57 |
| ATOM | 2398 | OW | WAT | W | 91 | 63.064 | 39.695 | 2.916 | 1.00 | 43.85 |
| ATOM | 2399 | OW | WAT | W | 92 | 44.680 | 44.699 | −10.376 | 1.00 | 43.51 |
| ATOM | 2400 | OW | WAT | W | 93 | 58.406 | 35.599 | −6.121 | 1.00 | 38.86 |
| ATOM | 2401 | OW | WAT | W | 94 | 65.511 | 37.766 | −5.710 | 1.00 | 44.17 |
| ATOM | 2402 | OW | WAT | W | 95 | 35.202 | 41.176 | −8.372 | 1.00 | 39.64 |
| ATOM | 2403 | OW | WAT | W | 96 | 59.077 | 37.991 | 9.698 | 1.00 | 41.74 |
| ATOM | 2404 | OW | WAT | W | 97 | 48.313 | 46.012 | −0.543 | 1.00 | 44.30 |
| ATOM | 2405 | OW | WAT | W | 98 | 46.910 | 25.873 | −11.080 | 1.00 | 41.07 |
| ATOM | 2406 | OW | WAT | W | 99 | 27.832 | 48.115 | 32.625 | 1.00 | 43.53 |
| ATOM | 2407 | OW | WAT | W | 100 | 25.948 | 27.573 | −0.013 | 1.00 | 44.20 |
| ATOM | 2408 | OW | WAT | W | 101 | 40.339 | 42.692 | 31.798 | 1.00 | 40.88 |
| ATOM | 2409 | OW | WAT | W | 102 | 25.203 | 38.977 | 1.188 | 1.00 | 40.14 |
| ATOM | 2410 | OW | WAT | W | 103 | 56.734 | 32.333 | 13.668 | 1.00 | 43.42 |
| ATOM | 2411 | OW | WAT | W | 104 | 34.264 | 33.194 | −10.599 | 1.00 | 39.67 |
| ATOM | 2412 | OW | WAT | W | 105 | 42.861 | 26.116 | −13.065 | 1.00 | 44.04 |
| ATOM | 2413 | OW | WAT | W | 106 | 52.016 | 40.040 | 10.676 | 1.00 | 46.02 |
| ATOM | 2414 | OW | WAT | W | 107 | 39.444 | 31.402 | 31.394 | 1.00 | 41.55 |
| ATOM | 2415 | OW | WAT | W | 108 | 48.736 | 22.281 | 15.374 | 1.00 | 45.69 |
| ATOM | 2416 | OW | WAT | W | 109 | 50.157 | 41.915 | −17.620 | 1.00 | 45.70 |
| ATOM | 2417 | OW | WAT | W | 110 | 59.124 | 22.710 | −6.607 | 1.00 | 45.49 |
| ATOM | 2418 | OW | WAT | W | 111 | 50.889 | 33.664 | −14.586 | 1.00 | 41.37 |
| ATOM | 2419 | OW | WAT | W | 112 | 46.675 | 44.120 | 3.894 | 1.00 | 44.02 |
| ATOM | 2420 | OW | WAT | W | 113 | 57.152 | 44.496 | −9.434 | 1.00 | 46.30 |
| ATOM | 2421 | OW | WAT | W | 114 | 54.350 | 40.757 | −16.203 | 1.00 | 47.28 |

TABLE 4-continued

Structural coordinates for AKT3lkd(T305D, S472D) (SEQ ID NO:2).

| ATOM | 2422 | OW | WAT | W | 115 | 37.867 | 42.808 | −11.505 | 1.00 | 51.34 |
|---|---|---|---|---|---|---|---|---|---|---|
| ATOM | 2423 | OW | WAT | W | 116 | 42.955 | 39.455 | −15.566 | 1.00 | 52.60 |
| ATOM | 2424 | OW | WAT | W | 501 | 45.718 | 37.899 | 14.859 | 1.00 | 30.70 |
| ATOM | 2425 | OW | WAT | W | 502 | 40.000 | 35.763 | 20.419 | 1.00 | 42.61 |
| ATOM | 2426 | OW | WAT | W | 503 | 43.475 | 46.755 | 9.075 | 1.00 | 38.67 |
| ATOM | 2427 | OW | WAT | W | 504 | 42.281 | 37.355 | 21.118 | 1.00 | 41.76 |
| ATOM | 2428 | OW | WAT | W | 505 | 35.608 | 39.557 | 19.222 | 1.00 | 38.00 |
| ATOM | 2429 | OW | WAT | W | 506 | 41.644 | 43.127 | 14.022 | 1.00 | 45.82 |
| ATOM | 2430 | OW | WAT | W | 507 | 39.192 | 33.451 | 24.966 | 1.00 | 30.27 |
| ATOM | 2431 | OW | WAT | W | 508 | 43.875 | 40.943 | 24.898 | 1.00 | 41.15 |
| END | | | | | | | | | | |

TABLE 5

Structural coordinates for AKT3lkd(pT305, S472D).

REMARK This is the long kinase domain with T472D mutation
REMARK and S305 phosphorylated: AKT3lkd(pT305, S472D)
REMARK
CRYST1 Unit Cell Dimensions: a = 48.830 b = 72.970 c = 95.220 α = 90.00
β = 90.00 γ = 90.00 Space group: P2₁2₁2₁

| ORIGX1 | 1.000000 | 0.000000 | 0.000000 | 0.00000 | | | | |
|---|---|---|---|---|---|---|---|---|
| ORIGX2 | 0.000000 | 1.000000 | 0.000000 | 0.00000 | | | | |
| ORIGX3 | 0.000000 | 0.000000 | 1.000000 | 0.00000 | | | | |
| SCALE1 | 0.020479 | 0.000000 | 0.000000 | 0.00000 | | | | |
| SCALE2 | 0.000000 | 0.013704 | 0.000000 | 0.00000 | | | | |
| SCALE3 | 0.000000 | 0.000000 | 0.010502 | 0.00000 | | | | |
| ATOM | 1 | N | ARG | A | 142 | 18.726 | 53.528 | 16.884 | 1.00 | 58.66 |
| ATOM | 2 | CA | ARG | A | 142 | 20.132 | 53.454 | 17.251 | 1.00 | 58.48 |
| ATOM | 3 | C | ARG | A | 142 | 20.293 | 52.930 | 18.671 | 1.00 | 61.84 |
| ATOM | 4 | O | ARG | A | 142 | 19.352 | 52.964 | 19.468 | 1.00 | 60.89 |
| ATOM | 5 | CB | ARG | A | 142 | 20.796 | 54.829 | 17.122 | 1.00 | 59.45 |
| ATOM | 6 | CG | ARG | A | 142 | 20.317 | 55.642 | 15.930 | 1.00 | 72.38 |
| ATOM | 7 | CD | ARG | A | 142 | 18.947 | 56.264 | 16.196 | 1.00 | 85.80 |
| ATOM | 8 | NE | ARG | A | 142 | 18.416 | 56.948 | 15.020 | 1.00 | 96.22 |
| ATOM | 9 | CZ | ARG | A | 142 | 17.173 | 56.806 | 14.569 | 1.00 | 111.34 |
| ATOM | 10 | NH1 | ARG | A | 142 | 16.325 | 56.002 | 15.196 | 1.00 | 98.56 |
| ATOM | 11 | NH2 | ARG | A | 142 | 16.780 | 57.464 | 13.487 | 1.00 | 98.92 |
| ATOM | 12 | N | LYS | A | 143 | 21.486 | 52.433 | 18.979 | 1.00 | 58.18 |
| ATOM | 13 | CA | LYS | A | 143 | 21.777 | 51.915 | 20.308 | 1.00 | 57.58 |
| ATOM | 14 | C | LYS | A | 143 | 22.657 | 52.901 | 21.053 | 1.00 | 60.94 |
| ATOM | 15 | O | LYS | A | 143 | 23.320 | 53.750 | 20.441 | 1.00 | 59.86 |
| ATOM | 16 | CB | LYS | A | 143 | 22.468 | 50.555 | 20.215 | 1.00 | 59.57 |
| ATOM | 17 | CG | LYS | A | 143 | 21.708 | 49.530 | 19.389 | 1.00 | 67.11 |
| ATOM | 18 | CD | LYS | A | 143 | 20.368 | 49.195 | 20.015 | 1.00 | 74.53 |
| ATOM | 19 | CE | LYS | A | 143 | 20.165 | 47.692 | 20.112 | 1.00 | 83.50 |
| ATOM | 20 | NZ | LYS | A | 143 | 18.777 | 47.291 | 19.759 | 1.00 | 91.32 |
| ATOM | 21 | N | THR | A | 144 | 22.664 | 52.793 | 22.375 | 1.00 | 57.46 |
| ATOM | 22 | CA | THR | A | 144 | 23.460 | 53.695 | 23.194 | 1.00 | 57.38 |
| ATOM | 23 | C | THR | A | 144 | 24.492 | 52.955 | 24.016 | 1.00 | 60.59 |
| ATOM | 24 | O | THR | A | 144 | 24.374 | 51.757 | 24.254 | 1.00 | 59.64 |
| ATOM | 25 | CB | THR | A | 144 | 22.579 | 54.503 | 24.167 | 1.00 | 66.03 |
| ATOM | 26 | OG1 | THR | A | 144 | 21.267 | 53.927 | 24.228 | 1.00 | 65.90 |
| ATOM | 27 | CG2 | THR | A | 144 | 22.486 | 55.956 | 23.724 | 1.00 | 64.61 |
| ATOM | 28 | N | MET | A | 145 | 25.469 | 53.702 | 24.516 | 1.00 | 57.24 |
| ATOM | 29 | CA | MET | A | 145 | 26.490 | 53.143 | 25.378 | 1.00 | 57.08 |
| ATOM | 30 | C | MET | A | 145 | 25.810 | 52.605 | 26.632 | 1.00 | 59.69 |
| ATOM | 31 | O | MET | A | 145 | 26.417 | 51.882 | 27.419 | 1.00 | 59.68 |
| ATOM | 32 | CB | MET | A | 145 | 27.504 | 54.224 | 25.755 | 1.00 | 59.68 |
| ATOM | 33 | CG | MET | A | 145 | 28.938 | 53.792 | 25.613 | 1.00 | 63.96 |
| ATOM | 34 | SD | MET | A | 145 | 29.059 | 52.041 | 25.252 | 1.00 | 68.85 |
| ATOM | 35 | CE | MET | A | 145 | 29.109 | 51.330 | 26.898 | 1.00 | 65.46 |
| ATOM | 36 | N | ASN | A | 146 | 24.534 | 52.955 | 26.792 | 1.00 | 54.86 |
| ATOM | 37 | CA | ASN | A | 146 | 23.732 | 52.544 | 27.943 | 1.00 | 53.92 |
| ATOM | 38 | C | ASN | A | 146 | 22.860 | 51.319 | 27.657 | 1.00 | 55.57 |
| ATOM | 39 | O | ASN | A | 146 | 22.099 | 50.878 | 28.518 | 1.00 | 54.75 |
| ATOM | 40 | CB | ASN | A | 146 | 22.852 | 53.710 | 28.416 | 1.00 | 55.19 |
| ATOM | 41 | CG | ASN | A | 146 | 23.623 | 55.017 | 28.528 | 1.00 | 78.81 |
| ATOM | 42 | OD1 | ASN | A | 146 | 24.022 | 55.424 | 29.620 | 1.00 | 75.19 |
| ATOM | 43 | ND2 | ASN | A | 146 | 23.840 | 55.679 | 27.395 | 1.00 | 69.26 |
| ATOM | 44 | N | ASP | A | 147 | 22.987 | 50.760 | 26.455 | 1.00 | 51.10 |
| ATOM | 45 | CA | ASP | A | 147 | 22.200 | 49.581 | 26.071 | 1.00 | 50.02 |
| ATOM | 46 | C | ASP | A | 147 | 22.895 | 48.264 | 26.436 | 1.00 | 51.36 |
| ATOM | 47 | O | ASP | A | 147 | 22.280 | 47.194 | 26.401 | 1.00 | 50.54 |
| ATOM | 48 | CB | ASP | A | 147 | 21.913 | 49.602 | 24.565 | 1.00 | 52.07 |

TABLE 5-continued

Structural coordinates for AKT3lkd(pT305, S472D).

| ATOM | 49 | CG | ASP | A | 147 | 20.736 | 50.492 | 24.202 | 1.00 | 62.19 |
|---|---|---|---|---|---|---|---|---|---|---|
| ATOM | 50 | OD1 | ASP | A | 147 | 19.587 | 49.996 | 24.209 | 1.00 | 62.15 |
| ATOM | 51 | OD2 | ASP | A | 147 | 20.968 | 51.677 | 23.869 | 1.00 | 68.26 |
| ATOM | 52 | N | PHE | A | 148 | 24.177 | 48.337 | 26.762 | 1.00 | 46.09 |
| ATOM | 53 | CA | PHE | A | 148 | 24.931 | 47.127 | 27.058 | 1.00 | 45.08 |
| ATOM | 54 | C | PHE | A | 148 | 25.528 | 47.059 | 28.455 | 1.00 | 47.05 |
| ATOM | 55 | O | PHE | A | 148 | 25.762 | 48.082 | 29.105 | 1.00 | 46.54 |
| ATOM | 56 | CB | PHE | A | 148 | 26.039 | 46.933 | 26.020 | 1.00 | 46.75 |
| ATOM | 57 | CG | PHE | A | 148 | 25.584 | 47.140 | 24.604 | 1.00 | 48.11 |
| ATOM | 58 | CD1 | PHE | A | 148 | 25.286 | 46.055 | 23.792 | 1.00 | 51.31 |
| ATOM | 59 | CD2 | PHE | A | 148 | 25.460 | 48.414 | 24.084 | 1.00 | 50.05 |
| ATOM | 60 | CE1 | PHE | A | 148 | 24.864 | 46.245 | 22.488 | 1.00 | 52.10 |
| ATOM | 61 | CE2 | PHE | A | 148 | 25.036 | 48.610 | 22.781 | 1.00 | 52.98 |
| ATOM | 62 | CZ | PHE | A | 148 | 24.739 | 47.526 | 21.985 | 1.00 | 51.04 |
| ATOM | 63 | N | ASP | A | 149 | 25.820 | 45.835 | 28.882 | 1.00 | 42.15 |
| ATOM | 64 | CA | ASP | A | 149 | 26.484 | 45.585 | 30.153 | 1.00 | 40.93 |
| ATOM | 65 | C | ASP | A | 149 | 27.968 | 45.437 | 29.841 | 1.00 | 42.05 |
| ATOM | 66 | O | ASP | A | 149 | 28.343 | 44.640 | 28.984 | 1.00 | 40.83 |
| ATOM | 67 | CB | ASP | A | 149 | 25.981 | 44.280 | 30.763 | 1.00 | 42.40 |
| ATOM | 68 | CG | ASP | A | 149 | 24.634 | 44.430 | 31.433 | 1.00 | 50.43 |
| ATOM | 69 | OD1 | ASP | A | 149 | 24.210 | 45.586 | 31.682 | 1.00 | 50.89 |
| ATOM | 70 | OD2 | ASP | A | 149 | 24.004 | 43.389 | 31.714 | 1.00 | 52.71 |
| ATOM | 71 | N | TYR | A | 150 | 28.798 | 46.232 | 30.500 | 1.00 | 36.96 |
| ATOM | 72 | CA | TYR | A | 150 | 30.236 | 46.174 | 30.287 | 1.00 | 36.18 |
| ATOM | 73 | C | TYR | A | 150 | 30.807 | 45.029 | 31.117 | 1.00 | 34.98 |
| ATOM | 74 | O | TYR | A | 150 | 30.824 | 45.087 | 32.355 | 1.00 | 32.84 |
| ATOM | 75 | CB | TYR | A | 150 | 30.874 | 47.503 | 30.668 | 1.00 | 38.76 |
| ATOM | 76 | CG | TYR | A | 150 | 32.380 | 47.454 | 30.832 | 1.00 | 42.09 |
| ATOM | 77 | CD1 | TYR | A | 150 | 33.177 | 46.737 | 29.949 | 1.00 | 44.27 |
| ATOM | 78 | CD2 | TYR | A | 150 | 33.002 | 48.139 | 31.861 | 1.00 | 43.25 |
| ATOM | 79 | CE1 | TYR | A | 150 | 34.551 | 46.711 | 30.094 | 1.00 | 44.93 |
| ATOM | 80 | CE2 | TYR | A | 150 | 34.374 | 48.105 | 32.015 | 1.00 | 44.00 |
| ATOM | 81 | CZ | TYR | A | 150 | 35.139 | 47.400 | 31.132 | 1.00 | 49.32 |
| ATOM | 82 | OH | TYR | A | 150 | 36.505 | 47.388 | 31.283 | 1.00 | 49.29 |
| ATOM | 83 | N | LEU | A | 151 | 31.217 | 43.957 | 30.443 | 1.00 | 28.79 |
| ATOM | 84 | CA | LEU | A | 151 | 31.687 | 42.768 | 31.143 | 1.00 | 27.37 |
| ATOM | 85 | C | LEU | A | 151 | 33.173 | 42.703 | 31.402 | 1.00 | 28.20 |
| ATOM | 86 | O | LEU | A | 151 | 33.598 | 42.325 | 32.495 | 1.00 | 26.43 |
| ATOM | 87 | CB | LEU | A | 151 | 31.217 | 41.491 | 30.441 | 1.00 | 27.49 |
| ATOM | 88 | CG | LEU | A | 151 | 29.701 | 41.345 | 30.220 | 1.00 | 32.42 |
| ATOM | 89 | CD1 | LEU | A | 151 | 29.384 | 39.960 | 29.680 | 1.00 | 32.21 |
| ATOM | 90 | CD2 | LEU | A | 151 | 28.947 | 41.601 | 31.508 | 1.00 | 36.38 |
| ATOM | 91 | N | LYS | A | 152 | 33.981 | 43.049 | 30.402 | 1.00 | 23.11 |
| ATOM | 92 | CA | LYS | A | 152 | 35.423 | 42.953 | 30.569 | 1.00 | 22.67 |
| ATOM | 93 | C | LYS | A | 152 | 36.193 | 43.675 | 29.476 | 1.00 | 27.94 |
| ATOM | 94 | O | LYS | A | 152 | 35.784 | 43.680 | 28.313 | 1.00 | 27.28 |
| ATOM | 95 | CB | LYS | A | 152 | 35.826 | 41.471 | 30.572 | 1.00 | 24.77 |
| ATOM | 96 | CG | LYS | A | 152 | 37.310 | 41.212 | 30.703 | 1.00 | 31.86 |
| ATOM | 97 | CD | LYS | A | 152 | 37.561 | 39.811 | 31.216 | 1.00 | 33.14 |
| ATOM | 98 | CE | LYS | A | 152 | 38.957 | 39.688 | 31.800 | 1.00 | 36.72 |
| ATOM | 99 | NZ | LYS | A | 152 | 39.279 | 38.278 | 32.104 | 1.00 | 39.43 |
| ATOM | 100 | N | LEU | A | 153 | 37.322 | 44.264 | 29.845 | 1.00 | 25.76 |
| ATOM | 101 | CA | LEU | A | 153 | 38.182 | 44.915 | 28.867 | 1.00 | 26.54 |
| ATOM | 102 | C | LEU | A | 153 | 38.962 | 43.808 | 28.134 | 1.00 | 31.51 |
| ATOM | 103 | O | LEU | A | 153 | 39.615 | 42.968 | 28.768 | 1.00 | 31.42 |
| ATOM | 104 | CB | LEU | A | 153 | 39.149 | 45.888 | 29.562 | 1.00 | 26.71 |
| ATOM | 105 | CG | LEU | A | 153 | 40.271 | 46.467 | 28.692 | 1.00 | 31.20 |
| ATOM | 106 | CD1 | LEU | A | 153 | 39.699 | 47.487 | 27.720 | 1.00 | 30.82 |
| ATOM | 107 | CD2 | LEU | A | 153 | 41.370 | 47.102 | 29.576 | 1.00 | 33.93 |
| ATOM | 108 | N | LEU | A | 154 | 38.836 | 43.766 | 26.809 | 1.00 | 28.49 |
| ATOM | 109 | CA | LEU | A | 154 | 39.500 | 42.737 | 26.014 | 1.00 | 28.27 |
| ATOM | 110 | C | LEU | A | 154 | 40.851 | 43.199 | 25.458 | 1.00 | 35.49 |
| ATOM | 111 | O | LEU | A | 154 | 41.688 | 42.380 | 25.098 | 1.00 | 35.47 |
| ATOM | 112 | CB | LEU | A | 154 | 38.596 | 42.279 | 24.868 | 1.00 | 27.74 |
| ATOM | 113 | CG | LEU | A | 154 | 37.301 | 41.579 | 25.292 | 1.00 | 31.07 |
| ATOM | 114 | CD1 | LEU | A | 154 | 36.494 | 41.171 | 24.076 | 1.00 | 31.01 |
| ATOM | 115 | CD2 | LEU | A | 154 | 37.586 | 40.383 | 26.187 | 1.00 | 31.74 |
| ATOM | 116 | N | GLY | A | 155 | 41.043 | 44.507 | 25.356 | 1.00 | 34.47 |
| ATOM | 117 | CA | GLY | A | 155 | 42.298 | 45.026 | 24.816 | 1.00 | 35.50 |
| ATOM | 118 | C | GLY | A | 155 | 42.265 | 46.527 | 24.644 | 1.00 | 41.53 |
| ATOM | 119 | O | GLY | A | 155 | 41.205 | 47.125 | 24.522 | 1.00 | 40.11 |
| ATOM | 120 | N | LYS | A | 156 | 43.444 | 47.132 | 24.640 | 1.00 | 42.08 |
| ATOM | 121 | CA | LYS | A | 156 | 43.556 | 48.570 | 24.505 | 1.00 | 43.67 |
| ATOM | 122 | C | LYS | A | 156 | 44.754 | 48.938 | 23.633 | 1.00 | 51.53 |
| ATOM | 123 | O | LYS | A | 156 | 45.728 | 48.185 | 23.544 | 1.00 | 51.22 |
| ATOM | 124 | CB | LYS | A | 156 | 43.684 | 49.221 | 25.888 | 1.00 | 45.92 |
| ATOM | 125 | CG | LYS | A | 156 | 43.196 | 50.662 | 25.950 | 1.00 | 61.54 |
| ATOM | 126 | CD | LYS | A | 156 | 43.696 | 51.355 | 27.207 | 1.00 | 71.99 |

TABLE 5-continued

Structural coordinates for AKT3lkd(pT305, S472D).

| ATOM | 127 | CE  | LYS | A | 156 | 42.924 | 52.635 | 27.483 | 1.00 | 81.90 |
| --- | --- | --- | --- | --- | --- | --- | --- | --- | --- | --- |
| ATOM | 128 | NZ  | LYS | A | 156 | 42.938 | 52.987 | 28.930 | 1.00 | 90.38 |
| ATOM | 129 | N   | GLY | A | 157 | 44.669 | 50.096 | 22.984 | 1.00 | 50.80 |
| ATOM | 130 | CA  | GLY | A | 157 | 45.740 | 50.568 | 22.113 | 1.00 | 51.78 |
| ATOM | 131 | C   | GLY | A | 157 | 45.602 | 52.064 | 21.841 | 1.00 | 58.15 |
| ATOM | 132 | O   | GLY | A | 157 | 44.679 | 52.713 | 22.331 | 1.00 | 57.87 |
| ATOM | 133 | N   | THR | A | 158 | 46.528 | 52.608 | 21.055 | 1.00 | 56.42 |
| ATOM | 134 | CA  | THR | A | 158 | 46.505 | 54.027 | 20.729 | 1.00 | 56.61 |
| ATOM | 135 | C   | THR | A | 158 | 45.166 | 54.422 | 20.123 | 1.00 | 60.17 |
| ATOM | 136 | O   | THR | A | 158 | 44.628 | 55.489 | 20.425 | 1.00 | 59.94 |
| ATOM | 137 | CB  | THR | A | 158 | 47.635 | 54.400 | 19.756 | 1.00 | 67.84 |
| ATOM | 138 | OG1 | THR | A | 158 | 47.589 | 53.537 | 18.611 | 1.00 | 70.34 |
| ATOM | 139 | CG2 | THR | A | 158 | 48.988 | 54.259 | 20.438 | 1.00 | 66.27 |
| ATOM | 140 | N   | PHE | A | 159 | 44.623 | 53.547 | 19.278 | 1.00 | 56.31 |
| ATOM | 141 | CA  | PHE | A | 159 | 43.348 | 53.804 | 18.619 | 1.00 | 55.57 |
| ATOM | 142 | C   | PHE | A | 159 | 42.190 | 53.726 | 19.584 | 1.00 | 56.20 |
| ATOM | 143 | O   | PHE | A | 159 | 41.121 | 54.272 | 19.326 | 1.00 | 56.15 |
| ATOM | 144 | CB  | PHE | A | 159 | 43.128 | 52.824 | 17.465 | 1.00 | 57.78 |
| ATOM | 145 | CG  | PHE | A | 159 | 43.885 | 53.176 | 16.217 | 1.00 | 59.65 |
| ATOM | 146 | CD1 | PHE | A | 159 | 44.615 | 52.212 | 15.537 | 1.00 | 62.98 |
| ATOM | 147 | CD2 | PHE | A | 159 | 43.868 | 54.472 | 15.723 | 1.00 | 61.88 |
| ATOM | 148 | CE1 | PHE | A | 159 | 45.317 | 52.536 | 14.388 | 1.00 | 63.97 |
| ATOM | 149 | CE2 | PHE | A | 159 | 44.567 | 54.799 | 14.576 | 1.00 | 64.69 |
| ATOM | 150 | CZ  | PHE | A | 159 | 45.295 | 53.831 | 13.910 | 1.00 | 62.78 |
| ATOM | 151 | N   | GLY | A | 160 | 42.393 | 53.021 | 20.689 | 1.00 | 50.48 |
| ATOM | 152 | CA  | GLY | A | 160 | 41.348 | 52.883 | 21.695 | 1.00 | 49.04 |
| ATOM | 153 | C   | GLY | A | 160 | 41.393 | 51.515 | 22.381 | 1.00 | 49.73 |
| ATOM | 154 | O   | GLY | A | 160 | 42.468 | 51.011 | 22.741 | 1.00 | 49.03 |
| ATOM | 155 | N   | LYS | A | 161 | 40.220 | 50.919 | 22.555 | 1.00 | 43.87 |
| ATOM | 156 | CA  | LYS | A | 161 | 40.113 | 49.630 | 23.223 | 1.00 | 41.76 |
| ATOM | 157 | C   | LYS | A | 161 | 38.932 | 48.813 | 22.720 | 1.00 | 41.97 |
| ATOM | 158 | O   | LYS | A | 161 | 38.078 | 49.304 | 21.972 | 1.00 | 41.45 |
| ATOM | 159 | CB  | LYS | A | 161 | 39.964 | 49.840 | 24.725 | 1.00 | 43.86 |
| ATOM | 160 | CG  | LYS | A | 161 | 38.538 | 50.153 | 25.150 | 1.00 | 52.70 |
| ATOM | 161 | CD  | LYS | A | 161 | 38.486 | 51.346 | 26.089 | 1.00 | 63.36 |
| ATOM | 162 | CE  | LYS | A | 161 | 37.051 | 51.758 | 26.381 | 1.00 | 75.01 |
| ATOM | 163 | NZ  | LYS | A | 161 | 36.078 | 51.045 | 25.504 | 1.00 | 84.77 |
| ATOM | 164 | N   | VAL | A | 162 | 38.883 | 47.561 | 23.155 | 1.00 | 35.02 |
| ATOM | 165 | CA  | VAL | A | 162 | 37.796 | 46.670 | 22.805 | 1.00 | 33.30 |
| ATOM | 166 | C   | VAL | A | 162 | 37.309 | 46.017 | 24.089 | 1.00 | 34.80 |
| ATOM | 167 | O   | VAL | A | 162 | 38.115 | 45.578 | 24.902 | 1.00 | 33.57 |
| ATOM | 168 | CB  | VAL | A | 162 | 38.266 | 45.586 | 21.819 | 1.00 | 36.84 |
| ATOM | 169 | CG1 | VAL | A | 162 | 37.146 | 44.589 | 21.560 | 1.00 | 36.43 |
| ATOM | 170 | CG2 | VAL | A | 162 | 38.724 | 46.232 | 20.512 | 1.00 | 36.97 |
| ATOM | 171 | N   | ILE | A | 163 | 35.995 | 46.002 | 24.286 | 1.00 | 30.82 |
| ATOM | 172 | CA  | ILE | A | 163 | 35.417 | 45.438 | 25.487 | 1.00 | 30.42 |
| ATOM | 173 | C   | ILE | A | 163 | 34.320 | 44.428 | 25.205 | 1.00 | 31.43 |
| ATOM | 174 | O   | ILE | A | 163 | 33.570 | 44.548 | 24.232 | 1.00 | 31.48 |
| ATOM | 175 | CB  | ILE | A | 163 | 34.872 | 46.544 | 26.418 | 1.00 | 34.07 |
| ATOM | 176 | CG1 | ILE | A | 163 | 33.691 | 47.250 | 25.761 | 1.00 | 35.11 |
| ATOM | 177 | CG2 | ILE | A | 163 | 35.959 | 47.545 | 26.737 | 1.00 | 35.33 |
| ATOM | 178 | CD1 | ILE | A | 163 | 33.489 | 48.661 | 26.244 | 1.00 | 44.52 |
| ATOM | 179 | N   | LEU | A | 164 | 34.225 | 43.429 | 26.067 | 1.00 | 25.64 |
| ATOM | 180 | CA  | LEU | A | 164 | 33.207 | 42.410 | 25.952 | 1.00 | 24.93 |
| ATOM | 181 | C   | LEU | A | 164 | 31.956 | 42.955 | 26.608 | 1.00 | 30.69 |
| ATOM | 182 | O   | LEU | A | 164 | 32.006 | 43.437 | 27.742 | 1.00 | 30.39 |
| ATOM | 183 | CB  | LEU | A | 164 | 33.657 | 41.121 | 26.675 | 1.00 | 24.94 |
| ATOM | 184 | CG  | LEU | A | 164 | 32.613 | 40.022 | 26.881 | 1.00 | 29.43 |
| ATOM | 185 | CD1 | LEU | A | 164 | 32.148 | 39.403 | 25.555 | 1.00 | 30.19 |
| ATOM | 186 | CD2 | LEU | A | 164 | 33.131 | 38.955 | 27.823 | 1.00 | 31.63 |
| ATOM | 187 | N   | VAL | A | 165 | 30.838 | 42.910 | 25.888 | 1.00 | 28.34 |
| ATOM | 188 | CA  | VAL | A | 165 | 29.571 | 43.408 | 26.418 | 1.00 | 28.77 |
| ATOM | 189 | C   | VAL | A | 165 | 28.463 | 42.379 | 26.249 | 1.00 | 36.00 |
| ATOM | 190 | O   | VAL | A | 165 | 28.582 | 41.426 | 25.470 | 1.00 | 34.41 |
| ATOM | 191 | CB  | VAL | A | 165 | 29.128 | 44.731 | 25.723 | 1.00 | 32.00 |
| ATOM | 192 | CG1 | VAL | A | 165 | 30.147 | 45.844 | 25.938 | 1.00 | 31.17 |
| ATOM | 193 | CG2 | VAL | A | 165 | 28.879 | 44.507 | 24.229 | 1.00 | 32.13 |
| ATOM | 194 | N   | ARG | A | 166 | 27.382 | 42.573 | 26.986 | 1.00 | 36.03 |
| ATOM | 195 | CA  | ARG | A | 166 | 26.211 | 41.732 | 26.849 | 1.00 | 37.06 |
| ATOM | 196 | C   | ARG | A | 166 | 25.065 | 42.663 | 26.513 | 1.00 | 44.19 |
| ATOM | 197 | O   | ARG | A | 166 | 24.934 | 43.738 | 27.110 | 1.00 | 43.48 |
| ATOM | 198 | CB  | ARG | A | 166 | 25.915 | 40.969 | 28.142 | 1.00 | 37.83 |
| ATOM | 199 | CG  | ARG | A | 166 | 24.581 | 40.231 | 28.124 | 1.00 | 43.05 |
| ATOM | 200 | CD  | ARG | A | 166 | 24.100 | 39.917 | 29.523 | 1.00 | 48.31 |
| ATOM | 201 | NE  | ARG | A | 166 | 24.890 | 38.853 | 30.137 | 1.00 | 47.29 |
| ATOM | 202 | CZ  | ARG | A | 166 | 25.537 | 38.978 | 31.287 | 1.00 | 50.96 |
| ATOM | 203 | NH1 | ARG | A | 166 | 25.474 | 40.118 | 31.962 | 1.00 | 33.38 |
| ATOM | 204 | NH2 | ARG | A | 166 | 26.239 | 37.965 | 31.764 | 1.00 | 32.07 |

TABLE 5-continued

Structural coordinates for AKT3lkd(pT305, S472D).

| ATOM | 205 | N   | GLU | A | 167 | 24.286 | 42.302 | 25.499 | 1.00 | 43.14 |
|------|-----|-----|-----|---|-----|--------|--------|--------|------|-------|
| ATOM | 206 | CA  | GLU | A | 167 | 23.150 | 43.114 | 25.104 | 1.00 | 43.82 |
| ATOM | 207 | C   | GLU | A | 167 | 22.050 | 42.906 | 26.134 | 1.00 | 49.03 |
| ATOM | 208 | O   | GLU | A | 167 | 21.550 | 41.788 | 26.305 | 1.00 | 48.91 |
| ATOM | 209 | CB  | GLU | A | 167 | 22.649 | 42.726 | 23.710 | 1.00 | 45.23 |
| ATOM | 210 | CG  | GLU | A | 167 | 21.462 | 43.567 | 23.227 | 1.00 | 56.98 |
| ATOM | 211 | CD  | GLU | A | 167 | 21.263 | 43.499 | 21.720 | 1.00 | 74.13 |
| ATOM | 212 | OE1 | GLU | A | 167 | 21.261 | 44.563 | 21.067 | 1.00 | 58.80 |
| ATOM | 213 | OE2 | GLU | A | 167 | 21.101 | 42.380 | 21.191 | 1.00 | 69.93 |
| ATOM | 214 | N   | LYS | A | 168 | 21.716 | 43.975 | 26.849 | 1.00 | 46.61 |
| ATOM | 215 | CA  | LYS | A | 168 | 20.693 | 43.934 | 27.899 | 1.00 | 47.14 |
| ATOM | 216 | C   | LYS | A | 168 | 19.437 | 43.205 | 27.444 | 1.00 | 52.71 |
| ATOM | 217 | O   | LYS | A | 168 | 19.098 | 42.137 | 27.968 | 1.00 | 52.51 |
| ATOM | 218 | CB  | LYS | A | 168 | 20.328 | 45.361 | 28.340 | 1.00 | 49.47 |
| ATOM | 219 | CG  | LYS | A | 168 | 21.231 | 45.936 | 29.421 | 1.00 | 60.30 |
| ATOM | 220 | CD  | LYS | A | 168 | 21.453 | 47.429 | 29.220 | 1.00 | 67.19 |
| ATOM | 221 | CE  | LYS | A | 168 | 21.518 | 48.161 | 30.545 | 1.00 | 75.04 |
| ATOM | 222 | NZ  | LYS | A | 168 | 21.956 | 47.264 | 31.644 | 1.00 | 84.39 |
| ATOM | 223 | N   | ALA | A | 169 | 18.755 | 43.784 | 26.461 | 1.00 | 50.17 |
| ATOM | 224 | CA  | ALA | A | 169 | 17.513 | 43.215 | 25.938 | 1.00 | 50.20 |
| ATOM | 225 | C   | ALA | A | 169 | 17.641 | 41.770 | 25.463 | 1.00 | 53.52 |
| ATOM | 226 | O   | ALA | A | 169 | 16.827 | 40.918 | 25.820 | 1.00 | 53.84 |
| ATOM | 227 | CB  | ALA | A | 169 | 16.954 | 44.099 | 24.819 | 1.00 | 50.94 |
| ATOM | 228 | N   | SER | A | 170 | 18.659 | 41.500 | 24.652 | 1.00 | 48.94 |
| ATOM | 229 | CA  | SER | A | 170 | 18.850 | 40.175 | 24.070 | 1.00 | 48.06 |
| ATOM | 230 | C   | SER | A | 170 | 19.548 | 39.142 | 24.958 | 1.00 | 49.60 |
| ATOM | 231 | O   | SER | A | 170 | 19.216 | 37.957 | 24.915 | 1.00 | 48.78 |
| ATOM | 232 | CB  | SER | A | 170 | 19.596 | 40.290 | 22.739 | 1.00 | 52.01 |
| ATOM | 233 | OG  | SER | A | 170 | 20.986 | 40.476 | 22.950 | 1.00 | 59.64 |
| ATOM | 234 | N   | GLY | A | 171 | 20.558 | 39.578 | 25.704 | 1.00 | 44.76 |
| ATOM | 235 | CA  | GLY | A | 171 | 21.340 | 38.664 | 26.537 | 1.00 | 43.71 |
| ATOM | 236 | C   | GLY | A | 171 | 22.517 | 38.090 | 25.732 | 1.00 | 45.61 |
| ATOM | 237 | O   | GLY | A | 171 | 23.273 | 37.241 | 26.222 | 1.00 | 44.86 |
| ATOM | 238 | N   | LYS | A | 172 | 22.661 | 38.559 | 24.494 | 1.00 | 40.76 |
| ATOM | 239 | CA  | LYS | A | 172 | 23.727 | 38.103 | 23.610 | 1.00 | 39.67 |
| ATOM | 240 | C   | LYS | A | 172 | 25.027 | 38.874 | 23.819 | 1.00 | 40.63 |
| ATOM | 241 | O   | LYS | A | 172 | 25.018 | 40.081 | 24.080 | 1.00 | 39.65 |
| ATOM | 242 | CB  | LYS | A | 172 | 23.285 | 38.189 | 22.140 | 1.00 | 42.22 |
| ATOM | 243 | CG  | LYS | A | 172 | 22.135 | 37.254 | 21.788 | 1.00 | 55.98 |
| ATOM | 244 | CD  | LYS | A | 172 | 21.515 | 37.608 | 20.442 | 1.00 | 67.09 |
| ATOM | 245 | CE  | LYS | A | 172 | 20.613 | 36.487 | 19.940 | 1.00 | 77.01 |
| ATOM | 246 | NZ  | LYS | A | 172 | 19.508 | 37.006 | 19.084 | 1.00 | 86.91 |
| ATOM | 247 | N   | TYR | A | 173 | 26.143 | 38.166 | 23.679 | 1.00 | 35.58 |
| ATOM | 248 | CA  | TYR | A | 173 | 27.459 | 38.745 | 23.868 | 1.00 | 34.31 |
| ATOM | 249 | C   | TYR | A | 173 | 28.038 | 39.278 | 22.573 | 1.00 | 36.31 |
| ATOM | 250 | O   | TYR | A | 173 | 27.919 | 38.653 | 21.521 | 1.00 | 35.10 |
| ATOM | 251 | CB  | TYR | A | 173 | 28.405 | 37.711 | 24.487 | 1.00 | 34.94 |
| ATOM | 252 | CG  | TYR | A | 173 | 27.875 | 37.128 | 25.779 | 1.00 | 35.98 |
| ATOM | 253 | CD1 | TYR | A | 173 | 28.071 | 37.786 | 26.993 | 1.00 | 37.67 |
| ATOM | 254 | CD2 | TYR | A | 173 | 27.099 | 35.976 | 25.776 | 1.00 | 36.46 |
| ATOM | 255 | CE1 | TYR | A | 173 | 27.546 | 37.281 | 28.179 | 1.00 | 37.81 |
| ATOM | 256 | CE2 | TYR | A | 173 | 26.574 | 35.460 | 26.953 | 1.00 | 37.62 |
| ATOM | 257 | CZ  | TYR | A | 173 | 26.801 | 36.116 | 28.153 | 1.00 | 44.88 |
| ATOM | 258 | OH  | TYR | A | 173 | 26.286 | 35.601 | 29.323 | 1.00 | 44.40 |
| ATOM | 259 | N   | TYR | A | 174 | 28.685 | 40.430 | 22.665 | 1.00 | 31.75 |
| ATOM | 260 | CA  | TYR | A | 174 | 29.331 | 41.048 | 21.523 | 1.00 | 31.27 |
| ATOM | 261 | C   | TYR | A | 174 | 30.641 | 41.644 | 21.959 | 1.00 | 32.46 |
| ATOM | 262 | O   | TYR | A | 174 | 30.921 | 41.755 | 23.154 | 1.00 | 29.88 |
| ATOM | 263 | CB  | TYR | A | 174 | 28.452 | 42.161 | 20.951 | 1.00 | 32.97 |
| ATOM | 264 | CG  | TYR | A | 174 | 27.125 | 41.672 | 20.427 | 1.00 | 35.94 |
| ATOM | 265 | CD1 | TYR | A | 174 | 27.039 | 41.004 | 19.211 | 1.00 | 37.79 |
| ATOM | 266 | CD2 | TYR | A | 174 | 25.956 | 41.867 | 21.156 | 1.00 | 36.84 |
| ATOM | 267 | CE1 | TYR | A | 174 | 25.824 | 40.550 | 18.730 | 1.00 | 38.78 |
| ATOM | 268 | CE2 | TYR | A | 174 | 24.740 | 41.417 | 20.687 | 1.00 | 37.89 |
| ATOM | 269 | CZ  | TYR | A | 174 | 24.673 | 40.769 | 19.473 | 1.00 | 45.18 |
| ATOM | 270 | OH  | TYR | A | 174 | 23.456 | 40.325 | 19.009 | 1.00 | 45.57 |
| ATOM | 271 | N   | ALA | A | 175 | 31.442 | 42.042 | 20.986 | 1.00 | 29.14 |
| ATOM | 272 | CA  | ALA | A | 175 | 32.685 | 42.721 | 21.261 | 1.00 | 29.11 |
| ATOM | 273 | C   | ALA | A | 175 | 32.490 | 44.152 | 20.785 | 1.00 | 33.57 |
| ATOM | 274 | O   | ALA | A | 175 | 32.115 | 44.379 | 19.635 | 1.00 | 32.50 |
| ATOM | 275 | CB  | ALA | A | 175 | 33.827 | 42.064 | 20.513 | 1.00 | 30.10 |
| ATOM | 276 | N   | MET | A | 176 | 32.656 | 45.116 | 21.684 | 1.00 | 30.63 |
| ATOM | 277 | CA  | MET | A | 176 | 32.495 | 46.512 | 21.303 | 1.00 | 30.35 |
| ATOM | 278 | C   | MET | A | 176 | 33.814 | 47.232 | 21.146 | 1.00 | 35.54 |
| ATOM | 279 | O   | MET | A | 176 | 34.593 | 47.346 | 22.091 | 1.00 | 35.73 |
| ATOM | 280 | CB  | MET | A | 176 | 31.563 | 47.274 | 22.250 | 1.00 | 32.39 |
| ATOM | 281 | CG  | MET | A | 176 | 31.414 | 48.745 | 21.853 | 1.00 | 35.59 |
| ATOM | 282 | SD  | MET | A | 176 | 30.505 | 49.769 | 23.045 | 1.00 | 39.70 |

TABLE 5-continued

Structural coordinates for AKT3lkd(pT305, S472D).

| ATOM | 283 | CE | MET | A | 176 | 28.941 | 48.971 | 23.115 | 1.00 | 35.76 |
|---|---|---|---|---|---|---|---|---|---|---|
| ATOM | 284 | N | LYS | A | 177 | 34.080 | 47.692 | 19.931 | 1.00 | 33.27 |
| ATOM | 285 | CA | LYS | A | 177 | 35.301 | 48.406 | 19.639 | 1.00 | 34.58 |
| ATOM | 286 | C | LYS | A | 177 | 35.048 | 49.887 | 19.820 | 1.00 | 44.50 |
| ATOM | 287 | O | LYS | A | 177 | 34.107 | 50.434 | 19.247 | 1.00 | 44.39 |
| ATOM | 288 | CB | LYS | A | 177 | 35.752 | 48.130 | 18.200 | 1.00 | 36.54 |
| ATOM | 289 | CG | LYS | A | 177 | 37.164 | 48.614 | 17.886 | 1.00 | 46.90 |
| ATOM | 290 | CD | LYS | A | 177 | 37.669 | 48.058 | 16.544 | 1.00 | 52.56 |
| ATOM | 291 | CE | LYS | A | 177 | 36.888 | 48.633 | 15.363 | 1.00 | 52.83 |
| ATOM | 292 | NZ | LYS | A | 177 | 37.673 | 48.590 | 14.087 | 1.00 | 56.74 |
| ATOM | 293 | N | ILE | A | 178 | 35.876 | 50.530 | 20.640 | 1.00 | 45.03 |
| ATOM | 294 | CA | ILE | A | 178 | 35.746 | 51.960 | 20.894 | 1.00 | 46.32 |
| ATOM | 295 | C | ILE | A | 178 | 37.008 | 52.680 | 20.448 | 1.00 | 52.58 |
| ATOM | 296 | O | ILE | A | 178 | 38.071 | 52.515 | 21.045 | 1.00 | 51.94 |
| ATOM | 297 | CB | ILE | A | 178 | 35.487 | 52.257 | 22.381 | 1.00 | 49.85 |
| ATOM | 298 | CG1 | ILE | A | 178 | 34.021 | 51.984 | 22.730 | 1.00 | 50.13 |
| ATOM | 299 | CG2 | ILE | A | 178 | 35.853 | 53.708 | 22.703 | 1.00 | 51.07 |
| ATOM | 300 | CD1 | ILE | A | 178 | 33.833 | 50.969 | 23.832 | 1.00 | 57.92 |
| ATOM | 301 | N | LEU | A | 179 | 36.892 | 53.457 | 19.374 | 1.00 | 51.52 |
| ATOM | 302 | CA | LEU | A | 179 | 38.033 | 54.185 | 18.833 | 1.00 | 52.12 |
| ATOM | 303 | C | LEU | A | 179 | 37.940 | 55.686 | 19.098 | 1.00 | 57.50 |
| ATOM | 304 | O | LEU | A | 179 | 36.887 | 56.304 | 18.907 | 1.00 | 56.84 |
| ATOM | 305 | CB | LEU | A | 179 | 38.178 | 53.922 | 17.330 | 1.00 | 52.23 |
| ATOM | 306 | CG | LEU | A | 179 | 37.652 | 52.582 | 16.810 | 1.00 | 56.96 |
| ATOM | 307 | CD1 | LEU | A | 179 | 37.403 | 52.661 | 15.316 | 1.00 | 57.02 |
| ATOM | 308 | CD2 | LEU | A | 179 | 38.629 | 51.456 | 17.136 | 1.00 | 59.88 |
| ATOM | 309 | N | LYS | A | 180 | 39.046 | 56.265 | 19.554 | 1.00 | 55.51 |
| ATOM | 310 | CA | LYS | A | 180 | 39.097 | 57.691 | 19.827 | 1.00 | 55.80 |
| ATOM | 311 | C | LYS | A | 180 | 39.191 | 58.447 | 18.505 | 1.00 | 59.98 |
| ATOM | 312 | O | LYS | A | 180 | 40.176 | 58.321 | 17.784 | 1.00 | 59.20 |
| ATOM | 313 | CB | LYS | A | 180 | 40.294 | 58.020 | 20.716 | 1.00 | 58.85 |
| ATOM | 314 | CG | LYS | A | 180 | 40.172 | 57.483 | 22.141 | 1.00 | 77.23 |
| ATOM | 315 | CD | LYS | A | 180 | 40.052 | 55.962 | 22.150 | 1.00 | 88.67 |
| ATOM | 316 | CE | LYS | A | 180 | 38.977 | 55.492 | 23.122 | 1.00 | 99.33 |
| ATOM | 317 | NZ | LYS | A | 180 | 38.903 | 54.003 | 23.203 | 1.00 | 106.95 |
| ATOM | 318 | N | LYS | A | 181 | 38.140 | 59.190 | 18.173 | 1.00 | 57.61 |
| ATOM | 319 | CA | LYS | A | 181 | 38.095 | 59.945 | 16.920 | 1.00 | 58.28 |
| ATOM | 320 | C | LYS | A | 181 | 39.364 | 60.771 | 16.696 | 1.00 | 64.60 |
| ATOM | 321 | O | LYS | A | 181 | 40.027 | 60.643 | 15.663 | 1.00 | 64.38 |
| ATOM | 322 | CB | LYS | A | 181 | 36.866 | 60.859 | 16.886 | 1.00 | 60.34 |
| ATOM | 323 | CG | LYS | A | 181 | 35.615 | 60.244 | 17.493 | 1.00 | 68.69 |
| ATOM | 324 | CD | LYS | A | 181 | 34.376 | 61.046 | 17.137 | 1.00 | 75.36 |
| ATOM | 325 | CE | LYS | A | 181 | 33.122 | 60.399 | 17.689 | 1.00 | 84.46 |
| ATOM | 326 | NZ | LYS | A | 181 | 31.894 | 61.157 | 17.314 | 1.00 | 92.28 |
| ATOM | 327 | N | GLU | A | 182 | 39.689 | 61.619 | 17.671 | 1.00 | 62.63 |
| ATOM | 328 | CA | GLU | A | 182 | 40.859 | 62.486 | 17.584 | 1.00 | 63.07 |
| ATOM | 329 | C | GLU | A | 182 | 42.113 | 61.732 | 17.164 | 1.00 | 68.01 |
| ATOM | 330 | O | GLU | A | 182 | 43.030 | 62.315 | 16.583 | 1.00 | 67.80 |
| ATOM | 331 | CB | GLU | A | 182 | 41.092 | 63.222 | 18.907 | 1.00 | 64.55 |
| ATOM | 332 | CG | GLU | A | 182 | 39.828 | 63.459 | 19.718 | 1.00 | 75.01 |
| ATOM | 333 | CD | GLU | A | 182 | 39.659 | 62.449 | 20.840 | 1.00 | 97.31 |
| ATOM | 334 | OE1 | GLU | A | 182 | 40.658 | 61.795 | 21.212 | 1.00 | 93.56 |
| ATOM | 335 | OE2 | GLU | A | 182 | 38.524 | 62.301 | 21.341 | 1.00 | 90.25 |
| ATOM | 336 | N | VAL | A | 183 | 42.151 | 60.435 | 17.447 | 1.00 | 64.94 |
| ATOM | 337 | CA | VAL | A | 183 | 43.296 | 59.615 | 17.064 | 1.00 | 65.11 |
| ATOM | 338 | C | VAL | A | 183 | 43.190 | 59.202 | 15.597 | 1.00 | 69.24 |
| ATOM | 339 | O | VAL | A | 183 | 44.166 | 59.274 | 14.850 | 1.00 | 68.68 |
| ATOM | 340 | CB | VAL | A | 183 | 43.441 | 58.353 | 17.956 | 1.00 | 69.08 |
| ATOM | 341 | CG1 | VAL | A | 183 | 42.688 | 57.178 | 17.354 | 1.00 | 68.97 |
| ATOM | 342 | CG2 | VAL | A | 183 | 44.909 | 58.001 | 18.146 | 1.00 | 68.83 |
| ATOM | 343 | N | ILE | A | 184 | 41.991 | 58.796 | 15.186 | 1.00 | 66.16 |
| ATOM | 344 | CA | ILE | A | 184 | 41.756 | 58.378 | 13.807 | 1.00 | 66.11 |
| ATOM | 345 | C | ILE | A | 184 | 42.110 | 59.503 | 12.832 | 1.00 | 70.50 |
| ATOM | 346 | O | ILE | A | 184 | 42.849 | 59.293 | 11.869 | 1.00 | 70.18 |
| ATOM | 347 | CB | ILE | A | 184 | 40.289 | 57.939 | 13.586 | 1.00 | 69.06 |
| ATOM | 348 | CG1 | ILE | A | 184 | 40.023 | 56.605 | 14.285 | 1.00 | 69.13 |
| ATOM | 349 | CG2 | ILE | A | 184 | 39.985 | 57.820 | 12.097 | 1.00 | 70.02 |
| ATOM | 350 | CD1 | ILE | A | 184 | 40.675 | 55.429 | 13.607 | 1.00 | 73.88 |
| ATOM | 351 | N | ILE | A | 185 | 41.595 | 60.701 | 13.102 | 1.00 | 67.23 |
| ATOM | 352 | CA | ILE | A | 185 | 41.880 | 61.859 | 12.260 | 1.00 | 66.95 |
| ATOM | 353 | C | ILE | A | 185 | 43.386 | 62.027 | 12.096 | 1.00 | 71.31 |
| ATOM | 354 | O | ILE | A | 185 | 43.932 | 61.809 | 11.014 | 1.00 | 70.81 |
| ATOM | 355 | CB | ILE | A | 185 | 41.293 | 63.155 | 12.861 | 1.00 | 69.87 |
| ATOM | 356 | CG1 | ILE | A | 185 | 41.673 | 63.282 | 14.337 | 1.00 | 70.41 |
| ATOM | 357 | CG2 | ILE | A | 185 | 39.783 | 63.181 | 12.704 | 1.00 | 70.37 |
| ATOM | 358 | CD1 | ILE | A | 185 | 42.694 | 64.366 | 14.620 | 1.00 | 78.11 |
| ATOM | 359 | N | ALA | A | 186 | 44.056 | 62.392 | 13.187 | 1.00 | 68.38 |
| ATOM | 360 | CA | ALA | A | 186 | 45.497 | 62.600 | 13.174 | 1.00 | 68.20 |

TABLE 5-continued

Structural coordinates for AKT3lkd(pT305, S472D).

| ATOM | 361 | C | ALA | A | 186 | 46.250 | 61.371 | 12.670 | 1.00 | 72.09 |
|---|---|---|---|---|---|---|---|---|---|---|
| ATOM | 362 | O | ALA | A | 186 | 47.405 | 61.467 | 12.248 | 1.00 | 72.04 |
| ATOM | 363 | CB | ALA | A | 186 | 45.986 | 63.000 | 14.554 | 1.00 | 68.94 |
| ATOM | 364 | N | LYS | A | 187 | 45.595 | 60.216 | 12.710 | 1.00 | 68.20 |
| ATOM | 365 | CA | LYS | A | 187 | 46.215 | 58.983 | 12.235 | 1.00 | 67.71 |
| ATOM | 366 | C | LYS | A | 187 | 45.963 | 58.808 | 10.738 | 1.00 | 70.60 |
| ATOM | 367 | O | LYS | A | 187 | 46.590 | 57.972 | 10.083 | 1.00 | 70.19 |
| ATOM | 368 | CB | LYS | A | 187 | 45.681 | 57.773 | 13.011 | 1.00 | 70.29 |
| ATOM | 369 | CG | LYS | A | 187 | 46.324 | 57.568 | 14.388 | 1.00 | 84.22 |
| ATOM | 370 | CD | LYS | A | 187 | 47.832 | 57.774 | 14.344 | 1.00 | 93.14 |
| ATOM | 371 | CE | LYS | A | 187 | 48.487 | 57.296 | 15.630 | 1.00 | 102.61 |
| ATOM | 372 | NZ | LYS | A | 187 | 49.499 | 58.266 | 16.131 | 1.00 | 111.11 |
| ATOM | 373 | N | ASP | A | 188 | 45.047 | 59.615 | 10.205 | 1.00 | 66.63 |
| ATOM | 374 | CA | ASP | A | 188 | 44.691 | 59.560 | 8.788 | 1.00 | 66.19 |
| ATOM | 375 | C | ASP | A | 188 | 43.951 | 58.263 | 8.467 | 1.00 | 68.40 |
| ATOM | 376 | O | ASP | A | 188 | 44.174 | 57.654 | 7.422 | 1.00 | 67.96 |
| ATOM | 377 | CB | ASP | A | 188 | 45.944 | 59.687 | 7.913 | 1.00 | 68.25 |
| ATOM | 378 | CG | ASP | A | 188 | 46.499 | 61.105 | 7.882 | 1.00 | 80.64 |
| ATOM | 379 | OD1 | ASP | A | 188 | 45.712 | 62.058 | 8.090 | 1.00 | 81.91 |
| ATOM | 380 | OD2 | ASP | A | 188 | 47.717 | 61.268 | 7.649 | 1.00 | 85.97 |
| ATOM | 381 | N | GLU | A | 189 | 43.075 | 57.842 | 9.377 | 1.00 | 63.75 |
| ATOM | 382 | CA | GLU | A | 189 | 42.315 | 56.602 | 9.203 | 1.00 | 62.68 |
| ATOM | 383 | C | GLU | A | 189 | 40.808 | 56.849 | 9.200 | 1.00 | 64.15 |
| ATOM | 384 | O | GLU | A | 189 | 40.025 | 55.970 | 9.561 | 1.00 | 63.55 |
| ATOM | 385 | CB | GLU | A | 189 | 42.675 | 55.599 | 10.304 | 1.00 | 64.00 |
| ATOM | 386 | CG | GLU | A | 189 | 44.154 | 55.571 | 10.660 | 1.00 | 73.98 |
| ATOM | 387 | CD | GLU | A | 189 | 44.821 | 54.269 | 10.271 | 1.00 | 91.66 |
| ATOM | 388 | OE1 | GLU | A | 189 | 45.515 | 53.676 | 11.123 | 1.00 | 80.34 |
| ATOM | 389 | OE2 | GLU | A | 189 | 44.654 | 53.837 | 9.111 | 1.00 | 87.79 |
| ATOM | 390 | N | VAL | A | 190 | 40.409 | 58.045 | 8.781 | 1.00 | 58.93 |
| ATOM | 391 | CA | VAL | A | 190 | 38.999 | 58.417 | 8.740 | 1.00 | 57.60 |
| ATOM | 392 | C | VAL | A | 190 | 38.206 | 57.650 | 7.678 | 1.00 | 58.46 |
| ATOM | 393 | O | VAL | A | 190 | 37.246 | 56.946 | 7.993 | 1.00 | 57.27 |
| ATOM | 394 | CB | VAL | A | 190 | 38.825 | 59.930 | 8.508 | 1.00 | 61.47 |
| ATOM | 395 | CG1 | VAL | A | 190 | 37.359 | 60.311 | 8.591 | 1.00 | 61.22 |
| ATOM | 396 | CG2 | VAL | A | 190 | 39.649 | 60.720 | 9.523 | 1.00 | 61.33 |
| ATOM | 397 | N | ALA | A | 191 | 38.588 | 57.820 | 6.420 | 1.00 | 54.10 |
| ATOM | 398 | CA | ALA | A | 191 | 37.900 | 57.144 | 5.327 | 1.00 | 53.52 |
| ATOM | 399 | C | ALA | A | 191 | 38.021 | 55.635 | 5.500 | 1.00 | 56.88 |
| ATOM | 400 | O | ALA | A | 191 | 37.063 | 54.892 | 5.272 | 1.00 | 56.17 |
| ATOM | 401 | CB | ALA | A | 191 | 38.476 | 57.576 | 3.990 | 1.00 | 54.20 |
| ATOM | 402 | N | HIS | A | 192 | 39.195 | 55.194 | 5.941 | 1.00 | 52.97 |
| ATOM | 403 | CA | HIS | A | 192 | 39.441 | 53.778 | 6.159 | 1.00 | 52.38 |
| ATOM | 404 | C | HIS | A | 192 | 38.417 | 53.184 | 7.109 | 1.00 | 53.22 |
| ATOM | 405 | O | HIS | A | 192 | 37.806 | 52.157 | 6.817 | 1.00 | 53.71 |
| ATOM | 406 | CB | HIS | A | 192 | 40.858 | 53.553 | 6.710 | 1.00 | 53.70 |
| ATOM | 407 | CG | HIS | A | 192 | 41.044 | 52.219 | 7.366 | 1.00 | 57.42 |
| ATOM | 408 | ND1 | HIS | A | 192 | 41.838 | 52.040 | 8.479 | 1.00 | 59.29 |
| ATOM | 409 | CD2 | HIS | A | 192 | 40.527 | 51.001 | 7.074 | 1.00 | 59.20 |
| ATOM | 410 | CE1 | HIS | A | 192 | 41.802 | 50.770 | 8.845 | 1.00 | 58.68 |
| ATOM | 411 | NE2 | HIS | A | 192 | 41.013 | 50.118 | 8.008 | 1.00 | 58.97 |
| ATOM | 412 | N | THR | A | 193 | 38.233 | 53.828 | 8.254 | 1.00 | 46.92 |
| ATOM | 413 | CA | THR | A | 193 | 37.289 | 53.341 | 9.242 | 1.00 | 45.74 |
| ATOM | 414 | C | THR | A | 193 | 35.858 | 53.223 | 8.713 | 1.00 | 47.90 |
| ATOM | 415 | O | THR | A | 193 | 35.200 | 52.208 | 8.914 | 1.00 | 47.11 |
| ATOM | 416 | CB | THR | A | 193 | 37.303 | 54.197 | 10.522 | 1.00 | 53.73 |
| ATOM | 417 | OG1 | THR | A | 193 | 38.632 | 54.236 | 11.061 | 1.00 | 51.28 |
| ATOM | 418 | CG2 | THR | A | 193 | 36.366 | 53.609 | 11.553 | 1.00 | 52.57 |
| ATOM | 419 | N | LEU | A | 194 | 35.374 | 54.268 | 8.050 | 1.00 | 43.66 |
| ATOM | 420 | CA | LEU | A | 194 | 34.007 | 54.264 | 7.525 | 1.00 | 43.08 |
| ATOM | 421 | C | LEU | A | 194 | 33.780 | 53.182 | 6.470 | 1.00 | 45.53 |
| ATOM | 422 | O | LEU | A | 194 | 32.734 | 52.531 | 6.450 | 1.00 | 44.56 |
| ATOM | 423 | CB | LEU | A | 194 | 33.638 | 55.637 | 6.967 | 1.00 | 43.23 |
| ATOM | 424 | CG | LEU | A | 194 | 32.787 | 56.496 | 7.905 | 1.00 | 47.98 |
| ATOM | 425 | CD1 | LEU | A | 194 | 33.285 | 56.385 | 9.343 | 1.00 | 48.08 |
| ATOM | 426 | CD2 | LEU | A | 194 | 32.755 | 57.949 | 7.447 | 1.00 | 50.49 |
| ATOM | 427 | N | THR | A | 195 | 34.764 | 53.009 | 5.596 | 1.00 | 41.71 |
| ATOM | 428 | CA | THR | A | 195 | 34.702 | 52.012 | 4.532 | 1.00 | 42.03 |
| ATOM | 429 | C | THR | A | 195 | 34.639 | 50.607 | 5.118 | 1.00 | 45.83 |
| ATOM | 430 | O | THR | A | 195 | 33.780 | 49.807 | 4.747 | 1.00 | 45.26 |
| ATOM | 431 | CB | THR | A | 195 | 35.930 | 52.117 | 3.610 | 1.00 | 51.71 |
| ATOM | 432 | OG1 | THR | A | 195 | 35.915 | 53.381 | 2.936 | 1.00 | 52.12 |
| ATOM | 433 | CG2 | THR | A | 195 | 35.926 | 50.992 | 2.578 | 1.00 | 51.85 |
| ATOM | 434 | N | GLU | A | 196 | 35.543 | 50.322 | 6.053 | 1.00 | 42.97 |
| ATOM | 435 | CA | GLU | A | 196 | 35.579 | 49.025 | 6.722 | 1.00 | 42.95 |
| ATOM | 436 | C | GLU | A | 196 | 34.246 | 48.737 | 7.408 | 1.00 | 46.67 |
| ATOM | 437 | O | GLU | A | 196 | 33.725 | 47.622 | 7.344 | 1.00 | 45.95 |
| ATOM | 438 | CB | GLU | A | 196 | 36.697 | 49.006 | 7.765 | 1.00 | 44.51 |

TABLE 5-continued

Structural coordinates for AKT3lkd(pT305, S472D).

| ATOM | 439 | CG | GLU | A | 196 | 36.188 | 48.912 | 9.207 | 1.00 | 58.01 |
|---|---|---|---|---|---|---|---|---|---|---|
| ATOM | 440 | CD | GLU | A | 196 | 37.023 | 49.725 | 10.184 | 1.00 | 81.05 |
| ATOM | 441 | OE1 | GLU | A | 196 | 36.645 | 49.790 | 11.377 | 1.00 | 76.55 |
| ATOM | 442 | OE2 | GLU | A | 196 | 38.059 | 50.289 | 9.761 | 1.00 | 74.31 |
| ATOM | 443 | N | SER | A | 197 | 33.708 | 49.743 | 8.084 | 1.00 | 42.81 |
| ATOM | 444 | CA | SER | A | 197 | 32.449 | 49.589 | 8.800 | 1.00 | 42.35 |
| ATOM | 445 | C | SER | A | 197 | 31.351 | 49.150 | 7.844 | 1.00 | 45.10 |
| ATOM | 446 | O | SER | A | 197 | 30.640 | 48.165 | 8.094 | 1.00 | 44.48 |
| ATOM | 447 | CB | SER | A | 197 | 32.055 | 50.911 | 9.467 | 1.00 | 46.15 |
| ATOM | 448 | OG | SER | A | 197 | 30.814 | 50.791 | 10.144 | 1.00 | 54.00 |
| ATOM | 449 | N | ARG | A | 198 | 31.216 | 49.886 | 6.749 | 1.00 | 40.56 |
| ATOM | 450 | CA | ARG | A | 198 | 30.193 | 49.596 | 5.750 | 1.00 | 40.55 |
| ATOM | 451 | C | ARG | A | 198 | 30.242 | 48.142 | 5.286 | 1.00 | 43.64 |
| ATOM | 452 | O | ARG | A | 198 | 29.214 | 47.466 | 5.212 | 1.00 | 43.45 |
| ATOM | 453 | CB | ARG | A | 198 | 30.349 | 50.532 | 4.551 | 1.00 | 41.02 |
| ATOM | 454 | CG | ARG | A | 198 | 29.253 | 51.575 | 4.438 | 1.00 | 54.84 |
| ATOM | 455 | CD | ARG | A | 198 | 29.807 | 52.916 | 3.982 | 1.00 | 67.24 |
| ATOM | 456 | NE | ARG | A | 198 | 30.671 | 52.783 | 2.811 | 1.00 | 74.86 |
| ATOM | 457 | CZ | ARG | A | 198 | 31.546 | 53.704 | 2.420 | 1.00 | 89.34 |
| ATOM | 458 | NH1 | ARG | A | 198 | 31.677 | 54.831 | 3.108 | 1.00 | 73.86 |
| ATOM | 459 | NH2 | ARG | A | 198 | 32.294 | 53.494 | 1.344 | 1.00 | 79.22 |
| ATOM | 460 | N | VAL | A | 199 | 31.445 | 47.672 | 4.981 | 1.00 | 39.55 |
| ATOM | 461 | CA | VAL | A | 199 | 31.641 | 46.310 | 4.505 | 1.00 | 39.20 |
| ATOM | 462 | C | VAL | A | 199 | 31.215 | 45.260 | 5.528 | 1.00 | 42.43 |
| ATOM | 463 | O | VAL | A | 199 | 30.479 | 44.333 | 5.200 | 1.00 | 41.86 |
| ATOM | 464 | CB | VAL | A | 199 | 33.107 | 46.066 | 4.105 | 1.00 | 42.97 |
| ATOM | 465 | CG1 | VAL | A | 199 | 33.383 | 44.568 | 3.950 | 1.00 | 42.68 |
| ATOM | 466 | CG2 | VAL | A | 199 | 33.435 | 46.819 | 2.831 | 1.00 | 42.74 |
| ATOM | 467 | N | LEU | A | 200 | 31.699 | 45.396 | 6.761 | 1.00 | 39.39 |
| ATOM | 468 | CA | LEU | A | 200 | 31.382 | 44.425 | 7.816 | 1.00 | 39.58 |
| ATOM | 469 | C | LEU | A | 200 | 29.905 | 44.449 | 8.177 | 1.00 | 43.03 |
| ATOM | 470 | O | LEU | A | 200 | 29.343 | 43.446 | 8.632 | 1.00 | 42.27 |
| ATOM | 471 | CB | LEU | A | 200 | 32.239 | 44.683 | 9.065 | 1.00 | 39.66 |
| ATOM | 472 | CG | LEU | A | 200 | 33.587 | 43.954 | 9.106 | 1.00 | 44.45 |
| ATOM | 473 | CD1 | LEU | A | 200 | 33.665 | 42.889 | 8.022 | 1.00 | 44.59 |
| ATOM | 474 | CD2 | LEU | A | 200 | 34.749 | 44.920 | 8.992 | 1.00 | 47.57 |
| ATOM | 475 | N | LYS | A | 201 | 29.286 | 45.605 | 7.971 | 1.00 | 39.92 |
| ATOM | 476 | CA | LYS | A | 201 | 27.881 | 45.816 | 8.288 | 1.00 | 39.99 |
| ATOM | 477 | C | LYS | A | 201 | 26.956 | 45.185 | 7.266 | 1.00 | 43.59 |
| ATOM | 478 | O | LYS | A | 201 | 25.956 | 44.562 | 7.624 | 1.00 | 43.75 |
| ATOM | 479 | CB | LYS | A | 201 | 27.589 | 47.321 | 8.347 | 1.00 | 43.16 |
| ATOM | 480 | CG | LYS | A | 201 | 26.951 | 47.791 | 9.638 | 1.00 | 59.20 |
| ATOM | 481 | CD | LYS | A | 201 | 27.462 | 49.169 | 10.032 | 1.00 | 69.46 |
| ATOM | 482 | CE | LYS | A | 201 | 26.441 | 50.249 | 9.721 | 1.00 | 79.35 |
| ATOM | 483 | NZ | LYS | A | 201 | 25.384 | 50.329 | 10.768 | 1.00 | 86.93 |
| ATOM | 484 | N | ASN | A | 202 | 27.270 | 45.393 | 5.990 | 1.00 | 39.45 |
| ATOM | 485 | CA | ASN | A | 202 | 26.422 | 44.940 | 4.890 | 1.00 | 38.79 |
| ATOM | 486 | C | ASN | A | 202 | 26.828 | 43.622 | 4.250 | 1.00 | 40.96 |
| ATOM | 487 | O | ASN | A | 202 | 26.396 | 43.307 | 3.141 | 1.00 | 40.89 |
| ATOM | 488 | CB | ASN | A | 202 | 26.343 | 46.022 | 3.818 | 1.00 | 42.53 |
| ATOM | 489 | CG | ASN | A | 202 | 25.072 | 46.836 | 3.912 | 1.00 | 72.51 |
| ATOM | 490 | OD1 | ASN | A | 202 | 24.797 | 47.453 | 4.939 | 1.00 | 65.44 |
| ATOM | 491 | ND2 | ASN | A | 202 | 24.265 | 46.805 | 2.854 | 1.00 | 67.06 |
| ATOM | 492 | N | THR | A | 203 | 27.660 | 42.856 | 4.939 | 1.00 | 34.32 |
| ATOM | 493 | CA | THR | A | 203 | 28.100 | 41.567 | 4.432 | 1.00 | 33.10 |
| ATOM | 494 | C | THR | A | 203 | 27.774 | 40.497 | 5.453 | 1.00 | 35.83 |
| ATOM | 495 | O | THR | A | 203 | 27.770 | 40.755 | 6.661 | 1.00 | 36.43 |
| ATOM | 496 | CB | THR | A | 203 | 29.607 | 41.553 | 4.202 | 1.00 | 39.08 |
| ATOM | 497 | OG1 | THR | A | 203 | 30.266 | 42.022 | 5.384 | 1.00 | 34.80 |
| ATOM | 498 | CG2 | THR | A | 203 | 29.974 | 42.447 | 3.024 | 1.00 | 37.14 |
| ATOM | 499 | N | ARG | A | 204 | 27.523 | 39.291 | 4.971 | 1.00 | 29.79 |
| ATOM | 500 | CA | ARG | A | 204 | 27.224 | 38.158 | 5.842 | 1.00 | 28.81 |
| ATOM | 501 | C | ARG | A | 204 | 27.944 | 36.936 | 5.297 | 1.00 | 29.19 |
| ATOM | 502 | O | ARG | A | 204 | 27.603 | 36.437 | 4.231 | 1.00 | 28.19 |
| ATOM | 503 | CB | ARG | A | 204 | 25.713 | 37.890 | 5.887 | 1.00 | 32.47 |
| ATOM | 504 | CG | ARG | A | 204 | 25.337 | 36.410 | 5.992 | 1.00 | 48.06 |
| ATOM | 505 | CD | ARG | A | 204 | 23.837 | 36.215 | 6.255 | 1.00 | 62.65 |
| ATOM | 506 | NE | ARG | A | 204 | 23.405 | 36.884 | 7.479 | 1.00 | 75.58 |
| ATOM | 507 | CZ | ARG | A | 204 | 23.153 | 36.260 | 8.627 | 1.00 | 90.68 |
| ATOM | 508 | NH1 | ARG | A | 204 | 23.285 | 34.942 | 8.711 | 1.00 | 75.51 |
| ATOM | 509 | NH2 | ARG | A | 204 | 22.771 | 36.955 | 9.692 | 1.00 | 79.41 |
| ATOM | 510 | N | HIS | A | 205 | 28.970 | 36.494 | 6.010 | 1.00 | 23.87 |
| ATOM | 511 | CA | HIS | A | 205 | 29.720 | 35.305 | 5.622 | 1.00 | 22.81 |
| ATOM | 512 | C | HIS | A | 205 | 30.242 | 34.611 | 6.883 | 1.00 | 25.55 |
| ATOM | 513 | O | HIS | A | 205 | 30.567 | 35.271 | 7.882 | 1.00 | 23.51 |
| ATOM | 514 | CB | HIS | A | 205 | 30.888 | 35.685 | 4.672 | 1.00 | 22.56 |
| ATOM | 515 | CG | HIS | A | 205 | 31.579 | 34.500 | 4.073 | 1.00 | 25.40 |
| ATOM | 516 | ND1 | HIS | A | 205 | 31.249 | 33.995 | 2.834 | 1.00 | 26.58 |

TABLE 5-continued

Structural coordinates for AKT3lkd(pT305, S472D).

| ATOM | 517 | CD2 | HIS | A | 205 | 32.509 | 33.662 | 4.584 | 1.00 | 26.10 |
|------|-----|-----|-----|---|-----|--------|--------|-------|------|-------|
| ATOM | 518 | CE1 | HIS | A | 205 | 31.992 | 32.934 | 2.580 | 1.00 | 25.74 |
| ATOM | 519 | NE2 | HIS | A | 205 | 32.759 | 32.705 | 3.631 | 1.00 | 26.54 |
| ATOM | 520 | N | PRO | A | 206 | 30.278 | 33.283 | 6.846 | 1.00 | 23.66 |
| ATOM | 521 | CA | PRO | A | 206 | 30.695 | 32.479 | 7.987 | 1.00 | 23.09 |
| ATOM | 522 | C | PRO | A | 206 | 32.068 | 32.833 | 8.538 | 1.00 | 22.73 |
| ATOM | 523 | O | PRO | A | 206 | 32.328 | 32.691 | 9.729 | 1.00 | 23.10 |
| ATOM | 524 | CB | PRO | A | 206 | 30.712 | 31.051 | 7.410 | 1.00 | 25.01 |
| ATOM | 525 | CG | PRO | A | 206 | 29.706 | 31.067 | 6.365 | 1.00 | 30.46 |
| ATOM | 526 | CD | PRO | A | 206 | 29.682 | 32.461 | 5.783 | 1.00 | 25.36 |
| ATOM | 527 | N | PHE | A | 207 | 32.957 | 33.272 | 7.668 | 1.00 | 17.19 |
| ATOM | 528 | CA | PHE | A | 207 | 34.314 | 33.564 | 8.082 | 1.00 | 16.36 |
| ATOM | 529 | C | PHE | A | 207 | 34.640 | 35.050 | 8.178 | 1.00 | 22.56 |
| ATOM | 530 | O | PHE | A | 207 | 35.801 | 35.435 | 8.272 | 1.00 | 20.73 |
| ATOM | 531 | CB | PHE | A | 207 | 35.297 | 32.832 | 7.169 | 1.00 | 17.57 |
| ATOM | 532 | CG | PHE | A | 207 | 35.022 | 31.365 | 7.072 | 1.00 | 18.73 |
| ATOM | 533 | CD1 | PHE | A | 207 | 34.829 | 30.609 | 8.224 | 1.00 | 20.46 |
| ATOM | 534 | CD2 | PHE | A | 207 | 34.800 | 30.770 | 5.830 | 1.00 | 20.62 |
| ATOM | 535 | CE1 | PHE | A | 207 | 34.487 | 29.248 | 8.138 | 1.00 | 21.01 |
| ATOM | 536 | CE2 | PHE | A | 207 | 34.448 | 29.419 | 5.729 | 1.00 | 23.09 |
| ATOM | 537 | CZ | PHE | A | 207 | 34.304 | 28.659 | 6.872 | 1.00 | 21.32 |
| ATOM | 538 | N | LEU | A | 208 | 33.604 | 35.875 | 8.135 | 1.00 | 22.17 |
| ATOM | 539 | CA | LEU | A | 208 | 33.767 | 37.325 | 8.222 | 1.00 | 22.11 |
| ATOM | 540 | C | LEU | A | 208 | 33.085 | 37.788 | 9.514 | 1.00 | 26.10 |
| ATOM | 541 | O | LEU | A | 208 | 31.962 | 37.376 | 9.810 | 1.00 | 24.37 |
| ATOM | 542 | CB | LEU | A | 208 | 33.094 | 37.997 | 7.021 | 1.00 | 22.98 |
| ATOM | 543 | CG | LEU | A | 208 | 33.884 | 38.107 | 5.706 | 1.00 | 28.94 |
| ATOM | 544 | CD1 | LEU | A | 208 | 33.050 | 38.863 | 4.644 | 1.00 | 29.23 |
| ATOM | 545 | CD2 | LEU | A | 208 | 35.211 | 38.824 | 5.950 | 1.00 | 32.96 |
| ATOM | 546 | N | THR | A | 209 | 33.775 | 38.618 | 10.287 | 1.00 | 23.94 |
| ATOM | 547 | CA | THR | A | 209 | 33.223 | 39.124 | 11.543 | 1.00 | 24.04 |
| ATOM | 548 | C | THR | A | 209 | 32.019 | 40.012 | 11.246 | 1.00 | 29.24 |
| ATOM | 549 | O | THR | A | 209 | 32.115 | 40.938 | 10.446 | 1.00 | 27.43 |
| ATOM | 550 | CB | THR | A | 209 | 34.263 | 39.960 | 12.301 | 1.00 | 33.16 |
| ATOM | 551 | OG1 | THR | A | 209 | 35.241 | 39.091 | 12.884 | 1.00 | 34.35 |
| ATOM | 552 | CG2 | THR | A | 209 | 33.588 | 40.769 | 13.398 | 1.00 | 33.51 |
| ATOM | 553 | N | SER | A | 210 | 30.874 | 39.705 | 11.855 | 1.00 | 28.46 |
| ATOM | 554 | CA | SER | A | 210 | 29.685 | 40.507 | 11.612 | 1.00 | 29.38 |
| ATOM | 555 | C | SER | A | 210 | 29.605 | 41.736 | 12.514 | 1.00 | 33.91 |
| ATOM | 556 | O | SER | A | 210 | 29.788 | 41.640 | 13.735 | 1.00 | 31.30 |
| ATOM | 557 | CB | SER | A | 210 | 28.407 | 39.665 | 11.705 | 1.00 | 34.64 |
| ATOM | 558 | OG | SER | A | 210 | 28.256 | 39.090 | 12.991 | 1.00 | 46.13 |
| ATOM | 559 | N | LEU | A | 211 | 29.382 | 42.894 | 11.891 | 1.00 | 32.32 |
| ATOM | 560 | CA | LEU | A | 211 | 29.244 | 44.173 | 12.607 | 1.00 | 33.64 |
| ATOM | 561 | C | LEU | A | 211 | 27.752 | 44.387 | 12.812 | 1.00 | 39.64 |
| ATOM | 562 | O | LEU | A | 211 | 27.021 | 44.625 | 11.853 | 1.00 | 39.37 |
| ATOM | 563 | CB | LEU | A | 211 | 29.847 | 45.315 | 11.769 | 1.00 | 34.00 |
| ATOM | 564 | CG | LEU | A | 211 | 29.687 | 46.767 | 12.241 | 1.00 | 39.31 |
| ATOM | 565 | CD1 | LEU | A | 211 | 29.514 | 46.853 | 13.753 | 1.00 | 39.54 |
| ATOM | 566 | CD2 | LEU | A | 211 | 30.890 | 47.594 | 11.783 | 1.00 | 42.12 |
| ATOM | 567 | N | LYS | A | 212 | 27.293 | 44.212 | 14.049 | 1.00 | 37.90 |
| ATOM | 568 | CA | LYS | A | 212 | 25.858 | 44.273 | 14.372 | 1.00 | 38.32 |
| ATOM | 569 | C | LYS | A | 212 | 25.275 | 45.682 | 14.502 | 1.00 | 44.50 |
| ATOM | 570 | O | LYS | A | 212 | 24.235 | 45.983 | 13.920 | 1.00 | 45.17 |
| ATOM | 571 | CB | LYS | A | 212 | 25.554 | 43.453 | 15.621 | 1.00 | 40.36 |
| ATOM | 572 | CG | LYS | A | 212 | 24.181 | 43.730 | 16.222 | 1.00 | 51.63 |
| ATOM | 573 | CD | LYS | A | 212 | 23.425 | 42.431 | 16.488 | 1.00 | 59.58 |
| ATOM | 574 | CE | LYS | A | 212 | 21.995 | 42.504 | 15.944 | 1.00 | 66.86 |
| ATOM | 575 | NZ | LYS | A | 212 | 21.262 | 41.213 | 16.129 | 1.00 | 72.40 |
| ATOM | 576 | N | TYR | A | 213 | 25.920 | 46.526 | 15.302 | 1.00 | 41.40 |
| ATOM | 577 | CA | TYR | A | 213 | 25.470 | 47.898 | 15.482 | 1.00 | 41.73 |
| ATOM | 578 | C | TYR | A | 213 | 26.644 | 48.847 | 15.404 | 1.00 | 49.12 |
| ATOM | 579 | O | TYR | A | 213 | 27.797 | 48.464 | 15.624 | 1.00 | 48.79 |
| ATOM | 580 | CB | TYR | A | 213 | 24.769 | 48.096 | 16.841 | 1.00 | 41.91 |
| ATOM | 581 | CG | TYR | A | 213 | 23.696 | 47.090 | 17.180 | 1.00 | 42.77 |
| ATOM | 582 | CD1 | TYR | A | 213 | 22.561 | 46.960 | 16.398 | 1.00 | 44.76 |
| ATOM | 583 | CD2 | TYR | A | 213 | 23.789 | 46.320 | 18.332 | 1.00 | 43.13 |
| ATOM | 584 | CE1 | TYR | A | 213 | 21.568 | 46.047 | 16.725 | 1.00 | 45.38 |
| ATOM | 585 | CE2 | TYR | A | 213 | 22.807 | 45.416 | 18.672 | 1.00 | 44.12 |
| ATOM | 586 | CZ | TYR | A | 213 | 21.691 | 45.287 | 17.874 | 1.00 | 52.70 |
| ATOM | 587 | OH | TYR | A | 213 | 20.714 | 44.374 | 18.216 | 1.00 | 55.32 |
| ATOM | 588 | N | SER | A | 214 | 26.334 | 50.105 | 15.139 | 1.00 | 48.53 |
| ATOM | 589 | CA | SER | A | 214 | 27.325 | 51.161 | 15.089 | 1.00 | 49.89 |
| ATOM | 590 | C | SER | A | 214 | 26.654 | 52.401 | 15.669 | 1.00 | 57.60 |
| ATOM | 591 | O | SER | A | 214 | 25.494 | 52.678 | 15.365 | 1.00 | 56.88 |
| ATOM | 592 | CB | SER | A | 214 | 27.756 | 51.426 | 13.645 | 1.00 | 53.88 |
| ATOM | 593 | OG | SER | A | 214 | 29.013 | 52.078 | 13.601 | 1.00 | 65.30 |
| ATOM | 594 | N | PHE | A | 215 | 27.348 | 53.102 | 16.558 | 1.00 | 57.28 |

TABLE 5-continued

Structural coordinates for AKT3lkd(pT305, S472D).

| ATOM | 595 | CA | PHE | A | 215 | 26.783 | 54.301 | 17.159 | 1.00 | 58.33 |
|---|---|---|---|---|---|---|---|---|---|---|
| ATOM | 596 | C | PHE | A | 215 | 27.781 | 55.412 | 17.411 | 1.00 | 65.01 |
| ATOM | 597 | O | PHE | A | 215 | 28.993 | 55.227 | 17.271 | 1.00 | 64.56 |
| ATOM | 598 | CB | PHE | A | 215 | 25.911 | 53.998 | 18.383 | 1.00 | 60.40 |
| ATOM | 599 | CG | PHE | A | 215 | 26.675 | 53.508 | 19.571 | 1.00 | 62.27 |
| ATOM | 600 | CD1 | PHE | A | 215 | 26.984 | 52.168 | 19.704 | 1.00 | 65.43 |
| ATOM | 601 | CD2 | PHE | A | 215 | 27.044 | 54.379 | 20.581 | 1.00 | 64.77 |
| ATOM | 602 | CE1 | PHE | A | 215 | 27.671 | 51.708 | 20.807 | 1.00 | 66.55 |
| ATOM | 603 | CE2 | PHE | A | 215 | 27.729 | 53.926 | 21.689 | 1.00 | 67.75 |
| ATOM | 604 | CZ | PHE | A | 215 | 28.051 | 52.590 | 21.797 | 1.00 | 65.78 |
| ATOM | 605 | N | GLN | A | 216 | 27.251 | 56.582 | 17.738 | 1.00 | 63.95 |
| ATOM | 606 | CA | GLN | A | 216 | 28.044 | 57.785 | 17.883 | 1.00 | 64.91 |
| ATOM | 607 | C | GLN | A | 216 | 28.150 | 58.327 | 19.306 | 1.00 | 71.10 |
| ATOM | 608 | O | GLN | A | 216 | 27.232 | 58.185 | 20.118 | 1.00 | 70.54 |
| ATOM | 609 | CB | GLN | A | 216 | 27.481 | 58.874 | 16.960 | 1.00 | 66.36 |
| ATOM | 610 | CG | GLN | A | 216 | 26.196 | 58.462 | 16.204 | 1.00 | 85.10 |
| ATOM | 611 | CD | GLN | A | 216 | 25.024 | 58.124 | 17.135 | 1.00 | 108.04 |
| ATOM | 612 | OE1 | GLN | A | 216 | 25.218 | 57.823 | 18.319 | 1.00 | 103.72 |
| ATOM | 613 | NE2 | GLN | A | 216 | 23.816 | 58.092 | 16.580 | 1.00 | 101.36 |
| ATOM | 614 | N | THR | A | 217 | 29.273 | 58.991 | 19.572 | 1.00 | 69.59 |
| ATOM | 615 | CA | THR | A | 217 | 29.531 | 59.644 | 20.852 | 1.00 | 70.25 |
| ATOM | 616 | C | THR | A | 217 | 30.425 | 60.851 | 20.576 | 1.00 | 75.24 |
| ATOM | 617 | O | THR | A | 217 | 31.079 | 60.913 | 19.533 | 1.00 | 74.97 |
| ATOM | 618 | CB | THR | A | 217 | 30.235 | 58.707 | 21.854 | 1.00 | 80.52 |
| ATOM | 619 | OG1 | THR | A | 217 | 31.233 | 57.933 | 21.176 | 1.00 | 81.89 |
| ATOM | 620 | CG2 | THR | A | 217 | 29.226 | 57.776 | 22.511 | 1.00 | 79.49 |
| ATOM | 621 | N | LYS | A | 218 | 30.427 | 61.811 | 21.501 | 1.00 | 72.51 |
| ATOM | 622 | CA | LYS | A | 218 | 31.196 | 63.054 | 21.359 | 1.00 | 72.52 |
| ATOM | 623 | C | LYS | A | 218 | 32.579 | 62.923 | 20.706 | 1.00 | 76.32 |
| ATOM | 624 | O | LYS | A | 218 | 32.923 | 63.710 | 19.822 | 1.00 | 76.24 |
| ATOM | 625 | CB | LYS | A | 218 | 31.303 | 63.784 | 22.703 | 1.00 | 75.14 |
| ATOM | 626 | CG | LYS | A | 218 | 30.122 | 64.698 | 23.011 | 1.00 | 88.76 |
| ATOM | 627 | CD | LYS | A | 218 | 30.564 | 65.945 | 23.768 | 1.00 | 97.01 |
| ATOM | 628 | CE | LYS | A | 218 | 29.602 | 66.277 | 24.904 | 1.00 | 105.00 |
| ATOM | 629 | NZ | LYS | A | 218 | 29.497 | 67.747 | 25.136 | 1.00 | 111.97 |
| ATOM | 630 | N | ASP | A | 219 | 33.361 | 61.931 | 21.130 | 1.00 | 72.48 |
| ATOM | 631 | CA | ASP | A | 219 | 34.706 | 61.742 | 20.571 | 1.00 | 71.96 |
| ATOM | 632 | C | ASP | A | 219 | 35.126 | 60.271 | 20.451 | 1.00 | 74.13 |
| ATOM | 633 | O | ASP | A | 219 | 36.319 | 59.960 | 20.373 | 1.00 | 73.73 |
| ATOM | 634 | CB | ASP | A | 219 | 35.737 | 62.514 | 21.390 | 1.00 | 73.95 |
| ATOM | 635 | CG | ASP | A | 219 | 35.421 | 62.512 | 22.870 | 1.00 | 85.43 |
| ATOM | 636 | OD1 | ASP | A | 219 | 34.562 | 61.710 | 23.293 | 1.00 | 86.12 |
| ATOM | 637 | OD2 | ASP | A | 219 | 36.024 | 63.319 | 23.610 | 1.00 | 91.93 |
| ATOM | 638 | N | ARG | A | 220 | 34.147 | 59.373 | 20.418 | 1.00 | 68.93 |
| ATOM | 639 | CA | ARG | A | 220 | 34.432 | 57.947 | 20.309 | 1.00 | 67.67 |
| ATOM | 640 | C | ARG | A | 220 | 33.604 | 57.273 | 19.219 | 1.00 | 68.58 |
| ATOM | 641 | O | ARG | A | 220 | 32.463 | 57.659 | 18.960 | 1.00 | 68.16 |
| ATOM | 642 | CB | ARG | A | 220 | 34.188 | 57.258 | 21.653 | 1.00 | 67.96 |
| ATOM | 643 | CG | ARG | A | 220 | 34.846 | 57.956 | 22.836 | 1.00 | 78.40 |
| ATOM | 644 | CD | ARG | A | 220 | 36.265 | 57.451 | 23.053 | 1.00 | 89.64 |
| ATOM | 645 | NE | ARG | A | 220 | 36.815 | 57.892 | 24.332 | 1.00 | 99.78 |
| ATOM | 646 | CZ | ARG | A | 220 | 37.195 | 57.071 | 25.309 | 1.00 | 114.90 |
| ATOM | 647 | NH1 | ARG | A | 220 | 37.078 | 55.758 | 25.161 | 1.00 | 101.73 |
| ATOM | 648 | NH2 | ARG | A | 220 | 37.686 | 57.566 | 26.439 | 1.00 | 101.86 |
| ATOM | 649 | N | LEU | A | 221 | 34.181 | 56.254 | 18.591 | 1.00 | 62.59 |
| ATOM | 650 | CA | LEU | A | 221 | 33.480 | 55.500 | 17.553 | 1.00 | 60.91 |
| ATOM | 651 | C | LEU | A | 221 | 33.132 | 54.113 | 18.083 | 1.00 | 59.97 |
| ATOM | 652 | O | LEU | A | 221 | 34.019 | 53.323 | 18.386 | 1.00 | 59.51 |
| ATOM | 653 | CB | LEU | A | 221 | 34.336 | 55.387 | 16.292 | 1.00 | 61.11 |
| ATOM | 654 | CG | LEU | A | 221 | 33.552 | 55.420 | 14.978 | 1.00 | 66.12 |
| ATOM | 655 | CD1 | LEU | A | 221 | 32.816 | 56.746 | 14.830 | 1.00 | 66.32 |
| ATOM | 656 | CD2 | LEU | A | 221 | 34.468 | 55.170 | 13.793 | 1.00 | 68.80 |
| ATOM | 657 | N | CYS | A | 222 | 31.836 | 53.838 | 18.217 | 1.00 | 53.15 |
| ATOM | 658 | CA | CYS | A | 222 | 31.373 | 52.563 | 18.762 | 1.00 | 51.56 |
| ATOM | 659 | C | CYS | A | 222 | 30.901 | 51.556 | 17.709 | 1.00 | 51.00 |
| ATOM | 660 | O | CYS | A | 222 | 29.974 | 51.828 | 16.944 | 1.00 | 49.67 |
| ATOM | 661 | CB | CYS | A | 222 | 30.280 | 52.796 | 19.801 | 1.00 | 52.02 |
| ATOM | 662 | SG | CYS | A | 222 | 30.768 | 53.922 | 21.149 | 1.00 | 56.02 |
| ATOM | 663 | N | PHE | A | 223 | 31.525 | 50.375 | 17.711 | 1.00 | 44.76 |
| ATOM | 664 | CA | PHE | A | 223 | 31.182 | 49.303 | 16.767 | 1.00 | 42.71 |
| ATOM | 665 | C | PHE | A | 223 | 30.899 | 47.999 | 17.504 | 1.00 | 42.02 |
| ATOM | 666 | O | PHE | A | 223 | 31.804 | 47.387 | 18.075 | 1.00 | 40.72 |
| ATOM | 667 | CB | PHE | A | 223 | 32.322 | 49.083 | 15.769 | 1.00 | 44.77 |
| ATOM | 668 | CG | PHE | A | 223 | 32.633 | 50.285 | 14.920 | 1.00 | 46.77 |
| ATOM | 669 | CD1 | PHE | A | 223 | 31.670 | 50.832 | 14.091 | 1.00 | 50.12 |
| ATOM | 670 | CD2 | PHE | A | 223 | 33.906 | 50.840 | 14.922 | 1.00 | 49.84 |
| ATOM | 671 | CE1 | PHE | A | 223 | 31.959 | 51.927 | 13.300 | 1.00 | 51.39 |
| ATOM | 672 | CE2 | PHE | A | 223 | 34.204 | 51.935 | 14.129 | 1.00 | 52.88 |

TABLE 5-continued

Structural coordinates for AKT3lkd(pT305, S472D).

| ATOM | 673 | CZ | PHE | A | 223 | 33.230 | 52.480 | 13.320 | 1.00 | 50.84 |
| ATOM | 674 | N | VAL | A | 224 | 29.646 | 47.572 | 17.492 | 1.00 | 36.13 |
| ATOM | 675 | CA | VAL | A | 224 | 29.272 | 46.344 | 18.169 | 1.00 | 35.50 |
| ATOM | 676 | C | VAL | A | 224 | 29.424 | 45.164 | 17.226 | 1.00 | 37.42 |
| ATOM | 677 | O | VAL | A | 224 | 28.606 | 44.957 | 16.331 | 1.00 | 36.51 |
| ATOM | 678 | CB | VAL | A | 224 | 27.854 | 46.403 | 18.727 | 1.00 | 39.30 |
| ATOM | 679 | CG1 | VAL | A | 224 | 27.490 | 45.081 | 19.386 | 1.00 | 39.01 |
| ATOM | 680 | CG2 | VAL | A | 224 | 27.725 | 47.556 | 19.724 | 1.00 | 39.11 |
| ATOM | 681 | N | MET | A | 225 | 30.489 | 44.403 | 17.431 | 1.00 | 32.85 |
| ATOM | 682 | CA | MET | A | 225 | 30.799 | 43.278 | 16.568 | 1.00 | 32.63 |
| ATOM | 683 | C | MET | A | 225 | 30.645 | 41.936 | 17.260 | 1.00 | 34.21 |
| ATOM | 684 | O | MET | A | 225 | 30.704 | 41.836 | 18.487 | 1.00 | 31.55 |
| ATOM | 685 | CB | MET | A | 225 | 32.215 | 43.431 | 16.013 | 1.00 | 35.71 |
| ATOM | 686 | CG | MET | A | 225 | 32.409 | 44.693 | 15.209 | 1.00 | 40.53 |
| ATOM | 687 | SD | MET | A | 225 | 34.121 | 45.242 | 15.227 | 1.00 | 46.26 |
| ATOM | 688 | CE | MET | A | 225 | 34.641 | 44.682 | 13.609 | 1.00 | 43.24 |
| ATOM | 689 | N | GLU | A | 226 | 30.482 | 40.894 | 16.458 | 1.00 | 30.70 |
| ATOM | 690 | CA | GLU | A | 226 | 30.333 | 39.556 | 16.975 | 1.00 | 30.41 |
| ATOM | 691 | C | GLU | A | 226 | 31.556 | 39.162 | 17.833 | 1.00 | 33.09 |
| ATOM | 692 | O | GLU | A | 226 | 32.696 | 39.501 | 17.505 | 1.00 | 32.62 |
| ATOM | 693 | CB | GLU | A | 226 | 30.047 | 38.576 | 15.821 | 1.00 | 32.37 |
| ATOM | 694 | CG | GLU | A | 226 | 31.081 | 37.520 | 15.553 | 1.00 | 39.58 |
| ATOM | 695 | CD | GLU | A | 226 | 30.662 | 36.591 | 14.401 | 1.00 | 47.03 |
| ATOM | 696 | OE1 | GLU | A | 226 | 30.611 | 37.055 | 13.235 | 1.00 | 25.39 |
| ATOM | 697 | OE2 | GLU | A | 226 | 30.322 | 35.418 | 14.672 | 1.00 | 39.96 |
| ATOM | 698 | N | TYR | A | 227 | 31.298 | 38.541 | 18.981 | 1.00 | 28.59 |
| ATOM | 699 | CA | TYR | A | 227 | 32.379 | 38.147 | 19.898 | 1.00 | 28.09 |
| ATOM | 700 | C | TYR | A | 227 | 33.055 | 36.846 | 19.459 | 1.00 | 31.81 |
| ATOM | 701 | O | TYR | A | 227 | 32.405 | 35.820 | 19.319 | 1.00 | 32.42 |
| ATOM | 702 | CB | TYR | A | 227 | 31.847 | 38.012 | 21.326 | 1.00 | 28.33 |
| ATOM | 703 | CG | TYR | A | 227 | 32.894 | 37.608 | 22.339 | 1.00 | 28.42 |
| ATOM | 704 | CD1 | TYR | A | 227 | 34.022 | 38.384 | 22.549 | 1.00 | 30.51 |
| ATOM | 705 | CD2 | TYR | A | 227 | 32.755 | 36.443 | 23.075 | 1.00 | 28.93 |
| ATOM | 706 | CE1 | TYR | A | 227 | 34.997 | 38.001 | 23.469 | 1.00 | 30.66 |
| ATOM | 707 | CE2 | TYR | A | 227 | 33.732 | 36.048 | 23.991 | 1.00 | 29.16 |
| ATOM | 708 | CZ | TYR | A | 227 | 34.836 | 36.835 | 24.186 | 1.00 | 32.30 |
| ATOM | 709 | OH | TYR | A | 227 | 35.794 | 36.454 | 25.098 | 1.00 | 30.98 |
| ATOM | 710 | N | VAL | A | 228 | 34.360 | 36.914 | 19.225 | 1.00 | 27.78 |
| ATOM | 711 | CA | VAL | A | 228 | 35.151 | 35.756 | 18.777 | 1.00 | 27.81 |
| ATOM | 712 | C | VAL | A | 228 | 36.239 | 35.505 | 19.827 | 1.00 | 28.90 |
| ATOM | 713 | O | VAL | A | 228 | 37.071 | 36.373 | 20.070 | 1.00 | 26.26 |
| ATOM | 714 | CB | VAL | A | 228 | 35.828 | 36.083 | 17.421 | 1.00 | 32.23 |
| ATOM | 715 | CG1 | VAL | A | 228 | 36.566 | 34.899 | 16.895 | 1.00 | 32.02 |
| ATOM | 716 | CG2 | VAL | A | 228 | 34.788 | 36.577 | 16.418 | 1.00 | 32.40 |
| ATOM | 717 | N | ASN | A | 229 | 36.222 | 34.328 | 20.458 | 1.00 | 26.74 |
| ATOM | 718 | CA | ASN | A | 229 | 37.157 | 34.057 | 21.561 | 1.00 | 26.64 |
| ATOM | 719 | C | ASN | A | 229 | 38.150 | 32.896 | 21.392 | 1.00 | 29.67 |
| ATOM | 720 | O | ASN | A | 229 | 38.681 | 32.381 | 22.378 | 1.00 | 27.19 |
| ATOM | 721 | CB | ASN | A | 229 | 36.382 | 33.904 | 22.890 | 1.00 | 28.45 |
| ATOM | 722 | CG | ASN | A | 229 | 35.640 | 32.562 | 22.993 | 1.00 | 40.09 |
| ATOM | 723 | OD1 | ASN | A | 229 | 35.233 | 31.985 | 21.984 | 1.00 | 31.42 |
| ATOM | 724 | ND2 | ASN | A | 229 | 35.486 | 32.065 | 24.215 | 1.00 | 27.73 |
| ATOM | 725 | N | GLY | A | 230 | 38.408 | 32.492 | 20.153 | 1.00 | 26.35 |
| ATOM | 726 | CA | GLY | A | 230 | 39.346 | 31.396 | 19.894 | 1.00 | 26.51 |
| ATOM | 727 | C | GLY | A | 230 | 40.780 | 31.881 | 19.879 | 1.00 | 29.98 |
| ATOM | 728 | O | GLY | A | 230 | 41.709 | 31.093 | 19.746 | 1.00 | 30.39 |
| ATOM | 729 | N | GLY | A | 231 | 40.954 | 33.189 | 19.984 | 1.00 | 27.17 |
| ATOM | 730 | CA | GLY | A | 231 | 42.284 | 33.793 | 20.051 | 1.00 | 27.00 |
| ATOM | 731 | C | GLY | A | 231 | 42.806 | 34.325 | 18.713 | 1.00 | 30.73 |
| ATOM | 732 | O | GLY | A | 231 | 42.358 | 33.898 | 17.645 | 1.00 | 29.11 |
| ATOM | 733 | N | GLU | A | 232 | 43.793 | 35.224 | 18.789 | 1.00 | 27.82 |
| ATOM | 734 | CA | GLU | A | 232 | 44.419 | 35.803 | 17.594 | 1.00 | 27.61 |
| ATOM | 735 | C | GLU | A | 232 | 45.366 | 34.810 | 16.913 | 1.00 | 29.19 |
| ATOM | 736 | O | GLU | A | 232 | 46.228 | 34.221 | 17.560 | 1.00 | 27.09 |
| ATOM | 737 | CB | GLU | A | 232 | 45.219 | 37.049 | 17.969 | 1.00 | 29.33 |
| ATOM | 738 | CG | GLU | A | 232 | 44.385 | 38.245 | 18.385 | 1.00 | 42.70 |
| ATOM | 739 | CD | GLU | A | 232 | 45.166 | 39.549 | 18.276 | 1.00 | 69.76 |
| ATOM | 740 | OE1 | GLU | A | 232 | 45.938 | 39.703 | 17.304 | 1.00 | 68.89 |
| ATOM | 741 | OE2 | GLU | A | 232 | 45.041 | 40.399 | 19.181 | 1.00 | 65.72 |
| ATOM | 742 | N | LEU | A | 233 | 45.236 | 34.651 | 15.600 | 1.00 | 25.73 |
| ATOM | 743 | CA | LEU | A | 233 | 46.141 | 33.739 | 14.884 | 1.00 | 25.64 |
| ATOM | 744 | C | LEU | A | 233 | 47.560 | 34.232 | 14.999 | 1.00 | 29.88 |
| ATOM | 745 | O | LEU | A | 233 | 48.488 | 33.444 | 15.051 | 1.00 | 29.05 |
| ATOM | 746 | CB | LEU | A | 233 | 45.743 | 33.586 | 13.409 | 1.00 | 26.00 |
| ATOM | 747 | CG | LEU | A | 233 | 44.751 | 32.444 | 13.152 | 1.00 | 31.94 |
| ATOM | 748 | CD1 | LEU | A | 233 | 44.455 | 32.306 | 11.663 | 1.00 | 32.36 |
| ATOM | 749 | CD2 | LEU | A | 233 | 45.280 | 31.116 | 13.744 | 1.00 | 34.00 |
| ATOM | 750 | N | PHE | A | 234 | 47.735 | 35.548 | 15.046 | 1.00 | 29.28 |

TABLE 5-continued

Structural coordinates for AKT3lkd(pT305, S472D).

| ATOM | 751 | CA | PHE | A | 234 | 49.076 | 36.092 | 15.201 | 1.00 | 30.90 |
|------|-----|-----|-----|---|-----|--------|--------|--------|------|-------|
| ATOM | 752 | C | PHE | A | 234 | 49.716 | 35.518 | 16.463 | 1.00 | 35.55 |
| ATOM | 753 | O | PHE | A | 234 | 50.886 | 35.174 | 16.476 | 1.00 | 35.08 |
| ATOM | 754 | CB | PHE | A | 234 | 49.058 | 37.621 | 15.290 | 1.00 | 33.76 |
| ATOM | 755 | CG | PHE | A | 234 | 50.418 | 38.218 | 15.520 | 1.00 | 36.81 |
| ATOM | 756 | CD1 | PHE | A | 234 | 50.982 | 38.216 | 16.791 | 1.00 | 41.25 |
| ATOM | 757 | CD2 | PHE | A | 234 | 51.172 | 38.686 | 14.458 | 1.00 | 40.08 |
| ATOM | 758 | CE1 | PHE | A | 234 | 52.256 | 38.727 | 17.003 | 1.00 | 42.98 |
| ATOM | 759 | CE2 | PHE | A | 234 | 52.451 | 39.193 | 14.662 | 1.00 | 43.68 |
| ATOM | 760 | CZ | PHE | A | 234 | 52.992 | 39.212 | 15.936 | 1.00 | 42.02 |
| ATOM | 761 | N | PHE | A | 235 | 48.923 | 35.403 | 17.516 | 1.00 | 33.64 |
| ATOM | 762 | CA | PHE | A | 235 | 49.425 | 34.881 | 18.784 | 1.00 | 34.21 |
| ATOM | 763 | C | PHE | A | 235 | 49.638 | 33.383 | 18.744 | 1.00 | 32.84 |
| ATOM | 764 | O | PHE | A | 235 | 50.654 | 32.885 | 19.217 | 1.00 | 30.60 |
| ATOM | 765 | CB | PHE | A | 235 | 48.529 | 35.308 | 19.944 | 1.00 | 37.60 |
| ATOM | 766 | CG | PHE | A | 235 | 48.663 | 36.768 | 20.297 | 1.00 | 41.05 |
| ATOM | 767 | CD1 | PHE | A | 235 | 49.871 | 37.426 | 20.101 | 1.00 | 45.45 |
| ATOM | 768 | CD2 | PHE | A | 235 | 47.579 | 37.492 | 20.777 | 1.00 | 44.30 |
| ATOM | 769 | CE1 | PHE | A | 235 | 50.002 | 38.777 | 20.398 | 1.00 | 47.01 |
| ATOM | 770 | CE2 | PHE | A | 235 | 47.702 | 38.840 | 21.076 | 1.00 | 47.64 |
| ATOM | 771 | CZ | PHE | A | 235 | 48.912 | 39.486 | 20.883 | 1.00 | 46.25 |
| ATOM | 772 | N | HIS | A | 236 | 48.727 | 32.664 | 18.098 | 1.00 | 27.59 |
| ATOM | 773 | CA | HIS | A | 236 | 48.903 | 31.217 | 17.962 | 1.00 | 26.89 |
| ATOM | 774 | C | HIS | A | 236 | 50.166 | 30.888 | 17.171 | 1.00 | 30.50 |
| ATOM | 775 | O | HIS | A | 236 | 50.947 | 30.024 | 17.568 | 1.00 | 30.35 |
| ATOM | 776 | CB | HIS | A | 236 | 47.697 | 30.583 | 17.277 | 1.00 | 27.06 |
| ATOM | 777 | CG | HIS | A | 236 | 46.471 | 30.560 | 18.124 | 1.00 | 29.97 |
| ATOM | 778 | ND1 | HIS | A | 236 | 46.387 | 29.831 | 19.294 | 1.00 | 31.63 |
| ATOM | 779 | CD2 | HIS | A | 236 | 45.270 | 31.170 | 17.971 | 1.00 | 30.75 |
| ATOM | 780 | CE1 | HIS | A | 236 | 45.188 | 30.000 | 19.826 | 1.00 | 30.91 |
| ATOM | 781 | NE2 | HIS | A | 236 | 44.489 | 30.799 | 19.036 | 1.00 | 30.77 |
| ATOM | 782 | N | LEU | A | 237 | 50.353 | 31.553 | 16.034 | 1.00 | 27.37 |
| ATOM | 783 | CA | LEU | A | 237 | 51.531 | 31.288 | 15.206 | 1.00 | 27.34 |
| ATOM | 784 | C | LEU | A | 237 | 52.822 | 31.677 | 15.958 | 1.00 | 35.35 |
| ATOM | 785 | O | LEU | A | 237 | 53.815 | 30.961 | 15.910 | 1.00 | 35.02 |
| ATOM | 786 | CB | LEU | A | 237 | 51.445 | 32.054 | 13.882 | 1.00 | 26.73 |
| ATOM | 787 | CG | LEU | A | 237 | 52.553 | 31.800 | 12.865 | 1.00 | 29.81 |
| ATOM | 788 | CD1 | LEU | A | 237 | 52.554 | 30.335 | 12.404 | 1.00 | 29.31 |
| ATOM | 789 | CD2 | LEU | A | 237 | 52.407 | 32.744 | 11.682 | 1.00 | 29.69 |
| ATOM | 790 | N | SER | A | 238 | 52.782 | 32.812 | 16.658 | 1.00 | 35.11 |
| ATOM | 791 | CA | SER | A | 238 | 53.947 | 33.300 | 17.406 | 1.00 | 36.16 |
| ATOM | 792 | C | SER | A | 238 | 54.394 | 32.316 | 18.488 | 1.00 | 42.67 |
| ATOM | 793 | O | SER | A | 238 | 55.544 | 32.348 | 18.932 | 1.00 | 43.81 |
| ATOM | 794 | CB | SER | A | 238 | 53.657 | 34.668 | 18.026 | 1.00 | 40.21 |
| ATOM | 795 | OG | SER | A | 238 | 52.998 | 34.528 | 19.278 | 1.00 | 49.07 |
| ATOM | 796 | N | ARG | A | 239 | 53.480 | 31.444 | 18.904 | 1.00 | 39.29 |
| ATOM | 797 | CA | ARG | A | 239 | 53.757 | 30.438 | 19.927 | 1.00 | 38.83 |
| ATOM | 798 | C | ARG | A | 239 | 54.166 | 29.105 | 19.317 | 1.00 | 40.58 |
| ATOM | 799 | O | ARG | A | 239 | 54.993 | 28.381 | 19.874 | 1.00 | 39.81 |
| ATOM | 800 | CB | ARG | A | 239 | 52.510 | 30.209 | 20.789 | 1.00 | 39.97 |
| ATOM | 801 | CG | ARG | A | 239 | 52.266 | 31.254 | 21.846 | 1.00 | 51.29 |
| ATOM | 802 | CD | ARG | A | 239 | 51.039 | 30.892 | 22.672 | 1.00 | 61.23 |
| ATOM | 803 | NE | ARG | A | 239 | 51.254 | 31.084 | 24.103 | 1.00 | 72.02 |
| ATOM | 804 | CZ | ARG | A | 239 | 50.387 | 30.716 | 25.041 | 1.00 | 88.81 |
| ATOM | 805 | NH1 | ARG | A | 239 | 49.248 | 30.130 | 24.697 | 1.00 | 78.72 |
| ATOM | 806 | NH2 | ARG | A | 239 | 50.654 | 30.933 | 26.322 | 1.00 | 75.74 |
| ATOM | 807 | N | GLU | A | 240 | 53.548 | 28.752 | 18.197 | 1.00 | 34.65 |
| ATOM | 808 | CA | GLU | A | 240 | 53.829 | 27.475 | 17.559 | 1.00 | 32.99 |
| ATOM | 809 | C | GLU | A | 240 | 54.953 | 27.608 | 16.550 | 1.00 | 34.77 |
| ATOM | 810 | O | GLU | A | 240 | 55.491 | 26.607 | 16.068 | 1.00 | 34.09 |
| ATOM | 811 | CB | GLU | A | 240 | 52.567 | 26.925 | 16.896 | 1.00 | 34.41 |
| ATOM | 812 | CG | GLU | A | 240 | 51.557 | 26.349 | 17.889 | 1.00 | 47.12 |
| ATOM | 813 | CD | GLU | A | 240 | 50.275 | 25.892 | 17.220 | 1.00 | 65.71 |
| ATOM | 814 | OE1 | GLU | A | 240 | 49.580 | 25.023 | 17.787 | 1.00 | 67.68 |
| ATOM | 815 | OE2 | GLU | A | 240 | 49.954 | 26.411 | 16.134 | 1.00 | 58.17 |
| ATOM | 816 | N | ARG | A | 241 | 55.295 | 28.857 | 16.236 | 1.00 | 31.17 |
| ATOM | 817 | CA | ARG | A | 241 | 56.366 | 29.179 | 15.296 | 1.00 | 30.52 |
| ATOM | 818 | C | ARG | A | 241 | 55.937 | 28.990 | 13.841 | 1.00 | 30.82 |
| ATOM | 819 | O | ARG | A | 241 | 56.119 | 29.870 | 13.011 | 1.00 | 28.62 |
| ATOM | 820 | CB | ARG | A | 241 | 57.614 | 28.349 | 15.598 | 1.00 | 34.12 |
| ATOM | 821 | CG | ARG | A | 241 | 58.735 | 28.517 | 14.595 | 1.00 | 52.40 |
| ATOM | 822 | CD | ARG | A | 241 | 60.065 | 28.745 | 15.298 | 1.00 | 69.21 |
| ATOM | 823 | NE | ARG | A | 241 | 61.199 | 28.619 | 14.386 | 1.00 | 83.32 |
| ATOM | 824 | CZ | ARG | A | 241 | 62.286 | 27.896 | 14.642 | 1.00 | 99.72 |
| ATOM | 825 | NH1 | ARG | A | 241 | 62.387 | 27.226 | 15.785 | 1.00 | 86.81 |
| ATOM | 826 | NH2 | ARG | A | 241 | 63.274 | 27.844 | 13.757 | 1.00 | 87.03 |
| ATOM | 827 | N | VAL | A | 242 | 55.375 | 27.826 | 13.543 | 1.00 | 27.05 |
| ATOM | 828 | CA | VAL | A | 242 | 54.932 | 27.511 | 12.194 | 1.00 | 27.00 |

TABLE 5-continued

Structural coordinates for AKT3lkd(pT305, S472D).

| ATOM | 829 | C   | VAL | A | 242 | 53.742 | 26.551 | 12.261 | 1.00 | 29.07 |
|------|-----|-----|-----|---|-----|--------|--------|--------|------|-------|
| ATOM | 830 | O   | VAL | A | 242 | 53.631 | 25.748 | 13.200 | 1.00 | 27.91 |
| ATOM | 831 | CB  | VAL | A | 242 | 56.078 | 26.849 | 11.394 | 1.00 | 32.58 |
| ATOM | 832 | CG1 | VAL | A | 242 | 56.400 | 25.479 | 11.958 | 1.00 | 32.99 |
| ATOM | 833 | CG2 | VAL | A | 242 | 55.741 | 26.764 | 9.937  | 1.00 | 32.96 |
| ATOM | 834 | N   | PHE | A | 243 | 52.845 | 26.656 | 11.283 | 1.00 | 22.92 |
| ATOM | 835 | CA  | PHE | A | 243 | 51.684 | 25.764 | 11.173 | 1.00 | 21.25 |
| ATOM | 836 | C   | PHE | A | 243 | 52.018 | 24.699 | 10.133 | 1.00 | 23.07 |
| ATOM | 837 | O   | PHE | A | 243 | 52.774 | 24.957 | 9.208  | 1.00 | 23.62 |
| ATOM | 838 | CB  | PHE | A | 243 | 50.447 | 26.548 | 10.672 | 1.00 | 22.20 |
| ATOM | 839 | CG  | PHE | A | 243 | 49.876 | 27.512 | 11.678 | 1.00 | 22.97 |
| ATOM | 840 | CD1 | PHE | A | 243 | 50.166 | 27.387 | 13.039 | 1.00 | 25.77 |
| ATOM | 841 | CD2 | PHE | A | 243 | 49.060 | 28.560 | 11.264 | 1.00 | 24.47 |
| ATOM | 842 | CE1 | PHE | A | 243 | 49.631 | 28.256 | 13.958 | 1.00 | 25.82 |
| ATOM | 843 | CE2 | PHE | A | 243 | 48.500 | 29.437 | 12.189 | 1.00 | 26.80 |
| ATOM | 844 | CZ  | PHE | A | 243 | 48.803 | 29.298 | 13.542 | 1.00 | 24.84 |
| ATOM | 845 | N   | SER | A | 244 | 51.431 | 23.515 | 10.261 | 1.00 | 19.05 |
| ATOM | 846 | CA  | SER | A | 244 | 51.640 | 22.471 | 9.279  | 1.00 | 19.15 |
| ATOM | 847 | C   | SER | A | 244 | 51.002 | 22.936 | 7.962  | 1.00 | 21.67 |
| ATOM | 848 | O   | SER | A | 244 | 50.174 | 23.856 | 7.958  | 1.00 | 19.38 |
| ATOM | 849 | CB  | SER | A | 244 | 50.961 | 21.182 | 9.725  | 1.00 | 22.47 |
| ATOM | 850 | OG  | SER | A | 244 | 49.552 | 21.350 | 9.754  | 1.00 | 22.06 |
| ATOM | 851 | N   | GLU | A | 245 | 51.351 | 22.291 | 6.850  | 1.00 | 18.01 |
| ATOM | 852 | CA  | GLU | A | 245 | 50.731 | 22.682 | 5.588  | 1.00 | 18.30 |
| ATOM | 853 | C   | GLU | A | 245 | 49.231 | 22.420 | 5.632  | 1.00 | 21.42 |
| ATOM | 854 | O   | GLU | A | 245 | 48.464 | 23.173 | 5.060  | 1.00 | 18.66 |
| ATOM | 855 | CB  | GLU | A | 245 | 51.347 | 21.966 | 4.405  | 1.00 | 19.81 |
| ATOM | 856 | CG  | GLU | A | 245 | 52.836 | 22.164 | 4.287  | 1.00 | 25.96 |
| ATOM | 857 | CD  | GLU | A | 245 | 53.368 | 21.753 | 2.946  | 1.00 | 34.13 |
| ATOM | 858 | OE1 | GLU | A | 245 | 52.568 | 21.618 | 1.988  | 1.00 | 21.87 |
| ATOM | 859 | OE2 | GLU | A | 245 | 54.602 | 21.621 | 2.859  | 1.00 | 17.02 |
| ATOM | 860 | N   | ASP | A | 246 | 48.815 | 21.325 | 6.274  | 1.00 | 18.34 |
| ATOM | 861 | CA  | ASP | A | 246 | 47.374 | 21.028 | 6.312  | 1.00 | 18.78 |
| ATOM | 862 | C   | ASP | A | 246 | 46.594 | 21.994 | 7.194  | 1.00 | 20.90 |
| ATOM | 863 | O   | ASP | A | 246 | 45.447 | 22.329 | 6.905  | 1.00 | 19.87 |
| ATOM | 864 | CB  | ASP | A | 246 | 47.093 | 19.581 | 6.689  | 1.00 | 20.90 |
| ATOM | 865 | CG  | ASP | A | 246 | 45.670 | 19.153 | 6.321  | 1.00 | 33.01 |
| ATOM | 866 | OD1 | ASP | A | 246 | 45.260 | 19.364 | 5.149  | 1.00 | 31.14 |
| ATOM | 867 | OD2 | ASP | A | 246 | 44.937 | 18.705 | 7.219  | 1.00 | 38.14 |
| ATOM | 868 | N   | ARG | A | 247 | 47.220 | 22.452 | 8.270  | 1.00 | 18.16 |
| ATOM | 869 | CA  | ARG | A | 247 | 46.571 | 23.428 | 9.140  | 1.00 | 18.23 |
| ATOM | 870 | C   | ARG | A | 247 | 46.434 | 24.744 | 8.370  | 1.00 | 20.51 |
| ATOM | 871 | O   | ARG | A | 247 | 45.416 | 25.420 | 8.456  | 1.00 | 19.39 |
| ATOM | 872 | CB  | ARG | A | 247 | 47.370 | 23.640 | 10.432 | 1.00 | 16.80 |
| ATOM | 873 | CG  | ARG | A | 247 | 46.845 | 24.793 | 11.283 | 1.00 | 26.90 |
| ATOM | 874 | CD  | ARG | A | 247 | 47.177 | 24.595 | 12.731 | 1.00 | 31.53 |
| ATOM | 875 | NE  | ARG | A | 247 | 46.528 | 25.583 | 13.580 | 1.00 | 26.90 |
| ATOM | 876 | CZ  | ARG | A | 247 | 46.982 | 25.949 | 14.772 | 1.00 | 38.55 |
| ATOM | 877 | NH1 | ARG | A | 247 | 48.077 | 25.385 | 15.262 | 1.00 | 34.58 |
| ATOM | 878 | NH2 | ARG | A | 247 | 46.334 | 26.863 | 15.483 | 1.00 | 22.06 |
| ATOM | 879 | N   | THR | A | 248 | 47.467 | 25.081 | 7.590  | 1.00 | 16.47 |
| ATOM | 880 | CA  | THR | A | 248 | 47.465 | 26.316 | 6.786  | 1.00 | 16.24 |
| ATOM | 881 | C   | THR | A | 248 | 46.441 | 26.223 | 5.643  | 1.00 | 19.61 |
| ATOM | 882 | O   | THR | A | 248 | 45.786 | 27.211 | 5.298  | 1.00 | 19.26 |
| ATOM | 883 | CB  | THR | A | 248 | 48.880 | 26.644 | 6.227  | 1.00 | 21.25 |
| ATOM | 884 | OG1 | THR | A | 248 | 49.809 | 26.754 | 7.321  | 1.00 | 18.64 |
| ATOM | 885 | CG2 | THR | A | 248 | 48.865 | 27.996 | 5.431  | 1.00 | 16.69 |
| ATOM | 886 | N   | ARG | A | 249 | 46.307 | 25.023 | 5.076  | 1.00 | 16.83 |
| ATOM | 887 | CA  | ARG | A | 249 | 45.324 | 24.757 | 4.023  | 1.00 | 16.08 |
| ATOM | 888 | C   | ARG | A | 249 | 43.919 | 25.018 | 4.564  | 1.00 | 18.71 |
| ATOM | 889 | O   | ARG | A | 249 | 43.103 | 25.642 | 3.917  | 1.00 | 17.41 |
| ATOM | 890 | CB  | ARG | A | 249 | 45.432 | 23.300 | 3.592  | 1.00 | 15.96 |
| ATOM | 891 | CG  | ARG | A | 249 | 44.316 | 22.841 | 2.619  | 1.00 | 17.50 |
| ATOM | 892 | CD  | ARG | A | 249 | 44.504 | 21.351 | 2.250  | 1.00 | 20.39 |
| ATOM | 893 | NE  | ARG | A | 249 | 45.675 | 21.179 | 1.383  | 1.00 | 21.35 |
| ATOM | 894 | CZ  | ARG | A | 249 | 46.823 | 20.620 | 1.752  | 1.00 | 27.98 |
| ATOM | 895 | NH1 | ARG | A | 249 | 46.965 | 20.087 | 2.966  | 1.00 | 19.38 |
| ATOM | 896 | NH2 | ARG | A | 249 | 47.818 | 20.545 | 0.877  | 1.00 | 17.68 |
| ATOM | 897 | N   | PHE | A | 250 | 43.659 | 24.547 | 5.771  | 1.00 | 17.63 |
| ATOM | 898 | CA  | PHE | A | 250 | 42.352 | 24.745 | 6.397  | 1.00 | 16.95 |
| ATOM | 899 | C   | PHE | A | 250 | 42.032 | 26.240 | 6.525  | 1.00 | 18.05 |
| ATOM | 900 | O   | PHE | A | 250 | 40.987 | 26.695 | 6.055  | 1.00 | 17.38 |
| ATOM | 901 | CB  | PHE | A | 250 | 42.308 | 24.078 | 7.767  | 1.00 | 18.51 |
| ATOM | 902 | CG  | PHE | A | 250 | 41.070 | 24.419 | 8.570  | 1.00 | 19.25 |
| ATOM | 903 | CD1 | PHE | A | 250 | 39.904 | 23.658 | 8.441  | 1.00 | 21.32 |
| ATOM | 904 | CD2 | PHE | A | 250 | 41.087 | 25.481 | 9.471  | 1.00 | 21.28 |
| ATOM | 905 | CE1 | PHE | A | 250 | 38.770 | 23.961 | 9.199  | 1.00 | 21.60 |
| ATOM | 906 | CE2 | PHE | A | 250 | 39.959 | 25.801 | 10.218 | 1.00 | 24.19 |

TABLE 5-continued

Structural coordinates for AKT3lkd(pT305, S472D).

| ATOM | 907 | CZ | PHE | A | 250 | 38.790 | 25.049 | 10.065 | 1.00 | 21.53 |
|---|---|---|---|---|---|---|---|---|---|---|
| ATOM | 908 | N | TYR | A | 251 | 42.935 | 27.002 | 7.138 | 1.00 | 15.29 |
| ATOM | 909 | CA | TYR | A | 251 | 42.731 | 28.460 | 7.294 | 1.00 | 14.97 |
| ATOM | 910 | C | TYR | A | 251 | 42.630 | 29.157 | 5.937 | 1.00 | 18.14 |
| ATOM | 911 | O | TYR | A | 251 | 41.738 | 29.980 | 5.712 | 1.00 | 17.37 |
| ATOM | 912 | CB | TYR | A | 251 | 43.857 | 29.086 | 8.121 | 1.00 | 16.33 |
| ATOM | 913 | CG | TYR | A | 251 | 43.896 | 28.604 | 9.540 | 1.00 | 16.96 |
| ATOM | 914 | CD1 | TYR | A | 251 | 42.705 | 28.303 | 10.233 | 1.00 | 18.75 |
| ATOM | 915 | CD2 | TYR | A | 251 | 45.106 | 28.380 | 10.174 | 1.00 | 18.74 |
| ATOM | 916 | CE1 | TYR | A | 251 | 42.743 | 27.813 | 11.546 | 1.00 | 18.07 |
| ATOM | 917 | CE2 | TYR | A | 251 | 45.156 | 27.895 | 11.461 | 1.00 | 20.21 |
| ATOM | 918 | CZ | TYR | A | 251 | 43.991 | 27.626 | 12.149 | 1.00 | 25.05 |
| ATOM | 919 | OH | TYR | A | 251 | 44.094 | 27.144 | 13.423 | 1.00 | 24.18 |
| ATOM | 920 | N | GLY | A | 252 | 43.566 | 28.851 | 5.051 | 1.00 | 15.48 |
| ATOM | 921 | CA | GLY | A | 252 | 43.578 | 29.430 | 3.695 | 1.00 | 15.31 |
| ATOM | 922 | C | GLY | A | 252 | 42.287 | 29.153 | 2.920 | 1.00 | 17.88 |
| ATOM | 923 | O | GLY | A | 252 | 41.756 | 30.038 | 2.244 | 1.00 | 17.02 |
| ATOM | 924 | N | ALA | A | 253 | 41.764 | 27.937 | 3.034 | 1.00 | 14.92 |
| ATOM | 925 | CA | ALA | A | 253 | 40.521 | 27.612 | 2.331 | 1.00 | 14.33 |
| ATOM | 926 | C | ALA | A | 253 | 39.355 | 28.484 | 2.851 | 1.00 | 16.79 |
| ATOM | 927 | O | ALA | A | 253 | 38.526 | 28.980 | 2.072 | 1.00 | 13.69 |
| ATOM | 928 | CB | ALA | A | 253 | 40.206 | 26.153 | 2.473 | 1.00 | 15.58 |
| ATOM | 929 | N | GLU | A | 254 | 39.279 | 28.650 | 4.169 | 1.00 | 14.94 |
| ATOM | 930 | CA | GLU | A | 254 | 38.209 | 29.459 | 4.766 | 1.00 | 14.52 |
| ATOM | 931 | C | GLU | A | 254 | 38.356 | 30.931 | 4.382 | 1.00 | 18.72 |
| ATOM | 932 | O | GLU | A | 254 | 37.381 | 31.605 | 4.074 | 1.00 | 18.82 |
| ATOM | 933 | CB | GLU | A | 254 | 38.154 | 29.249 | 6.294 | 1.00 | 15.75 |
| ATOM | 934 | CG | GLU | A | 254 | 37.713 | 27.783 | 6.630 | 1.00 | 18.12 |
| ATOM | 935 | CD | GLU | A | 254 | 37.330 | 27.575 | 8.086 | 1.00 | 24.68 |
| ATOM | 936 | OE1 | GLU | A | 254 | 36.515 | 26.652 | 8.377 | 1.00 | 21.86 |
| ATOM | 937 | OE2 | GLU | A | 254 | 37.911 | 28.244 | 8.942 | 1.00 | 21.72 |
| ATOM | 938 | N | ILE | A | 255 | 39.586 | 31.402 | 4.295 | 1.00 | 15.73 |
| ATOM | 939 | CA | ILE | A | 255 | 39.804 | 32.778 | 3.850 | 1.00 | 14.65 |
| ATOM | 940 | C | ILE | A | 255 | 39.419 | 32.895 | 2.358 | 1.00 | 19.30 |
| ATOM | 941 | O | ILE | A | 255 | 38.793 | 33.879 | 1.927 | 1.00 | 19.84 |
| ATOM | 942 | CB | ILE | A | 255 | 41.262 | 33.176 | 4.024 | 1.00 | 17.53 |
| ATOM | 943 | CG1 | ILE | A | 255 | 41.627 | 33.239 | 5.535 | 1.00 | 16.84 |
| ATOM | 944 | CG2 | ILE | A | 255 | 41.530 | 34.547 | 3.337 | 1.00 | 18.68 |
| ATOM | 945 | CD1 | ILE | A | 255 | 43.119 | 33.259 | 5.793 | 1.00 | 18.80 |
| ATOM | 946 | N | VAL | A | 256 | 39.789 | 31.895 | 1.573 | 1.00 | 15.18 |
| ATOM | 947 | CA | VAL | A | 256 | 39.455 | 31.921 | 0.130 | 1.00 | 14.97 |
| ATOM | 948 | C | VAL | A | 256 | 37.944 | 32.003 | −0.031 | 1.00 | 18.45 |
| ATOM | 949 | O | VAL | A | 256 | 37.433 | 32.761 | −0.858 | 1.00 | 17.21 |
| ATOM | 950 | CB | VAL | A | 256 | 39.992 | 30.681 | −0.606 | 1.00 | 17.94 |
| ATOM | 951 | CG1 | VAL | A | 256 | 39.301 | 30.514 | −2.006 | 1.00 | 17.70 |
| ATOM | 952 | CG2 | VAL | A | 256 | 41.494 | 30.796 | −0.770 | 1.00 | 18.03 |
| ATOM | 953 | N | SER | A | 257 | 37.231 | 31.254 | 0.793 | 1.00 | 16.73 |
| ATOM | 954 | CA | SER | A | 257 | 35.775 | 31.266 | 0.751 | 1.00 | 17.10 |
| ATOM | 955 | C | SER | A | 257 | 35.222 | 32.678 | 0.978 | 1.00 | 20.84 |
| ATOM | 956 | O | SER | A | 257 | 34.339 | 33.136 | 0.252 | 1.00 | 19.22 |
| ATOM | 957 | CB | SER | A | 257 | 35.195 | 30.309 | 1.802 | 1.00 | 19.55 |
| ATOM | 958 | OG | SER | A | 257 | 33.770 | 30.312 | 1.749 | 1.00 | 19.86 |
| ATOM | 959 | N | ALA | A | 258 | 35.742 | 33.361 | 1.987 | 1.00 | 18.38 |
| ATOM | 960 | CA | ALA | A | 258 | 35.259 | 34.713 | 2.307 | 1.00 | 18.32 |
| ATOM | 961 | C | ALA | A | 258 | 35.586 | 35.701 | 1.193 | 1.00 | 20.20 |
| ATOM | 962 | O | ALA | A | 258 | 34.762 | 36.521 | 0.836 | 1.00 | 19.37 |
| ATOM | 963 | CB | ALA | A | 258 | 35.834 | 35.199 | 3.633 | 1.00 | 19.01 |
| ATOM | 964 | N | LEU | A | 259 | 36.804 | 35.637 | 0.683 | 1.00 | 17.58 |
| ATOM | 965 | CA | LEU | A | 259 | 37.238 | 36.534 | −0.385 | 1.00 | 17.04 |
| ATOM | 966 | C | LEU | A | 259 | 36.436 | 36.326 | −1.684 | 1.00 | 22.15 |
| ATOM | 967 | O | LEU | A | 259 | 36.124 | 37.290 | −2.396 | 1.00 | 22.41 |
| ATOM | 968 | CB | LEU | A | 259 | 38.740 | 36.391 | −0.626 | 1.00 | 17.05 |
| ATOM | 969 | CG | LEU | A | 259 | 39.636 | 36.948 | 0.493 | 1.00 | 20.78 |
| ATOM | 970 | CD1 | LEU | A | 259 | 41.102 | 36.595 | 0.243 | 1.00 | 21.40 |
| ATOM | 971 | CD2 | LEU | A | 259 | 39.459 | 38.469 | 0.592 | 1.00 | 22.22 |
| ATOM | 972 | N | ASP | A | 260 | 36.116 | 35.073 | −1.989 | 1.00 | 18.28 |
| ATOM | 973 | CA | ASP | A | 260 | 35.325 | 34.729 | −3.184 | 1.00 | 18.19 |
| ATOM | 974 | C | ASP | A | 260 | 33.991 | 35.469 | −3.057 | 1.00 | 22.31 |
| ATOM | 975 | O | ASP | A | 260 | 33.520 | 36.134 | −4.006 | 1.00 | 21.59 |
| ATOM | 976 | CB | ASP | A | 260 | 35.076 | 33.214 | −3.200 | 1.00 | 19.13 |
| ATOM | 977 | CG | ASP | A | 260 | 34.209 | 32.756 | −4.384 | 1.00 | 26.19 |
| ATOM | 978 | OD1 | ASP | A | 260 | 34.255 | 33.387 | −5.460 | 1.00 | 24.58 |
| ATOM | 979 | OD2 | ASP | A | 260 | 33.590 | 31.690 | −4.266 | 1.00 | 26.42 |
| ATOM | 980 | N | TYR | A | 261 | 33.391 | 35.355 | −1.875 | 1.00 | 19.15 |
| ATOM | 981 | CA | TYR | A | 261 | 32.098 | 36.012 | −1.581 | 1.00 | 19.13 |
| ATOM | 982 | C | TYR | A | 261 | 32.187 | 37.539 | −1.697 | 1.00 | 22.28 |
| ATOM | 983 | O | TYR | A | 261 | 31.325 | 38.184 | −2.308 | 1.00 | 21.88 |
| ATOM | 984 | CB | TYR | A | 261 | 31.600 | 35.581 | −0.191 | 1.00 | 21.35 |

TABLE 5-continued

Structural coordinates for AKT3lkd(pT305, S472D).

| ATOM | 985 | CG | TYR | A | 261 | 30.554 | 36.504 | 0.421 | 1.00 | 24.45 |
|------|-----|-----|-----|---|-----|--------|--------|--------|------|-------|
| ATOM | 986 | CD1 | TYR | A | 261 | 29.210 | 36.367 | 0.109 | 1.00 | 26.31 |
| ATOM | 987 | CD2 | TYR | A | 261 | 30.926 | 37.518 | 1.308 | 1.00 | 25.79 |
| ATOM | 988 | CE1 | TYR | A | 261 | 28.241 | 37.216 | 0.682 | 1.00 | 27.00 |
| ATOM | 989 | CE2 | TYR | A | 261 | 29.984 | 38.354 | 1.868 | 1.00 | 26.01 |
| ATOM | 990 | CZ | TYR | A | 261 | 28.649 | 38.206 | 1.547 | 1.00 | 29.91 |
| ATOM | 991 | OH | TYR | A | 261 | 27.725 | 39.050 | 2.126 | 1.00 | 28.11 |
| ATOM | 992 | N | LEU | A | 262 | 33.235 | 38.116 | −1.131 | 1.00 | 19.79 |
| ATOM | 993 | CA | LEU | A | 262 | 33.419 | 39.578 | −1.178 | 1.00 | 20.08 |
| ATOM | 994 | C | LEU | A | 262 | 33.614 | 40.056 | −2.609 | 1.00 | 24.51 |
| ATOM | 995 | O | LEU | A | 262 | 32.943 | 40.986 | −3.064 | 1.00 | 25.23 |
| ATOM | 996 | CB | LEU | A | 262 | 34.590 | 40.012 | −0.296 | 1.00 | 20.05 |
| ATOM | 997 | CG | LEU | A | 262 | 34.356 | 39.837 | 1.219 | 1.00 | 24.63 |
| ATOM | 998 | CD1 | LEU | A | 262 | 35.662 | 40.011 | 1.979 | 1.00 | 24.27 |
| ATOM | 999 | CD2 | LEU | A | 262 | 33.290 | 40.821 | 1.733 | 1.00 | 27.27 |
| ATOM | 1000 | N | HIS | A | 263 | 34.506 | 39.390 | −3.329 | 1.00 | 21.16 |
| ATOM | 1001 | CA | HIS | A | 263 | 34.785 | 39.719 | −4.731 | 1.00 | 20.51 |
| ATOM | 1002 | C | HIS | A | 263 | 33.499 | 39.608 | −5.577 | 1.00 | 28.53 |
| ATOM | 1003 | O | HIS | A | 263 | 33.230 | 40.454 | −6.436 | 1.00 | 30.35 |
| ATOM | 1004 | CB | HIS | A | 263 | 35.854 | 38.760 | −5.285 | 1.00 | 19.95 |
| ATOM | 1005 | CG | HIS | A | 263 | 37.226 | 39.004 | −4.736 | 1.00 | 21.65 |
| ATOM | 1006 | ND1 | HIS | A | 263 | 37.499 | 40.023 | −3.849 | 1.00 | 22.40 |
| ATOM | 1007 | CD2 | HIS | A | 263 | 38.398 | 38.362 | −4.943 | 1.00 | 21.17 |
| ATOM | 1008 | CE1 | HIS | A | 263 | 38.780 | 39.992 | −3.536 | 1.00 | 20.66 |
| ATOM | 1009 | NE2 | HIS | A | 263 | 39.348 | 39.005 | −4.191 | 1.00 | 20.86 |
| ATOM | 1010 | N | SER | A | 264 | 32.709 | 38.572 | −5.324 | 1.00 | 25.71 |
| ATOM | 1011 | CA | SER | A | 264 | 31.450 | 38.380 | −6.058 | 1.00 | 26.64 |
| ATOM | 1012 | C | SER | A | 264 | 30.518 | 39.583 | −5.838 | 1.00 | 31.39 |
| ATOM | 1013 | O | SER | A | 264 | 29.647 | 39.864 | −6.666 | 1.00 | 31.10 |
| ATOM | 1014 | CB | SER | A | 264 | 30.757 | 37.085 | −5.621 | 1.00 | 31.61 |
| ATOM | 1015 | OG | SER | A | 264 | 31.466 | 35.951 | −6.100 | 1.00 | 46.38 |
| ATOM | 1016 | N | GLY | A | 265 | 30.722 | 40.288 | −4.726 | 1.00 | 27.74 |
| ATOM | 1017 | CA | GLY | A | 265 | 29.938 | 41.472 | −4.395 | 1.00 | 28.00 |
| ATOM | 1018 | C | GLY | A | 265 | 30.681 | 42.735 | −4.809 | 1.00 | 32.90 |
| ATOM | 1019 | O | GLY | A | 265 | 30.321 | 43.854 | −4.396 | 1.00 | 32.86 |
| ATOM | 1020 | N | LYS | A | 266 | 31.722 | 42.554 | −5.615 | 1.00 | 28.92 |
| ATOM | 1021 | CA | LYS | A | 266 | 32.538 | 43.658 | −6.099 | 1.00 | 29.13 |
| ATOM | 1022 | C | LYS | A | 266 | 33.233 | 44.442 | −4.992 | 1.00 | 32.40 |
| ATOM | 1023 | O | LYS | A | 266 | 33.476 | 45.644 | −5.130 | 1.00 | 33.03 |
| ATOM | 1024 | CB | LYS | A | 266 | 31.713 | 44.601 | −6.991 | 1.00 | 31.77 |
| ATOM | 1025 | CG | LYS | A | 266 | 30.879 | 43.881 | −8.054 | 1.00 | 43.06 |
| ATOM | 1026 | CD | LYS | A | 266 | 31.722 | 42.933 | −8.875 | 1.00 | 55.44 |
| ATOM | 1027 | CE | LYS | A | 266 | 31.114 | 41.530 | −8.908 | 1.00 | 69.44 |
| ATOM | 1028 | NZ | LYS | A | 266 | 31.823 | 40.637 | −9.872 | 1.00 | 80.26 |
| ATOM | 1029 | N | ILE | A | 267 | 33.556 | 43.765 | −3.893 | 1.00 | 25.64 |
| ATOM | 1030 | CA | ILE | A | 267 | 34.246 | 44.416 | −2.789 | 1.00 | 24.07 |
| ATOM | 1031 | C | ILE | A | 267 | 35.672 | 43.900 | −2.741 | 1.00 | 26.11 |
| ATOM | 1032 | O | ILE | A | 267 | 35.895 | 42.701 | −2.842 | 1.00 | 25.33 |
| ATOM | 1033 | CB | ILE | A | 267 | 33.604 | 44.050 | −1.448 | 1.00 | 26.68 |
| ATOM | 1034 | CG1 | ILE | A | 267 | 32.234 | 44.723 | −1.294 | 1.00 | 27.43 |
| ATOM | 1035 | CG2 | ILE | A | 267 | 34.546 | 44.387 | −0.295 | 1.00 | 25.48 |
| ATOM | 1036 | CD1 | ILE | A | 267 | 31.368 | 44.090 | −0.189 | 1.00 | 33.69 |
| ATOM | 1037 | N | VAL | A | 268 | 36.630 | 44.795 | −2.586 | 1.00 | 23.13 |
| ATOM | 1038 | CA | VAL | A | 268 | 38.042 | 44.385 | −2.447 | 1.00 | 23.39 |
| ATOM | 1039 | C | VAL | A | 268 | 38.343 | 44.568 | −0.967 | 1.00 | 27.13 |
| ATOM | 1040 | O | VAL | A | 268 | 38.114 | 45.647 | −0.433 | 1.00 | 25.95 |
| ATOM | 1041 | CB | VAL | A | 268 | 38.971 | 45.284 | −3.263 | 1.00 | 27.30 |
| ATOM | 1042 | CG1 | VAL | A | 268 | 40.444 | 44.906 | −3.025 | 1.00 | 26.87 |
| ATOM | 1043 | CG2 | VAL | A | 268 | 38.616 | 45.199 | −4.761 | 1.00 | 27.18 |
| ATOM | 1044 | N | TYR | A | 269 | 38.756 | 43.498 | −0.284 | 1.00 | 22.72 |
| ATOM | 1045 | CA | TYR | A | 269 | 38.947 | 43.583 | 1.170 | 1.00 | 22.96 |
| ATOM | 1046 | C | TYR | A | 269 | 40.056 | 44.521 | 1.592 | 1.00 | 25.91 |
| ATOM | 1047 | O | TYR | A | 269 | 39.870 | 45.360 | 2.492 | 1.00 | 25.83 |
| ATOM | 1048 | CB | TYR | A | 269 | 39.122 | 42.210 | 1.826 | 1.00 | 24.68 |
| ATOM | 1049 | CG | TYR | A | 269 | 38.889 | 42.285 | 3.313 | 1.00 | 26.03 |
| ATOM | 1050 | CD1 | TYR | A | 269 | 37.651 | 42.691 | 3.811 | 1.00 | 27.93 |
| ATOM | 1051 | CD2 | TYR | A | 269 | 39.925 | 42.088 | 4.210 | 1.00 | 26.03 |
| ATOM | 1052 | CE1 | TYR | A | 269 | 37.444 | 42.849 | 5.162 | 1.00 | 30.00 |
| ATOM | 1053 | CE2 | TYR | A | 269 | 39.730 | 42.254 | 5.561 | 1.00 | 27.07 |
| ATOM | 1054 | CZ | TYR | A | 269 | 38.483 | 42.617 | 6.035 | 1.00 | 35.09 |
| ATOM | 1055 | OH | TYR | A | 269 | 38.268 | 42.757 | 7.386 | 1.00 | 37.10 |
| ATOM | 1056 | N | ARG | A | 270 | 41.228 | 44.340 | 0.992 | 1.00 | 21.50 |
| ATOM | 1057 | CA | ARG | A | 270 | 42.387 | 45.205 | 1.250 | 1.00 | 21.03 |
| ATOM | 1058 | C | ARG | A | 270 | 43.089 | 44.962 | 2.567 | 1.00 | 25.12 |
| ATOM | 1059 | O | ARG | A | 270 | 44.300 | 45.120 | 2.664 | 1.00 | 26.77 |
| ATOM | 1060 | CB | ARG | A | 270 | 41.958 | 46.705 | 1.220 | 1.00 | 20.05 |
| ATOM | 1061 | CG | ARG | A | 270 | 41.472 | 47.233 | −0.108 | 1.00 | 31.32 |
| ATOM | 1062 | CD | ARG | A | 270 | 41.350 | 48.773 | −0.019 | 1.00 | 42.19 |

TABLE 5-continued

Structural coordinates for AKT3lkd(pT305, S472D).

| ATOM | 1063 | NE  | ARG | A | 270 | 40.671 | 49.366 | −1.169 | 1.00 | 56.79 |
| ---- | ---- | --- | --- | - | --- | ------ | ------ | ------ | ---- | ----- |
| ATOM | 1064 | CZ  | ARG | A | 270 | 40.605 | 50.678 | −1.400 | 1.00 | 68.44 |
| ATOM | 1065 | NH1 | ARG | A | 270 | 41.175 | 51.531 | −0.553 | 1.00 | 50.44 |
| ATOM | 1066 | NH2 | ARG | A | 270 | 39.971 | 51.137 | −2.473 | 1.00 | 54.71 |
| ATOM | 1067 | N   | ASP | A | 271 | 42.320 | 44.654 | 3.595  | 1.00 | 23.00 |
| ATOM | 1068 | CA  | ASP | A | 271 | 42.848 | 44.566 | 4.964  | 1.00 | 22.28 |
| ATOM | 1069 | C   | ASP | A | 271 | 43.256 | 43.174 | 5.468  | 1.00 | 26.98 |
| ATOM | 1070 | O   | ASP | A | 271 | 43.441 | 42.979 | 6.675  | 1.00 | 26.38 |
| ATOM | 1071 | CB  | ASP | A | 271 | 41.846 | 45.185 | 5.938  | 1.00 | 23.81 |
| ATOM | 1072 | CG  | ASP | A | 271 | 41.735 | 46.691 | 5.786  | 1.00 | 34.34 |
| ATOM | 1073 | OD1 | ASP | A | 271 | 42.613 | 47.296 | 5.138  | 1.00 | 35.09 |
| ATOM | 1074 | OD2 | ASP | A | 271 | 40.783 | 47.270 | 6.341  | 1.00 | 40.98 |
| ATOM | 1075 | N   | LEU | A | 272 | 43.416 | 42.220 | 4.567  | 1.00 | 23.10 |
| ATOM | 1076 | CA  | LEU | A | 272 | 43.826 | 40.879 | 4.993  | 1.00 | 23.37 |
| ATOM | 1077 | C   | LEU | A | 272 | 45.273 | 40.893 | 5.478  | 1.00 | 27.02 |
| ATOM | 1078 | O   | LEU | A | 272 | 46.182 | 41.246 | 4.735  | 1.00 | 27.21 |
| ATOM | 1079 | CB  | LEU | A | 272 | 43.674 | 39.880 | 3.844  | 1.00 | 23.00 |
| ATOM | 1080 | CG  | LEU | A | 272 | 44.104 | 38.421 | 4.093  | 1.00 | 26.17 |
| ATOM | 1081 | CD1 | LEU | A | 272 | 43.363 | 37.845 | 5.258  | 1.00 | 26.75 |
| ATOM | 1082 | CD2 | LEU | A | 272 | 43.831 | 37.596 | 2.842  | 1.00 | 24.37 |
| ATOM | 1083 | N   | LYS | A | 273 | 45.467 | 40.531 | 6.739  | 1.00 | 23.00 |
| ATOM | 1084 | CA  | LYS | A | 273 | 46.792 | 40.422 | 7.322  | 1.00 | 22.87 |
| ATOM | 1085 | C   | LYS | A | 273 | 46.659 | 39.494 | 8.502  | 1.00 | 25.35 |
| ATOM | 1086 | O   | LYS | A | 273 | 45.565 | 39.263 | 8.984  | 1.00 | 23.89 |
| ATOM | 1087 | CB  | LYS | A | 273 | 47.315 | 41.805 | 7.777  | 1.00 | 25.18 |
| ATOM | 1088 | CG  | LYS | A | 273 | 46.446 | 42.491 | 8.790  | 1.00 | 29.31 |
| ATOM | 1089 | CD  | LYS | A | 273 | 46.934 | 43.928 | 9.051  | 1.00 | 39.76 |
| ATOM | 1090 | CE  | LYS | A | 273 | 46.637 | 44.832 | 7.858  | 1.00 | 46.69 |
| ATOM | 1091 | NZ  | LYS | A | 273 | 47.078 | 46.242 | 8.086  | 1.00 | 57.60 |
| ATOM | 1092 | N   | LEU | A | 274 | 47.766 | 38.931 | 8.955  | 1.00 | 23.65 |
| ATOM | 1093 | CA  | LEU | A | 274 | 47.716 | 37.969 | 10.053 | 1.00 | 23.68 |
| ATOM | 1094 | C   | LEU | A | 274 | 47.057 | 38.558 | 11.291 | 1.00 | 27.72 |
| ATOM | 1095 | O   | LEU | A | 274 | 46.300 | 37.876 | 11.988 | 1.00 | 24.97 |
| ATOM | 1096 | CB  | LEU | A | 274 | 49.112 | 37.444 | 10.384 | 1.00 | 23.70 |
| ATOM | 1097 | CG  | LEU | A | 274 | 49.184 | 36.318 | 11.411 | 1.00 | 27.73 |
| ATOM | 1098 | CD1 | LEU | A | 274 | 48.546 | 35.039 | 10.864 | 1.00 | 27.18 |
| ATOM | 1099 | CD2 | LEU | A | 274 | 50.657 | 36.072 | 11.791 | 1.00 | 31.40 |
| ATOM | 1100 | N   | GLU | A | 275 | 47.333 | 39.839 | 11.542 | 1.00 | 26.56 |
| ATOM | 1101 | CA  | GLU | A | 275 | 46.778 | 40.547 | 12.698 | 1.00 | 27.48 |
| ATOM | 1102 | C   | GLU | A | 275 | 45.251 | 40.687 | 12.629 | 1.00 | 30.83 |
| ATOM | 1103 | O   | GLU | A | 275 | 44.603 | 41.013 | 13.625 | 1.00 | 31.36 |
| ATOM | 1104 | CB  | GLU | A | 275 | 47.426 | 41.940 | 12.816 | 1.00 | 29.22 |
| ATOM | 1105 | CG  | GLU | A | 275 | 48.952 | 41.924 | 13.094 | 1.00 | 42.00 |
| ATOM | 1106 | CD  | GLU | A | 275 | 49.771 | 41.204 | 12.008 | 1.00 | 63.19 |
| ATOM | 1107 | OE1 | GLU | A | 275 | 49.420 | 41.297 | 10.809 | 1.00 | 41.92 |
| ATOM | 1108 | OE2 | GLU | A | 275 | 50.792 | 40.575 | 12.362 | 1.00 | 64.19 |
| ATOM | 1109 | N   | ASN | A | 276 | 44.682 | 40.456 | 11.451 | 1.00 | 25.02 |
| ATOM | 1110 | CA  | ASN | A | 276 | 43.227 | 40.556 | 11.273 | 1.00 | 23.79 |
| ATOM | 1111 | C   | ASN | A | 276 | 42.555 | 39.196 | 11.176 | 1.00 | 25.70 |
| ATOM | 1112 | O   | ASN | A | 276 | 41.437 | 39.071 | 10.691 | 1.00 | 24.86 |
| ATOM | 1113 | CB  | ASN | A | 276 | 42.890 | 41.407 | 10.057 | 1.00 | 19.52 |
| ATOM | 1114 | CG  | ASN | A | 276 | 43.022 | 42.889 | 10.348 | 1.00 | 34.17 |
| ATOM | 1115 | OD1 | ASN | A | 276 | 43.023 | 43.298 | 11.499 | 1.00 | 31.53 |
| ATOM | 1116 | ND2 | ASN | A | 276 | 43.176 | 43.681 | 9.319  | 1.00 | 24.05 |
| ATOM | 1117 | N   | LEU | A | 277 | 43.245 | 38.181 | 11.652 | 1.00 | 21.55 |
| ATOM | 1118 | CA  | LEU | A | 277 | 42.719 | 36.832 | 11.633 | 1.00 | 20.07 |
| ATOM | 1119 | C   | LEU | A | 277 | 42.630 | 36.318 | 13.059 | 1.00 | 24.54 |
| ATOM | 1120 | O   | LEU | A | 277 | 43.613 | 36.350 | 13.803 | 1.00 | 23.43 |
| ATOM | 1121 | CB  | LEU | A | 277 | 43.656 | 35.918 | 10.821 | 1.00 | 19.75 |
| ATOM | 1122 | CG  | LEU | A | 277 | 43.814 | 36.278 | 9.341  | 1.00 | 22.82 |
| ATOM | 1123 | CD1 | LEU | A | 277 | 44.722 | 35.258 | 8.696  | 1.00 | 21.85 |
| ATOM | 1124 | CD2 | LEU | A | 277 | 42.438 | 36.268 | 8.677  | 1.00 | 23.61 |
| ATOM | 1125 | N   | MET | A | 278 | 41.452 | 35.837 | 13.427 | 1.00 | 23.67 |
| ATOM | 1126 | CA  | MET | A | 278 | 41.227 | 35.257 | 14.735 | 1.00 | 25.20 |
| ATOM | 1127 | C   | MET | A | 278 | 40.499 | 33.930 | 14.560 | 1.00 | 27.09 |
| ATOM | 1128 | O   | MET | A | 278 | 39.984 | 33.630 | 13.488 | 1.00 | 26.17 |
| ATOM | 1129 | CB  | MET | A | 278 | 40.364 | 36.187 | 15.584 | 1.00 | 28.68 |
| ATOM | 1130 | CG  | MET | A | 278 | 41.049 | 37.482 | 15.984 | 1.00 | 34.46 |
| ATOM | 1131 | SD  | MET | A | 278 | 40.045 | 38.396 | 17.133 | 1.00 | 41.14 |
| ATOM | 1132 | CE  | MET | A | 278 | 39.742 | 37.159 | 18.373 | 1.00 | 38.12 |
| ATOM | 1133 | N   | LEU | A | 279 | 40.468 | 33.138 | 15.614 | 1.00 | 22.48 |
| ATOM | 1134 | CA  | LEU | A | 279 | 39.735 | 31.883 | 15.587 | 1.00 | 22.26 |
| ATOM | 1135 | C   | LEU | A | 279 | 38.498 | 32.008 | 16.457 | 1.00 | 25.93 |
| ATOM | 1136 | O   | LEU | A | 279 | 38.546 | 32.632 | 17.512 | 1.00 | 25.66 |
| ATOM | 1137 | CB  | LEU | A | 279 | 40.599 | 30.750 | 16.134 | 1.00 | 22.27 |
| ATOM | 1138 | CG  | LEU | A | 279 | 41.909 | 30.453 | 15.417 | 1.00 | 27.39 |
| ATOM | 1139 | CD1 | LEU | A | 279 | 42.590 | 29.246 | 16.106 | 1.00 | 27.90 |
| ATOM | 1140 | CD2 | LEU | A | 279 | 41.630 | 30.160 | 13.921 | 1.00 | 28.68 |

TABLE 5-continued

Structural coordinates for AKT3lkd(pT305, S472D).

| ATOM | 1141 | N   | ASP | A | 280 | 37.400 | 31.383 | 16.049 | 1.00 | 22.56 |
| ---- | ---- | --- | --- | - | --- | ------ | ------ | ------ | ---- | ----- |
| ATOM | 1142 | CA  | ASP | A | 280 | 36.216 | 31.357 | 16.915 | 1.00 | 22.37 |
| ATOM | 1143 | C   | ASP | A | 280 | 36.381 | 30.205 | 17.898 | 1.00 | 26.87 |
| ATOM | 1144 | O   | ASP | A | 280 | 37.367 | 29.474 | 17.840 | 1.00 | 24.50 |
| ATOM | 1145 | CB  | ASP | A | 280 | 34.900 | 31.252 | 16.131 | 1.00 | 23.66 |
| ATOM | 1146 | CG  | ASP | A | 280 | 34.787 | 29.956 | 15.302 | 1.00 | 25.44 |
| ATOM | 1147 | OD1 | ASP | A | 280 | 35.435 | 28.926 | 15.645 | 1.00 | 25.56 |
| ATOM | 1148 | OD2 | ASP | A | 280 | 33.973 | 29.956 | 14.346 | 1.00 | 23.02 |
| ATOM | 1149 | N   | LYS | A | 281 | 35.420 | 30.047 | 18.798 | 1.00 | 26.93 |
| ATOM | 1150 | CA  | LYS | A | 281 | 35.482 | 29.007 | 19.831 | 1.00 | 26.99 |
| ATOM | 1151 | C   | LYS | A | 281 | 35.729 | 27.612 | 19.281 | 1.00 | 29.53 |
| ATOM | 1152 | O   | LYS | A | 281 | 36.304 | 26.760 | 19.964 | 1.00 | 30.75 |
| ATOM | 1153 | CB  | LYS | A | 281 | 34.182 | 29.010 | 20.663 | 1.00 | 29.69 |
| ATOM | 1154 | CG  | LYS | A | 281 | 33.011 | 28.304 | 19.994 | 1.00 | 42.05 |
| ATOM | 1155 | CD  | LYS | A | 281 | 31.733 | 28.465 | 20.803 | 1.00 | 53.01 |
| ATOM | 1156 | CE  | LYS | A | 281 | 30.573 | 28.889 | 19.921 | 1.00 | 60.16 |
| ATOM | 1157 | NZ  | LYS | A | 281 | 29.593 | 27.789 | 19.731 | 1.00 | 71.08 |
| ATOM | 1158 | N   | ASP | A | 282 | 35.253 | 27.363 | 18.064 | 1.00 | 24.92 |
| ATOM | 1159 | CA  | ASP | A | 282 | 35.362 | 26.039 | 17.440 | 1.00 | 23.52 |
| ATOM | 1160 | C   | ASP | A | 282 | 36.659 | 25.849 | 16.625 | 1.00 | 26.31 |
| ATOM | 1161 | O   | ASP | A | 282 | 37.001 | 24.727 | 16.229 | 1.00 | 25.17 |
| ATOM | 1162 | CB  | ASP | A | 282 | 34.147 | 25.767 | 16.560 | 1.00 | 24.81 |
| ATOM | 1163 | CG  | ASP | A | 282 | 32.856 | 25.698 | 17.355 | 1.00 | 31.85 |
| ATOM | 1164 | OD1 | ASP | A | 282 | 32.853 | 25.048 | 18.420 | 1.00 | 31.80 |
| ATOM | 1165 | OD2 | ASP | A | 282 | 31.873 | 26.352 | 16.953 | 1.00 | 34.43 |
| ATOM | 1166 | N   | GLY | A | 283 | 37.386 | 26.938 | 16.401 | 1.00 | 22.80 |
| ATOM | 1167 | CA  | GLY | A | 283 | 38.661 | 26.870 | 15.662 | 1.00 | 21.74 |
| ATOM | 1168 | C   | GLY | A | 283 | 38.516 | 27.224 | 14.171 | 1.00 | 23.86 |
| ATOM | 1169 | O   | GLY | A | 283 | 39.450 | 27.012 | 13.385 | 1.00 | 20.79 |
| ATOM | 1170 | N   | HIS | A | 284 | 37.353 | 27.745 | 13.781 | 1.00 | 19.93 |
| ATOM | 1171 | CA  | HIS | A | 284 | 37.183 | 28.200 | 12.395 | 1.00 | 19.90 |
| ATOM | 1172 | C   | HIS | A | 284 | 37.690 | 29.632 | 12.346 | 1.00 | 24.41 |
| ATOM | 1173 | O   | HIS | A | 284 | 37.746 | 30.309 | 13.378 | 1.00 | 24.47 |
| ATOM | 1174 | CB  | HIS | A | 284 | 35.708 | 28.153 | 11.955 | 1.00 | 20.11 |
| ATOM | 1175 | CG  | HIS | A | 284 | 35.204 | 26.769 | 11.716 | 1.00 | 22.64 |
| ATOM | 1176 | ND1 | HIS | A | 284 | 35.488 | 26.063 | 10.568 | 1.00 | 24.09 |
| ATOM | 1177 | CD2 | HIS | A | 284 | 34.434 | 25.958 | 12.480 | 1.00 | 24.35 |
| ATOM | 1178 | CE1 | HIS | A | 284 | 34.925 | 24.868 | 10.641 | 1.00 | 23.83 |
| ATOM | 1179 | NE2 | HIS | A | 284 | 34.300 | 24.771 | 11.802 | 1.00 | 24.00 |
| ATOM | 1180 | N   | ILE | A | 285 | 38.075 | 30.077 | 11.159 | 1.00 | 20.78 |
| ATOM | 1181 | CA  | ILE | A | 285 | 38.645 | 31.416 | 10.960 | 1.00 | 21.19 |
| ATOM | 1182 | C   | ILE | A | 285 | 37.609 | 32.498 | 11.083 | 1.00 | 24.09 |
| ATOM | 1183 | O   | ILE | A | 285 | 36.436 | 32.301 | 10.746 | 1.00 | 22.25 |
| ATOM | 1184 | CB  | ILE | A | 285 | 39.243 | 31.557 | 9.486  | 1.00 | 25.28 |
| ATOM | 1185 | CG1 | ILE | A | 285 | 40.709 | 31.099 | 9.432  | 1.00 | 26.87 |
| ATOM | 1186 | CG2 | ILE | A | 285 | 39.110 | 32.990 | 8.979  | 1.00 | 27.60 |
| ATOM | 1187 | CD1 | ILE | A | 285 | 41.692 | 32.093 | 10.058 | 1.00 | 34.62 |
| ATOM | 1188 | N   | LYS | A | 286 | 38.069 | 33.681 | 11.478 | 1.00 | 21.13 |
| ATOM | 1189 | CA  | LYS | A | 286 | 37.229 | 34.871 | 11.493 | 1.00 | 20.69 |
| ATOM | 1190 | C   | LYS | A | 286 | 38.096 | 36.058 | 11.073 | 1.00 | 24.88 |
| ATOM | 1191 | O   | LYS | A | 286 | 39.075 | 36.374 | 11.733 | 1.00 | 26.25 |
| ATOM | 1192 | CB  | LYS | A | 286 | 36.653 | 35.150 | 12.882 | 1.00 | 22.31 |
| ATOM | 1193 | CG  | LYS | A | 286 | 35.429 | 36.034 | 12.836 | 1.00 | 32.32 |
| ATOM | 1194 | CD  | LYS | A | 286 | 34.302 | 35.352 | 12.100 | 1.00 | 36.50 |
| ATOM | 1195 | CE  | LYS | A | 286 | 33.634 | 34.309 | 12.981 | 1.00 | 34.28 |
| ATOM | 1196 | NZ  | LYS | A | 286 | 32.281 | 33.926 | 12.478 | 1.00 | 34.39 |
| ATOM | 1197 | N   | ILE | A | 287 | 37.762 | 36.670 | 9.951  | 1.00 | 20.80 |
| ATOM | 1198 | CA  | ILE | A | 287 | 38.492 | 37.849 | 9.492  | 1.00 | 20.89 |
| ATOM | 1199 | C   | ILE | A | 287 | 37.928 | 39.028 | 10.264 | 1.00 | 28.14 |
| ATOM | 1200 | O   | ILE | A | 287 | 36.715 | 39.289 | 10.217 | 1.00 | 26.80 |
| ATOM | 1201 | CB  | ILE | A | 287 | 38.322 | 38.058 | 7.977  | 1.00 | 24.08 |
| ATOM | 1202 | CG1 | ILE | A | 287 | 38.835 | 36.807 | 7.230  | 1.00 | 23.64 |
| ATOM | 1203 | CG2 | ILE | A | 287 | 39.059 | 39.325 | 7.535  | 1.00 | 24.99 |
| ATOM | 1204 | CD1 | ILE | A | 287 | 38.442 | 36.748 | 5.758  | 1.00 | 27.05 |
| ATOM | 1205 | N   | THR | A | 288 | 38.785 | 39.659 | 11.071 | 1.00 | 27.25 |
| ATOM | 1206 | CA  | THR | A | 288 | 38.360 | 40.745 | 11.961 | 1.00 | 28.94 |
| ATOM | 1207 | C   | THR | A | 288 | 39.014 | 42.082 | 11.604 | 1.00 | 37.77 |
| ATOM | 1208 | O   | THR | A | 288 | 39.603 | 42.216 | 10.528 | 1.00 | 37.89 |
| ATOM | 1209 | CB  | THR | A | 288 | 38.648 | 40.386 | 13.456 | 1.00 | 32.52 |
| ATOM | 1210 | OG1 | THR | A | 288 | 40.060 | 40.303 | 13.667 | 1.00 | 34.15 |
| ATOM | 1211 | CG2 | THR | A | 288 | 38.039 | 39.037 | 13.810 | 1.00 | 31.11 |
| ATOM | 1212 | N   | ASP | A | 289 | 38.628 | 43.123 | 12.339 | 1.00 | 37.17 |
| ATOM | 1213 | C   | THR | A | 309 | 51.621 | 47.040 | 5.888  | 1.00 | 43.22 |
| ATOM | 1214 | O   | THR | A | 309 | 51.248 | 46.669 | 4.778  | 1.00 | 42.21 |
| ATOM | 1215 | N   | PRO | A | 310 | 52.754 | 47.708 | 6.073  | 1.00 | 39.90 |
| ATOM | 1216 | CA  | PRO | A | 310 | 53.654 | 47.996 | 4.958  | 1.00 | 39.00 |
| ATOM | 1217 | C   | PRO | A | 310 | 54.195 | 46.692 | 4.328  | 1.00 | 41.25 |
| ATOM | 1218 | O   | PRO | A | 310 | 54.402 | 46.610 | 3.109  | 1.00 | 39.94 |

TABLE 5-continued

Structural coordinates for AKT3lkd(pT305, S472D).

| ATOM | 1219 | CB | PRO | A | 310 | 54.791 | 48.773 | 5.629 | 1.00 | 40.69 |
|---|---|---|---|---|---|---|---|---|---|---|
| ATOM | 1220 | CG | PRO | A | 310 | 54.128 | 49.466 | 6.842 | 1.00 | 45.39 |
| ATOM | 1221 | CD | PRO | A | 310 | 52.787 | 48.763 | 7.100 | 1.00 | 40.84 |
| ATOM | 1222 | N | GLU | A | 311 | 54.427 | 45.690 | 5.171 | 1.00 | 37.82 |
| ATOM | 1223 | CA | GLU | A | 311 | 54.951 | 44.399 | 4.726 | 1.00 | 36.75 |
| ATOM | 1224 | C | GLU | A | 311 | 53.908 | 43.617 | 3.931 | 1.00 | 37.83 |
| ATOM | 1225 | O | GLU | A | 311 | 54.214 | 42.562 | 3.351 | 1.00 | 36.78 |
| ATOM | 1226 | CB | GLU | A | 311 | 55.414 | 43.569 | 5.929 | 1.00 | 38.19 |
| ATOM | 1227 | CG | GLU | A | 311 | 54.524 | 43.710 | 7.176 | 1.00 | 47.75 |
| ATOM | 1228 | CD | GLU | A | 311 | 54.771 | 45.012 | 7.941 | 1.00 | 63.57 |
| ATOM | 1229 | OE1 | GLU | A | 311 | 54.061 | 45.267 | 8.934 | 1.00 | 57.91 |
| ATOM | 1230 | OE2 | GLU | A | 311 | 55.669 | 45.783 | 7.542 | 1.00 | 52.21 |
| ATOM | 1231 | N | TYR | A | 312 | 52.674 | 44.112 | 3.936 | 1.00 | 32.50 |
| ATOM | 1232 | CA | TYR | A | 312 | 51.586 | 43.451 | 3.240 | 1.00 | 31.90 |
| ATOM | 1233 | C | TYR | A | 312 | 51.242 | 44.143 | 1.932 | 1.00 | 35.13 |
| ATOM | 1234 | O | TYR | A | 312 | 50.411 | 43.656 | 1.172 | 1.00 | 34.77 |
| ATOM | 1235 | CB | TYR | A | 312 | 50.339 | 43.394 | 4.126 | 1.00 | 32.68 |
| ATOM | 1236 | CG | TYR | A | 312 | 50.385 | 42.296 | 5.176 | 1.00 | 33.91 |
| ATOM | 1237 | CD1 | TYR | A | 312 | 50.959 | 42.528 | 6.413 | 1.00 | 35.61 |
| ATOM | 1238 | CD2 | TYR | A | 312 | 49.859 | 41.022 | 4.918 | 1.00 | 34.65 |
| ATOM | 1239 | CE1 | TYR | A | 312 | 51.019 | 41.538 | 7.381 | 1.00 | 36.87 |
| ATOM | 1240 | CE2 | TYR | A | 312 | 49.923 | 40.006 | 5.888 | 1.00 | 35.68 |
| ATOM | 1241 | CZ | TYR | A | 312 | 50.503 | 40.281 | 7.117 | 1.00 | 43.23 |
| ATOM | 1242 | OH | TYR | A | 312 | 50.553 | 39.320 | 8.103 | 1.00 | 43.97 |
| ATOM | 1243 | N | LEU | A | 313 | 51.852 | 45.299 | 1.686 | 1.00 | 30.68 |
| ATOM | 1244 | CA | LEU | A | 313 | 51.555 | 46.060 | 0.469 | 1.00 | 29.34 |
| ATOM | 1245 | C | LEU | A | 313 | 51.878 | 45.296 | −0.806 | 1.00 | 30.43 |
| ATOM | 1246 | O | LEU | A | 313 | 53.005 | 44.869 | −1.009 | 1.00 | 29.40 |
| ATOM | 1247 | CB | LEU | A | 313 | 52.318 | 47.392 | 0.467 | 1.00 | 29.28 |
| ATOM | 1248 | CG | LEU | A | 313 | 51.986 | 48.359 | 1.601 | 1.00 | 33.34 |
| ATOM | 1249 | CD1 | LEU | A | 313 | 52.729 | 49.681 | 1.390 | 1.00 | 33.96 |
| ATOM | 1250 | CD2 | LEU | A | 313 | 50.500 | 48.579 | 1.645 | 1.00 | 34.61 |
| ATOM | 1251 | N | ALA | A | 314 | 50.914 | 45.218 | −1.712 | 1.00 | 26.89 |
| ATOM | 1252 | CA | ALA | A | 314 | 51.145 | 44.539 | −2.995 | 1.00 | 27.17 |
| ATOM | 1253 | C | ALA | A | 314 | 51.972 | 45.444 | −3.920 | 1.00 | 31.91 |
| ATOM | 1254 | O | ALA | A | 314 | 51.908 | 46.676 | −3.819 | 1.00 | 31.62 |
| ATOM | 1255 | CB | ALA | A | 314 | 49.805 | 44.164 | −3.651 | 1.00 | 27.90 |
| ATOM | 1256 | N | PRO | A | 315 | 52.744 | 44.833 | −4.816 | 1.00 | 28.82 |
| ATOM | 1257 | CA | PRO | A | 315 | 53.590 | 45.594 | −5.736 | 1.00 | 28.69 |
| ATOM | 1258 | C | PRO | A | 315 | 52.822 | 46.638 | −6.543 | 1.00 | 31.85 |
| ATOM | 1259 | O | PRO | A | 315 | 53.316 | 47.752 | −6.741 | 1.00 | 31.05 |
| ATOM | 1260 | CB | PRO | A | 315 | 54.167 | 44.522 | −6.659 | 1.00 | 30.65 |
| ATOM | 1261 | CG | PRO | A | 315 | 54.127 | 43.262 | −5.843 | 1.00 | 34.81 |
| ATOM | 1262 | CD | PRO | A | 315 | 52.852 | 43.381 | −5.045 | 1.00 | 29.84 |
| ATOM | 1263 | N | GLU | A | 316 | 51.613 | 46.284 | −6.999 | 1.00 | 28.05 |
| ATOM | 1264 | CA | GLU | A | 316 | 50.800 | 47.199 | −7.799 | 1.00 | 27.52 |
| ATOM | 1265 | C | GLU | A | 316 | 50.315 | 48.406 | −7.002 | 1.00 | 34.56 |
| ATOM | 1266 | O | GLU | A | 316 | 50.040 | 49.472 | −7.575 | 1.00 | 35.06 |
| ATOM | 1267 | CB | GLU | A | 316 | 49.618 | 46.478 | −8.449 | 1.00 | 28.35 |
| ATOM | 1268 | CG | GLU | A | 316 | 48.609 | 45.951 | −7.473 | 1.00 | 28.96 |
| ATOM | 1269 | CD | GLU | A | 316 | 48.802 | 44.482 | −7.202 | 1.00 | 33.72 |
| ATOM | 1270 | OE1 | GLU | A | 316 | 49.961 | 44.023 | −7.241 | 1.00 | 24.60 |
| ATOM | 1271 | OE2 | GLU | A | 316 | 47.795 | 43.784 | −6.968 | 1.00 | 29.37 |
| ATOM | 1272 | N | VAL | A | 317 | 50.217 | 48.244 | −5.684 | 1.00 | 31.77 |
| ATOM | 1273 | CA | VAL | A | 317 | 49.809 | 49.333 | −4.810 | 1.00 | 32.42 |
| ATOM | 1274 | C | VAL | A | 317 | 51.003 | 50.263 | −4.655 | 1.00 | 37.64 |
| ATOM | 1275 | O | VAL | A | 317 | 50.870 | 51.482 | −4.718 | 1.00 | 37.43 |
| ATOM | 1276 | CB | VAL | A | 317 | 49.378 | 48.829 | −3.434 | 1.00 | 36.77 |
| ATOM | 1277 | CG1 | VAL | A | 317 | 49.359 | 49.983 | −2.429 | 1.00 | 36.70 |
| ATOM | 1278 | CG2 | VAL | A | 317 | 48.012 | 48.156 | −3.520 | 1.00 | 36.60 |
| ATOM | 1279 | N | LEU | A | 318 | 52.179 | 49.665 | −4.507 | 1.00 | 34.98 |
| ATOM | 1280 | CA | LEU | A | 318 | 53.437 | 50.409 | −4.421 | 1.00 | 35.95 |
| ATOM | 1281 | C | LEU | A | 318 | 53.699 | 51.195 | −5.720 | 1.00 | 42.84 |
| ATOM | 1282 | O | LEU | A | 318 | 54.141 | 52.345 | −5.683 | 1.00 | 42.19 |
| ATOM | 1283 | CB | LEU | A | 318 | 54.595 | 49.438 | −4.188 | 1.00 | 35.85 |
| ATOM | 1284 | CG | LEU | A | 318 | 54.677 | 48.801 | −2.803 | 1.00 | 40.60 |
| ATOM | 1285 | CD1 | LEU | A | 318 | 56.021 | 48.078 | −2.622 | 1.00 | 40.77 |
| ATOM | 1286 | CD2 | LEU | A | 318 | 54.476 | 49.850 | −1.736 | 1.00 | 43.06 |
| ATOM | 1287 | N | GLU | A | 319 | 53.457 | 50.552 | −6.861 | 1.00 | 42.01 |
| ATOM | 1288 | CA | GLU | A | 319 | 53.663 | 51.198 | −8.157 | 1.00 | 43.38 |
| ATOM | 1289 | C | GLU | A | 319 | 52.649 | 52.326 | −8.351 | 1.00 | 53.01 |
| ATOM | 1290 | O | GLU | A | 319 | 52.604 | 52.975 | −9.401 | 1.00 | 52.75 |
| ATOM | 1291 | CB | GLU | A | 319 | 53.595 | 50.186 | −9.294 | 1.00 | 44.73 |
| ATOM | 1292 | CG | GLU | A | 319 | 54.669 | 49.117 | −9.221 | 1.00 | 55.76 |
| ATOM | 1293 | CD | GLU | A | 319 | 55.547 | 49.083 | −10.456 | 1.00 | 78.58 |
| ATOM | 1294 | OE1 | GLU | A | 319 | 56.690 | 49.581 | −10.387 | 1.00 | 74.22 |
| ATOM | 1295 | OE2 | GLU | A | 319 | 55.101 | 48.546 | −11.492 | 1.00 | 75.75 |
| ATOM | 1296 | N | ASP | A | 320 | 51.865 | 52.571 | −7.305 | 1.00 | 53.92 |

TABLE 5-continued

Structural coordinates for AKT3lkd(pT305, S472D).

| ATOM | 1297 | CA | ASP | A | 320 | 50.898 | 53.662 | −7.281 | 1.00 | 55.52 |
|---|---|---|---|---|---|---|---|---|---|---|
| ATOM | 1298 | C | ASP | A | 320 | 49.675 | 53.455 | −8.163 | 1.00 | 61.17 |
| ATOM | 1299 | O | ASP | A | 320 | 49.688 | 52.656 | −9.102 | 1.00 | 60.69 |
| ATOM | 1300 | CB | ASP | A | 320 | 51.581 | 54.995 | −7.632 | 1.00 | 57.77 |
| ATOM | 1301 | CG | ASP | A | 320 | 51.392 | 56.051 | −6.554 | 1.00 | 70.56 |
| ATOM | 1302 | OD1 | ASP | A | 320 | 51.819 | 55.813 | −5.401 | 1.00 | 71.63 |
| ATOM | 1303 | OD2 | ASP | A | 320 | 50.824 | 57.123 | −6.863 | 1.00 | 77.03 |
| ATOM | 1304 | N | ASN | A | 321 | 48.621 | 54.195 | −7.839 | 1.00 | 59.27 |
| ATOM | 1305 | CA | ASN | A | 321 | 47.384 | 54.189 | −8.607 | 1.00 | 59.39 |
| ATOM | 1306 | C | ASN | A | 321 | 46.582 | 52.887 | −8.612 | 1.00 | 63.00 |
| ATOM | 1307 | O | ASN | A | 321 | 46.027 | 52.471 | −7.585 | 1.00 | 63.28 |
| ATOM | 1308 | CB | ASN | A | 321 | 47.634 | 54.668 | −10.038 | 1.00 | 61.21 |
| ATOM | 1309 | CG | ASN | A | 321 | 47.943 | 56.152 | −10.110 | 1.00 | 84.77 |
| ATOM | 1310 | OD1 | ASN | A | 321 | 47.038 | 56.984 | −10.158 | 1.00 | 76.91 |
| ATOM | 1311 | ND2 | ASN | A | 321 | 49.225 | 56.491 | −10.088 | 1.00 | 78.06 |
| ATOM | 1312 | N | ASP | A | 322 | 46.485 | 52.280 | −9.795 | 1.00 | 57.88 |
| ATOM | 1313 | CA | ASP | A | 322 | 45.664 | 51.092 | −10.009 | 1.00 | 56.47 |
| ATOM | 1314 | C | ASP | A | 322 | 45.955 | 49.842 | −9.172 | 1.00 | 56.87 |
| ATOM | 1315 | O | ASP | A | 322 | 47.073 | 49.621 | −8.703 | 1.00 | 57.05 |
| ATOM | 1316 | CB | ASP | A | 322 | 45.572 | 50.748 | −11.499 | 1.00 | 58.39 |
| ATOM | 1317 | CG | ASP | A | 322 | 44.989 | 51.889 | −12.330 | 1.00 | 70.26 |
| ATOM | 1318 | OD1 | ASP | A | 322 | 44.787 | 52.995 | −11.775 | 1.00 | 71.27 |
| ATOM | 1319 | OD2 | ASP | A | 322 | 44.716 | 51.673 | −13.531 | 1.00 | 76.32 |
| ATOM | 1320 | N | TYR | A | 323 | 44.916 | 49.029 | −9.021 | 1.00 | 49.71 |
| ATOM | 1321 | CA | TYR | A | 323 | 44.948 | 47.774 | −8.278 | 1.00 | 47.68 |
| ATOM | 1322 | C | TYR | A | 323 | 43.501 | 47.390 | −8.013 | 1.00 | 45.89 |
| ATOM | 1323 | O | TYR | A | 323 | 42.595 | 48.219 | −8.150 | 1.00 | 45.48 |
| ATOM | 1324 | CB | TYR | A | 323 | 45.724 | 47.916 | −6.956 | 1.00 | 49.53 |
| ATOM | 1325 | CG | TYR | A | 323 | 45.044 | 48.769 | −5.912 | 1.00 | 52.51 |
| ATOM | 1326 | CD1 | TYR | A | 323 | 43.965 | 48.284 | −5.183 | 1.00 | 54.62 |
| ATOM | 1327 | CD2 | TYR | A | 323 | 45.507 | 50.045 | −5.626 | 1.00 | 54.10 |
| ATOM | 1328 | CE1 | TYR | A | 323 | 43.351 | 49.056 | −4.219 | 1.00 | 56.21 |
| ATOM | 1329 | CE2 | TYR | A | 323 | 44.902 | 50.825 | −4.661 | 1.00 | 55.46 |
| ATOM | 1330 | CZ | TYR | A | 323 | 43.822 | 50.329 | −3.963 | 1.00 | 64.49 |
| ATOM | 1331 | OH | TYR | A | 323 | 43.217 | 51.106 | −3.001 | 1.00 | 68.42 |
| ATOM | 1332 | N | GLY | A | 324 | 43.268 | 46.135 | −7.663 | 1.00 | 36.70 |
| ATOM | 1333 | CA | GLY | A | 324 | 41.911 | 45.681 | −7.429 | 1.00 | 33.64 |
| ATOM | 1334 | C | GLY | A | 324 | 41.888 | 44.396 | −6.626 | 1.00 | 30.57 |
| ATOM | 1335 | O | GLY | A | 324 | 42.704 | 44.194 | −5.732 | 1.00 | 26.82 |
| ATOM | 1336 | N | ARG | A | 325 | 40.934 | 43.530 | −6.949 | 1.00 | 24.35 |
| ATOM | 1337 | CA | ARG | A | 325 | 40.762 | 42.282 | −6.213 | 1.00 | 22.82 |
| ATOM | 1338 | C | ARG | A | 325 | 42.044 | 41.473 | −6.066 | 1.00 | 24.88 |
| ATOM | 1339 | O | ARG | A | 325 | 42.206 | 40.750 | −5.095 | 1.00 | 23.82 |
| ATOM | 1340 | CB | ARG | A | 325 | 39.655 | 41.441 | −6.837 | 1.00 | 20.75 |
| ATOM | 1341 | CG | ARG | A | 325 | 39.966 | 41.000 | −8.257 | 1.00 | 26.97 |
| ATOM | 1342 | CD | ARG | A | 325 | 38.712 | 40.507 | −8.979 | 1.00 | 28.55 |
| ATOM | 1343 | NE | ARG | A | 325 | 38.957 | 40.393 | −10.415 | 1.00 | 32.10 |
| ATOM | 1344 | CZ | ARG | A | 325 | 39.702 | 39.450 | −10.980 | 1.00 | 41.48 |
| ATOM | 1345 | NH1 | ARG | A | 325 | 40.238 | 38.487 | −10.236 | 1.00 | 22.37 |
| ATOM | 1346 | NH2 | ARG | A | 325 | 39.892 | 39.456 | −12.299 | 1.00 | 31.77 |
| ATOM | 1347 | N | ALA | A | 326 | 42.946 | 41.574 | −7.047 | 1.00 | 21.30 |
| ATOM | 1348 | CA | ALA | A | 326 | 44.202 | 40.829 | −6.996 | 1.00 | 21.34 |
| ATOM | 1349 | C | ALA | A | 326 | 45.024 | 41.112 | −5.730 | 1.00 | 24.79 |
| ATOM | 1350 | O | ALA | A | 326 | 45.820 | 40.274 | −5.303 | 1.00 | 22.93 |
| ATOM | 1351 | CB | ALA | A | 326 | 45.037 | 41.082 | −8.263 | 1.00 | 22.43 |
| ATOM | 1352 | N | VAL | A | 327 | 44.869 | 42.307 | −5.153 | 1.00 | 21.47 |
| ATOM | 1353 | CA | VAL | A | 327 | 45.605 | 42.643 | −3.929 | 1.00 | 20.62 |
| ATOM | 1354 | C | VAL | A | 327 | 45.207 | 41.731 | −2.757 | 1.00 | 20.44 |
| ATOM | 1355 | O | VAL | A | 327 | 46.010 | 41.482 | −1.864 | 1.00 | 19.45 |
| ATOM | 1356 | CB | VAL | A | 327 | 45.412 | 44.137 | −3.493 | 1.00 | 25.62 |
| ATOM | 1357 | CG1 | VAL | A | 327 | 45.862 | 45.099 | −4.585 | 1.00 | 25.81 |
| ATOM | 1358 | CG2 | VAL | A | 327 | 43.993 | 44.402 | −3.109 | 1.00 | 25.43 |
| ATOM | 1359 | N | ASP | A | 328 | 43.984 | 41.203 | −2.781 | 1.00 | 17.44 |
| ATOM | 1360 | CA | ASP | A | 328 | 43.533 | 40.294 | −1.710 | 1.00 | 16.43 |
| ATOM | 1361 | C | ASP | A | 328 | 44.214 | 38.952 | −1.854 | 1.00 | 20.19 |
| ATOM | 1362 | O | ASP | A | 328 | 44.439 | 38.263 | −0.869 | 1.00 | 18.83 |
| ATOM | 1363 | CB | ASP | A | 328 | 42.007 | 40.098 | −1.732 | 1.00 | 17.36 |
| ATOM | 1364 | CG | ASP | A | 328 | 41.253 | 41.326 | −1.260 | 1.00 | 19.12 |
| ATOM | 1365 | OD1 | ASP | A | 328 | 41.853 | 42.176 | −0.587 | 1.00 | 18.08 |
| ATOM | 1366 | OD2 | ASP | A | 328 | 40.066 | 41.441 | −1.581 | 1.00 | 20.63 |
| ATOM | 1367 | N | TRP | A | 329 | 44.556 | 38.584 | −3.082 | 1.00 | 18.82 |
| ATOM | 1368 | CA | TRP | A | 329 | 45.241 | 37.311 | −3.315 | 1.00 | 18.73 |
| ATOM | 1369 | C | TRP | A | 329 | 46.717 | 37.432 | −2.932 | 1.00 | 21.74 |
| ATOM | 1370 | O | TRP | A | 329 | 47.333 | 36.476 | −2.465 | 1.00 | 19.59 |
| ATOM | 1371 | CB | TRP | A | 329 | 45.066 | 36.850 | −4.761 | 1.00 | 18.20 |
| ATOM | 1372 | CG | TRP | A | 329 | 43.625 | 36.628 | −5.137 | 1.00 | 18.80 |
| ATOM | 1373 | CD1 | TRP | A | 329 | 42.966 | 37.169 | −6.213 | 1.00 | 21.41 |
| ATOM | 1374 | CD2 | TRP | A | 329 | 42.636 | 35.916 | −4.380 | 1.00 | 18.77 |

TABLE 5-continued

Structural coordinates for AKT3lkd(pT305, S472D).

| ATOM | 1375 | NE1 | TRP | A | 329 | 41.654 | 36.793 | −6.201 | 1.00 | 19.84 |
|---|---|---|---|---|---|---|---|---|---|---|
| ATOM | 1376 | CE2 | TRP | A | 329 | 41.418 | 36.019 | −5.092 | 1.00 | 21.85 |
| ATOM | 1377 | CE3 | TRP | A | 329 | 42.678 | 35.135 | −3.211 | 1.00 | 20.46 |
| ATOM | 1378 | CZ2 | TRP | A | 329 | 40.246 | 35.400 | −4.665 | 1.00 | 21.74 |
| ATOM | 1379 | CZ3 | TRP | A | 329 | 41.495 | 34.520 | −2.771 | 1.00 | 21.98 |
| ATOM | 1380 | CH2 | TRP | A | 329 | 40.302 | 34.641 | −3.513 | 1.00 | 22.61 |
| ATOM | 1381 | N | TRP | A | 330 | 47.277 | 38.624 | −3.116 | 1.00 | 19.65 |
| ATOM | 1382 | CA | TRP | A | 330 | 48.641 | 38.890 | −2.696 | 1.00 | 19.82 |
| ATOM | 1383 | C | TRP | A | 330 | 48.666 | 38.736 | −1.171 | 1.00 | 21.51 |
| ATOM | 1384 | O | TRP | A | 330 | 49.510 | 38.009 | −0.622 | 1.00 | 21.91 |
| ATOM | 1385 | CB | TRP | A | 330 | 49.086 | 40.321 | −3.096 | 1.00 | 19.49 |
| ATOM | 1386 | CG | TRP | A | 330 | 50.422 | 40.726 | −2.474 | 1.00 | 21.00 |
| ATOM | 1387 | CD1 | TRP | A | 330 | 50.617 | 41.282 | −1.245 | 1.00 | 23.77 |
| ATOM | 1388 | CD2 | TRP | A | 330 | 51.726 | 40.579 | −3.061 | 1.00 | 21.27 |
| ATOM | 1389 | NE1 | TRP | A | 330 | 51.967 | 41.465 | −1.016 | 1.00 | 23.43 |
| ATOM | 1390 | CE2 | TRP | A | 330 | 52.665 | 41.038 | −2.115 | 1.00 | 25.10 |
| ATOM | 1391 | CE3 | TRP | A | 330 | 52.192 | 40.027 | −4.261 | 1.00 | 23.29 |
| ATOM | 1392 | CZ2 | TRP | A | 330 | 54.046 | 41.017 | −2.356 | 1.00 | 24.74 |
| ATOM | 1393 | CZ3 | TRP | A | 330 | 53.569 | 40.006 | −4.495 | 1.00 | 24.89 |
| ATOM | 1394 | CH2 | TRP | A | 330 | 54.471 | 40.489 | −3.544 | 1.00 | 25.35 |
| ATOM | 1395 | N | GLY | A | 331 | 47.688 | 39.355 | −0.513 | 1.00 | 17.33 |
| ATOM | 1396 | CA | GLY | A | 331 | 47.539 | 39.309 | 0.957 | 1.00 | 17.63 |
| ATOM | 1397 | C | GLY | A | 331 | 47.411 | 37.859 | 1.433 | 1.00 | 20.98 |
| ATOM | 1398 | O | GLY | A | 331 | 48.001 | 37.469 | 2.452 | 1.00 | 20.15 |
| ATOM | 1399 | N | LEU | A | 332 | 46.659 | 37.055 | 0.686 | 1.00 | 18.02 |
| ATOM | 1400 | CA | LEU | A | 332 | 46.502 | 35.631 | 1.040 | 1.00 | 17.25 |
| ATOM | 1401 | C | LEU | A | 332 | 47.853 | 34.928 | 0.965 | 1.00 | 20.49 |
| ATOM | 1402 | O | LEU | A | 332 | 48.187 | 34.110 | 1.820 | 1.00 | 19.31 |
| ATOM | 1403 | CB | LEU | A | 332 | 45.522 | 34.933 | 0.108 | 1.00 | 16.55 |
| ATOM | 1404 | CG | LEU | A | 332 | 45.311 | 33.434 | 0.442 | 1.00 | 18.98 |
| ATOM | 1405 | CD1 | LEU | A | 332 | 44.540 | 33.248 | 1.783 | 1.00 | 18.45 |
| ATOM | 1406 | CD2 | LEU | A | 332 | 44.574 | 32.736 | −0.701 | 1.00 | 21.44 |
| ATOM | 1407 | N | GLY | A | 333 | 48.611 | 35.237 | −0.083 | 1.00 | 17.20 |
| ATOM | 1408 | CA | GLY | A | 333 | 49.941 | 34.674 | −0.255 | 1.00 | 16.74 |
| ATOM | 1409 | C | GLY | A | 333 | 50.828 | 35.001 | 0.956 | 1.00 | 20.34 |
| ATOM | 1410 | O | GLY | A | 333 | 51.508 | 34.126 | 1.493 | 1.00 | 19.04 |
| ATOM | 1411 | N | VAL | A | 334 | 50.839 | 36.266 | 1.363 | 1.00 | 17.09 |
| ATOM | 1412 | CA | VAL | A | 334 | 51.664 | 36.684 | 2.492 | 1.00 | 17.07 |
| ATOM | 1413 | C | VAL | A | 334 | 51.235 | 35.964 | 3.777 | 1.00 | 20.90 |
| ATOM | 1414 | O | VAL | A | 334 | 52.062 | 35.472 | 4.525 | 1.00 | 20.83 |
| ATOM | 1415 | CB | VAL | A | 334 | 51.606 | 38.234 | 2.726 | 1.00 | 21.93 |
| ATOM | 1416 | CG1 | VAL | A | 334 | 52.462 | 38.614 | 3.955 | 1.00 | 22.17 |
| ATOM | 1417 | CG2 | VAL | A | 334 | 52.099 | 38.994 | 1.474 | 1.00 | 22.21 |
| ATOM | 1418 | N | VAL | A | 335 | 49.931 | 35.884 | 4.020 | 1.00 | 17.52 |
| ATOM | 1419 | CA | VAL | A | 335 | 49.441 | 35.202 | 5.221 | 1.00 | 17.08 |
| ATOM | 1420 | C | VAL | A | 335 | 49.778 | 33.695 | 5.235 | 1.00 | 19.27 |
| ATOM | 1421 | O | VAL | A | 335 | 50.220 | 33.160 | 6.249 | 1.00 | 18.72 |
| ATOM | 1422 | CB | VAL | A | 335 | 47.915 | 35.390 | 5.409 | 1.00 | 21.69 |
| ATOM | 1423 | CG1 | VAL | A | 335 | 47.403 | 34.490 | 6.548 | 1.00 | 21.76 |
| ATOM | 1424 | CG2 | VAL | A | 335 | 47.606 | 36.867 | 5.731 | 1.00 | 21.52 |
| ATOM | 1425 | N | MET | A | 336 | 49.523 | 33.013 | 4.121 | 1.00 | 14.38 |
| ATOM | 1426 | CA | MET | A | 336 | 49.792 | 31.593 | 4.033 | 1.00 | 14.25 |
| ATOM | 1427 | C | MET | A | 336 | 51.283 | 31.296 | 4.094 | 1.00 | 19.86 |
| ATOM | 1428 | O | MET | A | 336 | 51.692 | 30.292 | 4.671 | 1.00 | 19.51 |
| ATOM | 1429 | CB | MET | A | 336 | 49.169 | 31.015 | 2.788 | 1.00 | 15.39 |
| ATOM | 1430 | CG | MET | A | 336 | 47.626 | 30.944 | 2.909 | 1.00 | 16.49 |
| ATOM | 1431 | SD | MET | A | 336 | 46.841 | 30.055 | 1.541 | 1.00 | 18.06 |
| ATOM | 1432 | CE | MET | A | 336 | 47.242 | 28.296 | 1.975 | 1.00 | 15.86 |
| ATOM | 1433 | N | TYR | A | 337 | 52.089 | 32.188 | 3.518 | 1.00 | 17.24 |
| ATOM | 1434 | CA | TYR | A | 337 | 53.559 | 32.053 | 3.564 | 1.00 | 17.21 |
| ATOM | 1435 | C | TYR | A | 337 | 54.014 | 32.120 | 5.028 | 1.00 | 22.42 |
| ATOM | 1436 | O | TYR | A | 337 | 54.803 | 31.284 | 5.495 | 1.00 | 21.79 |
| ATOM | 1437 | CB | TYR | A | 337 | 54.230 | 33.189 | 2.766 | 1.00 | 18.57 |
| ATOM | 1438 | CG | TYR | A | 337 | 55.764 | 33.083 | 2.711 | 1.00 | 20.24 |
| ATOM | 1439 | CD1 | TYR | A | 337 | 56.553 | 33.398 | 3.832 | 1.00 | 22.53 |
| ATOM | 1440 | CD2 | TYR | A | 337 | 56.402 | 32.591 | 1.587 | 1.00 | 20.77 |
| ATOM | 1441 | CE1 | TYR | A | 337 | 57.954 | 33.282 | 3.787 | 1.00 | 22.18 |
| ATOM | 1442 | CE2 | TYR | A | 337 | 57.807 | 32.449 | 1.544 | 1.00 | 21.56 |
| ATOM | 1443 | CZ | TYR | A | 337 | 58.567 | 32.810 | 2.638 | 1.00 | 27.28 |
| ATOM | 1444 | OH | TYR | A | 337 | 59.958 | 32.661 | 2.593 | 1.00 | 28.87 |
| ATOM | 1445 | N | GLU | A | 338 | 53.493 | 33.111 | 5.750 | 1.00 | 20.76 |
| ATOM | 1446 | CA | GLU | A | 338 | 53.826 | 33.308 | 7.167 | 1.00 | 20.56 |
| ATOM | 1447 | C | GLU | A | 338 | 53.467 | 32.066 | 7.961 | 1.00 | 22.86 |
| ATOM | 1448 | O | GLU | A | 338 | 54.227 | 31.611 | 8.804 | 1.00 | 23.55 |
| ATOM | 1449 | CB | GLU | A | 338 | 53.021 | 34.466 | 7.739 | 1.00 | 22.25 |
| ATOM | 1450 | CG | GLU | A | 338 | 53.442 | 35.839 | 7.314 | 1.00 | 32.75 |
| ATOM | 1451 | CD | GLU | A | 338 | 52.710 | 36.901 | 8.098 | 1.00 | 46.74 |
| ATOM | 1452 | OE1 | GLU | A | 338 | 53.214 | 37.291 | 9.167 | 1.00 | 32.26 |

TABLE 5-continued

Structural coordinates for AKT3lkd(pT305, S472D).

| ATOM | 1453 | OE2 | GLU | A | 338 | 51.569 | 37.242 | 7.717 | 1.00 | 37.90 |
|---|---|---|---|---|---|---|---|---|---|---|
| ATOM | 1454 | N | MET | A | 339 | 52.269 | 31.547 | 7.719 | 1.00 | 19.29 |
| ATOM | 1455 | CA | MET | A | 339 | 51.791 | 30.362 | 8.436 | 1.00 | 18.55 |
| ATOM | 1456 | C | MET | A | 339 | 52.675 | 29.134 | 8.222 | 1.00 | 23.43 |
| ATOM | 1457 | O | MET | A | 339 | 53.042 | 28.444 | 9.180 | 1.00 | 24.45 |
| ATOM | 1458 | CB | MET | A | 339 | 50.353 | 30.047 | 8.046 | 1.00 | 19.32 |
| ATOM | 1459 | CG | MET | A | 339 | 49.348 | 31.040 | 8.592 | 1.00 | 21.08 |
| ATOM | 1460 | SD | MET | A | 339 | 47.667 | 30.595 | 8.119 | 1.00 | 23.73 |
| ATOM | 1461 | CE | MET | A | 339 | 46.762 | 32.010 | 8.822 | 1.00 | 20.84 |
| ATOM | 1462 | N | MET | A | 340 | 52.990 | 28.849 | 6.963 | 1.00 | 20.45 |
| ATOM | 1463 | CA | MET | A | 340 | 53.775 | 27.658 | 6.622 | 1.00 | 20.85 |
| ATOM | 1464 | C | MET | A | 340 | 55.283 | 27.824 | 6.805 | 1.00 | 25.66 |
| ATOM | 1465 | O | MET | A | 340 | 55.984 | 26.850 | 7.035 | 1.00 | 25.45 |
| ATOM | 1466 | CB | MET | A | 340 | 53.496 | 27.251 | 5.177 | 1.00 | 22.88 |
| ATOM | 1467 | CG | MET | A | 340 | 52.340 | 26.317 | 5.021 | 1.00 | 25.81 |
| ATOM | 1468 | SD | MET | A | 340 | 52.150 | 25.851 | 3.282 | 1.00 | 28.54 |
| ATOM | 1469 | CE | MET | A | 340 | 50.933 | 27.085 | 2.725 | 1.00 | 25.44 |
| ATOM | 1470 | N | CYS | A | 341 | 55.778 | 29.050 | 6.654 | 1.00 | 23.77 |
| ATOM | 1471 | CA | CYS | A | 341 | 57.216 | 29.307 | 6.749 | 1.00 | 24.07 |
| ATOM | 1472 | C | CYS | A | 341 | 57.699 | 29.902 | 8.070 | 1.00 | 29.70 |
| ATOM | 1473 | O | CYS | A | 341 | 58.901 | 29.878 | 8.363 | 1.00 | 30.29 |
| ATOM | 1474 | CB | CYS | A | 341 | 57.714 | 30.129 | 5.553 | 1.00 | 23.57 |
| ATOM | 1475 | SG | CYS | A | 341 | 57.274 | 29.432 | 3.935 | 1.00 | 27.17 |
| ATOM | 1476 | N | GLY | A | 342 | 56.780 | 30.460 | 8.850 | 1.00 | 26.48 |
| ATOM | 1477 | CA | GLY | A | 342 | 57.125 | 31.020 | 10.152 | 1.00 | 27.13 |
| ATOM | 1478 | C | GLY | A | 342 | 57.752 | 32.421 | 10.103 | 1.00 | 32.99 |
| ATOM | 1479 | O | GLY | A | 342 | 58.353 | 32.865 | 11.078 | 1.00 | 32.15 |
| ATOM | 1480 | N | ARG | A | 343 | 57.609 | 33.108 | 8.970 | 1.00 | 29.66 |
| ATOM | 1481 | CA | ARG | A | 343 | 58.138 | 34.461 | 8.822 | 1.00 | 29.18 |
| ATOM | 1482 | C | ARG | A | 343 | 57.562 | 35.130 | 7.577 | 1.00 | 31.07 |
| ATOM | 1483 | O | ARG | A | 343 | 57.074 | 34.454 | 6.675 | 1.00 | 28.97 |
| ATOM | 1484 | CB | ARG | A | 343 | 59.663 | 34.426 | 8.720 | 1.00 | 29.94 |
| ATOM | 1485 | CG | ARG | A | 343 | 60.163 | 33.843 | 7.423 | 1.00 | 38.65 |
| ATOM | 1486 | CD | ARG | A | 343 | 61.670 | 33.928 | 7.323 | 1.00 | 56.02 |
| ATOM | 1487 | NE | ARG | A | 343 | 62.093 | 34.399 | 6.009 | 1.00 | 68.77 |
| ATOM | 1488 | CZ | ARG | A | 343 | 63.361 | 34.530 | 5.636 | 1.00 | 86.78 |
| ATOM | 1489 | NH1 | ARG | A | 343 | 64.338 | 34.232 | 6.486 | 1.00 | 73.49 |
| ATOM | 1490 | NH2 | ARG | A | 343 | 63.654 | 34.968 | 4.418 | 1.00 | 76.50 |
| ATOM | 1491 | N | LEU | A | 344 | 57.667 | 36.455 | 7.515 | 1.00 | 27.27 |
| ATOM | 1492 | CA | LEU | A | 344 | 57.189 | 37.210 | 6.360 | 1.00 | 26.86 |
| ATOM | 1493 | C | LEU | A | 344 | 58.045 | 36.888 | 5.148 | 1.00 | 29.32 |
| ATOM | 1494 | O | LEU | A | 344 | 59.230 | 36.600 | 5.278 | 1.00 | 28.43 |
| ATOM | 1495 | CB | LEU | A | 344 | 57.224 | 38.722 | 6.637 | 1.00 | 27.22 |
| ATOM | 1496 | CG | LEU | A | 344 | 56.032 | 39.320 | 7.414 | 1.00 | 32.20 |
| ATOM | 1497 | CD1 | LEU | A | 344 | 54.728 | 39.043 | 6.704 | 1.00 | 31.69 |
| ATOM | 1498 | CD2 | LEU | A | 344 | 55.991 | 38.781 | 8.828 | 1.00 | 35.56 |
| ATOM | 1499 | N | PRO | A | 345 | 57.435 | 36.909 | 3.967 | 1.00 | 26.12 |
| ATOM | 1500 | CA | PRO | A | 345 | 58.161 | 36.632 | 2.735 | 1.00 | 26.00 |
| ATOM | 1501 | C | PRO | A | 345 | 59.119 | 37.785 | 2.409 | 1.00 | 32.63 |
| ATOM | 1502 | O | PRO | A | 345 | 60.121 | 37.598 | 1.712 | 1.00 | 31.28 |
| ATOM | 1503 | CB | PRO | A | 345 | 57.055 | 36.563 | 1.677 | 1.00 | 27.11 |
| ATOM | 1504 | CG | PRO | A | 345 | 55.915 | 37.339 | 2.247 | 1.00 | 30.79 |
| ATOM | 1505 | CD | PRO | A | 345 | 56.008 | 37.213 | 3.730 | 1.00 | 26.20 |
| ATOM | 1506 | N | PHE | A | 346 | 58.783 | 38.976 | 2.899 | 1.00 | 31.50 |
| ATOM | 1507 | CA | PHE | A | 346 | 59.595 | 40.170 | 2.649 | 1.00 | 32.30 |
| ATOM | 1508 | C | PHE | A | 346 | 59.700 | 40.973 | 3.917 | 1.00 | 38.83 |
| ATOM | 1509 | O | PHE | A | 346 | 58.687 | 41.402 | 4.467 | 1.00 | 36.28 |
| ATOM | 1510 | CB | PHE | A | 346 | 58.948 | 41.050 | 1.562 | 1.00 | 33.50 |
| ATOM | 1511 | CG | PHE | A | 346 | 58.658 | 40.323 | 0.284 | 1.00 | 34.39 |
| ATOM | 1512 | CD1 | PHE | A | 346 | 59.687 | 39.930 | −0.551 | 1.00 | 36.39 |
| ATOM | 1513 | CD2 | PHE | A | 346 | 57.347 | 40.054 | −0.093 | 1.00 | 35.93 |
| ATOM | 1514 | CE1 | PHE | A | 346 | 59.423 | 39.271 | −1.729 | 1.00 | 37.31 |
| ATOM | 1515 | CE2 | PHE | A | 346 | 57.078 | 39.387 | −1.264 | 1.00 | 38.40 |
| ATOM | 1516 | CZ | PHE | A | 346 | 58.111 | 39.002 | −2.091 | 1.00 | 36.57 |
| ATOM | 1517 | N | TYR | A | 347 | 60.926 | 41.186 | 4.390 | 1.00 | 40.72 |
| ATOM | 1518 | CA | TYR | A | 347 | 61.130 | 41.983 | 5.592 | 1.00 | 43.26 |
| ATOM | 1519 | C | TYR | A | 347 | 62.412 | 42.814 | 5.605 | 1.00 | 50.26 |
| ATOM | 1520 | O | TYR | A | 347 | 63.468 | 42.368 | 5.151 | 1.00 | 49.29 |
| ATOM | 1521 | CB | TYR | A | 347 | 61.052 | 41.135 | 6.854 | 1.00 | 45.82 |
| ATOM | 1522 | CG | TYR | A | 347 | 61.363 | 41.934 | 8.102 | 1.00 | 49.93 |
| ATOM | 1523 | CD1 | TYR | A | 347 | 60.498 | 42.928 | 8.549 | 1.00 | 52.60 |
| ATOM | 1524 | CD2 | TYR | A | 347 | 62.558 | 41.751 | 8.788 | 1.00 | 51.29 |
| ATOM | 1525 | CE1 | TYR | A | 347 | 60.799 | 43.690 | 9.673 | 1.00 | 54.25 |
| ATOM | 1526 | CE2 | TYR | A | 347 | 62.864 | 42.506 | 9.908 | 1.00 | 52.55 |
| ATOM | 1527 | CZ | TYR | A | 347 | 61.979 | 43.470 | 10.345 | 1.00 | 61.53 |
| ATOM | 1528 | OH | TYR | A | 347 | 62.279 | 44.213 | 11.465 | 1.00 | 65.11 |
| ATOM | 1529 | N | ASN | A | 348 | 62.307 | 44.012 | 6.172 | 1.00 | 49.52 |
| ATOM | 1530 | CA | ASN | A | 348 | 63.441 | 44.918 | 6.314 | 1.00 | 50.58 |

TABLE 5-continued

Structural coordinates for AKT3lkd(pT305, S472D).

| ATOM | 1531 | C | ASN | A | 348 | 63.023 | 46.122 | 7.150 | 1.00 | 56.55 |
|---|---|---|---|---|---|---|---|---|---|---|
| ATOM | 1532 | O | ASN | A | 348 | 61.879 | 46.573 | 7.074 | 1.00 | 55.61 |
| ATOM | 1533 | CB | ASN | A | 348 | 63.958 | 45.371 | 4.947 | 1.00 | 52.95 |
| ATOM | 1534 | CG | ASN | A | 348 | 64.862 | 46.588 | 5.040 | 1.00 | 80.86 |
| ATOM | 1535 | OD1 | ASN | A | 348 | 65.758 | 46.650 | 5.885 | 1.00 | 72.92 |
| ATOM | 1536 | ND2 | ASN | A | 348 | 64.614 | 47.573 | 4.187 | 1.00 | 76.10 |
| ATOM | 1537 | N | GLN | A | 349 | 63.943 | 46.615 | 7.971 | 1.00 | 55.41 |
| ATOM | 1538 | CA | GLN | A | 349 | 63.671 | 47.760 | 8.837 | 1.00 | 56.04 |
| ATOM | 1539 | C | GLN | A | 349 | 63.527 | 49.036 | 8.011 | 1.00 | 60.60 |
| ATOM | 1540 | O | GLN | A | 349 | 62.634 | 49.851 | 8.256 | 1.00 | 59.97 |
| ATOM | 1541 | CB | GLN | A | 349 | 64.783 | 47.918 | 9.881 | 1.00 | 57.59 |
| ATOM | 1542 | CG | GLN | A | 349 | 65.292 | 46.596 | 10.455 | 1.00 | 75.44 |
| ATOM | 1543 | CD | GLN | A | 349 | 66.158 | 45.827 | 9.470 | 1.00 | 97.91 |
| ATOM | 1544 | OE1 | GLN | A | 349 | 65.820 | 44.710 | 9.069 | 1.00 | 93.10 |
| ATOM | 1545 | NE2 | GLN | A | 349 | 67.262 | 46.437 | 9.054 | 1.00 | 91.60 |
| ATOM | 1546 | N | ASP | A | 350 | 64.405 | 49.199 | 7.029 | 1.00 | 58.22 |
| ATOM | 1547 | CA | ASP | A | 350 | 64.335 | 50.349 | 6.137 | 1.00 | 58.50 |
| ATOM | 1548 | C | ASP | A | 350 | 63.095 | 50.158 | 5.286 | 1.00 | 62.78 |
| ATOM | 1549 | O | ASP | A | 350 | 63.145 | 49.510 | 4.238 | 1.00 | 62.38 |
| ATOM | 1550 | CB | ASP | A | 350 | 65.580 | 50.417 | 5.239 | 1.00 | 60.53 |
| ATOM | 1551 | CG | ASP | A | 350 | 65.613 | 51.673 | 4.372 | 1.00 | 71.97 |
| ATOM | 1552 | OD1 | ASP | A | 350 | 66.724 | 52.121 | 4.013 | 1.00 | 72.63 |
| ATOM | 1553 | OD2 | ASP | A | 350 | 64.531 | 52.206 | 4.043 | 1.00 | 78.01 |
| ATOM | 1554 | N | HIS | A | 351 | 61.975 | 50.702 | 5.745 | 1.00 | 59.83 |
| ATOM | 1555 | CA | HIS | A | 351 | 60.715 | 50.553 | 5.030 | 1.00 | 59.72 |
| ATOM | 1556 | C | HIS | A | 351 | 60.715 | 51.178 | 3.638 | 1.00 | 62.06 |
| ATOM | 1557 | O | HIS | A | 351 | 59.674 | 51.596 | 3.129 | 1.00 | 62.36 |
| ATOM | 1558 | CB | HIS | A | 351 | 59.530 | 51.020 | 5.887 | 1.00 | 60.84 |
| ATOM | 1559 | CG | HIS | A | 351 | 59.151 | 50.044 | 6.960 | 1.00 | 64.57 |
| ATOM | 1560 | ND1 | HIS | A | 351 | 58.208 | 50.322 | 7.927 | 1.00 | 66.53 |
| ATOM | 1561 | CD2 | HIS | A | 351 | 59.601 | 48.790 | 7.223 | 1.00 | 66.60 |
| ATOM | 1562 | CE1 | HIS | A | 351 | 58.090 | 49.282 | 8.737 | 1.00 | 66.08 |
| ATOM | 1563 | NE2 | HIS | A | 351 | 58.923 | 48.339 | 8.330 | 1.00 | 66.44 |
| ATOM | 1564 | N | GLU | A | 352 | 61.896 | 51.194 | 3.020 | 1.00 | 56.23 |
| ATOM | 1565 | CA | GLU | A | 352 | 62.088 | 51.691 | 1.667 | 1.00 | 54.77 |
| ATOM | 1566 | C | GLU | A | 352 | 62.773 | 50.569 | 0.890 | 1.00 | 55.30 |
| ATOM | 1567 | O | GLU | A | 352 | 62.436 | 50.303 | −0.262 | 1.00 | 54.99 |
| ATOM | 1568 | CB | GLU | A | 352 | 62.971 | 52.948 | 1.674 | 1.00 | 56.27 |
| ATOM | 1569 | CG | GLU | A | 352 | 62.913 | 53.768 | 0.388 | 1.00 | 66.44 |
| ATOM | 1570 | CD | GLU | A | 352 | 64.115 | 54.697 | 0.225 | 1.00 | 88.46 |
| ATOM | 1571 | OE1 | GLU | A | 352 | 64.203 | 55.378 | −0.821 | 1.00 | 80.03 |
| ATOM | 1572 | OE2 | GLU | A | 352 | 64.968 | 54.747 | 1.141 | 1.00 | 82.63 |
| ATOM | 1573 | N | LYS | A | 353 | 63.717 | 49.897 | 1.549 | 1.00 | 49.27 |
| ATOM | 1574 | CA | LYS | A | 353 | 64.411 | 48.753 | 0.962 | 1.00 | 48.05 |
| ATOM | 1575 | C | LYS | A | 353 | 63.458 | 47.559 | 1.003 | 1.00 | 49.03 |
| ATOM | 1576 | O | LYS | A | 353 | 63.543 | 46.653 | 0.176 | 1.00 | 48.38 |
| ATOM | 1577 | CB | LYS | A | 353 | 65.682 | 48.425 | 1.751 | 1.00 | 50.92 |
| ATOM | 1578 | CG | LYS | A | 353 | 66.652 | 49.594 | 1.886 | 1.00 | 68.65 |
| ATOM | 1579 | CD | LYS | A | 353 | 67.784 | 49.271 | 2.856 | 1.00 | 79.68 |
| ATOM | 1580 | CE | LYS | A | 353 | 69.134 | 49.727 | 2.308 | 1.00 | 89.85 |
| ATOM | 1581 | NZ | LYS | A | 353 | 70.271 | 49.028 | 2.972 | 1.00 | 98.41 |
| ATOM | 1582 | N | LEU | A | 354 | 62.550 | 47.577 | 1.973 | 1.00 | 43.79 |
| ATOM | 1583 | CA | LEU | A | 354 | 61.534 | 46.544 | 2.089 | 1.00 | 43.44 |
| ATOM | 1584 | C | LEU | A | 354 | 60.672 | 46.613 | 0.834 | 1.00 | 46.51 |
| ATOM | 1585 | O | LEU | A | 354 | 60.253 | 45.593 | 0.300 | 1.00 | 46.01 |
| ATOM | 1586 | CB | LEU | A | 354 | 60.661 | 46.786 | 3.320 | 1.00 | 43.26 |
| ATOM | 1587 | CG | LEU | A | 354 | 59.249 | 46.211 | 3.208 | 1.00 | 47.79 |
| ATOM | 1588 | CD1 | LEU | A | 354 | 59.297 | 44.680 | 3.128 | 1.00 | 47.82 |
| ATOM | 1589 | CD2 | LEU | A | 354 | 58.365 | 46.677 | 4.357 | 1.00 | 50.19 |
| ATOM | 1590 | N | PHE | A | 355 | 60.430 | 47.835 | 0.367 | 1.00 | 42.72 |
| ATOM | 1591 | CA | PHE | A | 355 | 59.639 | 48.066 | −0.831 | 1.00 | 42.31 |
| ATOM | 1592 | C | PHE | A | 355 | 60.370 | 47.532 | −2.048 | 1.00 | 45.44 |
| ATOM | 1593 | O | PHE | A | 355 | 59.748 | 47.089 | −3.017 | 1.00 | 44.95 |
| ATOM | 1594 | CB | PHE | A | 355 | 59.352 | 49.562 | −1.005 | 1.00 | 44.37 |
| ATOM | 1595 | CG | PHE | A | 355 | 58.291 | 50.085 | −0.082 | 1.00 | 46.15 |
| ATOM | 1596 | CD1 | PHE | A | 355 | 57.610 | 49.229 | 0.768 | 1.00 | 49.44 |
| ATOM | 1597 | CD2 | PHE | A | 355 | 57.991 | 51.437 | −0.045 | 1.00 | 48.84 |
| ATOM | 1598 | CE1 | PHE | A | 355 | 56.643 | 49.707 | 1.628 | 1.00 | 50.47 |
| ATOM | 1599 | CE2 | PHE | A | 355 | 57.019 | 51.921 | 0.811 | 1.00 | 51.84 |
| ATOM | 1600 | CZ | PHE | A | 355 | 56.343 | 51.053 | 1.647 | 1.00 | 49.94 |
| ATOM | 1601 | N | GLU | A | 356 | 61.700 | 47.571 | −1.995 | 1.00 | 41.89 |
| ATOM | 1602 | CA | GLU | A | 356 | 62.526 | 47.071 | −3.087 | 1.00 | 41.15 |
| ATOM | 1603 | C | GLU | A | 356 | 62.373 | 45.560 | −3.168 | 1.00 | 42.86 |
| ATOM | 1604 | O | GLU | A | 356 | 62.222 | 44.991 | −4.249 | 1.00 | 41.96 |
| ATOM | 1605 | CB | GLU | A | 356 | 63.998 | 47.438 | −2.862 | 1.00 | 42.69 |
| ATOM | 1606 | CG | GLU | A | 356 | 64.718 | 47.910 | −4.119 | 1.00 | 53.07 |
| ATOM | 1607 | CD | GLU | A | 356 | 64.993 | 49.407 | −4.111 | 1.00 | 78.91 |
| ATOM | 1608 | OE1 | GLU | A | 356 | 64.886 | 50.031 | −3.029 | 1.00 | 82.04 |

TABLE 5-continued

Structural coordinates for AKT3lkd(pT305, S472D).

| ATOM | 1609 | OE2 | GLU | A | 356 | 65.333 | 49.957 | −5.183 | 1.00 | 70.75 |
|---|---|---|---|---|---|---|---|---|---|---|
| ATOM | 1610 | N | LEU | A | 357 | 62.402 | 44.915 | −2.009 | 1.00 | 38.50 |
| ATOM | 1611 | CA | LEU | A | 357 | 62.241 | 43.469 | −1.942 | 1.00 | 37.74 |
| ATOM | 1612 | C | LEU | A | 357 | 60.863 | 43.091 | −2.475 | 1.00 | 38.53 |
| ATOM | 1613 | O | LEU | A | 357 | 60.734 | 42.205 | −3.319 | 1.00 | 38.34 |
| ATOM | 1614 | CB | LEU | A | 357 | 62.409 | 42.980 | −0.496 | 1.00 | 38.12 |
| ATOM | 1615 | CG | LEU | A | 357 | 63.784 | 43.221 | 0.139 | 1.00 | 43.56 |
| ATOM | 1616 | CD1 | LEU | A | 357 | 63.690 | 43.201 | 1.647 | 1.00 | 44.09 |
| ATOM | 1617 | CD2 | LEU | A | 357 | 64.789 | 42.190 | −0.350 | 1.00 | 46.92 |
| ATOM | 1618 | N | ILE | A | 358 | 59.838 | 43.793 | −2.009 | 1.00 | 33.47 |
| ATOM | 1619 | CA | ILE | A | 358 | 58.483 | 43.508 | −2.454 | 1.00 | 32.32 |
| ATOM | 1620 | C | ILE | A | 358 | 58.399 | 43.654 | −3.958 | 1.00 | 34.58 |
| ATOM | 1621 | O | ILE | A | 358 | 57.848 | 42.807 | −4.644 | 1.00 | 31.11 |
| ATOM | 1622 | CB | ILE | A | 358 | 57.443 | 44.418 | −1.779 | 1.00 | 34.88 |
| ATOM | 1623 | CG1 | ILE | A | 358 | 57.269 | 44.027 | −0.306 | 1.00 | 34.56 |
| ATOM | 1624 | CG2 | ILE | A | 358 | 56.090 | 44.318 | −2.513 | 1.00 | 35.46 |
| ATOM | 1625 | CD1 | ILE | A | 358 | 56.420 | 44.993 | 0.484 | 1.00 | 38.87 |
| ATOM | 1626 | N | LEU | A | 359 | 58.998 | 44.715 | −4.470 | 1.00 | 33.72 |
| ATOM | 1627 | CA | LEU | A | 339 | 58.948 | 44.990 | −5.893 | 1.00 | 35.14 |
| ATOM | 1628 | C | LEU | A | 359 | 59.884 | 44.156 | −6.753 | 1.00 | 41.67 |
| ATOM | 1629 | O | LEU | A | 359 | 59.565 | 43.857 | −7.896 | 1.00 | 41.66 |
| ATOM | 1630 | CB | LEU | A | 359 | 59.177 | 46.482 | −6.156 | 1.00 | 35.54 |
| ATOM | 1631 | CG | LEU | A | 359 | 57.925 | 47.362 | −6.073 | 1.00 | 41.20 |
| ATOM | 1632 | CD1 | LEU | A | 359 | 58.296 | 48.832 | −5.918 | 1.00 | 42.14 |
| ATOM | 1633 | CD2 | LEU | A | 359 | 57.040 | 47.154 | −7.297 | 1.00 | 44.71 |
| ATOM | 1634 | N | MET | A | 360 | 61.040 | 43.787 | −6.210 | 1.00 | 40.82 |
| ATOM | 1635 | CA | MET | A | 360 | 62.056 | 43.103 | −7.007 | 1.00 | 41.73 |
| ATOM | 1636 | C | MET | A | 360 | 62.462 | 41.669 | −6.639 | 1.00 | 44.79 |
| ATOM | 1637 | O | MET | A | 360 | 62.836 | 40.893 | −7.513 | 1.00 | 44.50 |
| ATOM | 1638 | CB | MET | A | 360 | 63.310 | 43.977 | −7.107 | 1.00 | 44.82 |
| ATOM | 1639 | CG | MET | A | 360 | 63.059 | 45.376 | −7.692 | 1.00 | 49.88 |
| ATOM | 1640 | SD | MET | A | 360 | 63.036 | 45.369 | −9.494 | 1.00 | 55.50 |
| ATOM | 1641 | CE | MET | A | 360 | 61.359 | 44.771 | −9.829 | 1.00 | 52.01 |
| ATOM | 1642 | N | GLU | A | 361 | 62.456 | 41.338 | −5.354 | 1.00 | 41.11 |
| ATOM | 1643 | CA | GLU | A | 361 | 62.930 | 40.027 | −4.920 | 1.00 | 40.48 |
| ATOM | 1644 | C | GLU | A | 361 | 62.001 | 38.842 | −5.116 | 1.00 | 42.74 |
| ATOM | 1645 | O | GLU | A | 361 | 60.805 | 38.897 | −4.796 | 1.00 | 41.08 |
| ATOM | 1646 | CB | GLU | A | 361 | 63.432 | 40.069 | −3.477 | 1.00 | 42.09 |
| ATOM | 1647 | CG | GLU | A | 361 | 64.278 | 38.862 | −3.077 | 1.00 | 53.57 |
| ATOM | 1648 | CD | GLU | A | 361 | 65.552 | 39.258 | −2.340 | 1.00 | 78.37 |
| ATOM | 1649 | OE1 | GLU | A | 361 | 65.505 | 39.385 | −1.098 | 1.00 | 77.86 |
| ATOM | 1650 | OE2 | GLU | A | 361 | 66.597 | 39.442 | −3.002 | 1.00 | 72.56 |
| ATOM | 1651 | N | ASP | A | 362 | 62.584 | 37.744 | −5.585 | 1.00 | 39.07 |
| ATOM | 1652 | CA | ASP | A | 362 | 61.863 | 36.497 | −5.736 | 1.00 | 39.01 |
| ATOM | 1653 | C | ASP | A | 362 | 61.771 | 35.872 | −4.353 | 1.00 | 41.02 |
| ATOM | 1654 | O | ASP | A | 362 | 62.645 | 36.077 | −3.515 | 1.00 | 40.12 |
| ATOM | 1655 | CB | ASP | A | 362 | 62.610 | 35.563 | −6.681 | 1.00 | 41.29 |
| ATOM | 1656 | CG | ASP | A | 362 | 62.145 | 35.695 | −8.115 | 1.00 | 55.98 |
| ATOM | 1657 | OD1 | ASP | A | 362 | 60.943 | 35.987 | −8.326 | 1.00 | 56.91 |
| ATOM | 1658 | OD2 | ASP | A | 362 | 62.977 | 35.500 | −9.033 | 1.00 | 62.64 |
| ATOM | 1659 | N | ILE | A | 363 | 60.687 | 35.152 | −4.095 | 1.00 | 36.84 |
| ATOM | 1660 | CA | ILE | A | 363 | 60.487 | 34.546 | −2.789 | 1.00 | 36.15 |
| ATOM | 1661 | C | ILE | A | 363 | 61.346 | 33.299 | −2.598 | 1.00 | 38.24 |
| ATOM | 1662 | O | ILE | A | 363 | 61.649 | 32.598 | −3.558 | 1.00 | 38.05 |
| ATOM | 1663 | CB | ILE | A | 363 | 59.005 | 34.170 | −2.569 | 1.00 | 39.72 |
| ATOM | 1664 | CG1 | ILE | A | 363 | 58.572 | 34.544 | −1.160 | 1.00 | 40.18 |
| ATOM | 1665 | CG2 | ILE | A | 363 | 58.786 | 32.698 | −2.823 | 1.00 | 41.47 |
| ATOM | 1666 | CD1 | ILE | A | 363 | 58.289 | 36.019 | −0.997 | 1.00 | 48.46 |
| ATOM | 1667 | N | LYS | A | 364 | 61.731 | 33.042 | −1.350 | 1.00 | 33.43 |
| ATOM | 1668 | CA | LYS | A | 364 | 62.498 | 31.845 | −0.994 | 1.00 | 33.42 |
| ATOM | 1669 | C | LYS | A | 364 | 61.652 | 30.962 | −0.056 | 1.00 | 34.62 |
| ATOM | 1670 | O | LYS | A | 364 | 60.824 | 31.469 | 0.711 | 1.00 | 33.82 |
| ATOM | 1671 | CB | LYS | A | 364 | 63.817 | 32.230 | −0.321 | 1.00 | 35.69 |
| ATOM | 1672 | CG | LYS | A | 364 | 64.910 | 32.667 | −1.301 | 1.00 | 46.61 |
| ATOM | 1673 | CD | LYS | A | 364 | 64.586 | 32.236 | −2.728 | 1.00 | 52.42 |
| ATOM | 1674 | CE | LYS | A | 364 | 65.845 | 31.881 | −3.509 | 1.00 | 62.94 |
| ATOM | 1675 | NZ | LYS | A | 364 | 65.773 | 32.323 | −4.939 | 1.00 | 70.36 |
| ATOM | 1676 | N | PHE | A | 365 | 61.868 | 29.652 | −0.120 | 1.00 | 29.86 |
| ATOM | 1677 | CA | PHE | A | 365 | 61.084 | 28.692 | 0.670 | 1.00 | 28.97 |
| ATOM | 1678 | C | PHE | A | 365 | 61.953 | 27.754 | 1.489 | 1.00 | 35.60 |
| ATOM | 1679 | O | PHE | A | 365 | 63.072 | 27.446 | 1.104 | 1.00 | 35.87 |
| ATOM | 1680 | CB | PHE | A | 365 | 60.254 | 27.796 | −0.280 | 1.00 | 30.16 |
| ATOM | 1681 | CG | PHE | A | 365 | 59.289 | 28.540 | −1.152 | 1.00 | 30.81 |
| ATOM | 1682 | CD1 | PHE | A | 365 | 58.208 | 29.212 | −0.601 | 1.00 | 32.83 |
| ATOM | 1683 | CD2 | PHE | A | 365 | 59.404 | 28.489 | −2.540 | 1.00 | 32.45 |
| ATOM | 1684 | CE1 | PHE | A | 365 | 57.296 | 29.874 | −1.408 | 1.00 | 33.31 |
| ATOM | 1685 | CE2 | PHE | A | 365 | 58.496 | 29.147 | −3.350 | 1.00 | 34.71 |
| ATOM | 1686 | CZ | PHE | A | 365 | 57.442 | 29.840 | −2.786 | 1.00 | 32.54 |

TABLE 5-continued

Structural coordinates for AKT3lkd(pT305, S472D).

| ATOM | 1687 | N   | PRO | A | 366 | 61.385 | 27.192 | 2.551  | 1.00 | 33.54 |
|------|------|-----|-----|---|-----|--------|--------|--------|------|-------|
| ATOM | 1688 | CA  | PRO | A | 366 | 62.073 | 26.134 | 3.283  | 1.00 | 33.52 |
| ATOM | 1689 | C   | PRO | A | 366 | 62.178 | 25.003 | 2.253  | 1.00 | 35.75 |
| ATOM | 1690 | O   | PRO | A | 366 | 61.258 | 24.798 | 1.458  | 1.00 | 33.85 |
| ATOM | 1691 | CB  | PRO | A | 366 | 61.069 | 25.756 | 4.378  | 1.00 | 35.11 |
| ATOM | 1692 | CG  | PRO | A | 366 | 60.229 | 26.982 | 4.557  | 1.00 | 38.91 |
| ATOM | 1693 | CD  | PRO | A | 366 | 60.114 | 27.570 | 3.191  | 1.00 | 34.20 |
| ATOM | 1694 | N   | ARG | A | 367 | 63.319 | 24.329 | 2.198  | 1.00 | 32.42 |
| ATOM | 1695 | CA  | ARG | A | 367 | 63.514 | 23.280 | 1.196  | 1.00 | 31.60 |
| ATOM | 1696 | C   | ARG | A | 367 | 62.462 | 22.147 | 1.244  | 1.00 | 33.40 |
| ATOM | 1697 | O   | ARG | A | 367 | 62.022 | 21.653 | 0.201  | 1.00 | 35.54 |
| ATOM | 1698 | CB  | ARG | A | 367 | 64.932 | 22.700 | 1.296  | 1.00 | 34.03 |
| ATOM | 1699 | CG  | ARG | A | 367 | 65.903 | 23.234 | 0.242  | 1.00 | 45.84 |
| ATOM | 1700 | CD  | ARG | A | 367 | 67.307 | 22.655 | 0.440  | 1.00 | 53.48 |
| ATOM | 1701 | NE  | ARG | A | 367 | 67.534 | 22.237 | 1.823  | 1.00 | 55.25 |
| ATOM | 1702 | CZ  | ARG | A | 367 | 68.429 | 21.325 | 2.192  | 1.00 | 63.15 |
| ATOM | 1703 | NH1 | ARG | A | 367 | 69.191 | 20.734 | 1.282  | 1.00 | 50.29 |
| ATOM | 1704 | NH2 | ARG | A | 367 | 68.561 | 21.005 | 3.468  | 1.00 | 45.40 |
| ATOM | 1705 | N   | THR | A | 368 | 62.069 | 21.742 | 2.445  | 1.00 | 26.70 |
| ATOM | 1706 | CA  | THR | A | 368 | 61.124 | 20.636 | 2.613  | 1.00 | 24.61 |
| ATOM | 1707 | C   | THR | A | 368 | 59.655 | 21.004 | 2.365  | 1.00 | 26.85 |
| ATOM | 1708 | O   | THR | A | 368 | 58.779 | 20.145 | 2.474  | 1.00 | 25.69 |
| ATOM | 1709 | CB  | THR | A | 368 | 61.228 | 20.032 | 4.006  | 1.00 | 33.60 |
| ATOM | 1710 | OG1 | THR | A | 368 | 61.056 | 21.074 | 4.972  | 1.00 | 38.29 |
| ATOM | 1711 | CG2 | THR | A | 368 | 62.623 | 19.352 | 4.211  | 1.00 | 29.92 |
| ATOM | 1712 | N   | LEU | A | 369 | 59.375 | 22.278 | 2.087  | 1.00 | 23.45 |
| ATOM | 1713 | CA  | LEU | A | 369 | 57.991 | 22.670 | 1.790  | 1.00 | 22.86 |
| ATOM | 1714 | C   | LEU | A | 369 | 57.559 | 21.871 | 0.557  | 1.00 | 23.98 |
| ATOM | 1715 | O   | LEU | A | 369 | 58.370 | 21.617 | −0.342 | 1.00 | 23.77 |
| ATOM | 1716 | CB  | LEU | A | 369 | 57.896 | 24.169 | 1.517  | 1.00 | 23.24 |
| ATOM | 1717 | CG  | LEU | A | 369 | 56.486 | 24.736 | 1.653  | 1.00 | 28.43 |
| ATOM | 1718 | CD1 | LEU | A | 369 | 56.005 | 24.611 | 3.107  | 1.00 | 29.20 |
| ATOM | 1719 | CD2 | LEU | A | 369 | 56.433 | 26.182 | 1.176  | 1.00 | 29.74 |
| ATOM | 1720 | N   | SER | A | 370 | 56.313 | 21.427 | 0.529  | 1.00 | 18.98 |
| ATOM | 1721 | CA  | SER | A | 370 | 55.837 | 20.589 | −0.586 | 1.00 | 18.13 |
| ATOM | 1722 | C   | SER | A | 370 | 55.846 | 21.330 | −1.900 | 1.00 | 22.96 |
| ATOM | 1723 | O   | SER | A | 370 | 55.763 | 22.554 | −1.929 | 1.00 | 22.75 |
| ATOM | 1724 | CB  | SER | A | 370 | 54.429 | 20.009 | −0.301 | 1.00 | 21.20 |
| ATOM | 1725 | OG  | SER | A | 370 | 53.386 | 20.960 | −0.560 | 1.00 | 18.28 |
| ATOM | 1726 | N   | SER | A | 371 | 55.891 | 20.581 | −2.998 | 1.00 | 19.39 |
| ATOM | 1727 | CA  | SER | A | 371 | 55.870 | 21.197 | −4.319 | 1.00 | 19.03 |
| ATOM | 1728 | C   | SER | A | 371 | 54.587 | 22.000 | −4.523 | 1.00 | 21.88 |
| ATOM | 1729 | O   | SER | A | 371 | 54.618 | 23.097 | −5.059 | 1.00 | 19.01 |
| ATOM | 1730 | CB  | SER | A | 371 | 55.988 | 20.144 | −5.419 | 1.00 | 19.35 |
| ATOM | 1731 | OG  | SER | A | 371 | 55.898 | 20.745 | −6.691 | 1.00 | 26.58 |
| ATOM | 1732 | N   | ASP | A | 372 | 53.462 | 21.452 | −4.083 | 1.00 | 19.44 |
| ATOM | 1733 | CA  | ASP | A | 372 | 52.168 | 22.159 | −4.271 | 1.00 | 18.75 |
| ATOM | 1734 | C   | ASP | A | 372 | 52.121 | 23.469 | −3.453 | 1.00 | 22.08 |
| ATOM | 1735 | O   | ASP | A | 372 | 51.577 | 24.485 | −3.904 | 1.00 | 20.89 |
| ATOM | 1736 | CB  | ASP | A | 372 | 51.011 | 21.244 | −3.880 | 1.00 | 19.13 |
| ATOM | 1737 | CG  | ASP | A | 372 | 50.719 | 20.189 | −4.916 | 1.00 | 21.48 |
| ATOM | 1738 | OD1 | ASP | A | 372 | 51.293 | 20.230 | −6.033 | 1.00 | 23.50 |
| ATOM | 1739 | OD2 | ASP | A | 372 | 49.882 | 19.327 | −4.631 | 1.00 | 21.29 |
| ATOM | 1740 | N   | ALA | A | 373 | 52.678 | 23.437 | −2.242 | 1.00 | 19.83 |
| ATOM | 1741 | CA  | ALA | A | 373 | 52.735 | 24.633 | −1.402 | 1.00 | 19.68 |
| ATOM | 1742 | C   | ALA | A | 373 | 53.599 | 25.709 | −2.065 | 1.00 | 21.73 |
| ATOM | 1743 | O   | ALA | A | 373 | 53.218 | 26.888 | −2.130 | 1.00 | 19.08 |
| ATOM | 1744 | CB  | ALA | A | 373 | 53.273 | 24.283 | 0.002  | 1.00 | 20.46 |
| ATOM | 1745 | N   | LYS | A | 374 | 54.765 | 25.307 | −2.565 | 1.00 | 18.72 |
| ATOM | 1746 | CA  | LYS | A | 374 | 55.647 | 26.253 | −3.251 | 1.00 | 18.46 |
| ATOM | 1747 | C   | LYS | A | 374 | 54.957 | 26.868 | −4.473 | 1.00 | 21.29 |
| ATOM | 1748 | O   | LYS | A | 374 | 55.054 | 28.074 | −4.716 | 1.00 | 21.17 |
| ATOM | 1749 | CB  | LYS | A | 374 | 56.952 | 25.547 | −3.674 | 1.00 | 20.33 |
| ATOM | 1750 | CG  | LYS | A | 374 | 57.895 | 25.297 | −2.491 | 1.00 | 22.93 |
| ATOM | 1751 | CD  | LYS | A | 374 | 59.173 | 24.544 | −2.957 | 1.00 | 26.03 |
| ATOM | 1752 | CE  | LYS | A | 374 | 60.038 | 24.126 | −1.780 | 1.00 | 34.24 |
| ATOM | 1753 | NZ  | LYS | A | 374 | 61.037 | 23.083 | −2.191 | 1.00 | 36.50 |
| ATOM | 1754 | N   | SER | A | 375 | 54.250 | 26.038 | −5.228 | 1.00 | 18.00 |
| ATOM | 1755 | CA  | SER | A | 375 | 53.533 | 26.501 | −6.411 | 1.00 | 18.16 |
| ATOM | 1756 | C   | SER | A | 375 | 52.440 | 27.520 | −6.012 | 1.00 | 21.16 |
| ATOM | 1757 | O   | SER | A | 375 | 52.290 | 28.580 | −6.633 | 1.00 | 19.94 |
| ATOM | 1758 | CB  | SER | A | 375 | 52.886 | 25.309 | −7.117 | 1.00 | 20.20 |
| ATOM | 1759 | OG  | SER | A | 375 | 52.101 | 25.733 | −8.210 | 1.00 | 25.61 |
| ATOM | 1760 | N   | LEU | A | 376 | 51.677 | 27.186 | −4.981 | 1.00 | 18.00 |
| ATOM | 1761 | CA  | LEU | A | 376 | 50.596 | 28.059 | −4.522 | 1.00 | 16.91 |
| ATOM | 1762 | C   | LEU | A | 376 | 51.138 | 29.417 | −4.103 | 1.00 | 20.41 |
| ATOM | 1763 | O   | LEU | A | 376 | 50.671 | 30.442 | −4.561 | 1.00 | 19.35 |
| ATOM | 1764 | CB  | LEU | A | 376 | 49.865 | 27.425 | −3.333 | 1.00 | 16.65 |

TABLE 5-continued

Structural coordinates for AKT3lkd(pT305, S472D).

| ATOM | 1765 | CG | LEU | A | 376 | 48.701 | 28.274 | −2.790 | 1.00 | 20.52 |
|---|---|---|---|---|---|---|---|---|---|---|
| ATOM | 1766 | CD1 | LEU | A | 376 | 47.474 | 28.213 | −3.716 | 1.00 | 22.61 |
| ATOM | 1767 | CD2 | LEU | A | 376 | 48.333 | 27.845 | −1.361 | 1.00 | 21.65 |
| ATOM | 1768 | N | LEU | A | 377 | 52.097 | 29.406 | −3.183 | 1.00 | 19.57 |
| ATOM | 1769 | CA | LEU | A | 377 | 52.683 | 30.632 | −2.665 | 1.00 | 19.48 |
| ATOM | 1770 | C | LEU | A | 377 | 53.340 | 31.458 | −3.755 | 1.00 | 22.54 |
| ATOM | 1771 | O | LEU | A | 377 | 53.236 | 32.685 | −3.767 | 1.00 | 20.68 |
| ATOM | 1772 | CB | LEU | A | 377 | 53.686 | 30.315 | −1.537 | 1.00 | 19.02 |
| ATOM | 1773 | CG | LEU | A | 377 | 53.098 | 29.643 | −0.289 | 1.00 | 22.15 |
| ATOM | 1774 | CD1 | LEU | A | 377 | 54.207 | 29.402 | 0.732 | 1.00 | 21.62 |
| ATOM | 1775 | CD2 | LEU | A | 377 | 51.964 | 30.508 | 0.317 | 1.00 | 24.89 |
| ATOM | 1776 | N | SER | A | 378 | 54.011 | 30.786 | −4.678 | 1.00 | 21.38 |
| ATOM | 1777 | CA | SER | A | 378 | 54.645 | 31.480 | −5.802 | 1.00 | 20.74 |
| ATOM | 1778 | C | SER | A | 378 | 53.595 | 32.175 | −6.656 | 1.00 | 23.50 |
| ATOM | 1779 | O | SER | A | 378 | 53.784 | 33.307 | −7.096 | 1.00 | 22.37 |
| ATOM | 1780 | CB | SER | A | 378 | 55.419 | 30.488 | −6.674 | 1.00 | 23.20 |
| ATOM | 1781 | OG | SER | A | 378 | 56.620 | 30.094 | −6.040 | 1.00 | 28.59 |
| ATOM | 1782 | N | GLY | A | 379 | 52.507 | 31.465 | −6.928 | 1.00 | 20.50 |
| ATOM | 1783 | CA | GLY | A | 379 | 51.426 | 31.992 | −7.761 | 1.00 | 19.38 |
| ATOM | 1784 | C | GLY | A | 379 | 50.723 | 33.195 | −7.137 | 1.00 | 21.80 |
| ATOM | 1785 | O | GLY | A | 379 | 50.365 | 34.151 | −7.839 | 1.00 | 21.68 |
| ATOM | 1786 | N | LEU | A | 380 | 50.497 | 33.143 | −5.827 | 1.00 | 17.36 |
| ATOM | 1787 | CA | LEU | A | 380 | 49.800 | 34.224 | −5.137 | 1.00 | 16.69 |
| ATOM | 1788 | C | LEU | A | 380 | 50.689 | 35.435 | −5.033 | 1.00 | 20.38 |
| ATOM | 1789 | O | LEU | A | 380 | 50.215 | 36.562 | −4.954 | 1.00 | 19.69 |
| ATOM | 1790 | CB | LEU | A | 380 | 49.375 | 33.772 | −3.716 | 1.00 | 15.96 |
| ATOM | 1791 | CG | LEU | A | 380 | 48.314 | 32.653 | −3.694 | 1.00 | 18.24 |
| ATOM | 1792 | CD1 | LEU | A | 380 | 48.141 | 32.127 | −2.259 | 1.00 | 16.46 |
| ATOM | 1793 | CD2 | LEU | A | 380 | 46.963 | 33.183 | −4.232 | 1.00 | 17.00 |
| ATOM | 1794 | N | LEU | A | 381 | 51.993 | 35.195 | −5.027 | 1.00 | 19.21 |
| ATOM | 1795 | CA | LEU | A | 381 | 52.960 | 36.282 | −4.892 | 1.00 | 18.72 |
| ATOM | 1796 | C | LEU | A | 381 | 53.618 | 36.740 | −6.190 | 1.00 | 22.79 |
| ATOM | 1797 | O | LEU | A | 381 | 54.629 | 37.462 | −6.172 | 1.00 | 21.36 |
| ATOM | 1798 | CB | LEU | A | 381 | 53.986 | 35.964 | −3.807 | 1.00 | 18.56 |
| ATOM | 1799 | CG | LEU | A | 381 | 53.371 | 35.780 | −2.409 | 1.00 | 22.59 |
| ATOM | 1800 | CD1 | LEU | A | 381 | 54.387 | 35.326 | −1.381 | 1.00 | 23.94 |
| ATOM | 1801 | CD2 | LEU | A | 381 | 52.596 | 37.029 | −1.920 | 1.00 | 24.20 |
| ATOM | 1802 | N | ILE | A | 382 | 52.982 | 36.415 | −7.305 | 1.00 | 20.25 |
| ATOM | 1803 | CA | ILE | A | 382 | 53.443 | 36.867 | −8.610 | 1.00 | 20.34 |
| ATOM | 1804 | C | ILE | A | 382 | 53.319 | 38.383 | −8.548 | 1.00 | 24.32 |
| ATOM | 1805 | O | ILE | A | 382 | 52.361 | 38.904 | −7.976 | 1.00 | 22.63 |
| ATOM | 1806 | CB | ILE | A | 382 | 52.583 | 36.258 | −9.760 | 1.00 | 23.68 |
| ATOM | 1807 | CG1 | ILE | A | 382 | 53.127 | 34.873 | −10.155 | 1.00 | 24.15 |
| ATOM | 1808 | CG2 | ILE | A | 382 | 52.592 | 37.161 | −10.989 | 1.00 | 25.03 |
| ATOM | 1809 | CD1 | ILE | A | 382 | 52.076 | 33.942 | −10.785 | 1.00 | 30.57 |
| ATOM | 1810 | N | LYS | A | 383 | 54.345 | 39.094 | −9.009 | 1.00 | 22.49 |
| ATOM | 1811 | CA | LYS | A | 383 | 54.345 | 40.554 | −8.875 | 1.00 | 23.59 |
| ATOM | 1812 | C | LYS | A | 383 | 53.306 | 41.251 | −9.727 | 1.00 | 26.39 |
| ATOM | 1813 | O | LYS | A | 383 | 52.710 | 42.256 | −9.305 | 1.00 | 25.37 |
| ATOM | 1814 | CB | LYS | A | 383 | 55.747 | 41.138 | −9.119 | 1.00 | 27.49 |
| ATOM | 1815 | CG | LYS | A | 383 | 56.574 | 41.337 | −7.831 | 1.00 | 39.69 |
| ATOM | 1816 | CD | LYS | A | 383 | 57.457 | 40.133 | −7.533 | 1.00 | 44.10 |
| ATOM | 1817 | CE | LYS | A | 383 | 58.706 | 40.531 | −6.739 | 1.00 | 36.51 |
| ATOM | 1818 | NZ | LYS | A | 383 | 58.562 | 40.300 | −5.256 | 1.00 | 32.22 |
| ATOM | 1819 | N | ASP | A | 384 | 53.110 | 40.736 | −10.935 | 1.00 | 25.14 |
| ATOM | 1820 | CA | ASP | A | 384 | 52.149 | 41.297 | −11.881 | 1.00 | 25.34 |
| ATOM | 1821 | C | ASP | A | 384 | 50.750 | 40.789 | −11.539 | 1.00 | 29.01 |
| ATOM | 1822 | O | ASP | A | 384 | 50.489 | 39.594 | −11.614 | 1.00 | 29.17 |
| ATOM | 1823 | CB | ASP | A | 384 | 52.535 | 40.889 | −13.313 | 1.00 | 26.59 |
| ATOM | 1824 | CG | ASP | A | 384 | 51.611 | 41.493 | −14.367 | 1.00 | 32.11 |
| ATOM | 1825 | OD1 | ASP | A | 384 | 50.605 | 42.124 | −13.990 | 1.00 | 30.48 |
| ATOM | 1826 | OD2 | ASP | A | 384 | 51.911 | 41.346 | −15.573 | 1.00 | 33.04 |
| ATOM | 1827 | N | PRO | A | 385 | 49.859 | 41.695 | −11.140 | 1.00 | 26.88 |
| ATOM | 1828 | CA | PRO | A | 385 | 48.504 | 41.297 | −10.720 | 1.00 | 26.59 |
| ATOM | 1829 | C | PRO | A | 385 | 47.701 | 40.587 | −11.805 | 1.00 | 29.49 |
| ATOM | 1830 | O | PRO | A | 385 | 46.850 | 39.746 | −11.501 | 1.00 | 28.29 |
| ATOM | 1831 | CB | PRO | A | 385 | 47.844 | 42.625 | −10.325 | 1.00 | 28.11 |
| ATOM | 1832 | CG | PRO | A | 385 | 48.693 | 43.692 | −10.979 | 1.00 | 32.49 |
| ATOM | 1833 | CD | PRO | A | 385 | 50.076 | 43.151 | −11.006 | 1.00 | 27.66 |
| ATOM | 1834 | N | ASN | A | 386 | 47.977 | 40.923 | −13.072 | 1.00 | 25.61 |
| ATOM | 1835 | CA | ASN | A | 386 | 47.304 | 40.292 | −14.196 | 1.00 | 25.39 |
| ATOM | 1836 | C | ASN | A | 386 | 47.659 | 38.822 | −14.307 | 1.00 | 27.85 |
| ATOM | 1837 | O | ASN | A | 386 | 46.881 | 38.029 | −14.823 | 1.00 | 29.05 |
| ATOM | 1838 | CB | ASN | A | 386 | 47.718 | 40.976 | −15.507 | 1.00 | 28.97 |
| ATOM | 1839 | CG | ASN | A | 386 | 47.502 | 42.448 | −15.468 | 1.00 | 53.07 |
| ATOM | 1840 | OD1 | ASN | A | 386 | 46.437 | 42.911 | −15.071 | 1.00 | 42.25 |
| ATOM | 1841 | ND2 | ASN | A | 386 | 48.530 | 43.209 | −15.824 | 1.00 | 49.07 |
| ATOM | 1842 | N | LYS | A | 387 | 48.869 | 38.479 | −13.888 | 1.00 | 23.68 |

TABLE 5-continued

Structural coordinates for AKT3lkd(pT305, S472D).

| ATOM | 1843 | CA | LYS | A | 387 | 49.369 | 37.116 | −14.014 | 1.00 | 22.50 |
|---|---|---|---|---|---|---|---|---|---|---|
| ATOM | 1844 | C | LYS | A | 387 | 49.364 | 36.329 | −12.696 | 1.00 | 25.49 |
| ATOM | 1845 | O | LYS | A | 387 | 49.688 | 35.137 | −12.672 | 1.00 | 23.96 |
| ATOM | 1846 | CB | LYS | A | 387 | 50.790 | 37.138 | −14.596 | 1.00 | 25.46 |
| ATOM | 1847 | CG | LYS | A | 387 | 50.883 | 37.785 | −15.986 | 1.00 | 30.60 |
| ATOM | 1848 | CD | LYS | A | 387 | 52.320 | 37.796 | −16.488 | 1.00 | 40.13 |
| ATOM | 1849 | CE | LYS | A | 387 | 52.414 | 38.400 | −17.886 | 1.00 | 50.34 |
| ATOM | 1850 | NZ | LYS | A | 387 | 53.435 | 37.708 | −18.711 | 1.00 | 62.72 |
| ATOM | 1851 | N | ARG | A | 388 | 49.004 | 37.003 | −11.615 | 1.00 | 21.24 |
| ATOM | 1852 | CA | ARG | A | 388 | 48.958 | 36.388 | −10.285 | 1.00 | 20.49 |
| ATOM | 1853 | C | ARG | A | 388 | 47.850 | 35.346 | −10.234 | 1.00 | 22.29 |
| ATOM | 1854 | O | ARG | A | 388 | 46.841 | 35.465 | −10.947 | 1.00 | 20.52 |
| ATOM | 1855 | CB | ARG | A | 388 | 48.660 | 37.477 | −9.252 | 1.00 | 21.30 |
| ATOM | 1856 | CG | ARG | A | 388 | 48.752 | 37.029 | −7.792 | 1.00 | 25.22 |
| ATOM | 1857 | CD | ARG | A | 388 | 48.613 | 38.231 | −6.870 | 1.00 | 23.14 |
| ATOM | 1858 | NE | ARG | A | 388 | 49.642 | 39.237 | −7.161 | 1.00 | 23.98 |
| ATOM | 1859 | CZ | ARG | A | 388 | 49.466 | 40.553 | −7.046 | 1.00 | 31.41 |
| ATOM | 1860 | NH1 | ARG | A | 388 | 48.306 | 41.047 | −6.624 | 1.00 | 23.30 |
| ATOM | 1861 | NH2 | ARG | A | 388 | 50.467 | 41.374 | −7.336 | 1.00 | 18.11 |
| ATOM | 1862 | N | LEU | A | 389 | 48.025 | 34.339 | −9.374 | 1.00 | 18.09 |
| ATOM | 1863 | CA | LEU | A | 389 | 47.010 | 33.308 | −9.178 | 1.00 | 17.75 |
| ATOM | 1864 | C | LEU | A | 389 | 45.811 | 33.982 | −8.531 | 1.00 | 21.21 |
| ATOM | 1865 | O | LEU | A | 389 | 45.940 | 34.655 | −7.502 | 1.00 | 20.73 |
| ATOM | 1866 | CB | LEU | A | 389 | 47.547 | 32.199 | −8.240 | 1.00 | 17.25 |
| ATOM | 1867 | CG | LEU | A | 389 | 46.643 | 30.984 | −7.974 | 1.00 | 21.15 |
| ATOM | 1868 | CD1 | LEU | A | 389 | 46.442 | 30.203 | −9.252 | 1.00 | 20.93 |
| ATOM | 1869 | CD2 | LEU | A | 389 | 47.274 | 30.073 | −6.892 | 1.00 | 21.97 |
| ATOM | 1870 | N | GLY | A | 390 | 44.652 | 33.826 | −9.144 | 1.00 | 19.03 |
| ATOM | 1871 | CA | GLY | A | 390 | 43.434 | 34.469 | −8.647 | 1.00 | 18.94 |
| ATOM | 1872 | C | GLY | A | 390 | 43.147 | 35.809 | −9.363 | 1.00 | 24.96 |
| ATOM | 1873 | O | GLY | A | 390 | 42.065 | 36.362 | −9.230 | 1.00 | 24.47 |
| ATOM | 1874 | N | GLY | A | 391 | 44.112 | 36.291 | −10.139 | 1.00 | 23.27 |
| ATOM | 1875 | CA | GLY | A | 391 | 43.997 | 37.580 | −10.840 | 1.00 | 23.37 |
| ATOM | 1876 | C | GLY | A | 391 | 43.264 | 37.506 | −12.195 | 1.00 | 26.77 |
| ATOM | 1877 | O | GLY | A | 391 | 42.955 | 38.539 | −12.790 | 1.00 | 25.74 |
| ATOM | 1878 | N | GLY | A | 392 | 43.001 | 36.291 | −12.668 | 1.00 | 23.92 |
| ATOM | 1879 | CA | GLY | A | 392 | 42.270 | 36.082 | −13.927 | 1.00 | 23.81 |
| ATOM | 1880 | C | GLY | A | 392 | 40.770 | 36.339 | −13.713 | 1.00 | 26.91 |
| ATOM | 1881 | O | GLY | A | 392 | 40.344 | 36.697 | −12.607 | 1.00 | 25.95 |
| ATOM | 1882 | N | PRO | A | 393 | 39.975 | 36.145 | −14.768 | 1.00 | 23.35 |
| ATOM | 1883 | CA | PRO | A | 393 | 38.532 | 36.422 | −14.706 | 1.00 | 23.31 |
| ATOM | 1884 | C | PRO | A | 393 | 37.732 | 35.497 | −13.813 | 1.00 | 25.15 |
| ATOM | 1885 | O | PRO | A | 393 | 36.626 | 35.847 | −13.400 | 1.00 | 25.18 |
| ATOM | 1886 | CB | PRO | A | 393 | 38.076 | 36.271 | −16.168 | 1.00 | 24.81 |
| ATOM | 1887 | CG | PRO | A | 393 | 39.109 | 35.417 | −16.796 | 1.00 | 29.22 |
| ATOM | 1888 | CD | PRO | A | 393 | 40.401 | 35.788 | −16.133 | 1.00 | 24.38 |
| ATOM | 1889 | N | ASP | A | 394 | 38.273 | 34.312 | −13.520 | 1.00 | 20.27 |
| ATOM | 1890 | CA | ASP | A | 394 | 37.567 | 33.360 | −12.647 | 1.00 | 18.01 |
| ATOM | 1891 | C | ASP | A | 394 | 37.908 | 33.621 | −11.164 | 1.00 | 21.99 |
| ATOM | 1892 | O | ASP | A | 394 | 37.405 | 32.934 | −10.269 | 1.00 | 20.39 |
| ATOM | 1893 | CB | ASP | A | 394 | 37.872 | 31.916 | −13.034 | 1.00 | 18.76 |
| ATOM | 1894 | CG | ASP | A | 394 | 36.627 | 31.052 | −13.070 | 1.00 | 24.34 |
| ATOM | 1895 | OD1 | ASP | A | 394 | 36.756 | 29.824 | −13.246 | 1.00 | 24.63 |
| ATOM | 1896 | OD2 | ASP | A | 394 | 35.518 | 31.597 | −12.862 | 1.00 | 26.30 |
| ATOM | 1897 | N | ASP | A | 395 | 38.758 | 34.621 | −10.933 | 1.00 | 18.66 |
| ATOM | 1898 | CA | ASP | A | 395 | 39.098 | 35.064 | −9.578 | 1.00 | 18.47 |
| ATOM | 1899 | C | ASP | A | 395 | 39.415 | 33.916 | −8.631 | 1.00 | 20.81 |
| ATOM | 1900 | O | ASP | A | 395 | 40.312 | 33.126 | −8.893 | 1.00 | 19.47 |
| ATOM | 1901 | CB | ASP | A | 395 | 37.939 | 35.906 | −9.020 | 1.00 | 20.34 |
| ATOM | 1902 | CG | ASP | A | 395 | 38.305 | 36.624 | −7.740 | 1.00 | 22.20 |
| ATOM | 1903 | OD1 | ASP | A | 395 | 39.303 | 37.377 | −7.739 | 1.00 | 21.87 |
| ATOM | 1904 | OD2 | ASP | A | 395 | 37.567 | 36.456 | −6.751 | 1.00 | 22.80 |
| ATOM | 1905 | N | ALA | A | 396 | 38.659 | 33.819 | −7.535 | 1.00 | 18.80 |
| ATOM | 1906 | CA | ALA | A | 396 | 38.889 | 32.764 | −6.519 | 1.00 | 18.66 |
| ATOM | 1907 | C | ALA | A | 396 | 38.889 | 31.317 | −7.060 | 1.00 | 20.75 |
| ATOM | 1908 | O | ALA | A | 396 | 39.584 | 30.459 | −6.533 | 1.00 | 18.89 |
| ATOM | 1909 | CB | ALA | A | 396 | 37.900 | 32.908 | −5.342 | 1.00 | 19.90 |
| ATOM | 1910 | N | LYS | A | 397 | 38.104 | 31.045 | −8.106 | 1.00 | 17.25 |
| ATOM | 1911 | CA | LYS | A | 397 | 38.081 | 29.692 | −8.663 | 1.00 | 17.07 |
| ATOM | 1912 | C | LYS | A | 397 | 39.461 | 29.217 | −9.107 | 1.00 | 19.08 |
| ATOM | 1913 | O | LYS | A | 397 | 39.729 | 28.010 | −9.141 | 1.00 | 18.39 |
| ATOM | 1914 | CB | LYS | A | 397 | 37.072 | 29.568 | −9.807 | 1.00 | 19.81 |
| ATOM | 1915 | CG | LYS | A | 397 | 35.591 | 29.625 | −9.345 | 1.00 | 30.01 |
| ATOM | 1916 | CD | LYS | A | 397 | 35.352 | 30.755 | −8.382 | 1.00 | 34.59 |
| ATOM | 1917 | CE | LYS | A | 397 | 33.893 | 30.842 | −7.961 | 1.00 | 51.02 |
| ATOM | 1918 | NZ | LYS | A | 397 | 33.422 | 32.257 | −7.949 | 1.00 | 59.40 |
| ATOM | 1919 | N | GLU | A | 398 | 40.327 | 30.155 | −9.488 | 1.00 | 15.74 |
| ATOM | 1920 | CA | GLU | A | 398 | 41.701 | 29.806 | −9.920 | 1.00 | 16.17 |

TABLE 5-continued

Structural coordinates for AKT3lkd(pT305, S472D).

| ATOM | 1921 | C | GLU | A | 398 | 42.448 | 29.152 | −8.733 | 1.00 | 20.07 |
| --- | --- | --- | --- | --- | --- | --- | --- | --- | --- | --- |
| ATOM | 1922 | O | GLU | A | 398 | 43.212 | 28.183 | −8.886 | 1.00 | 18.78 |
| ATOM | 1923 | CB | GLU | A | 398 | 42.463 | 31.078 | −10.332 | 1.00 | 17.46 |
| ATOM | 1924 | CG | GLU | A | 398 | 42.011 | 31.697 | −11.626 | 1.00 | 27.71 |
| ATOM | 1925 | CD | GLU | A | 398 | 43.069 | 32.647 | −12.203 | 1.00 | 34.68 |
| ATOM | 1926 | OE1 | GLU | A | 398 | 44.214 | 32.641 | −11.703 | 1.00 | 25.96 |
| ATOM | 1927 | OE2 | GLU | A | 398 | 42.740 | 33.426 | −13.108 | 1.00 | 32.39 |
| ATOM | 1928 | N | ILE | A | 399 | 42.255 | 29.707 | −7.555 | 1.00 | 17.40 |
| ATOM | 1929 | CA | ILE | A | 399 | 42.899 | 29.156 | −6.357 | 1.00 | 16.71 |
| ATOM | 1930 | C | ILE | A | 399 | 42.208 | 27.879 | −5.893 | 1.00 | 18.83 |
| ATOM | 1931 | O | ILE | A | 399 | 42.860 | 26.897 | −5.529 | 1.00 | 18.08 |
| ATOM | 1932 | CB | ILE | A | 399 | 42.904 | 30.170 | −5.211 | 1.00 | 19.99 |
| ATOM | 1933 | CG1 | ILE | A | 399 | 43.852 | 31.322 | −5.559 | 1.00 | 21.69 |
| ATOM | 1934 | CG2 | ILE | A | 399 | 43.389 | 29.492 | −3.919 | 1.00 | 19.00 |
| ATOM | 1935 | CD1 | ILE | A | 399 | 43.164 | 32.610 | −5.872 | 1.00 | 30.08 |
| ATOM | 1936 | N | MET | A | 400 | 40.882 | 27.878 | −5.916 | 1.00 | 14.37 |
| ATOM | 1937 | CA | MET | A | 400 | 40.127 | 26.681 | −5.534 | 1.00 | 14.70 |
| ATOM | 1938 | C | MET | A | 400 | 40.513 | 25.472 | −6.370 | 1.00 | 18.34 |
| ATOM | 1939 | O | MET | A | 400 | 40.424 | 24.332 | −5.905 | 1.00 | 17.85 |
| ATOM | 1940 | CB | MET | A | 400 | 38.617 | 26.943 | −5.639 | 1.00 | 17.02 |
| ATOM | 1941 | CG | MET | A | 400 | 38.149 | 28.093 | −4.771 | 1.00 | 21.31 |
| ATOM | 1942 | SD | MET | A | 400 | 36.357 | 28.447 | −4.974 | 1.00 | 26.85 |
| ATOM | 1943 | CE | MET | A | 400 | 36.109 | 29.701 | −3.614 | 1.00 | 25.40 |
| ATOM | 1944 | N | ARG | A | 401 | 40.951 | 25.720 | −7.600 | 1.00 | 17.29 |
| ATOM | 1945 | CA | ARG | A | 401 | 41.337 | 24.641 | −8.500 | 1.00 | 17.39 |
| ATOM | 1946 | C | ARG | A | 401 | 42.827 | 24.279 | −8.390 | 1.00 | 21.84 |
| ATOM | 1947 | O | ARG | A | 401 | 43.287 | 23.334 | −9.042 | 1.00 | 21.91 |
| ATOM | 1948 | CB | ARG | A | 401 | 41.010 | 25.016 | −9.969 | 1.00 | 15.01 |
| ATOM | 1949 | CG | ARG | A | 401 | 39.495 | 25.012 | −10.329 | 1.00 | 22.11 |
| ATOM | 1950 | CD | ARG | A | 401 | 39.280 | 25.097 | −11.876 | 1.00 | 23.33 |
| ATOM | 1951 | NE | ARG | A | 401 | 39.824 | 26.324 | −12.462 | 1.00 | 23.56 |
| ATOM | 1952 | CZ | ARG | A | 401 | 39.123 | 27.434 | −12.660 | 1.00 | 28.96 |
| ATOM | 1953 | NH1 | ARG | A | 401 | 37.857 | 27.490 | −12.320 | 1.00 | 25.44 |
| ATOM | 1954 | NH2 | ARG | A | 401 | 39.698 | 28.496 | −13.194 | 1.00 | 26.81 |
| ATOM | 1955 | N | HIS | A | 402 | 43.582 | 25.027 | −7.593 | 1.00 | 18.82 |
| ATOM | 1956 | CA | HIS | A | 402 | 45.044 | 24.786 | −7.483 | 1.00 | 17.10 |
| ATOM | 1957 | C | HIS | A | 402 | 45.328 | 23.425 | −6.878 | 1.00 | 19.02 |
| ATOM | 1958 | O | HIS | A | 402 | 44.614 | 22.974 | −5.984 | 1.00 | 15.47 |
| ATOM | 1959 | CB | HIS | A | 402 | 45.755 | 25.923 | −6.664 | 1.00 | 17.53 |
| ATOM | 1960 | CG | HIS | A | 402 | 47.258 | 25.867 | −6.736 | 1.00 | 20.00 |
| ATOM | 1961 | ND1 | HIS | A | 402 | 48.014 | 25.069 | −5.901 | 1.00 | 21.12 |
| ATOM | 1962 | CD2 | HIS | A | 402 | 48.132 | 26.435 | −7.605 | 1.00 | 21.21 |
| ATOM | 1963 | CE1 | HIS | A | 402 | 49.293 | 25.181 | −6.225 | 1.00 | 20.57 |
| ATOM | 1964 | NE2 | HIS | A | 402 | 49.391 | 26.003 | −7.258 | 1.00 | 20.73 |
| ATOM | 1965 | N | SER | A | 403 | 46.397 | 22.771 | −7.333 | 1.00 | 17.31 |
| ATOM | 1966 | CA | SER | A | 403 | 46.748 | 21.452 | −6.789 | 1.00 | 16.94 |
| ATOM | 1967 | C | SER | A | 403 | 46.837 | 21.442 | −5.239 | 1.00 | 18.80 |
| ATOM | 1968 | O | SER | A | 403 | 46.499 | 20.437 | −4.593 | 1.00 | 16.66 |
| ATOM | 1969 | CB | SER | A | 403 | 48.085 | 20.967 | −7.391 | 1.00 | 24.16 |
| ATOM | 1970 | OG | SER | A | 403 | 49.153 | 21.819 | −6.974 | 1.00 | 33.68 |
| ATOM | 1971 | N | PHE | A | 404 | 47.293 | 22.547 | −4.641 | 1.00 | 15.26 |
| ATOM | 1972 | CA | PHE | A | 404 | 47.433 | 22.604 | −3.152 | 1.00 | 14.73 |
| ATOM | 1973 | C | PHE | A | 404 | 46.122 | 22.304 | −2.412 | 1.00 | 18.72 |
| ATOM | 1974 | O | PHE | A | 404 | 46.114 | 21.766 | −1.286 | 1.00 | 19.57 |
| ATOM | 1975 | CB | PHE | A | 404 | 47.967 | 23.971 | −2.689 | 1.00 | 15.73 |
| ATOM | 1976 | CG | PHE | A | 404 | 48.248 | 24.037 | −1.198 | 1.00 | 16.55 |
| ATOM | 1977 | CD1 | PHE | A | 404 | 49.404 | 23.461 | −0.667 | 1.00 | 18.69 |
| ATOM | 1978 | CD2 | PHE | A | 404 | 47.358 | 24.649 | −0.335 | 1.00 | 16.80 |
| ATOM | 1979 | CE1 | PHE | A | 404 | 49.664 | 23.501 | 0.725 | 1.00 | 18.89 |
| ATOM | 1980 | CE2 | PHE | A | 404 | 47.615 | 24.715 | 1.046 | 1.00 | 19.53 |
| ATOM | 1981 | CZ | PHE | A | 404 | 48.765 | 24.125 | 1.575 | 1.00 | 18.32 |
| ATOM | 1982 | N | PHE | A | 405 | 45.023 | 22.661 | −3.046 | 1.00 | 15.24 |
| ATOM | 1983 | CA | PHE | A | 405 | 43.669 | 22.458 | −2.469 | 1.00 | 15.05 |
| ATOM | 1984 | C | PHE | A | 405 | 42.927 | 21.283 | −3.143 | 1.00 | 20.39 |
| ATOM | 1985 | O | PHE | A | 405 | 41.702 | 21.174 | −3.048 | 1.00 | 18.93 |
| ATOM | 1986 | CB | PHE | A | 405 | 42.849 | 23.741 | −2.663 | 1.00 | 15.49 |
| ATOM | 1987 | CG | PHE | A | 405 | 43.315 | 24.899 | −1.811 | 1.00 | 16.01 |
| ATOM | 1988 | CD1 | PHE | A | 405 | 43.137 | 24.877 | −0.422 | 1.00 | 16.55 |
| ATOM | 1989 | CD2 | PHE | A | 405 | 43.932 | 26.008 | −2.392 | 1.00 | 16.07 |
| ATOM | 1990 | CE1 | PHE | A | 405 | 43.570 | 25.940 | 0.375 | 1.00 | 16.92 |
| ATOM | 1991 | CE2 | PHE | A | 405 | 44.354 | 27.101 | −1.594 | 1.00 | 17.73 |
| ATOM | 1992 | CZ | PHE | A | 405 | 44.157 | 27.057 | −0.201 | 1.00 | 15.65 |
| ATOM | 1993 | N | SER | A | 406 | 43.662 | 20.448 | −3.871 | 1.00 | 17.70 |
| ATOM | 1994 | CA | SER | A | 406 | 43.037 | 19.338 | −4.619 | 1.00 | 19.05 |
| ATOM | 1995 | C | SER | A | 406 | 42.097 | 18.386 | −3.816 | 1.00 | 23.15 |
| ATOM | 1996 | O | SER | A | 406 | 41.253 | 17.712 | −4.400 | 1.00 | 23.55 |
| ATOM | 1997 | CB | SER | A | 406 | 44.106 | 18.518 | −5.359 | 1.00 | 21.81 |
| ATOM | 1998 | OG | SER | A | 406 | 44.837 | 17.751 | −4.438 | 1.00 | 25.70 |

TABLE 5-continued

Structural coordinates for AKT3lkd(pT305, S472D).

| ATOM | 1999 | N | GLY | A | 407 | 42.222 | 18.337 | −2.502 | 1.00 | 18.87 |
|---|---|---|---|---|---|---|---|---|---|---|
| ATOM | 2000 | CA | GLY | A | 407 | 41.346 | 17.422 | −1.731 | 1.00 | 19.43 |
| ATOM | 2001 | C | GLY | A | 407 | 40.164 | 18.120 | −1.050 | 1.00 | 23.19 |
| ATOM | 2002 | O | GLY | A | 407 | 39.393 | 17.492 | −0.305 | 1.00 | 24.17 |
| ATOM | 2003 | N | VAL | A | 408 | 40.019 | 19.414 | −1.309 | 1.00 | 17.56 |
| ATOM | 2004 | CA | VAL | A | 408 | 39.019 | 20.231 | −0.634 | 1.00 | 16.73 |
| ATOM | 2005 | C | VAL | A | 408 | 37.675 | 20.319 | −1.338 | 1.00 | 18.98 |
| ATOM | 2006 | O | VAL | A | 408 | 37.605 | 20.622 | −2.535 | 1.00 | 17.82 |
| ATOM | 2007 | CB | VAL | A | 408 | 39.544 | 21.673 | −0.438 | 1.00 | 20.09 |
| ATOM | 2008 | CG1 | VAL | A | 408 | 38.480 | 22.564 | 0.182 | 1.00 | 19.09 |
| ATOM | 2009 | CG2 | VAL | A | 408 | 40.810 | 21.665 | 0.423 | 1.00 | 20.60 |
| ATOM | 2010 | N | ASN | A | 409 | 36.607 | 20.111 | −0.563 | 1.00 | 15.71 |
| ATOM | 2011 | CA | ASN | A | 409 | 35.244 | 20.265 | −1.066 | 1.00 | 16.45 |
| ATOM | 2012 | C | ASN | A | 409 | 34.799 | 21.677 | −0.650 | 1.00 | 17.39 |
| ATOM | 2013 | O | ASN | A | 409 | 34.651 | 21.966 | 0.528 | 1.00 | 15.82 |
| ATOM | 2014 | CB | ASN | A | 409 | 34.320 | 19.192 | −0.468 | 1.00 | 18.42 |
| ATOM | 2015 | CG | ASN | A | 409 | 32.883 | 19.353 | −0.918 | 1.00 | 26.77 |
| ATOM | 2016 | OD1 | ASN | A | 409 | 32.263 | 20.370 | −0.656 | 1.00 | 20.78 |
| ATOM | 2017 | ND2 | ASN | A | 409 | 32.376 | 18.377 | −1.664 | 1.00 | 20.04 |
| ATOM | 2018 | N | TRP | A | 410 | 34.689 | 22.566 | −1.628 | 1.00 | 15.83 |
| ATOM | 2019 | CA | TRP | A | 410 | 34.407 | 23.988 | −1.360 | 1.00 | 17.68 |
| ATOM | 2020 | C | TRP | A | 410 | 33.047 | 24.332 | −0.730 | 1.00 | 21.52 |
| ATOM | 2021 | O | TRP | A | 410 | 32.923 | 25.316 | 0.014 | 1.00 | 19.70 |
| ATOM | 2022 | CB | TRP | A | 410 | 34.745 | 24.845 | −2.577 | 1.00 | 16.78 |
| ATOM | 2023 | CG | TRP | A | 410 | 36.221 | 24.819 | −2.851 | 1.00 | 16.93 |
| ATOM | 2024 | CD1 | TRP | A | 410 | 36.897 | 23.911 | −3.633 | 1.00 | 19.77 |
| ATOM | 2025 | CD2 | TRP | A | 410 | 37.217 | 25.585 | −2.177 | 1.00 | 16.57 |
| ATOM | 2026 | NE1 | TRP | A | 410 | 38.249 | 24.108 | −3.527 | 1.00 | 18.38 |
| ATOM | 2027 | CE2 | TRP | A | 410 | 38.477 | 25.147 | −2.652 | 1.00 | 19.91 |
| ATOM | 2028 | CE3 | TRP | A | 410 | 37.173 | 26.601 | −1.207 | 1.00 | 17.44 |
| ATOM | 2029 | CZ2 | TRP | A | 410 | 39.674 | 25.671 | −2.176 | 1.00 | 19.04 |
| ATOM | 2030 | CZ3 | TRP | A | 410 | 38.377 | 27.174 | −0.785 | 1.00 | 18.46 |
| ATOM | 2031 | CH2 | TRP | A | 410 | 39.604 | 26.706 | −1.268 | 1.00 | 19.19 |
| ATOM | 2032 | N | GLN | A | 411 | 32.040 | 23.505 | −0.975 | 1.00 | 19.24 |
| ATOM | 2033 | CA | GLN | A | 411 | 30.759 | 23.734 | −0.295 | 1.00 | 19.84 |
| ATOM | 2034 | C | GLN | A | 411 | 30.952 | 23.380 | 1.177 | 1.00 | 22.47 |
| ATOM | 2035 | O | GLN | A | 411 | 30.497 | 24.100 | 2.051 | 1.00 | 22.38 |
| ATOM | 2036 | CB | GLN | A | 411 | 29.642 | 22.890 | −0.891 | 1.00 | 22.11 |
| ATOM | 2037 | CG | GLN | A | 411 | 28.234 | 23.235 | −0.310 | 1.00 | 30.04 |
| ATOM | 2038 | CD | GLN | A | 411 | 27.859 | 24.716 | −0.501 | 1.00 | 39.57 |
| ATOM | 2039 | OE1 | GLN | A | 411 | 27.461 | 25.402 | 0.439 | 1.00 | 36.47 |
| ATOM | 2040 | NE2 | GLN | A | 411 | 28.010 | 25.201 | −1.707 | 1.00 | 31.94 |
| ATOM | 2041 | N | ASP | A | 412 | 31.665 | 22.277 | 1.445 | 1.00 | 18.09 |
| ATOM | 2042 | CA | ASP | A | 412 | 31.936 | 21.878 | 2.822 | 1.00 | 17.12 |
| ATOM | 2043 | C | ASP | A | 412 | 32.685 | 22.992 | 3.550 | 1.00 | 21.21 |
| ATOM | 2044 | O | ASP | A | 412 | 32.453 | 23.235 | 4.730 | 1.00 | 21.15 |
| ATOM | 2045 | CB | ASP | A | 412 | 32.752 | 20.602 | 2.887 | 1.00 | 18.43 |
| ATOM | 2046 | CG | ASP | A | 412 | 31.911 | 19.362 | 2.668 | 1.00 | 22.48 |
| ATOM | 2047 | OD1 | ASP | A | 412 | 30.651 | 19.467 | 2.695 | 1.00 | 17.17 |
| ATOM | 2048 | OD2 | ASP | A | 412 | 32.507 | 18.283 | 2.533 | 1.00 | 21.89 |
| ATOM | 2049 | N | VAL | A | 413 | 33.605 | 23.659 | 2.851 | 1.00 | 16.85 |
| ATOM | 2050 | CA | VAL | A | 413 | 34.357 | 24.743 | 3.491 | 1.00 | 16.02 |
| ATOM | 2051 | C | VAL | A | 413 | 33.390 | 25.804 | 3.978 | 1.00 | 21.77 |
| ATOM | 2052 | O | VAL | A | 413 | 33.434 | 26.226 | 5.136 | 1.00 | 21.88 |
| ATOM | 2053 | CB | VAL | A | 413 | 35.352 | 25.407 | 2.508 | 1.00 | 18.33 |
| ATOM | 2054 | CG1 | VAL | A | 413 | 35.853 | 26.768 | 3.097 | 1.00 | 17.65 |
| ATOM | 2055 | CG2 | VAL | A | 413 | 36.523 | 24.475 | 2.236 | 1.00 | 17.87 |
| ATOM | 2056 | N | TYR | A | 414 | 32.533 | 26.253 | 3.076 | 1.00 | 19.89 |
| ATOM | 2057 | CA | TYR | A | 414 | 31.543 | 27.302 | 3.403 | 1.00 | 20.93 |
| ATOM | 2058 | C | TYR | A | 414 | 30.591 | 26.860 | 4.531 | 1.00 | 24.44 |
| ATOM | 2059 | O | TYR | A | 414 | 30.274 | 27.645 | 5.453 | 1.00 | 23.55 |
| ATOM | 2060 | CB | TYR | A | 414 | 30.743 | 27.672 | 2.152 | 1.00 | 22.06 |
| ATOM | 2061 | CG | TYR | A | 414 | 29.712 | 28.758 | 2.397 | 1.00 | 24.82 |
| ATOM | 2062 | CD1 | TYR | A | 414 | 28.460 | 28.447 | 2.900 | 1.00 | 27.48 |
| ATOM | 2063 | CD2 | TYR | A | 414 | 30.010 | 30.097 | 2.161 | 1.00 | 25.57 |
| ATOM | 2064 | CE1 | TYR | A | 414 | 27.509 | 29.438 | 3.132 | 1.00 | 28.69 |
| ATOM | 2065 | CE2 | TYR | A | 414 | 29.051 | 31.111 | 2.387 | 1.00 | 25.90 |
| ATOM | 2066 | CZ | TYR | A | 414 | 27.814 | 30.765 | 2.873 | 1.00 | 32.67 |
| ATOM | 2067 | OH | TYR | A | 414 | 26.876 | 31.735 | 3.117 | 1.00 | 34.54 |
| ATOM | 2068 | N | ASP | A | 415 | 30.181 | 25.596 | 4.481 | 1.00 | 21.18 |
| ATOM | 2069 | CA | ASP | A | 415 | 29.258 | 25.035 | 5.483 | 1.00 | 20.56 |
| ATOM | 2070 | C | ASP | A | 415 | 29.929 | 24.682 | 6.813 | 1.00 | 25.39 |
| ATOM | 2071 | O | ASP | A | 415 | 29.281 | 24.128 | 7.723 | 1.00 | 24.95 |
| ATOM | 2072 | CB | ASP | A | 415 | 28.506 | 23.833 | 4.895 | 1.00 | 21.40 |
| ATOM | 2073 | CG | ASP | A | 415 | 27.521 | 24.244 | 3.822 | 1.00 | 28.35 |
| ATOM | 2074 | OD1 | ASP | A | 415 | 27.004 | 25.370 | 3.911 | 1.00 | 27.83 |
| ATOM | 2075 | OD2 | ASP | A | 415 | 27.324 | 23.494 | 2.853 | 1.00 | 28.14 |
| ATOM | 2076 | N | LYS | A | 416 | 31.209 | 25.036 | 6.944 | 1.00 | 22.20 |

TABLE 5-continued

Structural coordinates for AKT3lkd(pT305, S472D).

| ATOM | 2077 | CA | LYS | A | 416 | 31.976 | 24.773 | 8.167 | 1.00 | 21.83 |
|---|---|---|---|---|---|---|---|---|---|---|
| ATOM | 2078 | C | LYS | A | 416 | 32.002 | 23.287 | 8.491 | 1.00 | 26.44 |
| ATOM | 2079 | O | LYS | A | 416 | 31.930 | 22.877 | 9.666 | 1.00 | 26.25 |
| ATOM | 2080 | CB | LYS | A | 416 | 31.421 | 25.589 | 9.353 | 1.00 | 23.47 |
| ATOM | 2081 | CG | LYS | A | 416 | 31.872 | 27.048 | 9.343 | 1.00 | 21.07 |
| ATOM | 2082 | CD | LYS | A | 416 | 30.951 | 27.959 | 10.185 | 1.00 | 27.93 |
| ATOM | 2083 | CE | LYS | A | 416 | 31.242 | 27.818 | 11.672 | 1.00 | 32.81 |
| ATOM | 2084 | NZ | LYS | A | 416 | 30.359 | 28.714 | 12.531 | 1.00 | 34.38 |
| ATOM | 2085 | N | LYS | A | 417 | 32.141 | 22.481 | 7.448 | 1.00 | 22.99 |
| ATOM | 2086 | CA | LYS | A | 417 | 32.184 | 21.034 | 7.599 | 1.00 | 22.35 |
| ATOM | 2087 | C | LYS | A | 417 | 33.617 | 20.458 | 7.599 | 1.00 | 28.62 |
| ATOM | 2088 | O | LYS | A | 417 | 33.809 | 19.271 | 7.829 | 1.00 | 28.93 |
| ATOM | 2089 | CB | LYS | A | 417 | 31.306 | 20.352 | 6.543 | 1.00 | 23.54 |
| ATOM | 2090 | CG | LYS | A | 417 | 29.818 | 20.416 | 6.875 | 1.00 | 31.26 |
| ATOM | 2091 | CD | LYS | A | 417 | 28.989 | 19.768 | 5.799 | 1.00 | 33.33 |
| ATOM | 2092 | CE | LYS | A | 417 | 27.521 | 20.169 | 5.918 | 1.00 | 40.83 |
| ATOM | 2093 | NZ | LYS | A | 417 | 26.757 | 19.759 | 4.697 | 1.00 | 40.93 |
| ATOM | 2094 | N | LEU | A | 418 | 34.618 | 21.305 | 7.378 | 1.00 | 26.95 |
| ATOM | 2095 | CA | LEU | A | 418 | 36.012 | 20.849 | 7.474 | 1.00 | 26.71 |
| ATOM | 2096 | C | LEU | A | 418 | 36.308 | 20.754 | 8.979 | 1.00 | 27.56 |
| ATOM | 2097 | O | LEU | A | 418 | 35.856 | 21.585 | 9.751 | 1.00 | 24.48 |
| ATOM | 2098 | CB | LEU | A | 418 | 36.975 | 21.887 | 6.868 | 1.00 | 27.70 |
| ATOM | 2099 | CG | LEU | A | 418 | 37.033 | 22.129 | 5.347 | 1.00 | 33.05 |
| ATOM | 2100 | CD1 | LEU | A | 418 | 38.356 | 22.802 | 4.970 | 1.00 | 33.73 |
| ATOM | 2101 | CD2 | LEU | A | 418 | 36.838 | 20.859 | 4.563 | 1.00 | 35.37 |
| ATOM | 2102 | N | VAL | A | 419 | 37.060 | 19.746 | 9.391 | 1.00 | 23.87 |
| ATOM | 2103 | CA | VAL | A | 419 | 37.396 | 19.605 | 10.803 | 1.00 | 24.25 |
| ATOM | 2104 | C | VAL | A | 419 | 38.577 | 20.485 | 11.140 | 1.00 | 26.15 |
| ATOM | 2105 | O | VAL | A | 419 | 39.642 | 20.333 | 10.567 | 1.00 | 25.08 |
| ATOM | 2106 | CB | VAL | A | 419 | 37.728 | 18.153 | 11.167 | 1.00 | 28.88 |
| ATOM | 2107 | CG1 | VAL | A | 419 | 37.971 | 18.038 | 12.669 | 1.00 | 28.94 |
| ATOM | 2108 | CG2 | VAL | A | 419 | 36.597 | 17.235 | 10.731 | 1.00 | 29.00 |
| ATOM | 2109 | N | PRO | A | 420 | 38.380 | 21.440 | 12.049 | 1.00 | 23.65 |
| ATOM | 2110 | CA | PRO | A | 420 | 39.466 | 22.353 | 12.406 | 1.00 | 23.38 |
| ATOM | 2111 | C | PRO | A | 420 | 40.641 | 21.577 | 13.009 | 1.00 | 28.46 |
| ATOM | 2112 | O | PRO | A | 420 | 40.459 | 20.761 | 13.910 | 1.00 | 28.05 |
| ATOM | 2113 | CB | PRO | A | 420 | 38.828 | 23.279 | 13.440 | 1.00 | 25.01 |
| ATOM | 2114 | CG | PRO | A | 420 | 37.350 | 23.231 | 13.135 | 1.00 | 29.24 |
| ATOM | 2115 | CD | PRO | A | 420 | 37.113 | 21.799 | 12.712 | 1.00 | 24.46 |
| ATOM | 2116 | N | PRO | A | 421 | 41.844 | 21.839 | 12.501 | 1.00 | 26.58 |
| ATOM | 2117 | CA | PRO | A | 421 | 43.044 | 21.139 | 12.959 | 1.00 | 26.63 |
| ATOM | 2118 | C | PRO | A | 421 | 43.431 | 21.472 | 14.394 | 1.00 | 29.43 |
| ATOM | 2119 | O | PRO | A | 421 | 44.067 | 20.671 | 15.067 | 1.00 | 30.38 |
| ATOM | 2120 | CB | PRO | A | 421 | 44.128 | 21.621 | 11.981 | 1.00 | 28.95 |
| ATOM | 2121 | CG | PRO | A | 421 | 43.567 | 22.877 | 11.372 | 1.00 | 34.07 |
| ATOM | 2122 | CD | PRO | A | 421 | 42.103 | 22.605 | 11.273 | 1.00 | 28.92 |
| ATOM | 2123 | N | PHE | A | 422 | 43.030 | 22.649 | 14.855 | 1.00 | 24.07 |
| ATOM | 2124 | CA | PHE | A | 422 | 43.329 | 23.093 | 16.207 | 1.00 | 24.43 |
| ATOM | 2125 | C | PHE | A | 422 | 42.041 | 23.578 | 16.861 | 1.00 | 28.00 |
| ATOM | 2126 | O | PHE | A | 422 | 41.342 | 24.425 | 16.313 | 1.00 | 26.28 |
| ATOM | 2127 | CB | PHE | A | 422 | 44.368 | 24.236 | 16.193 | 1.00 | 26.23 |
| ATOM | 2128 | CG | PHE | A | 422 | 44.486 | 24.965 | 17.520 | 1.00 | 28.15 |
| ATOM | 2129 | CD1 | PHE | A | 422 | 45.162 | 24.390 | 18.584 | 1.00 | 32.16 |
| ATOM | 2130 | CD2 | PHE | A | 422 | 43.889 | 26.203 | 17.703 | 1.00 | 29.94 |
| ATOM | 2131 | CE1 | PHE | A | 422 | 45.236 | 25.037 | 19.817 | 1.00 | 33.01 |
| ATOM | 2132 | CE2 | PHE | A | 422 | 43.974 | 26.860 | 18.919 | 1.00 | 33.10 |
| ATOM | 2133 | CZ | PHE | A | 422 | 44.644 | 26.269 | 19.982 | 1.00 | 31.81 |
| ATOM | 2134 | N | LYS | A | 423 | 41.701 | 23.013 | 18.012 | 1.00 | 26.09 |
| ATOM | 2135 | CA | LYS | A | 423 | 40.492 | 23.422 | 18.708 | 1.00 | 27.20 |
| ATOM | 2136 | C | LYS | A | 423 | 40.856 | 24.296 | 19.912 | 1.00 | 33.51 |
| ATOM | 2137 | O | LYS | A | 423 | 41.530 | 23.836 | 20.832 | 1.00 | 31.56 |
| ATOM | 2138 | CB | LYS | A | 423 | 39.677 | 22.202 | 19.131 | 1.00 | 30.51 |
| ATOM | 2139 | CG | LYS | A | 423 | 39.471 | 21.178 | 18.007 | 1.00 | 39.35 |
| ATOM | 2140 | CD | LYS | A | 423 | 38.529 | 21.710 | 16.917 | 1.00 | 41.21 |
| ATOM | 2141 | CE | LYS | A | 423 | 37.116 | 21.929 | 17.463 | 1.00 | 38.73 |
| ATOM | 2142 | NZ | LYS | A | 423 | 36.096 | 22.128 | 16.402 | 1.00 | 38.60 |
| ATOM | 2143 | N | PRO | A | 424 | 40.474 | 25.579 | 19.866 | 1.00 | 31.78 |
| ATOM | 2144 | CA | PRO | A | 424 | 40.790 | 26.496 | 20.960 | 1.00 | 31.98 |
| ATOM | 2145 | C | PRO | A | 424 | 40.273 | 25.909 | 22.277 | 1.00 | 37.71 |
| ATOM | 2146 | O | PRO | A | 424 | 39.154 | 25.391 | 22.345 | 1.00 | 36.43 |
| ATOM | 2147 | CB | PRO | A | 424 | 40.017 | 27.770 | 20.587 | 1.00 | 33.45 |
| ATOM | 2148 | CG | PRO | A | 424 | 39.942 | 27.720 | 19.088 | 1.00 | 37.02 |
| ATOM | 2149 | CD | PRO | A | 424 | 39.759 | 26.260 | 18.765 | 1.00 | 32.34 |
| ATOM | 2150 | N | GLN | A | 425 | 41.104 | 25.960 | 23.307 | 1.00 | 36.87 |
| ATOM | 2151 | CA | GLN | A | 425 | 40.736 | 25.377 | 24.600 | 1.00 | 37.81 |
| ATOM | 2152 | C | GLN | A | 425 | 39.989 | 26.357 | 25.497 | 1.00 | 43.24 |
| ATOM | 2153 | O | GLN | A | 425 | 40.503 | 26.792 | 26.528 | 1.00 | 42.96 |
| ATOM | 2154 | CB | GLN | A | 425 | 41.969 | 24.827 | 25.310 | 1.00 | 39.20 |

TABLE 5-continued

Structural coordinates for AKT3lkd(pT305, S472D).

| ATOM | 2155 | CG  | GLN | A | 425 | 42.540 | 23.575 | 24.657 | 1.00 | 52.11 |
|------|------|-----|-----|---|-----|--------|--------|--------|------|-------|
| ATOM | 2156 | CD  | GLN | A | 425 | 41.484 | 22.507 | 24.423 | 1.00 | 72.94 |
| ATOM | 2157 | OE1 | GLN | A | 425 | 40.807 | 22.498 | 23.392 | 1.00 | 68.53 |
| ATOM | 2158 | NE2 | GLN | A | 425 | 41.329 | 21.607 | 25.388 | 1.00 | 66.76 |
| ATOM | 2159 | N   | VAL | A | 426 | 38.771 | 26.694 | 25.093 | 1.00 | 41.06 |
| ATOM | 2160 | CA  | VAL | A | 426 | 37.938 | 27.606 | 25.853 | 1.00 | 41.42 |
| ATOM | 2161 | C   | VAL | A | 426 | 36.853 | 26.805 | 26.537 | 1.00 | 45.39 |
| ATOM | 2162 | O   | VAL | A | 426 | 36.396 | 25.794 | 26.020 | 1.00 | 45.35 |
| ATOM | 2163 | CB  | VAL | A | 426 | 37.291 | 28.670 | 24.949 | 1.00 | 45.79 |
| ATOM | 2164 | CG1 | VAL | A | 426 | 38.347 | 29.639 | 24.423 | 1.00 | 45.74 |
| ATOM | 2165 | CG2 | VAL | A | 426 | 36.534 | 28.007 | 23.804 | 1.00 | 45.70 |
| ATOM | 2166 | N   | THR | A | 427 | 36.460 | 27.248 | 27.717 | 1.00 | 42.10 |
| ATOM | 2167 | CA  | THR | A | 427 | 35.458 | 26.549 | 28.494 | 1.00 | 42.26 |
| ATOM | 2168 | C   | THR | A | 427 | 34.052 | 26.967 | 28.086 | 1.00 | 45.93 |
| ATOM | 2169 | O   | THR | A | 427 | 33.090 | 26.217 | 28.268 | 1.00 | 45.74 |
| ATOM | 2170 | CB  | THR | A | 427 | 35.649 | 26.830 | 29.985 | 1.00 | 52.97 |
| ATOM | 2171 | OG1 | THR | A | 427 | 36.525 | 25.846 | 30.547 | 1.00 | 55.12 |
| ATOM | 2172 | CG2 | THR | A | 427 | 34.320 | 26.806 | 30.705 | 1.00 | 52.32 |
| ATOM | 2173 | N   | SER | A | 428 | 33.937 | 28.163 | 27.523 | 1.00 | 41.63 |
| ATOM | 2174 | CA  | SER | A | 428 | 32.639 | 28.682 | 27.120 | 1.00 | 41.30 |
| ATOM | 2175 | C   | SER | A | 428 | 32.750 | 29.708 | 26.001 | 1.00 | 44.61 |
| ATOM | 2176 | O   | SER | A | 428 | 33.850 | 30.081 | 25.592 | 1.00 | 43.97 |
| ATOM | 2177 | CB  | SER | A | 428 | 31.943 | 29.322 | 28.314 | 1.00 | 44.16 |
| ATOM | 2178 | OG  | SER | A | 428 | 32.614 | 30.503 | 28.706 | 1.00 | 50.06 |
| ATOM | 2179 | N   | GLU | A | 429 | 31.596 | 30.182 | 25.544 | 1.00 | 40.61 |
| ATOM | 2180 | CA  | GLU | A | 429 | 31.518 | 31.182 | 24.485 | 1.00 | 39.95 |
| ATOM | 2181 | C   | GLU | A | 429 | 31.988 | 32.540 | 24.993 | 1.00 | 42.98 |
| ATOM | 2182 | O   | GLU | A | 429 | 32.272 | 33.440 | 24.205 | 1.00 | 43.28 |
| ATOM | 2183 | CB  | GLU | A | 429 | 30.072 | 31.310 | 23.991 | 1.00 | 41.37 |
| ATOM | 2184 | CG  | GLU | A | 429 | 29.180 | 32.122 | 24.942 | 1.00 | 52.46 |
| ATOM | 2185 | CD  | GLU | A | 429 | 27.701 | 32.016 | 24.608 | 1.00 | 72.16 |
| ATOM | 2186 | OE1 | GLU | A | 429 | 27.285 | 32.556 | 23.560 | 1.00 | 65.26 |
| ATOM | 2187 | OE2 | GLU | A | 429 | 26.949 | 31.428 | 25.414 | 1.00 | 64.05 |
| ATOM | 2188 | N   | THR | A | 430 | 32.050 | 32.698 | 26.310 | 1.00 | 38.13 |
| ATOM | 2189 | CA  | THR | A | 430 | 32.462 | 33.970 | 26.892 | 1.00 | 36.94 |
| ATOM | 2190 | C   | THR | A | 430 | 33.884 | 33.958 | 27.420 | 1.00 | 37.73 |
| ATOM | 2191 | O   | THR | A | 430 | 34.464 | 35.010 | 27.653 | 1.00 | 37.89 |
| ATOM | 2192 | CB  | THR | A | 430 | 31.503 | 34.444 | 27.996 | 1.00 | 46.85 |
| ATOM | 2193 | OG1 | THR | A | 430 | 31.482 | 33.487 | 29.062 | 1.00 | 49.49 |
| ATOM | 2194 | CG2 | THR | A | 430 | 30.100 | 34.619 | 27.441 | 1.00 | 44.71 |
| ATOM | 2195 | N   | ASP | A | 431 | 34.436 | 32.758 | 27.601 | 1.00 | 31.80 |
| ATOM | 2196 | CA  | ASP | A | 431 | 35.813 | 32.567 | 28.081 | 1.00 | 31.17 |
| ATOM | 2197 | C   | ASP | A | 431 | 36.785 | 33.546 | 27.406 | 1.00 | 34.47 |
| ATOM | 2198 | O   | ASP | A | 431 | 36.884 | 33.581 | 26.184 | 1.00 | 33.04 |
| ATOM | 2199 | CB  | ASP | A | 431 | 36.238 | 31.123 | 27.794 | 1.00 | 32.81 |
| ATOM | 2200 | CG  | ASP | A | 431 | 37.478 | 30.714 | 28.548 | 1.00 | 38.99 |
| ATOM | 2201 | OD1 | ASP | A | 431 | 38.209 | 31.601 | 29.033 | 1.00 | 39.51 |
| ATOM | 2202 | OD2 | ASP | A | 431 | 37.753 | 29.494 | 28.602 | 1.00 | 41.73 |
| ATOM | 2203 | N   | THR | A | 432 | 37.463 | 34.365 | 28.212 | 1.00 | 30.10 |
| ATOM | 2204 | CA  | THR | A | 432 | 38.372 | 35.386 | 27.692 | 1.00 | 29.51 |
| ATOM | 2205 | C   | THR | A | 432 | 39.831 | 34.949 | 27.772 | 1.00 | 32.66 |
| ATOM | 2206 | O   | THR | A | 432 | 40.736 | 35.753 | 27.599 | 1.00 | 32.44 |
| ATOM | 2207 | CB  | THR | A | 432 | 38.218 | 36.694 | 28.464 | 1.00 | 35.66 |
| ATOM | 2208 | OG1 | THR | A | 432 | 38.445 | 36.449 | 29.865 | 1.00 | 33.69 |
| ATOM | 2209 | CG2 | THR | A | 432 | 36.811 | 37.267 | 28.268 | 1.00 | 30.73 |
| ATOM | 2210 | N   | ARG | A | 433 | 40.033 | 33.661 | 28.012 | 1.00 | 29.89 |
| ATOM | 2211 | CA  | ARG | A | 433 | 41.354 | 33.069 | 28.168 | 1.00 | 30.69 |
| ATOM | 2212 | C   | ARG | A | 433 | 42.407 | 33.578 | 27.182 | 1.00 | 34.75 |
| ATOM | 2213 | O   | ARG | A | 433 | 43.495 | 34.010 | 27.575 | 1.00 | 33.80 |
| ATOM | 2214 | CB  | ARG | A | 433 | 41.230 | 31.556 | 28.049 | 1.00 | 31.93 |
| ATOM | 2215 | CG  | ARG | A | 433 | 42.523 | 30.833 | 27.789 | 1.00 | 43.37 |
| ATOM | 2216 | CD  | ARG | A | 433 | 42.319 | 29.347 | 27.988 | 1.00 | 53.66 |
| ATOM | 2217 | NE  | ARG | A | 433 | 40.947 | 29.048 | 28.411 | 1.00 | 65.78 |
| ATOM | 2218 | CZ  | ARG | A | 433 | 40.633 | 28.269 | 29.442 | 1.00 | 79.86 |
| ATOM | 2219 | NH1 | ARG | A | 433 | 41.588 | 27.700 | 30.165 | 1.00 | 67.43 |
| ATOM | 2220 | NH2 | ARG | A | 433 | 39.362 | 28.064 | 29.756 | 1.00 | 67.77 |
| ATOM | 2221 | N   | TYR | A | 434 | 42.098 | 33.501 | 25.903 | 1.00 | 31.36 |
| ATOM | 2222 | CA  | TYR | A | 434 | 43.059 | 33.908 | 24.894 | 1.00 | 31.25 |
| ATOM | 2223 | C   | TYR | A | 434 | 43.301 | 35.418 | 24.896 | 1.00 | 36.35 |
| ATOM | 2224 | O   | TYR | A | 434 | 44.393 | 35.876 | 24.593 | 1.00 | 37.87 |
| ATOM | 2225 | CB  | TYR | A | 434 | 42.680 | 33.340 | 23.512 | 1.00 | 31.95 |
| ATOM | 2226 | CG  | TYR | A | 434 | 42.805 | 31.810 | 23.450 | 1.00 | 32.11 |
| ATOM | 2227 | CD1 | TYR | A | 434 | 41.687 | 30.993 | 23.543 | 1.00 | 33.73 |
| ATOM | 2228 | CD2 | TYR | A | 434 | 44.057 | 31.198 | 23.389 | 1.00 | 33.10 |
| ATOM | 2229 | CE1 | TYR | A | 434 | 41.801 | 29.597 | 23.493 | 1.00 | 32.97 |
| ATOM | 2230 | CE2 | TYR | A | 434 | 44.180 | 29.811 | 23.359 | 1.00 | 33.81 |
| ATOM | 2231 | CZ  | TYR | A | 434 | 43.049 | 29.022 | 23.415 | 1.00 | 40.00 |
| ATOM | 2232 | OH  | TYR | A | 434 | 43.175 | 27.656 | 23.417 | 1.00 | 40.44 |

TABLE 5-continued

Structural coordinates for AKT3lkd(pT305, S472D).

| ATOM | 2233 | N | PHE | A | 435 | 42.306 | 36.187 | 25.327 | 1.00 | 31.96 |
|---|---|---|---|---|---|---|---|---|---|---|
| ATOM | 2234 | CA | PHE | A | 435 | 42.472 | 37.634 | 25.430 | 1.00 | 32.01 |
| ATOM | 2235 | C | PHE | A | 435 | 43.369 | 37.995 | 26.635 | 1.00 | 40.01 |
| ATOM | 2236 | O | PHE | A | 435 | 44.215 | 38.904 | 26.546 | 1.00 | 38.47 |
| ATOM | 2237 | CB | PHE | A | 435 | 41.112 | 38.318 | 25.576 | 1.00 | 33.18 |
| ATOM | 2238 | CG | PHE | A | 435 | 40.324 | 38.365 | 24.304 | 1.00 | 34.20 |
| ATOM | 2239 | CD1 | PHE | A | 435 | 39.303 | 37.468 | 24.076 | 1.00 | 36.88 |
| ATOM | 2240 | CD2 | PHE | A | 435 | 40.648 | 39.275 | 23.309 | 1.00 | 36.24 |
| ATOM | 2241 | CE1 | PHE | A | 435 | 38.594 | 37.493 | 22.887 | 1.00 | 38.20 |
| ATOM | 2242 | CE2 | PHE | A | 435 | 39.944 | 39.306 | 22.127 | 1.00 | 38.84 |
| ATOM | 2243 | CZ | PHE | A | 435 | 38.907 | 38.417 | 21.920 | 1.00 | 37.22 |
| ATOM | 2244 | N | ASP | A | 436 | 43.174 | 37.271 | 27.744 | 1.00 | 40.23 |
| ATOM | 2245 | CA | ASP | A | 436 | 43.899 | 37.518 | 29.000 | 1.00 | 41.95 |
| ATOM | 2246 | C | ASP | A | 436 | 45.372 | 37.867 | 28.822 | 1.00 | 51.85 |
| ATOM | 2247 | O | ASP | A | 436 | 46.238 | 36.997 | 28.844 | 1.00 | 51.64 |
| ATOM | 2248 | CB | ASP | A | 436 | 43.735 | 36.347 | 29.970 | 1.00 | 43.53 |
| ATOM | 2249 | CG | ASP | A | 436 | 42.331 | 36.259 | 30.547 | 1.00 | 48.98 |
| ATOM | 2250 | OD1 | ASP | A | 436 | 42.072 | 35.326 | 31.339 | 1.00 | 50.72 |
| ATOM | 2251 | OD2 | ASP | A | 436 | 41.491 | 37.114 | 30.212 | 1.00 | 49.33 |
| ATOM | 2252 | N | GLU | A | 437 | 45.634 | 39.163 | 28.633 | 1.00 | 52.77 |
| ATOM | 2253 | CA | GLU | A | 437 | 46.990 | 39.676 | 28.421 | 1.00 | 54.13 |
| ATOM | 2254 | C | GLU | A | 437 | 47.208 | 40.958 | 29.229 | 1.00 | 60.26 |
| ATOM | 2255 | O | GLU | A | 437 | 47.419 | 40.912 | 30.448 | 1.00 | 60.71 |
| ATOM | 2256 | CB | GLU | A | 437 | 47.219 | 39.972 | 26.933 | 1.00 | 55.59 |
| ATOM | 2257 | CG | GLU | A | 437 | 46.968 | 38.793 | 26.016 | 1.00 | 66.59 |
| ATOM | 2258 | CD | GLU | A | 437 | 48.228 | 38.016 | 25.720 | 1.00 | 86.17 |
| ATOM | 2259 | OE1 | GLU | A | 437 | 48.344 | 36.867 | 26.200 | 1.00 | 80.34 |
| ATOM | 2260 | OE2 | GLU | A | 437 | 49.109 | 38.559 | 25.022 | 1.00 | 81.35 |
| ATOM | 2261 | N | GLU | A | 438 | 47.024 | 42.099 | 28.567 | 1.00 | 56.97 |
| TER | 2262 | | GLU | A | 479 | | | | | |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank Accession Numbers and publications are cited throughout this application, the disclosures of which are incorporated herein by reference in their entireties.

We claim:

1. An isolated polypeptide consisting of an amino acid sequence selected from the group consisting of the amino acid sequence of SEQ ID NO: 1, the amino acid sequence of amino acids 24-347 of SEQ ID NO: 1, and the amino acid sequence of amino acids 28-347 of SEQ ID NO: 1.

2. A crystal of a polypeptide consisting of the amino acid sequence of amino acids 28-347 of SEQ ID NO: 1, the crystal having space group $P2_12_12_1$ and unit cell dimensions selected from the group consisting of:

1) a=48.679 Å, b=73.357 Å, and c=95.468 Å,
2) a=49.093 Å, b=73.528 Å, and c=95.559 Å, and
3) a=49.015 Å, b=73.365 Å, and c=95.375 Å.

3. A composition comprising the isolated polypeptide of claim 1 complexed with a polypeptide comprising an amino acid sequence selected from the group consisting of the amino acid sequence of SEQ ID NO: 6 and the amino acid sequence of SEQ ID NO: 14.

4. An aqueous solution comprising the isolated polypeptide of claim 1 and a buffer.

5. An aqueous solution comprising the composition of claim 3 and a buffer.

* * * * *

SEQUENCE LISTING

```
<160> NUMBER OF SEQ ID NOS: 25

<210> SEQ ID NO 1
<211> LENGTH: 347
<212> TYPE: PRT
<213> ORGANISM: Artificial Sequence
<220> FEATURE:
<223> OTHER INFORMATION: AKT3 short kinase domain
<220> FEATURE:
<221> NAME/KEY: MISC_FEATURE
<222> LOCATION: (194)..(194)
<223> OTHER INFORMATION: optional phosphothreonine
<220> FEATURE:
<221> NAME/KEY: MISC_FEATURE
<222> LOCATION: (194)..(194)
<223> OTHER INFORMATION: optional threonine
<220> FEATURE:
<221> NAME/KEY: MISC_FEATURE
<222> LOCATION: (194)..(194)
<223> OTHER INFORMATION: optionally Aspartic acid
<220> FEATURE:
<221> NAME/KEY: MISC_FEATURE
<222> LOCATION: (1)..(27)
<223> OTHER INFORMATION: optionally deleted
<220> FEATURE:
<221> NAME/KEY: MISC_FEATURE
<222> LOCATION: (1)..(23)
<223> OTHER INFORMATION: optionally deleted

<400> SEQUENCE: 1
```

```
Met Ser Tyr Tyr His His His His His Asp Tyr Asp Ile Pro Thr
1               5                   10                  15

Thr Glu Asn Leu Tyr Phe Gln Gly Ala Met Asp His His Lys Arg Lys
            20                  25                  30

Thr Met Asn Asp Phe Asp Tyr Leu Lys Leu Leu Gly Lys Gly Thr Phe
        35                  40                  45

Gly Lys Val Ile Leu Val Arg Glu Lys Ala Ser Gly Lys Tyr Tyr Ala
    50                  55                  60

Met Lys Ile Leu Lys Lys Glu Val Ile Ile Ala Lys Asp Glu Val Ala
65                  70                  75                  80

His Thr Leu Thr Glu Ser Arg Val Leu Lys Asn Thr Arg His Pro Phe
                85                  90                  95

Leu Thr Ser Leu Lys Tyr Ser Phe Gln Thr Lys Asp Arg Leu Cys Phe
            100                 105                 110

Val Met Glu Tyr Val Asn Gly Gly Glu Leu Phe Phe His Leu Ser Arg
        115                 120                 125

Glu Arg Val Phe Ser Glu Asp Arg Thr Arg Phe Tyr Gly Ala Glu Ile
    130                 135                 140

Val Ser Ala Leu Asp Tyr Leu His Ser Gly Lys Ile Val Tyr Arg Asp
145                 150                 155                 160

Leu Lys Leu Glu Asn Leu Met Leu Asp Lys Asp Gly His Ile Lys Ile
                165                 170                 175

Thr Asp Phe Gly Leu Cys Lys Glu Gly Ile Thr Asp Ala Ala Thr Met
            180                 185                 190

Lys Xaa Phe Cys Gly Thr Pro Glu Tyr Leu Ala Pro Glu Val Leu Glu
        195                 200                 205

Asp Asn Asp Tyr Gly Arg Ala Val Asp Trp Trp Gly Leu Gly Val Val
210                 215                 220

Met Tyr Glu Met Met Cys Gly Arg Leu Pro Phe Tyr Asn Gln Asp His
225                 230                 235                 240

Glu Lys Leu Phe Glu Leu Ile Leu Met Glu Asp Ile Lys Phe Pro Arg
                245                 250                 255

Thr Leu Ser Ser Asp Ala Lys Ser Leu Leu Ser Gly Leu Leu Ile Lys
            260                 265                 270

Asp Pro Asn Lys Arg Leu Gly Gly Gly Pro Asp Asp Ala Lys Glu Ile
        275                 280                 285

Met Arg His Ser Phe Phe Ser Gly Val Asn Trp Gln Asp Val Tyr Asp
    290                 295                 300

Lys Lys Leu Val Pro Pro Phe Lys Pro Gln Val Thr Ser Glu Thr Asp
305                 310                 315                 320

Thr Arg Tyr Phe Asp Glu Glu Phe Thr Ala Gln Thr Ile Thr Ile Thr
                325                 330                 335

Pro Pro Glu Lys Tyr Asp Glu Asp Gly Met Asp
            340                 345

<210> SEQ ID NO 2
<211> LENGTH: 368
<212> TYPE: PRT
<213> ORGANISM: Artificial Sequence
<220> FEATURE:
<223> OTHER INFORMATION: AKT3 long kinase domain
<220> FEATURE:
<221> NAME/KEY: MISC_FEATURE
<222> LOCATION: (194)..(194)
<223> OTHER INFORMATION: optional phosphothreonine
<220> FEATURE:
<221> NAME/KEY: MISC_FEATURE
<222> LOCATION: (194)..(194)
```

```
<223> OTHER INFORMATION: optionally Asp.
<220> FEATURE:
<221> NAME/KEY: MISC_FEATURE
<222> LOCATION: (194)..(194)
<223> OTHER INFORMATION: optionally threonine
<220> FEATURE:
<221> NAME/KEY: MISC_FEATURE
<222> LOCATION: (361)..(361)
<223> OTHER INFORMATION: optionally phosphoserine
<220> FEATURE:
<221> NAME/KEY: MISC_FEATURE
<222> LOCATION: (361)..(361)
<223> OTHER INFORMATION: optionally serine
<220> FEATURE:
<221> NAME/KEY: MISC_FEATURE
<222> LOCATION: (361)..(361)
<223> OTHER INFORMATION: optionally Asp.
<220> FEATURE:
<221> NAME/KEY: MISC_FEATURE
<222> LOCATION: (1)..(27)
<223> OTHER INFORMATION: optionally deleted
<220> FEATURE:
<221> NAME/KEY: MISC_FEATURE
<222> LOCATION: (1)..(23)
<223> OTHER INFORMATION: optionally deleted

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Asp His Lys Arg Lys
            20                  25                  30

Thr Met Asn Asp Phe Asp Tyr Leu Lys Leu Leu Gly Lys Gly Thr Phe
        35                  40                  45

Gly Lys Val Ile Leu Val Arg Glu Lys Ala Ser Gly Lys Tyr Tyr Ala
50                  55                  60

Met Lys Ile Leu Lys Lys Glu Val Ile Ile Ala Lys Asp Glu Val Ala
65                  70                  75                  80

His Thr Leu Thr Glu Ser Arg Val Leu Lys Asn Thr Arg His Pro Phe
                85                  90                  95

Leu Thr Ser Leu Lys Tyr Ser Phe Gln Thr Lys Asp Arg Leu Cys Phe
            100                 105                 110

Val Met Glu Tyr Val Asn Gly Gly Glu Leu Phe Phe His Leu Ser Arg
        115                 120                 125

Glu Arg Val Phe Ser Glu Asp Arg Thr Arg Phe Tyr Gly Ala Glu Ile
    130                 135                 140

Val Ser Ala Leu Asp Tyr Leu His Ser Gly Lys Ile Val Tyr Arg Asp
145                 150                 155                 160

Leu Lys Leu Glu Asn Leu Met Leu Asp Lys Asp Gly His Ile Lys Ile
                165                 170                 175

Thr Asp Phe Gly Leu Cys Lys Glu Gly Ile Thr Asp Ala Ala Thr Met
            180                 185                 190

Lys Xaa Phe Cys Gly Thr Pro Glu Tyr Leu Ala Pro Glu Val Leu Glu
        195                 200                 205

Asp Asn Asp Tyr Gly Arg Ala Val Asp Trp Trp Gly Leu Gly Val Val
    210                 215                 220

Met Tyr Glu Met Met Cys Gly Arg Leu Pro Phe Tyr Asn Gln Asp His
225                 230                 235                 240

Glu Lys Leu Phe Glu Leu Ile Leu Met Glu Asp Ile Lys Phe Pro Arg
                245                 250                 255

Thr Leu Ser Ser Asp Ala Lys Ser Leu Leu Ser Gly Leu Leu Ile Lys
            260                 265                 270

Asp Pro Asn Lys Arg Leu Gly Gly Gly Pro Asp Asp Ala Lys Glu Ile
```

```
                    275                 280                 285
Met Arg His Ser Phe Phe Ser Gly Val Asn Trp Gln Asp Val Tyr Asp
    290                 295                 300

Lys Lys Leu Val Pro Pro Phe Lys Pro Gln Val Thr Ser Glu Thr Asp
305                 310                 315                 320

Thr Arg Tyr Phe Asp Glu Glu Phe Thr Ala Gln Thr Ile Thr Ile Thr
                325                 330                 335

Pro Pro Glu Lys Tyr Asp Glu Asp Gly Met Asp Cys Met Asp Asn Glu
            340                 345                 350

Arg Arg Pro His Phe Pro Gln Phe Xaa Tyr Ser Ala Ser Gly Arg Glu
        355                 360                 365

<210> SEQ ID NO 3
<211> LENGTH: 479
<212> TYPE: PRT
<213> ORGANISM: Artificial Sequence
<220> FEATURE:
<223> OTHER INFORMATION: AKT3 full length sequence
<220> FEATURE:
<221> NAME/KEY: MISC_FEATURE
<222> LOCATION: (305)..(305)
<223> OTHER INFORMATION: optional phosphothreonine
<220> FEATURE:
<221> NAME/KEY: MISC_FEATURE
<222> LOCATION: (305)..(305)
<223> OTHER INFORMATION: optionally threonine
<220> FEATURE:
<221> NAME/KEY: MISC_FEATURE
<222> LOCATION: (305)..(305)
<223> OTHER INFORMATION: optionally Asp.
<220> FEATURE:
<221> NAME/KEY: MISC_FEATURE
<222> LOCATION: (472)..(472)
<223> OTHER INFORMATION: optional phosphoserine
<220> FEATURE:
<221> NAME/KEY: MISC_FEATURE
<222> LOCATION: (472)..(472)
<223> OTHER INFORMATION: optionally Asp.
<220> FEATURE:
<221> NAME/KEY: MISC_FEATURE
<222> LOCATION: (472)..(472)
<223> OTHER INFORMATION: optionally serine

<400> SEQUENCE: 3

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160
```

Lys Val Ile Leu Val Arg Glu Lys Ala Ser Gly Lys Tyr Tyr Ala Met
            165                 170                 175

Lys Ile Leu Lys Lys Glu Val Ile Ile Ala Lys Asp Glu Val Ala His
        180                 185                 190

Thr Leu Thr Glu Ser Arg Val Leu Lys Asn Thr Arg His Pro Phe Leu
            195                 200                 205

Thr Ser Leu Lys Tyr Ser Phe Gln Thr Lys Asp Arg Leu Cys Phe Val
        210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
            245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
        290                 295                 300

Xaa Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
            325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
        370                 375                 380

Pro Asn Lys Arg Leu Gly Gly Pro Asp Asp Ala Lys Glu Ile Met
385                 390                 395                 400

Arg His Ser Phe Phe Ser Gly Val Asn Trp Gln Asp Val Tyr Asp Lys
            405                 410                 415

Lys Leu Val Pro Pro Phe Lys Pro Gln Val Thr Ser Glu Thr Asp Thr
        420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
        450                 455                 460

Arg Pro His Phe Pro Gln Phe Xaa Tyr Ser Ala Ser Gly Arg Glu
465                 470                 475

<210> SEQ ID NO 4
<211> LENGTH: 6
<212> TYPE: PRT
<213> ORGANISM: Artificial Sequence
<220> FEATURE:
<223> OTHER INFORMATION: TEV cleavage site

<400> SEQUENCE: 4

Glu Asn Leu Tyr Phe Gln
1               5

<210> SEQ ID NO 5
<211> LENGTH: 3
<212> TYPE: PRT
<213> ORGANISM: Artificial Sequence
<220> FEATURE:

```
<223> OTHER INFORMATION: Akt3 Kinase Domain start

<400> SEQUENCE: 5

His His Lys
 1

<210> SEQ ID NO 6
<211> LENGTH: 11
<212> TYPE: PRT
<213> ORGANISM: Artificial Sequence
<220> FEATURE:
<223> OTHER INFORMATION: GSK-3 peptide

<400> SEQUENCE: 6

Gly Arg Pro Arg Thr Ser Ser Phe Ala Glu Gly
 1               5                  10

<210> SEQ ID NO 7
<211> LENGTH: 36
<212> TYPE: DNA
<213> ORGANISM: Artificial Sequence
<220> FEATURE:
<223> OTHER INFORMATION: common 5' primer

<400> SEQUENCE: 7
actgccatgg atcatcataa aagaaagaca atgaat                              36

<210> SEQ ID NO 8
<211> LENGTH: 31
<212> TYPE: DNA
<213> ORGANISM: Artificial Sequence
<220> FEATURE:
<223> OTHER INFORMATION: AKT3skd, 3' primer

<400> SEQUENCE: 8
gatcgaattc ttattctcgt ccacttgcag a                                   31

<210> SEQ ID NO 9
<211> LENGTH: 40
<212> TYPE: DNA
<213> ORGANISM: Artificial Sequence
<220> FEATURE:
<223> OTHER INFORMATION: AKT3lkd 3' primer

<400> SEQUENCE: 9
gatcgaattc tcagtccata ccatcctcat catatttttc                          40

<210> SEQ ID NO 10
<211> LENGTH: 5
<212> TYPE: PRT
<213> ORGANISM: Artificial Sequence
<220> FEATURE:
<223> OTHER INFORMATION: AKT3skd start sequence

<400> SEQUENCE: 10

His His Lys Arg Lys
 1               5

<210> SEQ ID NO 11
<211> LENGTH: 26
<212> TYPE: PRT
<213> ORGANISM: Artificial Sequence
<220> FEATURE:
<223> OTHER INFORMATION: N-terminal tag

<400> SEQUENCE: 11

Met Tyr Ser His His His His His His Asp Tyr Asp Ile Pro Thr Thr
```

```
                1               5                  10                  15

Glu Asn Leu Tyr Phe Gln Gly Ala Met Asp
            20                  25

<210> SEQ ID NO 12
<211> LENGTH: 6
<212> TYPE: PRT
<213> ORGANISM: Artificial Sequence
<220> FEATURE:
<223> OTHER INFORMATION: TEV protease consensus cleavage site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 12

Glu Xaa Xaa Tyr Xaa Gln
1               5

<210> SEQ ID NO 13
<211> LENGTH: 8
<212> TYPE: PRT
<213> ORGANISM: Artificial Sequence
<220> FEATURE:
<223> OTHER INFORMATION: FLAG tag

<400> SEQUENCE: 13

Asp Tyr Lys Asp Asp Asp Asp Lys
1               5

<210> SEQ ID NO 14
<211> LENGTH: 7
<212> TYPE: PRT
<213> ORGANISM: Artificial Sequence
<220> FEATURE:
<223> OTHER INFORMATION: AKT3 substrate peptide

<400> SEQUENCE: 14

Arg Pro Arg Ala Ala Thr Phe
1               5

<210> SEQ ID NO 15
<211> LENGTH: 12
<212> TYPE: PRT
<213> ORGANISM: Artificial Sequence
<220> FEATURE:
<223> OTHER INFORMATION: domain boundary

<400> SEQUENCE: 15

Thr Pro Pro Glu Lys Tyr Asp Glu Asp Gly Met Asp
1               5                   10

<210> SEQ ID NO 16
<211> LENGTH: 9
<212> TYPE: PRT
<213> ORGANISM: Artificial Sequence
<220> FEATURE:
<223> OTHER INFORMATION: domain boundary

<400> SEQUENCE: 16

His His Lys Arg Lys Thr Met Asn Asp
1               5

<210> SEQ ID NO 17
```

```
<211> LENGTH: 1041
<212> TYPE: DNA
<213> ORGANISM: Artificial Sequence
<220> FEATURE:
<223> OTHER INFORMATION: AKT3 skd
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
```

-continued

```
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (285)..(285)
```

-continued

```
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (408)..(408)
```

-continued

```
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (540)..(540)
```

```
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (660)..(660)
```

```
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(795)
```

-continued

```
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (921)..(921)
```

```
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t

<400> SEQUENCE: 17
atgwsntayt aycaycayca ycaycaycay gaytaygaya thccnacnac ngaraayytn      60 tayttyc

-continued

```
aarytnytng gnaarggnac nttyggnaar gtnathytng tnmgngaraa rgcnwsnggn    180
aartaytayg cnatgaarat hytnaaraar gargtnatha thgcnaarga ygargtngcn    240
cayacnytna cngarwsnmg ngtnytnaar aayacnmgnc ayccnttyyt nacnwsnytn    300
aartaywsnt tycaracnaa rgaymgnytn tgyttygtna tggartaygt naayggnggn    360
garytnttyt tycayytnws nmgngarmgn gtnttywsng argaymgnac nmgnttytay    420
ggngcngara thgtnwsngc nytngaytay ytncaywsng gnaarathgt ntaymgngay    480
ytnaarytng araayytnat gytngayaar gayggncaya thaarathac ngayttyggn    540
ytntgyaarg arggnathac ngaygcngcn acnatgaara cnttytgygg nacnccngar    600
tayytngcnc cngargtnyt ngargayaay gaytayggnm gngcngtnga ytggtggggn    660
ytnggngtng tnatgtayga ratgatgtgy ggnmgnytnc cnttytayaa ycargaycay    720
garaarytnt tygarytnat hytnatggar gayathaart tyccnmgnac nytnwsnwsn    780
gaygcnaarw snytnytnws nggnytnytn athaargayc cnaayaarmg nytnggnggn    840
ggnccngayg aygcnaarga rathatgmgn caywsnttyt tywsnggngt naaytggcar    900
gaygtntayg ayaaraaryt ngtnccnccn ttyaarccnc argtnacnws ngaracngay    960
acnmgntayt tygaygarga rttyacngcn caracnatha cnathacncc nccngaraar   1020
taygaygarg ayggnatgga y                                             1041
```

<210> SEQ ID NO 18
<211> LENGTH: 1104
<212> TYPE: DNA
<213> ORGANISM: Artificial Sequence
<220> FEATURE:
<223> OTHER INFORMATION: AKT3 lkd
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:

-continued

```
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
```

-continued

```
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
```

-continued

```
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
```

-continued

```
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
```

```
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
```

-continued

```
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
```

```
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
```

```
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t

<400> SEQUENCE: 18
atgwsntayt aycaycayca ycaycaycay gaytaygaya thccnacnac ngaraayytn      60
tayttycarg gngcnatgga ycaycayaar mgnaaracna tgaaygaytt ygaytayytn     120
aarytnytng gnaarggnac nttyggnaar gtnathytng tnmgngaraa rgcnwsnggn     180
aartaytayg cnatgaaart hytnaaraar gargtnatha thgcnaarga ygargtngcn     240
cayacnytna cngarwsnmg ngtnytnaar aayacnmgnc ayccnttyyt nacnwsnytn     300
```

-continued

```
aartaywsnt tycaracnaa rgaymgnytn tgyttygtna tggartaygt naayggnggn    360
garytnttyt tycayytnws nmgngarmgn gtnttywsng argaymgnac nmgnttytay    420
ggngcngara thgtnwsngc nytngaytay ytncaywsng gnaarathgt ntaymgngay    480
ytnaarytng araayytnat gytngayaar gayggncaya thaarathac ngayttyggn    540
ytntgyaarg arggnathac ngaygcngcn acnatgaara cnttytgygg nacnccngar    600
tayytngcnc cngargtnyt ngargayaay gaytayggnm gngcngtnga ytggtggggn    660
ytnggngtng tnatgtayga ratgatgtgy ggnmgnytnc cnttytayaa ycargaycay    720
garaarytnt tygarytnat hytnatggar gayathaart tyccnmgnac nytnwsnwsn    780
gaygcnaarw snytnytnws nggnytnytn athaargayc cnaayaarmg nytnggnggn    840
ggnccngayg aygcnaarga rathatgmgn caywsnttyt tywsnggngt naaytggcar    900
gaygtntayg ayaaraaryt ngtnccnccn ttyaarccnc argtnacnws ngaracngay    960
acnmgntayt tygaygarga rttyacngcn caracnatha cnathacncc nccngaraar   1020
taygaygarg ayggnatgga ytgyatggay aaygarmgnm gnccncaytt yccncartty   1080
wsntaywsng cnwsnggnmg ngar                                          1104
```

<210> SEQ ID NO 19
<211> LENGTH: 5
<212> TYPE: PRT
<213> ORGANISM: Artificial Sequence
<220> FEATURE:
<223> OTHER INFORMATION: enterokinase cleavage site

<400> SEQUENCE: 19

```
Asp Asp Asp Asp Lys
1               5
```

<210> SEQ ID NO 20
<211> LENGTH: 4
<212> TYPE: PRT
<213> ORGANISM: Artificial Sequence
<220> FEATURE:
<223> OTHER INFORMATION: factor Xa cleavage site

<400> SEQUENCE: 20

```
Ile Asp Gly Arg
1
```

<210> SEQ ID NO 21
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 21

```
Leu Val Pro Arg Gly Ser
1               5
```

<210> SEQ ID NO 22
<211> LENGTH: 8
<212> TYPE: PRT
<213> ORGANISM: Artificial Sequence
<220> FEATURE:
<223> OTHER INFORMATION: Prescission cleavage site

<400> SEQUENCE: 22

```
Leu Glu Val Leu Phe Gln Gly Pro
1               5
```

```
<210> SEQ ID NO 23
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 23

Glu Gln Leu Tyr Phe Gln Gly
1               5

<210> SEQ ID NO 24
<211> LENGTH: 7
<212> TYPE: PRT
<213> ORGANISM: Artificial Sequence
<220> FEATURE:
<223> OTHER INFORMATION: 3C protease cleavage site

<400> SEQUENCE: 24

Glu Thr Leu Phe Gln Gly Pro
1               5

<210> SEQ ID NO 25
<211> LENGTH: 5
<212> TYPE: PRT
<213> ORGANISM: Artificial Sequence
<220> FEATURE:
<223> OTHER INFORMATION: sortase A cleavage site

<400> SEQUENCE: 25

Leu Pro Glu Thr Gly
1               5
```